(12) United States Patent
Senger et al.

(10) Patent No.: US 11,484,560 B2
(45) Date of Patent: Nov. 1, 2022

(54) STABILISING FATTY ACID COMPOSITIONS

(71) Applicant: BASF PLANT SCIENCE COMPANY GMBH, Ludwigshafen (DE)

(72) Inventors: Toralf Senger, Durham, NC (US); Heiko A. Haertel, Berlin (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

(21) Appl. No.: 15/525,463

(22) PCT Filed: Nov. 13, 2015

(86) PCT No.: PCT/EP2015/076605
§ 371 (c)(1),
(2) Date: May 9, 2017

(87) PCT Pub. No.: WO2016/075310
PCT Pub. Date: May 19, 2016

(65) Prior Publication Data
US 2018/0291389 A1    Oct. 11, 2018

Related U.S. Application Data

(60) Provisional application No. 62/234,373, filed on Sep. 29, 2015, provisional application No. 62/079,622, filed on Nov. 14, 2014.

(51) Int. Cl.
| | | |
|---|---|---|
| C12N 15/82 | (2006.01) | |
| A61K 36/31 | (2006.01) | |
| C12Q 1/6895 | (2018.01) | |
| C12N 9/02 | (2006.01) | |
| C12N 9/00 | (2006.01) | |
| A61K 31/202 | (2006.01) | |

(52) U.S. Cl.
CPC ............ *A61K 36/31* (2013.01); *C12Q 1/6895* (2013.01); *A61K 31/202* (2013.01); *C12N 9/0071* (2013.01); *C12N 9/93* (2013.01); *C12N 15/8247* (2013.01); *C12Y 114/19* (2013.01); *C12Y 114/19003* (2013.01); *C12Y 114/19006* (2013.01); *C12Y 602/01003* (2013.01)

(58) Field of Classification Search
None
See application file for complete search history.

(56) References Cited

U.S. PATENT DOCUMENTS

| | | |
|---|---|---|
| 5,827,289 A | 10/1998 | Reiley et al. |
| 6,303,849 B1 | 10/2001 | Potts et al. |
| 6,462,258 B1 * | 10/2002 | Fincher ............... C12N 9/1092 800/300 |
| 6,689,880 B2 | 2/2004 | Chen et al. |
| 6,733,974 B1 | 5/2004 | Feazel |
| 6,740,488 B2 | 5/2004 | Rangwala et al. |
| 6,818,807 B2 | 11/2004 | Trolinder et al. |
| 6,825,400 B2 | 11/2004 | Behr et al. |
| 6,893,826 B1 | 5/2005 | Hillyard et al. |
| 6,900,014 B1 | 5/2005 | Weston et al. |
| 7,371,930 B1 | 5/2008 | Knerr |
| 7,423,198 B2 | 9/2008 | Yao et al. |
| 8,999,411 B2 | 4/2015 | Froman et al. |
| 10,035,989 B2 | 7/2018 | Cirpus et al. |
| 10,760,089 B2 | 9/2020 | Andre |
| 10,829,775 B2 | 11/2020 | Andre |
| 11,033,593 B2 | 6/2021 | Senger et al. |
| 2006/0051847 A1 | 3/2006 | Gunnarsson et al. |
| 2013/0288377 A1 | 10/2013 | Champagne et al. |
| 2014/0220215 A1 | 8/2014 | Iassonova et al. |
| 2015/0299676 A1 | 10/2015 | Walsh et al. |
| 2016/0369290 A1 | 12/2016 | Cirpus et al. |

FOREIGN PATENT DOCUMENTS

| | | |
|---|---|---|
| AU | 2011289381 A1 | 1/2013 |
| CN | 101400798 A | 4/2009 |
| JP | 2007527716 A | 10/2007 |
| WO | WO-93/10241 A1 | 5/1993 |
| WO | WO-94/13814 A1 | 6/1994 |
| WO | WO-95/27791 A1 | 10/1995 |
| WO | WO-96/24674 A1 | 8/1996 |
| WO | WO-98/55631 A1 | 12/1998 |
| WO | WO-98/55632 A1 | 12/1998 |

(Continued)

OTHER PUBLICATIONS

McConnell et al. (Nature, 411:709-713, 2001).*
Hanzawa et al. (PNAS, 102:7748-7753, 2005).*
Wishart et al. (JBC, 270:26782-26785, 1995).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
Doerks et al., (TIG, 14:248-250, 1998).*
Smith et al. (Nature Biotechnology, 15:1222-1223, 1997).*
Bork et al. (TIG, 12:425-427, 1996).*

(Continued)

*Primary Examiner* — Vinod Kumar
(74) *Attorney, Agent, or Firm* — Marshall, Gerstein & Borun LLP

(57) ABSTRACT

Assay method, comprising providing a plant capable of expressing a delta-12 desaturase, wherein said delta-12 desaturase has at least 50% total amino acid sequence identity to at least one of the sequences SEQ ID NO. 328 to 336, and/or at least 59% total amino acid sequence similarity to at least one of the sequences SEQ ID NO. 328 to 336, and wherein the plant is also capable of expressing at least one or more enzymes of unsaturated fatty acid metabolism, of which enzymes at least one is capable of using linoleic acid as a substrate, and of which enzymes at least one is supposedly connected to a plant metabolic property, growing the plant, and measuring said plant metabolic property for said plant.

3 Claims, 91 Drawing Sheets

Specification includes a Sequence Listing.

(56) References Cited

FOREIGN PATENT DOCUMENTS

| WO | WO-99/64616 A2 | 12/1999 | | |
|---|---|---|---|---|
| WO | WO-00/18889 A2 | 4/2000 | | |
| WO | WO-01/059128 A2 | 8/2001 | | |
| WO | WO-02/26946 A2 | 4/2002 | | |
| WO | WO-2002/052024 A2 | 7/2002 | | |
| WO | WO-02/102970 A2 | 12/2002 | | |
| WO | WO-2003/078639 A2 | 9/2003 | | |
| WO | WO-2003/089452 A2 | 10/2003 | | |
| WO | WO-2003/093482 A2 | 11/2003 | | |
| WO | WO-2004/071467 A2 | 8/2004 | | |
| WO | WO-2004/087902 A2 | 10/2004 | | |
| WO | WO-2004/090123 A2 | 10/2004 | | |
| WO | WO-2005/007845 A2 | 1/2005 | | |
| WO | WO-2005/012316 A2 | 2/2005 | | |
| WO | WO-2005/083053 A2 | 9/2005 | | |
| WO | WO-2005/083093 A2 | 9/2005 | | |
| WO | WO-2005/118814 A2 | 12/2005 | | |
| WO | WO-2006/008099 A2 | 1/2006 | | |
| WO | WO-2006/012325 A1 | 2/2006 | | |
| WO | WO-2006/024509 A2 | 3/2006 | | |
| WO | WO-2006/069710 A1 | 7/2006 | | |
| WO | WO-2006/100241 A2 | 9/2006 | | |
| WO | WO-2007/096387 A1 | 8/2007 | | |
| WO | WO-2008/022963 A2 | 2/2008 | | |
| WO | WO-2009/111263 A1 | 9/2009 | | |
| WO | WO-2009/130291 A2 | 10/2009 | | |
| WO | WO-2010/023202 A2 | 3/2010 | | |
| WO | WO-2010023202 A2 | * 3/2010 | ............... | C12N 9/00 |
| WO | WO-2010/066703 A2 | 6/2010 | | |
| WO | WO-2011/006948 A1 | 1/2011 | | |
| WO | WO-2011006948 A1 | * 1/2011 | ........... | C07K 14/435 |
| WO | WO-2011/161093 A1 | 12/2011 | | |
| WO | WO-2013/049227 A2 | 4/2013 | | |
| WO | WO-2013/153404 A1 | 10/2013 | | |
| WO | WO-2013153404 A1 | * 10/2013 | ........... | C12N 9/0083 |
| WO | WO-2013/185184 A2 | 12/2013 | | |
| WO | WO-2015/089587 A1 | 6/2015 | | |

OTHER PUBLICATIONS

Bahrani et al. (Can. J. Plant Sci., 88:419-423, 2008).*
Arondel, et al., "Map-based Cloning of a Gene Controlling Omega-3 Fatty Acid Desaturation in *Arabidopsis*c", Science vol. 258, Issue 5086, Nov. 20, 1992, pp. 1353-1355.
Bai, et al., "X-ray Structure of a Mammalian Stearoyl-CoA Desaturase", Nature, Aug. 2015, vol. 524, pp. 252-256.
Bligh, et al., "A Rapid Method of Total Lipid Extraction and Purification", Canadian Journal of Biochemistry and Physiology, vol. 37, Issue 1, 1959, pp. 911-917.
Browse et al., Fatty acid composition of leaf lipids determined after combined digestion and fatty acid methyl ester formation from fresh tissue, Anal. Biochem., 152(1):141-5 (1986).
Cahoon et al., Biosynthetic origin of conjugated double bonds: production of fatty acid components of high-value drying oils in transgenic soybean embryos, Proc. Natl. Acad. Sci. USA, 96(22):12935-40 (1999).
Cutler, et al., "Abscisic Acid: Emergence of a Core Signaling Network", Annual Review of Plant Biology, vol. 61, 2010, pp. 651-679.
Datar et al. Cell and Cell Debris Removal: Centrifugation and Crossflow Filtration, pp. 472-503 IN: Rehm et al. (eds.), Biotechnology, Second, Completely Revised Edition, vol. 3 (Bioprocessing) edited by Stephanopoulos, Weinheim, Germany: VCH (1993).
De Block, et al., "Transformation of *Brassica napus* and *Brassica oleracea* Using Agrobacterium Tumefaciens and the Expression of the Bar and Neo Genes in the Transgenic Plants", Plant Physiol., v.91(2):694-701 (1989).
Domergue, et al., Acyl Carriers Used as Substrates by the Desaturases and Elongases Involved in Very Long-chain Polyunsaturated Fatty Acids Biosynthesis Reconstituted in Yeast, J. Biol. Chem., 278(37):35115-26 (2003).

Domergue, et al., "In Vivo Characterization of the First Acyl-CoA Δ6-Desaturase from a Member of the Plant Kingdom, the Microalga *Ostreococcus tauri*", Biochem. J., 389(Pt. 2):483-90 (2005).
Dubos, et al., "Integrating Bioinformatic Resources to Predict Transcription Factors Interacting with Cis-Sequences Conserved in Co-Regulated Genes", BMC Genomics, 15:317 (2014).
Focks, et al., "Wrinkled1: A Novel, Low-Seed-Oil Mutant of *Arabidopsis* with a Deficiency in the Seed-Specific Regulation of Carbohydrate Metabolism", Plant Physiol., 118(1):91-101 (1998).
Fujiwara et al., Seed-specific repression of GUS activity in tobacco plants by antisense RNA, Plant Mol. Biol., 20(6):1059-69 (1992).
Griffiths, et al., Delta 6- and Delta 12-desaturase Activities and Phosphatidic Acid Formation in Microsomal Preparations from the Developing Cotyledons of Common Borage (*Borango officinalis*), Biochem. J., 252(3):641-7 (1988).
Hull et al., Analysis of the promoter of an abscisic acid responsive late embryogenesis abundant gene of *Arabidopsis thaliana*, Plant Sci., 14:181-92 (1996).
International Preliminary Report on Patentability, International Application No. PCT/EP2015/076630, dated May 16, 2017.
International Search Report and Written Opinion for PCT Patent Application No. PCT/EP2015/076605, dated Feb. 24, 2016, 13 pages.
International Search Report and Written Opinion, International Application No. PCT/EP2015/076630, dated Mar. 7, 2016.
Jain, et al., "Identification of a Novel Lysophospholipid Acyltransferase in *Saccharomyces cerevisiae*", J. Biol. Chem., 282(42):30562-9 (2007).
Kargiotidou, et al., "Low Temperature and Light Regulate Delta 12 Fatty Acid Desaturases (FAD2) at a Transcriptional Level in Cotton (*Gossypium hirsutum*)", J. Exp. Bot., 49(8):2043-56 (2008).
Knutzon, et al., "Identification of Delta5-dehydratase from Mortierella Alpina by Heterologous Expression in Bakers' Yeast and Canola", J. Biol. Chem., 273(45):29360-6 (1998).
Livak et al., Analysis of relative gene expression data using real-time quantitative PCR and the 2(-Delta Delta C(T)) Method, Methods, 25(4):402-8 (2001).
Meesapyodsuk, et al., "The Front-end Desaturase: Structure, Function, Evolution and Biotechnological Use", Lipids, vol. 47, Issue 3, Mar. 2012, pp. 227-237.
Okayasu, et al., "Purification and Partial Characterization of Linoleoyl-CoA Desaturase from Rat Liver Microsomes", Archives of Biochemistry and Biophysics, 206(1):21-8 (1981).
Okuley, et al., "*Arabidopsis* FAD2 Gene Encodes the Enzyme that is Essential for Polyunsaturated Lipid Synthesis", The Plant Cell Online, vol. 6, Issue 1, Jan. 1994, pp. 147-158.
Paul, et al., "Members of the *Arabidopsis* FAE1-like 3-Ketoacyl-CoA Synthase Gene Family Substitute for the Elop Proteins of *Saccharomyces cerevisiae*", J. Biol. Chem., 281(14):9018-29 (2006).
Qi, et al., "Production of Very Long Chain Polyunsaturated Omega-3 and Omega-6 Fatty Acids in Plants", Nature Biotechnology, vol. 22, Issue 6, Jun. 2004, pp. 739-745.
Riekhof, et al., "Lysophosphatidylcholine Metabolism in *Saccharomyces cerevisiae* The Role of P-Type Atpases in Transport and in Broad Specificity Acyltransferase in Acylation", J. Biol. Chem., 282(51):36853-61 (2007).
Ruiz-Lopez, et al., "Successful High-level Accumulation of Fish Oil Omega-3 Long-Chain Polyunsaturated Fatty Acids in a Transgenic Oilseed Crop",Plant J., 77(2):198-208 (2014).
Ruuska, et al., "Contrapuntal Networks of Gene Expression during *Arabidopsis* Seed Filling", The Plant Cell Online, vol. 14, Issue 6, Jun. 2002, pp. 1191-1206.
Sarkar, et al., "Specificity Determinants for the Abscisic Acid Response Element", FEBS Open Bio, vol. 3, Issue 1, Jan. 1, 2013, pp. 101-105.
Shanklin, et al., "Desaturation and Related Modifications of Fatty Acids1", Annual Review of Plant Physiology and Plant Molecular Biology, vol. 49, Jun. 1998, pp. 611-641.
Shanklin, et al., "Stearoyl-acyl-carrier-protein desaturase from Higher Plants is Structurally Unrelated to the Animal and Fungal Homologs", Proc. Natl. Acad. Sci. USA, 88(6):2510-4 (1991).

(56) References Cited

OTHER PUBLICATIONS

Strittmatter et al., "Purification and Properties of Rat Liver Microsomal Stearyl Coenzyme A Desaturase", Proc. Natl. Acad. Sci. USA, 71(11):4565-9 (1974).
Stymne, et al., "Biosynthesis of γ-linolenic Acid in Cotyledons and Microsomal Preparations of the Developing Seeds of Common Borage (*Borago officinalis*)", Biochem. J., 240(2):385-93 (1986).
Tamaki, et al., "LPT1 Encodes a Membrane-bound O-Acyltransferase Involved in the Acylation of Lysophospholipids in the Yeast *Saccharomyces cerevisiae*", J. Biol. Chem., 282(47):34288-98 (2007).
Tang, et al., "Oleate Desaturase Enzymes of Soybean: Evidence of Regulation Through Differential Stability and Phosphorylation", Plant J., 44(3):433-46 (2005).
Vilardell et al., Regulation of the rab17 gene promoter in transgenic *Arabidopsis* wild-type, ABA-deficient and ABA-insensitive mutants, Plant Mol. Biol., 24(4):561-9 (1994).
Wang, et al., "Crystal Structure of Human Stearoyl-Coenzyme a Desaturase in Complex with Substrate", Nature Structural & Molecular Biology, vol. 22, 2015, pp. 581-585.
Wu, et al., "Stepwise Engineering to Produce High Yields of Very Long-Chain Polyunsaturated Fatty Acids in Plants", Nature Biotechnology, vol. 23, Issue 8, Aug. 1, 2005, pp. 1013-1017.
Xiao, et al., "Characterization of the Promoter and 5'-UTR Intron of Oleic Acid Desaturase (FAD2) Gene in *Brassica napus*", Gene, vol. 545, Issue 1, Jul. 2014, pp. 45-55.
Database EMBL [Online] 5, "Rattus Norvegicus clone CH230-506F12, Working Draft Sequence, Unordered Pieces.", XP002754369, retrieved from EBI accession No. EM_HTG:AC142370 (Mar. 29, 2003).
Database EMBL [Online], "Mus *Musculus domesticus* DNA, BAG Clone: B6Ng01-175K07, 3' End.", XP002754370, retrieved from EBI accession No. EM_GSS:GA003396, created Feb. 6, 2011).
International Search Report and Written Opinion for PCT Patent Application No. PCT/EP2015/076596, dated Mar. 11, 2016, 15 pages.
O'Malley, et al., "An Adapter Ligation-Mediated Pcr Method for High-Throughput Mapping of T-DNA Inserts in the *Arabidopsis* Genome", Nature Protocols, vol. 2, Issue 11, 2007, pp. 2910-2917.
Rychlik, et al, "A computer program for choosing optimal oligonudeotides for filter hybridization, sequencing and in vitro amplification of DNA", Nucleic Acids Research, 17(21):8543-51 (1989).
Wu, et al., "Stepwise Engineering to Produce High Yields of Very Long-Chain Polyunsaturated Fatty Acids in Plants", Nature Biotechnology, vol. 23, Issue 8, 2005, pp. 1013-1017.
Abidi et al., "Effect of Genetic Modification on the Distribution of Minor Constituents in Canola Oil", Journal of the American Oil Chemists' Society, vol. 76, Issue 4, pp. 463-467 (Apr. 1999).
Dolde, et al., "Tocopherols in Breeding Lines and Effects of Planting Location, Fatty Acid Composition, and Temperature During Development", JAOCS, 76:349-55 (Mar. 1999).
International Search Report and Written Opinion for PCT Patent Application No. PCT/EP2015/076608, dated Mar. 9, 2016, 13 pages.
Li, et al., "Correlations between Tocopherol and Fatty Acid Components in Germplasm Collections of *Brassica* Oilseeds", Journal of Agricultural and Food Chemistry, 61:34-40 (2013).
Quek, et al., "Commercial Extraction of Vitamin E from Food Sources" The Encyclopedia of Vitamin E, Eds. Preedy, et al., CABI Publishers, Oxford, U.K., 2007, pp. 140-152.
International Preliminary Report on Patentability, International Application No. PCT/EP2015/076596, dated May 16, 2017.
International Preliminary Report on Patentability, PCT application No. PCT/EP2015/076605, dated May 16, 2017.
International Preliminary Report on Patentability, PCT Application No. PCT/EP2015/076608, completed Feb. 28, 2017.
Akermoun et al., Complex lipid biosynthesis: phospholipid synthesis, Biochemical Society Transactions 28: 713-5 (2000).

Bafor et al., Ricinoleic acid biosynthesis and triacylglycerol assembly in microsomal preparations from developing castor-bean (*Ricinus communis*) endosperm, Biochem. J., 280(Pt.2):507-14 (Dec. 1991).
Banas et al., Biosynthesis of an Acetylenic Fatty Acid in Microsomal Preparations from Developing Seeds of *Crepis alpina*. In: *Physiology, Biochemistry and Molecular Biology of Plant Lipids* (Williams et al. eds.) pp. 57-59. Kluwer Academic Press, Dordrecht (1997).
Bates et al., Acyl Editing and Headgroup Exchange Are the Major Mechanisms That Direct Polyunsaturated Fatty Acid Flux into Triacylglycerols. Plant Physiology 160: 1530-1539 (2012).
Bernert et al., Analysis of Partial Reactions in the Overall Chain Elongation of Saturated and Unsaturated Fatty Acids by Rat Liver Microsomes. J. Biol. Chem. 252, 6736-6744 (1977).
Blombach et al., Acetohydroxyacid synthase, a novel target for improvement of L-lysine production by Corynebacterium glutamicum, Appl. Environ. Microbiol., 75(2):419-27 (Jan. 2009).
Broadwater et al., Desaturation and hydroxylation. Residues 148 and 324 of *Arabidopsis* FAD2, in addition to substrate chain length, exert a major influence in partitioning of catalytic specificity, J. Biol. Chem., 277(18):15613-20 (May 2002).
Broun et al., Catalytic plasticity of fatty acid modification enzymes underlying chemical diversity of plant lipids, Science, 282(5392):1315-7 (Nov. 1998).
Brown et al., Synthetic promoters for CHO cell engineering, Biotechnol. Bioeng., 111(8):1638-47 (Aug. 2014).
Calvo et al., Genetic connection between fatty acid metabolism and sporulation in Aspergillus nidulans, J. Biol. Chem., 276(28):25766-74 (Jul. 2001).
Certik et al., Desaturase-defective fungal mutants: useful tools for the regulation and overproduction of polyunsaturated fatty acids, Trends in Biotechnology, vol. 16, No. 12, Dec. 1, 1998, pp. 500-505.
Deal et al., Histone variants and modifications in plant gene regulation, Curr. Opin. Plant Biol., 14(2):116-22 (Apr. 2011).
Demeke et al., Influence of DNA extraction methods, PCR inhibitors and quantification methods on real-time PCR assay of biotechnology-derived traits, Anal. Bioanal. Chem., 396(6):1977-90 (Mar. 2010).
Denic et al., A molecular caliper mechanism for determining very long-chain fatty acid length, Cell, 130(4):663-77 (Aug. 2007).
Eiamsa-ard et al., Two novel Physcomitrella patens fatty acid elongases (ELOs): identification and functional characterization, Appl. Microbiol. Biotechnol., 97:3485-3497 (2013).
Fraser et al., Partial purification and photoaffinity labelling of sunflower acyl-CoA:lysophosphatidylcholine acyltransferase, Biochem. Soc. Trans., 28(6):715-8 (Dec. 2000).
Fukuda, Characterization of matrix attachment sites in the upstream region of a tobacco chitinase gene, Plant Mol. Biol., 39(5):1051-62 (Mar. 1999).
Giusto et al., Lipid metabolism in vertebrate retinal rod outer segments, Prog. Lipid Res., 39(4):315-91 (Jul. 2000).
Goffman, et al., "Genetic variation of tocopherol content in a germplasm collection of *Brassica napus* L.", Euphytica, vol. 125, May 2002, pp. 189-196.
Hamilton, A binary-BAC system for plant transformation with high-molecular-weight DNA, Gene, 200(1-2):107-16 (Oct. 1997).
Hattori et al., Experimentally determined sequence requirement of ACGT-containing abscisic acid response element, Plant Cell Physiol., 43(1):136-40 (Jan. 2002).
He et al, Agrobacterium-Mediated Transformation of Large DNA Fragments Using a BIBAC Vector System in Rice, Plant Molecular Biology Reporter, vol. 28, No. 4, Mar. 2, 2010, pp. 613-619.
Higo et al., Plant cis-acting regulatory DNA elements (PLACE) database: 1999, Nucleic Acids Res., 27(1):297-300 (Jan. 1999).
Hinnebusch, The scanning mechanism of eukaryotic translation initiation, Annu. Rev. Biochem., 83:779-812 (2014).
Horrocks et al., Health benefits of Docosahexaenoic acid (DHA), Pharmacol. Res., 40(3):211-25 (Sep. 1999).
Keller et al., Crystal structure of a bZIP/DNA complex at 2.2 A: determinants of DNA specific recognition, J. Mol. Biol., 254(4):657-67 (Dec. 1995).
Kim et al., Transcription factors that directly regulate the expression of CSLA9 encoding mannan synthase in *Arabidopsis thaliana*, Plant Mol. Biol., 84(4-5):577-87 (Mar. 2014).

(56) References Cited

OTHER PUBLICATIONS

Komori et al., Current status of binary vectors and superbinary vectors, Plant Physiol., 145(4):1155-60 (Dec. 2007).
Kong et al., Expression levels of domestic cDNA cassettes integrated in the nuclear genomes of various Chlamydomonas reinhardtii strains, J. Biosci. Bioeng., 117(5):613-6 (May 2014).
Kozak, Initiation of translation in prokaryotes and eukaryotes, Gene, 234(2):187-208 (Jul. 1999).
Lopez et al., Identification of novel motif patterns to decipher the promoter architecture of co-expressed genes in *Arabidopsis thaliana*, BMC Syst. Biol., 7 Suppl 3:S10 (Oct. 2013).
Lowenthal et al., Quantitative bottom-up proteomics depends on digestion conditions, Anal. Chem., 86(1):551-8 (Jan. 2014).
Machens et al., Identification of a novel type of WRKY transcription factor binding site in elicitor-responsive cis-sequences from *Arabidopsis thaliana*, Plant Mol. Biol., 84(4-5):371-85 (2014).
Makriyannis et al., Design and study of peptide-ligand affinity chromatography adsorbents: application to the case of trypsin purification from bovine pancreas, Biotechnol. Bioeng., 53(1):49-57 (Jan. 1997).
Mantle et al., Differentiation of Claviceps purpurea in axenic culture, J. Gen. Microbiol., 93(2):321-34 (Apr. 1976).
Meggendorfer et al., Functional nuclear topography of transcriptionally inducible extra-chromosomal transgene clusters, CHromosome Res., 18(4):401-17 (Jun. 2010).
Mendel, *Versuche über Pflanzenhybriden* Verhandlungen des naturforschenden Vereines in Brünn, Bd. IV für das Jahr, 1865 Abhandlungen:3-47 (1866).
Mey et al., The biotrophic, non-appressorium-forming grass pathogen Claviceps purpurea needs a Fus3/Pmk1 homologous mitogen-activated protein kinase for colonization of rye ovarian tissue, Mol. Plant Microbe Interact., 15(4):303-12 (Apr. 2002).
Meyer et al., Novel fatty acid elongases and their use for the reconstitution of docosahexaenoic acid biosynthesis, Journal of Lipid Research, 45:1899-1909 (2004).
Muino et al., Structural determinants of DNA recognition by plant MADS-domain transcription factors, Nucleic Acids Res., 42(4):2138-46 (Feb. 2014).
Murashige et al., A Revised Medium for Rapid Growth and Bio Assays with Tobacco Tissue Cultures. Physiologia Plantarum 15, 3:473-497 (1962).
Nakagawa et al., Diversity of preferred nucleotide sequences around the translation initiation codon in eukaryote genomes, Nucleic Acids Res., 36(3):861-71 (Feb. 2008).
Nishikata et al., Database construction for PromoterCAD: synthetic promoter design for mammals and plants, ACS Synth. Biol., 3(3):192-6 (Mar. 2014).
Parker et al., Local DNA topography correlates with functional noncoding regions of the human genome, Science, 324(5925):389-92 (Apr. 2009).
Petrie et al., Metabolic engineering Camelina sativa with fish oil-like levels of DHA, PLoS One, 9(1):e85061 (Jan. 2014).
Potts et al., Inheritance of fatty acid composition in *Brassica juncea*, Proceedings of the 10th International Rapeseed Congress, Sep. 26, 1999.
Proc et al., A quantitative study of the effects of chaotropic agents, surfactants, and solvents on the digestion efficiency of human plasma proteins by trypsin, J> Proteome Res., 9(10):5422-37 (Oct. 2010).
Ramamoorthy et al., Length and sequence dependent accumulation of simple sequence repeats in vertebrates: potential role in genome organization and regulation, Gene, 551(2):167-75 (Nov. 2014).
Schwender et al., "Rubisco without the Calvin cycle improves the carbon efficiency of developing green seeds", Nature, 432:779-82 (2004).
Shrestha et al., Int. J. Mol. Sci., Comparison of the substrate preferences of ω3 fatty acid desaturases for long chain polyunsaturated fatty acids, 20:3058 (2019).
Smith et al., Measurement of protein using bicinchoninic acid, Anal. Biochem., 150(1):76-85 (Oct. 1985).

Spector, Essentiality of fatty acids, Lipids, 34 Suppl: S1-3 (1999).
Stymne et al., Evidence for the reversibility of the acyl-CoA:lysophosphatidylcholine acyltransferase in microsomal preparations from developing safflower (*Carthamus tinctorius* L.) cotyledons and rat liver, Biochem. J., 233(2):305-14 (1984).
Sánchez-García et al., Differential temperature regulation of three sunflower microsomal oleate desaturase (FAD2) isoforms overexpressed in *Saccharomyces cerevisia*, Eur. J. Lipid Sci. Tech., 106:583-590 (2004).
Tudzynski et al., Biotechnology and genetics of ergot alkaloids, Appl. Microbiol. Biotechnol., 57(5-6):593-605 (Dec. 2001).
Tumaney et al., Synthesis of azidophospholipids and labeling of lysophosphatidylcholine acyltransferase from developing soybean cotyledons, Biochim. Biophys. Acta, 1439(1):47-56 (Jul. 1999).
Wachter et al., Synthetic CpG islands reveal DNA sequence determinants of chromatin structure, Elife, 3:e03397 (Sep. 2014).
Wang et al., ω3 fatty acid desaturases from microorganisms: structure, function, evolution, and biotechnological use, App. Microbiol., 97:10255-62 (2013).
Wijesundra, The influence of triacylglycerol structure on the oxidative stability of polyunsaturated oils, Lipid Technology, 20:199-202 (2008).
Yamashita et al., ATP-independent fatty acyl-coenzyme A synthesis from phospholipid: coenzyme A-dependent transacylation activity toward lysophosphatidic acid catalyzed by acyl-coenzyme A:lysophosphatidic acid acyltransferase, J. Biol. Chem., 276(29):26745-52 (Jul. 2001).
Abedi et al., Long-chain polyunsaturated fatty acid sources and evaluation of their nutritional and functional properties, Food Sci. Nutr., 2(5):443-63 (2014).
Barret et al., A rapeseed FAE1 gene is linked to the E1 locus associated with variation in the content of erucic acid, Theor. Appl. Genet., 96:177-86 (1998).
Batista et al., Nutritional and nutraceutical potential of rape (*Brassica napus* L. var. *napus*) and "tronchuda" cabbage (*Brassica oleraceae* L. var. *costata*) inflorescences, Food Chem. Toxicol., 49(6):1208-14 (2011).
Chen et al., MISSA is a highly efficient in vivo DNA assembly method for plant multiple-gene transformation, Plant Physiol., 153(1):41-51 (2010).
Del Villar et al., Amino acid substitutions that convert the protein substrate specificity of farnesyltransferase to that of geranylgeranyltransferase type I, J. Biol. Chem., 272(1):680-7 (1997).
Dubois et al., Fatty acid profiles of 80 vegetable oils with regard to their nutritional potential, Eur. J. Lipid Sci. Technol., 109:710-32 (2007).
Hamilton et al., Metabolic engineering of Phaeodactylum tricornutum for the enhanced accumulation of omega-3 long chain polyunsaturated fatty acids, Metab. Eng., 22(100):3-9 (2014).
Lee, et al., "Overexpression of *Arabidopsis* homogentisate phytyltransferase or tocopherol cyclase elevates vitamin E content by increasing gamma-tocopherol level in lettuce (*Lactuca sativa* L.)", Molecules and Cells, vol. 24, Issue 2, Oct. 1, 2007, pp. 301-306.
Multari et al., Effects of aromatic herb flavoring on carotenoids and volatile compounds in edible oil from blue sweet lupin (*Lupinus angustifolius*), Eur. J. Lipid Sci. Tech, pp. 1-10 (2018).
Nishimura et al.,Over-expression of tobacco knotted1-type class1 homeobox genes alters various leaf morphology, Plant Cell Physiol., 41(5):583-90 (2000).
Rossak et al., Expression of the FAE1 gene and FAE1 promoter activity in developing seeds of *Arabidopsis thaliana*, Plant Mol. Biol., 46(6):717-25 (2001).
Ruiz-Lopez et al., Modifying the lipid content and composition of plant seeds: engineering the production of LC-PUFA, Appl. Microbiol. Biotechnol., 99:143-54 (2015).
Ruiz-Lopez et al., Nutritional and bioactive compounds in Mexican lupin beans species: A mini-review, Nutrients, pp. 1-19 (2019).
Truksa et al., Molecular analysis of flax 2S storage protein conlinin and seed specific activity of its promoter, Plant Physiol, and Biochem., 41:141-7 (2003).

(56) References Cited

OTHER PUBLICATIONS

Vrinten et al., Production of polyunsaturated fatty acids in transgenic plants, Biotechnology and Genetic Engineering Reviews, 24:263-80 (2007).

Yan et al., Characterization of FAE1 in the zero erucic acid germplasm of *Brassica rapa* L, Breed Sci., 65(3):257-64 (2015).

Yang et al., Expression of the REB transcriptional activator in rice grains improves the yield of recombinant proteins whose genes are controlled by a Reb-responsive promoter, Proc. Natl. Acad. Sci. USA, 98(20):11438-43 (2001).

Zebarjadi et al., Transformation of rapeseed (*Brassica napus* L.) plants with sense and antisense constructs of the fatty acid elongase gene, Iranian J Biotechnol., 4(2):79-87 (2006).

Oliva et al., Stability of fatty acid profile in soybean genotypes with modified seed oil composition, Crop Sci., 46:2069-75 (2006).

\* cited by examiner

Formula used for pathway step conversion efficiency Ceff $C_{eff} = \dfrac{100}{S+P} \times P$

| Pathway Step | Product Stream | pre-requisite of product stream | | | | | | |
|---|---|---|---|---|---|---|---|---|
| d12Des | d12Des Product Stream 1 | 18:1n-9 | | | | | | |
| | d12Des Product Stream 2 | 18:3n-3 from 18:2n-6 via d15Des | | 18:2n-6 | 18:3n-6 | 20:3n-6 | 20:4n-6 | 22:4n-6 | 22:5n-6 |
| | | | | 18:3n-3 | 18:4n-3 | 20:4n-3 | 20:5n-3 | 22:5n-3 | 22:6n-3 |
| | d12Des Product Stream 3 | 20:2n-6 from 18:2n-5 via d6Elo | 20:2n-6 | | | | | | |
| | d12Des Product Stream 4 | 20:3n-3 from 18:3n-3 via d6Elo | 20:3n-3 | | | | | | |
| d6Des | d6Des Product Stream 1 | 18:2n-6 | 18:2n-6 | | 18:3n-6 | 20:3n-6 | 20:4n-6 | 22:4n-6 | 22:5n-6 |
| | d6Des Product Stream 2 | 18:3n-3 produced by o3Des | 18:3n-3 | | 18:4n-3 | 20:4n-3 | 20:5n-3 | 22:5n-3 | 22:6n-3 |
| d6Elo | d6Elo Product Stream 1 | 18:3n-6 produced by d6Des | | 18:3n-6 | | 20:3n-6 | 20:4n-6 | 22:4n-6 | 22:5n-6 |
| | d6Elo Product Stream 2 | 18:4n-3 produced by d6Des or o3Des | | 18:4n-3 | | 20:4n-3 | 20:5n-3 | 22:5n-3 | 22:6n-3 |
| d5Des | d5Des Product Stream 1 | 20:3n-6 produced by d6Elo | | | 20:3n-6 | | 20:4n-6 | 22:4n-6 | 22:5n-6 |
| | d5Des Product Stream 2 | 20:4n-3 produced by d6Elo or o3Des | | | 20:4n-3 | | 20:5n-3 | 22:5n-3 | 22:6n-3 |
| d5Elo | d5Elo Product Stream 1 | 20:4n-6 produced by d5Des | | | | | 20:4n-6 | 22:4n-6 | 22:5n-6 |
| | d5Elo Product Stream 2 | 20:4n-3 produced by d5Des or o3Des | | | | | 20:5n-3 | 22:5n-3 | 22:6n-3 |
| d4Des | d4Des Product Stream 1 | 20:4n-6 produced by d5Des | | | | | | 22:4n-6 | 22:5n-6 |
| | d4Des Product Stream 2 | 20:4n-3 produced by d5Des or o3Des | | | | | | 22:5n-3 | 22:6n-3 |
| o3Des | | List of all o6Des Fatty acid substrates | 18:2n-6 | 18:3n-6 | | 20:2n-6 | 20:3n-6 | 20:4n-6 | 22:4n-6 | 22:5n-6 |
| | | List of all o3Des Fatty acid products | 18:3n-3 | 18:4n-3 | | 20:3n-3 | 20:4n-3 | 20:5n-3 | 22:5n-3 | 22:6n-3 |

Fig. 2

Fig. 24
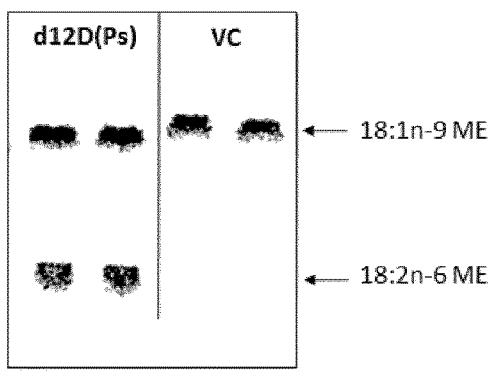
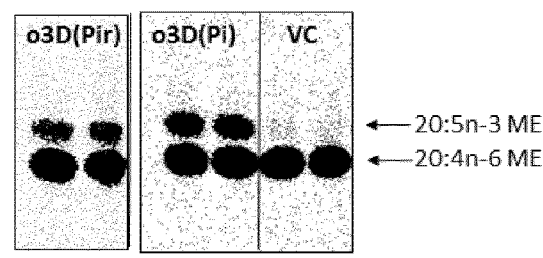
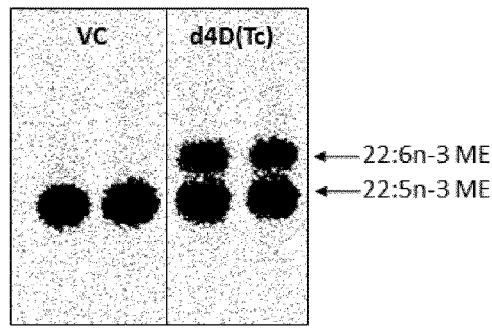
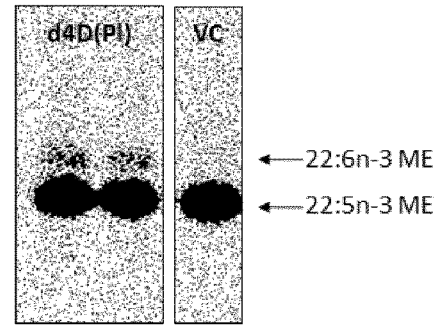

Fig. 25
A.
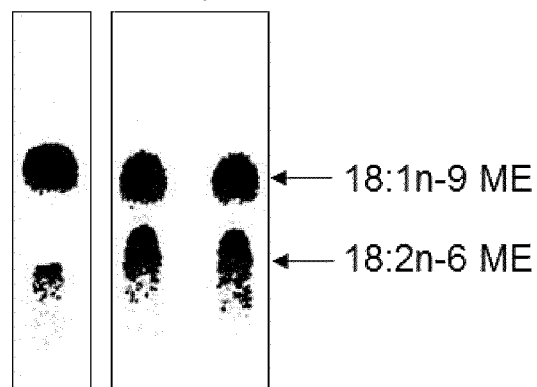
Delta-12 Desaturase (Ps) Activity
B.
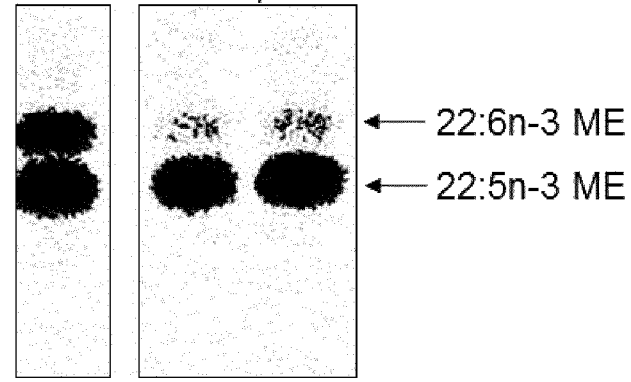
Delta-4 Desaturase Activity Fig. 26
A.
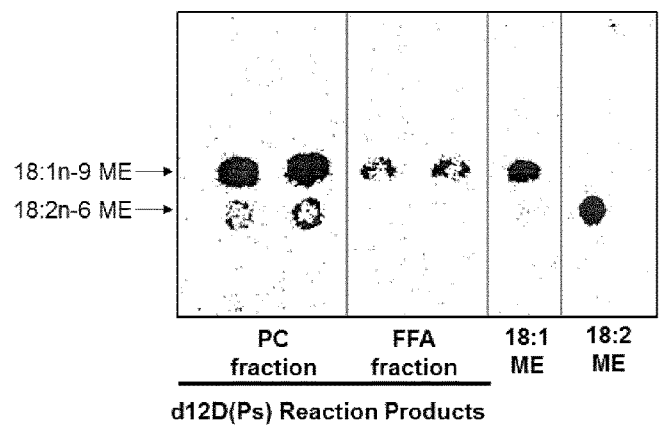
d12D(Ps) Reaction Products
B.
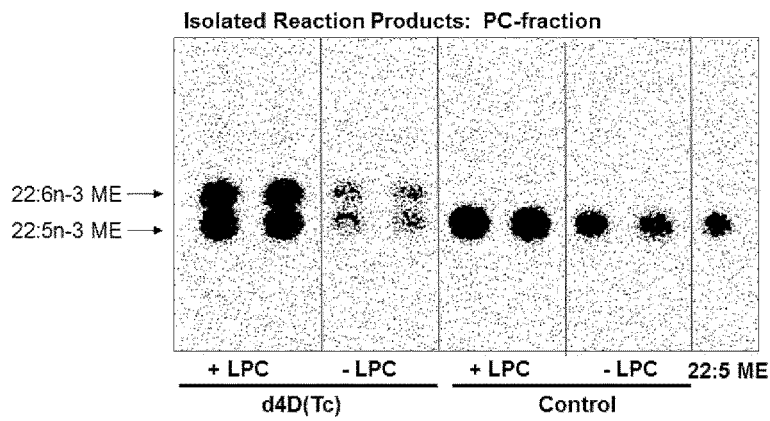
C.
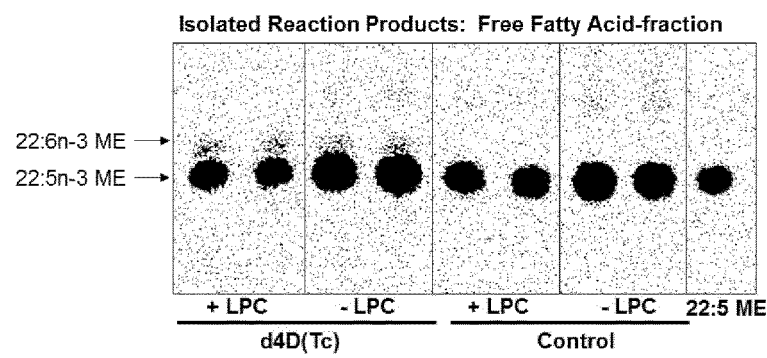
D.
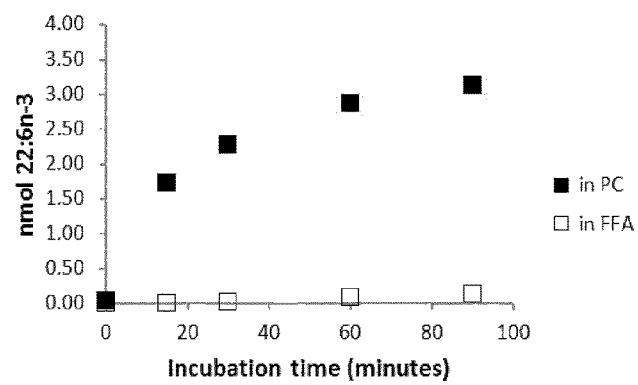

Fig. 27
A.
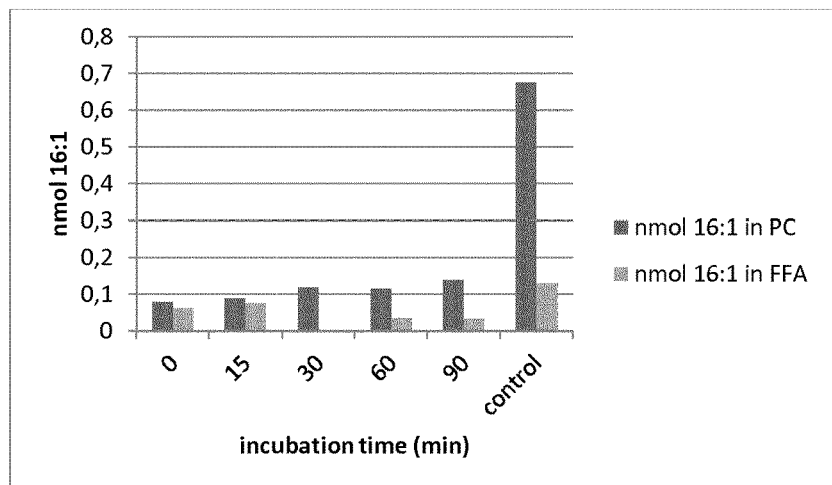
B.
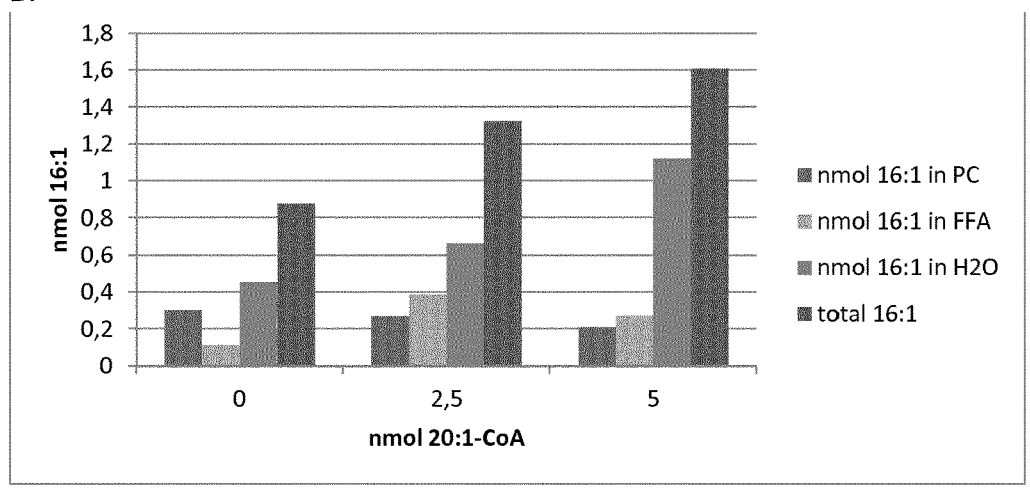
C.
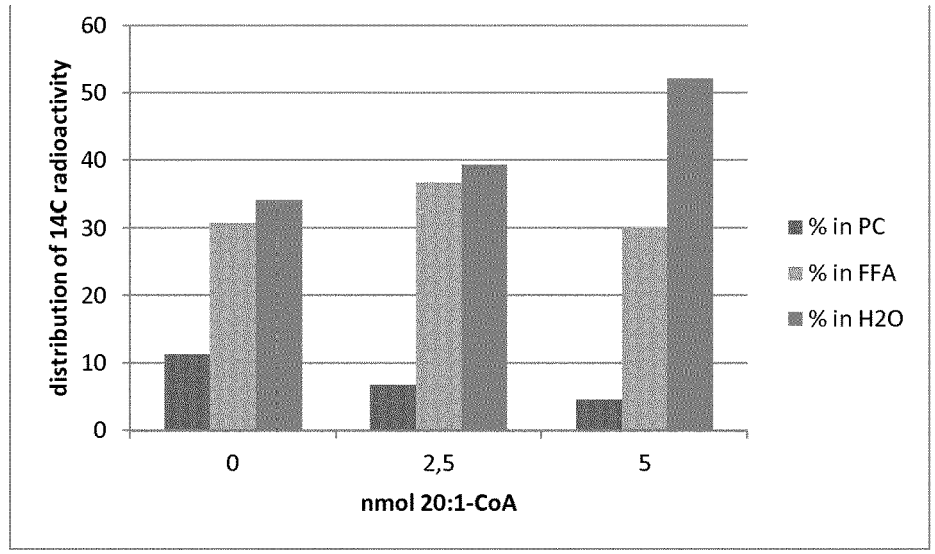

Fig. 28
A.
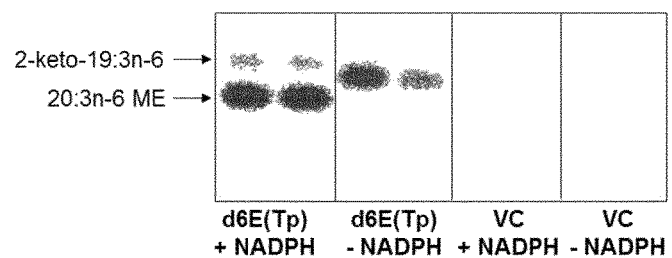
B.
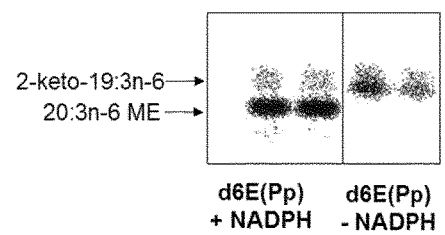
C.
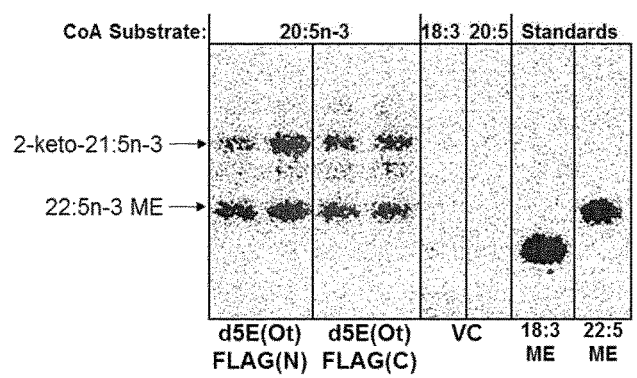

Fig. 29
A.
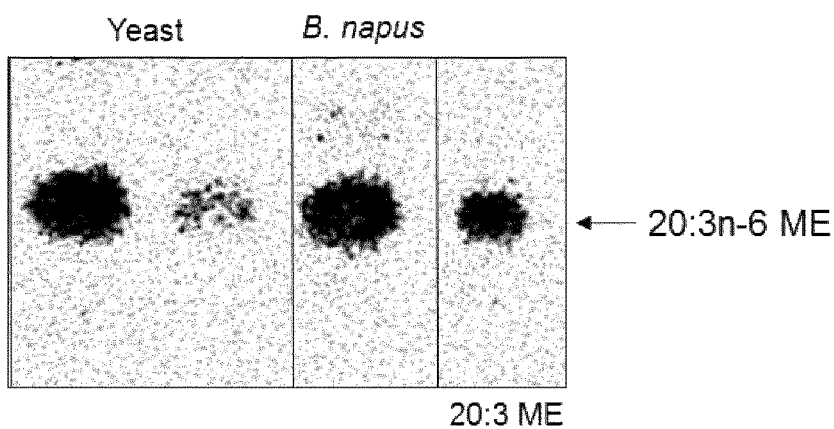
Delta-6 Elongase Activity
B.
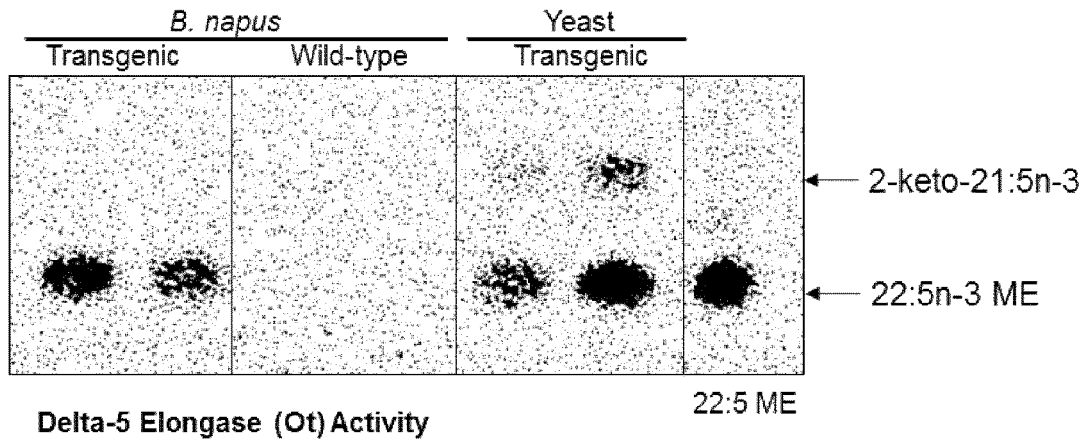
Delta-5 Elongase (Ot) Activity

Fig. 85
A.
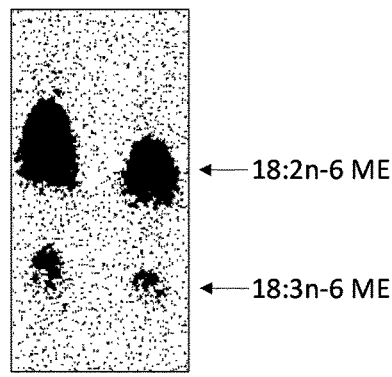
Delta-6 Desaturase (*Ostreococcus tauri*)
B.
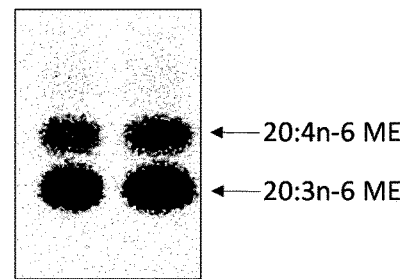
Delta-5 Desaturase (*Thraustochytrium* ssp.)
C.
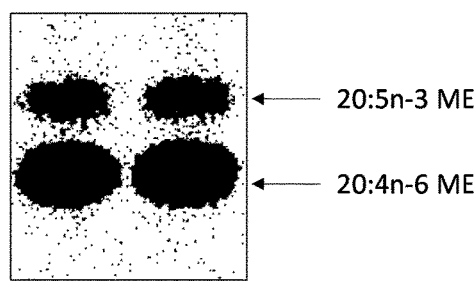
Omega-3 Desaturase Fig. 86
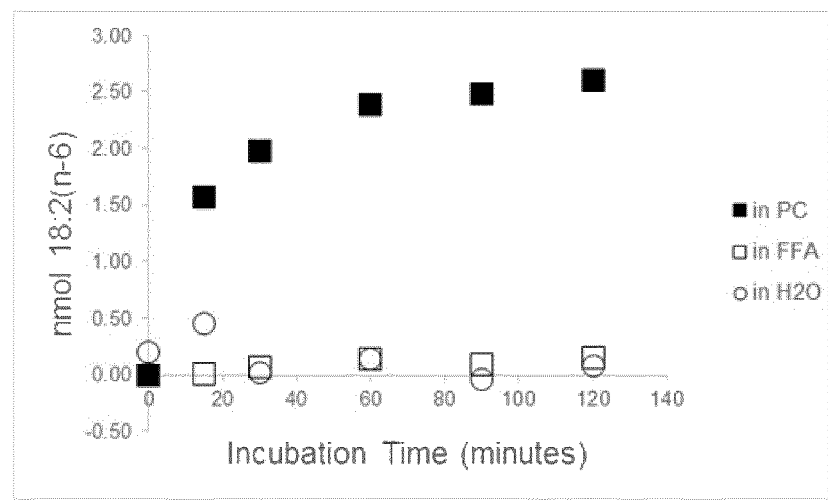
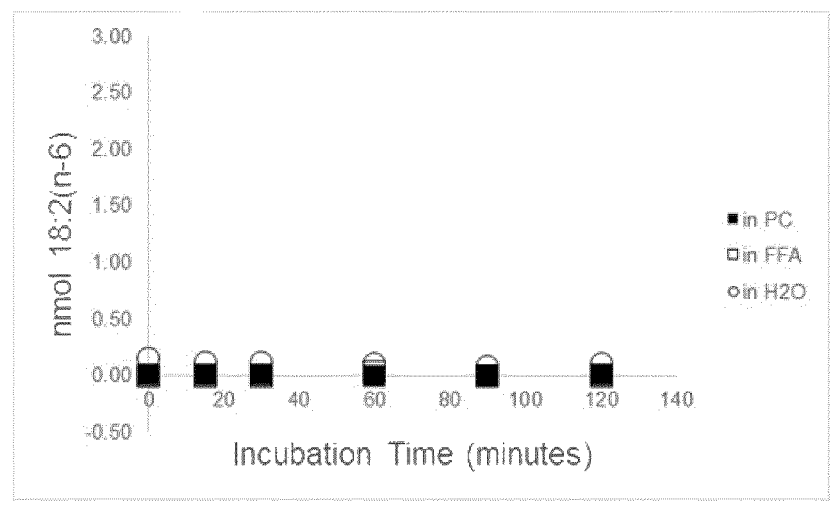

Fig. 87
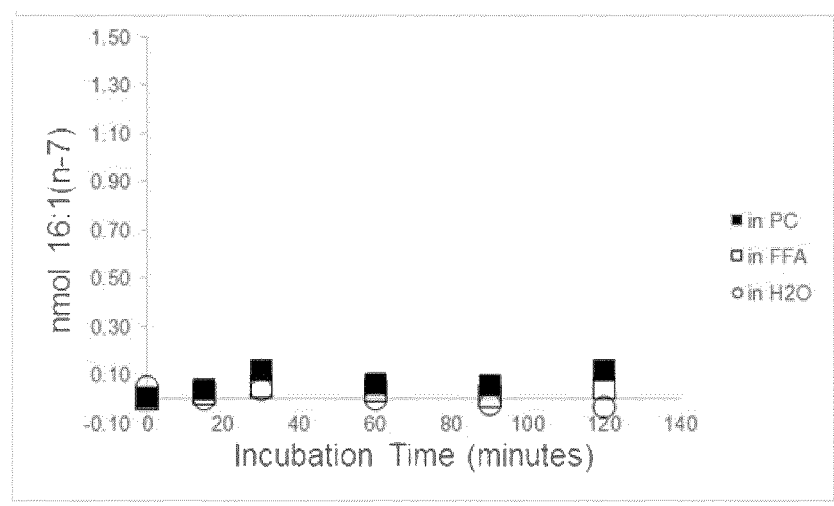
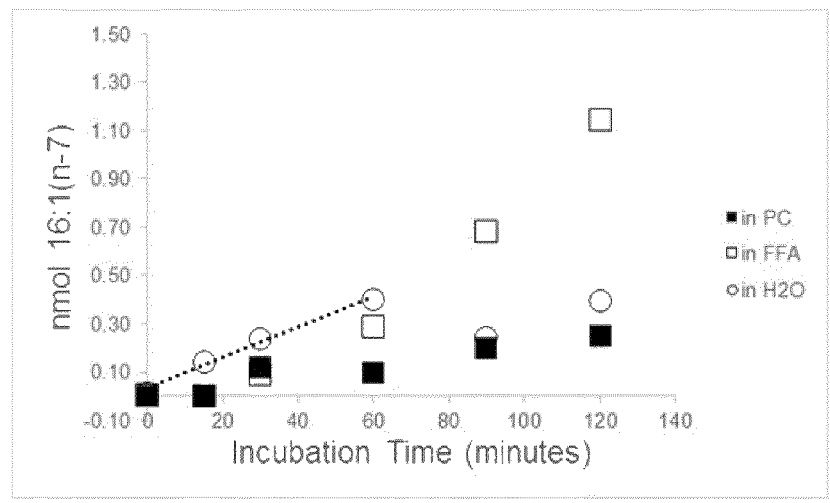

STABILISING FATTY ACID COMPOSITIONS

This application is a National Stage application of International Application No. PCT/EP2015/076605, filed Nov. 13, 2015, which claims the benefit of U.S. Provisional Patent Application No. 62/079,622, filed Nov. 14, 2014 and U.S. Provisional Patent Application No. 62/234,373, filed Sep. 29, 2015, which are incorporated herein by reference in their entirety.

FIELD OF THE INVENTION

Incorporation by Reference of Material Submitted Electronically

The Sequence Listing, which is a part of the present disclosure, is submitted concurrently with the specification as a text file. The name of the text file containing the Sequence Listing is "150219 Seqlisting.txt", which was created on May 9, 2017 and is 1,303,507 bytes in size. The subject matter of the Sequence Listing is incorporated herein in its entirety by reference.

The present invention is concerned with materials and methods for the production of genetically modified plants, particularly where the plants are for the production of at least one unsaturated or polyunsaturated fatty acid. The invention is also concerned with identification of genes conveying an unsaturated fatty acid metabolic property to a plant or plant cell, and generally relates to the field of Delta-12 desaturases.

BACKGROUND OF THE INVENTION

For the production of genetically modified plants it is not sufficient to test the effects of nucleic acid sequences in plants under greenhouse conditions. Unfortunately it has frequently been observed that plant metabolic properties differ in unpredictable ways when plants are grown in our field or under greenhouse conditions. Thus, when developing genetically modified plants having altered metabolic properties compared to the corresponding wild-type plant, it is necessary to test such plants in field trials.

However, field trials entail a variety of disadvantages compared to plant growth under greenhouse conditions: for example, field trial plots have frequently been vandalised or devastated by animals, rendering all work of creating the originally planted plants and sending them on the field useless. Further, field trials require completion of Norma Rose procedures of regulatory supervision, making field trials rather cumbersome. Also, the amount of practical work in raising enough plants for a future test, devising a plot layout to plant the plants, and planting and monitoring the plants is more labour intensive than testing plants under greenhouse conditions, particularly as plant maintenance and monitoring work can be highly automated in the greenhouse. Furthermore, growing plants in an automatic greenhouse allows to inspect plant parts that are not readily accessible on a field, for example because on a field the plants are grown too densely or the interesting plant part is growing underground, for example plant roots. Thus it is generally desired to reduce the number of necessary field trials.

This is particularly true in the field of production of polyunsaturated fatty acids. Plants generally cannot produce unsaturated fatty acids of at least 20 carbon atoms in length and comprising at least two double bonds. Thus, to develop plants for the production of such unsaturated fatty acids, it is necessary to install the whole metabolic process starting from linoleic acid or iPhone-linolenic acid. Even though potentially suitable elongates and desaturase genes are known in the art and have been tested at least in model plants, it is uncertain which combinations of genes and promoters will provide economically satisfactory yields of unsaturated fatty acids in a stable way, particularly under the environmental conditions that change from growth period to growth period. Thus, field trials cannot be avoided when developing plants for the production of unsaturated fatty acids. One of the factors that has to be a certain and by field trials is whether or not the composition of the plant oil will be as expected even under field conditions. It has unfortunately been observed that the composition of plant oils measured in individual plant seeds greatly differs even for seeds obtained from the very same plant, and particularly varies between plants grown under differing conditions. Thus, the composition of a plant oil obtained from harvesting a plurality of plants grown under field conditions cannot always reliably been predicted on the basis of oil composition analyses of individual plant seeds taken from plants grown under greenhouse conditions.

Reproducible production of a specific fatty acid profile is particularly important for commercial canola oil production. There is need to identify ways to reduce the variability in the fatty acid profile of canola oils produced in different environments.

The invention thus and generally aspires to remove or alleviate the above identified shortcomings and to provide materials and methods useful for reducing the number of field trials required for the manufacturing of a marketable plant variety producing unsaturated fatty acids. Further aspects and embodiments of the invention will become apparent below.

BRIEF DESCRIPTION OF THE FIGURES

FIG. 2: Formulas to calculate pathway step conversion efficiencies. S: substrate of pathway step. P: product of pathway step. Product was always the sum of the immediate product of the conversion at this pathway step, and all downstream products that passed this pathway step in order to be formed. E.g. DHA (22:6n-3 does possess a double bond that was a result of the delta-12-desaturation of oleic acid (18:1n-9) to linoleic acid (18:2n-6).

FIG. 24: Examples of Desaturase Enzyme Activity Heterologously Expressed in Yeast. [14C]Fatty acid methyl esters (ME's) were isolated from the enzymatic reactions, resolved by TLC as described for each specific enzyme and detected by electronic autoradiography using Instant Imager. In panel A Delta-12 Desaturase (Ps), c-d12Des(Ps_GA), activity was demonstrated by comparison of enzyme activity present in yeast microsomes isolated from a strain expressing the c-d12Des(Ps_GA) protein relative to microsomes isolated from a control strain containing an empty vector (VC). In panel B Omega-3 Desaturase activities, c-o3Des (Pir_GA) and c-o3Des(Pi_GA2), activities were demonstrated by comparison of enzyme activity from yeast microsomes isolated from strains expressing c-o3Des (Pir_GA) protein, c-o3Des(Pi_GA2) protein or an empty vector (VC) control. In panel C Delta-4 Desaturase (Tc), c-d4Des(Tc_GA), activity was demonstrated by comparison of enzyme activity from yeast microsomes isolated from a strain expressing the c-d4Des(Tc_GA) protein relative to microsomes isolated from a control strain containing an empty vector (VC). In panel D Delta-4 Desaturase (PI), c-d4Des(PI_GA)2, activity was demonstrated by comparison of enzyme activity from yeast microsomes isolated from a strain expressing the c-d4Des(PI_GA)2 protein relative to microsomes isolated from a control strain containing an empty vector (VC).

FIG. 25: Examples of Desaturase Enzyme Activity in transgenic Brassica napus. [14C]Fatty acid methyl esters (ME's) were isolated from the enzymatic reactions, resolved by TLC as described for each specific enzyme and detected by electronic autoradiography using Instant Imager. In panel A Delta-12 Desaturase (Ps), c-d12Des(Ps_GA), activity was demonstrated by comparison of enzyme activity from yeast microsomes isolated from a strain expressing the c-d12Des (Ps_GA) protein relative to microsomes isolated from transgenic B. napus containing the d12Des(Ps_GA2) gene. In panel B Delta-4 Desaturase (Tc), c-d4Des(Tc_GA), and Delta-4 Desaturase (PI) activities were demonstrated by comparison of enzyme activity from yeast microsomes isolated from a strain expressing the c-d4Des(Tc_GA) protein relative to microsomes isolated from transgenic B. napus containing the d4Des(Tc_GA3) and d4Des(PI_GA)2 genes.

FIG. 26: Examples of Desaturase Enzyme Reactions Showing Specificity for Acyl-lipid substrates. [14C]Fatty acid methyl esters (ME's) were isolated from the enzymatic reactions containing microsomes obtained from a yeast strain expressing the protein of interest, resolved by TLC as described for each specific enzyme and detected by electronic autoradiography using Instant Imager. In panel A Delta-12 Desaturase (Ps), c-d12Des(Ps_GA), desaturated enzyme products were only detected in the phosphatidylcholine fraction indicating the enzyme was specific for an acyl-lipid substrate. In panel B and panel C Delta-4 Desaturase (Tc), c-d4Des(Tc_GA), desaturated enzyme products were detected in the phosphatidylcholine fraction indicating the enzyme was specific for an acyl-lipid substrate. In panel D a time-course demonstrates the activity of the Delta-4 Desaturase (Tc), c-d4Des(Tc_GA).

FIG. 27: Examples of Desaturase Enzyme Reactions Showing Specificity for Acyl-CoA substrates. [14C]Fatty acid methyl esters (ME's) were isolated from the enzymatic reactions containing microsomes obtained from a yeast strain expressing the protein of interest, resolved by TLC as described for each specific enzyme and detected by electronic autoradiography using Instant Imager. In panel A PC was in situ labeled with substrate according to the method for determining lipid linked desaturation. Delta-9 Desaturase (Sc), d9D(Sc), desaturated enzyme products were very low in the phosphatidylcholine fraction, except for in the control reaction (none in situ labeled PC), indicating the enzyme cannot desaturate an acyl-lipid substrate. In panel B and C the incubation was done according to the method for determining acyl-CoA linked desaturation. In panel B the amount of radioactivity in the acyl-CoA fraction (MeOH/H2O-phase, called nmol 16:1 in H2O) was increasing when 20:1-CoA was added to the assay. This indicates that the added 20:1-CoA was competing with the radioactive substrate in formation of PC and free fatty acids. In panel C the amount of desaturated enzyme products was increased in the acyl-CoA fraction when 20:1-CoA was added to the assay, indicating that the desaturation was acyl-CoA linked.

FIG. 28: Examples of Elongase Enzyme Activity Heterologously Expressed in Yeast. [14C]Fatty acid methyl esters (ME's) were isolated from the enzymatic reactions, resolved by TLC as described for each specific enzyme and detected by electronic autoradiography using Instant Imager. All FAME's shown had similar Rf's as authentic standards. In the absence of [14C]malonyl-CoA no radioactive fatty acids were observed in any of these elongase reactions. In panel A delta-6 elongase (Tp), c-d6Elo(Tp_GA2), activity was demonstrated by comparison of enzyme activity present in yeast microsomes isolated from a strain expressing the c-d6Elo(Tp_GA2) protein relative to microsomes isolated from a control strain containing an empty vector (VC). In panel B, delta-6 elongase (Pp), c-d6Elo(Pp_GA2), was demonstrated by comparison of enzyme activity from yeast microsomes isolated from a strains expressing c-d6Elo (Pp_GA2) protein to microsomes isolated from a control strain containing an empty vector (VC), as shown in panel A. In panel C, delta-5 elongase (Ot), c-d5Elo(Ot_GA3), activity was demonstrated by comparison of enzyme activity present in yeast microsomes isolated from a strain expressing the d5E(Ot) protein relative to microsomes isolated from a control strain containing an empty vector (VC).

FIG. 29: Examples of Elongase Activity in transgenic *Brassica napus*. [14C]Fatty acid methyl esters (ME's) were isolated from the enzymatic reactions, resolved by TLC as described for each specific enzyme and detected by electronic autoradiography using Instant Imager. In panel A Delta-6 Elongase activity was demonstrated by comparison of enzyme activity from yeast microsomes isolated from a strain expressing the d6E(Pp_GA2) protein relative to microsomes isolated from transgenic *B. napus* containing the c-d6Elo(Pp_GA2) gene and the c-d6Elo(Tp_GA2) gene. In panel B the Delta-5 Elongase (Ot), d5Elo(Ot_GA3), activity was demonstrated by comparison of enzyme activity from yeast microsomes isolated from a strain expressing the c-d5Elo(Ot_GA3) protein relative to microsomes isolated from transgenic *B. napus* containing the d5Elo(Ot_GA3) and a wild-type *B. napus* (control).

FIG. 85. Examples of Desaturase Enzyme Activity in Transgenic *Brassica napus*. [14C]Fatty acid methyl esters (ME's) were isolated from the enzymatic reactions, resolved by TLC as described for each specific enzyme and detected by electronic autoradiography using an Instant Imager. Duplicate reactions are shown for each enzyme activity in Panels A-C. In Panel A delta-6 desaturase (*Ostreococcus tauri*) activity was demonstrated by the presence of [14C] 18:3n-6 ME using membranes isolated from transgenic *Brassica napus*. This desaturase activity was not present in membranes derived from a wild-type (Kumily) *B. napus*. In Panel B delta-5 desaturase (*Thraustochytrium* ssp.) activity was demonstrated by the presence of [14C]20:4n-6 ME using membranes isolated from transgenic *Brassica napus*. This desaturase activity was not present in membranes derived from a wild-type (Kumily) *B. napus*. In Panel C omega-3 desaturase activity was demonstrated by the presence of [14C]20:5n-3 ME using membranes isolated from transgenic *Brassica napus*. This desaturase activity was not present in membranes derived from a wild-type (Kumily) *B. napus*.

FIG. 86. Delta-12 desaturase (*Phytophthora sojae*), c-d12Des(Ps_GA), substrate preference.

Figure 1:
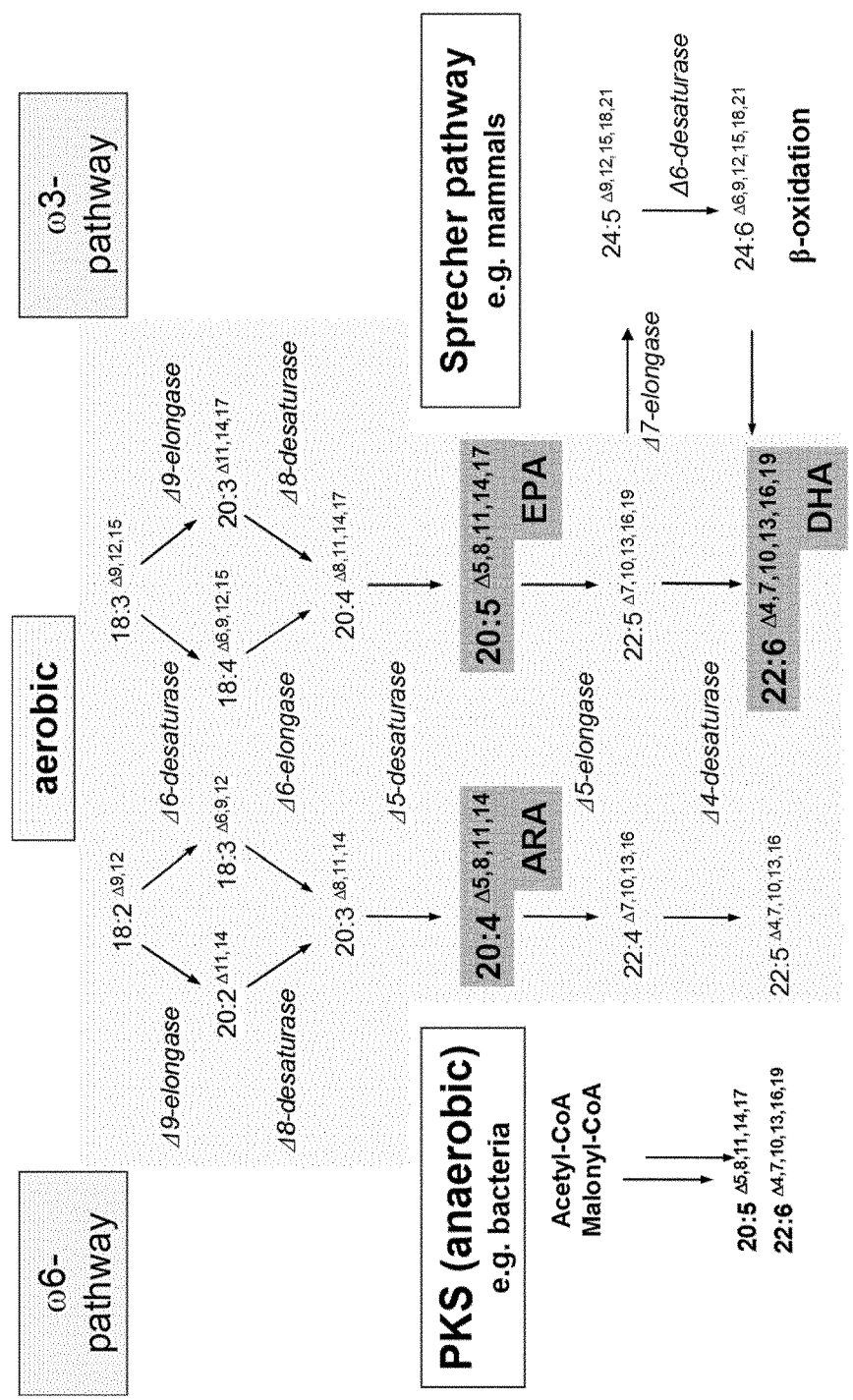
FIG. 1: Schematical figure of the different enzymatic activities leading to the production of ARA, EPA and DHA

During the course of the enzymatic reaction the following lipid pools were isolated: phosphatidylcholine (PC, ■), free fatty acid (FFA, •), and H2O (CoA, ○). In Panel A c-d12Des (Ps_GA) enzyme activity is shown using assay conditions to present the fatty acid substrate (18:1(n-9)) in the acyl-phosphatidylcholine form. Desaturated enzymatic product (18:2(n-6)) is found predominantly in the phosphatidylcholine (PC) pool, relative to the free fatty acid (FFA) or H2O (CoA) pools, indicating c-d12Des(Ps_GA) utilizes 18:1(n-9) attached to phosphatidylcholine as a substrate. In Panel B c-d12Des(Ps_GA) enzyme activity is shown using assay conditions to present the fatty acid substrate (18:1(n-9)) in the acyl-CoA form. Relative to Panel A, desaturated enzymatic product (18:2(n-6)) is not produced in the phosphatidylcholine (PC), free fatty acid (FFA) or H2O (CoA) pools indicating c-d12Des(Ps_GA) does not utilize 18:1(n-9) bound as an acyl-CoA ester.

FIG. 87. Delta-9 desaturase (*Saccharomyces cerevisiae*), d9Des(Sc) substrate preference. During the course of the enzymatic reaction the following lipid pools were isolated: phosphatidylcholine (PC, ■), free fatty acid (FFA, •), and H2O (CoA, ○). In Panel A d9Des(Sc) enzyme activity is shown using assay conditions to present the fatty acid substrate (16:0) in the acyl-phosphatidylcholine form. Relative to Panel B, desaturated enzymatic product (16:1(n-7)) is not produced in the phosphatidylcholine (PC), free fatty acid (FFA), or H2O (CoA) pools indicating d9Des(Sc) does not utilize 18:0 attached to phosphatidylcholine as a substrate. In Panel B d9Des(Sc) enzyme activity is shown using assay conditions to present the fatty acid substrate (16:0) in the acyl-CoA form. Desaturated enzymatic product (16:1(n-7)) is isolated in both the free fatty acid (FFA) and H2O (CoA) pools, but not the phosphatidylcholine (PC) pool. Furthermore, production of the desaturated enzymatic product (16:1(n-7)) in the H2O (CoA) pool is linear for the first 60 minutes of the assay as shown by the hashed line (r2=0.99). The high levels of [14C]16:1(n-7) detected in the FFA pool likely result from hydrolysis of the desaturated enzymatic product, 16:1(n-7)-CoA, by endogenous thioesterases present in the membrane preparations.

Figure 88:
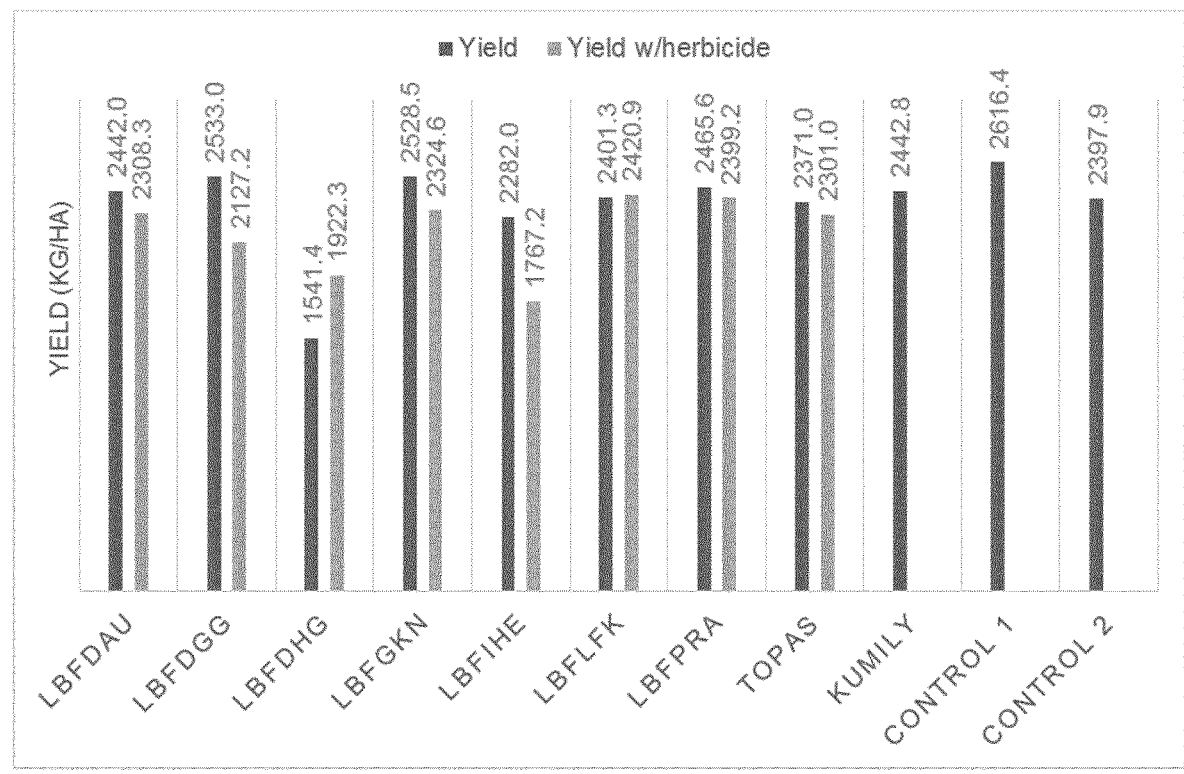

FIG. 88. Yield (kg seeds/ha) of canola plants grown in the field in 2014. Plants were either not treated (Yield) or were treated with 2× rate of imidazolinone herbicide (Yield w/herbicide).

Figure 89:
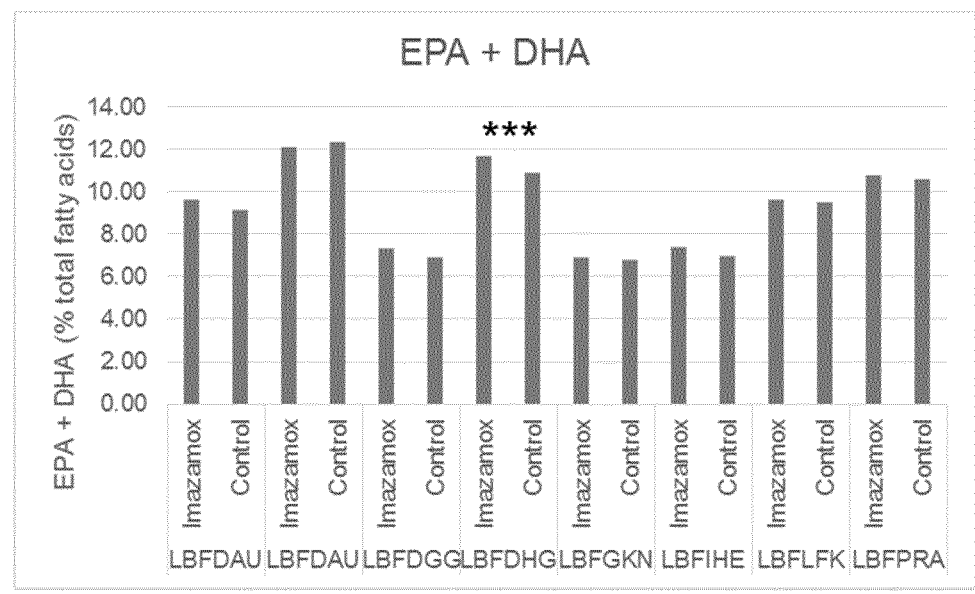

FIG. 89. EPA plus DHA content in seeds of plants grown in the field with (Imazamox) or without (control) herbicide treatment. *** denotes a significant difference between herbicide treatment and control as calculated by ANOVA, $p<0.05$.

Figure 90:
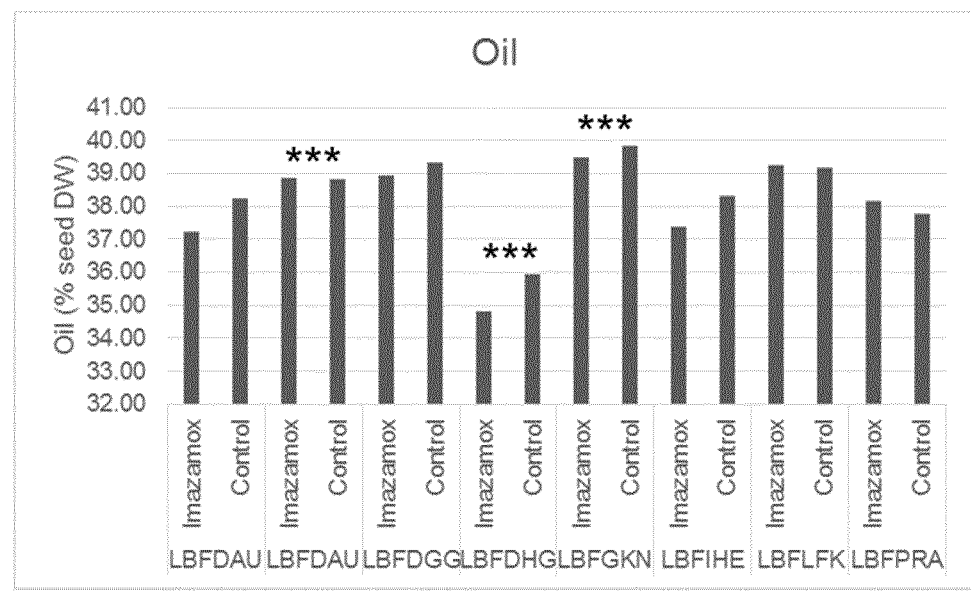

FIG. 90. Oil content in seeds of plants grown in the field with (Imazamox) or without (control) herbicide treatment. *** denotes a significant difference between herbicide treatment and control as calculated by ANOVA, $p<0.05$.

Figure 91:
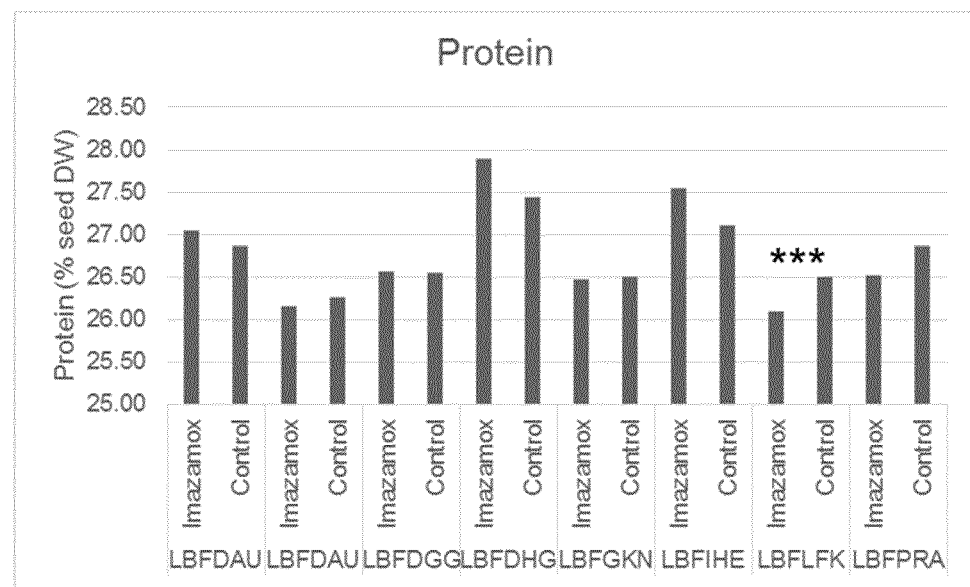

FIG. 91. Protein content in seeds of plants grown in the field with (Imazamox) or without (control) herbicide treatment. *** denotes a significant difference between herbicide treatment and control as calculated by ANOVA, $p<0.05$.

SUMMARY OF THE INVENTION

The invention thus generally provides an assay method, comprising:
i) providing a plant capable of expressing a delta-12 desaturase, wherein said delta-12 desaturase has at least 50% total amino acid sequence identity to at least one of the sequences SEQ ID NO. 328 to 336, and/or at least 59% total amino acid sequence similarity to at least one of the sequences SEQ ID NO. 328 to 336,
and wherein the plant is also capable of expressing at least one or more enzymes of unsaturated fatty acid metabolism, of which enzymes at least one is capable of using linoleic acid as a substrate, and of which enzymes at least one is supposedly connected to a plant metabolic property,
ii) growing the plant, and
iii) measuring said plant metabolic property for said plant.

The invention also provides an assay method, comprising:
i) providing a plant group, wherein the plants of said group are capable of expressing a delta-12 desaturase, wherein said delta-12 desaturase has at least 50% total amino acid sequence identity to at least one of the sequences SEQ ID NO. 328 to 336, and/or at least 59% total amino acid sequence similarity to at least one of the sequences SEQ ID NO. 328 to 336,
and wherein the plants of said group are capable of expressing at least one or more enzymes of unsaturated fatty acid metabolism, of which enzymes at least one is capable of using linoleic acid as a substrate, and of which enzymes at least one is supposedly connected to a plant metabolic property,
ii) growing the plants of the plant group, and
iii) measuring said plant metabolic property for plants of said plant group.

Further, the invention provides a method of identifying a gene for conveying an unsaturated fatty acid metabolic property to a plant, comprising:
i) producing a plant comprising said gene,
ii) performing an assay method according to the invention, wherein said gene is expressed and said plant metabolic property is measured, and
iii) evaluating said plant for the presence and/or intensity of said unsaturated fatty acid metabolic property.

Also provided is a method of increasing delta-12 desaturase activity in a plant, comprising growing a plant expressing a delta-12 desaturase, wherein said delta-12 desaturase has at least 50% total amino acid sequence identity to at least one of the sequences SEQ ID NO. 328 to 336, and/or at least 59% total amino acid sequence similarity to at least one of the sequences SEQ ID NO. 328 to 336.

Likewise the invention provides a method of stabilizing delta-12 desaturase activity in a plant, comprising growing a plant expressing a delta-12 desaturase, wherein said delta-12 desaturase has at least 50% total amino acid sequence identity to at least one of the sequences SEQ ID NO. 328 to 336, and/or at least 59% total amino acid sequence similarity to at least one of the sequences SEQ ID NO. 328 to 336.

Further provided is a method of producing one or more desired unsaturated fatty acids in a plant, comprising growing a plant,
said plant expressing, at least temporarily, a delta-12 desaturase, wherein said delta-12 desaturase has at least 50% total amino acid sequence identity to at least one of the sequences SEQ ID NO. 328 to 336, and/or at least 59% total amino acid sequence similarity to at least one of the sequences SEQ ID NO. 328 to 336, and
said plant expressing one or more further genes to convert linoleic acid to said one or more desired unsaturated fatty acids.

The invention also provides a nucleic acid comprising
a) a gene coding for a Delta-12 desaturase, wherein said delta-12 desaturase has at least 50% total amino acid sequence identity to at least one of the sequences SEQ ID NO. 328 to 336, and/or at least 59% total amino acid sequence similarity to at least one of the sequences SEQ ID NO. 328 to 336 and wherein the gene does not code for a Delta-12 desaturase of any of the exact sequences SEQ ID NO. 329 to 336, or
b) a gene coding for a Delta-12 desaturase, wherein said delta-12 desaturase has at least 50% total amino acid sequence identity to at least one of the sequences SEQ ID NO. 328 to 336, and/or at least 59% total amino acid sequence similarity to at least one of the sequences SEQ ID NO. 328 to 336 and wherein the gene is operably linked to an expression control sequence, and wherein the expression control sequence is heterologous to said gene if the gene codes for any of the exact sequences according to SEQ ID NO. 329 to 336.

In the context of the present invention is also provided a plant cell comprising a gene coding for a delta-12 desaturase, wherein said delta-12 desaturase has at least 50% total amino acid sequence identity to at least one of the sequences SEQ ID NO. 328 to 336, and/or at least 59% total amino acid sequence similarity to at least one of the sequences SEQ ID NO. 328 to 336.

And the invention provides a plant set comprising at least two plant groups,
wherein the plant or plants of each group are capable of expressing a delta-12 desaturase, wherein said delta-12 desaturase has at least 50% total amino acid sequence identity to at least one of the sequences SEQ ID NO. 328 to 336, and/or at least 59% total amino acid sequence similarity to at least one of the sequences SEQ ID NO. 328 to 336,
and wherein the plant or plants of said groups comprise one or more genes coding for at least one or more enzymes of unsaturated fatty acid metabolism, of which enzymes at least one is capable of using linoleic acid as a substrate, and of which enzymes at least one is supposedly connected to a plant metabolic property, and wherein the plants of said groups differ in the expression of at least one of the enzymes of unsaturated fatty acid metabolism.

DETAILED DESCRIPTION OF THE INVENTION

The present invention thus provides an assay method. The assay method of the present invention is particularly suitable for determining the presence and/or intensity of a metabolic property. The metabolic property depends directly or indirectly on the presence or concentration of at least one unsaturated fatty acid in a plant cell, preferably of a fatty acid having at least 18 carbon atoms in length and at least two carbon-carbon double bonds. Thus, the metabolic property preferably is or depends on the production of unsaturated fatty acids and even more polyunsaturated fatty acids in plant cells.

According to the present invention, unsaturated fatty acids preferably are polyunsaturated fatty acids, that is fatty acids comprising at least two, more preferably at least three and even more preferably at least or exactly 4 carbon-carbon double bonds. Unsaturated fatty acids including polyunsaturated fatty acids are generally known to the skilled person, important unsaturated fatty acids are categorised into a omega-3, omega-6 and omega-9 series, without any limitation intended. Unsaturated fatty acids of the omega-6 series include, for example, and without limitation, linoleic acid (18:2 n-6; LA), gamma-linolenic acid (18:3 n-6; GLA), di-homo-gamma-linolenic acid (C20:3 n-6; DGLA), arachidonic acid (C20:4 n-6; ARA), adrenic acid (also called docosatetraenoic acid or DTA; C22:4 n-6) and docosapentaenoic acid (C22:5 n-6). Unsaturated fatty acids of the omega-3 series include, for example and without limitation, alpha-linolenic acid (18:3 n-3, ALA), stearidonic acid (18:4 n-3; STA or SDA), eicosatrienoic acid (C20:3 n-3; ETA), eicosatetraenoic acid (C20:4 n-3; ETA), eicosapentaenoic acid (C20:5 n-3; EPA), docosapentaenoic acid (C22:5 n-3; DPA) and docosahexaenoic acid (C22:6 n-3; DHA). Unsaturated fatty acids also include fatty acids with greater than 22 carbons and 4 or more double bonds, for example and without limitation, C28:8 (n-3). Unsaturated fatty acids of the omega-9 series include, for example, and without limitation, mead acid (20:3 n-9; 5,8,11-eicosatrienoic acid), erucic acid (22:1 n-9; 13-docosenoic acid) and nervonic acid (24:1 n-9; 15-tetracosenoic acid). Further unsaturated fatty acids are eicosadienoic acid (C20:2d11,14; EDA) and eicosatrienoic acid (20:3d11,14,17; ETrA).

According to the present invention, the metabolic property preferably is the production and particularly preferably the yield of an omega-6 type and/or an omega-3 type unsaturated fatty acid. Such yield is preferably defined as the percentage of said fatty acid relative to the total fatty acids of an extract, preferably of a plant or seed oil. Thus, preferably the assay method of the present invention entails measuring the amount and/or concentration of an unsaturated fatty acid, preferably of an unsaturated fatty acid having at least 20 carbon atoms length and belonging to the omiga-3 or omega-6 series. The amount and/or concentration is determined on a plant extract, preferably a plant oil or plant lipids The term "lipids" refers to a complex mixture of molecules comprising compounds such as sterols, waxes, fat soluble vitamins such as tocopherols and carotenoid/retinoids, sphingolipids, phosphoglycerides, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as acetyl-coenzyme A esters. "Lipids" can be obtained from biological samples, such as fungi, algae, plants, leaves, seeds, or extracts thereof, by solvent extraction using protocols well known to those skilled in the art (for example, as described in Bligh, E. G., and Dyer, J. J. (1959) Can J. Biochem. Physiol. 37: 911-918).

The term "oil" refers to a fatty acid mixture comprising unsaturated and/or saturated fatty acids which are esterified to triglycerides. The oil may further comprise free fatty acids. Fatty acid content can be, e.g., determined by GC analysis after converting the fatty acids into the methyl esters by transesterification. The content of the various fatty acids in the oil or fat can vary, in particular depending on the source. It is known that most of the fatty acids in plant oil are esterified in triacylglycerides. In addition the oil of the invention may comprise other molecular species, such as monoacylglycerides, diacylglycerides, phospholipids, or any the molecules comprising lipids. Moreover, oil may comprise minor amounts of the polynucleotide or vector of the invention. Such low amounts, however, can be detected only by highly sensitive techniques such as PCR. Oil can be obtained by extraction of lipids from any lipid containing biological tissue and the amount of oil recovered is dependent on the amount of triacylglycerides present in the tissue. Extraction of oil from biological material can be achieved in a variety of ways, including solvent and mechanical extraction. Specifically, extraction of canola oil typically involves both solvent and mechanical extraction, the products of which are combined to form crude oil. The crude canola oil is further purified to remove phospholipids, free fatty acids, pigments and metals, and odiferous compounds by sequential degumming, refining, bleaching, and deodorizing. The final product after these steps is a refined, bleached, and deodorized oil comprising predominantly fatty acids in the form of triglycerides.

The assay method of the present invention comprises the step of providing a plant. According to the present invention, the term "plant" shall mean a plant or part thereof in any developmental stage. Particularly, the term "plant" herein is to be understood to indicate a callus, shoots, root, stem, branch, leaf, flower, pollen and/or seed, and/or any part thereof. The plant can be monocotyledonous or dicotyledonous and preferably is a crop plant. Crop plants include *Brassica* species, corn, alfalfa, sunflower, soybean, cotton, safflower, peanut, sorghum, wheat, millet and tobacco. The plant preferably is an oil plant. Preferred plants are of order Brassicales, particularly preferred of family Brassicaceae. Even more preferred are plants of tribus Aethionemeae, Alysseae, Alyssopsideae, Anastaticeae, Anchonieae, Aphragmeae, Arabideae, Asteae, Biscutelleae, Bivonaeeae, Boechereae, Brassiceae, Buniadeae, Calepineae, Camelineae, Cardamineae, Chorisporeae, Cochlearieae, Coluteocarpeae, Conringieae, Cremolobeae, Crucihimalayeae, Descurainieae, Dontostemoneae, Erysimeae, Euclidieae, Eudemeae, Eutremeae, Halimolobeae, Heliophileae, Hesperideae, Iberideae, Isatideae, Kernereae, Lepidieae, Malcolmieae, Megacarpaeeae, Microlepidieae, Noccaeeae, Notothlaspideae, Oreophytoneae, Physarieae, Schizopetaleae, Scoliaxoneae, Sisymbrieae, Smelowskieae, Stevenieae, Thelypodieae, Thlaspideae, Turritideae or Yinshanieae. Even more preferred are plants of genus *Aethionema, Moriera, Alyssoides, Alyssum, Aurinia, Berteroa, Bornmuellera, Bornmuellera x Leptoplax, Clastopus, Clypeola, Degenia, Fibigia, Galitzkya, Hormathophylla, Lepidotrichum, Leptoplax, Phyllolepidum, Physocardamum, Physoptychis, Straussiella, Alyssopsis, Calymmatium, Dielsiocharis, Olimarabidopsis, Anastatica, Cithareloma, Diceratella, Eigia, Eremobium, Farsetia, Lachnocapsa, Lobularia, Malcolmia, Maresia, Morettia,*

Notoceras, Parolinia, Anchonium, Eremoblastus, Iskandera, Matthiola, Micrantha, Microstigma, Petiniotia, Sterigmostemum, Synstemon, Zerdana, Aphragmus, Lignariella, Abdra, Arabis (rockcress), Arcyosperma, Athysanus, Aubrieta, Baimashania, Botschantzevia, Dendroarabis, Draba, Drabella, Erophila, Pachyneurum, Pseudodraba, Scapiarabis, Schivereckia, Sinoarabis, Tomostima, Asta, Biscutella, Megadenia, Bivonaea, Anelsonia, Boechera, Borodinia, Cusickiella, Nevada, Phoenicaulis, Polyctenium, Sandbergia, Ammosperma, Brassica, Brassica x Raphanus, Cakile, Carrichtera, Ceratocnemum, Coincya, Cordylocarpus, Crambe, Crambella, Didesmus, Diplotaxis, Douepea, Enarthrocarpus, Eremophyton, Eruca, Erucaria, Erucastrum, Euzomodendron, Fezia, Foleyola, Fortuynia, Guiraoa, Hemicrambe, Henophyton, Hirschfeldia, Kremeriella, Moricandia, Morisia, Muricaria, Nasturtiopsis, Orychophragmus, Otocarpus, Physorhynchus, Pseuderucaria, Psychine, Raffenaldia, Raphanus, Rapistrum, Rytidocarpus, Savignya, Schouwia, Sinapidendron, Sinapis, Succowia, Trachystoma, Vella, Zilla, Bunias, Calepina, Goldbachia, Leiocarpaea, Spirorhynchus, Camelina, Capsella, Catolobus, Cheesemania, Chrysochamela, Neslia, Noccidium, Pseudoarabidopsis, Aplanodes, Armoracia, Barbarea (winter cress), Cardamine (bittercresses), Iodanthus, Iti, Leavenworthia, Nasturtium, Neobeckia, Ornithocarpa, Planodes, Rorippa (yellowcress), Selenia, Sisymbrella, Chorispora, Diptychocarpus, Litwinowia, Neuroloma, Parrya, Pseudoclausia, Cochlearia, Ionopsidium, Callothlaspi, Coluteocarpus, Eunomia, Kotschyella, Noccaea, Vania, Conringia, Zuvanda, Cremolobus, Menonvillea, Crucihimalaya, Ladakiella, Transberingia, Descurainia, Hornungia, Hymenolobus, lanhedgea, Pritzelago, Robeschia, Tropidocarpum, Clausia, Dimorphostemon, Dontostemon, Erysimum, Syrenia, Atelanthera, Braya, Catenulina, Christolea, Cryptospora, Cymatocarpus, Dichasianthus, Dilophia, Euclidium, Lachnoloma, Leiospora, Lepidostemon, Leptaleum, Neotorularia, Octoceras, Phaeonychium, Pycnoplinthopsis, Pycnoplinthus, Rhammatophyllum, Shangrilaia, Sisymbriopsis, Solms-laubachia, Spryginia, Streptoloma, Tetracme, Aschersoniodoxa, Brayopsis, Dactylocardamum, Eudema, Onuris, Xerodraba, Chalcanthus, Eutrema, Pegaeophyton, Thellungiella, Exhalimolobos, Halimolobos, Mancoa, Pennellia, Sphaerocardamum, Heliophila (Cape stock), Hesperis, Tchihatchewia, Iberis, Teesdalia, Boreava, Chartoloma, Glastaria, Isatis, Myagrum, Pachypterygium, Sameraria, Schimpera, Tauscheria, Kernera, Rhizobotrya, Acanthocardamum, Coronopus, Cyphocardamum, Delpinophytum, Lepidium, Lithodraba, Stubendorffia, Winklera, Megacarpaea, Pugionium, Arabidella, Ballantinia, Blennodia, Carinavalva, Cuphonotus, Drabastrum, Geococcus, Harmsiodoxa, Irenepharsus, Menkea, Microlepidium, Pachycladon, Pachymitus, Phlegmatospermum, Scambopus, Stenopetalum, Notothlaspi, Murbeckiella, Oreophyton, Dimorphocarpa, Dithyrea, Lyrocarpa, Nerisyrenia, Paysonia, Physaria (bladderpods), Synthlipsis, Caulanthus, Mathewsia, Schizopetalon, Sibaropsis, Streptanthella, Werdermannia, Scoliaxon, Lycocarpus, Schoenocrambe, Sisymbrium, Hedinia, Smelowskia, Berteroella, Macropodium, Pseudoturritis, Ptilotrichum, Stevenia, Catadysia, Chaunanthus, Chilocardamum, Chlorocrambe, Coelophragmus, Dictyophragmus, Dryopetalon, Englerocharis, Guillenia, Hesperidanthus, Ivania, Mostacillastrum, Neuontobotrys, Phlebolobium, Polypsecadium, Pringlea, Pterygiosperma, Romanschulzia, Sarcodraba, Sibara, Stanleya, Streptanthus, Thelypodiopsis, Thelypodium, Thysanocarpus, Warea, Weberbauera, Alliaria, Didymophysa, Elburzia, Gagria, Graellsia, Pachyphragma, Parlatoria, Peltaria, Peltariopsis, Pseudocamelina, Pseudovesicaria, Sobolewskia, Thlaspi, Turritis, Hilliella, Yinshania. Most preferred are plants of species *Brassica aucheri*, *Brassica balearica*, *Brassica barrelieri*, *Brassica carinata*, *Brassica carinata* x *Brassica napus*, *Brassica carinata* x *Brassica rapa*, *Brassica carinata* x *Brassica juncea*, *Brassica cretica*, *Brassica deflexa*, *Brassica desnottesii*, *Brassica drepanensis*, *Brassica elongata*, *Brassica fruticulosa*, *Brassica gravinae*, *Brassica hilarionis*, *Brassica incana*, *Brassica insularis*, *Brassica juncea*, *Brassica macrocarpa*, *Brassica maurorum*, *Brassica montana*, *Brassica napus*, *Brassica napus* x *Brassica juncea*, *Brassica napus* x *Brassica nigra*, *Brassica nigra*, *Brassica oleracea*, *Brassica oxyrrhina*, *Brassica procumbens*, *Brassica rapa*, *Brassica repanda*, *Brassica rupestris*, *Brassica ruvo*, *Brassica souliei*, *Brassica spinescens*, *Brassica tournefortii* or *Brassica villosa*.

The plant of the assay method of the present invention is capable of expressing a Delta-12 desaturase as defined herein. The plant can be provided by any appropriate means. For example, the plant can be provided by transforming a plant cell with a nucleic acid comprising a gene coding for the Delta-12 desaturase of the present invention and raising such transformed plant cell to a plant sufficiently developed for measuring the plant metabolic property. According to the invention, a plant can also be provided in the form of an offspring of such transformed plant. Such offspring may be produced vegetatively from material of a parent plant, or may be produced by crossing a plant with another plant, preferably by inbreeding.

The plant is capable of expressing a Delta-12 desaturase. According to the invention, the term "capable of expressing a gene product" means that a cell will produce the gene product provided that the growth conditions of the sale are sufficient for production of said gene product. For example, a plant is capable of expressing a Delta-12 desaturase is a cell of said plant during any developmental stage of said plant will produce the corresponding Delta-12 desaturase. It goes without saying that where expression depends on human intervention, for example the application of an inductor, a plant is likewise considered capable of expressing the Delta-12 desaturase.

According to the invention, the plant is capable of expressing a Delta-12 desaturase, wherein said Delta-12 desaturase has at least 50% total amino acid sequence identity to any of the sequences SEQ ID NO. 328 to 336, and/or at least 59% total amino acid sequence similarity to any of the sequences SEQ ID NO. 328 to 336. A Delta-12 desaturase having this desired sequence identity and/or sequence similarity is also called a Delta-12 desaturase of the present invention. A Delta-12 desaturase according to the invention is an enzyme catalysing (at least) the conversion of oleic acid to linoleic acid. For a metabolic pathway for the production of unsaturated and polyunsaturated fatty acids, see for example figure one of WO2006100241. Examples of Delta-12 desaturases referred to herein are:

SEQ ID NO. 328 artificial Delta-12 desaturase sequence
SEQ ID NO. 329 Uniprot G5A275_PHYSP of *Phytophthora_sojae*
SEQ ID NO. 330 Uniprot H3G9L1_PHYRM of *Phytophthora_ramorum*
SEQ ID NO. 331 Uniprot G4XUM4_PHYIN of *Phytophthora_infestans*
SEQ ID NO. 332 Uniprot M4BXW8_HYAAE of *Hyaloperonospora_arabidopsidis*
SEQ ID NO. 333 Uniprot W2PDL4_PHYPN of *Phytophthora_parasitica*

SEQ ID NO. 334 Uniprot W2LW72_PHYPR of *Phytophthora_parasitica*

SEQ ID NO. 335 Uniprot W2ZYI2_PHYPR of *Phytophthora_parasitica*

SEQ ID NO. 336 Uniprot Q6UB74_9 STRA of *Saprolegnia diclina*

It has now surprisingly been found that expression of a Delta-12 desaturase of the present invention reduces the difference between fatty acid composition of plants grown under greenhouse and field conditions, respectively. This was unexpected, as plants generally are capable of expressing at least one Delta-12 desaturase even as wild type plants. However, as seen in the accompanying examples, the percentage of linoleic acid (and correspondingly also the concentration of other unsaturated fatty acids metabolically downstream of linoleic acid) differs between wild-type plants grown under greenhouse and field conditions, respectively. However, where plants express a delta-12 desaturases of the present invention, optionally in addition to the one or more type delta-12 desaturase(s), the difference in oil composition between plants raised in the greenhouse and plants raised under field conditions is greatly diminished or even removed. Thus, by making use of the delta-12 desaturases of the present invention it is possible to improve the delta-12 desaturases conversion efficiency in plants grown under greenhouse conditions. The assay method of the present invention hence effectively allows to simulate the influence of field conditions on a plant metabolic property, wherein said metabolic property is directly or indirectly connected to the presence and/or concentration of linoleic acid in a plant cell as described above. Using an assay method of the present invention therefore unexpectedly allows to screen plants for such metabolic properties with higher reliability and prediction accuracy of said plant metabolic property. Effectively the assay method of the present invention enables the skilled person to reduce the number of field trials required for development of a commercially viable plant variety producing unsaturated or even more preferably polyunsaturated fatty acids.

A gene coding for a Delta-12 desaturase of the present invention can be obtained by de novo synthesis. Starting from any of the amino acid sequences SEQ ID NO. 328 to 336, the skilled person can reverse-translate the selected sequence into a nucleic acid sequence and have the sequence synthesised. As described herein, the skilled person can also introduce one or more mutations, including insertions, substitutions and deletions to the amino acid sequence chosen or the corresponding nucleic acid sequence. For reverse translation, the skilled person can and should use nucleic acid codons such as to reflect codon frequency of the plant intended for expression of said Delta-12 desaturase of the present invention. By using any of the amino acid sequences according to SEQ ID NO. 328 to 336 as such or one or more mutations, the person can obtain using routine techniques and standard equipment, a Delta-12 desaturase having the beneficial properties described herein and exhibiting these beneficial properties in numerous plant species.

Instead of starting from any of the amino acid sequences according to SEQ ID NO. 328 to 336, the skilled person may also obtain a Delta-12 desaturase from any organism of class oomycetes, preferably of order Peronosporales, Pythiales or Saprolegniales, particularly preferably of genus *Basidiophora, Benua, Bremia, Erapthora, Graminivora, Hyaloperonospora, Novotelnova, Paraperonospora, Perofascia, Peronosclerospora, Peronospora, Phytophthora, Phytopythium, Plasmopara, Plasmoverna, Protobremia, Pseudoperonospora, Salisapiliaceae, Sclerophthora, Sclerospora* or *Viennotia*, or genus *Diasporangium, Elongisporangium, Globisporangium, Halophytophthora, Ovatisporangium, Pilasporangium* or *Pythium*, or genus *Achlya, Aphanomyces, Aplanes, Aplanopsis, Aquastella, Brevilegnia, Calyptralegnia, Dictyuchus, Geolegnia, lsoachlya, Leptolegnia, Newbya, Plectospira, Protoachlya, Pythiopsis, Saprolegnia, Scoliolegnia* or *Thraustotheca*. Methods for obtaining such Delta-12 desaturase nucleic acid and amino acid sequences are described for example in international publication WO 2006 100 241. Particularly preferably, the skilled person starts with a Delta-12 desaturase nucleic acid sequence obtainable or obtained from any member of the above genera, preferably the genera *Phytophthora, Hyaloperonospora* or *Saprolegnia*. Even more preferably, the skilled person starts by using the nucleic acid sequence coding for a Delta-12 desaturase obtainable or obtained from any member of species *Phytophthora sojae, Phytophthora parasitica, Phytophthora ramorum* or *Phytophthora infestans*.

The amino acid sequence of the Delta-12 desaturase of the present invention may be identical to any of the sequences according to SEQ ID NO. 328 to 336. However, in certain embodiments it is preferred that the amino acid sequence of the Delta-12 desaturase of the present invention is not the sequence according to SEQ ID NO. 328 and/or is not the amino acid sequence according to SEQ ID NO. 329 and/or is not the amino acid sequence according to SEQ ID NO. 330 and/or is not the amino acid sequence according to SEQ ID NO. 331 and/or is not the amino acid sequence according to SEQ ID NO. 332 and/or is not the amino acid sequence according to SEQ ID NO. 333 and/or is not the amino acid sequence according to SEQ ID NO. 334 and/or is not the amino acid sequence according to SEQ ID NO. 335 and/or is not the amino acid sequence according to SEQ ID NO. 336. Where the skilled person for any reason wants to avoid any one or more of the amino acid sequences according to SEQ ID NO. 328 to 336, the skilled person can use any of the remaining sequences of this set of sequences. However, the skilled person can also make up a new amino acid and corresponding nucleic acid sequence by selecting a base sequence from the set of amino acid sequences according to SEQ ID NO. 328 to 336 and introducing one or more mutations (insertions, substitutions and/or deletions) at appropriate positions of the base sequence to obtain a derived sequence. Generally, the skilled person will take into account that the higher the sequence identity and/or similarity between base sequence and derived sequence, the more will the corresponding derived Delta-12 desaturase resemble the Delta-12 desaturase activity that corresponds to the desaturase of the base sequence. Thus, if the skilled person uses a mutated Delta-12 desaturase according to the present invention and such mutated Delta-12 desaturase unexpectedly does not convey the benefits of a Delta-12 desaturase of the present invention, the skilled person should reduce the number of differences of the Delta-12 desaturase sequence to increase resemblance of any of the sequences according to SEQ ID NO. 328 to 336.

For substituting amino acids of a base sequence selected from any of the sequences SEQ ID NO. 328 to 336 without regard to the occurrence of amino acid in other of these sequences, the following applies, wherein letters indicate L amino acids using their common abbreviation and bracketed numbers indicate preference of replacement (higher numbers indicate higher preference): A may be replaced by any amino acid selected from S (1), C (0), G (0), T (0) or V (0). C may be replaced by A (0). D may be replaced by any amino acid selected from E (2), N (1), Q (0) or S (0). E may be replaced by any amino acid selected from D (2), Q (2), K (1), H (0), N (0), R (0) or S (0). F may be replaced by any amino acid selected from Y (3), W (1), I (0), L (0) or M (0). G may be replaced by any amino acid selected from A (0), N (0) or S (0). H may be replaced by any amino acid selected from Y (2), N (1), E (0), Q (0) or R (0). I may be replaced by any amino acid selected from V (3), L (2), M (1) or F (0). K may be replaced by any amino acid selected from R (2), E (1), Q (1), N (0) or S (0). L may be replaced by any amino acid selected from I (2), M (2), V (1) or F (0). M may be replaced by any amino acid selected from L (2), I (1), V (1), F (0) or Q (0). N may be replaced by any amino acid selected from D (1), H (1), S (1), E (0), G (0), K (0), Q (0), R (0) or T (0). Q may be replaced by any amino acid selected from E (2), K (1), R (1), D (0), H (0), M (0), N (0) or S (0). R may be replaced by any amino acid selected from K (2), Q (1), E (0), H (0) or N (0). S may be replaced by any amino acid selected from A (1), N (1), T (1), D (0), E (0), G (0), K (0) or Q (0). T may be replaced by any amino acid selected from S (1), A (0), N (0) or V (0). V may be replaced by any amino acid selected from I (3), L (1), M (1), A (0) or T (0). W may be replaced by any amino acid selected from Y (2) or F (1). Y may be replaced by any amino acid selected from F (3), H (2) or W (2).

According to the invention, sequence identity and similarity are calculated by pairwise alignment of two sequences according to the algorithm of Needleman and Wunsch (J. Mol. Biol. 1970, 48(3), 433-453) using, for amino acid sequence comparisons, a gap opening penalty of 12 and a gap extension penalty of 2 and applying the BLOSUM62 matrix, and using for nucleic acid sequence comparisons a gap opening penalty of 16 and a gap extension penalty of 4. Identity is then calculated as the number of identical positions in the alignment divided by the length of the alignment. Similarity is calculated as the number of positions where amino acids of both sequences have a weight of at least zero or larger in the BLOSUM62 matrix and then dividing this number by the length of the alignment.

The Delta-12 desaturase of the present invention preferably has at least 50% amino acid sequence identity to any of the sequences SEQ ID NO. 328 to 336. Most preferably, the Delta-12 desaturase of the present invention has at least 50% amino acid sequence identity to sequence SEQ ID NO. 329. This desaturase can be shown to be functional in numerous plant species, it is easy to obtain and conveys the benefits of the desaturase of the present invention. Preferably, the Delta-12 desaturase of the present invention has at least 55% amino acid sequence identity to any of the sequences SEQ ID NO. 328, 329, 330, 331, 332, 333, 334, 335, 336, 337, 338 and 339, wherein identity to SEQ ID NO. 329 is particularly preferred, even more preferably at least 65%, even more preferably at least 72%, even more preferably at least 78%, even more preferably at least 80%, even more preferably at least 82%, even more preferably at least 89%, even more preferably at least 91%, even more preferably at least 96%. The Delta-12 desaturase of the present invention preferably has at least 50% amino acid sequence identity to any of the sequences SEQ ID NO. 328 to 336. Most preferably, the Delta-12 desaturase of the present invention has at least 50% amino acid sequence identity to sequence SEQ ID NO. 329. This desaturase can be shown to be functional in numerous plant species, it is easy to obtain and conveys the benefits of the desaturase of the present invention. Preferably, the Delta-12 desaturase of the present invention has at least 60% amino acid sequence identity to any of the sequences SEQ ID NO. 1, 2, 3, 4, 5, 6, 7, 8 or 9, where similarity to SEQ ID NO. 329 is particularly preferred, even more preferably at least 73%, even more preferably at least 75%, even more preferably at least 89%, even more preferably at least 95%, even more preferably at least 96%, even more preferably at least 97%, even more preferably at least 98%, even more preferably at least 99%. Preferably, the delta-12 desaturase of the present invention has both the required or preferred minimal identity and the required or preferred minimal similarity. The higher the similarity and identity between the amino acid sequence of the Delta-12 desaturase of the present invention and the amino acid sequence according to SEQ ID NO. 1, 2, 3, 4, 5, 6, 7, 8 or 9, the more reliable will the Delta-12 desaturase of the present invention exhibit Delta-12 desaturase activity in a plant cell and convey the benefits of the present invention.

Preferably, the amino acid sequence of the Delta-12 desaturase of the present invention differs from the amino acid sequences according to any of SEQ ID NO. 328 to 336 only at such one or more positions where at least one of the amino acid sequences SEQ ID NO. 328 to 336 differs from at least one other of the sequences SEQ ID NO. 328 to 336, preferably not allowing any amino acid insertion or deletion. Preferably, the amino acid sequence of the Delta-12 desaturase of the invention can be thought to be the result of exchanging selected amino acids from one chosen base sequence of the sequences SEQ ID NO. 328 to 336 for the corresponding amino acid at the respective positions of any other of the sequences SEQ ID NO. 328 to 336. Also preferably, any mutation should increase the similarity, or, even more preferably, the identity, of the amino acid sequence of the Delta-12 desaturase of the present invention to that of a sequence according to SEQ ID NO. 328 to 336 and reduce the similarity or, even more preferably, the identity, to an amino acid sequence according to SEQ ID NO. 10 to 12.

For the reasons indicated above, the Delta-12 desaturase of the present invention preferably consists of the amino acid sequence SEQ ID NO. 329. Less preferably, the amino acid sequence of the Delta-12 desaturase of the present invention differs from the amino acid sequence according to SEQ ID NO. 329 only at such positions where any of the sequences SEQ ID NO. 338 or 330 to 336 differ from the amino acid sequence of SEQ ID NO. 329. More preferably, the Delta-12 desaturase of the present invention does not differ from the amino acid sequence of SEQ ID NO. 329 by an insertion or deletion and thus only comprises one or more substitutions. Even more preferably, the Delta-12 desaturase of the present invention consists of an amino acid sequence that differs from SEQ ID NO. 329 only by amino acids found at the corresponding position of any of the other amino acid sequence SEQ ID NO. 328 and 330-336.

The plant of the present invention is further capable of expressing at least one or more enzymes of unsaturated fatty acid metabolism. Preferably, such enzymes are capable of using an unsaturated fatty acid of the omega-6 and/or, more preferably, of the omega-3 series as a substrate. Preferred activities of the enzymes are: desaturase, elongase, ACS, acylglycerol-3-phosphate acyltransferase (AGPAT), choline phosphotransferase (CPT), diacylglycerol acyltransferase (DGAT), glycerol-3-phosphate acyltransferase (GPAT), lysophosphatidate acyltransferase (LPAT), lysophosphatidylcholine acyltransferase (LPCAT), lysophosphatidylethanolamine acyltransferase (LPEAT), lysophospholipid acyltransferase (LPLAT), phosphatidate phosphatase (PAP), phospholipid:diacylglycerol acyltransferase (PDAT), phosphatidylcholine:diacylglycerol choline phosphotransferase (PDCT), particularly Delta-8 desaturase, Delta-6 desaturase, Delta-5 desaturase, Delta-4 desaturase, Delta-9 elongase, Delta-6 elongase, Delta-5 elongase, omega-3 desaturase.

At least one of the enzymes is capable of using linoleic acid as substrate. Such enzymes are known to the skilled person as omega-3 desaturases, Delta-15 desaturases, Delta-9 along gazes and Delta-6 desaturases. It is possible that one or more enzymes of unsaturated fatty acid metabolism can have more than one activity. For example, it is common for omega-3 desaturases to be also Delta-15 desaturases and/or Delta-17 desaturases and/or Delta-19 desaturases. Further preferred enzymes of unsaturated fatty acid metabolic is our Delta-6 along gazes, Delta-8 desaturases, Delta-5 desaturases, Delta-5 elongates this and Delta-4 desaturases. At least one of these enzymes is supposedly connected to a plant metabolic property. Preferably, the metabolic property is the presence and/or concentration of the product of the respective enzyme. Thus, preferably the plant metabolic property is the presence and/or concentration of any of GL a, SDA, EDA, ETrA, the GLA, EDTA, ARA, EPA, DTA, DPA and DHA, wherein particularly preferred are the concentration of ARA, EPA and DHA.

In the assay method of the present invention, the plant is capable of expressing the Delta-12 desaturase of the present invention and at least one more enzyme of unsaturated fatty acid metabolic is and are grown. "Growing" for the present invention means to nurture plant material, preferably a plant can use, embryo or seed, such that cells of said plant material can develop and preferably multiply, such that at least one cell of the developed plant material can be expected to exhibit the plant metabolic property. For example, where the expression of a gene coding for an enzyme of unsaturated fatty acid metabolism, for example a desaturase or elongates, is under the control of a tissue-specific promoter, the plant material is grown such that the corresponding tissue develops.

The plant metabolic property is then measured by any suitable means. For example, the concentration of fatty acids in the form of free fatty acids or in the form of mono-, di- or triglycerides can be measured from extracts of plant material, preferably of plant seeds and most preferably from seed oil.

The assay method of the present invention preferably is not performed only on one plant but on a group of plants. This way, the measured plant metabolic properties will be statistically more significant than measurements taken only on plant material of a single plant, for example a single seed. Even though assay methods of the present invention preferably are performed on plant groups, assay methods of the present invention performed on single plants are also useful and beneficial. Such methods allow for a fast screening plants and thus are particularly suitable for high throughput evaluation of genes and gene combinations coding for enzymes of unsaturated fatty acid metabolism.

As indicated above, a preferred assay method of the present invention comprises 1) providing a plant group, wherein the plants of said group are capable of expressing a Delta-12 desaturase of the present invention,
and wherein the plants of said group are capable of expressing at least one or more enzymes of unsaturated fatty acid metabolism, of which enzymes at least one is capable of using linoleic acid as a substrate, and of which enzymes at least one is supposedly connected to a plant metabolic property,
2) growing the plants of the plant group, and
3) measuring said plant metabolic property for at least one, preferably at least 2 and even more preferably at least 3, 4, 5, 6 or more plants of said plant group.

As indicated above, the present invention aspires to and allows to reduce the number of field trials. Thus, the assay method of the present invention (performed on single plants or plant groups) is preferably performed such that the plant or plants are grown under greenhouse conditions. According to the present invention, greenhouse conditions are environmental conditions where intensity can be controlled and adjusted at will, and may also be referred to as controlled environment conditions. Greenhouse conditions are generally maintained using standard equipment, for example a germination chamber, a growth cabinet or a greenhouse. Such equipment particularly allows to control more than one environmental condition, preferably light, temperature (of growth material and of air bracket, humidity and growth medium composition, particularly water content, and the concentration of growth regulators like water, nutrients and protection agents like bactericides, fungicides, helminticides and insecticidal agents. Greenhouses, growth cabinets and germination chambers (that is according to the invention equipment for maintaining greenhouse conditions) also allow controlled changes of one or more of the aforementioned environmental conditions, for example in a diurnal rhythm to simulate for example short day or long day light conditions and/or drought or nutrient deficiency conditions. For automated greenhouses, such conditions can also be controlled for each individual plant or group of plants. Thus, for example greenhouse conditions allow to subject single or more plants to stress conditions at selected stages of plant development and for a selected duration.

For $Brassica$ species grown in the greenhouse, temperatures can range from 10° C. to 30° C., but the preferred conditions include 15-22° C. day and 12-20° C. night temperatures. Preferably, there is a 3° C. difference between night and day. Colder day and night temperatures can be used to slow the growth rate of plants or to assess the effect of temperature on plant growth. A preferred light cycle is 16 hrs light and 8 hrs dark. A shorter day length can be used to delay growth or to delay reproduction. The preferred light intensity is 200-300 micromoles of photons m-2 s-1, but it can range from 100-1200 micromoles of photons m-2 s-1. Humidity can range from 20-70%, with the preferred range being 30-50%. Lower humidity is useful to limit disease incidence.

The gene coding for the Delta-12 desaturase of the present invention preferably is operably linked to an expression control sequence to allow constitutive or non-constitutive expression of said gene. Expression control sequences according to the present invention are known to the skilled person as promoters, transcription factor binding sites and regulatory nucleic acids like for example RNAi. Preferably, the expression control sequence directs expression of the gene in a tissue-specific manner. Where the plant is an oil seed plant, preferably of a $Brassica$ species, expression of the gene preferably is specific to plant seeds in one or more of their developmental stages. According to the present invention, tissue-specific expression does not require the total absence of gene expression in any other tissue. However, tissue-specific expression for a selected tissue means that the maximum amount of mRNA transcript in this tissue is at least 2-fold, preferably at least 5-fold, even more preferably at least 10-fold, even more preferably at least 20-fold, even more preferably at least 50-fold and most preferably at least 100-fold the maximum amount of said mRNA in the other tissues. Furthermore, expression control sequences are known to the skilled person which allow induction or repression of expression by a signal applied by a user, for example application of an inductor like IPTG.

The Delta-12 desaturase of the present invention can be present in the plant or plants of the SA method of the present invention as a single copy gene or in multiple gene copies. It is an advantage of the present invention that even a single copy of the Delta-12 desaturase gene of the present invention can be shown to be sufficient for reducing or even removing differences in oil composition between plants grown under greenhouse and field conditions, and it can also be shown that a single copy of the Delta-12 desaturase gene of the present invention is sufficient for increasing Delta-12 desaturase conversion efficiencies as defined below. This is a considerable advantage, as the production of polyunsaturated fatty acids like EPA and DHA generally requires the introduction of at least 3 genes to provide the activities of a Delta-6 desaturase/Delta-6 elongase, Delta-9 elongase/Delta-8 desaturase, Delta-5 desaturase, Delta-5 elongase and/or Delta-4 desaturase. Thus, establishing a metabolic pathway for production of polyunsaturated fatty acids requires transformation of plants either by very long nucleic acid constructs (for example using a technique known in the art as BiBAC) or multiple transformations using shorter nucleic acid constructs. All of these techniques can be laborious, and labour intensity generally increases the more nucleic acids and/or the longer nucleic acids have to be introduced into a plant. Thus, the possibility of achieving the advantages conferred by the present invention by using only a single gene coding for the Delta-12 desaturase of the present invention allows the skilled person to materialise these benefits with minimal additional work. Also, expression of the 12 desaturase of the present invention does not require functional inactivation of one or more Delta-12 desaturase genes of the plant in question. The skilled person may even decide to prepare one or more plant varieties comprising one or another gene coding for a Delta-12 desaturase of the present invention under the control of a desired expression control sequence, for example a seed-specific promoter. Using such plant varieties, the skilled person can then introduce the genes of unsaturated fatty acid metabolism using normal constructs and without having to increase construct length by an additional Delta-12 desaturase gene and its corresponding expression control sequence.

Where the gene coding for the Delta-12 desaturase of the present invention is under the control of a seat-specific expression control sequence mRNA transcripts of the gene are preferably detectable, for example by qPCR, at least 25 days, more preferably at least 20 days and even more preferably at least 15 days after flowering of the plant. Also preferably, the maximum expression of the Delta-12 desaturase gene of the present invention is before 40 days after inflorescence, more preferably before 35 days after inflorescence and even more preferably before 33 days after inflorescence. Preferably, the maximum expression, for example as determined by qPCR, is from day 22 day 35 after inflorescence, even more preferably from day 21 to 31 after inflorescence. To achieve such expression pattern, the SBP promoter or, more preferably, the Napin promoter are particularly preferred. Thus, the present invention allows to materialise the benefits conferred by the use of the Delta-12 desaturase of the present invention without having to express said Delta-12 desaturase constitutively throughout the plant or constitutively throughout seed-development. Constitutive gene expression requires a plant cell to produce a gene product regardless of whether it is beneficial or even necessary or not. Thus, the present invention allows to minimise the stress inflicted upon the plant in question.

The Delta-12 desaturase of the present invention preferably is expressed in the same plant cell also expressing the other at least one or more enzymes of unsaturated fatty acid metabolism. It is possible but not necessary that the Delta-12 desaturase of the present invention is expressed at the same time as one, some or all of said other genes of unsaturated fatty acid metabolism. For example, the Delta-12 desaturase of the present invention may reach a maximum expression as determined by qPCR during the 1st two thirds of seed development time (preferably, as described above, during days 20 and 31 after inflorescence) with mRNA concentration of said Delta-12 desaturase gene being halved or even less at further stages of seed development, whereas the one or more other genes of unsaturated fatty acid metabolism may start to be or continue to be expressed even after maximal expression of the Delta-12 desaturase gene of the present invention. This is beneficial for reducing unwanted intermediary products in the formation of a polyunsaturated fatty acid. For example, where the skilled person desires to produce EPA and reduce the concentration of intermediates in the final plant oil, expression of the genes coding for Delta-6 desaturase, Delta-6 elongase and Delta-5 desaturase (or Delta-9 elongase, Delta-8 desaturase and Delta-5 desaturase) may be reduced or switched of in this sequence. Thus, the enzymes involved in late steps of product formation have the chance to consume some or all of the required intermediated products without these intermediate products being replenished by the enzymes involved in early steps of product formation. The resulting oil is then enriched in EPA and reduced in content of for example ALA, SDA and/or ETA.

According to the invention there is also provided a method of identifying a gene for conveying an unsaturated fatty acid metabolic property to a plant, comprising:
  i) producing a plant comprising said gene,
  ii) performing an assay method of the present invention, wherein said gene is expressed and said plant metabolic property is measured, and
  iii) evaluating said plant for the presence and/or intensity of said unsaturated fatty acid metabolic property.

As described herein, by using the Delta-12 desaturase of the present invention it is possible to obtain plant metabolic property measurements, preferably plant oil composition data, of plants grown under greenhouse conditions that approximate closely or are identical to paints grown under field conditions.

The invention also provides a method of increasing Delta-12 desaturase activity and/or of stabilising Delta-12 desaturase activity in a plant or part thereof or during developmental stages of a plant or part thereof, preferably during seed development, which methods comprise growing a plant expressing a Delta-12 desaturase of the present invention. As described herein, expression of the Delta-12 desaturase according to the present invention allows to simulate or approximate a plant metabolic property (preferably seed oil composition) obtainable or to be expected under field conditions by merely growing a corresponding plant or plants under greenhouse conditions. Thus, the use of the Delta-12 desaturase according to the present invention effectively reduces the impact of environmental influences (preferably of temperature and/or daily/seasonal temperature variation) on Delta-12 desaturase activity in the plant or plants, thus effectively stabilising or increasing Delta-12 desaturase activity. This also allows to produce unsaturated fatty acids downstream of linoleic acid, for example EPA, DPA and/or DHA, more reliably than without a Delta-12 desaturase of the present invention.

Thus, the invention also provides a method of producing one or more desired unsaturated fatty acids in a plant, comprising growing a plant, said plant expressing, at least temporarily, a Delta-12 desaturase of the present invention and one or more further genes to convert linoleic acid to said one or more desired unsaturated fatty acids. As indicated above, the one or more further genes coding for enzymes for the production of unsaturated fatty acids preferably comprise desaturases and elongases.

The invention also provides a nucleic acid comprising a gene coding for a Delta-12 desaturase of the present invention, wherein the gene does not code for a Delta-12 desaturase of any of the exact sequences SEQ ID NO. 329 to 336. Thus, the present invention provides a nucleic acid comprising a gene coding for a Delta-12 desaturase, wherein said Delta-12 desaturase has at least 50% total amino acid sequence identity to any of the sequences SEQ ID NO. 328 to 336 and/or at least 60% total amino acid sequence similarity to any of the sequences SEQ ID NO. 328 to 336, and wherein the sequence is not any of the sequences SEQ ID NO. 329 to 336. The amino acid sequence according to SEQ ID NO. 328 had not been described in the prior art. The aforementioned nucleic acid of the invention thus for the first time provides you nucleic acid sequences coding for Delta-12 desaturases of the present invention. Corresponding to the preferred Delta-12 desaturase amino acid sequences described above, the present invention provides corresponding nucleic acids comprising a gene coding for such preferred Delta-12 desaturase of the present invention.

The invention also provides a nucleic acid comprising a gene coding for a Delta-12 desaturase of the present invention, wherein the gene is operably linked to an expression control sequence, and wherein the expression control sequence is heterologous to said gene if the gene codes for any of the exact sequences according to SEQ ID NO. 329 to 336. Thus, the invention particularly provides combinations of promoters and genes not found in nature, and particularly not found in any organism of genus *Phytophthora*, *Hyaloperonospora* and *Saprolegnia*.

The nucleic acids of the present invention preferably are expression vectors or transformation constructs useful for transforming a plant cell and causing the Delta-12 desaturase gene of the present invention to be expressed at least temporarily during plant or plant cell development. Thus, the nucleic acids of the present invention facilitate to materialise the benefits conveyed by the present invention as described herein. Also, the invention provides purified Delta-12 desaturase polypeptides coded by any of the nucleic acids of the present invention.

According to the invention, there is also provided a plant cell comprising a gene coding for a Delta-12 desaturase of the present invention. Such plant cells can be obtained, as described above, by transformation of wild-type plant cells or offspring thereof, for example by crossing a plant comprising a gene coding for a Delta-12 desaturase of the invention with a plant not comprising such gene and selecting offspring, preferably seeds, which comprise said gene. This way it is easily possible to transfer the gene coding for a Delta-12 desaturase of the present invention from one germplasm to another. The plant cell of the present invention preferably comprises a gene coding for one of the preferred Delta-12 desaturases of the present invention to materialise the benefits conveyed by such preferred desaturase. Also as described above, the gene coding for the Delta-12 desaturase of the present invention preferably is operably linked to an expression control sequence, and it is particularly preferred that said expression control sequence directs expression to certain tissues and certain times of plant development, for example to developing seed tissue and the above indicated preferred times after flowering.

As the present invention provides an assay method which can, as described above, also be used for screening and comparison purposes, the present invention also provides a plant set comprising at least 2 plant groups, each consisting of one or more plants, wherein the plant or plants of each group are capable of expressing a Delta-12 desaturase of the present invention, and wherein the plant or plants of said groups comprise one or more genes coding for at least one or more enzymes of unsaturated fatty acid metabolism, of which enzymes at least one is capable of using linoleic acid as a substrate, and of which enzymes at least one is supposedly connected to a plant metabolic property, and wherein the plant or plants of said groups differ in the expression of at least one of the enzymes of unsaturated fatty acid metabolism. To differ in expression of at least one of the enzymes of unsaturated fatty acid metabolism, one gene present in the plant or plants of one group may be missing in the plant or plants of another group, or may be expressed at different times or in different tissues or in differing intensities. For example, the plants of 2 groups may both comprise a gene coding for a Delta-4 desaturase under the control of identical expression control sequences, but the Delta-4 desaturase nucleic acid sequences are derived from different organisms such that the amino acid sequences of the respective Delta-4 desaturases are unique for the plants of each of the groups. Instead of or additional to differing in the genes for Delta-4 desaturases, the groups can also differ in any other nucleic acid sequence coding for an enzyme of unsaturated fatty acid metabolism, included but not limited to omega-3 desaturases, Delta-6 desaturases, Delta-9 elongases, Delta-6 elongases, Delta-8 desaturases, Delta-5 desaturases and Delta-5 elongases.

As described above, the present invention allows to reduce the number of field trials for analysing plant metabolic properties, particularly of unsaturated fatty acid metabolism properties. Therefore the plants of the plant set of the present invention preferably are growing under greenhouse conditions. Even more preferably, at least one plant of at least one group of the plant set of the present invention is within at most 100 m distance to a plant of another group.

Where plants are grown in an automated greenhouse, in a growth chamber or germination chamber, it is allowable according to the invention to temporarily remove one or more plants from the greenhouse, growth chamber or germination chamber, respectively, for up to 1 hour per day, preferably for not more than 45 min, more preferably for not more than 30 min and most preferably for not more than 20 min per day. Thus, the invention allows to perform analyses done on the plant or plants outside of e.g. a greenhouse or in a separate chamber thereof where environmental conditions can differ from those of the location where the plant or plants are normally grown.

The invention and certain particular aspects thereof is hereinafter described by way of examples. These are intended to describe also additional objects, advantages, and novel features of this invention. They are not intended to limit the scope of the invention or of the claims.

EXAMPLES

Example 1: Materials and Methods

A. General Cloning Methods

Cloning methods as e.g. use of restriction endonucleases to cut double stranded DNA at specific sites, agarose gel electrophoreses, purification of DNA fragments, transfer of nucleic acids onto nitrocellulose and nylon membranes, joining of DNA-fragments, transformation of E. coli cells and culture of bacteria were performed as described in Sambrook et al. (1989) (Cold Spring Harbor Laboratory Press: ISBN 0-87965-309-6). Polymerase chain reaction was performed using Phusion™ High-Fidelity DNA Polymerase (NEB, Frankfurt, Germany) according to the manufactures instructions. In general, primers used in PCR were designed such, that at least 20 nucleotides of the 3' end of the primer anneal perfectly with the template to amplify. Restriction sites were added by attaching the corresponding nucleotides of the recognition sites to the 5' end of the primer. Fusion PCR, for example described by K. Heckman and L. R. Pease, Nature Protocols (2207) 2, 924-932 was used as an alternative method to join two fragments of interest, e.g. a promoter to a gene or a gene to a terminator. Gene Synthesis, as for example described by Czar et al. (Trends in Biotechnology, 2009, 27(2): 63-72), was performed by Life Technologies using their Geneart® service. The Geneart® technology, described in WO2013049227 allows production of genetic elements of a few basepair (bp) in length, and was used in this invention to produce entire plasmids of about 60,000 bp. Chemical synthesis of nucleotides to polynucleotides was employed for short DNA fragments, which were then combined in a sequential, modular fashion to fragments of increasing size using a combination of conventional cloning techniques as described in WO2013049227.

B. Different Types of Plant Transformation Plasmids Suitable to Transfer of Multiple Expression Cassettes Encoding Multiple Proteins into the Plant Genome.

For agrobacteria based plant transformation, DNA constructs preferably meet a number of criteria: (1) The construct carries a number of genetic elements that are intended to be inserted into the plant genome on a so called Transfer DNA (T-DNA) between a 'T-DNA Left Border' (LB) and 'T-DNA Right Border' (2) The construct replicates in E. coli, because most cloning steps require DNA multiplication steps in E. coli. (3) The construct replicates in Agrobacterium (e.g. A. tumefaciens or A. rhizogenes), because the plant transformation methods rely on using Agrobacterium to insert the genetic elements of interest into the plant genome of a cell that was infected by Agrobacterium. (4) The construct contains supporting genetic elements that encode proteins which are required for infection of the plant cell, and for transfer and integration of desired genetic elements into the plant genome of an plant cell infected by the Agrobacterium, or the construct was used in combination with a second construct containing such supporting genetic elements that was present in the same Agrobacterium cell. (5) The constructs can contain selection markers to facilitate selection or identification of bacterial cells that contain the entire construct, and of a plant cell(s) that contains the desired genetic elements. An overview of available plasmids was given in Komori et al (2007).

Agrobacteria mediated transformation results in an almost random integration (with some bias induced by a number of factors) of the desired genetic element into chromosomes of the plant cell. The goal of the transformation was to integrate the entire T-DNA from T-DNA Left border to T-DNA Right border into a random position of a random chromosome. It can also be desirable to integrate the entire T-DNA twice or three times into the genome, for example to increase the plant expression levels of genes encoded by the T-DNA. To avoid complex Mendelian segregation of multiple integrations, it was preferred to have all T-DNA insertions at one genomic location, (locus). Inserting more than 25,000 bp T-DNA into plant genomes has been found to be a particular challenge in the current invention. In particular, it has been found in this invention plasmids carrying a ColE1/pVS1 origin of replication for plasmid replication in E. coli and/or Agrobacterium, are not stable above ~25,000 bp. Such plasmids of the invention are described in Example 3. Because of this limitation, not more than ~4 to 5 gene expression cassettes can be transferred on one T-DNA containing plasmid into the plant genome. However, for the current invention up to 13 gene expression cassettes having a combined size of about 44,000 bp needed to be transferred into the plant genome. In contrast to plasmids containing the ColE1/pVS1 origin of replication for high copy plasmid replication in E. coli and/or Agrobacterium, BiBAC plasmids (Hammilton 1997) containing the F factor/pRi origin of replication for single copy plasmid replication in E. coli and/or Agrobacterium where found to be stable in this invention up to a size of ~60,000 bp. Such plasmids of the invention are described in Example 4. Both approaches described above were followed in the current invention.

Figure 3:
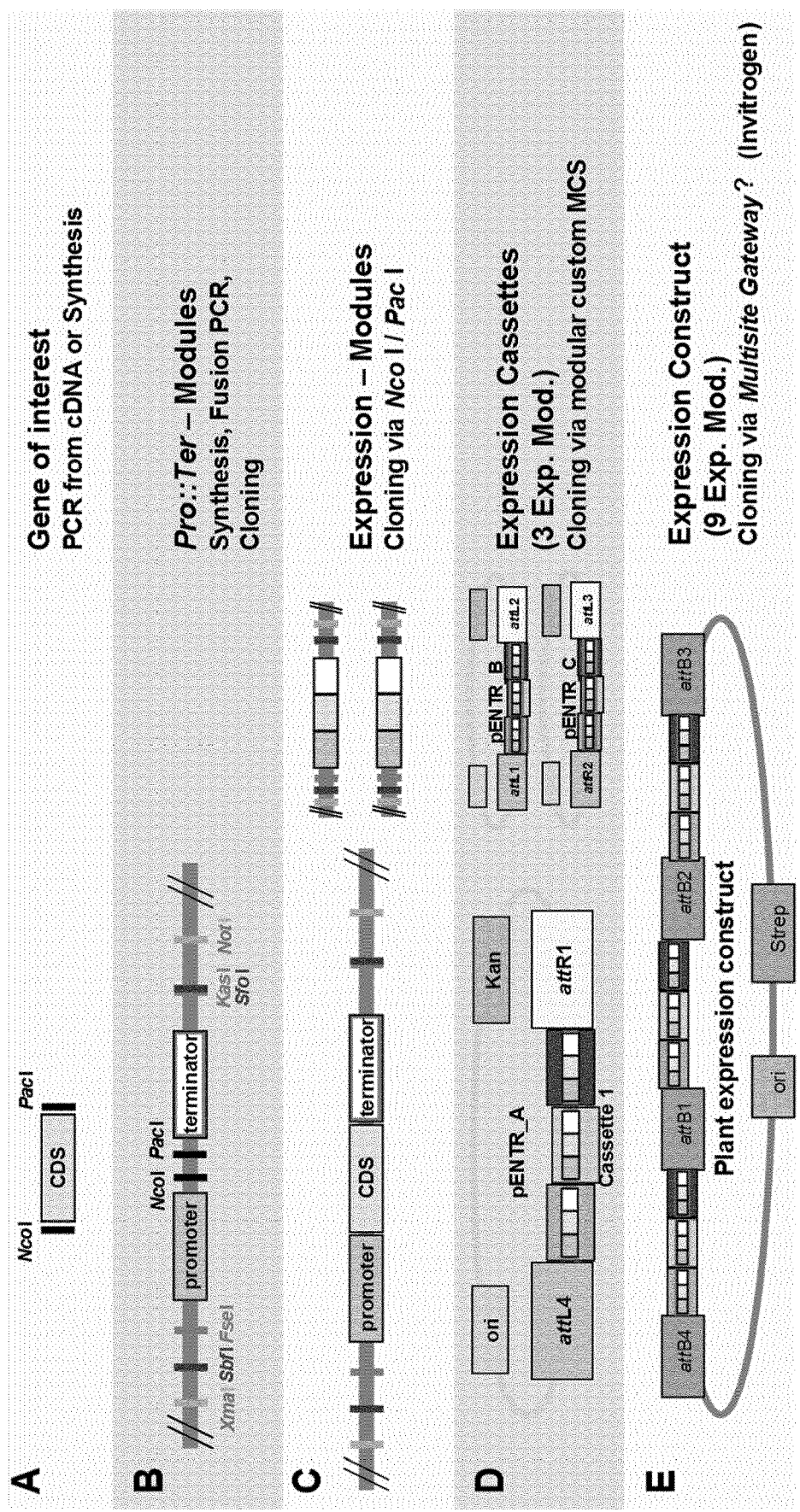
FIG. 3: Strategy employed for stepwise buildup of plant expression plasmids of the invention.
Figure 4:
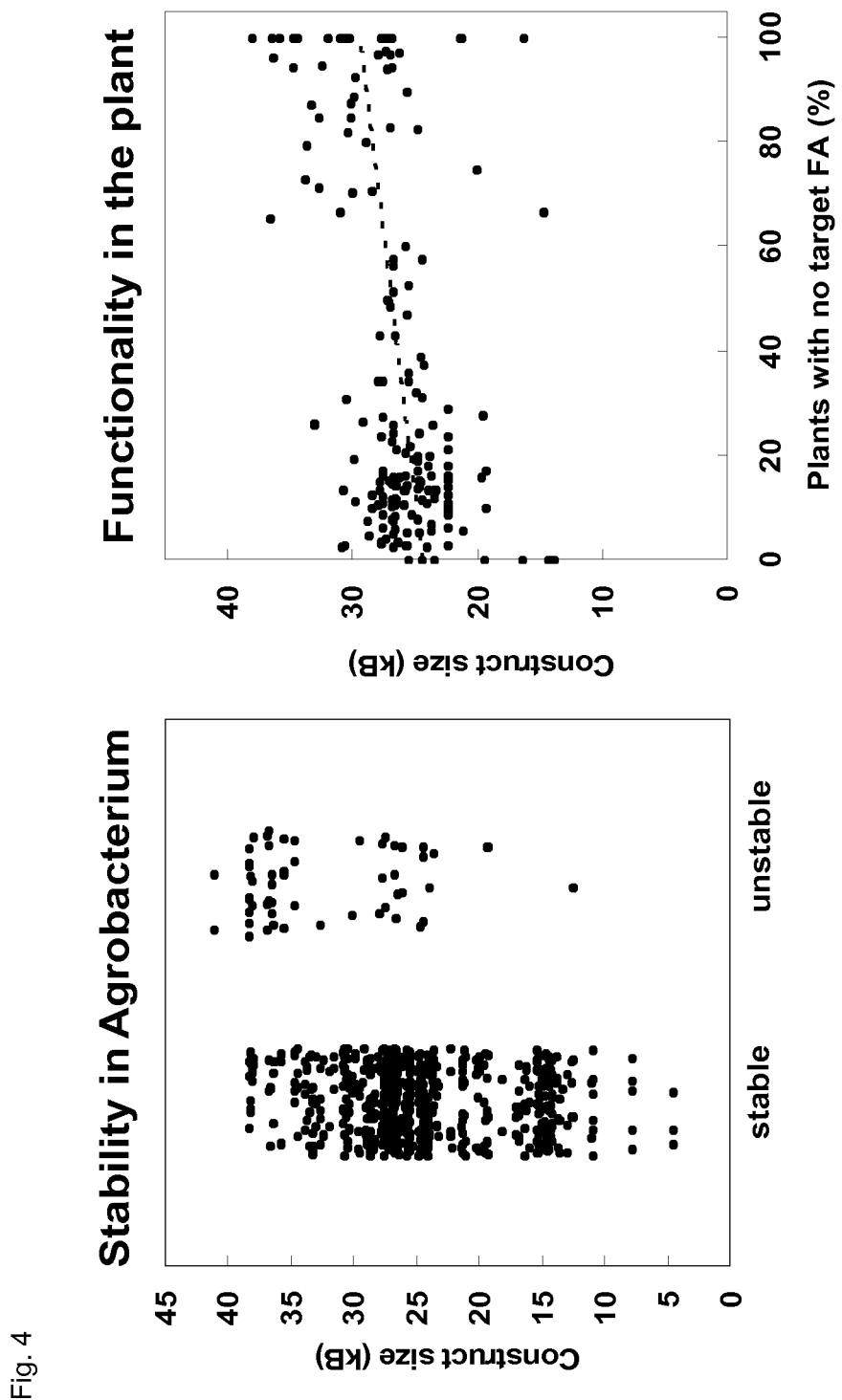
FIG. 4: Stabiliy of binary plant expression plasmids containing the ColE1/pVS1 origin of replication for plasmid replication in *E. coli*/Agrobacteria. Left Panel: Stability in *Agrobacterium* cells by isolating plasmid DNA from *Agrobacterium* cutures prior to usage of this culture for plant transformation, and subjecting the plasmid DNA to a restriction digest. An unexpected restriction pattern indicates disintegration/instability of the plasmid either in *E. coli* or in *Agrobacterium*. Right panel: Under the assumption at least one intact T-DNA from LB to RB was integrated into the plant genome during the transformation process most plants obtained via transformation of a given plasmid are expected to reach the desired trait encoded by the plasmid (here: production of novel fatty acids (FA) in the seeds). The decrease in the percentage of such 'functional' plants indicates instability either in Agrobacteria or during the transfer process into the plant or during the integration process into the genome. As can be seen, the proportion of non functional plants goes sharply up for plasmids above 25,000 bp size when ColE1/pVS1 containing plasmids are used.
Figure 5:
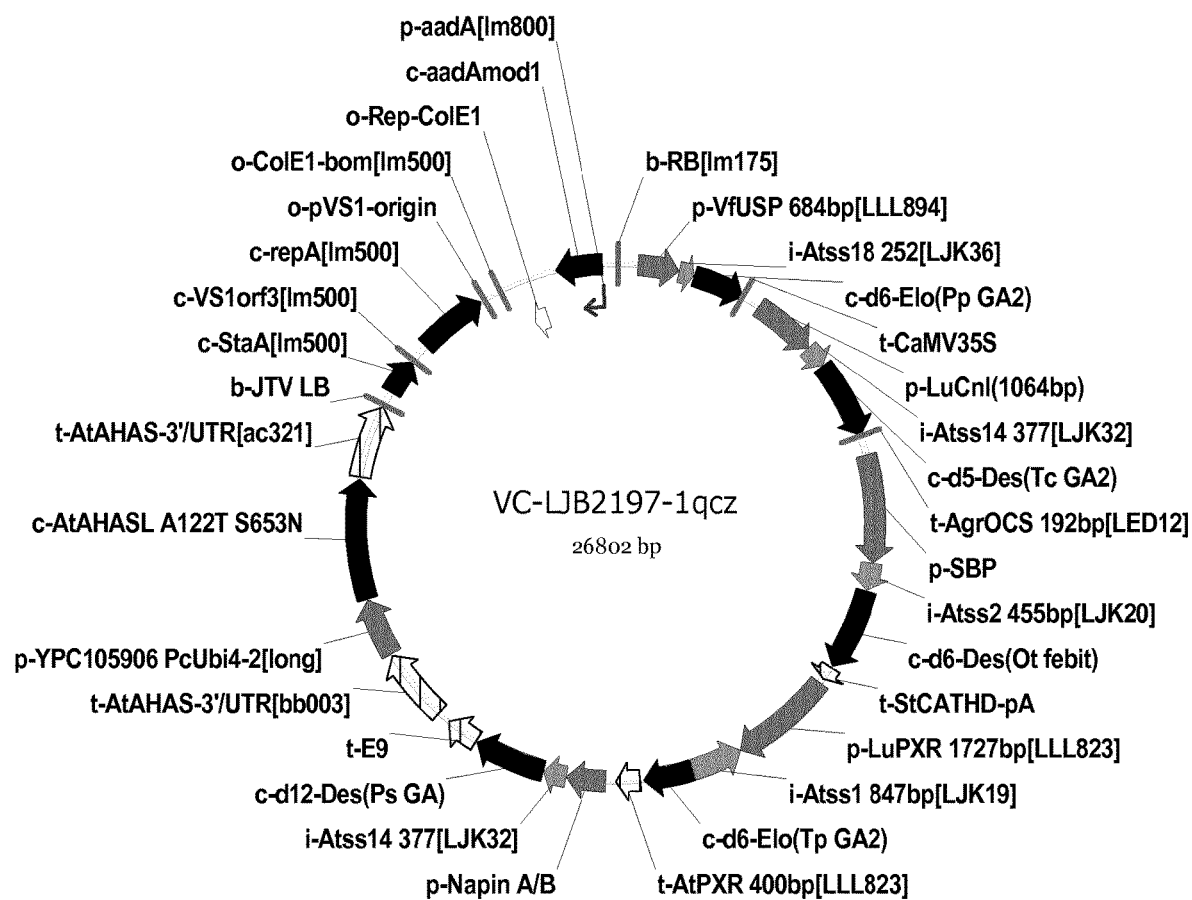
FIG. 5: Plasmid map of VC-LJB2197-1qcz indicating the position of genetic elements listed in table 1.
Figure 6:
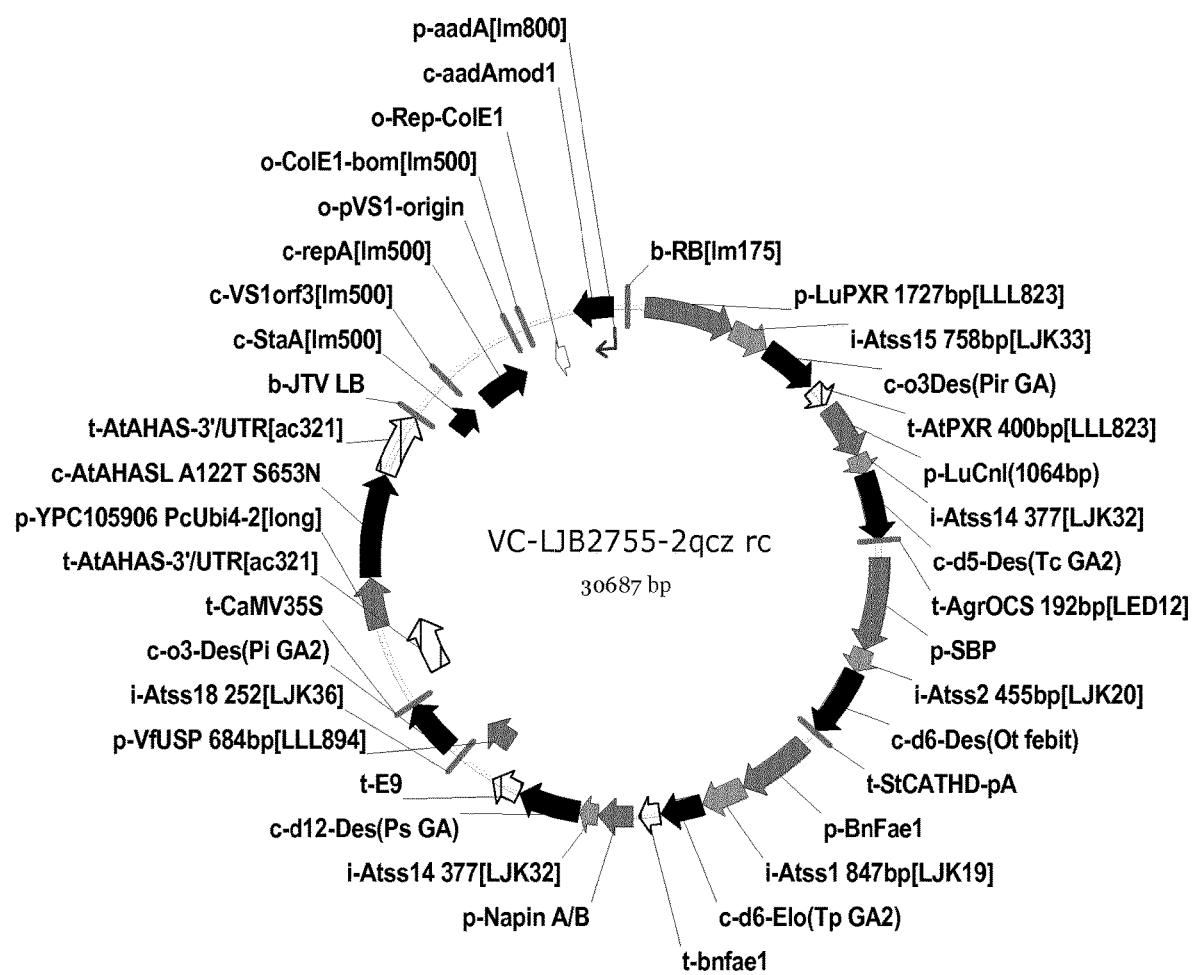
FIG. 6: Plasmid map of VC-LJB2755-2qcz rc indicating the position of genetic elements listed in table 2.
Figure 7:
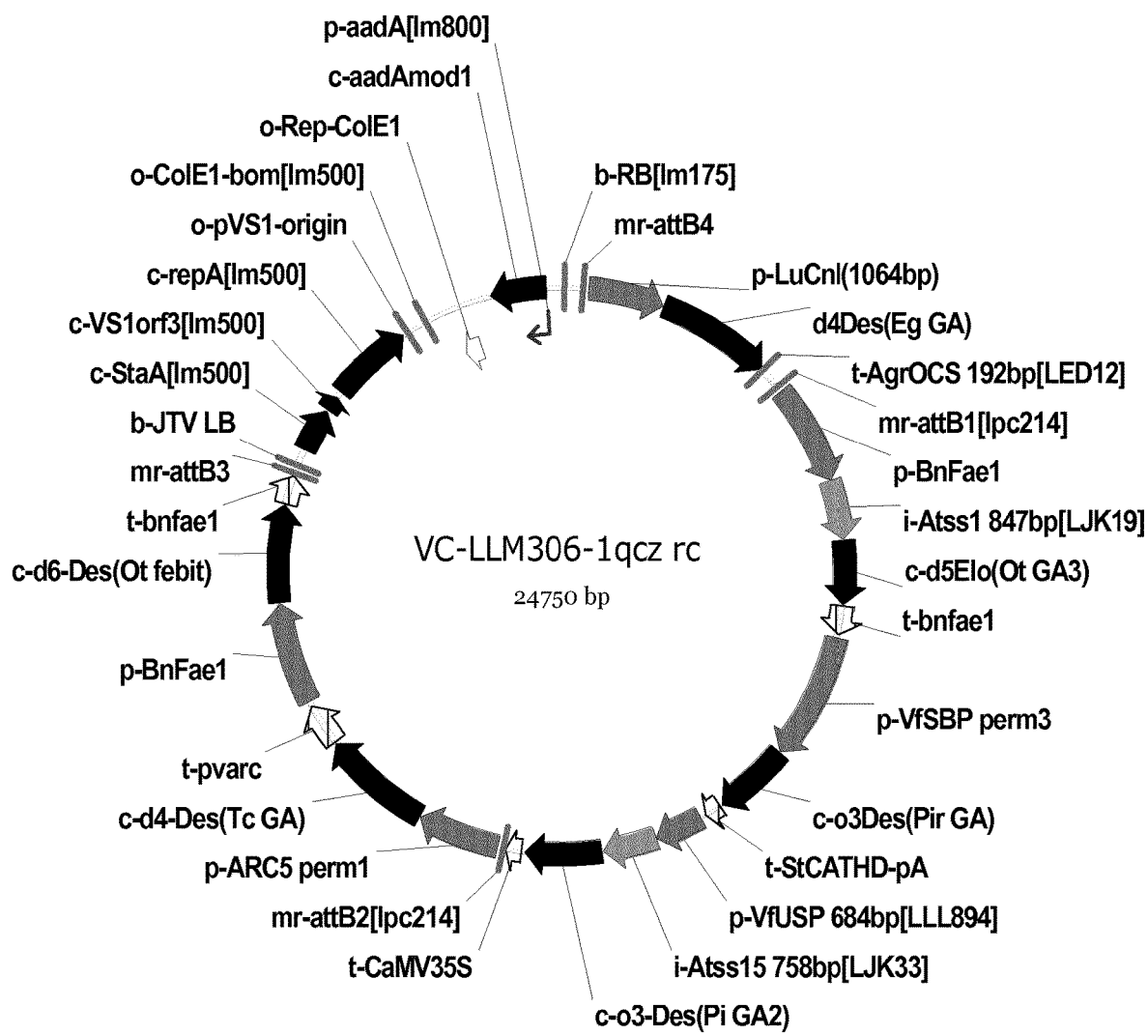
FIG. 7: Plasmid map of VC-LLM306-1qcz rc indicating the position of genetic elements listed in table 3.
Figure 8:
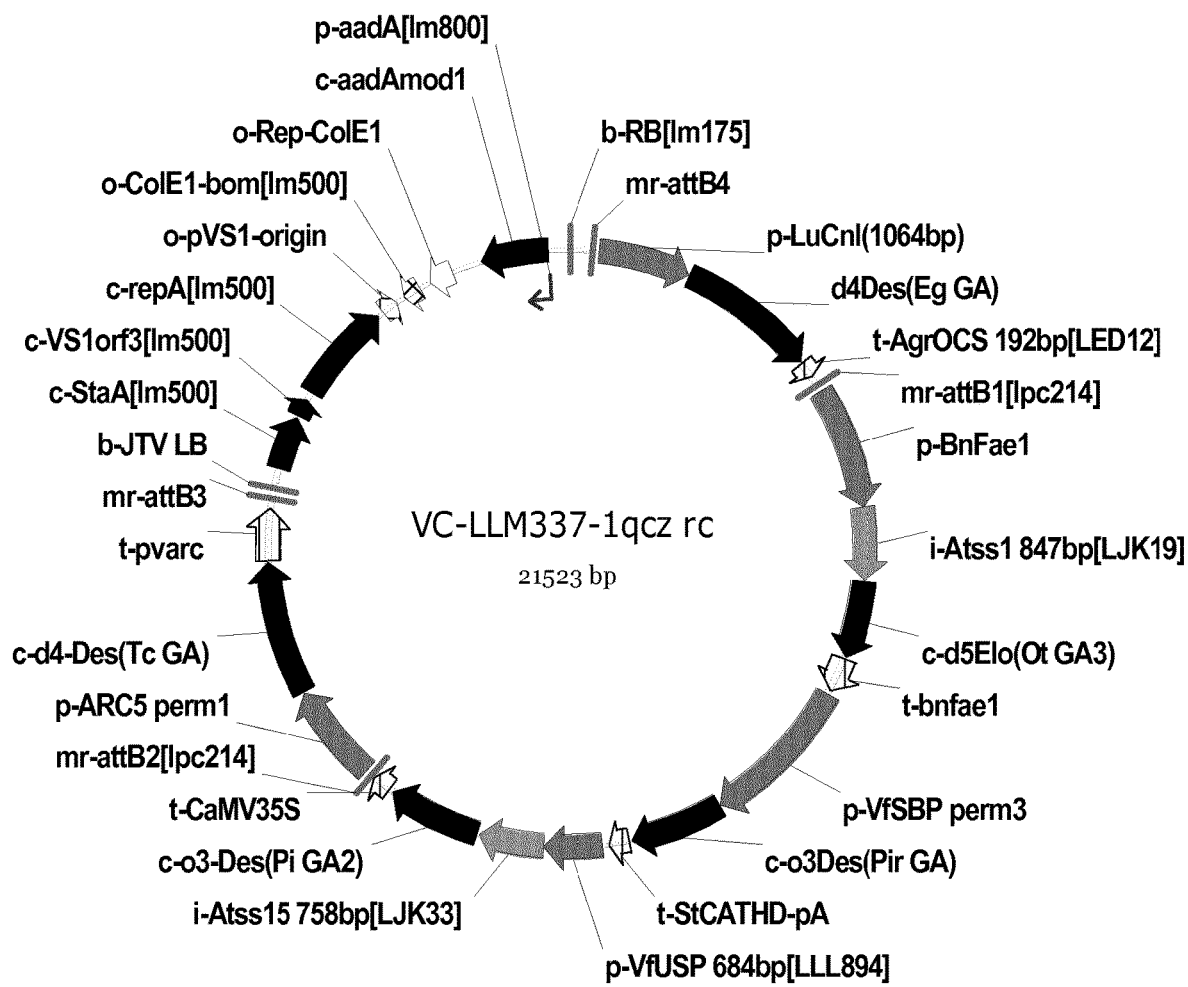
FIG. 8: Plasmid map of VC-LLM337-1qcz rc indicating the position of genetic elements listed in table 4.
Figure 9:
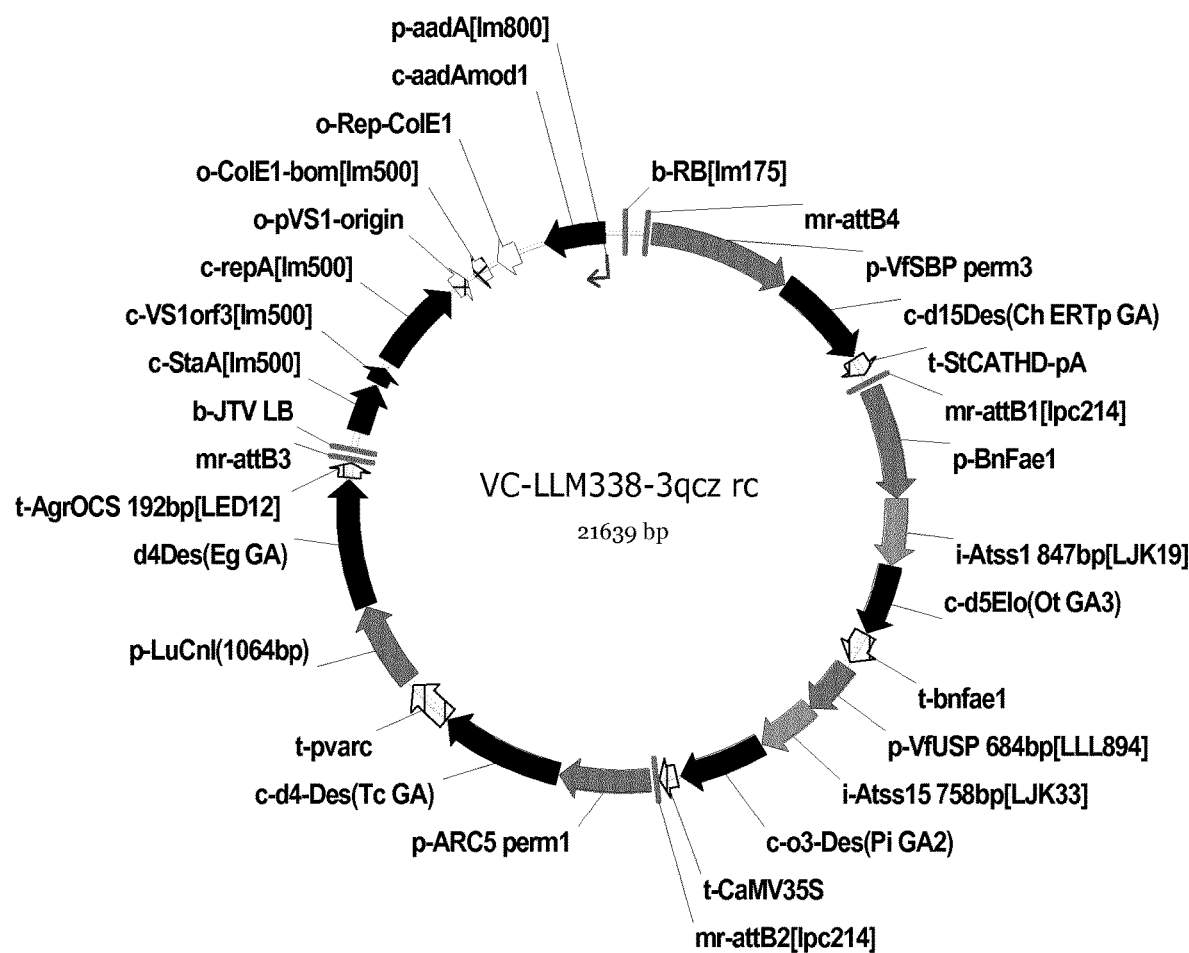
FIG. 9: Plasmid map of VC-LLM338-3qcz rc indicating the position of genetic elements listed in table 5.
Figure 10:
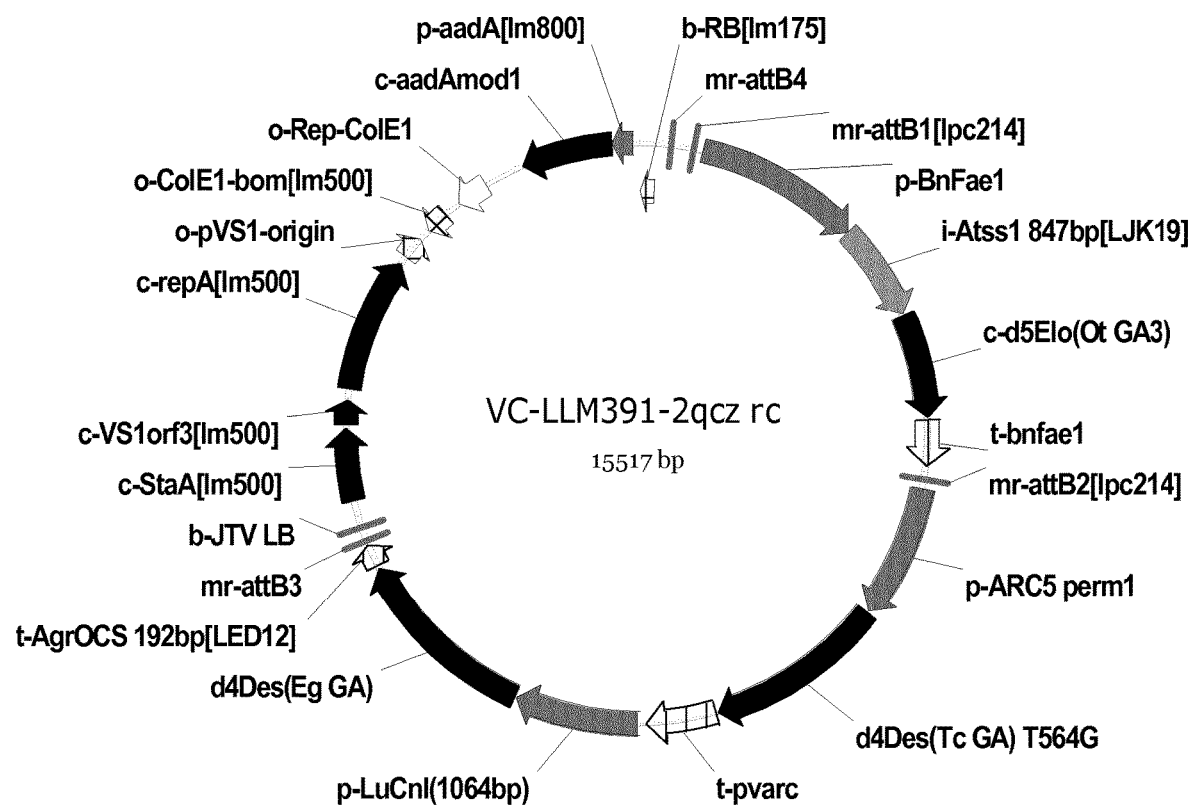
FIG. 10: Plasmid map of VC-LLM391-2qcz rc indicating the position of genetic elements listed in table 6.
Figure 11:
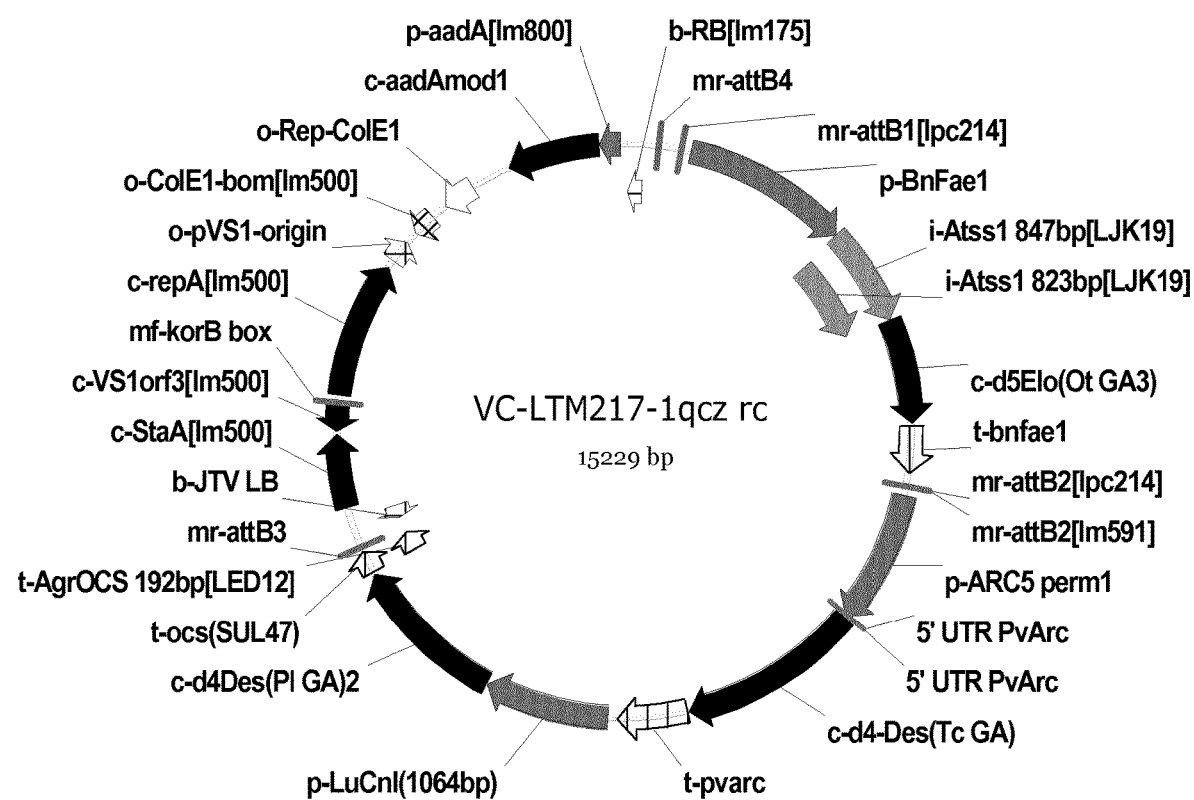
FIG. 11: Plasmid map of VC-LTM217-1qcz rc indicating the position of genetic elements listed in table 7.
Figure 12:
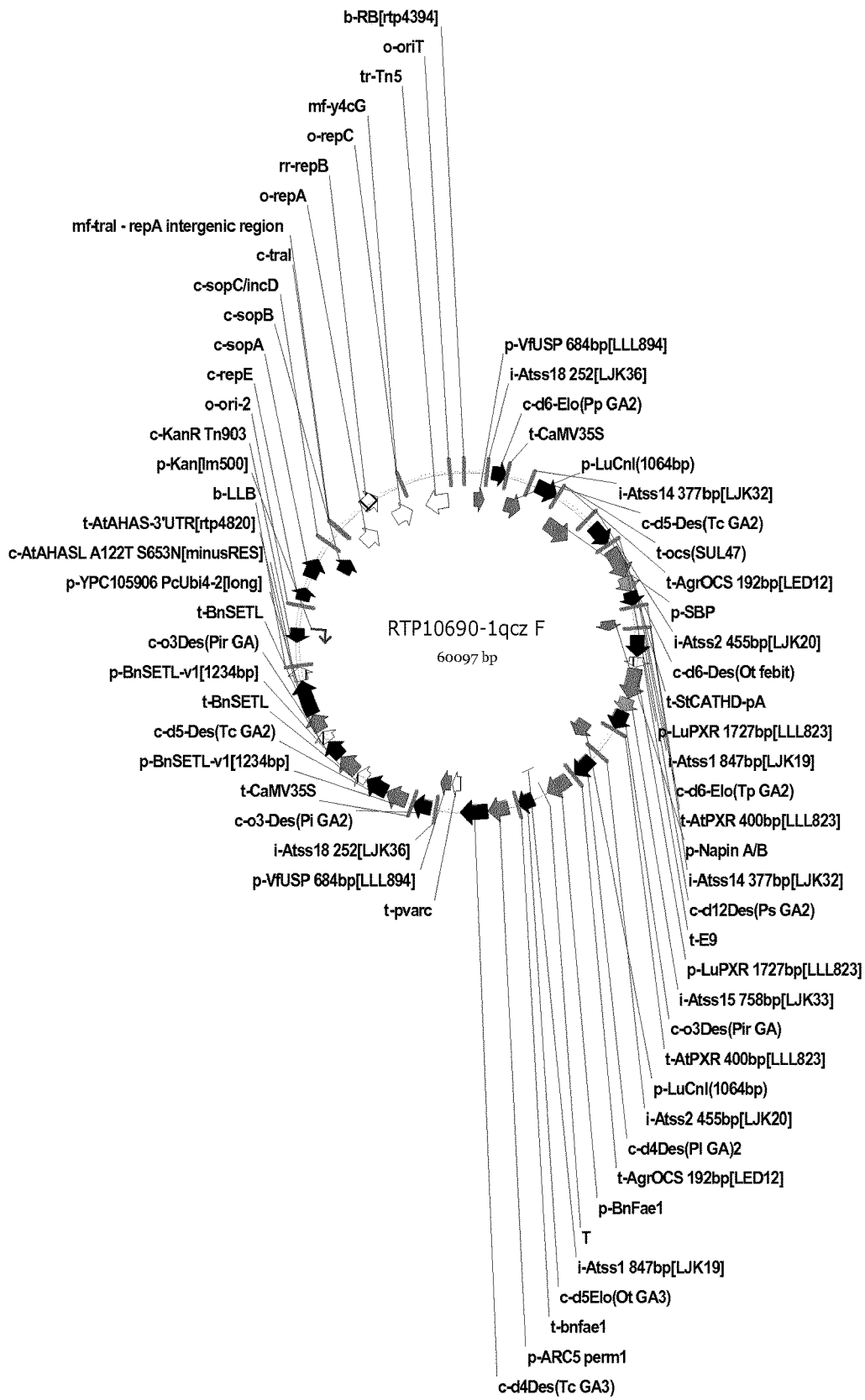
FIG. 12: Plasmid map of RTP10690-1qcz_F indicating the position of genetic elements listed in table 8.
Figure 13:
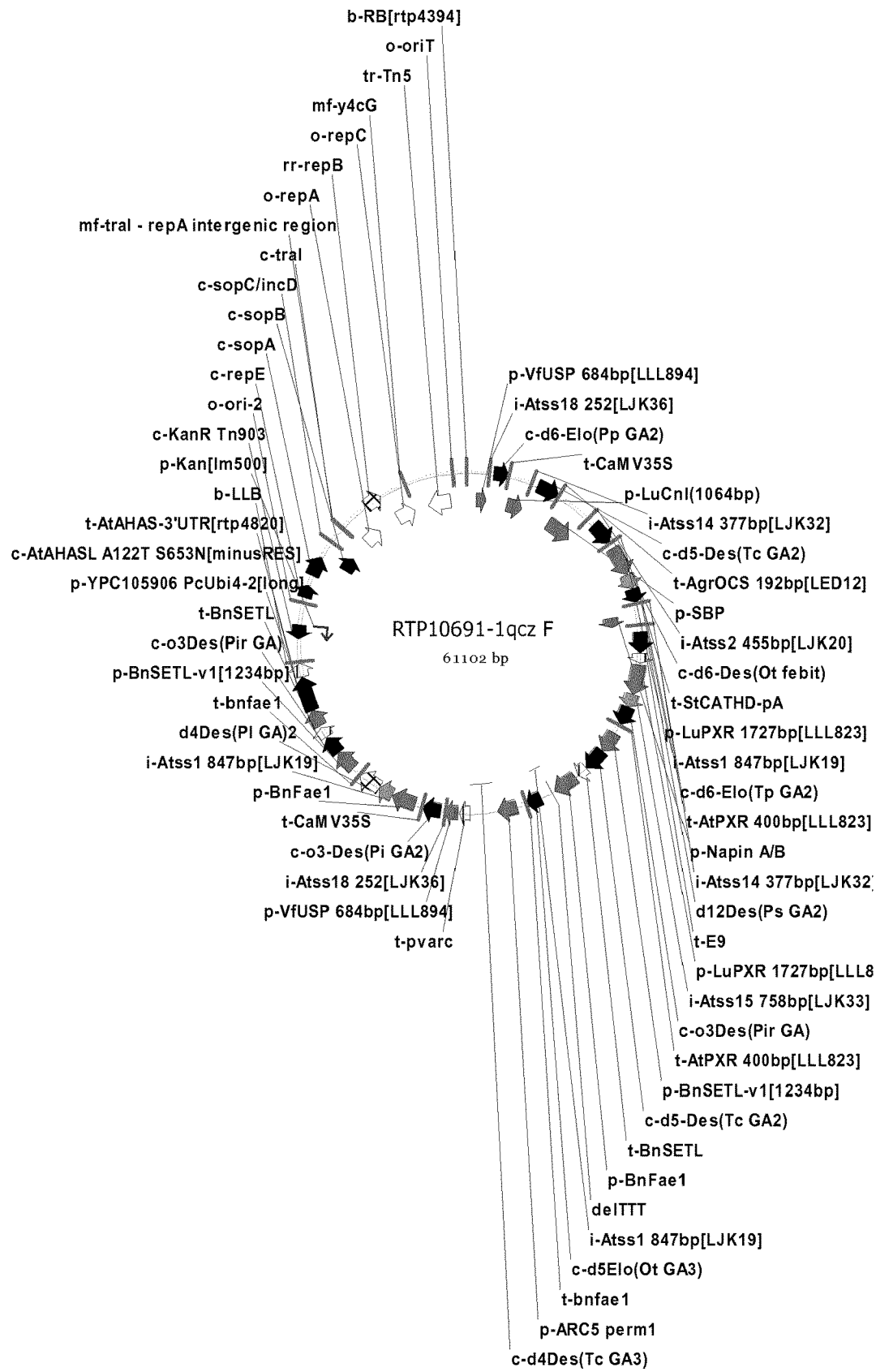
FIG. 13: Plasmid map of RTP10691-2qcz indicating the position of genetic elements listed in table 9.
Figure 14:
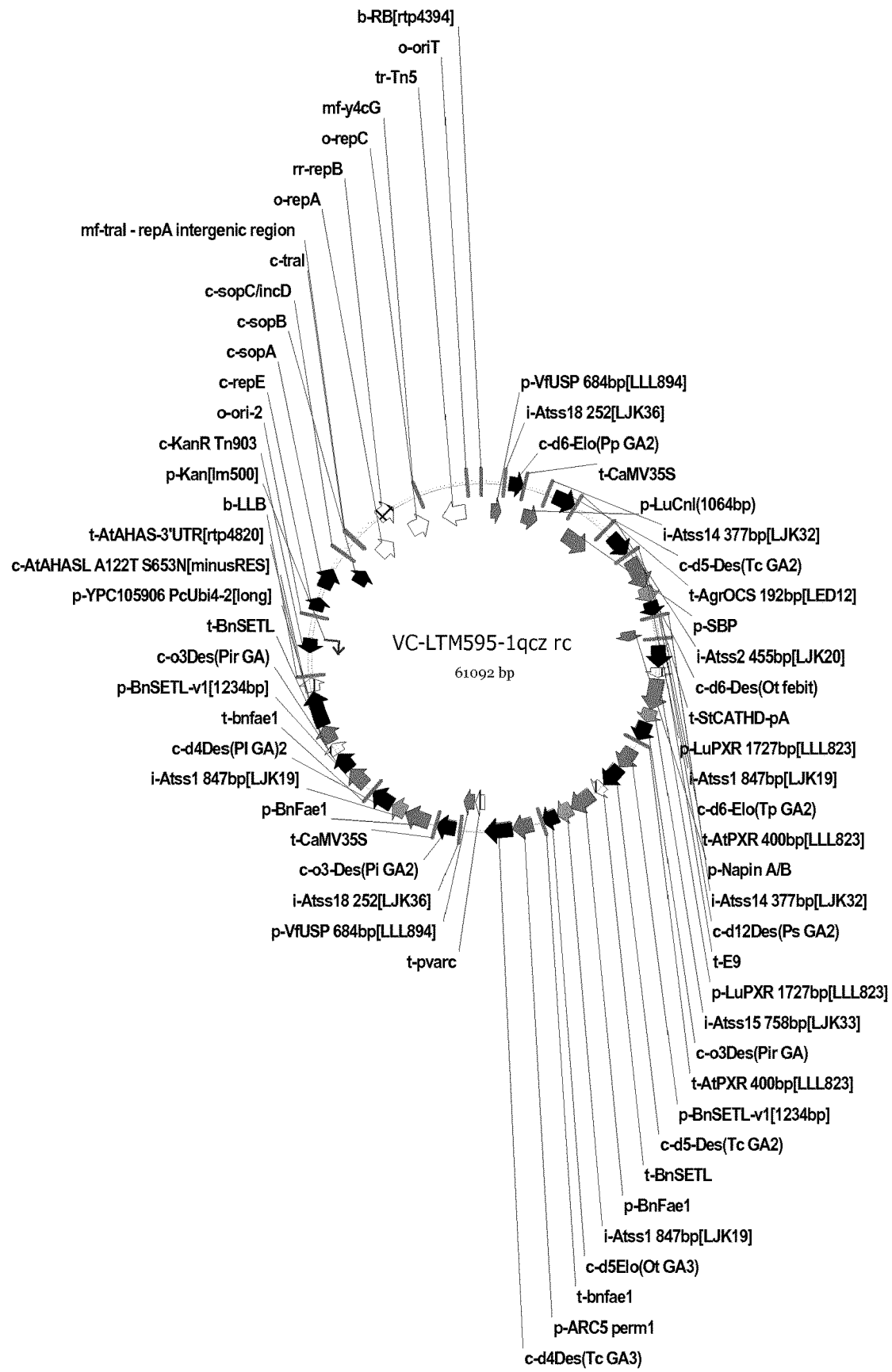
FIG. 14: Plasmid map of LTM595-1qcz rc indicating the position of genetic elements listed in table 10.
Figure 15:
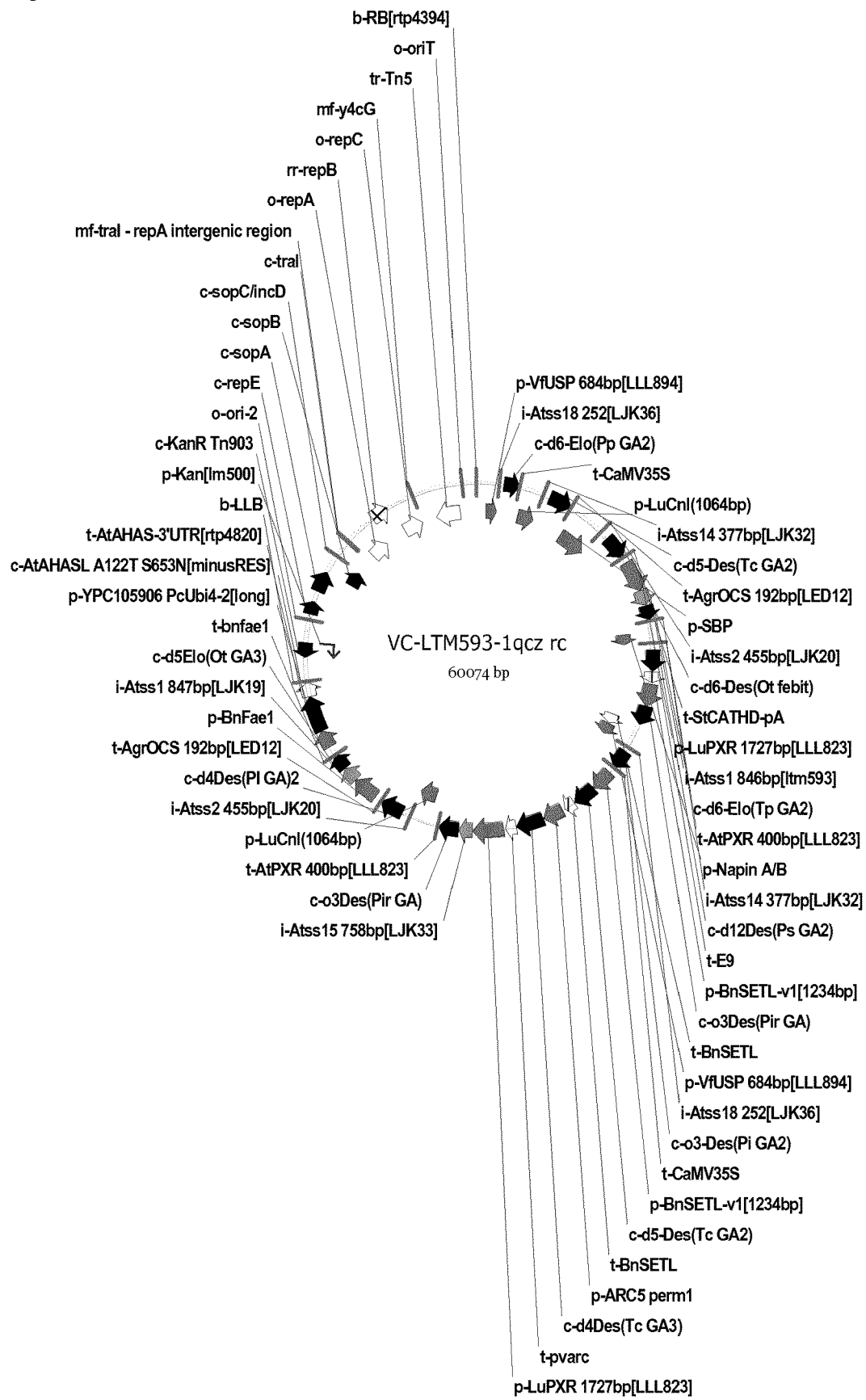
FIG. 15: Plasmid map of LTM593-1qcz rc indicating the position of genetic elements listed in table 11.
Figure 16:
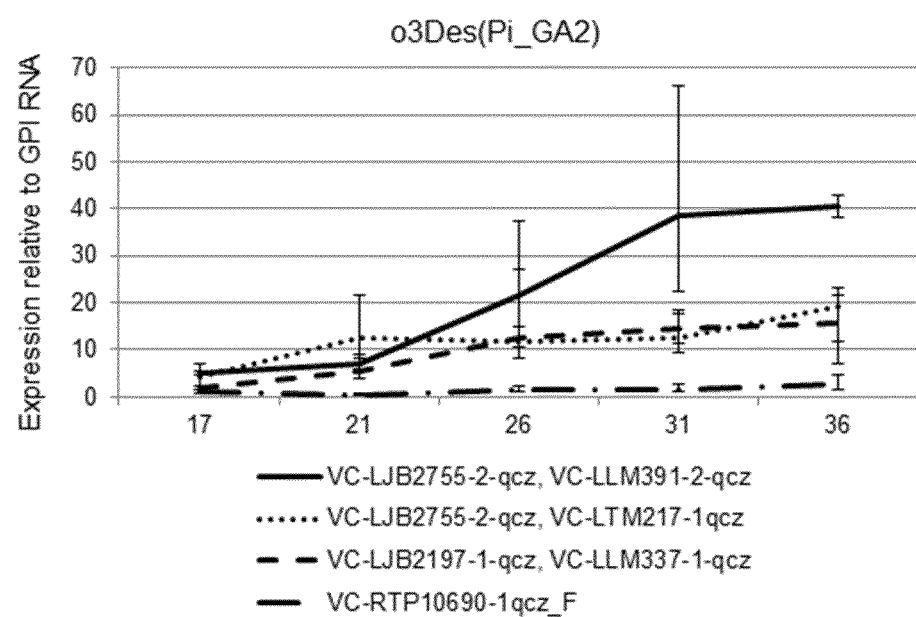
FIG. 16: Comparative transcript analysis o3Des(Pi_GA2) driven by the VfUSP promoter during seed development of single copy event of four different construct combinations.
Figure 17:
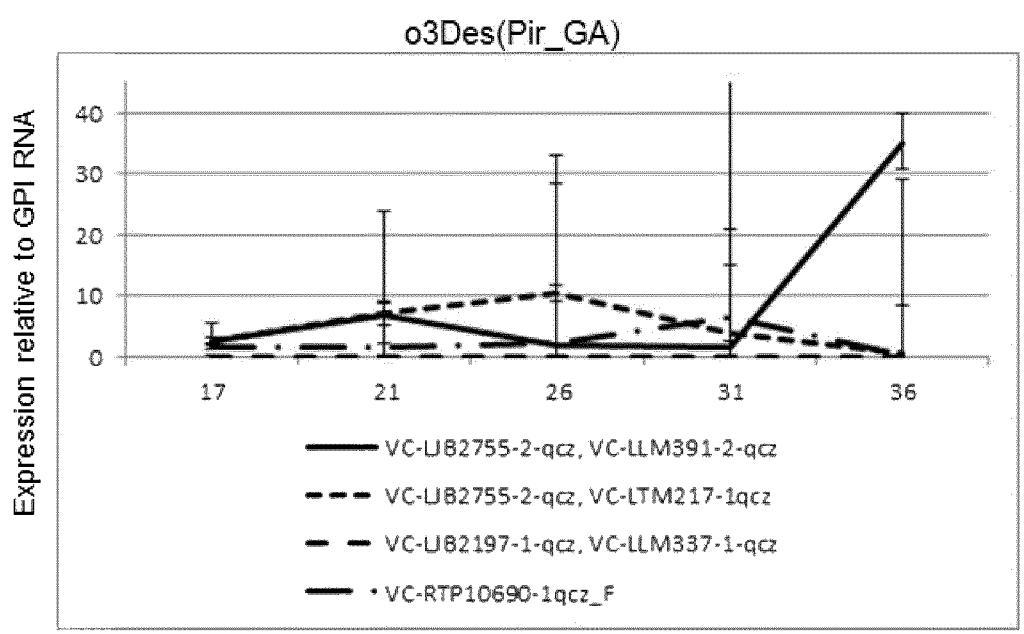
FIG. 17: Comparative transcript analysis of o3Des (Pir_GA) during seed development of single copy event of four different construct combinations. In VC-LJB2755-2qcz and VC-RTP10690-1qcz_F the gene was driven by the LuCnl promoter while in VC-LLM337-1qcz rc the gene was driven by the VfUSP promoter and was expressed at a lower level than the LuCnl o3Des(Pir_GA) combination.
Figure 18:
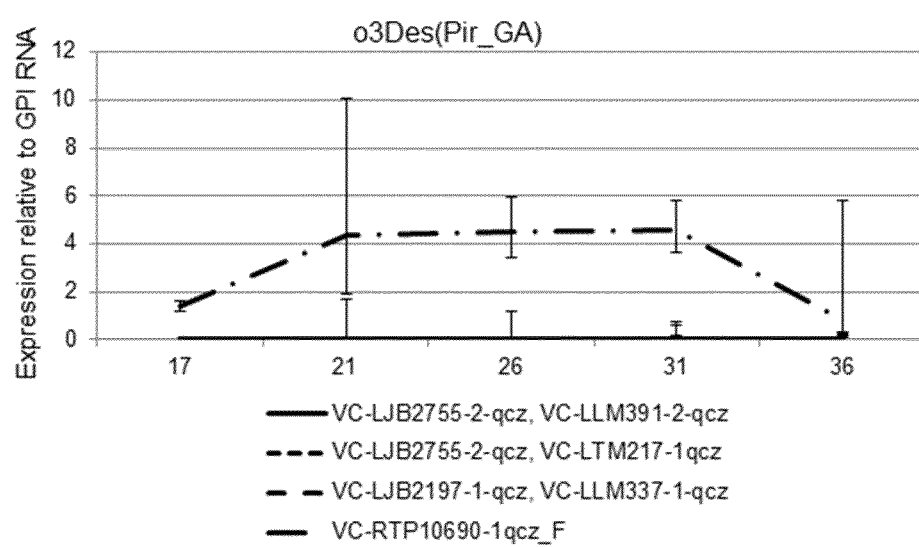
FIG. 18: Comparative transcript analysis of o3Des (Pir_GA) driven by the BnSETL promoter during seed development of single copy event of VC-RTP10690-1qcz_F.
Figure 19:
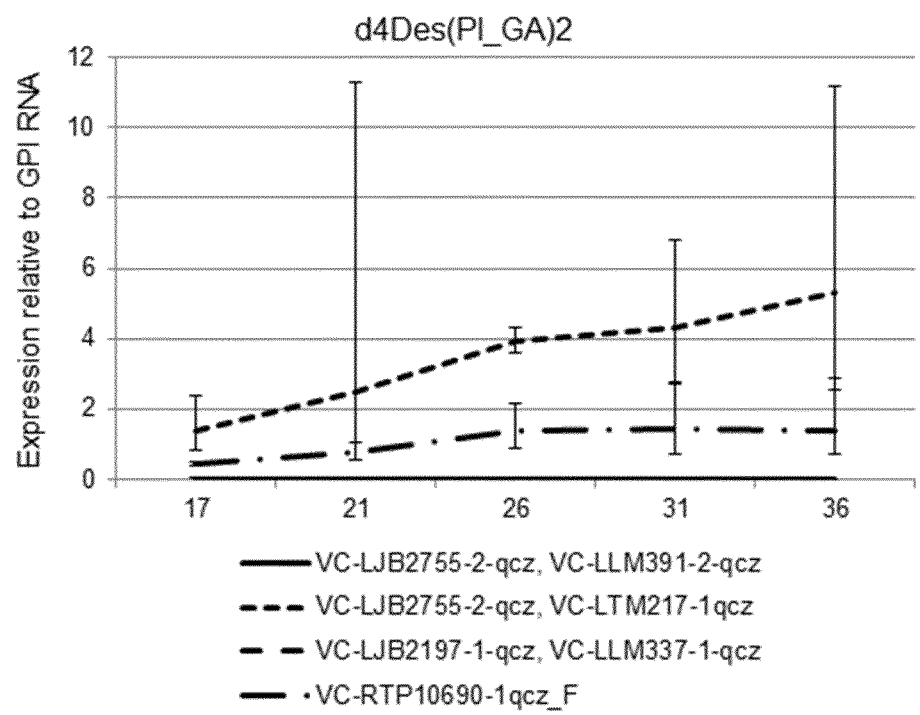
FIG. 19: Comparative transcript analysis of d4Des (PI_GA)2 driven by the LuCnl promoter during seed development of single copy event from VC-RTP10690-1qcz_F and VC-LTM217-1qcz rc, which was present with VC-LJB2755-1qcz. The other constructs lacked this particular d4Des.
Figure 20:
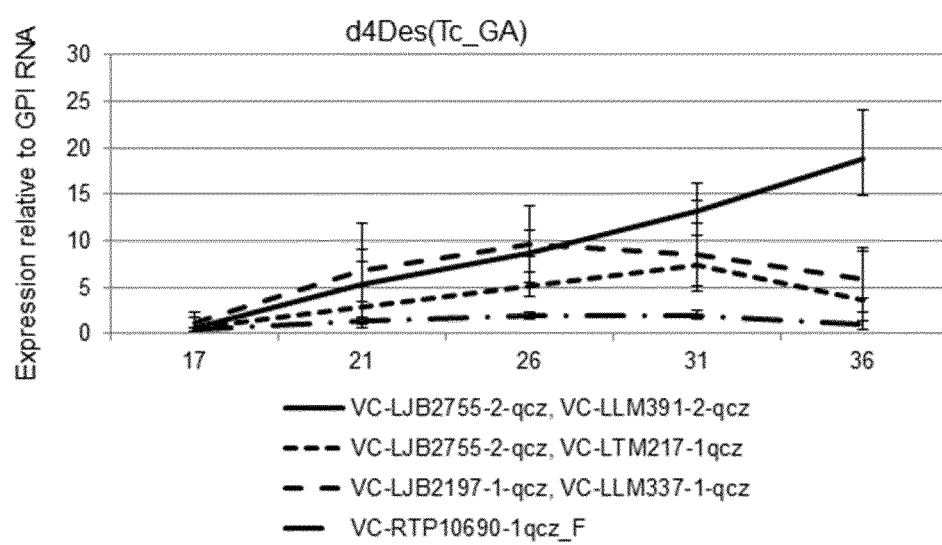
FIG. 20: Comparative transcript analysis of d4Des (Tc_GA) driven by the ARCS promoter during seed development of single copy event of four different construct combinations.
Figure 21:
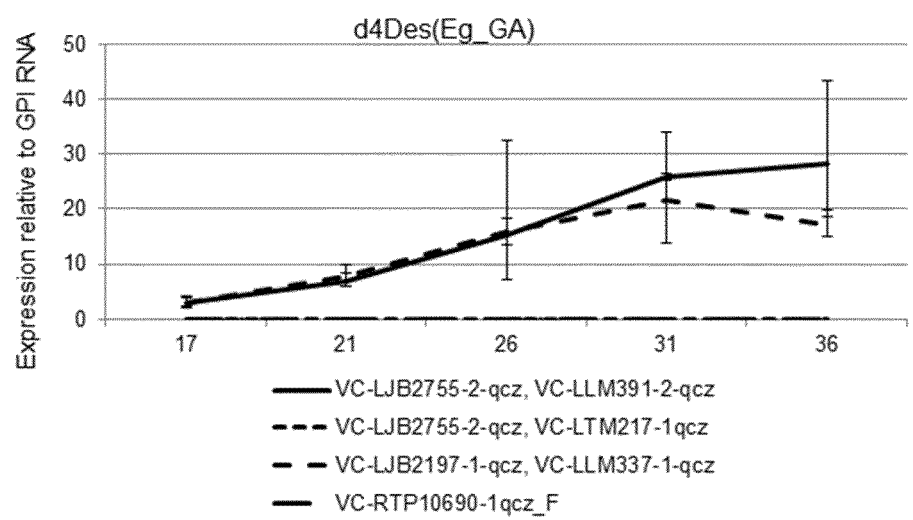
FIG. 21: Comparative transcript analysis of d4Des (Eg_GA) driven by the LuCnl promoter during seed development of single copy event of two different construct combinations; VC-LJB2755-2qcz, VC-LLM391-2qcz rc and VC-LJB2197-1qcz, VC-LLM337-1qcz rc.

C. Assembly of Genes Required for EPA and DHA Synthesis within T-Plasmids Containing the ColE1/pVS1 Origin of Replication For synthesis of VLC-PUFA in Brassica napus seeds, the set of genes encoding the proteins of the metabolic VLC-PUFA pathway were combined with expression elements (promoter, terminators, Introns) and transferred into binary t-plasmids that were used for agrobacteria mediated transformation of plants. Attributed to the large number of expression cassettes promoting expression of one protein each, two binary t-plasmids T-DNA where used for cloning of the complete set of proteins required for EPA and DHA synthesis. To this end, the general cloning strategy depicted in FIG. 3 was employed. While FIG. 3 depicts the general strategy, cloning of the final plant expression vectors described in example 10 to 14 was not restricted to this strategy; specifically a combination of all methods known to one skilled in the art, such as cloning, the use of restriction endonucleases for generation of sticky and blunt ends, synthesis and fusion PCR has been used. Following the modular cloning scheme depicted in FIG. 3, genes were either synthesized by GeneArt (Regensburg) or PCR-amplified using Phusion™ High-Fidelity DNA Polymerase (NEB, Frankfurt, Germany) according to the manufactures instructions from cDNA. In both cases an Nco I and/or Asc I restriction site at the 5' terminus, and a Pac I restriction site at the 3' terminus (FIG. 3A) were introduced to enable cloning of these genes between functional elements such as promoters and terminators using these restriction sites (see below in this example). Promoter-terminator modules or promoter-intron-terminator modules were created by complete synthesis by GeneArt (Regensburg) or by joining the corresponding expression elements using fusion PCR as described in example 1 and cloning the PCR-product into the TOPO-vector pCR2.1 (Invitrogen) according to the manufactures instructions (FIG. 3B). While joining terminator sequences to promoter sequences or promoter-intron sequences either via synthesis of whole cassettes or using fusion PCR, recognition sequences for the restriction endonucleases depicted in FIG. 3 were added to either side of the modules, and the recognition sites for the restriction endonucleases Nco I, Asc I and Pac I were introduced between promoter and terminator or between introns and terminator (see FIG. 3B). To obtain the final expression modules, PCR-amplified genes were cloned between promoter and terminator or intron and terminator via Nco I and/or Pac I restriction sites (FIG. 3C). Employing the custom multiple cloning site (MCS) up to three of those expression modules were combined as desired to expression cassettes harbored by either one of pENTR/A, pENTR/B or pENTR/C (FIG. 3D). Finally, the Multi-site Gateway™ System (Invitrogen) was used to combine three expression cassette harbored by pENTR/A, pENTR/B and pENTR/C (FIG. 3E) to obtain the final binary pSUN T-plasmids for plant transformation VC-LJB2197-1qcz, VC-LJB2755-2qcz rc, VC-LLM306-1qcz rc, VC-LLM337-1qcz rc, VC-LLM338-3qcz rc and VC-LLM391-2qcz rc. An overview of binary vectors and their usage was given by Hellens et al, Trends in Plant Science (2000) 5: 446-451.

The structure of the plamsids VC-LJB2197-1qcz, VC-LJB2755-2qcz rc, VC-LLM337-1qcz rc, and VC-LLM391-2qcz rc is given in the Table 1, Table 2, Table 4, and Table 6.

Nomeclature of genetic elements:
j-indicates a junction between two genetic elements
c-coding sequence
t-terminator
p-promotor
i-intron
T-DNA Transferred DNA
RB Right Border of the T-DNA
LB Left Border of the T-DNA

TABLE 1

Genetic Elements of plasmid VC-LJB2197-1qcz. Listed are the names of the elements, the position in VC-LJB2197-1qcz (note: start position was larger than stop position for elements encoded by the complementary strand of VC-LJB2197-1qcz), the function and source of the element. The T-DNA integrated into the plant genome during the transformation process was flanked by a right border (nucleotides 148 to 4 of VC-LJB2197-1qcz) and a left border (nucleotides 22232 to 22105 of VC-LJB2197-1qcz). Elements outside of that region (=vector backbone) are required for cloning and stable maintenance in *E. coli* and/or agrobacteria.

| Genetic Elements of plasmid VC-LJB2197-1qcz | From | To | Description, Function and Source of Element |
|---|---|---|---|
| b-RB[Im175] | 148 | 4 | Right border of T-DNA |
| p-VfUSP__684bp[LLL894] | 329 | 1012 | Promoter from UNKNOWN SEED PROTEIN gene USP (accession: X56240) from *Vicia faba* |
| i-Atss18__252[LJK36] | 1013 | 1264 | i-Atss18__252bp functional intron region; intron with partial 5'UTR, *Arabidopsis thaliana*, Locus At1g01170, +37 to +288 bp (numbering relative to start of transcription) (+72 to +282bp 5'UTR-Intron only) |
| c-d6Elo(Pp__GA2) | 1267 | 2139 | Delta-6 ELONGASE from *Physcomitrella patens* |
| t-CaMV35S | 2140 | 2355 | Terminator CaMV35S from 35S gene from Cauliflower mosaic virus |
| p-LuCnl(1064bp) | 2448 | 3511 | Promoter from CONLININ gene from *Linum usitatissimum* |
| i-Atss14__377[LJK32] | 3512 | 3888 | i-Atss14__377bp functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d5Des(Tc__GA2) | 3892 | 5211 | Delta-5 DESATURASE from *Thraustochytrium* sp. ATCC21685 |
| t-AgrOCS 192bp[LED12] | 5212 | 5403 | Terminator from OCTOPINE SYNTHASE gene OCS from *Agrobacterium tumefaciens* |
| p-SBP | 5539 | 7337 | Promoter from a SUCROSE-BINDING PROTEIN-RELATED gene from *Vicia faba* |
| i-Atss2__455bp[LJK20] | 7338 | 7792 | i-Atss2__455bp functional intron region; intron with partial 5'UTR, *Arabidopsis thaliana*, Locus At1g65090, +77 to +531bp (numbering relative to start of transcription) (+113 to +508bp 5'UTR-Intron only) |
| c-d6Des(Ot__febit) | 7802 | 9172 | Delta-6 DESATURASE from *Ostreococcus tauri* |
| t-StCATHD-pA | 9200 | 9434 | Terminator from CATHEPSIN D INHIBITOR gene [CATHD] from *Solanum tuberosum* [Potato] |
| p-LuPXR 1727bp[LLL823] | 9513 | 11239 | Promoter from PEROXIREDOXIN LIKE PROTEIN gene PXR from *Linum usitatissimum* |
| i-Atss1__847bp[LJK19] | 11240 | 12086 | i-Atss1__847bp functional intron region; intron with partial 5'UTR, *Arabidopsis thaliana*, Locus At1g62290 (aspartyl protease family protein), +1 to +847bp (numbering relative to start of transcription) (+19 to +841bp 5'UTR-Intron only); from QC1153-1/RTP6393. |
| c-d6Elo(Tp__GA2) | 12100 | 12918 | Delta-6 ELONGASE from *Thalassiosira pseudonana* |
| t-AtPXR 400bp[LLL823] | 12974 | 13373 | Terminator from PEROXIREDOXIN LIKE PROTEIN gene PXR (At1g48130) from *Arabidopsis thaliana* |
| p-Napin A/B | 13543 | 14206 | Promoter from napA/B gene (napin, seed storage protein) from *Brassica napus* |
| i-Atss14__377[LJK32] | 14207 | 14583 | i-Atss14__377bp functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d12Des(Ps__GA) | 14590 | 15786 | Delta-12 DESATURASE from *Phythophthora sojae* |
| t-E9 | 15805 | 16362 | Terminator from Small Subunit of RuBisCo rbcS gene (E9) from *Pisum sativum* |
| t-AtAHAS-3'/UTR[bb003] | 16576 | 17790 | Terminator from AtAHASL [csr1-2] of acetohydroxyacid synthase gene from *Arabidopsis* |
| p-PcUbi4-2[long] | 17823 | 18804 | Promoter from UBIQUITIN gene UBI4-2 with internal intron from *Petroselinum crispum* |
| c-AtAHASL__A122T_S653N | 18812 | 20824 | ACETOHYDROXYACID SYNTHASE LARGE-SUBUNIT gene/CDS with S653N(csr1-2) mutation and A122T SDM mutation from *Arabidopsis* |
| t-AtAHAS-3'/UTR[ac321] | 20849 | 22064 | Terminator from AtAHASL [csr1-2] of ACETOHYDROXYACID SYNTHASE gene from *Arabidopsis* |
| b-JTV__LB | 22232 | 22105 | Left border of T-DNA |
| c-StaA[Im500] | 22338 | 22967 | PVS1 partitioning protein |
| c-VS1orf3[Im500] | 23203 | 22988 | VS1orf3 |
| c-repA[Im500] | 23294 | 24469 | pVS1 replication protein [repA] gene/CDS |
| o-pVS1-origin | 24535 | 24729 | broad host-range replication origin of plasmid pVS1 (Genbank: AF133831, Itoh et al. 1984) |

TABLE 1-continued

Genetic Elements of plasmid VC-LJB2197-1qcz. Listed are the names of the elements, the position in VC-LJB2197-1qcz (note: start position was larger than stop position for elements encoded by the complementary strand of VC-LJB2197-1qcz), the function and source of the element. The T-DNA integrated into the plant genome during the transformation process was flanked by a right border (nucleotides 148 to 4 of VC-LJB2197-1qcz) and a left border (nucleotides 22232 to 22105 of VC-LJB2197-1qcz). Elements outside of that region (=vector backbone) are required for cloning and stable maintenance in *E. coli* and/or agrobacteria.

| Genetic Elements of plasmid VC-LJB2197-1qcz | From | To | Description, Function and Source of Element |
| --- | --- | --- | --- |
| o-ColE1-bom[Im500] | 25032 | 24830 | pBR322 bom site, partial, from AF234316 pCambia2301 |
| o-Rep-ColE1 | 25451 | 25171 | pBR322 origin of replication [*ecoli*] from AF234316 pCambia2301 |
| c-aadAmod1 | 26588 | 25797 | Codon Optimized Adenyltransferase [aadA] gene/CDS from SUN100 |
| p-aadA[Im800] | 26767 | 26589 | Adenyltransferase [aadA] Spectinomycin Prokaryotic promoter |

TABLE 2

Genetic Elements of plasmid VC-LJB2755-2qcz rc. Listed are the names of the elements, the position in VC-LJB2755-2qcz rc (note: start position was larger than stop position for elements encoded by the complementary strand of VC-LJB2755-2qcz rc), the function and source of the element. The T-DNA integrated into the plant genome during the transformation process was flanked by a right border (nucleotides 148 to 4 of VC-LJB2755-2qcz rc) and a left border (nucleotides 26117 to 25990 of VC-LJB2755-2qcz rc). Elements outside of that region (=vector backbone) are required for cloning and stable maintenance in *E. coli* and/or agrobacteria.

| Genetic Elements of plasmid VC-LJB2755-2qcz rc | From | To | Description, Function and Source of Element |
| --- | --- | --- | --- |
| b-RB[Im175] | 148 | 4 | Right border of T-DNA |
| p-LuPXR 1727bp[LLL823] | 342 | 2068 | Promoter from PEROXIREDOXIN LIKE PROTEIN gene PXR from *Linum usitatissimum* |
| i-Atss15__758bp[LJK33] | 2069 | 2826 | i-Atss15__758bp functional intron region; intron with partial 5'UTR, *Arabidopsis thaliana*, Locus At2g27040, +93 bp to +850 bp (numbering relative to start of transcription) (+128 to +847 bp 5'UTR-Intron only) |
| c-o3Des(Pir__GA) | 2842 | 3933 | Omega-3 DESATURASE from *Pythium irregulare* |
| t-AtPXR 400bp[LLL823] | 3990 | 4389 | Terminator from PEROXIREDOXIN LIKE PROTEIN gene PXR (At1g48130) from *Arabidopsis thaliana* |
| p-LuCnl(1064bp) | 4468 | 5531 | Promoter from CONLININ gene from *Linum usitatissimum* |
| i-Atss14__377[LJK32] | 5532 | 5908 | i-Atss14__377bp functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d5Des(Tc__GA2) | 5912 | 7231 | Delta-5 DESATURASE from *Thraustochytrium* sp. ATCC21685 |
| t-AgrOCS 192bp[LED12] | 7232 | 7423 | Terminator from OCTOPINE SYNTHASE gene OCS from *Agrobacterium tumefaciens* |
| p-SBP | 7559 | 9357 | Promoter from a SUCROSE BINDING RELATED-PROTEIN gene from *Vicia faba* |
| i-Atss2__455bp[LJK20] | 9358 | 9812 | i-Atss2__455bp functional intron region; intron with partial 5'UTR, *Arabidopsis thaliana*, Locus At1g65090, +77 to +531bp (numbering relative to start of transcription) (+113 to +508bp 5'UTR-Intron only) |
| c-d6Des(Ot__febit) | 9822 | 11192 | Delta-6 DESATURASE from *Ostreococcus tauri* |
| t-StCATHD-pA | 11220 | 11454 | Terminator from CATHEPSIN D INHIBITOR gene [CATHD] from *Solanum tuberosum* [Potato] |
| p-BnFae1 | 11533 | 12962 | Promoter from Beta-KETOACYL-CoA SYNTHASE (FAE1.1) gene from *Brassica napus* |
| i-Atss1__847bp[LJK19] | 12963 | 13809 | i-Atss1__847bp functional intron region; intron with partial 5'UTR, *Arabidopsis thaliana*, Locus At1g62290 (aspartyl protease family protein), +1 to +847bp (numbering relative to start of transcription) (+19 to +841bp 5'UTR-Intron only); from QC1153-1/RTP6393. |
| c-d6Elo(Tp__GA2) | 13812 | 14630 | Delta-6 ELONGASE from *Thalassiosira pseudonana* |
| t-bnFae1 | 14646 | 15045 | Terminator from FATTY ACID ELONGASE (FAE1, At4g34520; gene of *Arabidopsis thaliana* |
| p-Napin A/B | 15166 | 15829 | Promoter from napA/B gene (napin, seed storage protein) from *Brassica napus* |
| i-Atss14__377[LJK32] | 15830 | 16206 | i-Atss14__377bp functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d12Des(Ps__GA) | 16213 | 17409 | Delta-12 DESATURASE from *Phythophthora sojae* |
| t-E9 | 17428 | 17985 | Terminator from Small Subunit of RuBisCo rbcS gene (E9) from *Pisum sativum* |
| p-VfUSP__684bp[LLL894] | 18064 | 18747 | Promoter from UNKNOWN SEED PROTEIN gene USP (accession: X56240) from *Vicia faba* |
| i-Atss18__252[LJK36] | 18748 | 18999 | i-Atss18__252bp functional intron region; intron with partial 5'UTR, *Arabidopsis thaliana*, Locus At1g01170, +37 to +288 bp (numbering relative to start of transcription) (+72 to +282bp 5'UTR-Intron only) |
| c-o3Des(Pi__GA2) | 19010 | 20095 | Omega-3-DESATURASE from *Phythophthora infestans* |
| t-CaMV35S | 20104 | 20319 | Terminator CaMV35S from 35S gene from Cauliflower mosaic virus |
| t-AtAHAS-3'/UTR[ac321] | 20460 | 21675 | Terminator from AtAHASL [csr1-2] of ACETYOHYDROXYACID SYNTHASE gene from *Arabidopsis* |

TABLE 2-continued

Genetic Elements of plasmid VC-LJB2755-2qcz rc. Listed are the names of the elements, the position in VC-LJB2755-2qcz rc (note: start position was larger than stop position for elements encoded by the complementary strand of VC-LJB2755-2qcz rc), the function and source of the element. The T-DNA integrated into the plant genome during the transformation process was flanked by a right border (nucleotides 148 to 4 of VC-LJB2755-2qcz rc) and a left border (nucleotides 26117 to 25990 of VC-LJB2755-2qcz rc). Elements outside of that region (=vector backbone) are required for cloning and stable maintenance in *E. coli* and/or agrobacteria.

| Genetic Elements of plasmid VC-LJB2755-2qcz rc | From | To | Description, Function and Source of Element |
|---|---|---|---|
| p-PcUbi4-2[long] | 21708 | 22689 | Promoter from UBIQUITIN gene UBI4-2 with internal intron from *Petroselinum crispum* |
| c-AtAHASL__A122T__S653N | 22697 | 24709 | ACETOHYDROXYACID SYNTHASE LARGE-SUBUNIT gene/CDS with S653N(csr1-2) mutation and A122T SDM mutation from *Arabidopsis* |
| t-AtAHAS-3'/UTR[ac321] | 24734 | 25949 | Terminator from AtAHASL [csr1-2] of ACETOHYDROXYACID SYNTHASE gene from *Arabidopsis* |
| b-JTV_LB | 26117 | 25990 | Left border of T-DNA |
| c-StaA[lm500] | 26223 | 26852 | PVS1 partitioning protein |
| c-VS1orf3[lm500] | 27088 | 26873 | VS1orf3 |
| c-repA[lm500] | 27179 | 28354 | pVS1 replication protein [repA] gene/CDS |
| o-pVS1-origin | 28420 | 28614 | broad host-range replication origin of plasmid pVS1 (Genbank: AF133831, Itoh et al. 1984) |
| o-ColE1-bom[lm500] | 28917 | 28715 | pBR322 bom site, partial, from AF234316 pCambia2301 |
| o-Rep-ColE1 | 29336 | 29056 | pBR322 origin of replication [*E. coli*] from AF234316 pCambia2301 |
| c-aadAmod1 | 30473 | 29682 | Codon Optimized Adenyltransferase [aadA] gene/CDS from SUN100 |
| p-aadA[lm800] | 30652 | 30474 | Adenyltransferase [aadA] Spectinomycin Prokaryotic promoter |

TABLE 4

Genetic Elements of plasmid VC-LLM337-1qcz rc. Listed are the names of the elements, the position in VC-LLM337-1qcz rc (nucleotide number, note: start position was larger than stop position for elements encoded by the complementary strand of VC-LLM337-1qcz rc), the function and source of the element. The T-DNA integrated into the plant genome during the transformation process was flanked by a right border (nucleotides 148 to 4 of VC-LLM337-1qcz rc) and a left border (nucleotides 16953 to 16826 of VC-LLM337-1qcz rc. Elements outside of that region (=vector backbone) are required for cloning and stable maintenance in *E. coli* and/or agrobacteria.

| Genetic Elements of plasmid VC-LLM337-1qcz rc | From | To | Description, Function and Source of Element |
|---|---|---|---|
| b-RB[Im175] | 148 | 4 | Right border of T-DNA |
| p-LuCnl(1064bp) | 342 | 1405 | Promoter from CONLININ gene from *Linum usitatissimum* |
| c-d4Des(Eg_GA) | 1416 | 3041 | Delta-4 DESATURASE from *Euglena gracilis* |
| t-AgrOCS 192bp[LED12] | 3063 | 3254 | Terminator from OCTOPINE SYNTHASE gene OCS from *Agrobacterium tumefaciens* |
| p-BnFae1 | 3448 | 4877 | Promoter from Beta-KETOACYL-CoA SYNTHASE (FAE1.1) gene from *Brassica napus* |
| i-Atss1__847bp[LJK19] | 4878 | 5724 | i-Atss1__847bp functional intron region; intron with partial 5'UTR, *Arabidopsis thaliana*, Locus At1g62290 (aspartyl protease family protein), +1 to +847bp (numbering relative to start of transcription) (+19 to +841bp 5'UTR-Intron only); from QC1153-1/RTP6393. |
| c-d5Elo(Ot_GA3) | 5732 | 6634 | Delta-5 ELONGASE from *Ostreococcus tauri* |
| t-bnFae1 | 6651 | 7050 | Terminator from FATTY ACID ELONGASE (FAE1, At4g34520) gene of *Arabidopsis thaliana* |
| p-VfSBP__perm3 | 7099 | 8897 | Promoter derived from a promoter from a SUCROSE-BINDING PROTEIN-RELATED gene from *Vicia faba* |
| c-o3Des(Pir_GA) | 8901 | 9992 | Omega-3 DESATURASE from *Pythium irregulare* |
| t-StCATHD-pA | 10023 | 10257 | Terminator from CATHEPSIN D INHIBITOR gene [CATHD] from *Solanum tuberosum* [Potato] |
| p-VfUSP__684bp[LLL894] | 10331 | 11014 | Promoter from UNKNOWN SEED PROTEIN gene USP (accession: X56240) from *Vicia faba* |
| i-Atss15__758bp[LJK33] | 11015 | 11772 | i-Atss15__758bp functional intron region; intron with partial 5'UTR, *Arabidopsis thaliana*, Locus At2g27040, +93 bp to +850 bp (numbering relative to start of transcription) (+128 to +847 bp 5'UTR-Intron only) |
| c-o3Des(Pi_GA2) | 11789 | 12874 | Omega-3-DESATURASE from *Phythophthora infestans* |
| t-CaMV35S | 12924 | 13139 | Terminator CaMV35S from 35S gene from Cauliflower mosaic virus |
| p-ARC5__perm1 | 13259 | 14409 | Promoter derived from a promoter from ARCILINE 5 gene from *Phaseolus vulgaris* |
| c-d4Des(Tc_GA) | 14420 | 15979 | Delta-4 DESATURASE from *Thraustochytrium* sp. |
| t-pvarc | 15993 | 16592 | Terminator of ARC5 gene from *Phaseolus vulgaris* |
| b-JTV_LB | 16953 | 16826 | Left border of T-DNA |
| c-StaA[Im500] | 17059 | 17688 | PVS1 partitioning protein |
| c-VS1orf3[Im500] | 17924 | 17709 | VS1orf3 |
| c-repA[Im500] | 18015 | 19190 | pVS1 replication protein [repA] gene/CDS |
| o-pVS1-origin | 19256 | 19450 | broad host-range replication origin of plasmid pVS1 (Genbank: AF133831, Itoh et al. 1984) |

TABLE 4-continued

Genetic Elements of plasmid VC-LLM337-1qcz rc. Listed are the names of the elements, the position in VC-LLM337-1qcz rc (nucleotide number, note: start position was larger than stop position for elements encoded by the complementary strand of VC-LLM337-1qcz rc), the function and source of the element. The T-DNA integrated into the plant genome during the transformation process was flanked by a right border (nucleotides 148 to 4 of VC-LLM337-1qcz rc) and a left border (nucleotides 16953 to 16826 of VC-LLM337-1qcz rc). Elements outside of that region (=vector backbone) are required for cloning and stable maintenance in E. coli and/or agrobacteria.

| Genetic Elements of plasmid VC-LLM337-1qcz rc | From | To | Description, Function and Source of Element |
|---|---|---|---|
| o-ColE1-bom[Im500] | 19753 | 19551 | pBR322 bom site, partial, from AF234316 pCambia2301 |
| o-Rep-ColE1 | 20172 | 19892 | pBR322 origin of replication [E. coli] from AF234316 pCambia2301 |
| c-aadAmod1 | 21309 | 20518 | Codon Optimized Adenyltransferase [aadA] gene/CDS from SUN100 |
| p-aadA[Im800] | 21488 | 21310 | Adenyltransferase [aadA] Spectinomycin Prokaryotic promoter |

TABLE 6

Genetic Elements of plasmid VC-LLM391-2qcz rc rc. Listed are the names of the elements, the position in VC-LLM391-2qcz rc rc (nucleotide number, note: start position was larger than stop position for elements encoded by the complementary strand of VC-LLM391-2qcz rc rc), the function and source of the element. The T-DNA integrated into the plant genome during the transformation process was flanked by a right border (nucleotides 148 to 4 of VC-LLM391-2qcz rc rc) and a left border (nucleotides 10947 to 10820 of VC-LLM391-2qcz rc rc). Elements outside of that region (=vector backbone) are required for cloning and stable maintenance in E. coli and/or agrobacteria.

| Genetic Elements of plasmid VC-LLM391-2qcz rc | From | To | Description, Function and Source of Element |
|---|---|---|---|
| b-RB[Im175] | 148 | 4 | Right border of T-DNA |
| p-BnFae1 | 540 | 1969 | Promoter from Beta-KETOACYL-CoA SYNTHASE (FAE1.1) gene from Brassica napus |
| i-Atss1_847bp[LJK19] | 1970 | 2816 | i-Atss1_847bp functional intron region; intron with partial 5'UTR, Arabidopsis thaliana, Locus At1g62290 (aspartyl protease family protein), +1 to +847bp (numbering relative to start of transcription) (+19 to +841bp 5'UTR-Intron only); from QC1153-1/RTP6393. |
| c-d5Elo(Ot_GA3) | 2824 | 3726 | Delta-5 ELONGASE from Ostreococcus tauri |
| t-bnFae1 | 3743 | 4142 | Terminator from FATTY ACID ELONGASE (FAE1, At4g34520) gene of Arabidopsis thaliana |
| p-ARC5perm1 | 4335 | 5485 | Promoter derived from a promoter from ARCILINE 5 gene from Phaseolus vulgaris |
| c-d4Des(Tc_GA)_T564G | 5496 | 7055 | Delta-4 DESATURASE from Thraustochytrium spp. |
| t-pvarc | 7069 | 7668 | Terminator of Arc5 gene from Phaseolus vulgaris |
| p-LuCnl(1064bp) | 7747 | 8810 | Promoter from CONLININ gene from Linum usitatissimum |
| c-d4Des(Eg_GA) | 8821 | 10446 | Delta-4 DESATURASE from Euglena gracilis |
| t-AgrOCS 192bp[LED12] | 10468 | 10659 | Terminator from OCTOPINE SYNTHASE gene OCS from Agrobacterium tumefaciens |
| b-JTV_LB | 10947 | 10820 | Left border of T-DNA |
| c-StaA[Im500] | 11053 | 11682 | PVS1 partitioning protein |
| c-VS1orf3[Im500] | 11918 | 11703 | VS1orf3 |
| c-repA[Im500] | 12009 | 13184 | pVS1 replication protein [repA] gene/CDS |
| o-pVS1-origin | 13250 | 13444 | broad host-range replication origin of plasmid pVS1 (Genbank: AF133831, Itoh et al. 1984) |
| o-ColE1-bom[Im500] | 13747 | 13545 | pBR322 bom site, partial, from AF234316 pCambia2301 |
| o-Rep-ColE1 | 14166 | 13886 | pBR322 origin of replication [E. coli] from AF234316 pCambia2301 |
| c-aadAmod1 | 15303 | 14512 | Codon Optimized Adenyltransferase [aadA] gene/CDS from SUN100 |
| p-aadA[Im800] | 15482 | 15304 | Adenyltransferase [aadA] Spectinomycin Prokaryotic promoter |

D. Assembly of Genes Required for EPA and DHA Synthesis within BiBAC T-Plasmids Containing the F Factor/pRI Origin of Replication For synthesis of VLC-PUFA in Brassica napus seeds, the set of genes encoding the proteins of the metabolic VLC-PUFA pathway were combined with expression elements (promoter, terminators and introns) and transferred into a binary t-plasmid that was used for agrobacteria mediated transformation of plants. All expression cassettes have been combined onto a single binary T-plasmid. The advance of DNA synthesis allows numerous companies to offer services to use a combination of chemical synthesis and molecular biological techniques to synthesize de novo, without an initial template, polynucleotides up to the size of microbial genomes. Synthesis used in the construction of the plasmid described in this example was performed by Life Technologies using their Geneart® service. The Geneart® technology, described in WO2013049227 allows production of genetic elements of a few basepair (bp) length, and was used in this invention to produce the binary T-plasmid for plant transformation VC-LTM593-1qcz rc having a total size of ~61.000 bp. The structure of the plasmidVC-LTM593-1qcz rc is given in Table 11.

TABLE 11

Genetic Elements of plasmid VC-LTM593-1qcz rc. Listed are the names of the elements, the position in VC-LTM593-1qcz rc (nucleotide number, note: start position was larger than stop position for elements encoded by the complementary strand of VC-LTM593-1qcz rc), the function and source of the element. The T-DNA integrated into the plant genome during the transformation process was flanked by a right border (nucleotides 59895 to 148 of VC-LTM593-1qcz rc) and a left border (nucleotides 43830 to43695 of VC-LTM593-1qcz rc). Elements outside of that region (=vector backbone) are required for cloning and stable maintenance in *E. coli* and/or agrobacteria.

| Genetic Elements of plasmid VC-LTM593-1qcz rc | From | To | Description, Function and Source of Element |
|---|---|---|---|
| p-VfUSP__684bp[LLL894] | 329 | 1012 | Promoter from UNKNOWN SEED PROTEIN gene USP (accession: X56240) from *Vicia faba* |
| i-Atss18__252bp[LJK36] | 1013 | 1264 | i-Atss18__252bp functional intron region; intron with partial 5' UTR, *Arabidopsis thaliana*, Locus At1g01170, +37 to +288 bp (numbering relative to start of transcription) (+72 to +282bp 5'UTR-Intron only) |
| c-d6Elo(Pp__GA2) | 1267 | 2139 | Delta-6 ELONGASE from *Physcomitrella patens* |
| t-CaMV35S | 2140 | 2355 | Terminator CaMV35S from 35S gene from Cauliflower mosaic virus |
| p-LuCnl(1064bp) | 2448 | 3511 | Promoter from CONLININ gene from *Linum usitatissimum* |
| i-Atss14__377bp[LJK32] | 3512 | 3888 | i-Atss14__377bp[LJK32] functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d5Des(Tc__GA2) | 3892 | 5211 | Delta-5 DESATURASE from *Thraustochytrium* sp. ATCC21685 |
| t-AgrOCS 192bp[LED12] | 5212 | 5403 | Terminator from OCTOPINE SYNTHASE gene OCS from *Agrobacterium tumefaciens* |
| p-SBP | 5539 | 7337 | Promoter from a SUCROSE-BINDING PROTEIN-RELATED gene from *Vicia faba* |
| i-Atss2__455bp[LJK20] | 7338 | 7792 | i-Atss2__455bp functional intron region; intron with partial 5'UTR, *Arabidopsis thaliana*, Locus At1g65090, +77 to +531bp (numbering relative to start of transcription) (+113 to +508bp 5'UTR-Intron only) |
| c-d6Des(Ot__febit) | 7802 | 9172 | Delta-6 DESATURASE from *Ostreococcus tauri* |
| t-StCATHD-pA | 9200 | 9434 | Terminator from CATHEPSIN D INHIBITOR gene [CATHD] from *Solanum tuberosum* [Potato] |
| p-LuPXR 1727bp[LLL823] | 9513 | 11239 | Promoter from PEROXIREDOXIN LIKE protein gene PXR from *Linum usitatissimum* |
| i-Atss1__846bp[ltm593] | 11240 | 12085 | i-Atss1__847bp functional intron region; intron with partial 5' UTR, *Arabidopsis thaliana*, Locus At1g62290 (aspartyl protease family protein), +1 to +847bp (numbering relative to start of transcription) (+19 to +841bp 5'UTR-Intron only); 1 bp at poly T stretch shorter compared to original i-Atss1__847bp |
| c-d6Elo(Tp__GA2) | 12099 | 12917 | Delta-6 ELONGASE from *Thalassiosira pseudonana* |
| t-AtPXR 400bp[LLL823] | 12973 | 13372 | Terminator from peroxiredoxin like protein gene PXR (At1g48130) from *Arabidopsis thaliana* |
| p-Napin A/B | 13542 | 14205 | Promoter from napA/B gene (napin, seed storage protein) from *Brassica napus* |
| i-Atss14__377bp[LJK32] | 14206 | 14582 | i-Atss14__377bp[LJK32] functional intron region; intron with partial 5' UTR, *Arabidopsis thaliana*, Locus At5g63190, +166 to +542 bp (numbering relative to start of transcription) (+201 to +542 bp 5'UTR-Intron only) |
| c-d12Des(Ps__GA2) | 14589 | 15785 | Delta-12 DESATURASE from *Phythophthora sojae* |
| t-E9 | 15804 | 16361 | Terminator from Small Subunit of RuBisCo rbcS gene (E9) from *Pisum sativum* |
| p-BnSETL-v1[1234bp] | 16454 | 17687 | SETL-v1 *Brassica napus* promoter |
| c-o3Des(Pir__GA) | 17690 | 18781 | Omega-3 DESATURASE from *Pythium irregulare* |
| t-BnSETL | 18803 | 19416 | SETL-v1 *Brassica napus* terminator |
| p-VfUSP__684bp[LLL894] | 19495 | 20178 | Promoter from UNKNOWN SEED PROTEIN gene USP (accession: X56240) from *Vicia faba* |
| i-Atss18__252bp[LJK36] | 20179 | 20430 | i-Atss18__252bp functional intron region; intron with partial 5' UTR, *Arabidopsis thaliana*, Locus At1g01170, +37 to +288 bp (numbering relative to start of transcription) (+72 to +282bp 5'UTR-Intron only) |
| c-o3Des(Pi__GA2) | 20441 | 21526 | Omega-3-DESATURASE from *Phythophthora infestans* |
| t-CaMV35S | 21535 | 21750 | Terminator CaMV35S from 35S gene from Cauliflower mosaic virus |
| p-BnSETL-v1[1234bp] | 21886 | 23119 | SETL-v1 *Brassica napus* promoter |
| c-d5Des(Tc__GA2) | 23122 | 24441 | Delta-5 DESATURASE from *Thraustochytrium* sp. ATCC21685 |
| t-BnSETL | 24463 | 25076 | SETL-v1 *Brassica napus* terminator |
| p-ARC5__perm1 | 25223 | 26373 | Promoter derived from a promoter from ARCLINE 5 gene from *Phaseolus vulgaris* |
| c-d4Des(Tc__GA3) | 26384 | 27943 | Delta-4 DESATURASE from *Thraustochytrium* sp. |
| t-pvarc | 27957 | 28556 | Terminator of ARC5 gene from *Phaseolus vulgaris* |
| p-LuPXR 1727bp[LLL823] | 28649 | 30375 | Promoter from PEROXIREDOXIN LIKE protein gene PXR from *Linum usitatissimum* |
| i-Atss15__758bp[LJK33] | 30376 | 31133 | i-Atss15__758bp[LJK33] functional intron region; intron with partial 5'UTR, *Arabidopsis thaliana*, Locus At2g27040, +93 bp to +850 bp (numbering relative to start of transcription) (+128 to +847 bp 5'UTR-Intron only) |
| c-o3Des(Pir__GA) | 31149 | 32240 | Omega-3 DESATURASE from *Pythium irregulare* |
| t-AtPXR 400bp[LLL823] | 32297 | 32696 | Terminator from PEROXIREDOXIN LIKE protein gene PXR (At1g48130) from *Arabidopsis thaliana* |
| p-LuCnl(1064bp) | 32832 | 33895 | Promoter from CONLININ gene from *Linum usitatissimum* |
| i-Atss2__455bp[LJK20] | 33896 | 34350 | i-Atss2__455bp functional intron region; intron with partial 5'UTR, *Arabidopsis thaliana*, Locus At1g65090, +77 to +531bp (numbering relative to start of transcription) (+113 to +508bp 5'UTR-Intron only) |
| c-d4Des(Pl__GA)2 | 34360 | 35697 | Delta-4 DESATURASE from *Pavlova lutheri* |
| t-AgrOCS 192bp[LED12] | 35719 | 35910 | Terminator from OCTOPINE SYNTHASE gene OCS from *Agrobacterium tumefaciens* |
| p-BnFae1 | 36104 | 37533 | Promoter from Beta-KETOACYL-CoA SYNTHASE (FAE1.1) gene from *Brassica napus* |

TABLE 11-continued

Genetic Elements of plasmid VC-LTM593-1qcz rc. Listed are the names of the elements, the position in VC-LTM593-1qcz rc (nucleotide number, note: start position was larger than stop position for elements encoded by the complementary strand of VC-LTM593-1qcz rc), the function and source of the element. The T-DNA integrated into the plant genome during the transformation process was flanked by a right border (nucleotides 59895 to 148 of VC-LTM593-1qcz rc) and a left border (nucleotides 43830 to43695 of VC-LTM593-1qcz rc). Elements outside of that region (=vector backbone) are required for cloning and stable maintenance in E. coli and/or agrobacteria.

| Genetic Elements of plasmid VC-LTM593-1qcz rc | From | To | Description, Function and Source of Element |
|---|---|---|---|
| i-Atss1__847bp[LJK19] | 37534 | 38380 | i-Atss1__847bp functional intron region; intron with partial 5' UTR, *Arabidopsis thaliana*, Locus At1g62290 (aspartyl protease family protein), +1 to +847bp (numbering relative to start of transcription) (+19 to +841bp 5'UTR-Intron only); from QC1153-1/RTP6393. |
| c-d5Elo(Ot__GA3) | 38388 | 39290 | Delta-5 ELONGASE from *Ostreococcus tauri* |
| t-bnFae1 | 39307 | 39706 | Terminator from FATTY ACID ELONGASE (FAE1, At4g34520) gene of *Arabidopsis thaliana* |
| p-YPC105906__PcUbi4-2[long] | 39830 | 40806 | MTX Parsley UBI4-2 promoter with internal intron |
| c-AtAHASL__A122T__S653N[minusRES] | 40814 | 42826 | ACETOHYDROXYACID SYNTHASE LARGE-SUBUNIT gene/CDS from *Arabidopsis* with S653N (csr1-2) mutation and A122T SDM mutation minus restriction sites |
| t-AtAHAS-3'UTR[rtp4820] | 42827 | 43606 | *Arabidopsis* (dicot) AtAHASL 3' Un-translated Region [trimmed] terminator for ACETOHYDROXYACID SYNTHASE gene |
| b-LLB | 43830 | 43695 | Left T-DNA Left border from pTi15955 [Genbank #AF242881] |
| c-KanR__Tn903 | 45777 | 44962 | Kanamycin Resistance selection gene/CDS |
| p-Kan[lm500] | 45898 | 45778 | Promoter for Kanamycin resistance gene |
| o-ori-2 | 47051 | 47267 | ori-2 origin of replication |
| c-repE | 47361 | 48116 | repE gene/CDS |
| c-sopA | 48695 | 49870 | sapA gene/CDS |
| c-sopB | 49870 | 50841 | sopB gene/CDS |
| c-sopC/incD | 50914 | 51387 | incD/sopC partial gene/CDS |
| c-tral | 51890 | 51949 | tral gene/CDS |
| mf-tral - repA intergenic region | 51938 | 52300 | regulatory region of traR dependent quorum sensing regulon - containing 2 tra-boxes (see LI AND FARRAND JOURNAL OF BACTERIOLOGY, January 2000, p. 179-188) |
| o-repA | 52301 | 53518 | Rep-A gene from pTiC58 replicon (LI AND FARRAND JOURNAL OF BACTERIOLOGY, January 2000, p. 179 . . . 188) |
| rr-repB | 53748 | 54758 | rep-B gene from pTiC58 replicon (LI AND FARRAND JOURNAL OF BACTERIOLOGY, January 2000, p. 179 . . . 188) |
| o-repC | 54973 | 56292 | rep-C gene from pTiC58 replicon (LI AND FARRAND JOURNAL OF BACTERIOLOGY, January 2000, p. 179 . . . 188) |
| mf-y4cG | 56771 | 56301 | fragment of DNA invertase homolog; similar to *Rhizobium* sp. NGR234 pNGR234a Y4CG |
| tr-Tn5 | 58811 | 57250 | Transposon Tn5 sequence |
| o-oriT | 59107 | 59275 | oriT from pRK310 genbank file |
| b-RB[rtp4394] | 148 | 59895 | Right T-DNA Right border |

Figure 39:
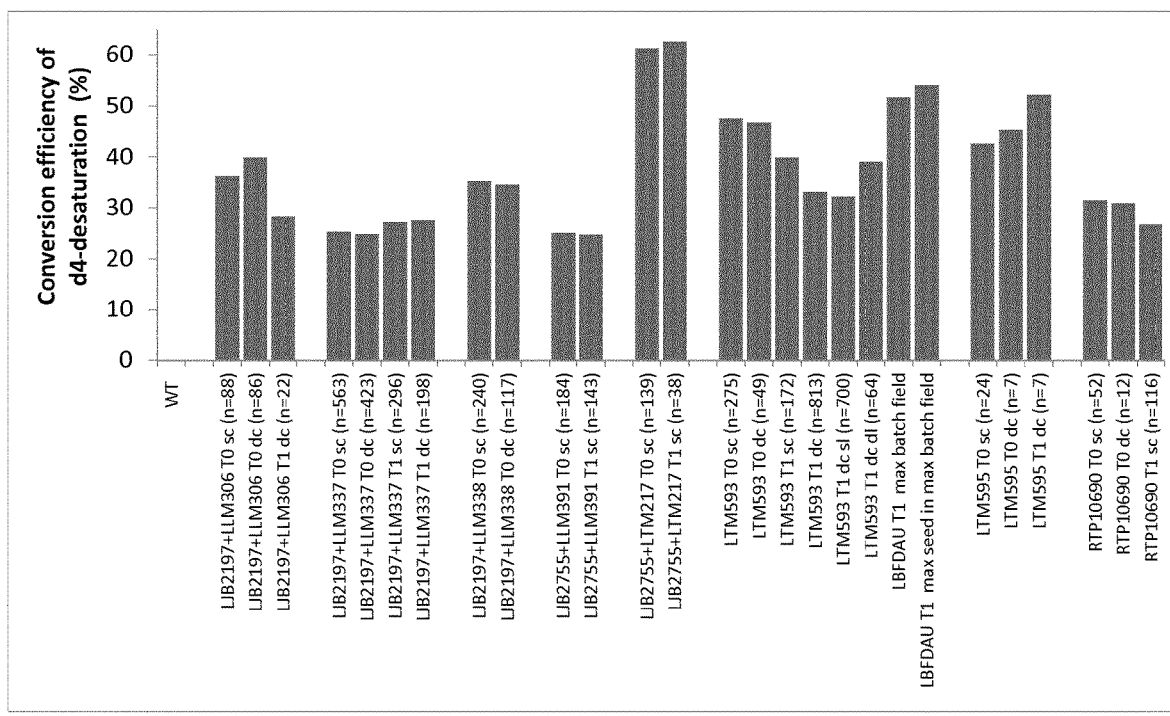
FIG. 39: Conversion efficiencies of delta-4-desturation in seed of transgenic *Brassica napus* and in *Brassica napus* wildtype seeds. See caption in FIG. 32 for further details.

Table 13 compares the order of the gene expression cassettes among all the different constructs and the construct combinations, using short terms for these expression cassettes, see Table 12 for definitions. The data in Examples 10 to 19 demonstrate significant differences among the different construct or construct combinations in terms of the PUFA profile measured in transgenic seed. The differences between constructs and the construct combinations were evident even when eliminating all other sources that affect PUFA levels (e.g. different environments, plant-to-plant variability, seed oil content, T-DNA copy number). For example VC-RTP10690-1qcz_F and VC-LMT593-1qcz rc are isogenic, i.e. the two constructs contained exactly the same gene expression cassettes. Because of the similarity between RTP10690-1qcz_F and VC-LMT593-1qcz one would expect exactly the same pathway step conversion efficiencies e.g. when comparing the average conversion efficiencies of all single copy events. However, FIG. 39 shows that VC-RTP10690-1qcz_F had a Delta-4 DESATURASE conversion efficiency of 32%, (average of T1 seeds of 52 single copy T0 events), whereas VC-LMT593-1qcz rc had a Delta-4 DESATURASE conversion efficiency of 47% (average of T1 seeds of 241 single copy T0 events). This was not expected, and can be explained by transcript levels, which in turn determine protein levels. The transcript levels are affected by the genetic elements that flank the Delta-4 DESATURASE cassettes in VC-LMT593-1qcz rc. The observations between the two constructs is an unexpected finding and indicates that not only the genome but also the T-DNA itself impacts the Delta-4 DESATURASE conversion efficiency, that was dependant on "gene dosage" as described in Example 19. Furthermore, the data in Example 10 to 19 demonstrate that it was possible to insulate expression cassettes from such effects. As can be seen in those Examples 10-19 all single copy events were capable of producing almost exactly the same VLC-PUFA levels when eliminating all other sources that affect PUFA levels (e.g. different environments, plant-to-plant variability, seed oil content). This was particularly striking when comparing all the single copy events in Example 18. Comparing the total C20+C22 VLC-PUFA content, which was largely only controlled by how much was converted by the delta-12 desaturase and by the delta-6 desaturase, it was striking to observe there was virtually no difference between e.g. the single copy event LANPMZ obtained from the construct combination VC-LJB2197-1qcz+VC-LLM337-1qcz rc, and all single copy events listed in Example 18. To this end, it is important to note that one side of the T-DNA that encodes either the entire pathway (Example 15 to 18) or at least the first steps of the pathway up to ARA and EPA production (Example 10 to 14) always contains the AHAS gene which confers herbicide tolerance but was not involved in the VLC-PUFA pathway. The other side of the T-DNA encodes either the entire pathway (Example 15 to 18) or at least the first steps of the pathway up to ARA and EPA production (Example 10 to 14) in most cases the Delta-6 ELONGASE from *Physcomitralla patens* (except in Example 13 and 14). As described in Example 19, the Delta-6 ELONGASE protein encoded by the *Physcomitrella patens* gene works close to maximum conversion efficiency (>90%), thus any increase in delta-6 elongase enzyme levels due to any effect that increases transcript levels will have virtually no effect on the C20 and C22 VLC-PUFA levels. Effectively, the T-DNA determining the total level of VLC-PUFA accumulation are flanked on both sides by genes where expression level differences will have no impact on the VLC-PUFA accumulation. As these two genes were encoded by expression cassettes that were several thousand bp in size, it appears the genes inside the T-DNA were shielded/insulated from any effects the genomic environment could have on the expression level of those genes (e.g. the delta-12-desaturase, compare with Example 19). This effect was consistent with the observation that double copy events differ considerably more in total C20 and C22 VLC-PUFA levels: As in many cases the additional T-DNA insertions are not complete (see Example 10 to 18), resulting in exposure of T-DNA internal genes are exposed to the genome. When these genes are susceptible to gene-dosage effects (the conversion efficiency of those genes depends on the amount of transcript and the derived amount of enzyme, compare with Example 19), then in some genomic locations the genomic environment boosted the transcript level.

TABLE 12

Definition of shorthands used for plant expression cassettes of this invention

| Cassette shorthand | Promoter | Intron | Coding sequence | Terminator |
| --- | --- | --- | --- | --- |
| USP/c-d6Elo(Pp_GA2) | p-VfUSP_684 bp[LLL894] | i-Atss18_252[LJK36] | c-d6Elo(Pp_GA2) | t-CaMV35S |
| PXR/c-o3Des(Pir_GA) | p-LuPXR 1727 bp[LLL823] | i-Atss15_758 bp[LJK33] | c-o3Des(Pir_GA) | t-AtPXR 400 bp[LLL823] |
| Conlinin/c-d5Des(Tc_GA2) | p-LuCnl(1064 bp) | i-Atss14_377[LJK32] | c-d5Des(Tc_GA2) | t-AgrOCS 192 bp[LED12] |
| SBP/c-d6Des(Ot_febit) | p-SBP | i-Atss2_455 bp[LJK20] | c-d6Des(Ot_febit) | t-StCATHD-pA |
| PXR/c-d6Elo(Tp_GA2) | p-LuPXR 1727 bp[LLL823] | i-Atss1_847 bp[LJK19] | c-d6Elo(Tp_GA2) | t-AtPXR 400 bp[LLL823] |
| Fae/c-d6Elo(Tp_GA2) | p-BnFae1 | i-Atss1_847 bp[LJK19] | c-d6Elo(Tp_GA2) | t-bnFae1 |
| Napin/c-d12Des(Ps_GA) | p-Napin A/B | i-Atss14_377[LJK32] | c-d12Des(Ps_GA) | t-E9 |
| USP/c-o3Des(Pi_GA2) | p-VfUSP_684 bp[LLL894] | i-Atss18_252[LJK36] | c-o3Des(Pi_GA2) | t-CaMV35S |
| UBI/AHAS | p-PcUbi4-2[long] | part of PcUBI promoter | c-AtAHASL_A122T_S653N | t-AtAHAS-3'/UTR[ac321] |
| Conlinin/d4Des(Eg) | p-LuCnl(1064 bp) | N/A | c-d4Des(Eg_GA) | t-AgrOCS 192 bp[LED12] |
| SBP/d15Des(Ch) | p-VfSBP_perm3 | N/A | c-d15Des(Ch_ERTp_GA) | t-StCATHD-pA |
| Conlinin/c-d4Des(PI_GA)2_var1 | p-LuCnl(1064 bp) | i-Atss2_455 bp[LJK20] | c-d4Des(PI_GA)2 | t-AgrOCS 192 bp[LED12] |
| SETL/c-d5Des(Tc_GA2) | p-BnSETL-v1[1234 bp] | N/A | c-d5Des(Tc_GA2) | t-BnSETL |
| SETL/c-o3Des(Pir_GA) | p-BnSETL-v1[1234 bp] | N/A | c-o3Des(Pir_GA) | t-BnSETL |
| FAE/c-d5Elo(Ot_GA3) | p-BnFAE1 | i-Atss1_847 bp[LJK19] | c-d5Elo(Ot_GA3) | t-bnFAE1 |
| SETL/c-o3Des(Pir_GA) | p-VfSBP_perm3 | N/A | c-o3Des(Pir_GA) | t-StCATHD-pA |
| ARC/c-d4Des(Tc_GA)_var1 | p-ARC5_perm1 | N/A | c-d4Des(Tc_GA) | t-pvarc |
| ARC/c-d4Des(Tc_GA)_var2 | p-ARC5_perm1 | N/A | c-d4Des(Tc_GA3) | t-pvarc |
| Conlinin/c-d4Des(PI_GA)2_var2 | p-LuCnl(1064 bp) | N/A | c-d4Des(PI_GA)2 | t-AgrOCS 192 bp[LED12] |
| FAE/c-d4Des(PI_GA)2 | p-BnFAE1 | i-Atss1_847 bp[LJK19] | c-d4Des(PI_GA)2 | t-bnFAE1 |

TABLE 13

Order and orientation of plant expression cassettes on T-DNAs. Per column, expression cassettes are abbreviated according to Table 12 and listed from top to bottom in the following way: The top row indicated the right border of the first T-DNA introduced into the plant genome; the following proteins are all listed according to sense orientation of transcription, pointing away from the right border. The end of the first T-DNA was indicated by 'LB'. In case a second T-DNA was used to transfer all pathway genes into the plant genome according to example 7 to 11, the right border of this T-DNA was indicated as 'RB2'. The expression cassettes of the second T-DNA are listed in the following rows. Empty cells have been introduced to facilitate comparison of the different constructs.

| VC-LJB2197-1qcz + VC-LLM306-1qcz rc | VC-LJB2197-1qcz + VC-LLM337-1qcz rc | VC-LJB2197-1qcz + VC-LLM338-3qcz rc | VC-LJB2755-2qcz + VC-LLM391-2qcz rc | VC-LJB2755-2qcz + VC-LLM217-1qcz rc | RTP10690-1qcz_F | RTP10691-2qcz | VC-LMT595-1qcz rc | VC-LMT593-1qcz rc |
|---|---|---|---|---|---|---|---|---|
| RB | RB | RB | RB | RB | RB | RB | RB | RB |
| USP/c- | USP/c- | USP/c- | PXR/c- | PXR/c- | USP/c- | USP/c- | USP/c- | USP/c- |
| d6Elo(Pp_GA2) | d6Elo(Pp_GA2) | d6Elo(Pp_GA2) | o3Des(Pir_GA) | o3Des(Pir_GA) | d6Elo(Pp_GA2) | d6Elo(Pp_GA2) | d6Elo(Pp_GA2) | d6Elo(Pp_GA2) |
| Conlinin/c- | Conlinin/c- | Conlinin/c- | Conlinin/c- | Conlinin/c- | Conlinin/c- | Conlinin/c- | Conlinin/c- | Conlinin/c- |
| d5Des(Tc_GA2) | d5Des(Tc_GA2) | d5Des(Tc_GA2) | d5Des(Tc_GA2) | d5Des(Tc_GA2) | d5Des(Tc_GA2) | d5Des(Tc_GA2) | d5Des(Tc_GA2) | d5Des(Tc_GA2) |
| SBP/c- | SBP/c- | SBP/c- | SBP/c- | SBP/c- | SBP/c- | SBP/c- | SBP/c- | SBP/c- |
| d6Des(Ot_febit) | d6Des(Ot_febit) | d6Des(Ot_febit) | d6Des(Ot_febit) | d6Des(Ot_febit) | d6Des(Ot_febit) | d6Des(Ot_febit) | d6Des(Ot_febit) | d6Des(Ot_febit) |
| PXR/c- | PXR/c- | PXR/c- | FAE/c- | FAE/c- | PXR/c- | PXR/c- | PXR/c- | PXR/c- |
| d6Elo(Tp_GA2) | d6Elo(Tp_GA2) | d6Elo(Tp_GA2) | d6Elo(Tp_GA2) | d6Elo(Tp_GA2) | d6Elo(Tp_GA2) | d6Elo(Tp_GA2) | d6Elo(Tp_GA2) | d6Elo(Tp_GA2) |
| Napin/c- | Napin/c- | Napin/c- | d12Des(Ps_GA) | d12Des(Ps_GA) | Napin/c- | Napin/c- | Napin/c- | Napin/c- |
| d12Des(Ps_GA) | d12Des(Ps_GA) | d12Des(Ps_GA) | USP/c- | USP/c- | d12Des(Ps_GA) | d12Des(Ps_GA) | d12Des(Ps_GA) | d12Des(Ps_GA) |
| | | | o3Des(Pi_GA2) | o3Des(Pi_GA2) | PXR/c- | PXR/c- | PXR/c- | |
| | | | UBI/AHAS | UBI/AHAS | o3Des(Pir_GA) | o3Des(Pir_GA) | o3Des(Pir_GA) | |
| UBI/AHAS | UBI/AHAS | UBI/AHAS | LB | LB | | | | |
| LB | LB | LB | RB2 | RB2 | | | | |
| RB2 | RB2 | RB2 | | | | | SETL/c- | SETL/c- |
| Conlinin/d4Des (Eg) | Conlinin/d4Des (Eg) | Conlinin/d4Des (Eg) | | | Conlinin/c- d4Des(Pl_GA2)_var1 | SETL/c- d5Des(Tc_GA2) | d5Des(Tc_GA2) | o3Des(Pir_GA) |
| FAE/c- | FAE/c- | FAE/c- | FAE/c- | FAE/c- | FAE/c- | FAE/c- | FAE/c- | USP/c- |
| d5Elo(Ot_GA3) | d5Elo(Ot_GA3) | d5Elo(Ot_GA3) | d5Elo(Ot_GA3) | d5Elo(Ot_GA3) | d5Elo(Ot_GA3) | d5Elo(Ot_GA3) | d5Elo(Ot_GA3) | o3Des(Pi_GA2) |
| SETL/c- | SETL/c- | | | | | | | SETL/c- |
| o3Des(Pir_GA) | o3Des(Pir_GA) | | | | | ARC/c- | ARC/c- | d5Des(Tc_GA2) |
| | | | | | ARC/c- | d4Des(Tc_GA)_var2 | d4Des(Tc_GA)_var2 | ARC/c- |
| | | | | ARC/c- | d4Des(Tc_GA)_var2 | USP/c- | USP/c- | d4Des(Tc_GA)_var2 |
| USP/c- | USP/c- | USP/c- | | d4Des(Tc_GA)_var1 | USP/c- | o3Des(Pi_GA2) | o3Des(Pi_GA2) | PXR/c- |
| o3Des(Pi_GA2) | o3Des(Pi_GA2) | o3Des(Pi_GA2) | | Conlinin/c- | o3Des(Pi_GA2) | | | o3Des(Pir_GA) |
| ARC/c- | ARC/c- | ARC/c- | ARC/c- | d4Des(Pl_GA2)_var2 | SETL/c- | SETL/c- | SETL/c- | Conlinin/c- |
| d4Des(Tc_GA)_var1 | d4Des(Tc_GA)_var1 | d4Des(Tc_GA)_var1 Conlinin/d4Des (Eg) | d4Des(Tc_GA)_var1 Conlinin/d4Des (Eg) | | d5Des(Tc_GA) | d5Des(Tc_GA) | d4Des(Pl_GA)2 | d4Des(Pl_GA)2_var1 |
| | | | | | | | FAE/c- | FAE/c- |
| | | | | | | | d5Elo(Ot_GA3) | d5Elo(Ot_GA3) |
| | | | | | SETL/c- | SETL/c- | SETL/c- | |
| | | | | | o3Des(Pir_GA) | o3Des(Pir_GA) | o3Des(Pir_GA) | |
| | | | | | UBI/AHAS | UBI/AHAS | UBI/AHAS | UBI/AHAS |
| LB2 | LB2 | LB2 | LB2 | LB2 | LB | LB | LB | LB |

E. Procedure for Production of Transgenic Plants Using a Co-Transformation Approach In general, the transgenic rapeseed plants were generated by a modified protocol according to DeBlock et al. 1989, Plant Physiology, 91:694-701). For the generation of rapeseed plants transgenic for two different T-DNAs, the binary vectors described in example 3 were transformed into *Agrobacterium rhizogenes* SHA001 (see WO2006024509 A2 for full description of the *Agrobacterium* used). For the transformation of rapeseed plants (cv. Kumily), a co-transformation strategy was used. Transformation was performed with two different agrobacteria strains harbouring one of the two different plasmids listed in Table 14 and described in detail in Example 3, Example 4, Example 6 and/or Example 7

TABLE 14

Overview of combinations used in Co-transformation Strategy described in Example 3 for generation of plants harboring two different T-DNAs

| ID of Combination | Plasmid containing T-DNA 1 harbored by *Agrobacterium tumefaciens* clone 1 | | Plasmid containing T-DNA 2 harbored by *Agrobacterium tumefaciens* clone 2 | |
|---|---|---|---|---|
| | Plasmid name | Selectable marker for transgenic plants | Plasmid name | Selectable marker for transgenic plants |
| A | VC-LJB2197-1qcz | AHAS | VC-LLM306-1qcz rc | None |
| B | VC-LJB2197-1qcz | AHAS | VC-LLM337-1qcz rc | None |
| C | VC-LJB2197-1qcz | AHAS | VC-LLM338-3qcz rc | None |
| D | VC-LJB2755-2qcz rc | AHAS | VC-LLM391-2qcz rc | None |
| E | VC-LJB2755-2qcz rc | AHAS | VC-LTM217-1qcz rc | None |

Overnight cultures of the two strains intended to be co-transformed were prepared in YEB medium with antibiotics (20 mg/L chloramphenicol, 5 mg/L tetracycline, 25 mg/L Spectinomycin) and grown at 28° C. On the next day the optical density of the culture was checked at 600 nm wave length. It reached about 1.0. Cultures of lower optical density were extended in cultivation period. Cultures with an optical density of above 1.3 were diluted with YEB medium to an OD of approximately 0.2 and cultured until they reach an OD of 1.0.

Cultures were pelleted at about 4000 g and re-suspended in liquid MS medium (Murashige and Skoog 1962), pH 5.8, 3% sucrose with 100 mg/L Acetosyringone to reach an $OD_{600nm}$ of 0.1.

The *Agrobacterium* suspensions corresponding to each of the two constructs to be co-transformed were mixed in equal parts and used for inoculation of hypocotyl segments prepared from 5 days old etiolated seedlings.

Germination took place on half concentrated MS medium, pH 5.6-5.8, 1% sucrose, at 23° C. in the dark for 5 days. Hypocotyl segments of 4 to 7 mm length were inoculated by dipping. Infected explants were transferred to petri dishes with co-cultivation medium (MS medium, pH 5.6, 3% sucrose, 0.6 g/L MES (2-(N-Morpholino)ethanesulfonic acid), 18 g/L mannitol, 0.7% phytoagar (Duchefa Biochemie, PO Box 809 2003 RV Haarlem, Netherlands, part number SKU:P1003), 100 mg/L Acetosyringone, 200 mg/L L-Cysteine, 1 mg/L 2,4D (2,4-Dichlorophenoxyacetic acid)) carrying one layer of Whatman filter paper on its surface. Petri dishes were sealed with tape and incubated at 23 C under long day conditions (16 h light/8 h darkness) for three days. After the three days co-cultivation period explants were transferred to MS medium, pH 5.6, 3% sucrose, 0.6 g/L MES, 18 g/L mannitol, 07% Phytoagar, 1 mg/L 2,4D and 500 mg/L Carbenicillin to prevent *Agrobacterium* growth and incubated for a recovery period under the same physical conditions as for the co-cultivation for 7 days.

For selective regeneration explants were transferred after the recovery period to MS medium, pH 5.8, 3% sucrose, 0.7% Phytoagar, 2.5 mg/L $AgNO_3$, 3 mg/L BAP (6-Benzylaminopurine), 0.1 mg/L GA (Gibberellic acid), 0.1 mg/L NAA (1-Naphthaleneacetic acid), 500 mg/L Carbenicillin, 100 nM Imazethapyr (Pursuit) and cultured for two weeks under long day conditions as described above. Sub-cultivation takes place every two weeks. Hormones were stepwise reduced as follows: BAP 3 to 0.5 to 0.05 mg/L; GA (Gibberellic acid) 0.1 to 0.25 to 0.25 mg/L; NAA 0.1 to 0 to 0 mg/L.

Developing shootlets could be harvested after the second cycle of selective regeneration. Shootlets were cut and transferred to either Elongation/rooting medium (MS medium, pH 5.8, 2% sucrose, 100 mg/L myo-inositol, 40 mg/L Adenine sulphate, 500 mg/L MES, 0.4% Sigma Agar, 150 mg/L Timentin, 0.1 mg/L IBA (Indole-3-butyric acid)) or to rock wool/stone wool or foam mats (Grodan, GRODAN Group P.O. Box 1160, 6040 KD Roermond The Netherlands, or Oasis, 919 Marvin Street, Kent, Ohio 44240 USA) watered with 1/10 Vol. of MS medium, pH 5.8 without sucrose under ex vitro long day conditions in covered boxes.

Shoots were elongated and rooted in in vitro medium and were transferred directly to soil.

Either in vitro shoots or GH adapted shoots were sampled for molecular analysis.

The following modifications were successfully tested for transformation and were alternatively used to the above described protocol, once they had been worked out.

Seeds were germinated under low light conditions (<50 μMol/$m^2$ s) using MSBS medium from Duchefa (Duchefa Biochemie, PO Box 809 2003 RV Haarlem, Netherlands), pH 5.8, 3% sucrose and 0.8% Oxoid agar. Germination under light conditions produces explants, which are more stable and easier to handle compared to etiolated hypocotyls.

The inoculation method can vary but the method used in the invention was inoculating explants in a bath of *Agrobacterium* cells under gentle shaking up to 4 min and sieving the explants after the incubation with shaking. Under this condition the $OD_{600nm}$ can be reduced up to 0.01. Medium were used either autoclaved (except antibiotics, hormones, additives such as L-cysteine, Acetosyringon, imidazolinone components) or filter sterilized prepared (Agar component autoclaved, allowed to cool to 42 C and then used).

F. Procedure for Production of Transgenic Plants Using BiBACs

For BiBAC transformation the same protocol as described for the co-transformation approach was used except that only one construct was used. According to the prokaryotic kanamycin resistance gene of binary plasmid 50 mg/L kanamycin was used instead of Spectinomycin for *Agrobacterium* growth. It was observed during the course of this work that *Agrobacterium* carrying BiBACs grow very slowly, often taking 18 hours to reach a liquid culture $OD_{600nm}$ considered optimal for use in plant transformation.

The table below gives an example for some key data documented during the transformation of the construct LTM593

| | VC-LTM593-1qcz rc |
|---|---|
| Explants inoculated | 37 600 |
| Shoots harvested | 2 630 |
| Shoots sampled and analyzed for gene AHAS | 1 543 |
| Transgenic events with gene AHAS | 1 050 |
| Transformation efficiency (%) | 2.8 |
| Percentage of events that grown on herbicide seelction plates but where confirmed using qPCR to lack the herbiced resitstance marker (%) | 32.0 |

The amount of single copy events produced by the plant transformation protocol described above was 45% and 38% of vector backbone-free events selected after transformation of the constructs LTM593 and LTM595, respectively, were single copy events (see Table 15).

TABLE 15

Statistics of single and double copy events with and without vector backbone in transformation experiments performed with the two BiBAC strains VC-LTM593-1qcz rc and VC-LTM595-1qcz rc

| | VC-LTM593-1qcz rc | | VC-LTM595-1qcz rc | |
|---|---|---|---|---|
| | # | % | # | % |
| Number of transgenic events confirmed to contain at least 1 copy of gene c-AtAHAS | 1050 | | 217 | |
| Single copy | 535 | 50 | 92 | 42 |
| Single copy, vector backbone-free | 478 | 45 | 83 | 38 |
| Double copy | 320 | 30 | 49 | 23 |
| Double copy vector backbone-free | 227 | 22 | 41 | 18 |

One important key finding for successful transformation was the choice of *Agrobacterium* strain. While the original method (see De Block et al. (1989) Plant Physiology 91:694-701) used the *Agrobacterium tumefaciens* strain C58C1pMP90, the described method was based on the *Agrobacterium rhizogenes* strain SHA001 (see WO2006024509 A2 for SHA001 and SHA017). Even within *Agrobacterium rhizogenes* strains we have realized a clear response of transformation success to the strain and construct used (see Table 16).

TABLE 16

Impact of *Agrobacterium rhizogenes* strains on transformation success of BiBACs

| | VC-RTP10690-1qcz_f | VC-LTM593-1qcz rc |
|---|---|---|
| Strain used | SHA017 | SHA001 |
| Number of inoculated explants | 60700 | 37600 |
| Regeneration efficiency (%) | 1.8 | 4.1 |
| Shoots samples and analysed for gene AHAS | 1084 | 1543 |
| Number of transgenic plants based on the presence of gene c-AHAS | 333 | 1050 |
| Transformation efficiency (TE) (%) | 0.6 | 2.8 |
| Percentage of events that grown on herbicide seelction plates but where confirmed using qPCR to lack the herbiced resitstance marker (%) | 69.3 | 32.0 |

TABLE 17

Transformation Efficiencies of the various plasmids and *Agrobacterium* strains used. With respect to the integration of the T-DNA, it was possible that multiple copies or single copies of intact or truncated or duplicated, or truncated and duplicated T-DNA's could be inserted into the genome. The terms copy or copies refer to the number of copies of a particular T-DNA or fragment of a T-DNA were inserted into the plant genome. The term locus refers to how many different locations within the plant genome the copy or copies of the T-DNA were inserted into. Locus is defined as region of disequilibrium within the genome an area which varies between plant species and even within cultivars of a given species. For the purpose of this definition this is within one genetic map unit or CentiMorgan.

| Outcome | VC-LJB2197-1qcz + VC-LLM337-1qcz rc | VC-LJB2755-2qcz rc + VC-LLM391-2qcz rc | VC-RTP10690-1qcz_f | VC-LTM593-1qcz rc |
|---|---|---|---|---|
| *Agrobacterium* strain | SHA001 | SHA001 | SHA017 | SHA001 |
| Transformation efficiency (TE) (%) based on the presence of gene AHAS | 17 | 19.7 | 0.6 | 2.8 |
| Percentage of events that grown on herbicide seelction plates but where confirmed using | 1.1 | 0.6 | 69.3 | 32.0 |

TABLE 17-continued

Transformation Efficiencies of the various plasmids and *Agrobacterium* strains used. With respect to the integration of the T-DNA, it was possible that multiple copies or single copies of intact or truncated or duplicated, or truncated and duplicated T-DNA's could be inserted into the genome. The terms copy or copies refer to the number of copies of a particular T-DNA or fragment of a T-DNA were inserted into the plant genome. The term locus refers to how many different locations within the plant genome the copy or copies of the T-DNA were inserted into. Locus is defined as region of disequilibrium within the genome an area which varies between plant species and even within cultivars of a given species. For the purpose of this definition this is within one genetic map unit or CentiMorgan.

| Outcome | VC-LJB2197-1qcz + VC-LLM337-1qcz rc | VC-LJB2755-2qcz rc + VC-LLM391-2qcz rc | VC-RTP10690-1qcz_f | VC-LTM593-1qcz rc |
|---|---|---|---|---|
| qPCR to lack the herbiced resitstance marker (%) | | | | |
| Genes of both T-DNAs present (% co-transformed) | 11.2 | 15.1 | n. a. | n. a. |
| % of single copy events one locus integration | 0 | 0 | 100 | 100 |
| Portion of selected "more copy events" (2 to 3 copies) with one locus integration | 0 | 0 | n.d. | 25 from 33 |

G. Seed Germination and Plant Growth in the Greenhouse and Field

Transformed plants were cultivated for seed production and phenotypic assessment in both the greenhouse and in the field. Greenhouse growth conditions were a sixteen hour light period followed by an eight hour dark period. The temperature was 20 degrees celsius during the light period (also called the day period) with a level of light corresponding to 200-300 micromoles of photons m-2 s-1 (this is the incident of light at the top of the plant and lights were adjusted in terms of distance from the plant to achieve this rate). During the day period the range of light in the greenhouse varied between 130 and 500 micromoles of photons m-2 s-1. Getting out of the day range just cited triggered either the use of artificial light to bring the level up to 200-300 micromoles of photons m-2 s-1 or shading and/or shut off of lights to bring the level back to 200-300 micromoles of photons m-2 s-1. The dark period (also referred to as the night period) temperature was 18 C. Four hours before the light period began the temperature was lowered to 15 C for the remainder of the dark period. Plants were irrigated and treated for insects as necessary. The soil type was 50% Floradur B Seed+50% Floradur B Cutting (including sand and perlite) provided by Floragard (Oldenburg, Germany). Plant growth was enhanced by nutrient supplementation. Nutrients were combined with the daily watering. A 0.1% (w/v) fertilizer solution (Hakaphos Blue 15(N)-10 (P)-15 (K), Compo GmbH & Co KG, Munster, Germany) was used to water the plants. Water was supplied on demand (e.g. depending on plant growth stage, water consumption etc.). To avoid cross-pollination, plants were bagged at the time when the first flowers opened. Plants were checked daily in order to ensure that all open flowers were covered by the bags. Open flowers that were not covered properly were removed.

For field grown plants, the plants were grown in six locations which correspond climatically to USDA growth zones 3a-4b and 5a, and five locations corresponding climatically to USDA growth zones 8a-9b and 11. The plants grown in the regions corresponding to USDA growth zones 3a-4b and 5a were grown in the summer and the plants grown in the regions corresponding to USDA growth zones 8a-9b and 11 were grown in the winter. Standard horticultural practices for canola were followed. Netting and other measures to protect from birds and insects were used as deemed necessary by the growers, as were herbicides and fertilizer applications. The planting density for all locations was eighty seeds per square meter with germination rate of 95 or better percent.

In the case where it was necessary to determine germination rates for the purpose of seed quality assurance or control, or where it was advantageous to germinate seeds to obtain cotyledons or seedling tissues, the following protocol was used:

150 mm by 15 mm petri-plates and Whatman (no. 2) filter paper cut into 120 mm disks were used. The filter paper was pre-moistened with sterile deionized water. One hundred seeds of the appropriate line were obtained and spread evenly across the pre-moistened filter paper.

Clean and sterile tweezers were used to spread the seeds to obtain the uniform pattern as shown above. Additional sterile water was added to ensure the seeds and paper were wetted, but not floating (see above image). The total amount of water used per petri-plate was approximately 20 milliliters. Three plates were done for each genotype tested. The plates were sealed with surgical tape, VWR (1050 Satellite Blvd.

Suwanee, Ga. 30024 USA) catalog number 56222-110. After the plates were sealed, they were then incubated in a germination chamber set to 90% humidity, set to a sixteen hour photoperiod with 20 degrees Celsius day temperature and 15 degrees Celsius night temperature. The light intensity was 90-120 micro-moles per square meter per second. Germination was scored twice, once at four days after placing the plates into the growth chamber and again at eight days after incubation.

H. Lipid Extraction and Lipid Analysis of Plant Oils

The results of genetic modifications in plants or on the production of a desired molecule, e.g. a certain fatty acid, were determined by growing the plant under suitable conditions, e.g. as described below, and analyzing the growth media and/or the cellular components for enhanced production of the desired molecule, e.g. lipids or a certain fatty acid. Lipids were extracted as described in the standard literature including Ullman, Encyclopedia of Industrial Chemistry, Bd. A2, S. 89-90 und S. 443-613, VCH: Weinheim (1985); Fallon, A., et al., (1987) "Applications of HPLC in Biochemistry" in: Laboratory Techniques in Biochemistry and Molecular Biology, Bd. 17; Rehm et al. (1993) Biotechnology, Bd. 3, Kapitel III: "Product recovery and purification", S. 469-714, VCH: Weinheim; Belter, P. A., et al. (1988) Bioseparations: downstream processing for Biotechnology, John Wiley and Sons; Kennedy, J. F., und Cabral, J. M. S. (1992) Recovery processes for biological Materials, John Wiley and Sons; Shaeiwitz, J. A., und Henry, J. D. (1988) Biochemical Separations, in: Ullmann's Encyclopedia of Industrial Chemistry, Bd. B3; Kapitel 11, S. 1-27, VCH: Weinheim; and Dechow, F. J. (1989) Separation and purification techniques in biotechnology, Noyes Publications.

It is acknowledged that extraction of lipids and fatty acids can be carried out using other protocols than those cited above, such as described in Cahoon et al. (1999) Proc. Natl. Acad. Sci. USA 96 (22):12935-12940, and Browse et al. (1986) Analytic Biochemistry 152:141-145. The protocols used for quantitative and qualitative analysis of lipids or fatty acids are described in Christie, William W., Advances in Lipid Methodology, Ayr/Scotland: Oily Press (Oily Press Lipid Library; 2); Christie, William W., Gas Chromatography and Lipids. A Practical Guide-Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) u.d.T.: Progress in the Chemistry of Fats and Other Lipids CODEN.

To generate transgenic plants containing the genetic elements described in examples 3 and 4 for production of EPA and DHA in seeds, rapeseed (*Brassica napus*) was transformed as described in examples 5 and 6. Selected plants containing the genetic elements described in examples 3 and 4 were grown until development of mature seeds under the conditions cited in Example 7. Fatty acids from harvested seeds were extracted as described above and analyzed using gas chromatography as described above. The content (levels) of fatty acids is expressed throughout the present invention as percentage (weight of a particular fatty acid) of the (total weight of all fatty acids). Seed oil content is expressed throughout the present invention as percentage of (oil weight) of the (total oil weight of seeds).

TABLE 18

Fatty acids analyzed using gas chromatography

| Systematic name | Trivial Name | Short hand 1 | Short hand 2 |
|---|---|---|---|
| Hexadecanoic acid | Palmitic acid | 16:0 | |
| (Z)-7-Hexadecenoic acid | | 16:1n-9 | |
| (Z,Z,Z)-7,10,13-Hexadecatrienoic acid | | 16:3n-3 | |
| Octadecanoic acid | Stearic acid | 18:0 | |
| (Z)-9-Octadecenoic acid | Oleic acid | 18:1n-9 | OA |
| (Z,Z)-9,12-Octadecadienoic acid | Linoleic acid | 18:2n-6 | LA |
| (Z,Z)-6,9-Octadecadienoic acid | | 18:2n-9 | |
| (Z,Z,Z)-9,12,15-Octadecatrienoic acid | alpha-Linolenic acid | 18:3n-3 | ALA |
| (Z,Z,Z)-6,9,12-Octadecatrienoic acid | gamma-Linolenic acid | 18:3n-6 | GLA |
| (Z,Z,Z,Z)-6,9,12,15-Octadecatetraenoic acid | Stearidonic acid | 18:4n-3 | SDA |
| Eicosanoic acid | Arachidic acid | 20:0 | |
| (Z)-11-Eicosenoic acid | Gondoic acid | 20:1n-9 | |
| (Z,Z)-11,14-Eicosadienoic acid | | 20:2n-6 | |
| (Z,Z)-11,14,17-Eicosatrienoic acid | | 20:3n-3 | |
| (Z,Z,Z)-8,11,14-Eicosatrienoic acid | Dihomo-gamma-linolenic acid | 20:3n-6 | DHGLA |
| (Z,Z,Z,Z)-8,11,14,17-Eicosatetraenoic acid | | 20:4n-3 | |
| (Z,Z,Z,Z)-5,8,11,14-Eicosatetraenoic acid | Arachidonic acid | 20:4n-6 | ARA |
| (Z,Z,Z,Z,Z)-5,8,11,14,17-Eicosapentaenoic acid | Timnodonic acid | 20:5n-3 | EPA |
| Docosanoic acid | Behenic acid | 22:0 | |
| (Z)-13-Docosenoic acid | Erucic acid | 22:1n-9 | |
| (Z,Z,Z,Z)-7,10,13,16-Docosatetraenoic acid | Adrenic acid | 22:4n-6 | DTA |
| (Z,Z,Z,Z,Z)-7,10,13,16,19-Docosapentaenoic acid | Clupanodonic acid | 22:5n-3 | DPAn-3 |
| (Z,Z,Z,Z,Z)-4,7,10,13,16-Docosapentaenoic acid | Osbond acid | 22:5n-6 | DPAn-6 |
| (Z,Z,Z,Z,Z,Z)-4,7,10,13,16,19-Docosahexaenoic acid | | 22:6n-3 | DHA |

I. Non-Destructive Analysis of Lipids in Single Cotyledons of Seedlings

Transformation of plants according to the methods described in Example 5 and Example 6 results in a random integration of the T-DNA into the genome. It was known that such integrations can also occur in a partial manner, furthermore multiple integrations of complete and partial T-DNAs can occur. A diploid plant contains one haploid chromosome set inherited from the ovule containing progenitor (for simplicity called the mother or female parent), and one haploid chromosome set inherited from the pollen donating progenitor (for simplicity called the father or male parent). In transformation of the T0 plant the T-DNA integrates into random position(s) of random chromosomes and will result in the maternal chromosome carrying the integration(s), and the corresponding paternal chromosome will not carry this integration, resulting in a seed heterozygous for the integration(s). Growing the T0 seed up results in a plant heterozygous for the T-DNA insert(s) and subsequent gametogenesis will result in both pollen and ovules that contain the T-DNA integration and in some pollen and ovules that do not carry the T-DNA insert(s), according to random segregation, as observed by Gregor Mendel (Mendel, 1866). Self pollination of the plant will result in seeds which will be segregating for the T-DNA insertion(s) according to the ratios observed by Gregor Mendel (Mendel, 1866) and which are now part of the basic general knowledge in the life sciences. Due to the Mendelian segregation; for each integration of the T-DNA, one quarter (~25%) of the T1 seed have lost the integration. 50% of the T1 seed will carry the T-DNA integration either on the maternal chromosome (25%), or paternal chromosome (25%); these seeds are 'heterozygous' or 'hemizygous' related to the T-DNA integration. The remaining quarter (~25%) of the T1 seed will carry the T-DNA on the maternal and paternal chromosome; these seeds are 'homozygous' related to the T-DNA integration. For plants that follow such a sexual propagation, it is essential to genetically fix the T-DNA integration(s), by selecting progenies that are homozygous for the T-DNA integration(s); otherwise the T-DNAs insertion(s) and the trait conferred by the T-DNA insertion(s) will continue to segregate and might be lost over a number of generations.

Figure 22:
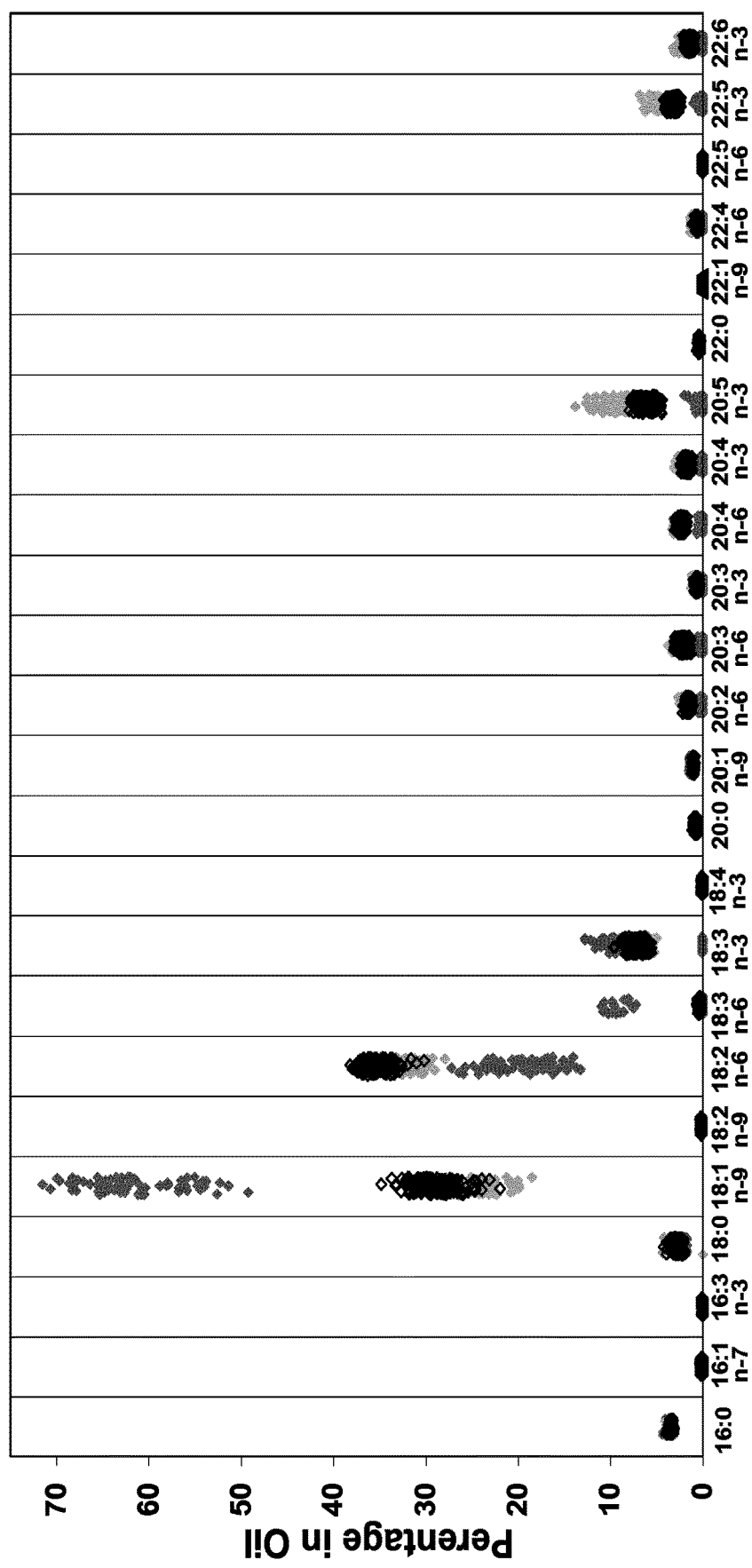
FIG. 22: Half Kernel Analysis of segregating T1 seeds of Event LANPMZ. A total of 288 seedlings where analysed. 71 of those seedlings were found to produce no significant amount of VLC-PUFA (dark grey diamonds) while containing >49% Oleic acid and <28% Linoleic acid. 71 seed of 288 seed correspond to 24.65% of the total analysed seed. All remaining seed were capable of producing DHA, indicating the presence of both T-DNA from construct VC-LJB2197-1qcz and VC-LLM337-1qcz rc. Among those seeds producing DHA, one can discriminate a group of 146 seeds showing medium VLC-PUFA levels (open diamonds), and a group of 71 seed showing high VLC-PUFA levels (light grey diamonds). The ratios of these three groups is 71:146:71, which corresponds to the Medelain 1:2:1 ratio (NULL: HETEROZYGOUS:HOMOZYGOUS) expected for a phenotype when all genes conveying this phenotype (in this case the two T-DNAs of plasmid VC-LJB2197-1qcz and VC-LLM337-1qcz rc) integrated into one locus in the genome.
Figure 23:
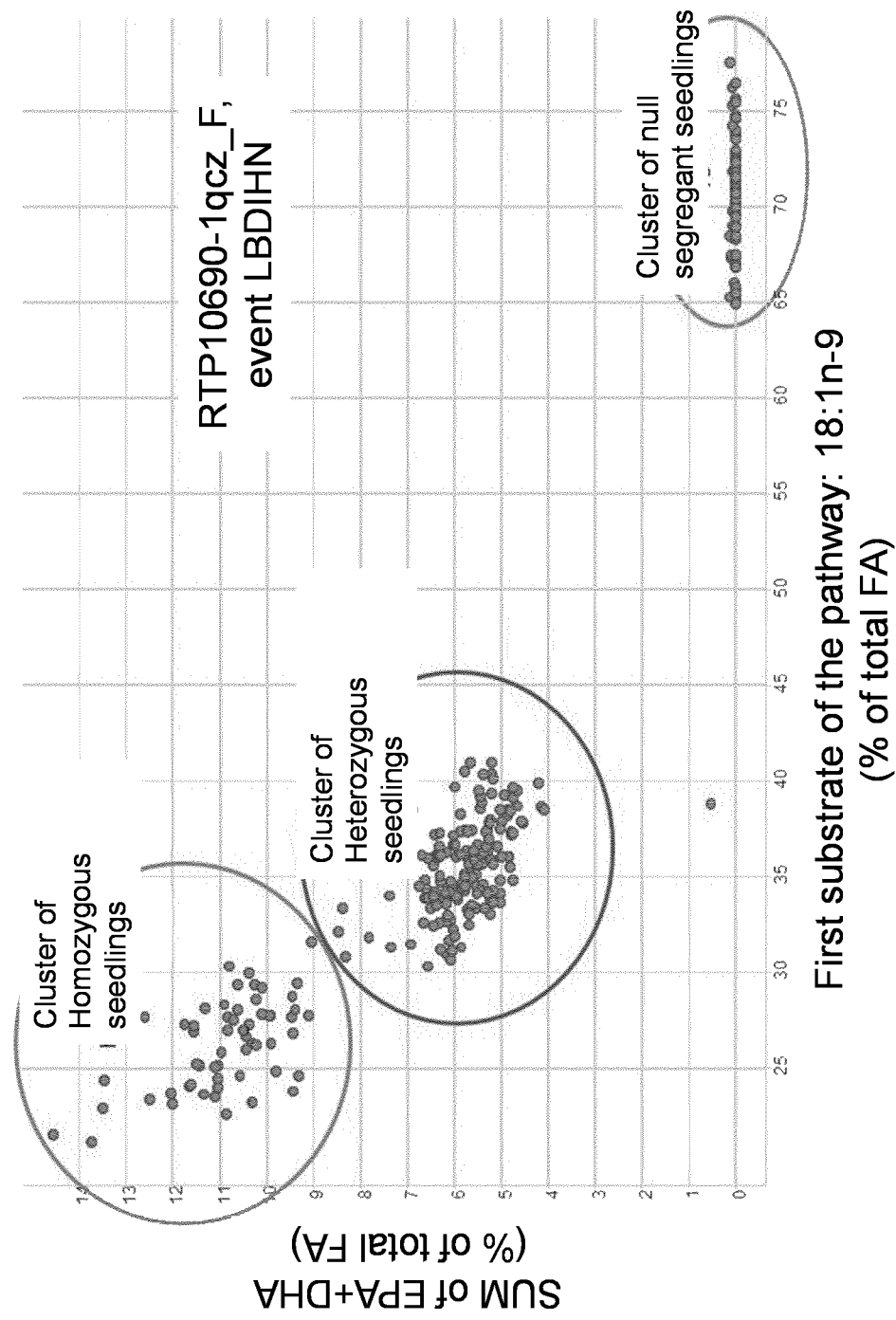
FIG. 23: Half Kernel Analysis of segregating T1 seeds of Event LBDIHN. A total of 288 seedlings where analysed. The levels of first substrate fatty acid of the pathway was plotted on the x-axis, the levels of the sum of two products of the pathways (EPA+DHA) was plotted on the y-axis. One can clearly see three clusters, where the ratio of the number of seeds in the these three clusters was 1:2:1 (Homozygous: Heterozygous:Null segregant). This segregation of the phenotype according to the first Mendelian law demonstrates a single locus insertion of the T-DNA of construct RTP10690-1qcz_F into the genome of B. napus cv Kumily.
Figure 30:
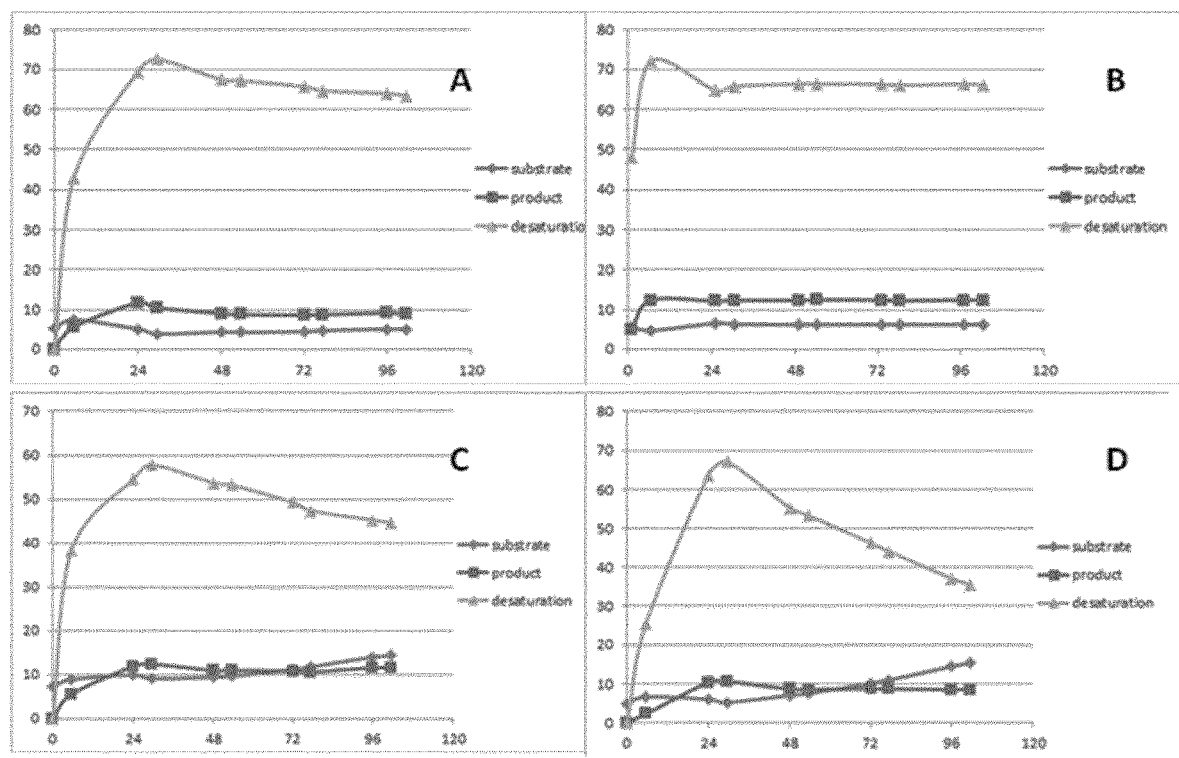
FIG. 30: Time course optimization. Yeast cells expressing the c-d5Des(Tc_GA2) were fed with 0.25 mM DHGLA and the production of ARA was determined by GC. Samples were collected starting immediately after feeding. In Panels A-D, Desaturation was represented as % Conversion vs Growth Time (hours) and Product and Substrate levels are represented as % Total Fatty acid vs Growth time (hours). Panel A pertains to samples supplied with DHGLA immediately after induction. Panel B is overnight induction (22 hrs) before feeding. Panel C is for cultures supplied with 3× normal DHGLA level. Panel D is for cultures supplied with normal rate of DHGLA (0.25 mM) daily.
Figure 31:
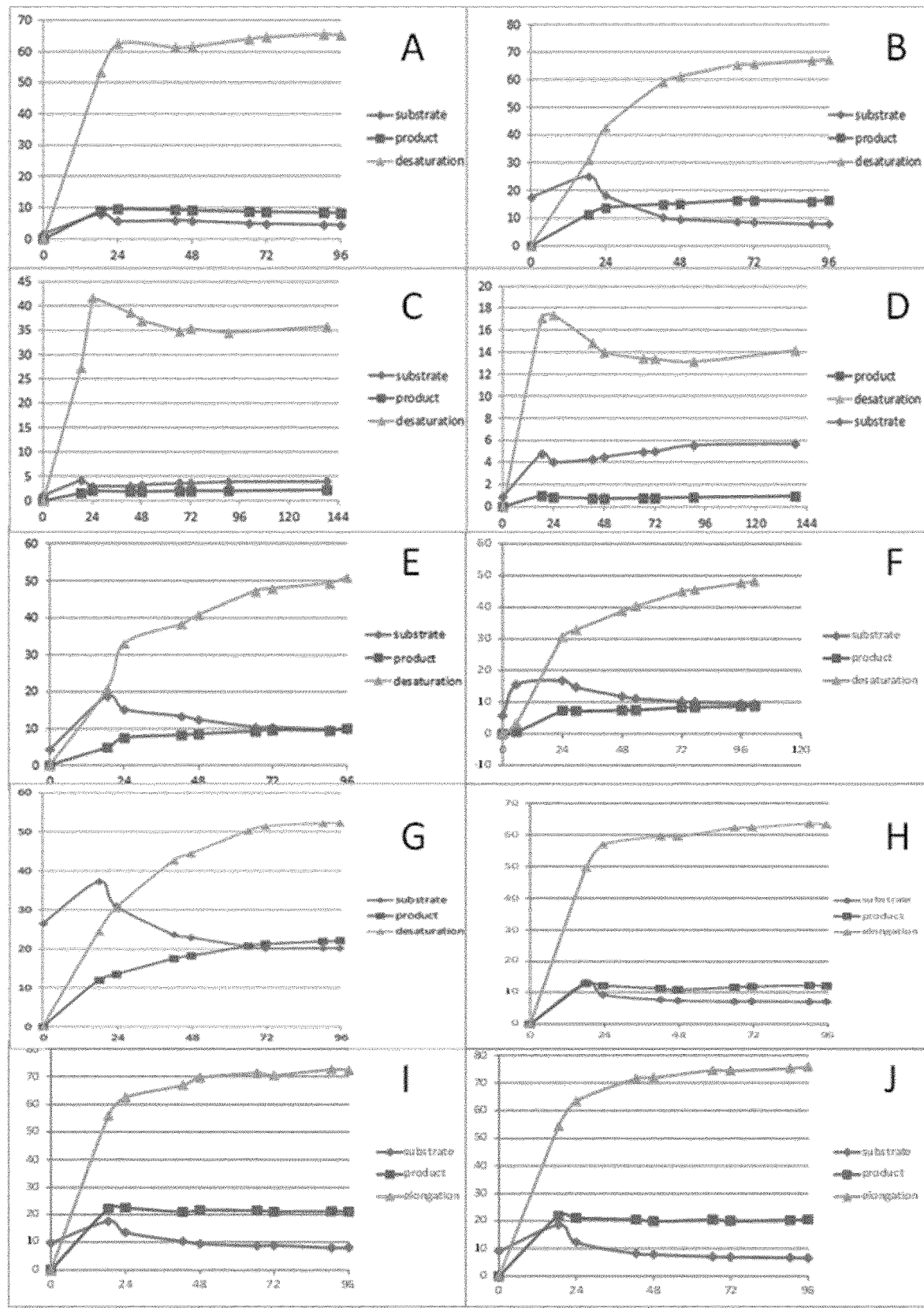
FIG. 31: Representative time course graphs for all desaturases and elongases. Yeast cells expressing each enzyme were supplied with 0.25 mM of preferred fatty acid substrate, and fatty acid profiles were obtained by GC at the indicated time points. In Panels A-J, Desaturation and Elongation were represented as % Conversion vs Growth Time (hours), and Product and Substrate levels were represented as % Total Fatty acid vs Growth time (hours). A. c-d5Des (Tc_GA2)+DHGLA B. c-d6Des(Ot_febit)+ALA C. c-d4Des (PI_GA)2+DTA D. c-d4Des(Tc_GA)+DTA E. c-o3Des (Pir_GA)+ARA F. c-o3Des(Pi_GA2)+ARA G. c-d12Des (Ps_GA)+OA H. c-d5Elo(Ot_GA3)+EPA I. c-d6Elo (Tp_GA2)+GLA J. c-d6Elo(Pp_GA2)+SDA.
Figure 32:
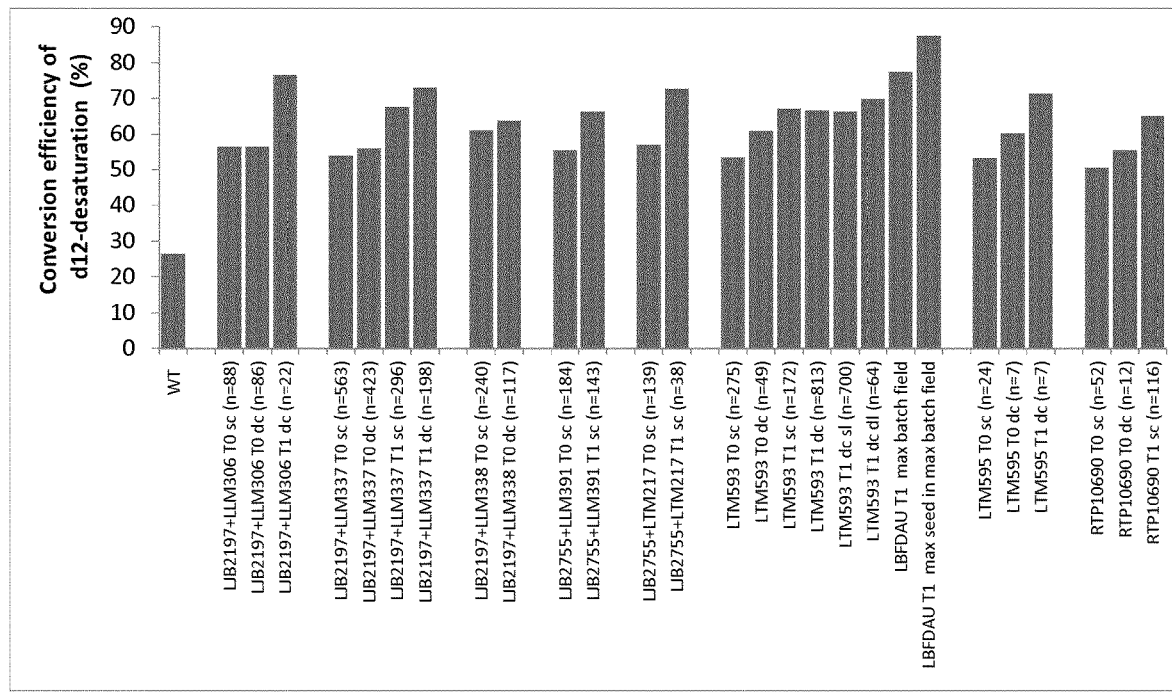
FIG. 32: Conversion efficiencies of delta-12-desaturation in seed of transgenic *Brassica napus* and in *Brassica napus* wildtype seeds. Shown are average conversion efficiencies of various plant populations, as well as the conversion efficiencies observed in a seedbacth of event LBFDAU having highest EPA+DHA levels, and those efficiencies observed in a single seed of that seedbatch, where this single seed had highest EPA+DHA levels among all 95 measured single seeds. Data were taken from Example 10 to Example 18. T0 and T1 designates the plant generation producing the seeds (all grown in the greenhouse except for the two LBFDAU datapoints)
Figure 33:
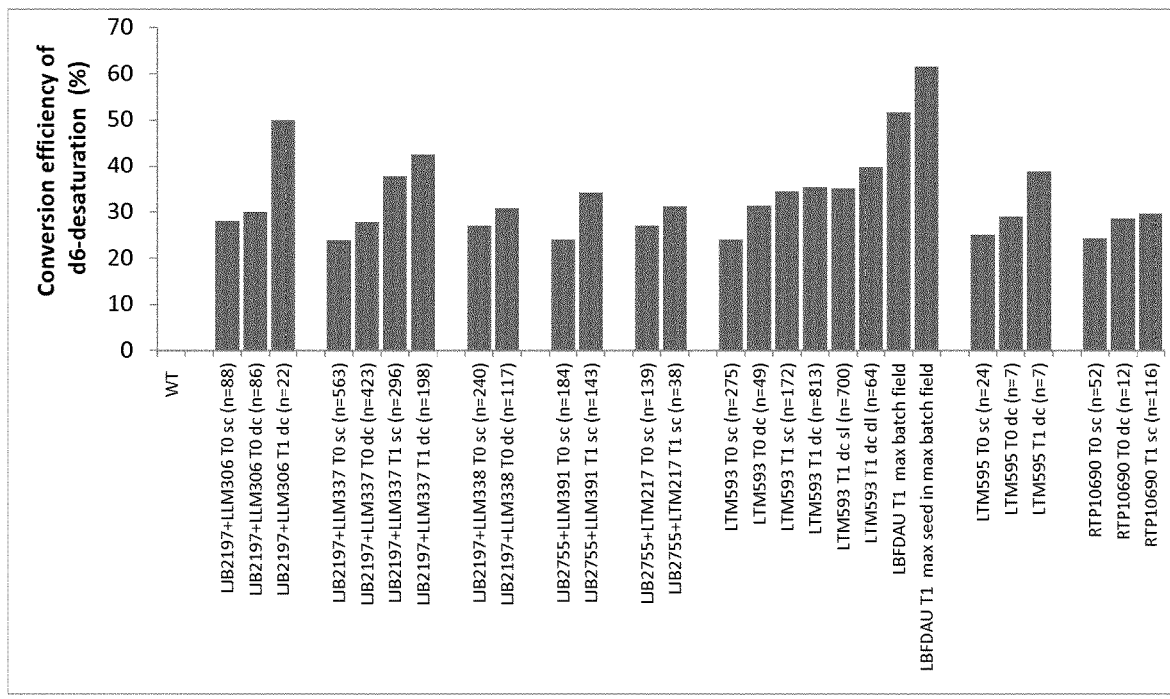
FIG. 33: Conversion efficiencies of delta-6-desaturation in seed of transgenic *Brassica napus* and in *Brassica napus* wildtype seeds. See caption in FIG. 32 for further details.
Figure 34:
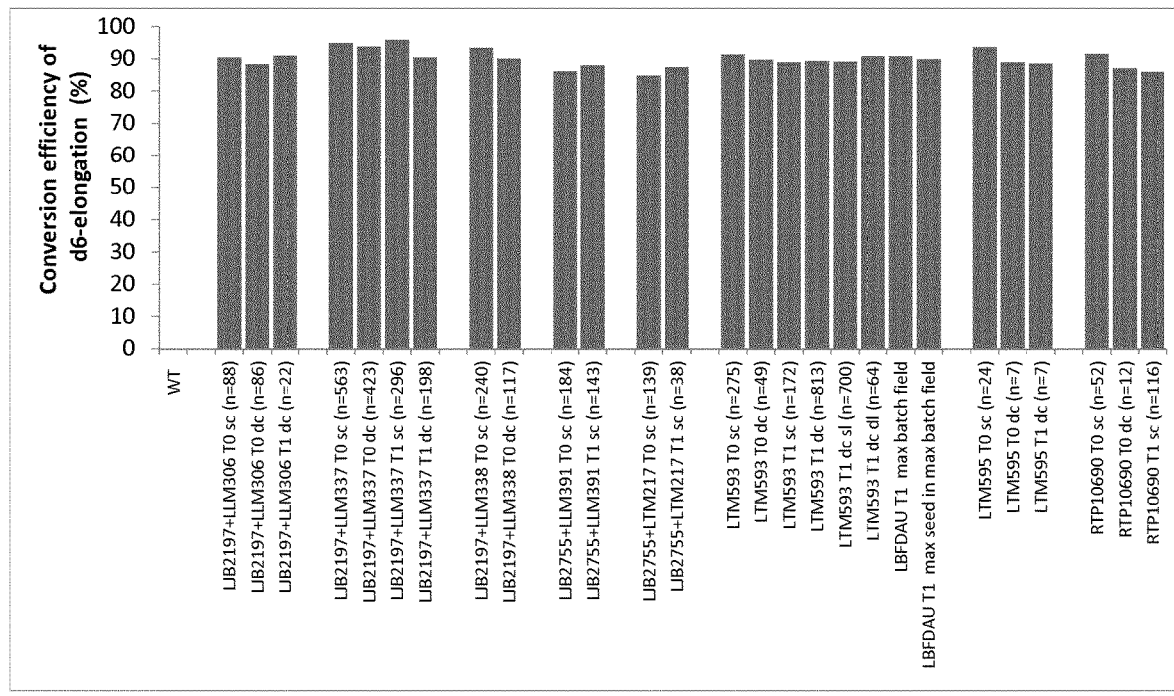
FIG. 34: Conversion efficiencies of delta-6-elongation in seed of transgenic *Brassica napus* and in *Brassica napus* wildtype seeds. See caption in FIG. 32 for further details.
Figure 35:
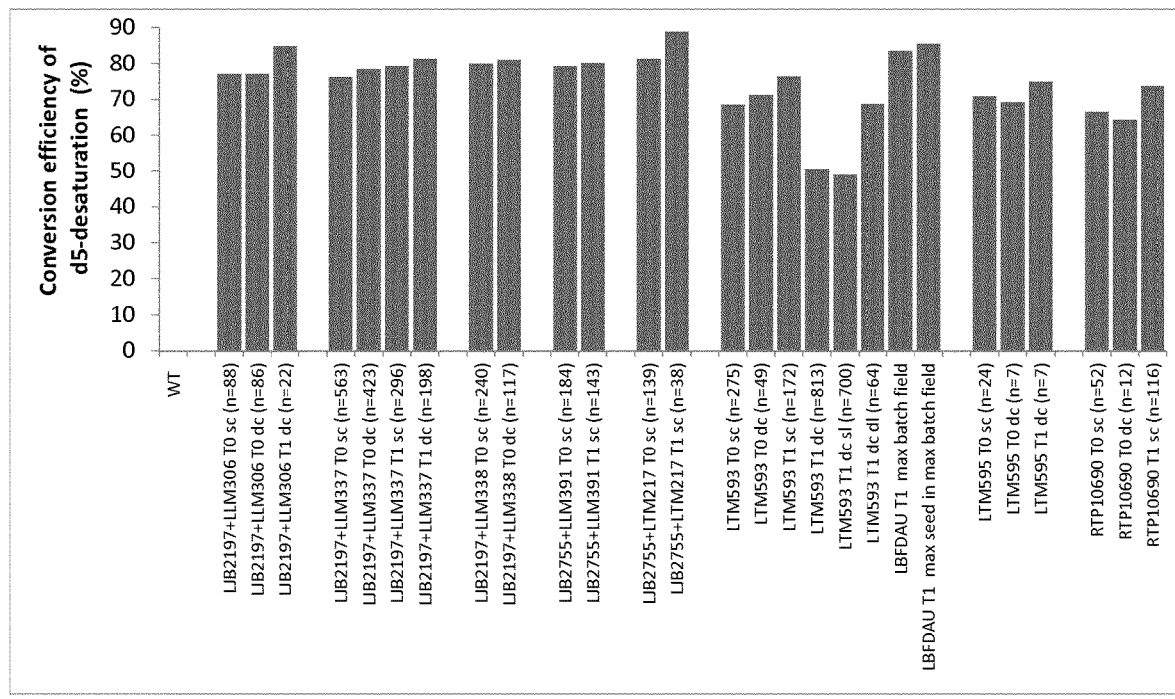
FIG. 35: Conversion efficiencies of delta-5-desaturation in seed of transgenic *Brassica napus* and in *Brassica napus* wildtype seeds. See caption in FIG. 32 for further details.
Figure 36:
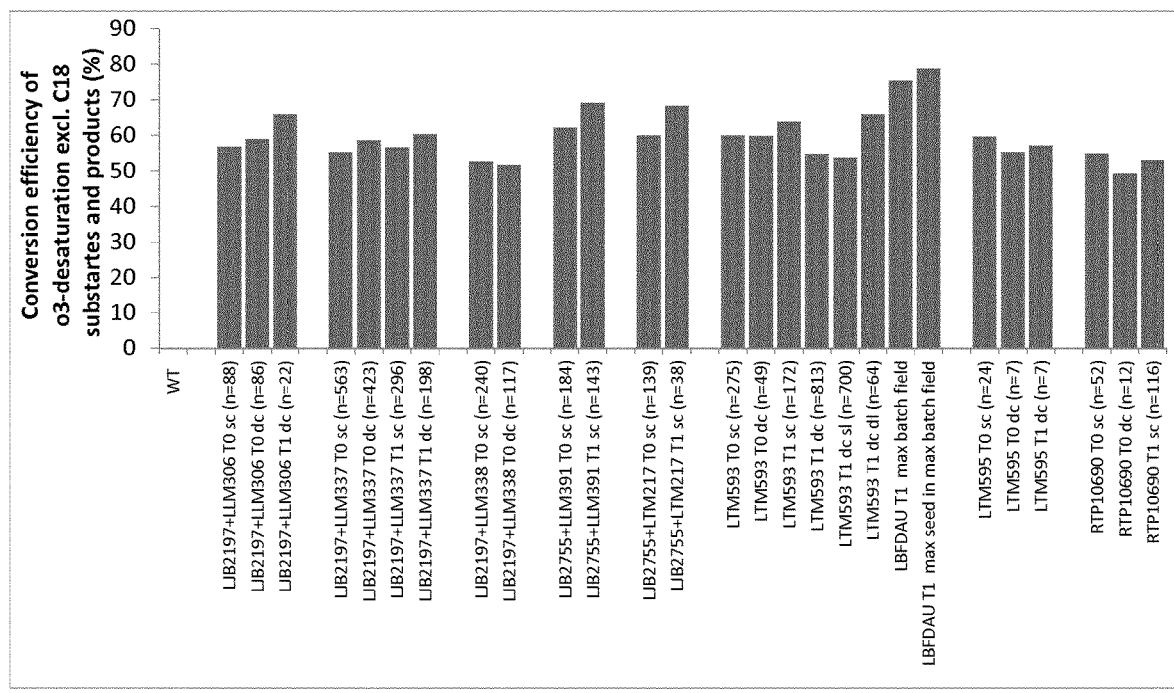
FIG. 36: Conversion efficiencies of omega-3 desaturation (excluding C18 fatty acids) in seed of transgenic *Brassica napus* and in *Brassica napus* wildtype seeds. See caption in FIG. 32 for further details.
Figure 37:
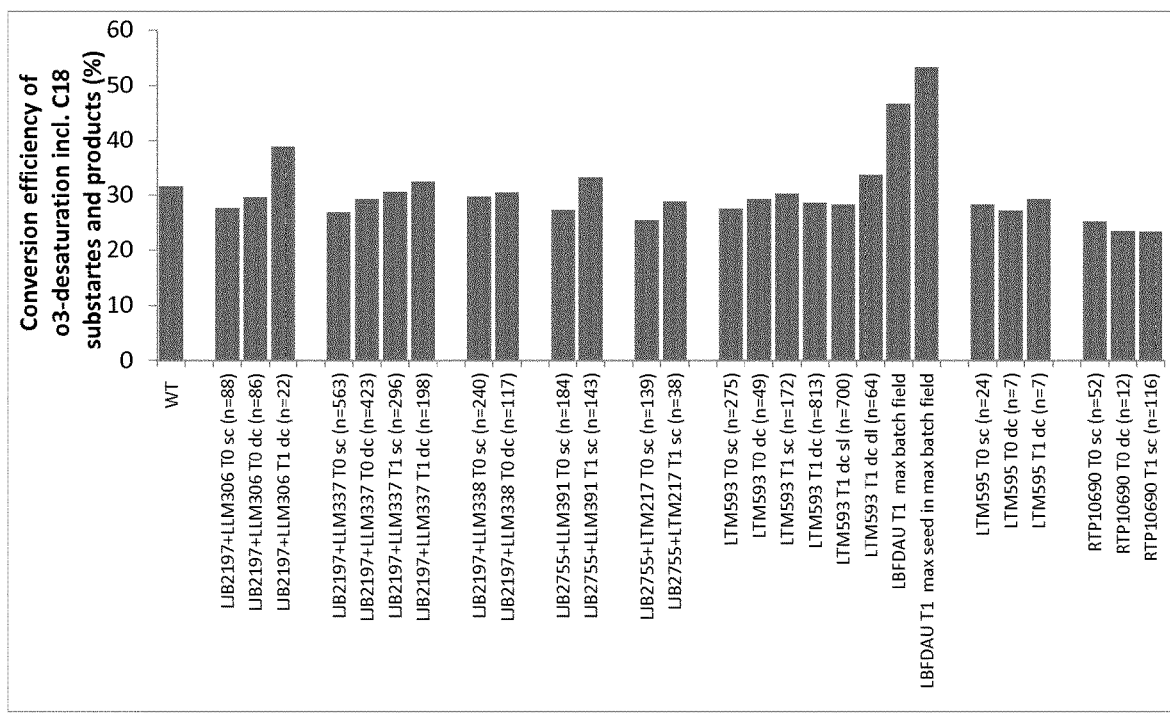
FIG. 37: Conversion efficiencies of omega-3 desaturation (including C18 fatty acids) in seed of transgenic *Brassica napus* and in *Brassica napus* wildtype seeds. See caption in FIG. 32 for further details.
Figure 38:
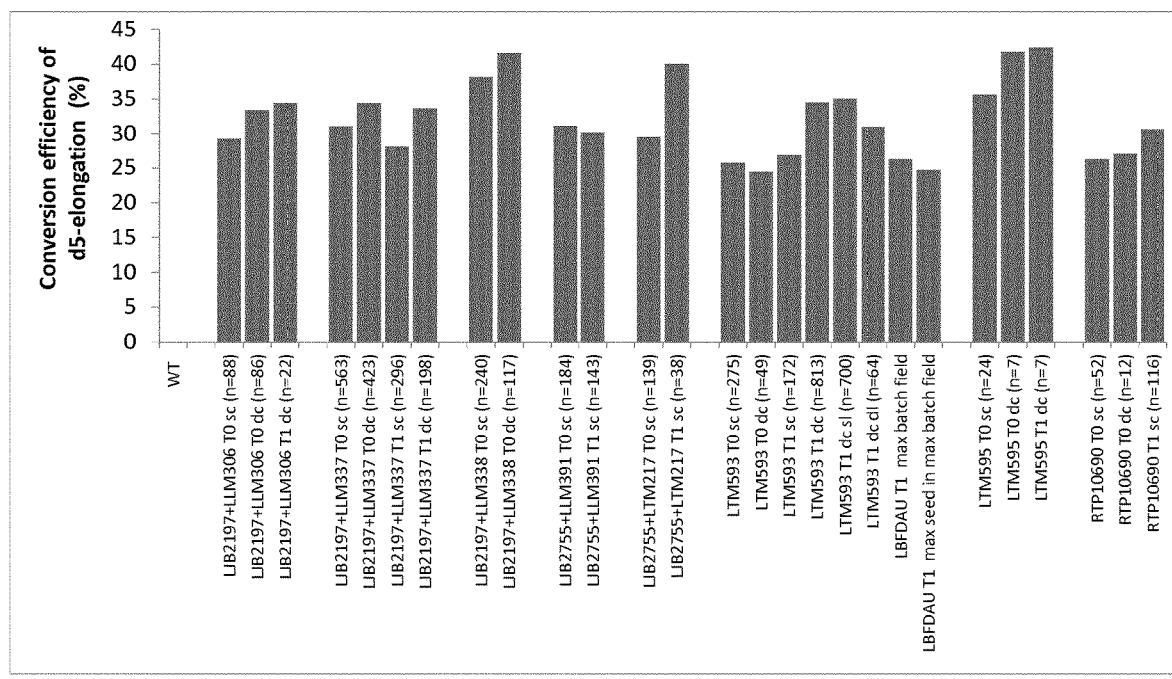
FIG. 38: Conversion efficiencies of delta-5-elongation in seed of transgenic *Brassica napus* and in *Brassica napus* wildtype seeds. See caption in FIG. 32 for further details.

In order to identify T1 seedlings where each T-DNA integration that was essential for the trait was present, ideally homozygous, one can perform quantitative PCR to measure the copy number of the T-DNA integration(s) directly. Alternatively one can analyse the trait conferred by the presence of the T-DNAs, which at least enables the identification of all seeds that do not contain all T-DNA of interest (null-segregants). For all constructs described in Example 10 to Example 14, and where indicated, a nondestructive analysis of VLC-PUFA production was performed. To this end, T1 seeds were germinated in the dark for three days on wet filter paper. After three days, one of the two cotyledons was cut off to subject it to lipid analysis as described in Example 8: Lipid extraction and lipid analysis of plant oils, the other cotyledon, including the hypocotyl and root, was planted in soil. As an example, the result from the lipid content analysis of these cotyledons from segregating T1 seedlings of event LANPMZ obtained from the construct combination described in Example 11 are shown in FIG. 22; the results of event LBDIHN obtained from the construct combination described in Example 15 are shown in FIG. 23. In both of these figures, it is observed that one quarter of the seed produce a significant amount of VLC-PUFA, while producing wildtype levels of Oleic acid. One can furthermore see in both figures two additional clusters of seedlings, see FIG. 23. Counting the number of seed in these respective clusters, a 1:2:1 segregation ratio was observed for the clusters that produce (~0 VLC-PUFA): (medium level of VLC-PUFAs): (high level of VLC-PUFAs). The observations demonstrate a relationship between 'gene dosage', that was the number of T-DNA copies present in the genome, and VLC-PUFA levels. For all constructs described in Example 10 to Example 13, and where indicated, this relationship was exploited to identify T1 plants where at least one T-DNA locus has become homozygous, or where multiple T-DNA integration loci are at least present, or some are homozygous while others still segregate. The applicability of this method can be demonstrated for event LANPMZ, see FIG. 22, all T1 seeds of event LANPMZ are capable of producing EPA and DHA. As this requires the presence of both T-DNAs, it can be concluded that at least one copy of the T-DNA of VC-LJB2197-1qcz and one copy of the T-DNA of VC-LLM337-1qcz rc have inserted into the genome, likely at the same locus. 13 T1 seedlings of those 288 seedlings of event LANPMZ having the highest VLC-PUFA levels have been selected and have been grown to mature plants. Copy number analysis on those 13 selected plants shown in Table 40 indicates that both T-DNAs are present in a single copy, and comparison of the T0 plant copy number results against the average result of the 13 T1 plants demonstrates that these single T-DNA insertions are homozygous (duplicated copy number). All results combined provide the information that the event LANPMZ contains the T-DNAs of construct VC-LJB2197-1qcz and the T-DNA of construct VC-LLM337-1qcz rc in one copy each, whereby both T-DNAs co-segregate in a single locus.

For a single T-DNA integration into the genome, 1 out of 4 T1 seed are expected to be homozygous for that T-DNA integration. For each additional T-DNA integration, just one quarter of all seed homozygous for all other T-DNA integrations are homozygous for the additional T-DNA integration, consequently for two T-DNA integration events into the genome 1 out of 16 T1 seed are expected to be homozygous for both T-DNA integration; for three T-DNA integration into the genome 1 out of 64 T1 seed are expected to be homozygous for all three T-DNA integration; for four T-DNA integration into the genome 1 out of 256 T1 seed are expected to be homozygous for all four T-DNA integration; and so forth. All plants Example 10 to Example 14 contain a minimum of two T-DNA insertion events (one from each plasmid) in order for the plant to contain all the necessary genes to generate all the required enzymes to reconstitute the PUFA pathway sufficiently to generate the VLC-PUFAs: DHA and EPA as well as ARA.

Example 2: Plants Containing the T-DNAs of Plasmid VC-LJB2197-1qcz and VC-LLM337-1qcz Rc (Combination B in Example 5) for Production of EPA and DHA in Seeds In this example, the genetic elements required for EPA and DHA synthesis were transferred into the plant genome on two different T-DNAs. To this end, the two different plasmids VC-LJB2197-1qcz and VC-LLM337-1qcz rc containing two different T-DNAs were cloned into agrobacteria, and plant tissue was incubated according to Example 5 at the same time with these two agrobacterial cultures that were identical apart from containing either VC-LJB2197-1qcz or VC-LLM337-1qcz rc. Due to the selectable herbicide resistance marker, regenerated plants contained the T-DNA of VC-LJB2197-1qcz. Only those plants were kept, that also contained the T-DNA of plasmid VC-LLM337-1qcz rc as confirmed by PCR, conducted as described in Example 24, which contains PCR protocols for both gene expression and copy number analysis. Only plants containing the T-DNA of plasmid VC-LJB2197-1qcz as well as the T-DNA of plasmid VC-LLM337-1qcz rc combined all the genetic elements required for EPA and DHA synthesis in seeds. The genetic elements of VC-LJB2197-1qcz and the function of each element were listed in Table 1. The genetic elements of VC-LLM337-1qcz rc and the function of each element were listed in Table 4. For convenience, all enzymes expressed in seeds of plants carrying both T-DNA of VC-LJB2197-1qcz and VC-LLM337-1qcz rc that were required for EPA and DHA synthesis are additionally listed on Table 35.

TABLE 35

Combined list of genes essential of EPA and DHA synthesis carried by the T-DNAs of plasmids VC-LJB2197-1qcz and VC-LLM337-1qcz rc.

| Genes encoding enzmyes for EPA and DHA synthesis | Plasmid containing T-DNA with the gene | Length | Enzymatic function and source of encoded protein |
|---|---|---|---|
| c-d12Des(Ps_GA) | VC-LJB2197-1qcz | 1196 | Delta-12 desaturase from *Phythophthora sojae* |
| c-d6Des(Ot_febit) | VC-LJB2197-1qcz | 1370 | Delta-6 desaturase from *Ostreococcus tauri* |
| c-d6Elo(Pp_GA2) | VC-LJB2197-1qcz | 872 | Delta-6 elongase from *Physcomitrella patens* |
| c-d6Elo(Tp_GA2) | VC-LJB2197-1qcz | 818 | Delta-6 elongase from *Thalassiosira pseudonana* |
| c-d5Des(Tc_GA2) | VC-LJB2197-1qcz | 1319 | Delta-5 desaturase from *Thraustochytrium* sp. ATCC21685 |
| c-o3Des(Pi_GA2) | VC-LLM337-1qcz rc | 1085 | Omega-3-desaturase from *Phythophthora infestans* |
| c-o3Des(Pir_GA) | VC-LLM337-1qcz rc | 1091 | Omega-3 desaturase from *Pythium irregulare* |
| c-d5Elo(Ot_GA3) | VC-LLM337-1qcz rc | 902 | Delta-5 elongase from *Ostreococcus tauri* |
| c-d4Des(Eg_GA) | VC-LLM337-1qcz rc | 1625 | Delta-4 desaturase from *Euglena gracilis* |
| c-d4Des(Tc_GA) | VC-LLM337-1qcz rc | 1559 | Delta-4 desaturase from *Thraustochytrium* sp. |

A. Fatty Acid Profiles, Copy Number Measurements, and Phenotypic Observations of T1 Plants Carrying T-DNAs of Plasmids VC-LJB2197-1qcz and VC-LLM337-1qcz Rc Cultivated in Greenhouses During Winter The data on Table 39 indicate that the integration of these two T-DNA's (VC-LJB2197-1qcz and VC-LLM337-1qcz rc), has occurred in such a way as to introduce copy number variation of individual genes on a given T-DNA (indicating truncations and deletions along with multiple copies being inserted). For example the event LAMABL on Table 39 was segregating for a single copy of AHAS (homozygous), two copies of j-t-StCAT_p2_p-LuPXR (homozygous), possibly three copies of c-d6Elo(Pp_GA) likely homozygous, though it could be three copies which are not homozygous for all three, and three copies of j-i-Atss18_c-d6Elo(Pp_GA2) (homozygous for all three). Data on Table 42 to Table 45 for fatty acid profile indicates some variation among the events, though not large differences. The highest event average for both DHA and EPA for the events listed on Table 41 was LAMRHL which has DHA of 1.9 and EPA of 10.5 with respect to percent of the total fatty acid content of the seed and contains what was likely a single copy of the T-DNA of VC-LJB2197-1qcz still segregating, while VC-LLM337-1qcz rc seems to be a single copy homozygous insertion. The event, LANMGC, with the lowest levels of EPA and DHA combined, contained EPA of 3.7 and 0.8 for DHA with respect to percent of the total fatty acid content of the seed. LANMGC appeared to be homozygous single copy for VC-LJB2197 and carried at least two separate integrations of VC-LLM337. For the highest single plant level of EPA and DHA, event LAMRHL had 5 percent of DHA and 13.7 percent of EPA with respect to percentage of total fatty acids in the seed, Table 43. The data indicate that the location of the insertion site is important for EPA and DHA accumulation in this combination of constructs. As seen in previous examples, comparison of single copy insertions versus double copy insertions revealed that between single copy and double copy containing plants there was an increase in VLC-PUFA levels, but between double and triple copy containing plants there was less distinction. Table 46 displays phenotypic scoring/assessment and shows some small differences in aerial phenotype among events and between the transformed plants and untransformed reference.

TABLE 40

Copy number measurement of T1 plants cultivated in the greenhouse of canola events containing the T-DNAs of plasmids VC-LJB2197-1qcz and VC-LLM337-1qcz rc. The events are indicated in the first column, along with the number of T1 plants that where measured per event. The T1 plants underwent a selection from 250 segregating T1 seedlings using half-kernel analysis, where the correlation of VCL-PUFA levels with copy number was employed to select for homozygous plants, or in the case of multilocus events to selecect for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

Copy number assays targeting the T-DNA of VC-LJB2197-1qcz. Assays are listed according to the position of the assay target along the T-DNA, with target c-AHAS located near the left T-DNA border and target j-i-Atss18_c-d6Elo(Pp_GA2) near the right T-DNA border. Copy number results obtained on the T0 plants are indicated in parentheses. Homozygosity was indicated if the average result of the selected T1 plants was about two fold higher than the T0 generation.

| Event | c-AHAS | j-t-E9-p3-2 | c-d6Elo(Tp_GA) | j-t-StCAT_p2_p- | j-t-CaMV_p-LuCnl-2 | c-d6Elo(Pp_GA) | j-i-Atss18_c-o3Des(Pir_GA3) |
|---|---|---|---|---|---|---|---|
| LALHCY (n = 15) | 2.9 (T0: 1.8) | 4.4 | | 4.6 | 3.5 | 1.9 (T0: 1.1) | 2.0 |
| LALIAO (n = 15) | 3 (T0: 1.8) | 2.7 | | 3.3 | 3.6 | 2.8 (T0: 1.9) | 3.1 |

TABLE 40-continued

Copy number measurement of T1 plants cultivated in the greenhouse of canola events containing the T-DNAs of plasmids VC-LJB2197-1qcz and VC-LLM337-1qcz rc. The events are indicated in the first column, along with the number of T1 plants that where measured per event. The T1 plants underwent a selection from 250 segregating T1 seedlings using half-kernel analysis, where the correlation of VCL-PUFA levels with copy number was employed to select for homozygous plants, or in the case of multilocus events to selecect for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

| | | | | | | |
|---|---|---|---|---|---|---|
| LALJKA (n = 15) | 2 (T0: 1.1) | 2.0 | 2.0 | 4.1 | 3.6 (T0: 1.9) | 3.8 |
| LALLTL (n = 11) | 1.7 (T0: 1.8) | 3.5 | 3.5 | 3.1 | 3.2 (T0: 3) | 3.2 |
| LALQAM (n = 15) | 3.4 (T0: 1.9) | 3.3 | 3.3 | 3.1 | 3.3 (T0: 1.9) | 3.3 |
| LALQDS (n = 14) | 2.7 (T0: 2) | 2.8 | 3.6 | 2.3 | 2.3 (T0: 2.2) | 2.3 |
| LALRCQ (n = 14) | 3.2 (T0: 2) | 3.2 | 3.3 | 3.0 | 3.2 (T0: 2.1) | 3.3 |
| LALWKF (n = 14) | 1.9 (T0: 1.2) | 1.9 | 4.8 | 4.8 | 4.7 (T0: 3.2) | 4.8 |
| LAMABL (n = 8) | 1.8 (T0: 1) | 1.9 | 3.6 | 5.8 | 5.2 (T0: 3.7) | 5.6 |
| LAMCKI (n = 10) | 2 (T0: 1) | 3.9 | 3.6 | 2.7 | 2.3 (T0: 1) | 2.0 |
| LAMCLE (n = 14) | 3 (T0: 2) | 3.0 | 4.3 | 4.2 | 4.2 (T0: 2.9) | 4.4 |
| LAMCLF (n = 9) | 1.6 (T0: 1) | 3.3 | 4.1 | 4.7 | 4.4 (T0: 2.8) | 3.8 |
| LAMEUB (n = 15) | 1.9 (T0: 1) | 2.1 | 3.6 | 3.9 | 3.7 (T0: 2.2) | 3.8 |
| LAMEUU (n = 13) | 1.9 (T0: 0.9) | 3.8 | 3.3 | 5.6 | 5.4 (T0: 2.8) | 5.2 |
| LAMFJO (n = 15) | 2 (T0: 1.1) | 2.1 | 2.0 | 2.1 | 2 (T0: 0.9) | 2.0 |
| LAMIRY (n = 10) | 1.9 (T0: 1) | 1.9 | 2.6 | 2.7 | 2.7 (T0: 2) | 2.8 |
| LAMJIC (n = 9) | 1.9 (T0: 1.1) | 1.7 | 1.6 | 2.5 | 1.8 (T0: 1) | 1.8 |
| LAMPJB (n = 13) | 2.8 (T0: 2) | 2.9 | 3.6 | 4.4 | 4.1 (T0: 3) | 4.1 |
| LAMQDL (n = 14) | 2 (T0: 1) | 2.1 | 2.3 | 2.6 | 2.3 (T0: 1) | 2.0 |
| LAMQNE (n = 14) | 2.6 (T0: 1.1) | 2.6 | 2.7 | 2.8 | 2.8 (T0: 1.3) | 2.5 |
| LAMQSF (n = 14) | 3.5 (T0:: 2.1) | 4.5 | 3.8 | 4.7 | 4.2 (T0: 3.2) | 4.0 |
| LAMRCO (n = 14) | 2.8 (T0: 1.9) | 3.7 | 6.6 | 6.5 | 6 (T0: 4.1) | 5.5 |
| LAMRDS (n = 15) | 3.2 (T0: 1.9) | 3.2 | 3.0 | 3.6 | 3 (T0: 1.8) | 3.0 |
| LAMRHL (n = 14) | 2 (T0: 1.3) | 2.2 | 3.2 | 2.8 | 2.1 (T0: 1.5) | 1.9 |
| LAMRJK (n = 15) | 3 (T0: 2) | 3.0 | 2.9 | 1.3 | 1.2 (T0: 0.9) | 1.0 |
| LAMRNQ (n = 9) | 2.2 (T0: 1.9) | 2.1 | 2.2 | 2.3 | 2.3 (T0: 2.1) | 2.1 |
| LAMVUB (n = 15) | 2.1 (T0: 1.1) | 2.1 | 2.1 | 2.7 | 2.1 (T0: 1) | 2.1 |
| LAMYDP (n = 14) | 3.9 (T0: 2) | 4.0 | 3.7 | 4.2 | 3.8 (T0: 1.9) | 3.9 |
| LANBCH (n = 14) | 3.5 (T0: 1.9) | 3.2 | 3.3 | 4.0 | 3.5 (T0: 2) | 3.4 |
| LANCEG (n = 4) | 4 (T0: 2.1) | 4.0 | 3.5 | 5.9 | 5.4 (T0: 2.9) | 3.6 |
| LANCOX (n = 10) | 2.2 (T0: 1) | 2.5 | 2.2 | 5.4 | 5.1 (T0: 4.3) | 4.5 |
| LANFEF (n = 15) | 2.1 (T0: 1.1) | 2.0 | 2.3 | 2.6 | 2.1 (T0: 1) | 2.1 |
| LANMGC (n = 15) | 4.2 (T0: 1.9) | 4.0 | 4.1 | 4.7 | 4.2 (T0: 2) | 4.2 |
| LANMOM (n = 10) | 1.4 (T0: 1.2) | 1.4 | 3.0 | 2.7 | 2 (T0: 1.1) | 1.5 |
| LANPMZ (n = 13) | 2.1 (T0: 1.1) | 2.1 | 2.0 | 2.3 | 2.2 (T0: 1) | 2.2 |
| LANTLE (n = 15) | 2.7 (T0: 2) | 2.8 | 2.7 | 3.3 | 2.8 (T0: 2) | 3.0 |
| LANTSP (n = 12) | 1.4 (T0: 1) | 1.3 | 2.9 | 3.7 | 3 (T0: 1.9) | 3.0 |
| LANUCB (n = 14) | 2 (T0: 1.1) | 2.1 | 4.6 | 4.5 | 3.5 (T0: 2.1) | 3.1 |
| LAOBGQ (n = 15) | 1.4 (T0: 1) | 1.4 | 6.1 | 5.2 | 4 (T0: 2.8) | 4.2 |
| LAOHLR (n = 14) | 1.9 (T0: 1.2) | 4.9 | 4.0 | 4.3 | 3.7 (T0: 2) | 3.1 |
| LAOJAT (n = 15) | 2.2 (T0: 1.9) | 3.4 | 3.2 | 3.8 | 3.4 (T0: 3) | 3.3 |

TABLE 40-continued

Copy number measurement of T1 plants cultivated in the greenhouse of canola events containing the T-DNAs of plasmids VC-LJB2197-1qcz and VC-LLM337-1qcz rc. The events are indicated in the first column, along with the number of T1 plants that where measured per event. The T1 plants underwent a selection from 250 segregating T1 seedlings using half-kernel analysis, where the correlation of VCL-PUFA levels with copy number was employed to select for homozygous plants, or in the case of multilocus events to seleecct for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

| | | | | | | |
|---|---|---|---|---|---|---|
| LAOKLP (n = 15) | 2.1 (T0: 0.8) | 2.1 | 2.1 | 2.5 | 2.2 (T0: 1) | 2.1 |
| LAOKTE (n = 15) | 3 (T0: 2) | 2.8 | 3.5 | 3.5 | 3.3 (T0: 2.1) | 3.2 |
| LAPKLS (n = 12) | 3.4 (T0: 2.1) | 3.1 | 3.6 | 4.2 | 3.1 (T0: 2.1) | 3.2 |
| LAPKXM (n = 15) | 3.2 (T0: 1.8) | 3.2 | 3.8 | 4.2 | 3.3 (T0: 2) | 3.4 |
| LAPKZJ (n = 15) | 3.3 (T0: 1.4) | 3.2 | 3.6 | 4.3 | 3.2 (T0: 1.9) | 3.3 |
| LAPWJD (n = 14) | 2.1 (T0: 1.1) | 2.0 | 2.3 | 2.8 | 2.1 (T0: 1) | 2.1 |
| LAPWLP (n = 14) | 1.3 (T0: 1.1) | 1.2 | 3.1 | 3.4 | 2.8 (T0: 1.9) | 2.9 |
| LAQYTA (n = 15) | 4.5 (T0: 2.8) | 5.1 | 5.0 | 3.2 | 2.6 (T0: 2.1) | 2.8 |
| LAQYUT (n = 15) | 4.3 (T0: 1.9) | 3.9 | 4.6 | 4.3 | 3 (T0: 2) | 2.8 |
| LAQYWQ (n = 15) | 2.6 (T0: 1.2) | 2.8 | 5.6 | 5.9 | 4.5 (T0: 3) | 4.6 |
| LAQZME (n = 12) | 1.4 (T0: 1.2) | 1.3 | 3.7 | 4.4 | 3.8 (T0: 2.3) | 4.0 |

Copy number assays targeting the T-DNA of VC-LLM337-1qcz rc. Assays are listed according to the position of the assay target along the T-DNA, with target j-t-PvARC-p3 located near the left T-DNA border and target c-d4Des(Eg_GA) near the right T-DNA border. Copy number results obtained on the T0 plants are indicated in parentheses. Homozygosity was indicated if the average result of the selected T1 plants was about two fold higher than the T0 generation.

| Event | j-t-PvARC-p3 | c-d4Des(Tc_GA) | j-i-Atss15_c-c-o3Des(Pi_GA2) | c-o3Des(Pir_GA) | j-p-VfSBPperm3-c-o3Des(Pir_GA) | j-i-Atss1_c-d5Elo(Ot_GA3) | c-d4Des-(Eg_GA) |
|---|---|---|---|---|---|---|---|
| LALHCY (n = 15) | 2.9 | 2.9 (T0: 2.1) | (T0: 2.6) | (T0: 2.1) | 4.5 | | 3.0 |
| LALIAO (n = 15) | 3.2 | 2.8 (T0: 2) | (T0: 2.2) | (T0: 1.9) | 2.9 | | 1.5 |
| LALJKA (n = 15) | 3.5 | 3.8 (T0: 2) | (T0: 1.9) | | 4.0 | | 5.5 |
| LALLTL (n = 11) | 2.3 | 2.4 (T0: 2) | (T0: 1.9) | | 2.3 | | 2.8 |
| LALQAM (n = 15) | 2.9 | 3.1 (T0: 2) | (T0: 2.1) | | 1.6 | | 1.6 |
| LALQDS (n = 14) | 2.8 | 2.9 (T0: 2) | (T0: 1.9) | | 4.0 | | 2.8 |
| LALRCQ (n = 14) | 3.0 | 3.2 (T0: 2.1) | (T0: 2.2) | | 4.4 | | 4.3 |
| LALWKF (n = 14) | 1.4 | 1.3 (T0: 1) | (T0: 1) | | 1.3 | | 1.3 |
| LAMABL (n = 8) | 1.9 | 1.8 (T0: 1) | (T0: 1) | (T0: 1.2) | 1.8 | | 3.5 |
| LAMCKI (n = 10) | 3.8 | 4 (T0: 1.9) | (T0: 2.1) | (T0: 1.8) | 3.9 | | 3.9 |
| LAMCLE (n = 14) | 2.5 | 2.4 (T0: 2) | (T0: 2) | (T0: 2.1) | 3.4 | | 1.3 |
| LAMCLF (n = 9) | 2.2 | 1.8 (T0: 2.1) | (T0: 1.9) | (T0: 1.4) | 1.8 | | 1.8 |
| LAMEUB (n = 15) | 1.3 | 1.2 (T0: 1) | (T0: 1) | | 1.2 | | 1.1 |
| LAMEUU (n = 13) | 3.1 | 3.8 (T0: 1.9) | (T0: 1.9) | | 3.7 | | 3.7 |
| LAMFJO (n = 15) | 1.1 | 1.1 (T0: 0.5) | (T0: 0.8) | | 1.2 | | 1.1 |
| LAMIRY (n = 10) | 1.7 | 2 (T0: 2.3) | (T0: 2) | | 3.1 | | 2.1 |
| LAMJIC (n = 9) | 2.3 | 1.8 (T0: 1) | (T0: 1) | | 1.8 | | 1.8 |
| LAMPJB (n = 13) | 2.6 | 2.8 (T0: 2.1) | (T0: 1) | (T0: 1.8) | 2.8 | | 2.6 |
| LAMQDL (n = 14) | 0.0 | 2.6 (T0: 2) | (T0: 1) | (T0: 1) | 1.3 | | 1.3 |
| LAMQNE (n = 14) | 2.0 | 1.5 (T0: 1.1) | (T0: 0.9) | (T0: 1.9) | 4.0 | | 4.2 |
| LAMQSF (n = 14) | 2.9 | 3.7 (T0: 3.9) | (T0: 4.2) | (T0: 2.2) | 3.6 | | 3.6 |
| LAMRCO (n = 14) | 1.8 | 1.3 (T0: 1.1) | (T0: 1) | (T0: 2.1) | 3.9 | | 2.5 |
| LAMRDS (n = 15) | 3.0 | 3 (T0: 2) | (T0: 1.9) | (T0: 1.7) | 3.1 | | 2.6 |
| LAMRHL (n = 14) | 4.1 | 3.8 (T0: 2.7) | (T0: 1.3) | (T0: 1.3) | 1.9 | | 2.0 |
| LAMRJK (n = 15) | 3.0 | 4.5 (T0: 2.9) | (T0: 1.9) | (T0: 1.7) | 2.9 | | 2.7 |
| LAMRNQ (n = 9) | 2.5 | 2 (T0: 1.9) | (T0: 2) | (T0: 1.9) | 2.0 | | 2.7 |
| LAMVUB (n = 15) | 0.6 | 0.8 (T0: 0.8) | (T0: 0.9) | | 1.1 | | 0.8 |
| LAMYDP (n = 14) | 3.2 | 3.4 (T0: 2.1) | (T0: 1.9) | (T0: 1.7) | 3.3 | | 3.2 |

TABLE 40-continued

Copy number measurement of T1 plants cultivated in the greenhouse of canola events containing the T-DNAs of plasmids VC-LJB2197-1qcz and VC-LLM337-1qcz rc. The events are indicated in the first column, along with the number of T1 plants that where measured per event. The T1 plants underwent a selection from 250 segregating T1 seedlings using half-kernel analysis, where the correlation of VCL-PUFA levels with copy number was employed to select for homozygous plants, or in the case of multilocus events to seleceet for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

| | | | | | | |
|---|---|---|---|---|---|---|
| LANBCH (n = 14) | 3.5 | 3 (T0: 1.8) | (T0: 2) | | 3.3 | 3.3 |
| LANCEG (n = 4) | 3.6 | 4.1 (T0: 2) | (T0: 2) | | 4.1 | 1.9 |
| LANCOX (n = 10) | 1.7 | 1.7 (T0: 1) | (T0: 1.1) | | 1.8 | 2.6 |
| LANFEF (n = 15) | 1.0 | 0.7 (T0: 1.1) | (T0: 1) | (T0: 1.8) | 2.9 | 2.9 |
| LANMGC (n = 15) | 2.2 | 3.8 (T0: 1.9) | (T0: 2) | | 4.0 | 6.0 |
| LANMOM (n = 10) | 3.5 | 2.9 (T0: 1.9) | (T0: 1.9) | | 2.9 | 4.8 |
| LANPMZ (n = 13) | 2.0 | 2.1 (T0: 1.1) | (T0: 1.1) | | 2.1 | 1.9 |
| LANTLE (n = 15) | 2.5 | 2.2 (T0: 2) | (T0: 1.9) | | 2.3 | 2.3 |
| LANTSP (n = 12) | 0.6 | 1.5 (T0: 0.9) | (T0: 1.6) | | 2.5 | 3.3 |
| LANUCB (n = 14) | 1.1 | 0.9 (T0: 2.1) | (T0: 2.8) | | 2.3 | 2.3 |
| LAOBGQ (n = 15) | 1.6 | 2.7 (T0: 1.8) | (T0: 2.1) | (T0: 1.8) | 2.8 | 4.0 |
| LAOHLR (n = 14) | 2.1 | 1.7 (T0: 1.1) | (T0: 1) | | 1.7 | 1.7 |
| LAOJAT (n = 15) | 2.3 | 2.2 (T0: 1.9) | (T0: 1.9) | (T0: 1.9) | 2.3 | 1.2 |
| LAOKLP (n = 15) | 1.4 | 1.2 (T0: 0.7) | (T0: 1) | (T0: 0.6) | 1.2 | 1.2 |
| LAOKTE (n = 15) | 3.0 | 2.4 (T0: 2) | (T0: 1.9) | (T0: 2.1) | 2.5 | 2.4 |
| LAPKLS (n = 12) | 2.5 | 1.9 (T0: 2) | (T0: 2.1) | | 2.0 | 2.1 |
| LAPKXM (n = 15) | 3.7 | 2.9 (T0: 1.9) | (T0: 1.9) | | 3.6 | 0.0 |
| LAPKZJ (n = 15) | 2.0 | 1.6 (T0: 2) | (T0: 1.9) | | 1.7 | 1.6 |
| LAPWJD (n = 14) | 2.4 | 2 (T0: 1) | (T0: 1) | | 2.2 | 2.1 |
| LAPWLP (n = 14) | 0.0 | 1.3 (T0: 1) | (T0: 1.1) | | 2.3 | 2.3 |
| LAQYTA (n = 15) | 2.4 | 2.2 (T0: 1.9) | (T0: 2) | (T0: 2.4) | 3.2 | 3.3 |
| LAQYUT (n = 15) | 3.6 | 2.8 (T0: 1.6) | (T0: 1.9) | (T0: 0.6) | 3.0 | 4.3 |
| LAQYWQ (n = 15) | 3.2 | 2.7 (T0: 2) | (T0: 1.9) | (T0: 2.2) | 2.6 | 1.4 |
| LAQZME (n = 12) | 1.8 | 1.4 (T0: 1.1) | (T0: 1.2) | (T0: 1.2) | 1.4 | 1.3 |

TABLE 41

Copy number measurement of T1 plants cultivated in the greenhouse of canola events containing the T-DNAs of plasmids VC-LJB2197-1qcz and VC-LLM337-1qcz rc. Plants of all events combined have been grouped into the categories indicated in the first column; sc: all T1 plants where the average of all copy number assays listed in this table was 1.51-2.49, dc: all T1 plants where the average of all copy number assays listed in this table was 3.51-4.49, tc: all T1 plants where the average of all copy number assays listed in this table was 5.51-6.49. The number of T1 plants fullfilling these criteria are displayed in parentheses.

Copy number assays targeting the T-DNA of VC-LJB2197-1qcz. Assays are listed according to the position of the assay target along the T-DNA, with assay A1 located near the left T-DNA border and assay A13 near the right T-DNA border. Copy number results obtained on the T0 plants are indicated in parentheses. Homozygosity was indicated if the average result of the selected T1 plants was about two fold higher than the T0 generation.

| Event | c-AHAS | j-t-E9-p3-2 | c-d6Elo (Tp_GA) | j-t-StCAT_p2_p- | j-t-CaMV_p-LuCnl- | c-d6Elo (Pp_GA) | j-i-Atss18_c-d6Elo(Pp_GA2) |
|---|---|---|---|---|---|---|---|
| sc (n = 296) | 1.9 | 2.1 | 2.6 | 2.7 | 2.4 | 2.3 | |
| dc (n = 198) | 3.4 | 3.7 | 4.2 | 4.8 | 4.2 | 4.2 | |
| tc (n = 2) | 4.0 | 5.6 | 7.6 | 7.5 | 7.1 | 6.3 | |

TABLE 41-continued

Copy number measurement of T1 plants cultivated in the greenhouse of canola events containing the T-DNAs of plasmids VC-LJB2197-1qcz and VC-LLM337-1qcz rc. Plants of all events combined have been grouped into the categories indicated in the first column; sc: all T1 plants where the average of all copy number assays listed in this table was 1.51-2.49, dc: all T1 plants where the average of all copy number assays listed in this table was 3.51-4.49, tc: all T1 plants where the average of all copy number assays listed in this table was 5.51-6.49. The number of T1 plants fullfilling these criteria are displayed in parentheses.

Copy number assays targeting the T-DNA of VC-LJB2197-1qcz. Assays are listed according to the position of the assay target along the T-DNA, with assay A1 located near the left T-DNA border and assay A13 near the right T-DNA border. Copy number results obtained on the T0 plants are indicated in parentheses. Homozygosity was indicated if the average result of the selected T1 plants was about two fold higher than the T0 generation.

| Event | j-t-PvARC-p3 | c-d4Des (Tc_GA) | c- | j-i-Atss15_c-o3Des(Pi_GA2) | c-o3Des (Pir_GA) | j-p-VfSBPperm3_c-o3Des(Pir_GA) | j-i-Atss1_c-d5Elo(Ot_GA3) | c-d4Des (Eg_GA) |
|---|---|---|---|---|---|---|---|---|
| sc (n = 296) | 1.5 | 1.6 | | | | 1.8 | | 1.7 |
| dc (n = 198) | 3.2 | 3.4 | | | | 3.8 | | 3.6 |
| tc (n = 2) | 4.6 | 4.4 | | | | 5.9 | | 4.7 |

TABLE 42

Fatty acid profiles of T2 seeds harvested from T1 cultivated in the greenhouse of canola events containing the T-DNAs of plasmids VC-LJB2197-1qcz and VC-LLM337-1qcz rc The events are indicated in the first column, along with the number of T2 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LALHCY (n = 15) | 4.9 ± 0.1 | 0.3 ± 0 | 0 ± 0 | 4 ± 0.2 | .7 ± 1 | 32 ± 0.9 | 1.2 ± 0.1 | 4.2 ± 0.4 | 2.2 ± 0.2 |
| LALIAO (n = 15) | 5 ± 0.2 | 0.2 ± 0 | 0 ± 0 | 2.9 ± 0.4 | 26.8 ± 3.4 | 30.8 ± 1.6 | 0.6 ± 0.2 | 5.5 ± 0.9 | 0.9 ± 0.4 |
| LALJKA (n = 15) | 5.4 ± 0.2 | 0.3 ± 0 | 0 ± 0 | 2.7 ± 0.5 | 25.3 ± 2.2 | 36.4 ± 1.1 | 0.6 ± 0.1 | 5.7 ± 0.5 | 2.2 ± 0.3 |
| LALLTL (n = 11) | 5 ± 0.2 | 0.3 ± 0 | 0 ± 0 | 3.6 ± 0.3 | 28.5 ± 4.4 | 31.5 ± 1.1 | 0.8 ± 0.2 | 4.6 ± 0.5 | 1.3 ± 0.4 |
| LALQAM (n = 15) | 5.4 ± 0.8 | 0.3 ± 0.1 | 0 ± 0 | 3.8 ± 0.2 | 23.3 ± 1.4 | 32.7 ± 1 | 0.5 ± 0.2 | 3.8 ± 0.3 | 1 ± 0.4 |
| LALQDS (n = 14) | 5 ± 0.1 | 0.3 ± 0 | 0 ± 0 | 3.2 ± 0.4 | 29.1 ± 2.4 | 35.7 ± 1.1 | 0.6 ± 0.1 | 6.2 ± 0.6 | 1 ± 0.2 |
| LALRCQ (n = 14) | 5.1 ± 0.1 | 0.3 ± 0 | 0 ± 0 | 4 ± 0.5 | 23 ± 1.1 | 33.2 ± 1.2 | 1 ± 0.2 | 3.5 ± 0.5 | 2.3 ± 0.2 |
| LALWKF (n = 14) | 5.3 ± 0.1 | 0.3 ± 0.1 | 0 ± 0 | 3.7 ± 0.3 | 26.7 ± 6.7 | 27.6 ± 3.6 | 1.3 ± 0.4 | 3.3 ± 0.3 | 2.2 ± 0.7 |
| LAMABL (n = 8) | 4.8 ± 0.2 | 0.3 ± 0 | 0 ± 0 | 3.3 ± 0.5 | 27.8 ± 6.3 | 30 ± 3.8 | 1.4 ± 0.2 | 3.7 ± 0.5 | 2.7 ± 0.7 |
| LAMCKI (n = 10) | 5.1 ± 0.1 | 0.2 ± 0 | 0 ± 0 | 3.5 ± 0.2 | 26.4 ± 0.7 | 33.8 ± 0.5 | 1.1 ± 0 | 4.2 ± 0.2 | 1.8 ± 0.2 |
| LAMCLE (n = 14) | 4.9 ± 0.2 | 0.2 ± 0.1 | 0 ± 0 | 3.4 ± 0.2 | 25.1 ± 2.4 | 32.2 ± 1.6 | 1.1 ± 0.3 | 3.5 ± 0.3 | 2.4 ± 0.6 |
| LAMCLF (n = 9) | 5.1 ± 0.1 | 0.3 ± 0 | 0 ± 0 | 3.6 ± 0.1 | 24.7 ± 3.5 | 28.5 ± 2 | 1.1 ± 0.6 | 2.8 ± 0.5 | 2 ± 0.6 |
| LAMEUB (n = 15) | 5 ± 0.2 | 0.3 ± 0.1 | 0 ± 0 | 3.8 ± 0.5 | 28.4 ± 5.6 | 29.7 ± 2.1 | 0.9 ± 0.3 | 3.4 ± 0.6 | 1.3 ± 0.4 |
| LAMEUU (n = 13) | 5 ± 0.1 | 0.1 ± 0.1 | 0 ± 0 | 3.3 ± 0.4 | 25.8 ± 4.8 | 34.3 ± 1.8 | 1.4 ± 0.3 | 4.2 ± 0.7 | 2.1 ± 0.4 |
| LAMFJO (n = 15) | 5.1 ± 0.7 | 0.2 ± 0.1 | 0 ± 0 | 3.5 ± 0.7 | 26.5 ± 1.9 | 32.9 ± 0.8 | 0.2 ± 0.1 | 4.5 ± 0.4 | 0.4 ± 0.1 |
| LAMIRY (n = 10) | 5 ± 0.2 | 0.3 ± 0 | 0 ± 0 | 3.5 ± 0.3 | 26.9 ± 6.8 | 30.9 ± 2.8 | 0.6 ± 0.1 | 4.6 ± 0.5 | 1.2 ± 0.3 |
| LAMJIC (n = 9) | 5.8 ± 0.4 | 0.2 ± 0.1 | 0 ± 0 | 3.1 ± 0.5 | 28.5 ± 6.6 | 33.1 ± 3.9 | 0.6 ± 0.2 | 5.3 ± 1.2 | 1.3 ± 0.6 |
| LAMPJB (n = 13) | 4.8 ± 0.1 | 0.1 ± 0 | 0 ± 0 | 3.1 ± 0.3 | 24.1 ± 1.7 | 33.6 ± 0.9 | 0.9 ± 0.2 | 3.7 ± 0.5 | 2.2 ± 0.5 |
| LAMQDL (n = 14) | 5 ± 0.5 | 0.2 ± 0 | 0 ± 0 | 2.7 ± 0.4 | 26.4 ± 2.2 | 31.2 ± 1 | 0.2 ± 0 | 5.2 ± 0.6 | 0.4 ± 0.1 |
| LAMQNE (n = 14) | 6.9 ± 1.3 | 0.3 ± 0.1 | 0 ± 0 | 2.7 ± 0.3 | 27.8 ± 2.6 | 31.8 ± 0.7 | 0.8 ± 0.1 | 4.9 ± 0.6 | 1.3 ± 0.1 |
| LAMQSF (n = 14) | 5.2 ± 0.1 | 0.3 ± 0 | 0 ± 0 | 3.4 ± 0.3 | 24.3 ± 2.7 | 31.5 ± 1.2 | 0.8 ± 0.4 | 4.5 ± 0.7 | 2 ± 0.8 |
| LAMRCO (n = 14) | 5.5 ± 0.6 | 0.3 ± 0.1 | 0 ± 0 | 4.4 ± 0.6 | 23.9 ± 6.8 | 28.4 ± 3.1 | 1.3 ± 0.4 | 2.7 ± 0.4 | 3.4 ± 0.8 |
| LAMRDS (n = 15) | 4.8 ± 0.1 | 0 ± 0 | 0 ± 0 | 3.6 ± 0.4 | 23.4 ± 1.7 | 32.7 ± 1.3 | 1.1 ± 0.2 | 3.4 ± 0.5 | 2.3 ± 0.3 |

TABLE 42-continued

Fatty acid profiles of T2 seeds harvested from T1 cultivated in the greenhouse of canola events containing the T-DNAs of plasmids VC-LJB2197-1qcz and VC-LLM337-1qcz rc The events are indicated in the first column, along with the number of T2 seed batches that were measured per event. Per seed batch a random selection of ~30 seed was measured in two technical repeats.

| | | | | | | | | | |
|---|---|---|---|---|---|---|---|---|---|
| LAMRHL (n = 14) | 6 ± 1 | 0.3 ± 0.1 | 0 ± 0 | 3.5 ± 0.5 | 26.5 ± 6 | 26.2 ± 3.9 | 0.6 ± 0.1 | 3.7 ± 0.8 | 1 ± 0.3 |
| LAMRJK (n = 15) | 4.9 ± 0.2 | 0.1 ± 0 | 0 ± 0 | 3.6 ± 0.4 | 26.4 ± 2.9 | 33 ± 1 | 1 ± 0.2 | 4.1 ± 0.6 | 2 ± 0.4 |
| LAMRNQ (n = 9) | 4.8 ± 0.1 | 0.2 ± 0 | 0 ± 0 | 2.7 ± 0.4 | 29.6 ± 3.8 | 32.2 ± 0.9 | 0.5 ± 0.1 | 5.1 ± 0.8 | 0.9 ± 0.2 |
| LAMVUB (n = 15) | 4.9 ± 0.3 | 0.2 ± 0 | 0 ± 0 | 3.6 ± 0.4 | 24.6 ± 1.9 | 33.4 ± 0.5 | 0.2 ± 0.1 | 4.8 ± 0.4 | 0.4 ± 0.1 |
| LAMYDP (n = 14) | 5.1 ± 0.5 | 0.2 ± 0.1 | 0 ± 0 | 4 ± 0.8 | 23.1 ± 2.3 | 31.7 ± 1.1 | 1.2 ± 0.1 | 4.1 ± 0.5 | 2.4 ± 0.3 |
| LANBCH (n = 14) | 4.7 ± 0.8 | 0.2 ± 0.1 | 0 ± 0 | 3.4 ± 0.4 | 25 ± 3.9 | 32.7 ± 1.5 | 0.8 ± 0.2 | 4.7 ± 0.5 | 1.5 ± 0.5 |
| LANCEG (n = 4) | 4.9 ± 0.1 | 0.1 ± 0.1 | 0 ± 0 | 3.3 ± 0.2 | 23.8 ± 1.2 | 33.2 ± 0.5 | 0.9 ± 0.1 | 3.7 ± 0.4 | 2 ± 0.3 |
| LANCOX (n = 10) | 5.1 ± 0.7 | 0.2 ± 0.1 | 0 ± 0 | 3.1 ± 0.2 | 25 ± 2.5 | 35.5 ± 1.3 | 0.7 ± 0.1 | 4.1 ± 0.3 | 2.1 ± 0.3 |
| LANFEF (n = 15) | 5.1 ± 0.3 | 0.1 ± 0.1 | 0 ± 0 | 3.5 ± 0.4 | 27.2 ± 1 | 34.3 ± 1.1 | 0.2 ± 0.1 | 4.5 ± 0.9 | 0.3 ± 0 |
| LANMGC (n = 15) | 5.6 ± 0.9 | 0.2 ± 0.1 | 0 ± 0 | 4 ± 0.5 | 25.1 ± 1.9 | 33.1 ± 1.8 | 1 ± 0.2 | 4.3 ± 0.3 | 2.1 ± 0.2 |
| LANMOM (n = 10) | 5.4 ± 0.4 | 0.2 ± 0 | 0 ± 0 | 2.8 ± 0.2 | 26.9 ± 3.1 | 31.8 ± 1.3 | 0.8 ± 0.2 | 4.9 ± 0.5 | 1.4 ± 0.4 |
| LANPMZ (n = 13) | 4.8 ± 0.6 | 0.2 ± 0.1 | 0 ± 0 | 3.7 ± 0.3 | 26.2 ± 1.4 | 34.4 ± 1 | 0.3 ± 0.1 | 5 ± 0.4 | 0.5 ± 0.1 |
| LANTLE (n = 15) | 5 ± 0.4 | 0.2 ± 0.1 | 0 ± 0 | 2.4 ± 0.4 | 26.7 ± 4 | 32.7 ± 1.2 | 0.4 ± 0.3 | 6.1 ± 0.8 | 1 ± 0.5 |
| LANTSP (n = 12) | 4.9 ± 0.2 | 0.2 ± 0 | 0.1 ± 0 | 3.3 ± 0.3 | 35.9 ± 6.9 | 26.8 ± 4 | 0.8 ± 0.2 | 4.6 ± 0.9 | 1.1 ± 0.4 |
| LANUCB (n = 14) | 5 ± 0.5 | 0.3 ± 0 | 0 ± 0 | 2.9 ± 0.4 | 28.2 ± 4.5 | 28.8 ± 2.2 | 1.5 ± 0.6 | 3.8 ± 0.8 | 2.7 ± 1.5 |
| LAOBGQ (n = 15) | 5.2 ± 0.4 | 0.2 ± 0.1 | 0 ± 0 | 3.5 ± 0.3 | 31.8 ± 7.9 | 29.2 ± 4.2 | 1.2 ± 0.4 | 3.9 ± 0.6 | 2.5 ± 0.7 |
| LAOHLR (n = 14) | 5.1 ± 0.2 | 0.2 ± 0 | 0 ± 0 | 3.5 ± 0.3 | 26.5 ± 6.1 | 33 ± 2.7 | 1.1 ± 0.2 | 3.7 ± 0.7 | 2.1 ± 0.4 |
| LAOJAT (n = 15) | 5.1 ± 0.5 | 0.1 ± 0.1 | 0 ± 0 | 2.8 ± 0.7 | 28.7 ± 4 | 34 ± 1.8 | 0.6 ± 0.1 | 5 ± 0.8 | 1.3 ± 0.4 |
| LAOKLP (n = 15) | 4.7 ± 0.4 | 0.2 ± 0 | 0 ± 0 | 3.1 ± 0.2 | 26 ± 2.2 | 32.5 ± 1.3 | 0.2 ± 0 | 5.2 ± 0.5 | 0.3 ± 0 |
| LAOKTE (n = 15) | 4.7 ± 0.3 | 0.2 ± 0.1 | 0.1 ± 0 | 2.8 ± 0.4 | 27.1 ± 7.8 | 31.4 ± 2.3 | 0.5 ± 0.3 | 5.5 ± 1.7 | 0.9 ± 0.6 |
| LAPKLS (n = 12) | 5.2 ± 0.3 | 0.2 ± 0.1 | 0 ± 0 | 3.7 ± 0.5 | 23.8 ± 1.9 | 33.6 ± 0.7 | 0.9 ± 0.1 | 4.1 ± 0.5 | 1.9 ± 0.4 |
| LAPKXM (n = 15) | 4.6 ± 0.3 | 0.2 ± 0 | 0 ± 0 | 3.2 ± 0.3 | 26.1 ± 2 | 32 ± 0.9 | 0.7 ± 0.2 | 5.2 ± 0.5 | 1.2 ± 0.4 |
| LAPKZJ (n = 15) | 5.1 ± 0.5 | 0.1 ± 0.1 | 0 ± 0 | 3.6 ± 0.4 | 24.6 ± 1.9 | 31.8 ± 1.6 | 0.4 ± 0.2 | 4.7 ± 0.7 | 0.6 ± 0.3 |
| LAPWJD (n = 14) | 5.1 ± 0.4 | 0.1 ± 0.1 | 0 ± 0 | 3.6 ± 0.1 | 7 ± 0.9 | 34 ± 0.7 | 0.3 ± 0.1 | 4.9 ± 0.2 | 0.5 ± 0.1 |
| LAPWLP (n = 14) | 4.5 ± 0.4 | 0.2 ± 0 | 0 ± 0 | 3 ± 0.3 | 32.5 ± 6.3 | 23.1 ± 3.7 | 0.5 ± 0.3 | 5.1 ± 0.8 | 0.5 ± 0.3 |
| LAQYTA (n = 15) | 5.6 ± 0.2 | 0 ± 0 | 0 ± 0 | 3.3 ± 0.3 | 24.7 ± 1.3 | 31.5 ± 1.3 | 1.3 ± 0.2 | 4.1 ± 0.5 | 2.1 ± 0.3 |
| LAQYUT (n = 15) | 5.5 ± 0.3 | 0.2 ± 0 | 0 ± 0 | 3.3 ± 0.3 | 26.6 ± 4 | 33.4 ± 1.5 | 1 ± 0.2 | 4 ± 0.6 | 2.2 ± 0.5 |
| LAQYWQ (n = 15) | 5.6 ± 0.2 | 0.2 ± 0.1 | 0 ± 0 | 3.9 ± 0.5 | 26.9 ± 6 | 30.3 ± 2.1 | 1.3 ± 0.4 | 4.1 ± 0.6 | 2.5 ± 0.8 |
| LAQZME (n = 12) | 5.3 ± 0.7 | 0.2 ± 0.1 | 0 ± 0 | 2.5 ± 0.2 | 33.3 ± 6.9 | 24.1 ± 4.6 | 0.5 ± 0.1 | 4.1 ± 0.5 | 0.9 ± 1 |

| Event | 18:4 n-3 | 20:0 | 20:1 n-9 | 20:2 n-6 | 20:3 n-3 | 20:3 n-6 | 20:4 n-3 | 20:4 n-6 | 20:5 n-3 |
|---|---|---|---|---|---|---|---|---|---|
| LALHCY (n = 15) | 0.3 ± 0 | 0.8 ± 0 | 0.3 ± 0.3 | 0.2 ± 0 | 0.1 ± 0 | 4.4 ± 1.4 | 2.5 ± 0.7 | 2.9 ± 0.4 | 8.1 ± 0.8 |
| LALIAO (n = 15) | 0.2 ± 0.1 | 0.7 ± 0.1 | 0.8 ± 0.1 | 1.2 ± 0.7 | 0.4 ± 0.3 | 2.5 ± 0.4 | 1.6 ± 0.1 | 3.7 ± 1.3 | 9.9 ± 2.5 |
| LALJKA (n = 15) | 0.5 ± 0.1 | 0.7 ± 0.1 | 0.6 ± 0 | 0.1 ± 0.1 | 0.1 ± 0 | 1.7 ± 1 | 1 ± 0.5 | 2.2 ± 0.5 | 6.9 ± 1.5 |
| LALLTL (n = 11) | 0.2 ± 0 | 0.8 ± 0 | 0.6 ± 0.3 | 0.6 ± 0.2 | 0.2 ± 0.1 | 2.6 ± 1 | 1.3 ± 0.6 | 6 ± 2.4 | 6.2 ± 1.5 |
| LALQAM (n = 15) | 0.1 ± 0 | 0.8 ± 0 | 0.7 ± 0.1 | 1.5 ± 0.9 | 0.4 ± 0.2 | 3.5 ± 0.8 | 1.5 ± 0.2 | 6.4 ± 1.4 | 8 ± 1.3 |
| LALQDS (n = 14) | 0.2 ± 0 | 0.8 ± 0.1 | 0.5 ± 0.2 | 0.4 ± 0.2 | 0.2 ± 0.1 | 1.5 ± 0.5 | 1 ± 0.2 | 2.4 ± 0.6 | 6.7 ± 0.7 |

TABLE 42-continued

Fatty acid profiles of T2 seeds harvested from T1 cultivated in the greenhouse of canola events containing the T-DNAs of plasmids VC-LJB2197-1qcz and VC-LLM337-1qcz rc The events are indicated in the first column, along with the number of T2 seed batches that were measured per event. Per seed batch a random selection of ~30 seed was measured in two technical repeats.

| | | | | | | | | | | |
|---|---|---|---|---|---|---|---|---|---|---|
| LALRCQ (n = 14) | 0.2 ± 0 | 0.8 ± 0.1 | 0.6 ± 0 | 0.2 ± 0.1 | 0 ± 0 | 5.1 ± 1.6 | 1.7 ± 0.4 | 4.1 ± 0.7 | 6.6 ± 0.9 |
| LALWKF (n = 14) | 0.3 ± 0.1 | 0.8 ± 0 | 0.7 ± 0.1 | 0.6 ± 0.5 | 0.2 ± 0.2 | 2.1 ± 0.5 | 0.9 ± 0.3 | 9.3 ± 2.7 | 8.8 ± 1.5 |
| LAMABL (n = 8) | 0.4 ± 0.1 | 0.8 ± 0.1 | 0.7 ± 0.1 | 0.3 ± 0.1 | 0 ± 0 | 1.3 ± 0.4 | 0.6 ± 0.1 | 7 ± 0.8 | 8.6 ± 1.7 |
| LAMCKI (n = 10) | 0.2 ± 0 | 0.8 ± 0 | 0.6 ± 0 | 0.1 ± 0 | 0 ± 0 | 3.9 ± 0.6 | 1.7 ± 0.2 | 2.9 ± 0.2 | 6.8 ± 0.6 |
| LAMCLE (n = 14) | 0.3 ± 0.1 | 0.8 ± 0 | 0.7 ± 0.1 | 0.4 ± 0.2 | 0 ± 0.1 | 2.3 ± 0.5 | 1 ± 0.2 | 5.8 ± 1.3 | 8.4 ± 1.3 |
| LAMCLF (n = 9) | 0.2 ± 0.1 | 0.8 ± 0 | 0.6 ± 0.1 | 1.4 ± 0.7 | 0.1 ± 0.1 | 2.8 ± 0.7 | 1 ± 0.2 | 9.7 ± 2.2 | 9.4 ± 1 |
| LAMEUB (n = 15) | 0.1 ± 0.1 | 0.9 ± 0.1 | 0.8 ± 0.1 | 1 ± 0.4 | 0.2 ± 0.1 | 2.7 ± 0.3 | 1.1 ± 0.3 | 8.4 ± 2.9 | 7.6 ± 1.9 |
| LAMEUU (n = 13) | 0.2 ± 0.1 | 0.9 ± 0.1 | 0.7 ± 0.1 | 0.2 ± 0.2 | 1.8 ± 1.8 | 1.4 ± 1.5 | 1.2 ± 0.3 | 3.1 ± 0.8 | 7.8 ± 1.1 |
| LAMFJO (n = 15) | 0 ± 0 | 0.9 ± 0.1 | 1 ± 0.1 | 2.2 ± 0.7 | 1.7 ± 1.9 | 3.7 ± 0.6 | 3 ± 0.3 | 4.7 ± 1.8 | 6.2 ± 0.7 |
| LAMIRY (n = 10) | 0.2 ± 0 | 0.8 ± 0 | 0.7 ± 0.2 | 1.1 ± 0.2 | 0.4 ± 0.1 | 2.4 ± 0.4 | 1.4 ± 0.3 | 4.5 ± 0.9 | 9.1 ± 2.1 |
| LAMJIC (n = 9) | 0.2 ± 0.1 | 0.8 ± 0.1 | 0.7 ± 0.1 | 0.5 ± 0.3 | 0.1 ± 0.1 | 2.6 ± 0.4 | 1.3 ± 0.3 | 3.9 ± 1.3 | 6.2 ± 1.8 |
| LAMPJB (n = 13) | 0.3 ± 0.1 | 0.8 ± 0.1 | 0.7 ± 0 | 0.4 ± 0.3 | 0 ± 0 | 2.8 ± 0.4 | 1.2 ± 0.2 | 5.5 ± 2.2 | 8.7 ± 1 |
| LAMQDL (n = 14) | 0.1 ± 0 | 0.7 ± 0.1 | 1 ± 0.1 | 2.8 ± 0.5 | 1 ± 0.2 | 3.7 ± 0.4 | 2.1 ± 0.4 | 4.7 ± 2 | 6.7 ± 1.2 |
| LAMQNE (n = 14) | 0.2 ± 0 | 0.7 ± 0.1 | 0.7 ± 0.1 | 0.4 ± 0.1 | 0.2 ± 0.1 | 4 ± 1.7 | 1.9 ± 0.8 | 2.7 ± 1 | 5.9 ± 1.1 |
| LAMQSF (n = 14) | 0.3 ± 0.1 | 0.8 ± 0.1 | 0.6 ± 0.1 | 0.6 ± 0.2 | 0.2 ± 0.2 | 1.9 ± 0.6 | 1.3 ± 0.5 | 4.1 ± 1.5 | 10.6 ± 1.7 |
| LAMRCO (n = 14) | 0.3 ± 0.1 | 1 ± 0.2 | 0.6 ± 0.1 | 0.4 ± 0.2 | 0.1 ± 0.1 | 3.7 ± 0.8 | 1.3 ± 0.3 | 5.7 ± 1.3 | 8.7 ± 1.7 |
| LAMRDS (n = 15) | 0.2 ± 0 | 0.9 ± 0.1 | 0.7 ± 0 | 0.2 ± 0.1 | 5.4 ± 0.9 | 0 ± 0.1 | 1.2 ± 0.1 | 3.4 ± 0.8 | 8.2 ± 0.7 |
| LAMRHL (n = 14) | 0.2 ± 0.1 | 0.9 ± 0.1 | 0.8 ± 0.2 | 1.6 ± 0.6 | 0.4 ± 0.1 | 3 ± 0.6 | 1.9 ± 0.4 | 4.6 ± 0.8 | 10.5 ± 1.9 |
| LAMRJK (n = 15) | 0.2 ± 0.1 | 0.9 ± 0.1 | 0.7 ± 0.1 | 0 ± 0.1 | 0.5 ± 1.4 | 2.6 ± 1.4 | 1.3 ± 0.3 | 4.4 ± 1.3 | 7.7 ± 1.2 |
| LAMRNQ (n = 9) | 0.1 ± 0 | 0.8 ± 0.1 | 0.9 ± 0 | 1.2 ± 0.2 | 0.3 ± 0.1 | 2.8 ± 0.7 | 1.3 ± 0.3 | 4.6 ± 1.3 | 6 ± 1.2 |
| LAMVUB (n = 15) | 0 ± 0 | 0.9 ± 0.1 | 1 ± 0.1 | 2.8 ± 0.5 | 1 ± 0.2 | 4 ± 0.4 | 2.4 ± 0.3 | 4 ± 1.4 | 6.7 ± 1 |
| LAMYDP (n = 14) | 0.3 ± 0 | 0.9 ± 0.1 | 0.6 ± 0 | 0.3 ± 0.1 | 0 ± 0 | 2.5 ± 0.4 | 1.3 ± 0.3 | 4.1 ± 0.8 | 10.3 ± 1.6 |
| LANBCH (n = 14) | 0.2 ± 0.1 | 0.8 ± 0.1 | 0.7 ± 0.1 | 0.5 ± 0.2 | 0.2 ± 0.1 | 2.3 ± 0.4 | 1.5 ± 0.2 | 3.5 ± 0.5 | 9.2 ± 1.8 |
| LANCEG (n = 4) | 0.3 ± 0 | 0.8 ± 0 | 0.7 ± 0 | 0.2 ± 0.1 | 5.5 ± 0.2 | 0.2 ± 0.1 | 0.7 ± 0.1 | 1.5 ± 0.4 | 10.8 ± 0.4 |
| LANCOX (n = 10) | 0.3 ± 0 | 0.8 ± 0.1 | 0.7 ± 0 | 0 ± 0 | 7.2 ± 2.4 | 0.2 ± 0.1 | 0.6 ± 0.1 | 1.6 ± 0.3 | 7.3 ± 1.5 |
| LANFEF (n = 15) | 0 ± 0 | 0.8 ± 0.1 | 1 ± 0 | 2.5 ± 0.3 | 0.8 ± 0.2 | 3.5 ± 0.5 | 1.6 ± 0.4 | 3.3 ± 1.4 | 5.5 ± 0.5 |
| LANMGC (n = 15) | 0.2 ± 0 | 0.9 ± 0.1 | 0.7 ± 0 | 0.2 ± 0 | 0 ± 0 | 7.9 ± 1.3 | 3.6 ± 0.7 | 1.4 ± 0.5 | 3.7 ± 1.3 |
| LANMOM (n = 10) | 0.2 ± 0.1 | 0.8 ± 0.1 | 0.7 ± 0.1 | 0.6 ± 0.3 | 0.2 ± 0.1 | 3 ± 0.3 | 1.2 ± 0.2 | 3.9 ± 0.5 | 8.6 ± 1.5 |
| LANPMZ (n = 13) | 0.1 ± 0 | 0.9 ± 0 | 0.9 ± 0.1 | 1.5 ± 0.3 | 0.5 ± 0.2 | 3 ± 0.2 | 3 ± 0.3 | 2.7 ± 0.3 | 6.9 ± 0.8 |
| LANTLE (n = 15) | 0.1 ± 0.1 | 0.6 ± 0.1 | 0.8 ± 0.2 | 1.4 ± 1 | 0.5 ± 0.5 | 2.5 ± 0.5 | 1.7 ± 0.4 | 3.9 ± 1.4 | 7.9 ± 1.9 |
| LANTSP (n = 12) | 0.2 ± 0.1 | 0.9 ± 0.1 | 0.9 ± 0.2 | 0.8 ± 0.3 | 0.2 ± 0.1 | 2.1 ± 0.4 | 1.2 ± 0.2 | 3.4 ± 0.9 | 6.6 ± 1.8 |
| LANUCB (n = 14) | 0.4 ± 0.3 | 0.7 ± 0.1 | 0.7 ± 0.1 | 0.5 ± 0.5 | 0.1 ± 0.1 | 2.2 ± 0.7 | 1.1 ± 0.3 | 5.7 ± 1.9 | 9.2 ± 1.4 |
| LAOBGQ (n = 15) | 0.4 ± 0.2 | 0.8 ± 0.1 | 0.7 ± 0.1 | 0.2 ± 0.2 | 0 ± 0 | 2.1 ± 0.9 | 1.1 ± 0.5 | 3.9 ± 0.6 | 7.3 ± 1.5 |
| LAOHLR (n = 14) | 0.2 ± 0 | 0.9 ± 0.1 | 0.7 ± 0.1 | 0.1 ± 0.1 | 0 ± 0 | 4.1 ± 1.6 | 1.4 ± 0.5 | 5.3 ± 0.8 | 6.8 ± 1.2 |
| LAOJAT (n = 15) | 0.1 ± 0.1 | 0.6 ± 0.1 | 0.8 ± 0.1 | 0.7 ± 0.4 | 0.1 ± 0.2 | 1.5 ± 0.5 | 0.9 ± 0.2 | 4.3 ± 0.7 | 7.9 ± 1.3 |
| LAOKLP (n = 15) | 0 ± 0 | 0.8 ± 0 | 1 ± 0 | 2.5 ± 0.7 | 1 ± 0.2 | 3.5 ± 0.4 | 2.1 ± 0.3 | 4.4 ± 1.6 | 6.5 ± 0.9 |
| LAOKTE (n = 15) | 0.1 ± 0.1 | 0.8 ± 0.1 | 0.8 ± 0.1 | 1.2 ± 0.7 | 0.4 ± 0.2 | 2.5 ± 0.8 | 1.6 ± 0.4 | 4.1 ± 2.2 | 8.2 ± 2.9 |

TABLE 42-continued

Fatty acid profiles of T2 seeds harvested from T1 cultivated in the greenhouse of canola events containing the T-DNAs of plasmids VC-LJB2197-1qcz and VC-LLM337-1qcz rc The events are indicated in the first column, along with the number of T2 seed batches that were measured per event. Per seed batch a random selection of ~30 seed was measured in two technical repeats.

| | | | | | | | | | |
|---|---|---|---|---|---|---|---|---|---|
| LAPKLS (n = 12) | 0.2 ± 0.1 | 0.8 ± 0.1 | 0.7 ± 0 | 0.4 ± 0.3 | 0.1 ± 0.1 | 3.1 ± 0.5 | 1.5 ± 0.4 | 6 ± 2.3 | 7.9 ± 1.5 |
| LAPKXM (n = 15) | 0.2 ± 0.1 | 0.8 ± 0.1 | 0.8 ± 0.1 | 0.9 ± 0.7 | 0.3 ± 0.3 | 2.3 ± 0.4 | 1.7 ± 0.2 | 3.1 ± 0.7 | 9.8 ± 2 |
| LAPKZJ (n = 15) | 0 ± 0 | 0.8 ± 0.1 | 0.9 ± 0.2 | 2.1 ± 0.8 | 0.8 ± 0.4 | 3.4 ± 0.5 | 2.1 ± 0.5 | 4.9 ± 2.1 | 7.7 ± 1.1 |
| LAPWJD (n = 14) | 0 ± 0 | 0.8 ± 0.1 | 0.9 ± 0.1 | 1.6 ± 0.4 | 0.6 ± 0.2 | 3.4 ± 0.2 | 2.2 ± 0.2 | 2.5 ± 0.3 | 6.2 ± 0.3 |
| LAPWLP (n = 14) | 0.1 ± 0.1 | 0.8 ± 0.1 | 1.2 ± 0.2 | 2.5 ± 0.9 | 0.9 ± 0.4 | 2.2 ± 0.4 | 1.8 ± 0.4 | 3.5 ± 0.7 | 10 ± 2.3 |
| LAQYTA (n = 15) | 0.1 ± 0.1 | 0.7 ± 0.1 | 0.6 ± 0 | 0.2 ± 0.2 | 0 ± 0 | 3.6 ± 1.6 | 1.6 ± 0.8 | 5.8 ± 2.6 | 8.2 ± 1.4 |
| LAQYUT (n = 15) | 0.2 ± 0.1 | 0.7 ± 0.1 | 0.6 ± 0.1 | 0.1 ± 0.1 | 0 ± 0 | 3.7 ± 2.1 | 1.5 ± 0.8 | 4.1 ± 1.4 | 7.1 ± 1.5 |
| LAQYWQ (n = 15) | 0.3 ± 0.1 | 0.8 ± 0.1 | 0.6 ± 0.1 | 0.2 ± 0.2 | 0 ± 0 | 2.3 ± 1.1 | 1.1 ± 0.6 | 6.5 ± 3 | 7.9 ± 2 |
| LAQZME (n = 12) | 0.2 ± 0.1 | 0.7 ± 0.1 | 1.1 ± 0.4 | 1.3 ± 1.1 | 0.6 ± 0.3 | 2.7 ± 0.2 | 1.8 ± 0.3 | 5.6 ± 0.5 | 8.2 ± 1.2 |

| Event | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|
| LALHCY (n = 15) | 0.3 ± 0 | 0 ± 0 | 1.3 ± 0.1 | 3.1 ± 0.3 | 0 ± 0 | 1.9 ± 0.2 | 1.2 ± 0.5 | |
| LALIAO (n = 15) | 0.3 ± 0.1 | 0 ± 0 | 0.7 ± 0.3 | 3.3 ± 1 | 0 ± 0 | 1.2 ± 0.4 | 0.2 ± 0.3 | 0.6 ± 0.2 |
| LALJKA (n = 15) | 0.3 ± 0 | 0 ± 0 | 1.3 ± 0.2 | 3.4 ± 0.9 | 0 ± 0 | 1.8 ± 0.4 | 0.6 ± 0.5 | |
| LALLTL (n = 11) | 0.3 ± 0 | 0 ± 0 | 1.1 ± 0.4 | 2.4 ± 0.6 | 0 ± 0.1 | 1.3 ± 0.4 | 0.6 ± 0.5 | |
| LALQAM (n = 15) | 0.3 ± 0 | 0 ± 0 | 0.9 ± 0.3 | 2.9 ± 0.7 | 0 ± 0 | 1.6 ± 0.4 | 0.3 ± 0.1 | |
| LALQDS (n = 14) | 0.3 ± 0 | 0 ± 0 | 0.7 ± 0.1 | 2.7 ± 0.3 | 0 ± 0 | 1 ± 0.2 | 0.3 ± 0.1 | |
| LALRCQ (n = 14) | 0.3 ± 0 | 0 ± 0 | 1.9 ± 0.3 | 2.8 ± 0.4 | 0 ± 0 | 1.8 ± 0.3 | 1.1 ± 0.4 | |
| LALWKF (n = 14) | 0.3 ± 0.1 | 0 ± 0 | 0.7 ± 0.3 | 2.9 ± 0.6 | 0 ± 0 | 1.6 ± 0.5 | 0.1 ± 0.1 | |
| LAMABL (n = 8) | 0.3 ± 0 | 0 ± 0 | 1.3 ± 0.3 | 3.2 ± 0.4 | 0 ± 0 | 1.4 ± 0.3 | 0.1 ± 0.1 | |
| LAMCKI (n = 10) | 0.3 ± 0 | 0 ± 0 | 1.2 ± 0.1 | 2.7 ± 0.3 | 0 ± 0 | 1.3 ± 0.1 | 0.9 ± 0.1 | |
| LAMCLE (n = 14) | 0.1 ± 0.1 | 0 ± 0 | 1.8 ± 0.4 | 3.4 ± 0.6 | 0 ± 0 | 1.8 ± 0.5 | 0.1 ± 0.2 | |
| LAMCLF (n = 9) | 0.3 ± 0 | 0 ± 0 | 1 ± 0.3 | 2.8 ± 0.5 | 0 ± 0 | 1.5 ± 0.3 | 0 ± 0.1 | |
| LAMEUB (n = 15) | 0.3 ± 0 | 0 ± 0 | 0.5 ± 0.2 | 2.2 ± 0.7 | 0 ± 0 | 1.2 ± 0.5 | 0.1 ± 0.1 | |
| LAMEUU (n = 13) | 0.2 ± 0.2 | 0 ± 0 | 1.4 ± 0.2 | 3 ± 0.4 | 0 ± 0 | 1.5 ± 0.3 | 0.3 ± 0.3 | |
| LAMFJO (n = 15) | 0.3 ± 0.1 | 0 ± 0 | 0.3 ± 0.2 | 2.2 ± 0.3 | 0 ± 0.1 | 1 ± 0.2 | 0.4 ± 0.3 | |
| LAMIRY (n = 10) | 0.3 ± 0 | 0 ± 0 | 1 ± 0.2 | 3 ± 0.6 | 0 ± 0 | 1.6 ± 0.4 | 0.5 ± 0.1 | |
| LAMJIC (n = 9) | 0.3 ± 0.1 | 0 ± 0 | 0.9 ± 0.3 | 2.6 ± 1 | 0 ± 0 | 1.4 ± 0.4 | 0.4 ± 0.1 | |
| LAMPJB (n = 13) | 0 ± 0.1 | 0 ± 0 | 1.5 ± 0.3 | 3.2 ± 0.4 | 0 ± 0 | 2 ± 0.3 | 0.1 ± 0.3 | |
| LAMQDL (n = 14) | 0.3 ± 0 | 0 ± 0 | 0.4 ± 0.1 | 2.7 ± 0.7 | 0 ± 0 | 0.8 ± 0.2 | 0.4 ± 0.2 | 1.1 ± 0.1 |
| LAMQNE (n = 14) | 0.3 ± 0 | 0 ± 0 | 1.2 ± 0.2 | 2.8 ± 0.6 | 0 ± 0 | 1.2 ± 0.3 | 0.8 ± 0.6 | 0.4 ± 0.1 |
| LAMQSF (n = 14) | 0.3 ± 0 | 0 ± 0 | 1.1 ± 0.2 | 3.6 ± 0.5 | 0 ± 0 | 1.8 ± 0.5 | 0.3 ± 0.3 | |
| LAMRCO (n = 14) | 0.4 ± 0.1 | 0 ± 0 | 1.8 ± 0.4 | 3.3 ± 0.8 | 0 ± 0 | 2.1 ± 0.6 | 0.4 ± 0.2 | 0.4 ± 0.1 |
| LAMRDS (n = 15) | 0.4 ± 0.1 | 0 ± 0 | 2 ± 0.4 | 3.5 ± 0.3 | 0 ± 0 | 1.8 ± 0.3 | 0.5 ± 0.3 | |
| LAMRHL (n = 14) | 0.4 ± 0 | 0 ± 0 | 1 ± 0.3 | 3.9 ± 1 | 0 ± 0 | 1.9 ± 0.5 | 0.3 ± 0.2 | 1.4 ± 0.4 |
| LAMRJK (n = 15) | 0.1 ± 0.2 | 0 ± 0 | 1.3 ± 0.4 | 3.2 ± 0.6 | 0 ± 0 | 1.5 ± 0.2 | 0.2 ± 0.4 | |
| LAMRNQ (n = 9) | 0.3 ± 0 | 0 ± 0 | 0.9 ± 0.1 | 2.4 ± 0.3 | 0 ± 0 | 1.2 ± 0.3 | 0.4 ± 0.2 | 0.6 ± 0.2 |

TABLE 42-continued

Fatty acid profiles of T2 seeds harvested from T1 cultivated in the greenhouse of canola events containing the T-DNAs of plasmids VC-LJB2197-1qcz and VC-LLM337-1qcz rc The events are indicated in the first column, along with the number of T2 seed batches that were measured per event. Per seed batch a random selection of ~30 seed was measured in two technical repeats.

| | | | | | | | | |
|---|---|---|---|---|---|---|---|---|
| LAMVUB (n = 15) | 0.4 ± 0 | 0 ± 0 | 0.5 ± 0.1 | 2.3 ± 0.4 | 0 ± 0 | 1.3 ± 0.3 | 0.6 ± 0.2 | |
| LAMYDP (n = 14) | 0.3 ± 0.1 | 0 ± 0 | 1.3 ± 0.3 | 3.6 ± 0.7 | 0 ± 0 | 2.1 ± 0.5 | 0.4 ± 0.2 | |
| LANBCH (n = 14) | 0.3 ± 0 | 0 ± 0 | 1.3 ± 0.4 | 3.7 ± 0.9 | 0 ± 0 | 2 ± 0.6 | 0.5 ± 0.1 | 0.3 ± 0 |
| LANCEG (n = 4) | 0.3 ± 0.1 | 0 ± 0 | 1.2 ± 0.1 | 3.8 ± 0.2 | 0 ± 0 | 1.7 ± 0.2 | 0 ± 0 | |
| LANCOX (n = 10) | 0.3 ± 0.1 | 0 ± 0 | 0.9 ± 0.4 | 2.7 ± 0.7 | 0 ± 0.1 | 1.4 ± 0.5 | 0 ± 0 | |
| LANFEF (n = 15) | 0.2 ± 0.1 | 0 ± 0 | 1 ± 0.1 | 2.2 ± 0.3 | 0 ± 0 | 1.1 ± 0.1 | 0.8 ± 0.2 | 0.9 ± 0 |
| LANMGC (n = 15) | 0.3 ± 0 | 0 ± 0 | 0.7 ± 0.2 | 1.5 ± 0.6 | 0 ± 0 | 0.8 ± 0.4 | 2.4 ± 0.6 | |
| LANMOM (n = 10) | 0.3 ± 0 | 0 ± 0 | 1.2 ± 0.2 | 3.7 ± 0.7 | 0 ± 0 | 1.5 ± 0.4 | 0.4 ± 0.1 | 0.3 ± 0.1 |
| LANPMZ (n = 13) | 0.4 ± 0 | 0 ± 0 | 0.8 ± 0.2 | 2.8 ± 0.6 | 0 ± 0 | 1.5 ± 0.3 | 0.7 ± 0.1 | 1 ± 0.1 |
| LANTLE (n = 15) | 0 ± 0.1 | 0 ± 0 | 0.7 ± 0.4 | 3.3 ± 0.8 | 0 ± 0 | 1.5 ± 0.4 | 0.1 ± 0.2 | 0.4 ± 0.2 |
| LANTSP (n = 12) | 0.4 ± 0 | 0 ± 0 | 1 ± 0.4 | 2.5 ± 0.7 | 0 ± 0 | 1.3 ± 0.4 | 0.4 ± 0.2 | 0.4 ± 0.3 |
| LANUCB (n = 14) | 0.2 ± 0.1 | 0 ± 0 | 0.9 ± 0.3 | 3.3 ± 0.5 | 0 ± 0 | 1.3 ± 0.4 | 0 ± 0.1 | 0.6 ± 0.5 |
| LAOBGQ (n = 15) | 0.2 ± 0.2 | 0 ± 0 | 1.1 ± 0.3 | 2.9 ± 0.6 | 0 ± 0 | 1.4 ± 0.4 | 0.1 ± 0.3 | 0.1 ± 0.1 |
| LAOHLR (n = 14) | 0.3 ± 0.1 | 0 ± 0 | 0.8 ± 0.2 | 2.3 ± 0.4 | 0 ± 0 | 1.2 ± 0.3 | 0.3 ± 0.3 | |
| LAOJAT (n = 15) | 0 ± 0 | 0 ± 0 | 0.8 ± 0.3 | 2.9 ± 0.4 | 0 ± 0 | 1.4 ± 0.3 | 0 ± 0 | 0.3 ± 0.1 |
| LAOKLP (n = 15) | 0.3 ± 0 | 0 ± 0 | 0.5 ± 0.1 | 2.5 ± 0.6 | 0 ± 0 | 1.2 ± 0.3 | 0.5 ± 0.2 | 1.1 ± 0.6 |
| LAOKTE (n = 15) | 0.3 ± 0.1 | 0 ± 0 | 0.9 ± 0.4 | 3 3 ± 1 | 0 ± 0 | 1.6 ± 0.6 | 0.4 ± 0.2 | 0.5 ± 0.2 |
| LAPKLS (n = 12) | 0.2 ± 0.1 | 0 ± 0 | 0.8 ± 0.3 | 2.6 ± 0.7 | 0 ± 0 | 1.4 ± 0.5 | 0.3 ± 0.3 | 0.4 ± 0.2 |
| LAPKXM (n = 15) | 0.3 ± 0 | 0 ± 0 | 0.9 ± 0.3 | 3.4 ± 0.7 | 0 ± 0 | 1.4 ± 0.4 | 0.4 ± 0.3 | 0.5 ± 0.2 |
| LAPKZJ (n = 15) | 0.2 ± 0.2 | 0 ± 0 | 0.6 ± 0.3 | 2.8 ± 0.5 | 0 ± 0 | 1.4 ± 0.3 | 0.4 ± 0.5 | 1 ± 0.2 |
| LAPWJD (n = 14) | 0.2 ± 0.2 | 0 ± 0 | 0.7 ± 0.1 | 2.5 ± 0.2 | 0 ± 0 | 1.3 ± 0.1 | 0.7 ± 0.1 | 0.8 ± 0.1 |
| LAPWLP (n = 14) | 0.3 ± 0 | 0 ± 0 | 0.7 ± 0.2 | 3.6 ± 1 | 0 ± 0 | 1.7 ± 0.6 | 0.2 ± 0.2 | 1.3 ± 0.4 |
| LAQYTA (n = 15) | 0 ± 0 | 0 ± 0 | 1 ± 0.2 | 2.9 ± 0.5 | 0 ± 0 | 1.4 ± 0.3 | 0.5 ± 0.7 | 0.5 ± 0.2 |
| LAQYUT (n = 15) | 0.1 ± 0.1 | 0 ± 0 | 1.1 ± 0.2 | 2.4 ± 0.5 | 0 ± 0 | 1.3 ± 0.3 | 0.5 ± 0.6 | 0.2 ± 0.2 |
| LAQYWQ (n = 15) | 0.1 ± 0.1 | 0 ± 0 | 0.8 ± 0.4 | 2.5 ± 0.7 | 0 ± 0 | 1.4 ± 0.6 | 0.2 ± 0.4 | 0.2 ± 0.2 |
| LAQZME (n = 12) | 0.3 ± 0 | 0 ± 0 | 0.7 ± 0.3 | 3 ± 0.5 | 0 ± 0 | 1.6 ± 0.6 | 0.1 ± 0.1 | 1.4 ± 1.1 |

TABLE 43

Fatty acid profiles of one T2 seed batch per event harvested from T1 plants cultivated in the greenhouse of canola events containing the T-DNAs of plasmids VC-LJB2197-1qcz and VC-LLM337-1qcz rc. The events are indicated in the first column. Fatty acid profiles of T2 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|---|---|---|---|---|---|---|---|---|---|---|---|---|
| LALHCY (n = 1) | 7.6 | 1.1 | 0.7 | 2.3 | 19.7 | 25.6 | 0.9 | 6.3 | 3.6 | 0.7 | 0.8 | 0.6 | 0.0 | 0.0 | 1.2 | 1.1 | 3.9 | 10.4 | 0.0 | 0.0 | 1.0 | 7.0 | 0.0 | 3.4 | 0.0 | 0.0 |
| LALIAO (n = 1) | 5.1 | 0.2 | 0.0 | 3.1 | 23.3 | 31.4 | 0.8 | 4.2 | 1.4 | 0.2 | 0.8 | 0.7 | 0.7 | 0.1 | 2.4 | 1.5 | 5.7 | 13.2 | 0.4 | 0.0 | 0.6 | 2.7 | 0.0 | 1.1 | 0.0 | 0.4 |
| LALJKA (n = 1) | 5.6 | 0.3 | 0.0 | 2.1 | 22.4 | 34.6 | 0.5 | 6.2 | 2.6 | 0.6 | 0.6 | 0.6 | 0.2 | 0.1 | 1.0 | 0.7 | 2.9 | 9.4 | 0.3 | 0.0 | 1.6 | 4.9 | 0.0 | 2.3 | 0.4 | |
| LALLTL (n = 1) | 5.4 | 0.3 | 0.0 | 3.6 | 24.5 | 31.8 | 0.9 | 5.0 | 1.7 | 0.3 | 0.8 | 0.6 | 0.3 | 0.2 | 2.8 | 1.9 | 2.8 | 8.6 | 0.3 | 0.0 | 1.7 | 3.7 | 0.0 | 2.2 | 1.1 | |
| LALQAM (n = 1) | 7.1 | 0.5 | 0.0 | 3.9 | 21.1 | 30.2 | 0.8 | 4.0 | 1.7 | 0.2 | 0.8 | 0.5 | 0.5 | 0.2 | 2.3 | 1.2 | 6.2 | 10.4 | 0.3 | 0.0 | 1.3 | 4.3 | 0.0 | 1.5 | 0.3 | |
| LALQDS (n = 1) | 5.3 | 0.3 | 0.0 | 3.4 | 25.3 | 35.7 | 0.7 | 6.1 | 1.4 | 0.3 | 0.8 | 0.0 | 0.3 | 0.2 | 1.6 | 1.2 | 2.4 | 8.3 | 0.4 | 0.0 | 0.9 | 3.4 | 0.0 | 1.5 | 0.4 | 0.0 |
| LALRCQ (n = 1) | 5.0 | 0.3 | 0.0 | 3.6 | 23.0 | 32.7 | 1.0 | 4.0 | 2.3 | 0.4 | 0.8 | 0.6 | 0.3 | 0.1 | 3.5 | 1.5 | 3.8 | 11.3 | 0.3 | 0.0 | 2.0 | 3.4 | 0.0 | 2.1 | 0.3 | 0.0 |
| LALWKF (n = 1) | 5.5 | 0.3 | 0.0 | 3.7 | 23.0 | 29.0 | 1.4 | 3.4 | 2.9 | 0.3 | 0.8 | 0.6 | 0.3 | 0.1 | 1.9 | 1.2 | 5.9 | 11.3 | 0.3 | 0.0 | 1.2 | 3.9 | 0.0 | 2.4 | 0.9 | 0.0 |
| LAMABL (n = 1) | 4.6 | 0.3 | 0.0 | 3.7 | 24.3 | 31.5 | 1.4 | 3.4 | 2.8 | 0.3 | 0.9 | 0.6 | 0.2 | 0.0 | 1.1 | 0.6 | 7.3 | 10.1 | 0.3 | 0.0 | 2.0 | 3.6 | 0.0 | 1.5 | 0.2 | 0.0 |
| LAMCKI (n = 1) | 5.1 | 0.3 | 0.0 | 3.4 | 25.6 | 33.0 | 1.1 | 4.2 | 2.0 | 0.4 | 0.8 | 0.6 | 0.1 | 0.0 | 3.9 | 1.8 | 3.1 | 7.7 | 0.3 | 0.0 | 1.3 | 3.0 | 0.0 | 1.5 | 0.9 | 0.0 |
| LAMCLE (n = 1) | 4.8 | 0.2 | 0.0 | 3.9 | 22.2 | 31.9 | 1.3 | 3.3 | 3.1 | 0.3 | 0.9 | 0.6 | 0.0 | 0.0 | 2.0 | 1.1 | 3.8 | 10.5 | 0.0 | 0.0 | 2.8 | 4.3 | 0.0 | 2.8 | 0.0 | 0.0 |
| LAMCLF (n = 1) | 5.2 | 0.3 | 0.0 | 3.8 | 24.0 | 27.7 | 1.7 | 3.1 | 3.1 | 0.3 | 0.8 | 0.5 | 0.7 | 0.0 | 1.9 | 0.9 | 7.5 | 11.2 | 0.3 | 0.0 | 1.3 | 3.6 | 0.0 | 1.9 | 0.2 | 0.0 |
| LAMEUB (n = 1) | 5.4 | 0.4 | 0.0 | 4.7 | 26.2 | 27.5 | 1.0 | 3.4 | 1.5 | 0.2 | 1.0 | 0.7 | 1.2 | 0.0 | 2.6 | 1.8 | 3.8 | 11.1 | 0.3 | 0.0 | 0.8 | 3.6 | 0.0 | 2.2 | 0.3 | 0.0 |
| LAMEUU (n = 1) | 10.9 | 1.2 | 1.0 | 2.9 | 16.4 | 27.3 | 0.0 | 8.4 | 2.3 | 0.7 | 1.0 | 0.7 | 0.6 | 0.0 | 2.9 | 0.7 | 4.5 | 6.6 | 0.3 | 0.0 | 1.4 | 6.3 | 0.0 | 4.5 | 0.2 | 0.0 |
| LAMFJO (n = 1) | 5.5 | 0.4 | 0.0 | 2.4 | 26.8 | 30.6 | 0.2 | 7.3 | 0.4 | 0.1 | 0.6 | 0.8 | 2.1 | 1.0 | 1.7 | 1.4 | 2.8 | 7.4 | 0.2 | 0.0 | 0.9 | 4.5 | 0.0 | 1.8 | 0.5 | 0.5 |
| LAMIRY (n = 1) | 5.1 | 0.3 | 0.0 | 3.7 | 23.0 | 30.3 | 0.7 | 4.5 | 1.4 | 0.1 | 0.8 | 0.7 | 1.1 | 0.3 | 2.4 | 1.6 | 4.4 | 11.6 | 0.3 | 0.0 | 1.1 | 3.7 | 0.0 | 2.0 | 0.5 | 0.0 |
| LAMJIC (n = 1) | 6.3 | 0.3 | 0.0 | 2.9 | 24.5 | 28.3 | 0.7 | 6.4 | 1.3 | 0.3 | 0.7 | 0.7 | 0.0 | 0.0 | 2.7 | 1.7 | 4.9 | 9.4 | 0.3 | 0.0 | 1.1 | 4.3 | 0.0 | 1.8 | 0.5 | 0.0 |
| LAMPJB (n = 1) | 4.9 | 0.2 | 0.0 | 3.2 | 24.2 | 32.0 | 1.1 | 4.0 | 2.7 | 0.4 | 0.8 | 0.7 | 0.7 | 0.0 | 2.2 | 1.1 | 4.0 | 10.3 | 0.0 | 0.0 | 1.8 | 4.0 | 0.0 | 2.4 | 0.5 | 0.0 |
| LAMQDL (n = 1) | 4.3 | 0.2 | 0.0 | 2.4 | 24.7 | 28.5 | 0.2 | 6.1 | 0.5 | 0.1 | 0.8 | 1.1 | 2.6 | 1.4 | 3.6 | 2.9 | 2.5 | 9.4 | 0.0 | 0.0 | 0.7 | 4.7 | 0.0 | 1.3 | 0.8 | 1.1 |
| LAMQNE (n = 1) | 7.6 | 0.4 | 0.0 | 2.7 | 25.4 | 30.7 | 0.7 | 4.7 | 1.4 | 0.2 | 0.7 | 0.6 | 0.5 | 0.2 | 3.0 | 1.5 | 3.6 | 7.8 | 0.3 | 0.0 | 1.4 | 3.7 | 0.0 | 1.7 | 0.8 | 0.3 |
| LAMQSF (n = 1) | 5.4 | 0.3 | 0.0 | 3.8 | 20.3 | 30.2 | 0.5 | 3.9 | 3.6 | 0.5 | 0.8 | 0.6 | 0.4 | 0.1 | 1.3 | 0.9 | 6.1 | 13.3 | 0.3 | 0.0 | 1.0 | 4.0 | 0.0 | 2.4 | 0.0 | 0.0 |
| LAMRCO (n = 1) | 6.7 | 0.4 | 0.0 | 4.2 | 14.8 | 26.6 | 1.0 | 2.4 | 4.7 | 0.5 | 1.0 | 0.4 | 0.3 | 0.0 | 3.9 | 1.5 | 6.7 | 12.3 | 0.4 | 0.0 | 2.6 | 5.3 | 0.0 | 3.5 | 0.5 | 0.0 |
| LAMRDS (n = 1) | 4.9 | 0.4 | 0.0 | 3.4 | 20.9 | 31.3 | 1.4 | 2.7 | 2.7 | 0.2 | 0.9 | 0.6 | 0.3 | 0.0 | 3.0 | 1.2 | 4.7 | 9.1 | 0.3 | 0.0 | 2.7 | 3.8 | 0.0 | 2.1 | 0.7 | 0.0 |
| LAMRHL (n = 1) | 6.4 | 0.3 | 0.0 | 4.0 | 19.7 | 23.4 | 0.8 | 2.6 | 1.1 | 0.4 | 1.0 | 0.7 | 1.9 | 0.5 | 4.4 | 2.7 | 4.7 | 13.7 | 0.3 | 0.0 | 1.3 | 5.0 | 0.0 | 2.8 | 0.6 | 1.8 |
| LAMRJK (n = 1) | 5.0 | 0.2 | 0.0 | 3.6 | 25.5 | 31.1 | 1.5 | 4.3 | 2.6 | 0.4 | 0.9 | 0.6 | 0.0 | 0.0 | 2.8 | 1.4 | 4.0 | 9.5 | 0.3 | 0.0 | 1.1 | 3.8 | 0.0 | 1.7 | 0.0 | 0.0 |
| LAMRNQ (n = 1) | 5.0 | 0.2 | 0.1 | 3.1 | 23.5 | 31.7 | 0.6 | 4.2 | 1.2 | 0.2 | 0.8 | 0.8 | 1.4 | 0.4 | 3.4 | 1.8 | 5.5 | 8.5 | 0.3 | 0.0 | 1.1 | 3.0 | 0.0 | 1.8 | 0.5 | 0.9 |
| LAMVUB (n = 1) | 4.3 | 0.2 | 0.0 | 3.2 | 21.9 | 33.5 | 0.2 | 4.8 | 0.4 | 0.1 | 0.8 | 1.0 | 3.0 | 1.2 | 3.7 | 2.4 | 4.7 | 8.4 | 0.3 | 0.0 | 0.6 | 3.0 | 0.0 | 1.7 | 0.6 | |
| LAMYDP (n = 1) | 3.4 | 0.1 | 0.0 | 2.9 | 19.2 | 29.9 | 1.1 | 4.6 | 2.8 | 0.4 | 0.7 | 0.7 | 0.4 | 0.1 | 2.0 | 1.5 | 4.2 | 14.1 | 0.3 | 0.0 | 1.9 | 5.7 | 0.0 | 3.3 | 0.5 | 0.2 |
| LANBCH (n = 1) | 3.7 | 0.1 | 0.0 | 3.2 | 19.5 | 31.2 | 1.0 | 4.7 | 2.2 | 0.4 | 0.8 | 0.7 | 0.3 | 0.0 | 1.9 | 1.6 | 4.5 | 12.5 | 0.3 | 0.0 | 2.1 | 5.7 | 0.0 | 3.2 | 0.0 | 0.3 |
| LANCEG (n = 1) | 5.0 | 0.0 | 0.0 | 3.7 | 22.4 | 33.6 | 0.8 | 4.1 | 2.0 | 0.3 | 0.9 | 0.6 | 0.1 | 0.0 | 0.4 | 0.7 | 1.3 | 11.2 | 0.2 | 0.0 | 1.2 | 4.0 | 0.0 | 2.0 | 0.0 | 0.0 |
| LANCOX (n = 1) | 4.9 | 0.2 | 0.0 | 3.2 | 22.1 | 33.9 | 0.6 | 4.4 | 2.3 | 0.4 | 0.8 | 0.6 | 0.0 | 5.5 | 0.3 | 0.8 | 1.6 | 6.3 | 0.0 | 0.0 | 1.4 | 4.1 | 0.0 | 2.6 | 0.0 | 0.0 |
| LANFEF (n = 1) | 5.3 | 0.0 | 0.0 | 2.5 | 28.8 | 32.0 | 0.0 | 6.0 | 0.3 | 0.0 | 0.6 | 1.0 | 2.7 | 1.1 | 2.7 | 1.6 | 2.4 | 6.3 | 0.0 | 0.0 | 1.0 | 2.9 | 0.0 | 1.1 | 0.9 | 0.8 |
| LANMGC (n = 1) | 5.2 | 0.2 | 0.0 | 3.4 | 25.2 | 33.1 | 1.0 | 4.1 | 2.2 | 0.2 | 0.8 | 0.6 | 0.2 | 0.0 | 5.1 | 2.3 | 2.7 | 6.5 | 0.3 | 0.0 | 1.1 | 2.6 | 0.0 | 1.4 | 1.3 | 0.0 |

TABLE 43-continued

Fatty acid profiles of one T2 seed batch per event harvested from T1 plants cultivated in the greenhouse of canola events containing the T-DNAs of plasmids VC-LJB2197-1qcz and VC-LLM337-1qcz rc. The events are indicated in the first column. Fatty acid profiles of T2 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|---|---|---|---|---|---|---|---|---|---|---|---|---|
| LANPMZ (n = 1) | 3.6 | 0.1 | 0.0 | 3.1 | 22.5 | 32.7 | 0.3 | 5.8 | 0.4 | 0.1 | 0.8 | 1.0 | 2.0 | 0.8 | 3.0 | 2.6 | 2.7 | 8.8 | 0.4 | 0.0 | 1.2 | 4.1 | 0.0 | 2.2 | 0.9 | 1.0 |
| LANMOM (n = 1) | 5.3 | 0.2 | 0.0 | 2.8 | 19.6 | 32.5 | 0.8 | 4.5 | 2.2 | 0.4 | 0.7 | 0.6 | 0.4 | 0.2 | 2.3 | 1.6 | 4.3 | 11.9 | 0.3 | 0.0 | 1.5 | 4.6 | 0.0 | 2.5 | 0.4 | 0.3 |
| LANTLE (n = 1) | 4.4 | 0.3 | 0.0 | 2.3 | 19.0 | 31.5 | 0.5 | 5.3 | 1.6 | 0.3 | 0.6 | 0.7 | 1.4 | 0.7 | 3.2 | 2.5 | 5.1 | 11.6 | 0.2 | 0.0 | 1.0 | 4.7 | 0.0 | 2.6 | 0.2 | 0.4 |
| LANTSP (n = 1) | 5.3 | 0.2 | 0.0 | 2.9 | 23.5 | 32.1 | 0.8 | 4.6 | 1.9 | 0.3 | 0.7 | 0.7 | 0.4 | 0.1 | 2.3 | 1.5 | 3.6 | 9.9 | 0.3 | 0.0 | 1.8 | 3.9 | 0.0 | 2.3 | 0.6 | 0.1 |
| LANUCB (n = 1) | 4.8 | 0.3 | 0.0 | 3.4 | 25.7 | 27.9 | 2.1 | 3.6 | 4.2 | 0.6 | 0.8 | 0.6 | 0.1 | 0.0 | 1.9 | 1.1 | 4.2 | 10.7 | 0.3 | 0.0 | 1.3 | 4.0 | 0.0 | 1.9 | 0.0 | 0.3 |
| LAOBGQ (n = 1) | 4.8 | 0.2 | 0.0 | 3.2 | 23.0 | 34.0 | 0.9 | 3.9 | 2.0 | 0.2 | 0.9 | 0.7 | 0.4 | 0.0 | 2.4 | 1.2 | 4.8 | 9.2 | 0.4 | 0.0 | 1.6 | 3.8 | 0.0 | 1.9 | 0.0 | 0.3 |
| LAOHLR (n = 1) | 5.5 | 0.2 | 0.0 | 3.2 | 21.7 | 34.5 | 1.1 | 3.2 | 2.3 | 0.2 | 0.8 | 0.7 | 0.0 | 0.0 | 4.6 | 1.6 | 6.0 | 8.4 | 0.3 | 0.0 | 1.1 | 2.6 | 0.0 | 1.6 | 0.3 | 0.2 |
| LAOJAT (n = 1) | 5.3 | 0.2 | 0.0 | 2.9 | 22.5 | 34.1 | 0.8 | 5.0 | 2.3 | 0.2 | 0.6 | 0.6 | 0.0 | 0.0 | 2.1 | 1.3 | 4.3 | 10.3 | 0.0 | 0.0 | 1.0 | 3.6 | 0.0 | 2.0 | 0.0 | 0.2 |
| LAOKLP (n = 1) | 5.0 | 0.2 | 0.0 | 3.1 | 22.9 | 32.5 | 0.2 | 5.5 | 0.4 | 0.3 | 0.8 | 1.0 | 3.0 | 1.3 | 3.2 | 2.5 | 3.4 | 8.4 | 0.3 | 0.0 | 0.7 | 3.3 | 0.0 | 1.8 | 0.6 | 0.0 |
| LAOKTE (n = 1) | 4.9 | 0.2 | 0.0 | 2.6 | 21.3 | 29.8 | 0.9 | 4.6 | 1.9 | 0.3 | 0.7 | 0.6 | 0.3 | 0.2 | 2.3 | 1.6 | 5.4 | 12.6 | 0.3 | 0.0 | 1.4 | 4.8 | 0.0 | 2.4 | 0.4 | 0.3 |
| LAPKLS (n = 1) | 5.7 | 0.3 | 0.0 | 3.8 | 20.0 | 32.5 | 1.1 | 3.9 | 3.0 | 0.4 | 0.8 | 0.6 | 0.0 | 0.0 | 3.1 | 2.0 | 4.0 | 10.6 | 0.2 | 0.0 | 1.4 | 3.5 | 0.0 | 2.3 | 0.6 | 0.1 |
| LAPKXM (n = 1) | 4.4 | 0.2 | 0.0 | 3.6 | 23.0 | 33.1 | 0.8 | 4.3 | 1.7 | 0.2 | 0.9 | 0.7 | 0.5 | 0.0 | 2.3 | 1.6 | 4.3 | 13.3 | 0.4 | 0.0 | 0.6 | 2.5 | 0.0 | 1.2 | 0.0 | 0.3 |
| LAPKZJ (n = 1) | 4.8 | 0.1 | 0.0 | 3.7 | 23.2 | 30.4 | 0.4 | 4.7 | 0.6 | 0.1 | 0.9 | 1.0 | 2.2 | 0.9 | 3.4 | 2.7 | 2.9 | 9.2 | 0.4 | 0.0 | 0.9 | 3.7 | 0.0 | 1.9 | 0.8 | 1.1 |
| LAPWJD (n = 1) | 5.5 | 0.1 | 0.0 | 3.5 | 25.6 | 35.2 | 0.4 | 4.6 | 0.7 | 0.0 | 0.8 | 0.8 | 1.5 | 0.6 | 3.4 | 2.1 | 2.7 | 6.6 | 0.2 | 0.0 | 0.8 | 2.4 | 0.0 | 1.4 | 0.6 | 0.7 |
| LAPWLP (n = 1) | 4.5 | 0.1 | 0.0 | 2.9 | 28.2 | 28.3 | 0.5 | 4.7 | 0.5 | 0.2 | 0.8 | 1.2 | 2.9 | 1.1 | 1.9 | 2.1 | 3.6 | 15.9 | 0.4 | 0.0 | 0.7 | 4.8 | 0.0 | 3.2 | 0.0 | 1.7 |
| LAQYTA (n = 1) | 5.3 | 0.0 | 0.0 | 3.0 | 24.8 | 30.1 | 1.2 | 4.3 | 2.1 | 0.1 | 0.7 | 0.6 | 0.4 | 0.0 | 2.1 | 1.1 | 7.5 | 10.2 | 0.0 | 0.0 | 0.9 | 3.7 | 0.0 | 1.5 | 0.0 | 0.5 |
| LAQYUT (n = 1) | 5.6 | 0.2 | 0.0 | 3.5 | 21.5 | 32.5 | 1.4 | 3.0 | 3.1 | 0.3 | 0.7 | 0.6 | 0.0 | 0.0 | 4.6 | 1.6 | 6.8 | 8.9 | 0.0 | 0.0 | 1.0 | 2.6 | 0.0 | 1.6 | 0.0 | 0.3 |
| LAQYWQ (n = 1) | 5.8 | 0.3 | 0.0 | 4.3 | 22.3 | 30.0 | 2.1 | 3.6 | 4.1 | 0.6 | 0.8 | 0.5 | 0.3 | 0.0 | 1.7 | 1.1 | 3.8 | 11.5 | 0.3 | 0.0 | 1.5 | 3.5 | 0.0 | 1.9 | 0.0 | 0.1 |
| LAQZME (n = 1) | 6.3 | 0.3 | 0.0 | 2.5 | 21.7 | 30.7 | 0.7 | 3.3 | 2.7 | 0.4 | 0.6 | 0.6 | 0.7 | 0.2 | 2.7 | 1.6 | 6.4 | 10.3 | 0.3 | 0.0 | 1.2 | 3.8 | 0.0 | 2.6 | 0.1 | 0.2 |

TABLE 44

Fatty acid profiles of T2 seeds harvested from T1 plants cultivated in the greenhouse of canola events containing the T-DNAs of plasmids VC-LJB2197-1qcz and VC-LLM337-1qcz rc. Plants of all events combined have been grouped into the categories indicated in the first column; as defined in Table 41. The number of T1 plants fullfilling these criteria are displayed in parentheses. Per seed batch a random selection of ~30 seed was measured in two technical repeats.

| Category of T1 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 |
|---|---|---|---|---|---|---|---|---|---|---|
| sc (n = 296) | 4.9 ± 0.5 | 0.2 ± 0.1 | 0 ± 0 | 3.2 ± 0.6 | 28.5 ± 5.4 | 31 ± 4 | 0.5 ± 0.3 | 4.7 ± 1 | 0.8 ± 0.5 | 0.1 ± 0.1 |
| dc (n = 198) | 5.1 ± 0.6 | 0.2 ± 0.1 | 0 ± 0 | 3.5 ± 0.6 | 23.7 ± 3.1 | 32.2 ± 2.5 | 1.1 ± 0.3 | 4.1 ± 0.7 | 2.3 ± 0.6 | 0.3 ± 0.1 |
| tc (n = 2) | 5.6 ± 0.4 | 0.3 ± 0 | 0 ± 0 | 4.4 ± 0.7 | 22 ± 1.5 | 30.2 ± 0.1 | 1.6 ± 0.7 | 3.6 ± 1.2 | 3.1 ± 0.7 | 0.4 ± 0.1 |

| Category of T1 plants | 20:0 | 20:1 n-9 | 20:2 n-6 | 20:3 n-3 | 20:3 n-6 | 20:4 n-3 | 20:4 n-6 | 20:5 n-3 | 22:0 | 22:1 n-9 |
|---|---|---|---|---|---|---|---|---|---|---|
| sc (n = 296) | 0.8 ± 0.1 | 0.9 ± 0.2 | 1.6 ± 0.9 | 0.7 ± 1.2 | 2.7 ± 0.9 | 1.6 ± 0.6 | 4.6 ± 2.3 | 7.2 ± 1.9 | 0.3 ± 0.1 | 0 ± 0 |
| dc (n = 198) | 0.8 ± 0.1 | 0.6 ± 0.1 | 0.3 ± 0.2 | 0.4 ± 1.4 | 3 ± 2 | 1.6 ± 0.8 | 4 ± 1.8 | 9.1 ± 2.8 | 0.3 ± 0.1 | 0 ± 0 |
| tc (n = 2) | 0.9 ± 0 | 0.6 ± 0 | 0.3 ± 0.1 | 0.1 ± 0.1 | 3.5 ± 1.5 | 1.7 ± 0.4 | 3.4 ± 1.1 | 9.7 ± 3 | 0.3 ± 0 | 0 ± 0 |

| Category of T1 plants | 22:4 n-6 | 22:5 n-3 | 22:5 n-6 | 22:6 n-3 | 22:4 n-3 | 20:2 n-9 |
|---|---|---|---|---|---|---|
| sc (n = 296) | 0.7 ± 0.3 | 2.7 ± 0.7 | 0 ± 0 | 1.3 ± 0.4 | 0.3 ± 0.3 | 0.9 ± 0.5 |
| dc (n = 198) | 1.4 ± 0.5 | 3.4 ± 1.2 | 0 ± 0 | 1.8 ± 0.6 | 0.6 ± 0.7 | 0.3 ± 0.2 |
| tc (n = 2) | 1.6 ± 0.2 | 3.6 ± 1.4 | 0 ± 0 | 2.2 ± 0.7 | 0.7 ± 0 | |

TABLE 45

Fatty acid profiles of T2 seeds harvested from T1 plants cultivated in the greenhouse of canola events containing the T-DNAs of plasmids VC-LJB2197-1qcz and VC-LLM337-1qcz rc. Plants of all events combined have been grouped into the categories indicated in the first column; as defined in Table 41. For each category, the fatty acid profile of the plant having the highest EPA ± DHA levels was shown. Per seed batch a random selection of ~30 seed was measured in two technical repeats.

| Category of T1 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 1) | 5.3 | 0.3 | 0.0 | 3.2 | 26.0 | 32.3 | 0.6 | 4.5 | 1.0 | 0.2 | 0.8 | 0.8 | 1.1 |
| dc (n = 1) | 4.5 | 0.1 | 0.0 | 2.9 | 28.2 | 18.2 | 0.5 | 4.7 | 0.5 | 0.2 | 0.8 | 1.2 | 2.9 |
| tc (n = 1) | 3.5 | 0.1 | 0.0 | 2.7 | 18.2 | 26.4 | 0.4 | 4.6 | 0.9 | 0.2 | 0.7 | 0.9 | 2.0 |

| Category of T1 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 0.4 | 1.8 | 1.1 | 5.7 | 9.3 | 0.4 | 0.0 | 0.7 | 3.2 | 0.0 | 1.4 | 0.0 | 0.0 |
| dc (n = 1) | 1.1 | 1.9 | 2.1 | 3.6 | 15.9 | 0.4 | 0.0 | 0.7 | 4.8 | 0.0 | 3.2 | 0.0 | 1.7 |
| tc (n = 1) | 0.7 | 2.2 | 1.9 | 5.5 | 16.7 | 0.3 | 0.0 | 1.2 | 6.6 | 0.0 | 3.3 | 0.2 | 1.0 |

TABLE 46

Phenotypic rating of T1 plants cultivated in the greenhouse of canola events containing the T-DNAs of plasmids VC-LJB2197-1qcz and VC-LLM337-1qcz rc. The events are indicated in the first column, along with the number of T1 plants that where rated per event.

| Event | DFF | DF | DL | DP | DS | FC | LD | LGC |
|---|---|---|---|---|---|---|---|---|
| LALHCY (n = 15) | 59.3 ± 2.6 | 1 ± 0 | 1 ± 0 | 1 ± 0 | 1.3 ± 0.5 | 3 ± 0 | 3 ± 0 | 5 ± 0 |
| LALIAO (n = 15) | 65.9 ± 3.2 | 1 ± 0 | 1.2 ± 0.8 | 1.3 ± 0.5 | 1.8 ± 0.7 | 3 ± 0 | 3 ± 0 | 5 ± 0 |
| LALJKA (n = 15) | 62.1 ± 5.5 | 1 ± 0 | 1 ± 0 | 1.1 ± 0.3 | 2.5 ± 2.2 | 3 ± 0 | 3 ± 0 | 5 ± 0 |

TABLE 46-continued

Phenotypic rating of T1 plants cultivated in the greenhouse of canola events containing the T-DNAs of plasmids VC-LJB2197-1qcz and VC-LLM337-1qcz rc. The events are indicated in the first column, along with the number of T1 plants that where rated per event.

| | | | | | | | | |
|---|---|---|---|---|---|---|---|---|
| LALLTL (n = 11) | 55.3 ± 2.2 | 1 ± 0 | 1 ± 0 | 1 ± 0 | 1.5 ± 0.7 | 3 ± 0 | 3 ± 0 | 5 ± 0 |
| LALQAM (n = 15) | 58.3 ± 2.8 | 1 ± 0 | 1 ± 0 | 1 ± 0 | 2.7 ± 2.1 | 3 ± 0 | 3 ± 0 | 5 ± 0 |
| LALQDS (n = 14) | 54.5 ± 3.1 | 1 ± 0 | 1 ± 0 | 1.6 ± 0.9 | 2.6 ± 1.8 | 3 ± 0 | 3 ± 0 | 5 ± 0 |
| LALRCQ (n = 14) | 61.7 ± 1.7 | 1 ± 0 | 1 ± 0 | 1 ± 0 | 2.1 ± 1.1 | 3 ± 0 | 3 ± 0 | 5 ± 0 |
| LALWKF (n = 14) | 62.1 ± 3.2 | 1 ± 0 | 1.4 ± 1.1 | 1 ± 0 | 1.4 ± 0.8 | 3 ± 0 | 3 ± 0 | 5 ± 0 |
| LAMABL (n = 8) | 56.1 ± 1.6 | 1 ± 0 | 2.9 ± 1.6 | 2.1 ± 0.6 | 6.5 ± 2 | 3 ± 0 | 3 ± 0 | 5 ± 0 |
| LAMCKI (n = 10) | 61.5 ± 2.4 | 1 ± 0 | 1 ± 0 | 1 ± 0 | 1.6 ± 0.7 | 3 ± 0 | 3 ± 0 | 5 ± 0 |
| LAMCLE (n = 14) | 65.4 ± 1.9 | 1 ± 0 | 1.4 ± 1.1 | 1.5 ± 0.8 | 2 ± 0.7 | 3 ± 0 | 3 ± 0 | 5 ± 0 |
| LAMCLF (n = 9) | 66.4 ± 4.3 | 1 ± 0 | 1.3 ± 1 | 1 ± 0 | 1.1 ± 0.3 | 3 ± 0 | 3 ± 0 | 5 ± 0 |
| LAMEUB (n = 15) | 57.7 ± 2.4 | 1 ± 0 | 1 ± 0 | 1.5 ± 0.7 | 4.5 ± 2.3 | 3 ± 0 | 3 ± 0 | 5 ± 0 |
| LAMEUU (n = 13) | 65.8 ± 3.6 | 1 ± 0 | 1.5 ± 1.1 | 1.5 ± 0.9 | 2.2 ± 1.9 | 3 ± 0 | 3 ± 0 | 5 ± 0 |
| LAMFJO (n = 15) | 64.7 ± 2.9 | 1 ± 0 | 1.6 ± 1.2 | 1.1 ± 0.3 | 3.7 ± 2.4 | 3 ± 0 | 3 ± 0 | 5 ± 0 |
| LAMIRY (n = 10) | 54.7 ± 2.3 | 1 ± 0 | 1 ± 0 | 1 ± 0 | 2.2 ± 2.1 | 3 ± 0 | 3 ± 0 | 5 ± 0 |
| LAMJIC (n = 9) | 60.1 ± 2.9 | 1 ± 0 | 2 ± 1.5 | 2.7 ± 2.5 | 5.3 ± 3.1 | 3 ± 0 | 3 ± 0 | 5 ± 0 |
| LAMPJB (n = 13) | 64.8 ± 2.5 | 1 ± 0 | 1.1 ± 0.3 | 1 ± 0 | 2.1 ± 0.8 | 3 ± 0 | 3 ± 0 | 5 ± 0 |
| LAMQDL (n = 14) | 67.9 ± 4.5 | 1 ± 0 | 1.2 ± 0.8 | 1.6 ± 0.8 | 2.6 ± 2.3 | 3 ± 0 | 3 ± 0 | 5 ± 0 |
| LAMQNE (n = 14) | 71.9 ± 6.2 | 1 ± 0 | 1.2 ± 0.8 | 1 ± 0 | 1.5 ± 1.3 | 3 ± 0 | 3 ± 0 | 5 ± 0 |
| LAMQSF (n = 14) | 61.1 ± 1.8 | 1 ± 0 | 1 ± 0 | 1 ± 0 | 1.6 ± 0.7 | 3 ± 0 | 3 ± 0 | 5 ± 0 |
| LAMRCO (n = 14) | 62.1 ± 2.9 | 1 ± 0 | 1 ± 0 | 1.6 ± 1 | 2.9 ± 1.7 | 3 ± 0 | 3 ± 0 | 5 ± 0 |
| LAMRDS (n = 15) | 63.7 ± 2.3 | 1 ± 0 | 1.4 ± 1.1 | 1.1 ± 0.3 | 1.9 ± 1.4 | 3 ± 0 | 3 ± 0 | 5 ± 0 |
| LAMRHL (n = 14) | 67.7 ± 4 | 1 ± 0 | 1 ± 0 | 1 ± 0 | 2.9 ± 2 | 3 ± 0 | 3 ± 0 | 5 ± 0 |
| LAMRJK (n = 15) | 63.4 ± 2.6 | 1 ± 0 | 1.3 ± 1 | 1 ± 0 | 3.5 ± 2 | 3 ± 0 | 3 ± 0 | 5 ± 0 |
| LAMRNQ (n = 9) | 63.1 ± 3 | 1 ± 0 | 1 ± 0 | 1 ± 0 | 1.1 ± 0.4 | 3 ± 0 | 3 ± 0 | 5 ± 0 |
| LAMVUB (n = 15) | 65.5 ± 3.3 | 1 ± 0 | 1 ± 0 | 1 ± 0 | 3.3 ± 2.6 | 3 ± 0 | 3 ± 0 | 5 ± 0 |
| LAMYDP (n = 14) | 64.1 ± 4.6 | 1 ± 0 | 1 ± 0 | 1 ± 0 | 1.9 ± 0.7 | 3 ± 0 | 3 ± 0 | 5 ± 0 |
| LANBCH (n = 14) | 64.4 ± 2.8 | 1 ± 0 | 1 ± 0 | 1 ± 0 | 1.1 ± 0.4 | 3 ± 0 | 3 ± 0 | 5 ± 0 |
| LANCEG (n = 4) | 67.3 ± 3.3 | 1 ± 0 | 1 ± 0 | 1.3 ± 0.5 | 1.3 ± 0.5 | 3 ± 0 | 3 ± 0 | 5 ± 0 |
| LANCOX (n = 10) | 66.3 ± 3.2 | 1 ± 0 | 1 ± 0 | 1.6 ± 0.8 | 4.2 ± 2.3 | 3 ± 0 | 3 ± 0 | 5 ± 0 |
| LANFEF (n = 15) | 67.4 ± 2.4 | 1 ± 0 | 1.2 ± 0.8 | 1.1 ± 0.4 | 1.5 ± 0.6 | 3 ± 0 | 3 ± 0 | 5 ± 0 |
| LANMGC (n = 15) | 64.2 ± 2 | 1 ± 0 | 1 ± 0 | 1 ± 0 | 2.3 ± 2.2 | 3 ± 0 | 3 ± 0 | 5 ± 0 |
| LANMOM (n = 10) | 65.9 ± 3.1 | 1 ± 0 | 1 ± 0 | 1 ± 0 | 1.4 ± 1 | 3 ± 0 | 3 ± 0 | 5 ± 0 |
| LANPMZ (n = 13) | 65.3 ± 3.1 | 1 ± 0 | 1 ± 0 | 1 ± 0 | 1.2 ± 0.4 | 3 ± 0 | 3 ± 0 | 5 ± 0 |
| LANTLE (n = 15) | 55.6 ± 2 | 1 ± 0 | 2.5 ± 1.7 | 3.1 ± 0.9 | 1.9 ± 1.8 | 3 ± 0 | 3 ± 0 | 5 ± 0 |
| LANTSP (n = 12) | 65.3 ± 3.4 | 1 ± 0 | 1 ± 0 | 1.2 ± 0.4 | 1.3 ± 0.5 | 3 ± 0 | 3 ± 0 | 5 ± 0 |
| LANUCB (n = 14) | 58.3 ± 2.2 | 1 ± 0 | 1.2 ± 0.8 | 2.6 ± 0.6 | 1.9 ± 0.8 | 3 ± 0 | 3 ± 0 | 5 ± 0 |
| LAOBGQ (n = 15) | 67.8 ± 3.4 | 1 ± 0 | 1 ± 0 | 1.1 ± 0.4 | 1.2 ± 0.4 | 3 ± 0 | 3 ± 0 | 5 ± 0 |
| LAOHLR (n = 14) | 61.7 ± 2.7 | 1 ± 0 | 1 ± 0 | 1 ± 0 | 1.1 ± 0.4 | 3 ± 0 | 3 ± 0 | 5 ± 0 |
| LAOJAT (n = 15) | 60.3 ± 2.8 | 1 ± 0 | 1 ± 0 | 1.4 ± 0.6 | 1.4 ± 0.5 | 3 ± 0 | 3 ± 0 | 5 ± 0 |
| LAOKLP (n = 15) | 62 ± 2.9 | 1 ± 0 | 1 ± 0 | 1.1 ± 0.4 | 1.9 ± 1.5 | 3 ± 0 | 3 ± 0 | 5 ± 0 |
| LAOKTE (n = 15) | 62.9 ± 3.7 | 1 ± 0 | 1.4 ± 1.1 | 1.7 ± 0.6 | 2.1 ± 1.1 | 3 ± 0 | 3 ± 0 | 5 ± 0 |

TABLE 46-continued

Phenotypic rating of T1 plants cultivated in the greenhouse of canola events containing the T-DNAs of plasmids VC-LJB2197-1qcz and VC-LLM337-1qcz rc. The events are indicated in the first column, along with the number of T1 plants that where rated per event.

| | | | | | | | | |
|---|---|---|---|---|---|---|---|---|
| LAPKLS (n = 12) | 66.3 ± 2.7 | 1 ± 0 | 1 ± 0 | 1.7 ± 0.9 | 1.9 ± 0.7 | 3 ± 0 | 3 ± 0 | 5 ± 0 |
| LAPKXM (n = 15) | 68.2 ± 3.2 | 1 ± 0 | 1.2 ± 0.8 | 1.9 ± 0.7 | 1.3 ± 0.5 | 3 ± 0 | 3 ± 0 | 5 ± 0 |
| LAPKZJ (n = 15) | 67.9 ± 2.7 | 1 ± 0 | 1.2 ± 0.8 | 1.1 ± 0.3 | 1.5 ± 0.5 | 3 ± 0 | 3 ± 0 | 5 ± 0 |
| LAPWJD (n = 14) | 68.3 ± 2.9 | 1 ± 0 | 1 ± 0 | 1.1 ± 0.4 | 1.7 ± 0.9 | 3 ± 0 | 3 ± 0 | 5 ± 0 |
| LAPWLP (n = 14) | 64.9 ± 4 | 1 ± 0 | 1.5 ± 1.3 | 2 ± 1.4 | 3.6 ± 3 | 3 ± 0 | 3 ± 0 | 5 ± 0 |
| LAQYTA (n = 15) | 59.2 ± 3.9 | 1 ± 0 | 1.2 ± 0.8 | 2.6 ± 0.8 | 2.1 ± 1.5 | 3 ± 0 | 3 ± 0 | 5 ± 0 |
| LAQYUT (n = 15) | 66.3 ± 3 | 1 ± 0 | 1 ± 0 | 1.1 ± 0.3 | 1.6 ± 0.5 | 3 ± 0 | 3 ± 0 | 5 ± 0 |
| LAQYWQ (n = 15) | 66.7 ± 4.6 | 1 ± 0 | 1 ± 0 | 1.6 ± 0.7 | 2.5 ± 1.8 | 3 ± 0 | 3 ± 0 | 5 ± 0 |
| LAQZME (n = 12) | 64.3 ± 4.7 | 3 ± 3.6 | 1.8 ± 1.5 | 1.5 ± 0.5 | 4.1 ± 3.4 | 3 ± 0 | 3 ± 0 | 5 ± 0 |

| Event | LF | NoL | PH | TKW | SC |
|---|---|---|---|---|---|
| LALHCY (n = 15) | 1.7 ± 1.1 | 4 ± 0 | 136 ± 3.9 | 4.7 ± 0.2 | 3.3 ± 1.1 |
| LALIAO (n = 15) | 1.3 ± 1.3 | 3.5 ± 0.9 | 124.3 ± 3.7 | 4 ± 0.5 | 3 ± 0.7 |
| LALJKA (n = 15) | 1.6 ± 1.8 | 3.6 ± 0.7 | 126 ± 5.1 | 4.6 ± 0.2 | 3.4 ± 2 |
| LALLTL (n = 11) | 1.2 ± 0.6 | 4 ± 0 | 128.6 ± 5.5 | 4.5 ± 0.2 | 2.2 ± 1.2 |
| LALQAM (n = 15) | 2.1 ± 2.3 | 4 ± 0 | 133.7 ± 4 | 4.8 ± 0.2 | 4.7 ± 1.8 |
| LALQDS (n = 14) | 1.9 ± 1.6 | 4 ± 0 | 127.1 ± 5.4 | 4.6 ± 0.2 | 3.4 ± 1.4 |
| LALRCQ (n = 14) | 1.9 ± 1.5 | 3.7 ± 0.7 | 127.1 ± 3.8 | 4.8 ± 0.3 | 3.3 ± 1.2 |
| LALWKF (n = 14) | 1.2 ± 0.6 | 4 ± 0 | 132.9 ± 5.8 | 4.5 ± 0.2 | 3.1 ± 0.8 |
| LAMABL (n = 8) | 5 ± 2.3 | 4 ± 0 | 123.1 ± 4.6 | 4.1 ± 0.4 | 5.3 ± 1.6 |
| LAMCKI (n = 10) | 1 ± 0 | 4 ± 0 | 131 ± 3.9 | 4.1 ± 0.2 | 2.8 ± 0.6 |
| LAMCLE (n = 14) | 1.3 ± 0.6 | 3.7 ± 0.7 | 124.3 ± 4.3 | 4.3 ± 0.3 | 3 ± 1 |
| LAMCLF (n = 9) | 1 ± 0 | 3.1 ± 1.1 | 121.1 ± 3.3 | 4 ± 0.5 | 2.1 ± 0.3 |
| LAMEUB (n = 15) | 3.9 ± 2.3 | 4 ± 0 | 128.3 ± 3.6 | 4.2 ± 0.4 | 3.1 ± 1 |
| LAMEUU (n = 13) | 2.1 ± 1.7 | 3.7 ± 0.8 | 126.2 ± 4.2 | 4.2 ± 0.4 | 3.2 ± 0.7 |
| LAMFJO (n = 15) | 2.3 ± 1.7 | 4 ± 0 | 123.7 ± 3.5 | 4.1 ± 0.5 | 4.1 ± 2.4 |
| LAMIRY (n = 10) | 1.6 ± 1.9 | 4 ± 0 | 123 ± 4.2 | 4.9 ± 0.2 | 3.3 ± 1.7 |
| LAMJIC (n = 9) | 3.6 ± 2 | 3.3 ± 1 | 111.1 ± 26.8 | 3.9 ± 0.7 | 4.4 ± 1.1 |
| LAMPJB (n = 13) | 1.5 ± 0.9 | 4 ± 0 | 123.5 ± 2.4 | 4.6 ± 0.3 | 3.8 ± 1.5 |
| LAMQDL (n = 14) | 1.6 ± 0.9 | 4 ± 0 | 117.1 ± 6.4 | 3.5 ± 0.4 | 3.8 ± 1.6 |
| LAMQNE (n = 14) | 1.1 ± 0.5 | 4 ± 0 | 119.3 ± 3.3 | 4.2 ± 0.3 | 3.6 ± 1.3 |
| LAMQSF (n = 14) | 1.1 ± 0.5 | 4 ± 0 | 123.9 ± 4 | 3.9 ± 0.5 | 2.6 ± 0.7 |
| LAMRCO (n = 14) | 2.1 ± 1.3 | 4 ± 0 | 119.3 ± 4.3 | 3.9 ± 0.4 | 3.9 ± 2.1 |
| LAMRDS (n = 15) | 1.4 ± 1.1 | 4 ± 0 | 125.7 ± 3.7 | 4.4 ± 0.4 | 2.7 ± 1.3 |
| LAMRHL (n = 14) | 2.7 ± 2.4 | 4 ± 0 | 122.1 ± 2.6 | 4.1 ± 0.5 | 4.1 ± 1.1 |
| LAMRJK (n = 15) | 2.5 ± 1.6 | 4 ± 0 | 124.7 ± 4.4 | 4.5 ± 0.4 | 3.8 ± 1.1 |
| LAMRNQ (n = 9) | 1 ± 0 | 4 ± 0 | 121.9 ± 2.6 | 3.8 ± 0.5 | 2.6 ± 1.3 |
| LAMVUB (n = 15) | 2.3 ± 1.9 | 4 ± 0 | 124.3 ± 4.2 | 4.6 ± 0.3 | 4.2 ± 2.2 |
| LAMYDP (n = 14) | 1.4 ± 0.9 | 4 ± 0 | 123.2 ± 3.7 | 4.5 ± 0.3 | 3.9 ± 1.4 |
| LANBCH (n = 14) | 1 ± 0 | 4 ± 0 | 123.9 ± 3.5 | 4.2 ± 0.2 | 3.1 ± 0.7 |
| LANCEG (n = 4) | 1 ± 0 | 4 ± 0 | 123.8 ± 2.5 | 4.1 ± 0.4 | 2.5 ± 0.6 |

TABLE 46-continued

Phenotypic rating of T1 plants cultivated in the greenhouse of canola events containing the T-DNAs of plasmids VC-LJB2197-1qcz and VC-LLM337-1qcz rc. The events are indicated in the first column, along with the number of T1 plants that where rated per event.

| Event | | | | | | |
|---|---|---|---|---|---|---|
| LANCOX (n = 10) | 2.9 ± 1.4 | 3.6 ± 0.8 | 127.5 ± 2.6 | 4.6 ± 0.3 | 4 ± 1.5 |
| LANFEF (n = 15) | 1.1 ± 0.5 | 4 ± 0 | 127 ± 3.2 | 4.7 ± 0.3 | 2.9 ± 0.5 |
| LANMGC (n = 15) | 1.7 ± 1.6 | 4 ± 0 | 123.7 ± 4 | 4.4 ± 0.3 | 3 ± 0.8 |
| LANMOM (n = 10) | 1.1 ± 0.3 | 4 ± 0 | 119.5 ± 3.7 | 3.4 ± 0.7 | 3.3 ± 1.2 |
| LANPMZ (n = 13) | 1 ± 0 | 4 ± 0 | 124.2 ± 3.4 | 4.4 ± 0.2 | 2.4 ± 0.5 |
| LANTLE (n = 15) | 1.3 ± 0.6 | 3.9 ± 0.5 | 106 ± 9.3 | 3.2 ± 0.3 | 2.6 ± 0.8 |
| LANTSP (n = 12) | 1.2 ± 0.6 | 4 ± 0 | 124.6 ± 4 | 4.1 ± 0.4 | 3.8 ± 1.3 |
| LANUCB (n = 14) | 1.4 ± 0.7 | 4 ± 0 | 117.9 ± 5.4 | 3.6 ± 0.3 | 3.1 ± 1 |
| LAOBGQ (n = 15) | 1 ± 0 | 4 ± 0 | 127 ± 3.2 | 4.2 ± 0.3 | 3.1 ± 0.6 |
| LAOHLR (n = 14) | 1 ± 0 | 3.9 ± 0.5 | 123.2 ± 4.2 | 4.2 ± 0.5 | 2.8 ± 0.7 |
| LAOJAT (n = 15) | 1 ± 0 | 4 ± 0 | 124.3 ± 5 | 4 ± 0.4 | 4.8 ± 1.6 |
| LAOKLP (n = 15) | 1 ± 0 | 4 ± 0 | 125.7 ± 3.2 | 4.1 ± 0.3 | 3.8 ± 1.9 |
| LAOKTE (n = 15) | 1.3 ± 1 | 4 ± 0 | 122.3 ± 4.2 | 3.7 ± 0.5 | 5.6 ± 2.7 |
| LAPKLS (n = 12) | 1.2 ± 0.6 | 2.8 ± 1 | 118.3 ± 6.2 | 4.2 ± 0.3 | 4.5 ± 1.4 |
| LAPKXM (n = 15) | 1 ± 0 | 3.2 ± 1 | 127.3 ± 2.6 | 4 ± 0.4 | 3.5 ± 0.5 |
| LAPKZJ (n = 15) | 1 ± 0 | 3.9 ± 0.5 | 127 ± 3.2 | 4.2 ± 0.3 | 3.3 ± 0.8 |
| LAPWJD (n = 14) | 1 ± 0 | 4 ± 0 | 126.1 ± 4 | 4.6 ± 0.3 | 3.1 ± 0.3 |
| LAPWLP (n = 14) | 2.6 ± 2.8 | 3.6 ± 0.9 | 119.3 ± 8.7 | 3.5 ± 0.4 | 4.1 ± 0.9 |
| LAQYTA (n = 15) | 1.7 ± 1 | 3.7 ± 0.7 | 111.3 ± 6.1 | 3.6 ± 0.3 | 4.2 ± 1.3 |
| LAQYUT (n = 15) | 1 ± 0 | 3.7 ± 0.7 | 126.3 ± 3 | 4.3 ± 0.2 | 3.7 ± 0.6 |
| LAQYWQ (n = 15) | 1.2 ± 0.6 | 4 ± 0 | 124 ± 3.9 | 4.1 ± 0.4 | 3.8 ± 0.7 |
| LAQZME (n = 12) | 2.8 ± 3.3 | 4 ± 0 | 124.2 ± 5.1 | 4.2 ± 0.4 | 4.8 ± 2.8 |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoL: number of lobes(#),
PH: plant height (cm),
TKW: thousand kernel weight (g),
SC: seed quality (1 = good, 9 = bad)

TABLE 47

Phenotypic rating of T1 plants cultivated in the greenhouse of canola events containing the T-DNAs of plasmids VC-LJB2197-1qcz and VC-LLM337-1qcz rc. Plants of all events combined have been grouped into the categories indicated in the first column; as defined in Table 41. The number of T1 plants fullfilling these criteria are displayed in parentheses.

| Category of T1 plants | DFF | DF | DL | DP | DS | FC | LD | LGC | LF | NoL | PH | TKW | SC |
|---|---|---|---|---|---|---|---|---|---|---|---|---|---|
| sc (n = 296) | 62.9 ± 4.8 | 1 ± 0 | 1.2 ± 0.7 | 1.4 ± 0.9 | 2.5 ± 2 | 3 ± 0 | 3 ± 0 | 5 ± 0 | 1.7 ± 1.6 | 3.9 ± 0.4 | 123.9 ± 8 | 4.2 ± 0.6 | 3.6 ± 1.6 |
| dc (n = 198) | 63.4 ± 4.5 | 1 ± 0.6 | 1.2 ± 0.7 | 1.2 ± 0.5 | 2 ± 1.6 | 3 ± 0 | 3 ± 0 | 5 ± 0 | 1.6 ± 1.4 | 3.8 ± 0.5 | 123.9 ± 10.4 | 4.2 ± 0.4 | 3.6 ± 1.6 |

TABLE 47-continued

Phenotypic rating of T1 plants cultivated in the greenhouse of canola events containing the T-DNAs of plasmids VC-LJB2197-1qcz and VC-LLM337-1qcz rc. Plants of all events combined have been grouped into the categories indicated in the first column; as defined in Table 41. The number of T1 plants fullfilling these criteria are displayed in parentheses.

| Category-of T1 plants | DFF | DF | DL | DP | DS | FC | LD | LGC | LF | NoL | PH | TKW | SC |
|---|---|---|---|---|---|---|---|---|---|---|---|---|---|
| tc (n = 2) | 59.5 ± 0.7 | 1 ± 0 | 1 ± 0 | 1 ± 0 | 1 ± 0 | 3 ± 0 | 3 ± 0 | 5 ± 0 | 1 ± 0 | 4 ± 0 | 125 ± 0 | 3.7 ± 0.1 | 3.5 ± 0.7 |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoL: number of lobes (#),
PH: plant height (cm),
TKW: thousand kernel weight (g),
SC: seed quality (1 = good, 9 = bad)

B. Fatty Acid Profiles, Copy Number Measurements, and Phenotypic Observations of T2 Plants Carrying T-DNAs of Plasmids VC-LJB2197-1qcz and VC-LLM337-1qcz Rc Cultivated in Greenhouses During Summer Table 48 shows the copy number analysis of select events. The events comprised one to two homozygous insertions and some had additional insertions still segregating. For example LANBCH segregated as homozygous for one T-DNA insertions for each construct, while LANPMZ segregated as homozygous for two T-DNA insertions for each construct. LALXOL seems to segregate for one insertion of VC-LLM337-1qcz rc, not homozygous, and for one homozygous insertion of LJB2197-1qcz_F with another copy which was not homozygous with the exception of the region around j-t-StCAT_p2_p-LuPXR, which seems to be a double copy event homozygous for each copy. For the T2 events selected, combined DHA and EPA levels were from nine to thirteen percent of the total fatty acids present in the seed. Whereas the selected T3 events had combined DHA and EPA levels varying from eleven to twenty three percent, with LALWPA having a DHA level of five percent and an EPA level of eighteen percent with respect to total fatty acid content in the seed, see Table 50. The selected events exhibited no morphological or anatomical defects relative to one another or to wild type.

TABLE 48

Copy number measurement of T2 plants cultivated in the greenhouse of canola events containing the T-DNAs of plasmids VC-LJB2197-1qcz and VC-LLM337-1qcz rc. The events are indicated in the first column, along with the number of T1 plants that where measured per event. As the T2 plants underwent two cylces of selecting homozygous plants, all plants of all events are homozygous for all T-DNA insertions. A copy number of ~2 therefore was indicative of one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

Copy number assays targeting the T-DNA of VC-LJB2197-1qcz. Assays are listed according to the position of the assay target along the T-DNA, with target c-AHAS located near the left T-DNA border and target j-i-Atss18_c-d6Elo(Pp_GA2) near the right T-DNA border.

| Event | c-AHAS | j-t-E9-p3-2 | c-d6Elo(Tp_GA) | j-t-StCAT_p2_p-LuPXR | j-t-CaMV_p-LuCnl-2 |
|---|---|---|---|---|---|
| LANBCH (n = 30) | 4.0 | 3.7 | 4.1 | 4.0 | 4.4 |
| LANPMZ (n = 74) | 2.0 | 2.0 | 2.0 | 2.0 | 1.6 |
| LAOIKC (n = 29) | 2.1 | 4.0 | 3.9 | 4.2 | 4.3 |
| LALHBO (n = 29) | 4.1 | 3.9 | 4.1 | 4.0 | 3.9 |
| LALRCH (n = 30) | 4.1 | 3.8 | 4.0 | 3.9 | 3.4 |
| LALWPA (n = 29) | 4.0 | 3.9 | 4.1 | 6.0 | 5.7 |
| LALXOL (n = 15) | 2.1 | 2.1 | 2.1 | 4.1 | 2.7 |
| LALXVM (n = 30) | 3.8 | 3.6 | 3.9 | 3.5 | 1.8 |
| LALZGS (n = 24) | 1.9 | 4.0 | 3.8 | 4.0 | 1.8 |
| LAMADR (n = 44) | 4.0 | 3.9 | 3.8 | 4.0 | 4.6 |
| LAMQJH (n = 30) | 4.0 | 4.0 | 4.0 | 3.9 | 2.9 |
| LAMQUI (n = 36) | 2.2 | 2.1 | 4.0 | 3.7 | 3.5 |
| LAMRUR (n = 30) | 3.6 | 3.7 | 3.4 | 3.7 | 4.1 |
| LANPSF (n = 30) | 4.0 | 4.0 | 3.8 | 3.9 | 4.1 |

TABLE 48-continued

Copy number measurement of T2 plants cultivated in the greenhouse of canola events containing the T-DNAs of plasmids VC-LJB2197-1qcz and VC-LLM337-1qcz rc. The events are indicated in the first column, along with the number of T1 plants that where measured per event. As the T2 plants underwent two cylces of selecting homozygous plants, all plants of all events are homozygous for all T-DNA insertions. A copy number of ~2 therefore was indicative of one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

| | Copy number assays targeting the T-DNA of VC-LJB2197-1qcz. Assays are listed according to the position of theassay target along the T-DNA, with target c-AHAS located near the left T-DNA border and target j-i-Atss18_c-d6Elo(Pp_GA2) near the right T-DNA border. | | Copy number assays targeting the T-DNA of VC-LLM337-1qcz rc. Assays are listed according to the position of the assay target along the T-DNA, with target j-t-PvARC-p3 located near the left T-DNA border and target c-d4Des(Eg_GA) near the right T-DNA border. | | |
|---|---|---|---|---|---|
| Event | c-d6Elo(Pp_GA) | j-i-Atss18_c-d6Elo(Pp_GA2) | j-t-PvARC-p3 | c-d4Des(Tc_GA) | c-o3Des(Pi_GA2_SN) |
| LANBCH (n = 30) | 4.0 | 3.8 | 2.9 | 3.9 | |
| LANPMZ (n = 74) | 2.0 | 2.0 | 1.8 | 2.1 | |
| LAOIKC (n = 29) | 4.1 | 4.3 | 2.3 | 2.0 | |
| LALHBO (n = 29) | 3.9 | 3.8 | 3.9 | 3.5 | |
| LALRCH (n = 30) | 4.1 | 4.0 | 3.9 | 4.1 | |
| LALWPA (n = 29) | 4.1 | 3.9 | 2.3 | 3.6 | |
| LALXOL (n = 15) | 2.0 | 2.1 | 0.9 | 1.2 | |
| LALXVM (n = 30) | 2.0 | 1.9 | 2.5 | 2.5 | |
| LALZGS (n = 24) | 2.0 | 2.0 | 2.1 | 2.0 | |
| LAMADR (n = 44) | 4.0 | 3.9 | 2.5 | 3.4 | |
| LAMQJH (n = 30) | 4.1 | 4.1 | 4.5 | 4.1 | |
| LAMQUI (n = 36) | 3.6 | 3.8 | 1.5 | 1.3 | |
| LAMRUR (n = 30) | 3.6 | 3.8 | 3.7 | 3.6 | |
| LANPSF (n = 30) | 3.9 | 4.1 | 1.5 | 3.5 | |

| | Copy number assays targeting the T-DNA of VC-LLM337-1qcz rc. Assays are listed according to the position of the assay target along the T-DNA, with target j-t-PvARC-p3 located near the left T-DNA border and target c-d4Des(Eg_GA) near the right T-DNA border. | | | | |
|---|---|---|---|---|---|
| Event | j-i-Atss15_c-o3Des(Pi_GA2) | c-o3Des(Pir_GA) | j-p-VfSBPperm3_c-o3Des(Pir_GA) | j-i-Atss1_c-d5Elo(Ot_GA3) | c-d4Des(Eg_GA) |
| LANBCH (n = 30) | | | 3.8 | 3.8 | 3.8 |
| LANPMZ (n = 74) | | | 2.0 | 2.0 | 2.1 |
| LAOIKC (n = 29) | | | 2.1 | 2.3 | 2.2 |
| LALHBO (n = 29) | | | 3.8 | 2.1 | 2.0 |
| LALRCH (n = 30) | | | 3.6 | 3.8 | 4.0 |
| LALWPA (n = 29) | | | 3.5 | 3.4 | 3.6 |
| LALXOL (n = 15) | | | 1.2 | 1.1 | 1.2 |
| LALXVM (n = 30) | | | 2.4 | 2.2 | 2.3 |
| LALZGS (n = 24) | | | 2.0 | 2.1 | 2.2 |
| LAMADR (n = 44) | | | 3.1 | 3.0 | 3.1 |
| LAMQJH (n = 30) | | | 4.0 | 3.9 | 4.2 |
| LAMQUI (n = 36) | | | 2.9 | 5.2 | 5.5 |
| LAMRUR (n = 30) | | | 3.8 | 4.3 | 3.9 |
| LANPSF (n = 30) | | | 3.4 | 4.3 | 3.9 |

TABLE 49

Fatty acid profiles of T3 seeds harvested from T2 cultivated in the greenhouse of canola events containing the T-DNAs of plasmids VC-LJB2197-1qcz and VC-LLM337-1qcz rc The events are indicated in the first column, along with the number of T3 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 |
|---|---|---|---|---|---|---|---|---|---|---|
| LANBCH (n = 30) | 4.5 ± 0.6 | 0.2 ± 0 | 0.1 ± 0 | 4 ± 0.2 | 22.2 ± 1.1 | 31.1 ± 0.7 | 1 ± 0.1 | 4 ± 0.2 | 1.8 ± 0.2 | 0.2 ± 0 |
| LANPMZ (n = 74) | 5 ± 0.4 | 0.2 ± 0 | 0 ± 0 | 3.6 ± 0.4 | 26.3 ± 2.1 | 35.2 ± 1.6 | 0.4 ± 0.1 | 4.6 ± 0.6 | 0.7 ± 0.2 | 0.1 ± 0.1 |
| LAOIKC (n = 29) | 5.1 ± 0.6 | 0.2 ± 0 | 0.1 ± 0 | 3.6 ± 0.3 | 22.1 ± 1.7 | 30.8 ± 1 | 0.9 ± 0.1 | 4 ± 0.3 | 1.8 ± 0.2 | 0.2 ± 0 |

TABLE 49-continued

Fatty acid profiles of T3 seeds harvested from T2 cultivated in the greenhouse of canola events containing the T-DNAs of plasmids VC-LJB2197-1qcz and VC-LLM337-1qcz rc The events are indicated in the first column, along with the number of T3 seed batches that were measured per event. Per seed batch a random selection of ~30 seed was measured in two technical repeats.

| Event | | | | | | | | | | |
|---|---|---|---|---|---|---|---|---|---|---|
| LALHBO (n = 29) | 4.4 ± 0.3 | 0.2 ± 0.1 | 0 ± 0 | 3.9 ± 0.4 | 19.6 ± 2.3 | 28.8 ± 1.5 | 0.6 ± 0.1 | 4.9 ± 0.3 | 1.3 ± 0.3 | 0.2 ± 0.1 |
| LALRCH (n = 30) | 4.6 ± 0.2 | 0.2 ± 0 | 0.1 ± 0 | 3.7 ± 0.3 | 22.3 ± 1.2 | 30.1 ± 1 | 0.9 ± 0.1 | 4.2 ± 0.2 | 1.6 ± 0.2 | 0.2 ± 0 |
| LALWPA (n = 29) | 4.4 ± 0.2 | 0.2 ± 0.1 | 0 ± 0 | 3.3 ± 0.2 | 17.3 ± 1.6 | 25.6 ± 1.4 | 1 ± 0.1 | 4.4 ± 0.4 | 2.3 ± 0.3 | 0.4 ± 0.1 |
| LALXOL (n = 15) | 4.4 ± 0.3 | 0.2 ± 0 | 0 ± 0 | 4.4 ± 0.6 | 21.4 ± 1.1 | 28.4 ± 1.2 | 0.4 ± 0.1 | 3.5 ± 0.3 | 0.8 ± 0.2 | 0.1 ± 0 |
| LALXVM (n = 30) | 4.5 ± 1 | 0.2 ± 0 | 0 ± 0 | 3.8 ± 0.4 | 21.3 ± 1.6 | 28.8 ± 1.7 | 0.7 ± 0.2 | 4.5 ± 0.6 | 1.2 ± 0.6 | 0.2 ± 0.1 |
| LALZGS (n = 24) | 4.5 ± 0.7 | 0.3 ± 0 | 0 ± 0 | 3.4 ± 0.5 | 21.8 ± 1.8 | 29.4 ± 1.4 | 0.6 ± 0.1 | 4.2 ± 0.5 | 1.2 ± 0.3 | 0.2 ± 0 |
| LAMADR (n = 44) | 3.7 ± 1.6 | 0.2 ± 0 | 0.1 ± 0 | 4 ± 0.5 | 22.3 ± 2.8 | 32.5 ± 1.5 | 0.8 ± 0.2 | 4.3 ± 0.6 | 1.9 ± 0.4 | 0.3 ± 0.1 |
| LAMQJH (n = 30) | 4.9 ± 0.3 | 0.3 ± 0 | 0.1 ± 0.1 | 3.8 ± 0.3 | 21.9 ± 1.7 | 30.9 ± 1.1 | 1 ± 0.2 | 4.3 ± 0.3 | 2.2 ± 0.2 | 0.3 ± 0.1 |
| LAMQUI (n = 36) | 3.2 ± 2 | 0.2 ± 0.1 | 0.1 ± 0 | 3.1 ± 0.8 | 25.1 ± 2.7 | 26 ± 1.4 | 1.1 ± 0.3 | 4.5 ± 0.9 | 1.5 ± 0.4 | 0.2 ± 0.1 |
| LAMRUR (n = 30) | 4.9 ± 0.3 | 0.2 ± 0 | 0.2 ± 0.1 | 3.9 ± 0.3 | 23.4 ± 1.7 | 32 ± 1.1 | 1.1 ± 0.2 | 4 ± 0.5 | 2.3 ± 0.3 | 0.3 ± 0 |
| LANPSF (n = 30) | 4.7 ± 0.2 | 0.3 ± 0 | 0.1 ± 0 | 3.9 ± 0.2 | 23.2 ± 1.3 | 30.9 ± 0.9 | 0.8 ± 0.1 | 4.5 ± 0.5 | 1.7 ± 0.3 | 0.3 ± 0 |
| WT Kumily (n = 46) | 5 ± 0.1 | 0.4 ± 0 | 0.2 ± 0 | 2.6 ± 0.1 | 66.3 ± 1.7 | 16.8 ± 1.3 | 0 ± 0 | 6.1 ± 0.4 | 0 ± 0 | 0 ± 0 |

| Event | 20:0 | 20:1 n-9 | 20:2 n-6 | 20:3 n-3 | 20:3 n-6 | 20:4 n-3 | 20:4 n-6 | 20:5 n-3 | 22:0 | 22:1 n-9 |
|---|---|---|---|---|---|---|---|---|---|---|
| LANBCH (n = 30) | 0.8 ± 0 | 0.6 ± 0 | 0.5 ± 0.1 | 0.1 ± 0 | 2.6 ± 0.3 | 1.8 ± 0.1 | 3.3 ± 0.1 | 11.4 ± 0.5 | 0.3 ± 0 | 0 ± 0 |
| LANPMZ (n = 74) | 0.8 ± 0.1 | 0.8 ± 0.1 | 1.1 ± 0.4 | 0.3 ± 0.2 | 2.4 ± 0.3 | 1.5 ± 0.2 | 3.1 ± 0.4 | 7.2 ± 0.8 | 0.3 ± 0.1 | 0 ± 0 |
| LAOIKC (n = 29) | 0.8 ± 0.1 | 0.6 ± 0 | 0.5 ± 0.1 | 0.1 ± 0 | 3.1 ± 0.8 | 1.6 ± 0.3 | 5.9 ± 0.5 | 10.3 ± 0.8 | 0.3 ± 0 | 0 ± 0 |
| LALHBO (n = 29) | 0.9 ± 0.1 | 0.7 ± 0 | 0.9 ± 0.3 | 0.3 ± 0.1 | 2.4 ± 0.3 | 2 ± 0.2 | 4.3 ± 0.3 | 13.4 ± 1.9 | 0.3 ± 0 | 0 ± 0 |
| LALRCH (n = 30) | 0.8 ± 0 | 0.7 ± 0 | 0.7 ± 0.2 | 0.2 ± 0.1 | 2.7 ± 0.3 | 1.8 ± 0.2 | 4 ± 0.4 | 11.2 ± 0.8 | 0.3 ± 0 | 0 ± 0 |
| LALWPA (n = 29) | 0.8 ± 0 | 0.7 ± 0 | 0.5 ± 0.2 | 0.2 ± 0 | 2 ± 0.2 | 1.6 ± 0.1 | 5.7 ± 0.7 | 14.8 ± 1.5 | 0.4 ± 0 | 0 ± 0 |
| LALXOL (n = 15) | 0.9 ± 0.1 | 0.9 ± 0.1 | 2.5 ± 0.5 | 0.5 ± 0.2 | 2.2 ± 0.3 | 1.3 ± 0.3 | 8.7 ± 2.1 | 11.6 ± 1.3 | 0.3 ± 0 | 0 ± 0 |
| LALXVM (n = 30) | 0.8 ± 0.1 | 0.8 ± 0.1 | 1.5 ± 0.8 | 0.5 ± 0.3 | 2.7 ± 0.3 | 1.9 ± 0.3 | 4.7 ± 0.9 | 11.7 ± 1.3 | 0.3 ± 0 | 0 ± 0 |
| LALZGS (n = 24) | 0.8 ± 0.1 | 0.7 ± 0.1 | 1.3 ± 0.3 | 0.3 ± 0.1 | 2.6 ± 0.3 | 1.8 ± 0.3 | 5.6 ± 0.6 | 12.1 ± 1.2 | 0.3 ± 0 | 0 ± 0 |
| LAMADR (n = 44) | 0.9 ± 0.1 | 0.7 ± 0 | 0.5 ± 0.2 | 0.1 ± 0 | 2.2 ± 0.4 | 1.4 ± 0.2 | 4.4 ± 2 | 10.8 ± 1.6 | 0.3 ± 0 | 0 ± 0 |
| LAMQJH (n = 30) | 0.8 ± 0 | 0.6 ± 0 | 0.2 ± 0.1 | 0 ± 0 | 3 ± 0.5 | 1.7 ± 0.2 | 3.4 ± 0.4 | 10.7 ± 1 | 0.3 ± 0.1 | 0 ± 0 |
| LAMQUI (n = 36) | 0.7 ± 0.1 | 0.8 ± 0.1 | 1.1 ± 0.7 | 0.3 ± 0.2 | 2.2 ± 0.4 | 1.3 ± 0.3 | 4.7 ± 1.7 | 11.6 ± 2.2 | 0.2 ± 0 | 0 ± 0 |
| LAMRUR (n = 30) | 0.8 ± 0.1 | 0.7 ± 0 | 0.2 ± 0.1 | 0 ± 0 | 2.9 ± 0.6 | 1.5 ± 0.2 | 4 ± 0.4 | 9.4 ± 0.9 | 0.2 ± 0.1 | 0 ± 0 |
| LANPSF (n = 30) | 0.8 ± 0.1 | 0.7 ± 0 | 0.5 ± 0.1 | 0.1 ± 0 | 2.2 ± 0.2 | 1.5 ± 0.1 | 3.7 ± 0.7 | 9.9 ± 0.8 | 0.3 ± 0 | 0 ± 0 |
| WT Kumily (n = 46) | 0.9 ± 0 | 1.2 ± 0 | 0 ± 0 | 0 ± 0 | 0 ± 0 | 0 ± 0 | 0 ± 0 | 0 ± 0 | 0.5 ± 0 | 0 ± 0 |

| Event | 22:4 n-6 | 22:5 n-3 | 22:5 n-6 | 22:6 n-3 | 22:4 n-3 | 20:2 n-9 |
|---|---|---|---|---|---|---|
| LANBCH (n = 30) | 1.7 ± 0.1 | 4.4 ± 0.2 | 0 ± 0 | 2.3 ± 0.2 | 0.6 ± 0.1 | 0.4 ± 0.1 |
| LANPMZ (n = 74) | 1 ± 0.1 | 2.9 ± 0.5 | 0 ± 0 | 1.5 ± 0.3 | 0.4 ± 0.1 | 0.5 ± 0.1 |
| LAOIKC (n = 29) | 1.3 ± 0.1 | 4 ± 0.3 | 0 ± 0 | 1.8 ± 0.2 | 0.4 ± 0.1 | 0.3 ± 0 |
| LALHBO (n = 29) | 1.3 ± 0.2 | 5.7 ± 0.8 | 0 ± 0 | 2.7 ± 0.4 | 0.4 ± 0.1 | 0.6 ± 0.1 |
| LALRCH (n = 30) | 1.8 ± 0.1 | 4.5 ± 0.4 | 0 ± 0 | 2.3 ± 0.4 | 0.6 ± 0.1 | 0.6 ± 0.2 |

TABLE 49-continued

Fatty acid profiles of T3 seeds harvested from T2 cultivated in the greenhouse of canola events containing the T-DNAs of plasmids VC-LJB2197-1qcz and VC-LLM337-1qcz rc The events are indicated in the first column, along with the number of T3 seed batches that were measured per event. Per seed batch a random selection of ~30 seed was measured in two technical repeats.

| Event | | | | | | |
|---|---|---|---|---|---|---|
| LALWPA (n = 29) | 2.1 ± 0.2 | 7.3 ± 0.8 | 0 ± 0 | 4 ± 0.7 | 0.5 ± 0.1 | 0.3 ± 0.1 |
| LALXOL (n = 15) | 0.8 ± 0.2 | 3.5 ± 0.8 | 0 ± 0 | 1.8 ± 0.4 | 0.1 ± 0.1 | 1 ± 0.2 |
| LALXVM (n = 30) | 1.4 ± 0.4 | 5.1 ± 0.8 | 0 ± 0 | 2.3 ± 0.3 | 0.4 ± 0.2 | 0.8 ± 0.4 |
| LALZGS (n = 24) | 1.2 ± 0.1 | 4.7 ± 0.6 | 0 ± 0 | 2.1 ± 0.4 | 0.2 ± 0.2 | 0.8 ± 0.2 |
| LAMADR (n = 44) | 1.6 ± 0.2 | 4.1 ± 0.5 | 0 ± 0 | 2.1 ± 0.3 | 0.5 ± 0.2 | 0.3 ± 0.1 |
| LAMQJH (n = 30) | 1.8 ± 0.2 | 4.4 ± 0.6 | 0 ± 0 | 2.3 ± 0.5 | 0.7 ± 0.1 | 0.2 ± 0 |
| LAMQUI (n = 36) | 2.4 ± 0.4 | 6.1 ± 0.9 | 0 ± 0 | 2.3 ± 0.6 | 0.6 ± 0.1 | 0.7 ± 0.3 |
| LAMRUR (n = 30) | 1.6 ± 0.2 | 3.7 ± 0.3 | 0 ± 0 | 1.9 ± 0.3 | 0.6 ± 0.1 | 0.2 ± 0.1 |
| LANPSF (n = 30) | 2.1 ± 0.2 | 4.4 ± 0.4 | 0 ± 0 | 2.3 ± 0.2 | 0.7 ± 0.2 | 0.3 ± 0.1 |
| WT Kumily (n = 46) | 0 ± 0 | 0 ± 0 | 0 ± 0 | 0 ± 0 | 0 ± 0 | 0 ± 0 |

TABLE 50

Fatty acid profiles of one T3 seed batch per event harvested from T2 plants cultivated in the greenhouse of canola events containing the T-DNAs of plasmids VC-LJB2197-1qcz and VC-LLM337-1qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LANBCH (n = 1) | 4.6 | 0.2 | 0.1 | 3.9 | 21.3 | 30.3 | 1.1 | 4.0 | 2.0 | 0.3 | 0.8 | 0.6 | 0.4 |
| LANPMZ (n = 1) | 4.6 | 0.3 | 0.1 | 4.0 | 22.6 | 32.2 | 0.3 | 5.2 | 0.7 | 0.1 | 0.9 | 0.8 | 1.4 |
| LAOIKC (n = 1) | 7.9 | 0.5 | 0.1 | 3.2 | 19.0 | 28.4 | 0.8 | 3.4 | 1.9 | 0.2 | 0.7 | 0.5 | 0.5 |
| LALHBO (n = 1) | 4.1 | 0.1 | 0.0 | 3.6 | 16.4 | 26.5 | 0.6 | 4.8 | 1.5 | 0.3 | 0.9 | 0.7 | 1.1 |
| LALRCH (n = 1) | 4.1 | 0.2 | 0.1 | 3.6 | 20.5 | 28.5 | 0.8 | 4.3 | 1.3 | 0.2 | 0.7 | 0.7 | 1.2 |
| LALWPA (n = 1) | 4.7 | 0.2 | 0.0 | 3.0 | 14.6 | 20.2 | 1.1 | 4.7 | 2.8 | 0.7 | 0.8 | 0.7 | 0.7 |
| LALXOL (n = 1) | 4.6 | 0.2 | 0.0 | 4.9 | 21.0 | 26.0 | 0.5 | 4.2 | 0.7 | 0.2 | 1.0 | 0.9 | 2.3 |
| LALXVM (n = 1) | 4.7 | 0.3 | 0.0 | 3.7 | 18.3 | 26.9 | 0.5 | 4.5 | 0.8 | 0.2 | 0.8 | 0.9 | 2.4 |
| LALZGS (n = 1) | 4.6 | 0.3 | 0.0 | 2.5 | 19.0 | 28.4 | 0.6 | 3.7 | 1.5 | 0.2 | 0.6 | 0.7 | 1.2 |
| LAMADR (n = 1) | 4.2 | 0.2 | 0.1 | 3.6 | 17.2 | 29.3 | 0.9 | 3.4 | 3.1 | 0.4 | 0.7 | 0.7 | 0.5 |
| LAMQJH (n = 1) | 4.8 | 0.3 | 0.1 | 3.0 | 17.7 | 28.1 | 0.7 | 4.6 | 2.3 | 0.4 | 0.7 | 0.6 | 0.4 |
| LAMQUI (n = 1) | 0.2 | 0.1 | 0.1 | 3.8 | 24.4 | 25.8 | 1.2 | 2.4 | 1.9 | 0.4 | 0.7 | 0.8 | 1.1 |
| LAMRUR (n = 1) | 4.9 | 0.2 | 0.3 | 4.2 | 20.3 | 32.0 | 1.1 | 3.2 | 2.7 | 0.3 | 0.8 | 0.6 | 0.0 |
| LANPSF (n = 1) | 4.7 | 0.3 | 0.0 | 3.9 | 20.8 | 30.7 | 0.8 | 4.1 | 2.0 | 0.3 | 0.8 | 0.6 | 0.5 |
| LANBCH (n = 1) | 4.6 | 0.2 | 0.1 | 3.9 | 21.3 | 30.3 | 1.1 | 4.0 | 2.0 | 0.3 | 0.8 | 0.6 | 0.4 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LANBCH (n = 1) | 0.1 | 2.5 | 1.8 | 3.3 | 12.4 | 0.3 | 0.0 | 1.8 | 4.8 | 0.0 | 2.5 | 0.7 | 0.3 |
| LANPMZ (n = 1) | 0.5 | 2.6 | 2.1 | 3.1 | 9.7 | 0.3 | 0.0 | 1.1 | 4.2 | 0.0 | 2.3 | 0.5 | 0.5 |
| LAOIKC (n = 1) | 0.1 | 3.0 | 1.6 | 6.5 | 12.2 | 0.3 | 0.0 | 1.5 | 4.6 | 0.0 | 2.2 | 0.3 | 0.4 |
| LALHBO (n = 1) | 0.4 | 2.7 | 2.3 | 4.3 | 16.6 | 0.4 | 0.0 | 1.4 | 7.0 | 0.0 | 3.5 | 0.5 | 0.6 |
| LALRCH (n = 1) | 0.3 | 2.7 | 2.0 | 4.6 | 12.3 | 0.3 | 0.0 | 1.8 | 5.0 | 0.0 | 3.3 | 0.6 | 1.0 |
| LALWPA (n = 1) | 0.2 | 1.6 | 1.6 | 5.4 | 18.1 | 0.4 | 0.0 | 2.0 | 10.0 | 0.0 | 5.7 | 0.5 | 0.4 |
| LALXOL (n = 1) | 0.9 | 2.1 | 1.9 | 3.4 | 14.0 | 0.4 | 0.0 | 1.1 | 5.4 | 0.0 | 2.7 | 0.4 | 1.1 |
| LALXVM (n = 1) | 0.8 | 2.7 | 2.2 | 4.7 | 14.3 | 0.3 | 0.0 | 1.1 | 5.6 | 0.0 | 2.8 | 0.4 | 1.1 |
| LALZGS (n = 1) | 0.3 | 2.7 | 1.9 | 7.0 | 14.1 | 0.2 | 0.0 | 1.4 | 5.5 | 0.0 | 2.9 | 0.0 | 0.7 |
| LAMADR (n = 1) | 0.1 | 2.6 | 1.5 | 5.8 | 14.7 | 0.3 | 0.0 | 2.1 | 5.1 | 0.0 | 2.7 | 0.5 | 0.3 |
| LAMQJH (n = 1) | 0.1 | 2.2 | 1.5 | 4.7 | 14.4 | 0.4 | 0.0 | 2.2 | 6.8 | 0.0 | 3.5 | 0.5 | 0.2 |
| LAMQUI (n = 1) | 0.3 | 2.2 | 1.6 | 4.0 | 14.9 | 0.2 | 0.0 | 2.2 | 7.3 | 0.0 | 3.1 | 0.6 | 0.8 |
| LAMRUR (n = 1) | 0.0 | 3.0 | 1.7 | 4.0 | 11.3 | 0.3 | 0.0 | 1.8 | 3.8 | 0.0 | 2.7 | 0.6 | 0.3 |
| LANPSF (n = 1) | 0.1 | 2.4 | 1.4 | 4.5 | 11.4 | 0.3 | 0.0 | 2.1 | 4.7 | 0.0 | 2.6 | 0.6 | 0.4 |
| LANBCH (n = 1) | 0.1 | 2.5 | 1.8 | 3.3 | 12.4 | 0.3 | 0.0 | 1.8 | 4.8 | 0.0 | 2.5 | 0.7 | 0.3 |

TABLE 51

Phenotypic rating of T2 plants cultivated in the greenhouse of canola events containing the T-DNAs of plasmids VC-LJB2197-1qcz and VC-LLM337-1qcz rc. The events are indicated in the first column, along with the number of T1 plants that where rated per event.

| Event | DFF | DF | DL | DP | DS | FC | LD | LGC |
|---|---|---|---|---|---|---|---|---|
| LALHCY (n = 1) | 59.1 ± 3.3 | 9 ± 0 | 8.9 ± 0.4 | 9 ± 0 | 7 ± 0.9 | 3 ± 0 | 3 ± 0 | 5 ± 0 |
| LANBCH (n = 30) | 51.9 ± 3.1 | 9 ± 0.2 | 8.5 ± 0.7 | 9 ± 0.2 | 8.1 ± 0.7 | 3 ± 0 | 3 ± 0 | 5 ± 0 |
| LANPMZ (n = 74) | 57.3 ± 1.6 | 9 ± 0 | 8.9 ± 0.4 | 9 ± 0 | 7.3 ± 0.7 | 3 ± 0 | 3 ± 0 | 5 ± 0 |
| LAOIKC (n = 29) | 65.2 ± 2.1 | 9 ± 0 | 7.1 ± 1.7 | 7.4 ± 1.1 | 6.2 ± 2.9 | 3 ± 0 | 3 ± 0 | 5 ± 0 |
| LALHBO (n = 29) | 61.3 ± 1.9 | 9 ± 0 | 7.9 ± 1.3 | 8.8 ± 0.4 | 7.3 ± 0.5 | 3 ± 0 | 3 ± 0 | 5.1 ± 0.4 |
| LALRCH (n = 30) | 61.3 ± 1.8 | 9 ± 0 | 8.2 ± 1.4 | 7.8 ± 1 | 7.7 ± 1.9 | 3 ± 0 | 3 ± 0 | 5 ± 0 |
| LALWPA (n = 29) | 60.4 ± 3.9 | 9 ± 0 | 9 ± 0 | 9 ± 0 | 7.6 ± 1.1 | 3 ± 0 | 3 ± 0 | 5 ± 0 |
| LALXOL (n = 15) | 60.7 ± 4.6 | 9 ± 0 | 8.9 ± 0.7 | 8.2 ± 0.8 | 7.6 ± 0.9 | 3 ± 0 | 3 ± 0 | 5 ± 0 |
| LALXVM (n = 30) | 56.7 ± 4 | 8.7 ± 1.3 | 9 ± 0 | 8.9 ± 0.4 | 7.3 ± 1.3 | 3 ± 0 | 3 ± 0 | 5 ± 0 |
| LALZGS (n = 24) | 56.9 ± 6 | 9 ± 0 | 8.4 ± 1.3 | 9 ± 0 | 7.8 ± 1 | 3 ± 0 | 3 ± 0 | 5 ± 0 |
| LAMADR (n = 44) | 59.9 ± 2.6 | 9 ± 0 | 8.7 ± 0.9 | 8.8 ± 0.5 | 7.5 ± 1.1 | 3 ± 0 | 3 ± 0 | 5 ± 0 |
| LAMQJH (n = 30) | 60.3 ± 3.1 | 9 ± 0 | 8.5 ± 1.1 | 8.3 ± 0.6 | 8.1 ± 0.9 | 3 ± 0 | 3 ± 0 | 5 ± 0 |
| LAMQUI (n = 36) | 59.6 ± 1.9 | 9 ± 0 | 9 ± 0 | 9 ± 0 | 8.3 ± 0.7 | 3 ± 0 | 3 ± 0 | 5 ± 0 |
| LAMRUR (n = 30) | 55.1 ± 2.9 | 9 ± 0 | 9 ± 0 | 9 ± 0 | 7.3 ± 0.8 | 3 ± 0 | 3 ± 0 | 5 ± 0 |
| LANPSF (n = 30) | 59.1 ± 3.3 | 9 ± 0 | 8.9 ± 0.4 | 9 ± 0 | 7 ± 0.9 | 3 ± 0 | 3 ± 0 | 5 ± 0 |
| WT Kumily (n = 46) | | | | | | | | |

| Event | LF | NoL | PH | TKW | SC | Oil | Protein |
|---|---|---|---|---|---|---|---|
| LALHCY (n = 1) | 7.5 ± 1.4 | 4 ± 0.2 | 129.2 ± 3.5 | | | | |
| LANBCH (n = 30) | 8 ± 0.7 | 5 ± 0.8 | 127.7 ± 6.6 | | | 35.2 ± 2.8 | 30 ± 2 |
| LANPMZ (n = 74) | 7.9 ± 1.1 | 4 ± 0 | 125.3 ± 5 | | | | |
| LAOIKC (n = 29) | 7.7 ± 2 | 4.1 ± 0.4 | 118.8 ± 5.8 | 4.9 ± 0.5 | 5.3 ± 2.3 | | |
| LALHBO (n = 29) | 7.7 ± 3 | 3.9 ± 0.4 | 128.3 ± 3.3 | | | | |
| LALRCH (n = 30) | 8.2 ± 1.3 | 3.8 ± 0.6 | 125 ± 3 | 5.2 ± 0.4 | 3.7 ± 1 | | |
| LALWPA (n = 29) | 7.6 ± 1.1 | 4.9 ± 0.8 | 127.3 ± 3.7 | | | | |
| LALXOL (n = 15) | 8.4 ± 0.9 | 4 ± 0.6 | 126 ± 4.6 | 5.4 ± 0.4 | 3.3 ± 1.3 | | |
| LALXVM (n = 30) | 7.3 ± 1.4 | 5.6 ± 1.3 | 121 ± 24.4 | | | | |
| LALZGS (n = 24) | 7.9 ± 0.9 | 5.1 ± 0.7 | 128.4 ± 5.5 | | | | |
| LAMADR (n = 44) | 8.2 ± 1.2 | 4 ± 0.2 | 126.5 ± 5.3 | | | | |
| LAMQJH (n = 30) | 8.6 ± 0.9 | 3.9 ± 0.3 | 124 ± 4.6 | 5.3 ± 0.4 | 4.7 ± 1.3 | | |
| LAMQUI (n = 36) | 8.3 ± 0.7 | 4.9 ± 0.5 | 129.3 ± 4.5 | | | | |
| LAMRUR (n = 30) | 7.4 ± 0.9 | 5.7 ± 0.8 | 126.8 ± 4.4 | | | | |

TABLE 51-continued

Phenotypic rating of T2 plants cultivated in the greenhouse of canola events containing the T-DNAs of plasmids VC-LJB2197-1qcz and VC-LLM337-1qcz rc. The events are indicated in the first column, along with the number of T1 plants that where rated per event.

| | | | | | |
|---|---|---|---|---|---|
| LANPSF (n = 30) | 7.5 ± 1.4 | 4 ± 0.2 | 129.2 ± 3.5 | | |
| WT Kumily (n = 46) | | | | 34.9 ± 1.1 | 32.2 ± 1 |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
Nol: number of lobes(#),
PH: plant height (cm),
TKW: thousand kernel weight (g),
SC: seed quality (1 = good, 9 = bad),
Oil: oil content (% of seed weight),
Protein: Protein content (% of seed cake without oil)

C. Fatty Acid Profiles of T2 Plants Carrying T-DNAs of Plasmids VC-LJB2197-1qcz and VC-LLM337-1qcz rc Cultivated in Field Trials in USDA Growth Zones 3a-4b and 5a During Summer.

Field data from the T3 seed indicate that field values are lower for EPA and DHA than what was observed in the greenhouse, with values ranging from six to thirteen percent of the total fatty acid content of the seed for EPA and DHA combined. These data show a difference in seed oil content observed in field studies compared to the greenhouse (e.g. comparing Table 54 with Table 51), see also Example 10. Results of this analysis are described in Example 20.

TABLE 52

Fatty acid profiles of T3 seeds harvested from T2 cultivated in the field in field trials, corresponding to USDA zones 3a-4b and zone 5a, of canola events containing the T-DNAs of plasmids VC-LJB2197-1qcz and VC-LLM337-1qcz rc The events are indicated in the first column, along with the number of T3 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-6 | 18:3 n-3 | 18:4 n-3 | 20:0 | 20:1 n-9 | 20:2 n-6 | 20:3 n-6 | 20:3 n-3 | 20:4 n-6 | 20:4 n-3 |
|---|---|---|---|---|---|---|---|---|---|---|---|---|---|---|---|---|---|
| LANBCH (n = 30) | 5.1 ± 0.2 | 0.4 ± 0 | 0 ± 0 | 2.6 ± 0.1 | 26 ± 1.9 | 31.3 ± 1 | 0.7 ± 0.1 | 6.2 ± 0.4 | 1.2 ± 0.2 | 0.2 ± 0 | 0.7 ± 0 | 0.7 ± 0 | 0.7 ± 0.1 | 1.9 ± 0.1 | 0.2 ± 0 | | 1.1 ± 0.1 |
| LANPMZ (n = 30) | 4.9 ± 0.1 | 0.3 ± 0 | 0 ± 0 | 2.4 ± 0.1 | 30.7 ± 1.5 | 32.1 ± 0.8 | 0.3 ± 0 | 6.9 ± 0.3 | 0.5 ± 0.1 | 0.1 ± 0 | 0.7 ± 0 | 0.9 ± 0 | 1.4 ± 0.3 | 2 ± 0.1 | 0.5 ± 0.1 | | 1.2 ± 0.1 |
| LAOIKC (n = 31) | 5.2 ± 0.2 | 0.3 ± 0 | 0 ± 0 | 2.5 ± 0.1 | 26 ± 2.2 | 31.4 ± 1.1 | 0.8 ± 0.1 | 5.5 ± 0.3 | 1.4 ± 0.2 | 0.2 ± 0 | 0.7 ± 0 | 0.7 ± 0 | 0.6 ± 0.1 | 2.4 ± 0.2 | 0.1 ± 0 | | 1.1 ± 0.1 |
| LALHBO (n = 29) | 5.1 ± 0.2 | 0.2 ± 0.1 | 0 ± 0 | 2.5 ± 0.2 | 28 ± 6.4 | 30.3 ± 2 | 0.6 ± 0.2 | 6.7 ± 1.1 | 1.1 ± 0.4 | 0.2 ± 0.1 | 0.7 ± 0 | 0.8 ± 0.1 | 0.9 ± 0.2 | 1.9 ± 0.4 | 0.3 ± 0.1 | | 1.1 ± 0.2 |
| LALWPA (n = 30) | 5 ± 0.4 | 0.3 ± 0 | 0 ± 0 | 2.2 ± 0.2 | 21.3 ± 2.7 | 28.8 ± 1.8 | 0.8 ± 0.1 | 5.5 ± 0.5 | 1.6 ± 0.3 | 0.3 ± 0.1 | 0.7 ± 0 | 0.8 ± 0 | 1 ± 0.2 | 2.3 ± 0.3 | 0.3 ± 0 | | 1.3 ± 0.1 |
| LALXOL (n = 29) | 5.1 ± 0.2 | 0.3 ± 0.1 | 0 ± 0 | 2.6 ± 0.2 | 26.8 ± 1.9 | 29.7 ± 1.8 | 0.4 ± 0.1 | 6 ± 0.8 | 0.8 ± 0.2 | 0.2 ± 0.1 | 0.7 ± 0 | 1 ± 0.1 | 2.1 ± 0.7 | 1.9 ± 0.2 | 0.5 ± 0.2 | | 1 ± 0.1 |
| LALXVM (n = 30) | 5 ± 0.3 | 0.3 ± 0.1 | 0 ± 0 | 2.4 ± 0.1 | 29 ± 4 | 29.9 ± 1.3 | 0.5 ± 0.1 | 6.3 ± 0.9 | 0.8 ± 0.2 | 0.2 ± 0.1 | 0.7 ± 0 | 0.9 ± 0.1 | 1.3 ± 0.4 | 2 ± 0.3 | 0.4 ± 0.1 | | 1.1 ± 0.1 |
| LALZGS (n = 29) | 5.1 ± 0.2 | 0.2 ± 0.1 | 0 ± 0 | 2.6 ± 0.2 | 25.1 ± 1.4 | 30.6 ± 1.2 | 0.6 ± 0.1 | 5.9 ± 0.4 | 1 ± 0.1 | 0.2 ± 0.1 | 0.7 ± 0 | 0.8 ± 0 | 1 ± 0.2 | 2.3 ± 0.1 | 0.3 ± 0.1 | | 1.2 ± 0.1 |
| LAMADR (n = 30) | 5.1 ± 0.1 | 0.2 ± 0.1 | 0 ± 0 | 2.7 ± 0.2 | 25.9 ± 1 | 32 ± 1.2 | 0.7 ± 0.1 | 5.9 ± 0.4 | 1.3 ± 0.2 | 0.2 ± 0.1 | 0.7 ± 0 | 0.8 ± 0 | 0.7 ± 0.1 | 2.1 ± 0.1 | 0.2 ± 0 | | 1 ± 0.1 |
| LAMQUI (n = 30) | 4.7 ± 0.2 | 0.3 ± 0.1 | 0 ± 0 | 2.5 ± 0.2 | 28.8 ± 1.9 | 29 ± 1.6 | 0.8 ± 0.2 | 5.7 ± 0.5 | 1.2 ± 0.2 | 0.2 ± 0.1 | 0.6 ± 0 | 0.9 ± 0.1 | 1 ± 0.3 | 1.7 ± 0.3 | 0.2 ± 0.1 | | 0.8 ± 0.1 |
| LAMRUR (n = 29) | 5.1 ± 0.3 | 0.3 ± 0 | 0 ± 0 | 2.6 ± 0.1 | 28.5 ± 2.3 | 32 ± 1.9 | 0.8 ± 0.2 | 5.8 ± 0.8 | 1.3 ± 0.2 | 0.2 ± 0 | 0.7 ± 0.1 | 0.7 ± 0.1 | 0.4 ± 0.1 | 2.1 ± 0.2 | 0 ± 0.1 | | 1 ± 0.1 |
| LANPSF (n = 28) | 5.1 ± 0.2 | 0.3 ± 0.1 | 0 ± 0 | 2.6 ± 0.1 | 26.9 ± 1.8 | 31.4 ± 1.4 | 0.7 ± 0.2 | 6.1 ± 0.7 | 1.2 ± 0.3 | 0.2 ± 0 | 0.7 ± 0 | 0.8 ± 0 | 0.7 ± 0.2 | 1.9 ± 0.2 | 0.2 ± 0.1 | | 1 ± 0.1 |
| WT Kumily (n = 60) | 5 ± 0.3 | 0.4 ± 0 | 0.1 ± 0.1 | 2 ± 0.1 | 56.2 ± 4.2 | 23.3 ± 1.7 | 0 ± 0.1 | 9.5 ± 0.7 | 0.1 ± 0.2 | 0 ± 0 | 0.7 ± 0 | 1.1 ± 0.1 | 0.1 ± 0.1 | 0.2 ± 0.3 | 0 ± 0 | | 0.1 ± 0.3 |

| Event | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|
| LANBCH (n = 30) | 3.4 ± 0.3 | 8.9 ± 0.8 | 0.3 ± 0 | 0 ± 0 | 1.4 ± 0.2 | 4.7 ± 0.4 | 0 ± 0 | 1.5 ± 0.2 | 0.4 ± 0.1 | 0.3 ± 0.1 |
| LANPMZ (n = 30) | 2.9 ± 0.2 | 5.8 ± 0.5 | 0.3 ± 0 | 0 ± 0 | 0.8 ± 0.1 | 3.3 ± 0.2 | 0 ± 0 | 1 ± 0.1 | 0.4 ± 0.1 | 0.5 ± 0.1 |
| LAOIKC (n = 31) | 5.7 ± 0.5 | 8 ± 0.6 | 0.2 ± 0 | 0 ± 0 | 1.1 ± 0.1 | 4.1 ± 0.3 | 0 ± 0 | 1.2 ± 0.2 | 0.1 ± 0.1 | 0.4 ± 0.1 |
| LALHBO (n = 29) | 3.8 ± 1 | 8.5 ± 2.1 | 0.3 ± 0 | 0 ± 0 | 0.9 ± 0.3 | 4.2 ± 1 | 0 ± 0 | 1.2 ± 0.3 | 0.1 ± 0.1 | 0.4 ± 0.1 |

TABLE 52-continued

Fatty acid profiles of T3 seeds harvested from T2 cultivated in the field in field trials, corresponding to USDA zones 3a-4b and zone 5a, of canola events containing the T-DNAs of plasmids VC-LJB2197-1qcz and VC-LLM337-1qcz rc The events are indicated in the first column, along with the number of T3 seed aliquots representing a plot were measured per event. Per seed batch a random selection of ~30 seed was measured in two technical repeats.

| | | | | | | | | | | |
|---|---|---|---|---|---|---|---|---|---|---|
| LAIWPA (n = 30) | 6 ± 1.4 | 11.1 ± 1.3 | 0.3 ± 0 | 0 ± 0 | 1.5 ± 0.1 | 5.9 ± 0.7 | 0 ± 0 | 2 ± 0.3 | 0.3 ± 0.2 | 0.5 ± 0.1 |
| LAIXOL (n = 29) | 5.5 ± 1.6 | 8.5 ± 1 | 0.3 ± 0 | 0 ± 0 | 0.8 ± 0.1 | 3.8 ± 0.6 | 0 ± 0 | 1.1 ± 0.2 | 0 ± 0 | 0.8 ± 0.2 |
| LAIXVM (n = 30) | 4.4 ± 1.3 | 7.7 ± 1.8 | 0.3 ± 0 | 0 ± 0 | 0.8 ± 0.2 | 3.9 ± 0.9 | 0 ± 0 | 1.1 ± 0.3 | 0.2 ± 0.1 | 0.6 ± 0.2 |
| LAIZGS (n = 29) | 5.7 ± 0.5 | 8.8 ± 0.5 | 0.2 ± 0.1 | 0 ± 0 | 0.9 ± 0.1 | 4.5 ± 0.2 | 0 ± 0 | 1.2 ± 0.1 | 0 ± 0.1 | 0.7 ± 0.1 |
| LAMADR (n = 30) | 4.7 ± 0.6 | 8 ± 0.7 | 0.3 ± 0 | 0 ± 0 | 1.3 ± 0.1 | 4.1 ± 0.3 | 0 ± 0 | 1.2 ± 0.1 | 0.2 ± 0.1 | 0.4 ± 0.1 |
| LAMQUI (n = 30) | 4.6 ± 0.9 | 7.6 ± 1 | 0.2 ± 0 | 0 ± 0 | 2.1 ± 0.3 | 4.6 ± 0.7 | 0 ± 0 | 1.4 ± 0.2 | 0.5 ± 0.1 | 0.5 ± 0.1 |
| LAMRUR (n = 29) | 3.8 ± 0.6 | 7.2 ± 0.7 | 0.2 ± 0.1 | 0 ± 0 | 1.3 ± 0.2 | 3.9 ± 0.4 | 0 ± 0 | 1.2 ± 0.2 | 0.3 ± 0.1 | 0.3 ± 0.1 |
| LANPSF (n = 28) | 3.9 ± 0.9 | 7.6 ± 1.1 | 0.3 ± 0 | 0 ± 0 | 1.7 ± 0.2 | 4.2 ± 0.4 | 0 ± 0 | 1.4 ± 0.2 | 0.6 ± 0.2 | 0.4 ± 0.1 |
| WT Kumily (n = 60) | 0.2 ± 0.5 | 0.4 ± 1.1 | 0.3 ± 0.1 | 0 ± 0 | 0 ± 0.2 | 0.2 ± 0.6 | 0 ± 0 | 0 ± 0.2 | | |

TABLE 53

Fatty acid profiles of one T3 seed batch per event harvested from T2 plants cultivated in field trials, corresponding to USDA zones 3a-4b and zone 5a, of canola events containing the T-DNAs of plasmids VC-LJB2197-1qcz and VC-LLM337-1qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LANBCH (n = 30) | 5.3 | 0.4 | 0.1 | 2.5 | 25.5 | 29.5 | 0.7 | 6.1 | 1.3 | 0.3 | 0.6 | 0.7 | 0.8 |
| LANPMZ (n = 30) | 5.1 | 0.3 | 0.0 | 2.3 | 27.1 | 31.5 | 0.2 | 6.9 | 0.4 | 0.1 | 0.7 | 0.9 | 2.1 |
| LAOIKC (n = 31) | 5.3 | 0.3 | 0.0 | 2.6 | 23.3 | 32.0 | 0.8 | 5.3 | 1.5 | 0.2 | 0.7 | 0.7 | 0.5 |
| LALHBO (n = 29) | 5.2 | 0.4 | 0.1 | 2.5 | 25.8 | 29.0 | 0.8 | 5.5 | 1.5 | 0.3 | 0.7 | 0.7 | 0.7 |
| LALWPA (n = 30) | 5.9 | 0.4 | 0.0 | 2.0 | 15.4 | 27.9 | 0.8 | 5.2 | 2.5 | 0.5 | 0.7 | 0.7 | 0.9 |
| LALXOL (n = 29) | 5.2 | 0.2 | 0.0 | 2.7 | 24.3 | 28.8 | 0.5 | 5.9 | 0.9 | 0.2 | 0.7 | 1.0 | 2.3 |
| LALXVM (n = 30) | 4.9 | 0.3 | 0.1 | 2.4 | 26.7 | 28.2 | 0.5 | 5.3 | 0.8 | 0.2 | 0.7 | 0.9 | 1.6 |
| LALZGS (n = 29) | 5.4 | 0.3 | 0.0 | 2.4 | 24.5 | 29.1 | 0.6 | 5.6 | 1.1 | 0.2 | 0.6 | 0.8 | 1.1 |
| LAMADR (n = 30) | 5.2 | 0.3 | 0.0 | 2.6 | 25.6 | 30.1 | 0.7 | 5.5 | 1.4 | 0.3 | 0.7 | 0.8 | 0.8 |
| LAMQUI (n = 30) | 4.4 | 0.4 | 0.0 | 2.3 | 26.7 | 26.2 | 0.9 | 5.3 | 1.2 | 0.2 | 0.6 | 0.9 | 1.3 |
| LAMRUR (n = 29) | 6.3 | 0.3 | 0.0 | 2.8 | 34.5 | 23.3 | 0.5 | 4.5 | 1.1 | 0.2 | 0.5 | 0.5 | 0.4 |
| LANPSF (n = 28) | 5.0 | 0.3 | 0.1 | 2.5 | 26.6 | 29.7 | 0.8 | 4.9 | 1.6 | 0.3 | 0.7 | 0.7 | 0.5 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LANBCH (n = 30) | 0.2 | 1.9 | 1.1 | 3.7 | 10.1 | 0.2 | 0.0 | 1.4 | 5.2 | 0.0 | 1.6 | 0.2 | 0.4 |
| LANPMZ (n = 30) | 0.8 | 2.4 | 1.5 | 3.0 | 6.8 | 0.3 | 0.0 | 0.9 | 4.1 | 0.0 | 1.4 | 0.5 | 0.6 |
| LAOIKC (n = 31) | 0.1 | 2.5 | 1.2 | 6.1 | 8.9 | 0.2 | 0.0 | 1.2 | 4.5 | 0.0 | 1.4 | 0.1 | 0.4 |
| LALHBO (n = 29) | 0.2 | 2.1 | 1.2 | 4.5 | 10.6 | 0.3 | 0.0 | 1.1 | 4.9 | 0.0 | 1.6 | 0.0 | 0.4 |
| LALWPA (n = 30) | 0.2 | 2.7 | 1.4 | 7.1 | 13.2 | 0.4 | 0.0 | 1.8 | 6.9 | 0.0 | 2.7 | 0.0 | 0.4 |
| LALXOL (n = 29) | 0.6 | 1.9 | 1.1 | 5.3 | 10.1 | 0.3 | 0.0 | 0.9 | 4.8 | 0.0 | 1.4 | 0.0 | 1.0 |
| LALXVM (n = 30) | 0.5 | 2.1 | 1.2 | 5.3 | 10.2 | 0.3 | 0.0 | 0.8 | 4.5 | 0.0 | 1.4 | 0.1 | 0.9 |
| LALZGS (n = 29) | 0.3 | 2.5 | 1.3 | 6.3 | 9.6 | 0.2 | 0.0 | 1.0 | 4.9 | 0.0 | 1.5 | 0.0 | 0.7 |
| LAMADR (n = 30) | 0.1 | 2.1 | 1.0 | 5.4 | 9.1 | 0.3 | 0.0 | 1.3 | 4.5 | 0.0 | 1.5 | 0.0 | 0.4 |
| LAMQUI (n = 30) | 0.3 | 2.0 | 1.0 | 5.0 | 9.8 | 0.2 | 0.0 | 2.4 | 6.0 | 0.0 | 1.7 | 0.6 | 0.7 |
| LAMRUR (n = 29) | 0.1 | 2.3 | 1.2 | 3.5 | 9.6 | 0.2 | 0.0 | 1.1 | 5.1 | 0.0 | 1.7 | 0.0 | 0.3 |
| LANPSF (n = 28) | 0.1 | 1.9 | 1.0 | 5.4 | 9.2 | 0.3 | 0.0 | 1.7 | 4.6 | 0.0 | 1.5 | 0.4 | 0.3 |

TABLE 54

Phenotypic rating of T2 plants cultivated in the field of canola events containing the T-DNAs of plasmids VC-LJB2197-1qcz and VC-LLM337-1qcz rc. The events are indicated in the first column, along with the number of field plots that where rated per event.

| Event | Oil | protein |
|---|---|---|
| LANBCH (n = 30) | 37.9 ± 1.2 | 27.9 ± 0.9 |
| LANPMZ (n = 30) | 38.7 ± 1 | 27.8 ± 0.9 |
| LAOIKC (n = 31) | 38.8 ± 1.1 | 28.1 ± 2.7 |
| LALHBO (n = 29) | 37.9 ± 1.4 | 28.2 ± 0.7 |
| LALWPA (n = 30) | 36.5 ± 1.4 | 28 ± 0.7 |
| LALXOL (n = 29) | 38.4 ± 1.1 | 27.7 ± 0.6 |
| LALXVM (n = 30) | 38.3 ± 1.1 | 27.7 ± 1 |
| LALZGS (n = 29) | 39.5 ± 0.7 | 27.2 ± 0.6 |
| LAMADR (n = 30) | 38.7 ± 0.9 | 27.6 ± 0.5 |
| LAMQUI (n = 30) | 38.3 ± 0.9 | 28.7 ± 0.8 |
| LAMRUR (n = 29) | 38.3 ± 1.1 | 27.8 ± 0.8 |
| LANPSF (n = 28) | 38.4 ± 1.1 | 27.6 ± 0.8 |
| WT Kumily (n = 60) | 38.7 ± 1.1 | |

Oil: oil content (% of seed weight), protein: Protein content (% of seed cake without oil)

D. Fatty Acid Profiles Copy Number Measurements, and Phenotypic Observations of T3 Plants Carrying T-DNAs of Plasmids VC-LJB2197-1qcz and VC-LLM337-1qcz Rc Cultivated in Greenhouses During Winter The data indicate that EPA and DHA are still being synthesized by the plant in the T4 seed/generation.

TABLE 55

Copy number measurement of T3 plants cultivated in the greenhouse of canola events containing the T-DNAs of plasmids VC-LJB2197-1qcz and VC-LLM337-1qcz rc. The events are indicated in the first column, along with the number of T3 plants that were measured per event. As the T3 plants underwent two cylces of selecting homozygous plants, all plants of all events are homozygous for all T-DNA insertions. A copy number of ~2 therefore was indicative for one homozygous locus, a copy number of ~4 indicative for two homozygous loci or indicative for one homozygous locus containing two copies of the target gene measured by the assay, and so forth.

Copy number assays targeting the T-DNA of VC-LJB2197-1qcz. Assays are listed according to the position of the assay target along the T-DNA, with target c-AHAS located near the left T-DNA border and target j-i-Atss18_c-d6Elo (Pp_GA2) near the right T-DNA border.

| Event | c-AHAS | j-t-E9-p3-2 | c-d6Elo (Tp_GA) | j-t-StCAT_p2_p-LuPXR | j-t-CaMV_p-LuCnl-2 | c-d6Elo (Pp_GA) | j-i-Atss18_c-d6Elo (Pp_GA2) |
|---|---|---|---|---|---|---|---|
| LANPMZ (n = 74) | 1.9 | | | | | 2 | 2.02 |

Copy number assays targeting the T-DNA of VC-LLM337-1qcz rc. Assays are listed according to the position of the assay target along the T-DNA, with target j-t-PvARC-p3 located near the left T-DNA border and target c-d4Des (Eg_GA) near the right T-DNA border.

| Event | j-t-PvARC-p3 | c-d4Des (Tc_GA) | c-o3Des (Pi_GA2_SNP) | j-i-Atss15_c-o3Des (Pi_GA2) | c-o3Des (Pir_GA) | j-p-VfSBPperm3_c-o3Des (Pir_GA) | j-i-Atss1_c-d5Elo (Ot_GA3) | c-d4Des (Eg_GA) |
|---|---|---|---|---|---|---|---|---|
| LANPMZ (n = 74) | | 1.94 | | | | 2.04 | | 1.88 |

TABLE 57

Fatty acid profiles of one T4 seed batch per event harvested from T3 plants cultivated in greenhouses of canola events containing the T-DNAs of plasmids VC-LJB2197-1qcz and VC-LLM337-1qcz rc. The events are indicated in the first column. Fatty acid profiles of T4 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LANPMZ (n = 1) | 4.9 | 0.2 | 0.0 | 4.0 | 19.5 | 38.5 | 0.5 | 3.6 | 1.6 | 0.2 | 1.0 | 0.7 | 0.4 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LANPMZ (n = 1) | 0.0 | 1.6 | 0.8 | 4.8 | 9.2 | 0.4 | 0.0 | 1.7 | 3.8 | 0.0 | 2.5 | 0.0 | 0.2 |

TABLE 56

Fatty acid profiles of T4 seeds harvested from T3 plants cultivated in greenhouses of canola events containing the T-DNAs of plasmids VC-LJB2197-1qcz and VC-LLM337-1qcz rc The events are indicated in the first column, along with the number of T4 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LANPMZ (n = 30) | 5.3 ± 0.3 | 0.2 ± 0 | 0 ± 0 | 3.6 ± 0.8 | 25.2 ± 5.3 | 38.1 ± 2.8 | 0.5 ± 0.1 | 4.1 ± 0.6 | 1.1 ± 0.3 |

| Event | 18:4 n-3 | 20:0 | 20:1 n-9 | 20:2 n-6 | 20:3 n-3 | 20:3 n-6 | 20:4 n-3 | 20:4 n-6 | 20:5 n-3 |
|---|---|---|---|---|---|---|---|---|---|
| LANPMZ (n = 30) | 0.1 ± 0.1 | 0.8 ± 0.2 | 0.7 ± 0 | 0.5 ± 0.1 | 0.1 ± 0.1 | 1.9 ± 0.2 | 0.9 ± 0.1 | 3.8 ± 0.6 | 6.9 ± 1.3 |

| Event | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|
| LANPMZ (n = 30) | 0.3 ± 0.1 | 0 ± 0 | 1.2 ± 0.4 | 2.6 ± 0.5 | 0 ± 0 | 1.5 ± 0.6 | 0.2 ± 0.1 | 0.3 ± 0.1 |

TABLE 58

Phenotypic rating of T3 plants cultivated in the greenhouse of canola events containing the T-DNAs of plasmids VC-LJB2197-1qcz and VC-LLM337-1qcz rc. The events are indicated in the first column, along with the number of T1 plants that where rated per event.

| Event | DFF | DF | DL | DP | DS | FC | LD | LGC | LF | NoL | PH | TKW | SC | Oil | Protein |
|---|---|---|---|---|---|---|---|---|---|---|---|---|---|---|---|
| LANPMZ (n = 30) | 42.4 ± 2 | 8.2 ± 0.8 | 8.7 ± 0.7 | 9 ± 0 | 8 ± 0.7 | 3 ± 0 | 5 ± 0 | 5 ± 0 | | 5.2 ± 0.8 | 128.5 ± 8.5 | | | | |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoL: number of lobes (#),
PH: plant height (cm),
TKW: thousand kernel weight (g),
SC: seed quality (1 = good, 9 = bad),
Oil: oil content (% of seed weight),
Protein: Protein content (% of seed cake without oil)

E. Fatty Acid Profiles and Phenotypes of T3 Plants Carrying T-DNAs of Plasmids VC-LJB2197-1qcz and VC-LLM337-1qcz rc Cultivated in Field Trials in USDA Growth Zones 8a-9a During Winter The data indicate that in the field the T4 seed are making EPA and DHA, but at lower levels than seen in the summer field trial (Part D). The greenhouse data show higher oil content compared to the summer field trials (Comparison of Table 61 with Table 54). This data was analyzed in detail in Example 20.

TABLE 60

Fatty acid profiles of one T4 seed batch per event harvested from T3 plants cultivated in the field in USDA growth zones 8a-9a of canola events containing the T-DNAs of plasmids VC-LJB2197-1qcz and VC-LLM337-1qcz rc. The events are indicated in the first column. Fatty acid profiles of T4 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LANPMZ (n = 1) | 4.9 | 0.3 | 0.0 | 2.3 | 31.2 | 32.0 | 0.2 | 7.6 | 0.4 | 0.1 | 0.6 | 0.9 | 1.6 |
| LAOIKC (n = 1) | 5.4 | 0.3 | 0.0 | 2.4 | 29.6 | 30.3 | 0.7 | 5.5 | 1.4 | 0.2 | 0.5 | 0.7 | 0.5 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LANPMZ (n = 1) | 0.6 | 1.6 | 1.1 | 2.8 | 5.7 | 0.2 | 0.0 | 0.8 | 3.3 | 0.0 | 1.1 | 0.4 | 0.5 |
| LAOIKC (n = 1) | 0.0 | 2.2 | 1.1 | 5.4 | 7.3 | 0.2 | 0.0 | 1.0 | 3.6 | 0.0 | 1.3 | 0.0 | 0.3 |

TABLE 59

Fatty acid profiles of T4 seeds harvested from T3 plants cultivated in the field in USDA growth zones 8a-9a of canola events containing the T-DNAs of plasmids VC-LJB2197-1qcz and VC-LLM337-1qcz rc The events are indicated in the first column, along with the number of T4 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LANPMZ (n = 56) | 5.2 ± 0.5 | 0.3 ± 0.1 | 0.1 ± 0.2 | 2.6 ± 0.5 | 35.6 ± 2.7 | 30.4 ± 1.8 | 0.3 ± 0.1 | 7.1 ± 0.5 | 0.5 ± 0.3 |
| LAOIKC (n = 16) | 5.3 ± 0.2 | 0.3 ± 0 | 0 ± 0 | 2.5 ± 0.2 | 32.6 ± 2.2 | 29.9 ± 0.9 | 0.7 ± 0.1 | 5.9 ± 0.4 | 1 ± 0.2 |
| WT Kumily (n = 83) | 5.1 ± 0.5 | 0.4 ± 0.1 | 0.1 ± 0.1 | 2.1 ± 0.5 | 59.1 ± 1.8 | 21.3 ± 1.5 | 0 ± 0.1 | 9.5 ± 0.7 | 0 ± 0.1 |

TABLE 59-continued

Fatty acid profiles of T4 seeds harvested from T3 plants cultivated in the field in USDA growth zones 8a-9a of canola events containing the T-DNAs of plasmids VC-LJB2197-1qcz and VC-LLM337-1qcz rc The events are indicated in the first column, along with the number of T4 seed aliquots representing a plot were measured per event. Per seed batch a random selection of ~30 seed was measured in two technical repeats.

| Event | 18:4 n-3 | 20:0 | 20:1 n-9 | 20:2 n-6 | 20:3 n-3 | 20:3 n-6 | 20:4 n-3 | 20:4 n-6 | 20:5 n-3 |
|---|---|---|---|---|---|---|---|---|---|
| LANPMZ (n = 56) | 0.1 ± 0.1 | 0.6 ± 0 | 0.9 ± 0.1 | 1.3 ± 0.3 | 0.4 ± 0.1 | 1.6 ± 0.2 | 1 ± 0.1 | 2.5 ± 0.3 | 4.5 ± 0.6 |
| LAOIKC (n = 16) | 0.2 ± 0 | 0.6 ± 0 | 0.7 ± 0 | 0.6 ± 0.1 | 0 ± 0 | 2.1 ± 0.1 | 1 ± 0.1 | 4.6 ± 0.4 | 6.2 ± 0.5 |
| WT Kumily (n = 83) | 0 ± 0 | 0.6 ± 0.1 | | 0.1 ± 0 | 0 ± 0 | 0 ± 0 | 0 ± 0 | 0 ± 0.1 | 0.1 ± 0.1 |

| Event | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|
| LANPMZ (n = 56) | 0.2 ± 0.1 | 0 ± 0 | 0.5 ± 0.3 | 2.6 ± 0.3 | 0 ± 0 | 0.7 ± 0.2 | 0.3 ± 0.1 | 0.5 ± 0.1 |
| LAOIKC (n = 16) | 0.2 ± 0 | 0 ± 0 | 0.8 ± 0.1 | 3.3 ± 0.2 | 0 ± 0 | 0.9 ± 0.2 | 0 ± 0.1 | 0.4 ± 0.1 |
| WT Kumily (n = 83) | 0.3 ± 0 | 0 ± 0 | 0 ± 0.1 | 0 ± 0.1 | 0 ± 0 | 0 ± 0 | 5.1 ± 0.5 | 0.4 ± 0.1 |

TABLE 61

Phenotypic rating of T3 plants cultivated in the field in USDA growth zones 8a-9b of canola events containing the T-DNAs of plasmids VC-LJB2197-1qcz and VC-LLM337-1qcz rc. The events are indicated in the first column, along with the number of field plots that where rated per event.

| Event | Oil | Protein |
|---|---|---|
| LANPMZ (n = 56) | 43.9 ± 7.8 | 23.2 ± 3.2 |
| LAOIKC (n = 16) | 42.6 ± 4 | 23.1 ± 3 |
| WT Kumily (n = 83) | 45.3 ± 3.9 | |

Oil: oil content in T4 seeds harvested from T3 plants (% of seed weight), Protein: Protein content in T4 seeds harvested from T3 plants (% of seed cake without oil)

F. Fatty Acid Profiles and Phenotypes of T4 Plants Carrying T-DNAs of Plasmids VC-LJB2197-1qcz and VC-LLM337-1qcz rc Cultivated in Field Trials in USDA Growth Zones 3a-4b and 5a During Summer.

The data indicate that through the T5 generation the transformants are still producing EPA and DHA at a level consistent with the field trial in summer 2012 (described in part D). An additional observation is that the oil levels are comparable between these two field trials.

TABLE 62

Fatty acid profiles of T5 seeds harvested from T4 plants cultivated in the filed in USDA growth zones 3a-4b and 5a of canola events containing the T-DNAs of plasmids VC-LJB2197-1qcz and VC-LLM337-1qcz rc The events are indicated in the first column, along with the number of T4 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LANPMZ (n = 124) | 4.5 ± 0.4 | 0.2 ± 0.1 | 0 ± 0 | 2.8 ± 0.4 | 34.7 ± 3.9 | 33 ± 4.8 | 0.1 ± 0.2 | 6.5 ± 0.8 | 0.6 ± 0.2 |
| WT Kumily (n = 56) | 4.5 ± 0.5 | 0.1 ± 0.1 | 0 ± 0 | 1.8 ± 1 | 60 ± 3.8 | 22.5 ± 3.6 | 0.6 ± 1.5 | 7.9 ± 2.2 | 0.1 ± 0.1 |

TABLE 62-continued

Fatty acid profiles of T5 seeds harvested from T4 plants cultivated in the filed in USDA growth zones 3a-4b and 5a of canola events containing the T-DNAs of plasmids VC-LJB2197-1qcz and VC-LLM337-1qcz rc The events are indicated in the first column, along with the number of T4 seed aliquots representing a plot were measured per event. Per seed batch a random selection of ~30 seed was measured in two technical repeats.

| Event | 18:4 n-3 | 20:0 | 20:1 n-9 | 20:2 n-6 | 20:3 n-3 | 20:3 n-6 | 20:4 n-3 | 20:4 n-6 |
|---|---|---|---|---|---|---|---|---|
| LANPMZ (n = 124) | 0.1 ± 0.1 | 0.7 ± 0.1 | 0.9 ± 0.1 | 0.7 ± 0.3 | 0.2 ± 0.1 | 1.7 ± 0.3 | 1.2 ± 1.3 | 2.8 ± 0.6 |
| WT Kumily (n = 56) | 0 ± 0 | 0.8 ± 0.2 | 1 ± 0.4 | 0.1 ± 0 | 0 ± 0 | 0.2 ± 0.8 | 0 ± 0 | 0 ± 0 |

| Event | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|
| LANPMZ (n = 124) | 4.3 ± 1.9 | 0.3 ± 0.1 | 0 ± 0 | 0.7 ± 0.4 | 2.8 ± 0.6 | 0 ± 0.2 | 0.8 ± 0.3 | 0.1 ± 0.2 | 0.4 ± 0.2 |
| WT Kumily (n = 56) | 0 ± 0.1 | 0.2 ± 0.2 | 0 ± 0 | 0 ± 0.1 | 0 ± 0 | 0 ± 0 | 0 ± 0 | 0 ± 0 | 0 ± 0 |

TABLE 63

Fatty acid profiles of one T5 seed batch per event harvested from T3 plants cultivated in the field in USDA growth zones 3a-4b and 5a of canola events containing the T-DNAs of plasmids VC-LJB2197-1qcz and VC-LLM337-1qcz rc. The events are indicated in the first column. Fatty acid profiles of T5 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LANPMZ (n = 1) | 5.6 | 0.3 | 0.0 | 2.7 | 21.8 | 32.3 | 0.0 | 6.3 | 0.9 | 0.0 | 0.8 | 0.8 | 1.5 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LANPMZ (n = 1) | 0.5 | 2.2 | 1.5 | 4.7 | 8.0 | 0.4 | 0.0 | 1.6 | 5.1 | 0.0 | 2.7 | 0.0 | 0.4 |

TABLE 64

Phenotypic rating of T4 plants cultivated in the field in USDA growth zones 3a-4b and 5a of canola events containing the T-DNAs of plasmids VC-LJB2197-1qcz and VC-LLM337-1qcz rc. The events are indicated in the first column, along with the number of field plots that were rated per event.

| Event | Oil | Protein |
|---|---|---|
| LANPMZ (n = 124) | 39.7 ± 2.7 | 25.8 ± 1.4 |
| WT Kumily (n = 56) | 40.6 ± 2.3 | 26.4 ± 1.3 |

Oil: oil content in T4 seeds harvested from T3 plants (% of seed weight), Protein: Protein content in T4 seeds harvested from T3 plants (% of seed cake without oil)

Example 3: Plants Containing the T-DNAs of Plasmid VC-LJB2755-2qcz rc and VC-LLM391-2Qcz rc (Combination D in Example 5) for Production of EPA and DHA in Seeds In this example, the genetic elements required for EPA and DHA synthesis were transferred into the plant genome on two different T-DNAs. To this end, the two different plasmids VC-LJB2755-2qcz rc and VC-LLM391-2qcz rc containing two different T-DNAs where cloned into agrobacteria, and plant tissue was incubated according to example 5 at the same time with these two agrobacterial cultures that are identical apart from containing either VC-LJB2755-2qcz rc or VC-LLM391-2qcz rc. Due to the selectable herbicide resistance marker, regenerated plants contained the T-DNA of VC-LJB2755-2qcz rc. Only those plants where kept, that also contained the T-DNA of plasmid VC-LLM391-2qcz rc as confirmed by PCR, conducted as described in example 5. Only plants containing the T-DNA of plasmid VC-LJB2755-2qcz rc as well as the T-DNA of plasmid VC-LLM391-2qcz rc combine all the genetic elements required for EPA and DHA synthesis in seeds. The genetic elements of VC-LJB2755-2qcz rc and the function of each element are listed in Table 2. The genetic elements of VC-LLM391-2qcz rc and the function of each element was listed in Table 6. For convenience, all enzymes expressed in seeds of plants carrying both T-DNA of VC-LJB2755-2qcz rc and VC-LLM391-2qcz rc that are required for EPA and DHA synthesis are additionally listed Table 70.

TABLE 70

Combined list of genes essential of EPA and DHA synthesis carried by the T-DNAs of plasmids VC-LJB2755-2qcz rc and VC-LLM391-2qcz rc.

| Genes encoding enzmyes for EPA and DHA synthesis | Plasmid containing T-DNA with the gene | Length (bp) | Enzymatic function and source of encoded protein |
|---|---|---|---|
| c-d12Des(Ps_GA) | VC-LJB2755-2qcz rc | 1196 | Delta-12 desaturase from *Phythophthora sojae* |
| c-d5Des(Tc_GA2) | VC-LJB2755-2qcz rc | 1319 | Delta-5 desaturase from *Thraustochytrium* sp. ATCC21685 |
| c-d6Des(Ot_febit) | VC-LJB2755-2qcz rc | 1370 | Delta-6 desaturase from *Ostreococcus tauri* |
| c-d6Elo(Tp_GA2) | VC-LJB2755-2qcz rc | 818 | Delta-6 elongase from *Thalassiosira pseudonana* |
| c-o3Des(Pi_GA2) | VC-LJB2755-2qcz rc | 1085 | Omega-3-desaturase from *Phythophthora infestans* |
| c-o3Des(Pir_GA) | VC-LJB2755-2qcz rc | 1091 | Omega-3 desaturase from *Pythium irregulare* |
| c-d5Elo(Ot_GA3) | VC-LLM391-2qcz rc | 902 | Delta-5 elongase from *Ostreococcus tauri* |
| c-d4Des(Eg_GA) | VC-LLM391-2qcz rc | 1625 | Delta-4 desaturase from *Euglena gracilis* |
| c-d4Des(Tc_GA)_T564G | VC-LLM391-2qcz rc | 1559 | Delta-4 desaturase from *Thraustochytrium* spp. |

A. Fatty Acid Profiles, Copy Number Measurements, and Phenotypic Observations of T1 Plants Carrying T-DNAs of Plasmids VC-LJB2755-2qcz rc and VC-LLM391-2qcz Rc Cultivated in Greenhouses During Winter.

The data on Table 75, Table 76, Table 77, Table 78, Table 79, Table 80, Table 81 and Table 82 demonstrate that this pair of constructs was successful in recapitulating the pathway to generate VLC-PUFA (C20 and C22, including EPA, DHA and ARA). The copy number for each gene varied from homozygous single insertion of the T-DNA to insertions of parts of the T-DNA's and/or deletions of the T-DNA after insertion into the genome. The fatty acid profile indicated that some events (see Table 78, event LAPCSC) were able to accumulate up to 18 percent EPA and DHA combined). Table 75 indicates that LAPCSC was largely homozygous for a single insertion of each T-DNA with the exception of region of j-p-LuPXR_i-Atss15 on construct VC-LJB2755-2qcz, which contained at least four copies of the regions around that marker. The data presented on Table 81 indicate there was no obvious alteration of the phenotype of the plants bearing T-DNA corresponding to the constructs VC-LJB2755-2qcz and VC-LLM391-2qcz rc.

TABLE 75

Copy number measurement of T1 plants cultivated in the greenhouse of canola events containing the T-DNAs of plasmids VC-LJB2755-2qcz rc and VC-LLM391-2qcz rc. The events are indicated in the first column, along with the number of T1 plants that were measured per event. The T1 plants underwent a selection from 250 segregating T1 seedlings using half-kernel analysis, where the correlation of VCL-PUFA levels with copy number was employed to select for homozygous plants, or on case of multilocus events to selecect for plants where one or more loci are homozygous. A copy number of ~2 therefore was indicative for one homozygous locus, a copy number of ~4 indicative for two homozygous loci or indicative for one omozygous locus containing two copies of the target gene measured by the assay, and so forth. Odd results of 3 and 5 indicate that at least some of the selected T1 plants carry a heterozygous locus.

Copy number assays targeting the T-DNA of VC-LJB2755-2qcz rc. Assays are listed according to the position of the assay target along the T-DNA, with target c-AHAS located near the left T-DNA border and target j-p-LuPXR_i-Atss15 near the right T-DNA border. Copy number results obtained on the T0 plants are indicated in parentheses. Homozygosity of all plants per event was indicated if the average result of the selected T1 plants was about two fold higher than the T0 generation.

| Event | c-AHAS | c-o3Des (Pi_GA) | j-i-Atss18_c-o3Des (Pi_GA2) | j-i-Atss14_c-d12Des (Ps_GA) | c-d6Elo (Tp_GA) | j-i-Atss1_c-d6Elo (Tp_GA2) | c-o3Des (Pir_GA) | j-p-LuPXR_i-Atss15 |
|---|---|---|---|---|---|---|---|---|
| LAPCTC (n = 11) | 1.3 (T0: 1.1) | | | 2.3 | | 2.1 | | 4.6 (T0: 3.6) |
| LAPCSC (n = 11) | 1.4 (T0: 1) | | | 2.7 | | 2.6 | | 5.1 (T0: 4) |
| LAPYTJ (n = 15) | 1.7 (T0: 0.9) | | | 3.2 | | 3.3 | | 3.2 (T0: 2.1) |
| LAQKQS (n = 15) | 1.5 (T0: 1.1) | | | 1.7 | | 1.4 | | 2 (T0: 1.3) |
| LAPARV (n = 15) | 2 (T0: 1.1) | | | 1.9 | | 2.0 | | 2 (T0: 1.1) |
| LAPCMY (n = 15) | 2 (T0: 1) | | | 2.0 | | 2.1 | | 2.2 (T0: 1.1) |
| LAPBOW (n = 15) | 2 (T0: 1) | | | 1.9 | | 2.1 | | 2 (T0: 1) |
| LAPAWA (n = 15) | 1.9 (T0: 1.1) | | | 2.0 | | 2.0 | | 2.1 (T0: 1.1) |
| LAPBYW (n = 13) | 2 (T0: 1) | | | 2.0 | | 2.2 | | 2.3 (T0: 1) |

TABLE 75-continued

Copy number measurement of T1 plants cultivated in the greenhouse of canola events containing the T-DNAs of plasmids VC-LJB2755-2qcz rc and VC-LLM391-2qcz rc. The events are indicated in the first column, along with the number of T1 plants that were measured per event. The T1 plants underwent a selection from 250 segregating T1 seedlings using half-kernel analysis, where the correlation of VCL-PUFA levels with copy number was employed to select for homozygous plants, or on case of multilocus events to selecect for plants where one or more loci are homozygous. A copy number of ~2 therefore was indicative for one homozygous locus, a copy number of ~4 indicative for two homozygous loci or indicative for one omozygous locus containing two copies of the target gene measured by the assay, and so forth. Odd results of 3 and 5 indicate that at least some of the selected T1 plants carry a heterozygous locus.

| | | | | |
|---|---|---|---|---|
| LAPQEP (n = 15) | 1.4 (T0: 0.9) | 2.8 | 2.6 | 4 (T0: 3.1) |
| LAODDN (n = 15) | 2.1 (T0: 1.1) | 2.0 | 2.1 | 2.1 (T0: 1.1) |
| LAPAUX (n = 10) | 1.5 (T0: 1) | 1.6 | 1.7 | 1.7 (T0: 1) |
| LAPZOJ (n = 10) | 1.8 (T0: 1) | 2.1 | 1.9 | 2 (T0: 1.1) |

Copy number assays targeting the T-DNA of VC-LLM391-2qcz rc. Assays are listed according to the position of the assay target along the T-DNA, with target c-d4Des(Eg_GA) located near the left T-DNA border and target j-i-Atss1_c-d5Elo (Ot_GA3) near the right T- DNA border. Copy number results obtained on the T0 plants are indicated in parentheses. Homozygosity was indicated if the average result of the selected T1 plants was about two fold higher than the T0 generation.

| Event | c-d4Des (Eg_GA) | j-t-PvARC-p-LuCnl | j-i-Atss2_c-d4Des (Tc_GA3) | c-d4Des (Tc_GA) | j-p-PvARC5_t-BnFAE | c-d5Elo (Ot_GA3) | j-i-Atss1_c-d5Elo (Ot_GA3) |
|---|---|---|---|---|---|---|---|
| LAPCTC (n = 11) | 1.7 (T0: 1) | N/A (T0: 1.2) | | 1.7 | | 1.7 (T0: 1.1) | |
| LAPCSC (n = 11) | 1.6 (T0: 1) | N/A (T0: 1) | | 1.7 | | 1.6 (T0: 1.1) | |
| LAPYTJ (n = 15) | 1.7 (T0: 1.1) | N/A (T0: 1.1) | | 1.8 | | 1.7 (T0: 1.1) | |
| LAQKQS (n = 15) | 1.4 (T0: 1) | N/A (T0: 1.1) | | 1.5 | | 1.4 (T0: 1) | |
| LAPARV (n = 15) | 1.2 (T0: 1.1) | N/A (T0: 0.9) | | 1.2 | | 1.2 (T0: 1.1) | |
| LAPCMY (n = 15) | 1.7 (T0: 1) | N/A (T0: 1.1) | | 1.7 | | 1.9 (T0: 1.2) | |
| LAPBOW (n = 15) | 2 (T0: 1) | N/A (T0: 1.2) | | 1.9 | | 2.1 (T0: 1.1) | |
| LAPAWA (n = 15) | 1.5 (T0: 1) | N/A (T0: 1) | | 1.5 | | 1.5 (T0: 1.2) | |
| LAPBYW (n = 13) | 1.3 (T0: 1) | N/A (T0: 0.8) | | 1.3 | | 1.5 (T0: 1.1) | |
| LAPQEP (n = 15) | 1.3 (T0: 0.9) | N/A (T0: 1.2) | | 1.4 | | 1.4 (T0: 1.1) | |
| LAODDN (n = 15) | 2 (T0: 1) | N/A (T0: 1.1) | | 2.0 | | 2.1 (T0: 1.1) | |
| LAPAUX (n = 10) | 1 (T0: 0.9) | N/A (T0: 0.8) | | 1.0 | | 1.1 (T0: 0.6) | |
| LAPZOJ (n = 10) | 1.8 (T0: 1) | N/A (T0: 1.2) | | 1.9 | | 1.9 (T0: 1) | |

TABLE 76

Copy number measurement of T1 plants cultivated in the greenhouse of canola events containing the T-DNAs of plasmids VC-LJB2755-2qcz rc and VC-LLM391-2qcz rc. Plants of all events combined have been grouped into the categories indicated in the first column; sc: all T1 plants where the average of all copy number assays listed in this table was 1.51-2.49, dc: all T1 plants where the average of all copy number assays listed in this table was 3.51-4.49, tc: all T1 plants where the average of all copy number assays listed in this table was 5.51-6.49. The number of T1 plants fulfilling these criteria are displayed in parentheses.

Copy number assays targeting the T-DNA of VC-LJB2755-2qcz rc. Assays are listed according to the position of the assay target along the T-DNA, with target c-AHAS located near the left T-DNA border and target j-p-LuPXR_i-Atss15 near the right T-DNA border. Copy number results obtained on the T0 plants are indicated in parentheses. Homozygosity of all plants per event was indicated if the average result of the selected T1 plants was about two fold higher than the T0 generation.

| Category of T1 plants | c-AHAS | j-i-Atss18_c-c-o3Des (Pi_GA) | j-i-Atss14_c-o3Des (Pi_GA2) | d12Des (Ps_GA) | c-d6Elo (Tp_GA) | j-i-Atss1_c-d6Elo (Tp_GA2) |
|---|---|---|---|---|---|---|
| sc (n = 140) | 1.8 | | 2.1 | | | 2.1 |

TABLE 76-continued

Copy number measurement of T1 plants cultivated in the greenhouse of canola events containing the T-DNAs of plasmids VC-LJB2755-2qcz rc and VC-LLM391-2qcz rc. Plants of all events combined have been grouped into the categories indicated in the first column; sc: all T1 plants where the average of all copy number assays listed in this table was 1.51-2.49, dc: all T1 plants where the average of all copy number assays listed in this table was 3.51-4.49, tc: all T1 plants where the average of all copy number assays listed in this table was 5.51-6.49. The number of T1 plants fulfilling these criteria are displayed in parentheses.

Copy number assays targeting the T-DNA of VC-LLM391-2qcz rc. Assays are listed according to the position of the assay target along the T-DNA, with target c-d4Des (Eg_GA) located near the left T-DNA border and target j-i-Atss1_c-d5Elo (Ot_GA3) near the right T-DNA border. Copy number results obtained on the T0 plants are indicated in parentheses. Homozygosity was indicated if the average result of the selected T1 plants was about two fold higher than the T0 generation.

| Category of T1 plants | c-o3Des (Pir_GA) | j-p-LuPXR_i-Atss15 | c-d4Des (Eg_GA) | j-t-PvARC-p-LuCnl | j-i-Atss2_c-d4Des (Tc_GA3) | c-d4Des (Tc_GA) | j-p-PvARC5_t-BnFAE | c-d5Elo (Ot_GA3) |
|---|---|---|---|---|---|---|---|---|
| sc (n = 140) | | 2.6 | 1.6 | | | 1.6 | | 1.6 |

TABLE 77

Fatty acid profiles of T2 seeds harvested from T1 plants cultivated in the greenhouse of canola events containing the T-DNAs of plasmids VC-LJB2755-2qcz rc and VC-LLM391-2qcz rc The events are indicated in the first column, along with the number of T2 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LAPCTC (n = 11) | 5.1 ± 0.2 | 0.3 ± 0 | 0 ± 0 | 3 ± 0.3 | 28.2 ± 5.5 | 28.9 ± 1.6 | 1.3 ± 0.2 | 5 ± 0.2 | 3 ± 0.5 |
| LAPCSC (n = 11) | 5.1 ± 0.1 | 0.3 ± 0 | 0 ± 0 | 3.2 ± 0.4 | 27.9 ± 4.2 | 28.8 ± 2.3 | 1.3 ± 0.2 | 4.9 ± 0.4 | 3.2 ± 0.6 |
| LAPYTJ (n = 15) | 5.9 ± 0.3 | 0.3 ± 0.1 | 0 ± 0 | 3.3 ± 0.6 | 26.5 ± 1.9 | 34 ± 1.6 | 0.9 ± 0.2 | 4.9 ± 0.7 | 2.1 ± 0.3 |
| LAQKQS (n = 15) | 5.3 ± 0.3 | 0.3 ± 0.1 | 0 ± 0 | 3.2 ± 0.6 | 32.7 ± 8 | 29.7 ± 2.7 | 1.1 ± 0.3 | 5.3 ± 0.5 | 2.6 ± 0.6 |
| LAPARV (n = 15) | 5.3 ± 0.2 | 0.3 ± 0 | 0 ± 0 | 3.5 ± 0.3 | 26.5 ± 1.9 | 36 ± 1.2 | 0.7 ± 0.1 | 5.4 ± 0.3 | 1.9 ± 0.2 |
| APCMY (n = 15) | 6.2 ± 1.3 | 0.3 ± 0.1 | 0 ± 0 | 2.4 ± 1.4 | 34 ± 8.6 | 26.7 ± 14.5 | 0.5 ± 0.3 | 6.5 ± 1.4 | 1.9 ± 0.4 |
| LAPBOW (n = 15) | 5.1 ± 0.6 | 0.2 ± 0.1 | 0 ± 0 | 2.9 ± 0.2 | 27.3 ± 2.6 | 34.9 ± 0.9 | 0.7 ± 0 | 5.6 ± 0.6 | 1.9 ± 0.2 |
| LAPAWA (n = 15) | 5.2 ± 0.1 | 0.3 ± 0 | 0 ± 0 | 3.1 ± 0.2 | 28.3 ± 1.3 | 35.9 ± 1.1 | 0.7 ± 0.1 | 5.3 ± 0.3 | 1.7 ± 0.2 |
| LAPBYW (n = 13) | 5.6 ± 0.3 | 0.3 ± 0.1 | 0 ± 0 | 2.6 ± 1.2 | 28.4 ± 1.2 | 36 ± 1.2 | 0.7 ± 0.1 | 5.4 ± 0.3 | 1.7 ± 0.2 |
| LAPQEP (n = 15) | 5 ± 0.3 | 0.3 ± 0 | 0 ± 0 | 2.7 ± 0.3 | 38.1 ± 5.8 | 26.7 ± 4 | 1.1 ± 0.3 | 6.1 ± 0.9 | 1.2 ± 0.2 |
| LAODDN (n = 15) | 5.2 ± 0.6 | 0.2 ± 0.1 | 0 ± 0 | 3.1 ± 0.3 | 28 ± 2 | 35.8 ± 1.1 | 0.7 ± 0.1 | 5.9 ± 0.4 | 1.6 ± 0.2 |
| LAPAUX (n = 10) | 5.5 ± 0.5 | 0.3 ± 0 | 0 ± 0 | 2.8 ± 0.3 | 31.3 ± 7.3 | 34.9 ± 2.5 | 0.5 ± 0.1 | 6.1 ± 0.6 | 1.5 ± 0.5 |
| LAPZOJ (n = 10) | 5.6 ± 0.6 | 0.3 ± 0 | 0 ± 0 | 3 ± 0.3 | 34.1 ± 6.8 | 33.5 ± 2.8 | 0.6 ± 0.2 | 6.5 ± 0.6 | 1.3 ± 0.3 |

| Event | 18:4 n-3 | 20:0 | 20:1 n-9 | 20:2 n-6 | 20:3 n-3 | 20:3 n-6 | 20:4 n-3 | 20:4 n-6 |
|---|---|---|---|---|---|---|---|---|
| LAPCTC (n = 11) | 0.8 ± 0.2 | 0.9 ± 0.1 | 0.7 ± 0.1 | 0.2 ± 0 | 0.1 ± 0 | 2.2 ± 0.4 | 1.8 ± 0.5 | 1.2 ± 0.4 |
| LAPCSC (n = 11) | 0.8 ± 0.2 | 0.9 ± 0.1 | 0.7 ± 0.1 | 0.2 ± 0.1 | 0.1 ± 0 | 2.1 ± 0.4 | 1.7 ± 0.5 | 1.3 ± 0.3 |
| LAPYTJ (n = 15) | 0.4 ± 0.1 | 0.8 ± 0.1 | 0.6 ± 0 | 0 ± 0 | 0 ± 0 | 2.2 ± 0.3 | 1.3 ± 0.3 | 2.9 ± 0.5 |
| LAQKQS (n = 15) | 0.6 ± 0.1 | 0.9 ± 0.2 | 0.7 ± 0.1 | 0.1 ± 0.1 | 0 ± 0 | 1.7 ± 0.6 | 1.3 ± 0.5 | 1.1 ± 0.2 |
| LAPARV (n = 15) | 0.4 ± 0.1 | 0.9 ± 0.1 | 0.7 ± 0 | 0 ± 0 | 0 ± 0 | 1.9 ± 0.3 | 1.4 ± 0.2 | 1.7 ± 0.3 |
| APCMY (n = 15) | 0.4 ± 0.1 | 1 ± 0.2 | 0.7 ± 0.1 | 0.1 ± 0.1 | 0 ± 0 | 2.5 ± 0.5 | 1.8 ± 0.4 | 1.6 ± 0.4 |
| LAPBOW (n = 15) | 0.4 ± 0 | 0.8 ± 0.1 | 0.7 ± 0 | 0.1 ± 0 | 0 ± 0 | 2 ± 0.3 | 1.4 ± 0.2 | 1.6 ± 0.1 |
| LAPAWA (n = 15) | 0.3 ± 0 | 0.8 ± 0.1 | 0.7 ± 0 | 0.1 ± 0.1 | 0 ± 0 | 2.1 ± 0.2 | 1.4 ± 0.2 | 1.6 ± 0.1 |

TABLE 77-continued

Fatty acid profiles of T2 seeds harvested from T1 plants cultivated in the greenhouse of canola events containing the T-DNAs of plasmids VC-LJB2755-2qcz rc and VC-LLM391-2qcz rc The events are indicated in the first column, along with the number of T2 seed batches that were measured per event. Per seed batch a random selection of ~30 seed was measured in two technical repeats.

| | | | | | | | | |
|---|---|---|---|---|---|---|---|---|
| LAPBYW (n = 13) | 0.4 ± 0 | 0.8 ± 0.1 | 0.7 ± 0 | 0.1 ± 0.1 | 0.1 ± 0.1 | 1.9 ± 0.2 | 1.4 ± 0.2 | 1.6 ± 0.1 |
| LAPQEP (n = 15) | 0.3 ± 0 | 0.8 ± 0.1 | 0.8 ± 0.1 | 0.2 ± 0.1 | 0.1 ± 0 | 1.6 ± 0.4 | 1.5 ± 0.4 | 0.7 ± 0.2 |
| LAODDN (n = 15) | 0.4 ± 0 | 0.8 ± 0.1 | 0.7 ± 0 | 0 ± 0 | 0 ± 0 | 2 ± 0.2 | 1.4 ± 0.2 | 1.2 ± 0.1 |
| LAPAUX (n = 10) | 0.4 ± 0.1 | 0.8 ± 0.1 | 0.7 ± 0.1 | 0.1 ± 0 | 0 ± 0 | 1.7 ± 0.5 | 1.2 ± 0.4 | 1.7 ± 0.5 |
| LAPZOJ (n = 10) | 0.3 ± 0.1 | 0.8 ± 0.1 | 0.7 ± 0.1 | 0 ± 0 | 0 ± 0 | 1.6 ± 0.4 | 1.1 ± 0.3 | 1 ± 0.2 |

| Event | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|
| LAPCTC (n = 11) | 10.9 ± 2.1 | 0.4 ± 0 | 0 ± 0 | 0.6 ± 0.2 | 3.5 ± 1.1 | 0 ± 0 | 1.3 ± 0.4 | 0.4 ± 0.2 | 0.2 ± 0.1 |
| LAPCSC (n = 11) | 11.4 ± 2.4 | 0.4 ± 0.1 | 0 ± 0 | 0.6 ± 0.1 | 3.4 ± 1 | 0 ± 0 | 1.2 ± 0.3 | 0.3 ± 0.1 | 0.2 ± 0.1 |
| LAPYTJ (n = 15) | 8.4 ± 1.7 | 0.1 ± 0.1 | 0 ± 0 | 0.9 ± 0.3 | 2.8 ± 0.5 | 0 ± 0 | 1.2 ± 0.3 | 0.2 ± 0.1 | 0.1 ± 0.1 |
| LAQKQS (n = 15) | 8.8 ± 3.2 | 0.2 ± 0.2 | 0 ± 0 | 0.5 ± 0.3 | 2.4 ± 0.6 | 0 ± 0 | 1 ± 0.4 | 0.2 ± 0.2 | 0.1 ± 0.1 |
| LAPARV (n = 15) | 8.4 ± 1.6 | 0.4 ± 0 | 0 ± 0 | 0.6 ± 0.2 | 2.4 ± 0.5 | 0 ± 0 | 1.2 ± 0.3 | 0.3 ± 0.2 | |
| APCMY (n = 15) | 7.9 ± 2 | 0.4 ± 0.1 | 0 ± 0 | 0.6 ± 0.3 | 2.6 ± 0.8 | 0 ± 0 | 1.2 ± 0.4 | 0.3 ± 0.2 | |
| LAPBOW (n = 15) | 7.8 ± 1.1 | 0.3 ± 0 | 0 ± 0 | 0.9 ± 0.2 | 3.1 ± 0.7 | 0 ± 0 | 1.3 ± 0.4 | 0.6 ± 0.1 | 0.1 ± 0 |
| LAPAWA (n = 15) | 7.4 ± 0.7 | 0.3 ± 0 | 0 ± 0 | 0.7 ± 0.2 | 2.2 ± 0.5 | 0 ± 0 | 1 ± 0.3 | 0.5 ± 0.2 | |
| LAPBYW (n = 13) | 7.9 ± 0.8 | 0.4 ± 0.1 | 0 ± 0 | 0.5 ± 0.2 | 2 ± 0.4 | 0 ± 0 | 1 ± 0.2 | 0.3 ± 0.2 | |
| LAPQEP (n = 15) | 7.7 ± 1.6 | 0.4 ± 0 | 0 ± 0 | 0.4 ± 0.1 | 2.8 ± 0.7 | 0 ± 0 | 0.7 ± 0.2 | 0.3 ± 0.1 | 0.2 ± 0.1 |
| LAODDN (n = 15) | 7.1 ± 0.9 | 0.4 ± 0 | 0 ± 0 | 0.8 ± 0.1 | 2.8 ± 0.4 | 0 ± 0 | 1.1 ± 0.3 | 0.6 ± 0.1 | 0.1 ± 0 |
| LAPAUX (n = 10) | 8.3 ± 3.4 | 0.4 ± 0 | 0 ± 0 | 0.2 ± 0.1 | 1.1 ± 0.4 | 0 ± 0 | 0.4 ± 0.2 | 0 ± 0.1 | |
| LAPZOJ (n = 10) | 5.5 ± 1.5 | 0.2 ± 0.1 | 0 ± 0 | 0.4 ± 0.2 | 2.2 ± 0.6 | 0 ± 0 | 0.8 ± 0.3 | 0.3 ± 0.2 | 0 ± 0 |

TABLE 78

Fatty acid profiles of one T2 seed batch per event harvested from T1 plants cultivated in the greenhouse of canola events containing the T-DNAs of plasmids VC-LJB2755-2qcz rc and VC-LLM391-2qcz rc. The events are indicated in the first column. Fatty acid profiles of T2 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPCTC (n = 1) | 5.1 | 0.3 | 0.0 | 2.7 | 25.2 | 29.7 | 1.3 | 4.8 | 2.6 | 0.5 | 0.8 | 0.6 | 0.3 |
| LAPCSC (n = 1) | 5.0 | 0.3 | 0.0 | 3.4 | 20.8 | 25.8 | 1.7 | 5.2 | 3.5 | 1.0 | 0.8 | 0.6 | 0.3 |
| LAPYTJ (n = 1) | 5.5 | 0.3 | 0.0 | 3.0 | 24.0 | 31.1 | 1.1 | 4.9 | 2.4 | 0.5 | 0.8 | 0.6 | 0.0 |
| LAQKQS (n = 1) | 5.8 | 0.3 | 0.0 | 3.6 | 24.4 | 31.3 | 1.4 | 4.7 | 3.9 | 0.9 | 0.8 | 0.6 | 0.0 |
| LAPARV (n = 1) | 5.3 | 0.2 | 0.0 | 3.2 | 24.3 | 34.2 | 0.6 | 5.6 | 2.0 | 0.5 | 0.8 | 0.6 | 0.1 |
| LAPCMY (n = 1) | 8.1 | 0.5 | 0.0 | 0.0 | 51.4 | 1.0 | 0.0 | 9.5 | 2.3 | 0.6 | 1.2 | 1.0 | 0.1 |
| LAPBOW (n = 1) | 3.8 | 0.1 | 0.0 | 2.3 | 21.5 | 33.7 | 0.7 | 6.7 | 2.3 | 0.6 | 0.7 | 0.7 | 0.1 |
| LAPAWA (n = 1) | 5.3 | 0.3 | 0.0 | 3.4 | 26.2 | 36.5 | 0.7 | 4.8 | 1.8 | 0.4 | 0.9 | 0.7 | 0.0 |
| LAPBYW (n = 1) | 5.5 | 0.3 | 0.0 | 0.0 | 29.4 | 36.1 | 0.6 | 5.8 | 1.8 | 0.4 | 0.8 | 0.8 | 0.1 |
| LAPQEP (n = 1) | 4.9 | 0.4 | 0.0 | 2.3 | 36.6 | 23.9 | 1.5 | 5.7 | 1.3 | 0.4 | 0.7 | 0.8 | 0.3 |
| LAODDN (n = 1) | 3.8 | 0.1 | 0.0 | 2.6 | 24.1 | 36.0 | 0.8 | 5.7 | 2.0 | 0.4 | 0.8 | 0.7 | 0.0 |
| LAPAUX (n = 1) | 5.5 | 0.3 | 0.0 | 3.1 | 25.6 | 33.6 | 0.7 | 5.4 | 1.9 | 0.4 | 0.8 | 0.6 | 0.1 |
| LAPZOJ (n = 1) | 5.7 | 0.3 | 0.0 | 2.1 | 25.8 | 31.3 | 0.4 | 7.9 | 2.2 | 0.7 | 0.6 | 0.6 | 0.0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPCTC (n = 1) | 0.1 | 2.4 | 1.9 | 1.9 | 14.1 | 0.3 | 0.0 | 0.4 | 3.3 | 0.0 | 1.0 | 0.2 | 0.3 |
| LAPCSC (n = 1) | 0.1 | 2.5 | 2.7 | 1.0 | 16.1 | 0.3 | 0.0 | 0.6 | 5.3 | 0.0 | 1.9 | 0.4 | 0.3 |
| LAPYTJ (n = 1) | 0.0 | 2.4 | 1.7 | 2.8 | 10.8 | 0.3 | 0.0 | 1.1 | 4.1 | 0.0 | 1.7 | 0.5 | 0.3 |

TABLE 78-continued

Fatty acid profiles of one T2 seed batch per event harvested from T1 plants cultivated in the greenhouse of canola events containing the T-DNAs of plasmids VC-LJB2755-2qcz rc and VC-LLM391-2qcz rc. The events are indicated in the first column. Fatty acid profiles of T2 seed batches having the highest EPA + DHA levels per event are shown. Per seed batch, a random selection of ~30 seed was measured in two technical repeats.

| | | | | | | | | | | | | | |
|---|---|---|---|---|---|---|---|---|---|---|---|---|---|
| LAQKQS (n = 1) | 0.0 | 2.2 | 1.8 | 1.5 | 13.8 | 0.0 | 0.0 | 0.0 | 1.8 | 0.0 | 1.0 | 0.0 | 0.0 |
| LAPARV (n = 1) | 0.0 | 2.0 | 1.5 | 2.3 | 11.9 | 0.3 | 0.0 | 0.6 | 2.4 | 0.0 | 1.1 | 0.3 | |
| LAPCMY (n = 1) | 0.0 | 2.9 | 2.1 | 2.4 | 12.5 | 0.5 | 0.0 | 0.3 | 2.6 | 0.0 | 0.8 | 0.0 | |
| LAPBOW (n = 1) | 0.1 | 2.2 | 1.8 | 2.0 | 10.8 | 0.4 | 0.0 | 1.5 | 5.2 | 0.0 | 2.1 | 0.7 | 0.1 |
| LAPAWA (n = 1) | 0.0 | 2.7 | 1.9 | 1.7 | 8.7 | 0.4 | 0.0 | 0.5 | 1.7 | 0.0 | 0.9 | 0.3 | |
| LAPBYW (n = 1) | 0.0 | 1.9 | 1.5 | 1.7 | 9.5 | 0.4 | 0.0 | 0.4 | 1.7 | 0.0 | 0.8 | 0.3 | |
| LAPQEP (n = 1) | 0.1 | 1.9 | 1.6 | 1.0 | 10.9 | 0.4 | 0.0 | 0.3 | 3.7 | 0.0 | 0.7 | 0.3 | 0.3 |
| LAODDN (n = 1) | 0.0 | 2.3 | 1.8 | 1.6 | 9.4 | 0.4 | 0.0 | 1.1 | 3.8 | 0.0 | 1.6 | 0.6 | 0.1 |
| LAPAUX (n = 1) | 0.0 | 2.4 | 1.7 | 2.3 | 12.8 | 0.3 | 0.0 | 0.2 | 1.5 | 0.0 | 0.5 | 0.0 | |
| LAPZOJ (n = 1) | 0.0 | 1.3 | 1.0 | 2.1 | 9.3 | 0.0 | 0.0 | 1.0 | 5.6 | 0.0 | 2.2 | 0.0 | 0.0 |

TABLE 79

Fatty acid profiles of T2 seeds harvested from T1 plants cultivated in the greenhouse of canola events containing the T-DNAs of plasmids VC-LJB2755-2qcz rc and VC-LLM391-2qcz rc. Plants of all events combined have been grouped into the categories indicated in the first column; as defined in Table 76. The number of T1 plants fullfilling these criteria are displayed in parentheses. Per seed batch a random selection of ~30 seed was measured in two technical repeats.

| | Category of T1 plants | | | | | | | | |
|---|---|---|---|---|---|---|---|---|---|
| | 16:0 | 16:1 n-7 | 16:3 n-3 | 18:0 | 18:1 n-9 | 18:2 n-6 | 18:2 n-9 | 18:3 n-3 | 18:3 n-6 |
| sc (n = 143) | 5.4 ± 0.7 | 0.3 ± 0.1 | 0 ± 0 | 2.9 ± 0.7 | 29.6 ± 5.5 | 32.8 ± 6.2 | 0.8 ± 0.3 | 5.6 ± 0.8 | 1.9 ± 0.6 |

| | Category of T1 plants | | | | | | | | |
|---|---|---|---|---|---|---|---|---|---|
| | 18:4 n-3 | 20:0 | 20:1 n-9 | 20:2 n-6 | 20:3 n-3 | 20:3 n-6 | 20:4 n-3 | 20:4 n-6 | 20:5 n-3 |
| sc (n = 143) | 0.4 ± 0.2 | 0.8 ± 0.1 | 0.7 ± 0.1 | 0.1 ± 0.1 | 0 ± 0 | 2 ± 0.4 | 1.5 ± 0.3 | 1.5 ± 0.5 | 8.3 ± 2 |

| | Category of T1 plants | | | | | | | | |
|---|---|---|---|---|---|---|---|---|---|
| | 22:0 | 22:1 n-9 | 22:4 n-6 | 22:5 n-3 | 22:5 n-6 | 22:6 n-3 | 22:4 n-3 | 20:2 n-9 | |
| sc (n = 143) | 0.3 ± 0.1 | 0 ± 0 | 0.6 ± 0.3 | 2.6 ± 0.7 | 0 ± 0 | 1.1 ± 0.4 | 0.4 ± 0.2 | 0.1 ± 0.1 | |

TABLE 80

Fatty acid profiles of T2 seeds harvested from T1 plants cultivated in the greenhouse of canola events containing the T-DNAs of plasmids VC-LJB2755-2qcz rc and VC-LLM391-2qcz rc. Plants of all events combined have been grouped into the categories indicated in the first column; as defined in Table 76. For each category, the fatty acid profile of the plant having the highest EPA + DHA levels was shown. Per seed batch a random selection of ~30 seed was measured in two technical repeats.

| | Category of T1 plants | | | | | | | | | | | |
|---|---|---|---|---|---|---|---|---|---|---|---|---|
| | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
| sc (n = 1) | 5.1 | 0.3 | 0.0 | 2.7 | 25.2 | 29.7 | 1.3 | 4.8 | 2.6 | 0.5 | 0.8 | 0.6 | 0.3 |

| | Category of T1 plants | | | | | | | | | | | |
|---|---|---|---|---|---|---|---|---|---|---|---|---|
| | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
| sc (n = 1) | 0.1 | 2.4 | 1.9 | 1.9 | 14.1 | 0.3 | 0.0 | 0.4 | 3.3 | 0.0 | 1.0 | 0.2 | 0.3 |

TABLE 81

Phenotypic rating of T1 plants cultivated in the greenhouse of canola events containing the T-DNAs of plasmids VC-LJB2755-2qcz rc and VC-LLM391-2qcz rc. The events are indicated in the first column, along with the number of T1 plants that where rated per event.

| Event | DFF | DF | DL | DP | DS | FC | LD | LGC | LF |
|---|---|---|---|---|---|---|---|---|---|
| LAPCTC (n = 11) | 67.5 ± 1.5 | 1 ± 0 | 1 ± 0 | 1 ± 0 | 1.8 ± 0.6 | 3 ± 0 | 3 ± 0 | 5 ± 0 | 1 ± 0 |
| LAPCSC (n = 11) | 68.6 ± 3.3 | 1 ± 0 | 1 ± 0 | 1 ± 0 | 1.7 ± 0.6 | 3 ± 0 | 3 ± 0 | 5 ± 0 | 1 ± 0 |
| LAPYTJ (n = 15) | 72.3 ± 7.1 | 1 ± 0 | 1.4 ± 1.1 | 1.1 ± 0.5 | 1.6 ± 0.8 | 3 ± 0 | 3 ± 0 | 5 ± 0 | 1.3 ± 0.7 |
| LAQKQS (n = 15) | 67.4 ± 4.4 | 1 ± 0 | 1.4 ± 0.8 | 1.1 ± 0.3 | 3.1 ± 1.6 | 3 ± 0 | 3 ± 0 | 5 ± 0 | 1.8 ± 1.5 |
| LAPARV (n = 15) | 68.1 ± 2.6 | 1 ± 0 | 1.2 ± 0.8 | 1 ± 0 | 2.3 ± 2.1 | 3 ± 0 | 3 ± 0 | 5 ± 0 | 1.3 ± 0.9 |
| LAPCMY (n = 15) | 68.7 ± 2.4 | 1 ± 0 | 1 ± 0 | 1 ± 0 | 1.7 ± 0.6 | 3 ± 0 | 3 ± 0 | 5 ± 0 | 1 ± 0 |
| LAPBOW (n = 15) | 68.1 ± 0.9 | 1 ± 0 | 1.2 ± 0.6 | 1 ± 0 | 1.2 ± 0.6 | 3 ± 0 | 3 ± 0 | 5 ± 0 | 1 ± 0 |
| LAPAWA (n = 15) | 66.5 ± 1.4 | 1 ± 0 | 1 ± 0 | 1 ± 0 | 1.2 ± 0.4 | 3 ± 0 | 3 ± 0 | 5 ± 0 | 1 ± 0 |
| LAPBYW (n = 13) | 65.7 ± 2.6 | 1 ± 0 | 1.2 ± 0.8 | 1.2 ± 0.6 | 1.7 ± 0.6 | 3 ± 0 | 3 ± 0 | 5 ± 0 | 1.2 ± 0.6 |
| LAPQEP (n = 15) | 66.9 ± 2.6 | 1 ± 0 | 1.2 ± 0.8 | 1 ± 0 | 1.7 ± 0.7 | 3 ± 0 | 3 ± 0 | 5 ± 0 | 1 ± 0 |
| LAODDN (n = 15) | 69.3 ± 2 | 1 ± 0 | 1 ± 0 | 1 ± 0 | 1.2 ± 0.4 | 3 ± 0 | 3 ± 0 | 5 ± 0 | 1 ± 0 |
| LAPAUX (n = 10) | 70 ± 4.5 | 1 ± 0 | 1.3 ± 0.9 | 1 ± 0 | 3.1 ± 2.3 | 3 ± 0 | 3 ± 0 | 5 ± 0 | 2.4 ± 2.1 |
| LAPZOJ (n = 10) | 68 ± 6.7 | 1 ± 0 | 1.2 ± 0.6 | 1 ± 0 | 1.1 ± 0.3 | 3 ± 0 | 3 ± 0 | 5 ± 0 | 1 ± 0 |

| Event | NoL | PH | TKW | SC | Oil | Protein |
|---|---|---|---|---|---|---|
| LAPCTC (n = 11) | 4 ± 0 | 129.5 ± 3.5 | 3.6 ± 0.6 | 3.6 ± 0.9 | | |
| LAPCSC (n = 11) | 3.6 ± 0.8 | 126.4 ± 3.2 | 3.2 ± 0.3 | 3.9 ± 0.5 | | |
| LAPYTJ (n = 15) | 4 ± 0 | 123 ± 4.9 | 3.6 ± 0.3 | 3.5 ± 0.8 | | |
| LAQKQS (n = 15) | 4 ± 0 | 130.3 ± 4.8 | 3.8 ± 0.5 | 3.7 ± 1 | | |
| LAPARV (n = 15) | 4 ± 0 | 128 ± 3.2 | 4 ± 0.6 | 3.9 ± 1.3 | | |
| LAPCMY (n = 15) | 3.9 ± 0.5 | 130.7 ± 1.8 | 3.6 ± 0.4 | 3.3 ± 0.7 | | |
| LAPBOW (n = 15) | 4 ± 0 | 127.3 ± 3.2 | 4 ± 0.4 | 3.7 ± 1 | 35.3 ± 1.3 | 29.2 ± 0.3 |
| LAPAWA (n = 15) | 4 ± 0 | 128.7 ± 3.5 | 3.7 ± 0.4 | 2.6 ± 0.5 | | |
| LAPBYW (n = 13) | 3.8 ± 0.6 | 128.1 ± 5.2 | 4 ± 0.5 | 3.9 ± 1.7 | | |
| LAPQEP (n = 15) | 4 ± 0 | 128 ± 4.6 | 3.2 ± 0.3 | 3.3 ± 0.6 | | |
| LAODDN (n = 15) | 4 ± 0 | 125.7 ± 3.2 | 3.9 ± 0.5 | 3.8 ± 1.2 | 36.6 ± 1.2 | 27.9 ± 0.4 |
| LAPAUX (n = 10) | 3.8 ± 0.6 | 130 ± 2.4 | 4.3 ± 0.5 | 4.5 ± 1.4 | | |
| LAPZOJ (n = 10) | 4 ± 0 | 126.5 ± 3.4 | 3.8 ± 0.6 | 3.3 ± 0.9 | | |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoL: number of lobes(#),
PH: plant height (cm),
TKW: thousand kernel weight (g),
SC: seed quality (1 = good, 9 = bad),
Oil: oil content (% of seed weight),
Protein: Protein content (% of seed cake without oil)

TABLE 82

Phenotypic rating of T1 plants cultivated in the greenhouse of canola events containing the T-DNAs of plasmids VC-LJB2755-2qcz rc and VC-LLM391-2qcz rc. Plants of all events combined have been grouped into the categories indicated in the first column; as defined in Table 76. The number of T1 plants fulfilling these criteria are displayed in parentheses.

| | Category of T1 plants | | | | | | | | |
|---|---|---|---|---|---|---|---|---|---|
| | DFF | DF | DL | DP | DS | FC | LD | LGC | LF |
| sc (n = 143; n = 30 for oil and protein) | 67.9 ± 3 | 1 ± 0 | 1.1 ± 0.5 | 1 ± 0.2 | 1.7 ± 1.1 | 3 ± 0 | 3 ± 0 | 5 ± 0 | 1.1 ± 0.7 |

TABLE 82-continued

Phenotypic rating of T1 plants cultivated in the greenhouse of canola events
containing the T-DNAs of plasmids VC-LJB2755-2qcz rc and VC-LLM391-2qcz rc.
Plants of all events combined have been grouped into the categories indicated
in the first column; as defined in Table 76. The number of T1 plants
fullfilling these criteria are displayed in parentheses.

| | Category of T1 plants | | | | | |
|---|---|---|---|---|---|---|
| | NoL | PH | TKW | SC | Oil | Protein |
| sc (n = 143; n = 30 for oil and protein) | 3.9 ± 0.3 | 127.9 ± 4 | 3.6 ± 0.4 | 3.5 ± 1.1 | 36 ± 1.4 | 28.5 ± 0.8 |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
Nol: number of lobes (#),
PH: plant height (cm),
TKW: thousand kernel weight (g),
SC: seed quality (1 = good, 9 = bad),
Oil: oil content (% of seed weight),
Protein: Protein content (% of seed cake without oil)

B. Fatty Acid Profiles, Copy Number Measurements, and Phenotypic Observations of T2 Plants Carrying T-DNAs of Plasmids VC-LJB2755-2qcz rc and VC-LLM391-2qcz Rc Cultivated in Greenhouses During Summer.

The data in Table 83 indicate the copy number of the selected events was a single insertion which was homozygous in the T3 seed. Fatty acid profile measurements, see Table 84 and Table 85, indicated the combination of T-DNAs from VC-LJB2755-2qcz and VC-LLM391-2qcz rc are capable of bringing in the VLC-PUFA pathway to successfully accumulate ARA, EPA and DHA. The data on Table 86 show that there was no significant impact on the aerial portion of the plant caused by VC-LJB2755-2qcz and VC-LLM391-2qcz rc.

TABLE 83

Copy number measurement of T2 plants cultivated in the greenhouse of canola events containing the T-DNAs of plasmids VC-LJB2755-2qcz rc and VC-LLM391-2qcz rc. The events are indicated in the first column, along with the number of T1 plants that were measured per event. As the T2 plants underwent two cylces of selecting homozygous plants, all plants of all events are homozygous for all T-DNA insertions. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

Copy number assays targeting the T-DNA of VC-LJB2755-2qcz rc. Assays are listed according to the position of the assay target along the T-DNA, with target c-AHAS located near the left T-DNA border and target j-p-LuPXR_i-Atss15 near the right T-DNA border.

| Event | c-AHAS | c-o3Des(Pi_GA) | j-i-Atss18_c-o3Des(Pi_GA2) | j-i-Atss14_c-d12Des(Ps_GA) | c-d6Elo(Tp_GA) |
|---|---|---|---|---|---|
| LAPBOW (n = 54) | 1.9 | 2.0 | | | |
| LAODDN (n = 63) | 1.9 | 2.0 | | | |

| | Copy number assays targeting the T-DNA of VC-LJB2755-2qcz rc. Assays are listed according to the position of the assay target along the T-DNA, with target c-AHAS located near the left T-DNA border and target j-p-LuPXR_i-Atss15 near the right T-DNA border. | | | Copy number assays targeting the T-DNA of VC-LLM391-2qcz rc. Assays are listed according to the position of the assay target along the T-DNA, with target c-d4Des(Eg_GA) located near the left T-DNA border and target j-i-Atss1_c-d5Elo(Ot_GA3) near the right T-DNA border. | | |
|---|---|---|---|---|---|---|
| Event | j-i-Atss1_c-d6Elo(Tp_GA2) | c-o3Des(Pir_GA) | j-p-LuPXR_i-Atss15 | c-d4Des(Eg_GA) | j-t-PvARC-p-LuCnl | j-i-Atss2_c-d4Des(Tc_GA3) |
| LAPBOW (n = 54) | | 2.0 | 2.4 | 2.0 | | |
| LAODDN (n = 63) | | 2.0 | 2.1 | 2.0 | | |

TABLE 83-continued

Copy number measurement of T2 plants cultivated in the greenhouse of canola events containing the T-DNAs of plasmids VC-LJB2755-2qcz rc and VC-LLM391-2qcz rc. The events are indicated in the first column, along with the number of T1 plants that were measured per event. As the T2 plants underwent two cylces of selecting homozygous plants, all plants of all events are homozygous for all T-DNA insertions. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

| | Copy number assays targeting the T-DNA of VC-LLM391-2qcz rc. Assays are listed according to the position of the assay target along the T-DNA, with target c-d4Des(Eg_GA) located near the left T-DNA border and target j-i-Atss1_c-d5Elo(Ot_GA3) near the right T-DNA border. | | | |
|---|---|---|---|---|
| Event | c-d4Des(Tc_GA) | j-p-PvARC5_t-BnFAE | c-d5Elo(Ot_GA3) | j-i-Atss1_c-d5Elo(Ot_GA3) |
| LAPBOW (n = 54) | | 2.0 | | 2.0 |
| LAODDN (n = 63) | | 2.0 | | 1.9 |

TABLE 84

Fatty acid profiles of T3 seeds harvested from T2 plants cultivated in the greenhouse of canola events containing the T-DNAs of plasmids VC-LJB2755-2qcz rc and VC-LLM391-2qcz rc. The events are indicated in the first column, along with the number of T3 seed batches that where measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LAPBOW (n = 54) | 5.3 ± 0.3 | 0.3 ± 0.1 | 0.2 ± 0.1 | 3.4 ± 0.2 | 26.8 ± 1.9 | 35.6 ± 2.1 | 0.6 ± 0.1 | 6.1 ± 0.8 | 1.6 ± 0.2 |
| LAODDN (n = 63) | 5.4 ± 0.4 | 0.3 ± 0.1 | 0.2 ± 0.1 | 3.5 ± 0.4 | 27.7 ± 2.4 | 35.4 ± 1.8 | 0.6 ± 0.1 | 6.5 ± 0.8 | 1.4 ± 0.2 |
| WT Kumily (n = 46) | 5 ± 0.1 | 0.4 ± 0 | 0.2 ± 0 | 2.6 ± 0.1 | 66.3 ± 1.7 | 16.8 ± 1.3 | 0 ± 0 | 6.1 ± 0.4 | 0 ± 0 |

| Event | 18:4 n-3 | 20:0 | 20:1 n-9 | 20:2 n-6 | 20:3 n-3 | 20:3 n-6 | 20:4 n-3 | 20:4 n-6 | 20:5 n-3 |
|---|---|---|---|---|---|---|---|---|---|
| LAPBOW (n = 54) | 0.4 ± 0.1 | 0.8 ± 0.1 | 0.7 ± 0 | 0.1 ± 0.1 | 0 ± 0 | 1.8 ± 0.3 | 1.4 ± 0.3 | 1.4 ± 0.2 | 7.1 ± 0.8 |
| LAODDN (n = 63) | 0.4 ± 0 | 0.8 ± 0.1 | 0.7 ± 0 | 0.1 ± 0.1 | 0 ± 0 | 1.8 ± 0.2 | 1.4 ± 0.2 | 1 ± 0.2 | 6.8 ± 0.6 |
| WT Kumily (n = 46) | 0 ± 0 | 0.9 ± 0 | 1.2 ± 0 | 0 ± 0 | 0 ± 0 | 0 ± 0 | 0 ± 0 | 0 ± 0 | 0 ± 0 |

| Event | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|
| LAPBOW (n = 54) | 0.3 ± 0.1 | 0 ± 0 | 1 ± 0.1 | 3.2 ± 0.5 | 0 ± 0 | 1.3 ± 0.3 | 0.6 ± 0.2 | 0.1 ± 0.1 |
| LAODDN (n = 63) | 0.3 ± 0.1 | 0 ± 0 | 0.8 ± 0.1 | 3 ± 0.3 | 0 ± 0 | 1.1 ± 0.3 | 0.6 ± 0.1 | 0.1 ± 0.1 |
| WT Kumily (n = 46) | 0.5 ± 0 | 0 ± 0 | 0 ± 0 | 0 ± 0 | 0 ± 0 | 0 ± 0 | 0 ± 0 | 0 ± 0 |

TABLE 85

Fatty acid profiles of one T3 seed batch per event harvested from T2 plants cultivated in the greenhouse of canola events containing the T-DNAs of plasmids VC-LJB2755-2qcz rc and VC-LLM391-2qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPBOW (n = 1) | 5.7 | 0.3 | 0.2 | 3.3 | 24.1 | 34.3 | 0.6 | 6.1 | 2.0 | 0.5 | 0.7 | 0.6 | 0.0 |
| LAODDN (n = 1) | 5.3 | 0.3 | 0.2 | 3.1 | 25.1 | 34.7 | 0.7 | 6.0 | 1.8 | 0.5 | 0.7 | 0.7 | 0.0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPBOW (n = 1) | 0.0 | 2.1 | 1.7 | 1.6 | 8.7 | 0.1 | 0.0 | 1.1 | 3.8 | 0.0 | 1.7 | 0.7 | 0.0 |
| LAODDN (n = 1) | 0.0 | 2.2 | 2.0 | 1.1 | 8.7 | 0.3 | 0.0 | 0.8 | 3.6 | 0.0 | 1.5 | 0.7 | 0.1 |

TABLE 86

Phenotypic rating of T2 plants cultivated in the greenhouse of canola events containing the T-DNAs of plasmids VC-LJB2755-2qcz rc and VC-LLM391-2qcz rc. The events are indicated in the first column, along with the number of T1 plants that where rated per event.

| Event | Oil | Protein |
|---|---|---|
| LAPBOW (n = 54) | 34.8 ± 2.9 | 30.8 ± 2.3 |
| LAODDN (n = 63) | 36.6 ± 3 | 28.6 ± 2.4 |
| WT Kumily (n = 46) | 34.9 ± 1.1 | 32.2 ± 1 |

Oil: oil content (% of seed weight), protein: Protein content (% of seed cake without oil)

C. Fatty Acid Profiles, Copy Number Measurements, and Phenotypic Observations of T2 Plants Carrying T-DNAs of Plasmids VC-LJB2755-2qcz rc and VC-LLM391-2qcz Rc Cultivated in Field Trials in USDA Growth Zones 3a-4b and 5a During the Summer Field data for the T3 seed from the events carrying the T-DNA from VC-LJB2755-2qcz and VC-LLM391-2qcz rc, shown in Table 87 and Table 88, indicate that the plants are capable of making VLC-PUFAs in the field (ARA, EPA and DHA), though not at the level observed in the greenhouse. However, there was also a difference in seed oil content observed compared to the greenhouse (e.g. comparing Table 89 with Table 86). These observations are in agreement with previous examples where it was observed that increased oil contents in the field grown plants concomitant with a decrease in VLC-PUFAs, in particular EPA, DHA and ARA. A more detailed description of the observations regarding oil content and VLC-PUFAs is given in Example 20.

TABLE 87

Fatty acid profiles of T3 seeds harvested from T2 cultivated in the field, corresponding to USDA growth zones 3a-4b and 5a, for field trials of canola events containing the T-DNAs of plasmids VC-LJB2755-2qcz rc and VC-LLM391-2qcz rc The events are indicated in the first column, along with the number of T3 seed aliquots representing a plot where measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LAPBOW (n = 31) | 5.3 ± 0.2 | 0.4 ± 0.1 | 0 ± 0 | 2.4 ± 0.1 | 31.9 ± 1.6 | 33.3 ± 1 | 0.6 ± 0.1 | 7.7 ± 0.5 | 1.4 ± 0.2 |
| LAODDN (n = 31) | 5.1 ± 0.2 | 0.4 ± 0 | 0.1 ± 0 | 2.5 ± 0.2 | 32.1 ± 2.3 | 33.4 ± 1.4 | 0.6 ± 0.1 | 7.9 ± 0.5 | 1.3 ± 0.2 |
| WT Kumily (n = 60) | 5 ± 0.3 | 0.4 ± 0 | 0.1 ± 0.1 | 2 ± 0.1 | 56.2 ± 4.2 | 23.3 ± 1.7 | 0 ± 0.1 | 9.5 ± 0.7 | 0.1 ± 0.2 |

| Event | 18:4 n-3 | 20:0 | 20:1 n-9 | 20:2 n-6 | 20:3 n-3 | 20:3 n-6 | 20:4 n-3 | 20:4 n-6 | 20:5 n-3 |
|---|---|---|---|---|---|---|---|---|---|
| LAPBOW (n = 31) | 0.4 ± 0.1 | 0.6 ± 0 | 0.7 ± 0 | 0.1 ± 0.1 | 0 ± 0 | 1.5 ± 0.1 | 0.9 ± 0.1 | 1.6 ± 0.2 | 5.5 ± 0.5 |
| LAODDN (n = 31) | 0.4 ± 0.1 | 0.6 ± 0 | 0.7 ± 0 | 0.2 ± 0.1 | 0.1 ± 0.1 | 1.3 ± 0.1 | 0.8 ± 0.1 | 1.4 ± 0.2 | 5.7 ± 0.7 |
| WT Kumily (n = 60) | 0 ± 0 | 0.7 ± 0 | 1.1 ± 0.1 | 0.1 ± 0.1 | 0 ± 0 | 0.2 ± 0.3 | 0.1 ± 0.3 | 0.2 ± 0.5 | 0.4 ± 1.1 |

TABLE 87-continued

Fatty acid profiles of T3 seeds harvested from T2 cultivated in the field, corresponding to USDA growth zones 3a-4b and 5a, for field trials of canola events containing the T-DNAs of plasmids VC-LJB2755-2qcz rc and VC-LLM391-2qcz rc The events are indicated in the first column, along with the number of T3 seed aliquots representing a plot where measured per event. Per seed batch a random selection of ~30 seed was measured in two technical repeats.

| Event | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|
| LAPBOW (n = 31) | 0.2 ± 0.1 | 0 ± 0 | 0.9 ± 0.1 | 3.1 ± 0.3 | 0 ± 0 | 0.8 ± 0.1 | 0.4 ± 0.1 | 0.1 ± 0.1 |
| LAODDN (n = 31) | 0.3 ± 0 | 0 ± 0 | 0.8 ± 0.1 | 3.1 ± 0.4 | 0 ± 0 | 0.8 ± 0.1 | 0.4 ± 0.1 | 0.1 ± 0 |
| WT Kumily (n = 60) | 0.3 ± 0.1 | 0 ± 0 | 0 ± 0.2 | 0.2 ± 0.6 | 0 ± 0 | 0 ± 0.2 | | |

TABLE 88

Fatty acid profiles of one T3 seed batch per event harvested from T2 plants cultivated in USDA growth zones 3a-4b and 5a for field trials of canola events containing the T-DNAs of plasmids VC-LJB2755-2qcz rc and VC-LLM391-2qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPBOW (n = 1) | 5.5 | 0.4 | 0.1 | 2.3 | 30.3 | 32.9 | 0.6 | 7.6 | 1.8 | 0.5 | 0.6 | 0.7 | 0.1 |
| LAODDN (n = 1) | 5.4 | 0.4 | 0.0 | 2.6 | 30.1 | 33.3 | 0.7 | 6.9 | 1.5 | 0.4 | 0.6 | 0.6 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPBOW (n = 1) | 0.0 | 1.6 | 1.0 | 1.7 | 6.5 | 0.1 | 0.0 | 1.0 | 3.5 | 0.0 | 1.1 | 0.2 | 0.1 |
| LAODDN (n = 1) | 0.0 | 1.5 | 0.9 | 1.8 | 6.8 | 0.2 | 0.0 | 1.0 | 3.5 | 0.0 | 0.9 | 0.4 | 0.1 |

TABLE 89

Phenotypic rating of T2 plants cultivated in USDA growth zones 3a-4b and 5a for field trials of canola events containing the T-DNAs of plasmids VC-LJB2755-2qcz rc and VC-LLM391-2qcz rc. The events are indicated in the first column, along with the number of field plots that where rated per event.

| Event | Oil | protein |
|---|---|---|
| LAPBOW (n = 31) | 38.7 ± 1.2 | 28 ± 1.1 |
| LAODDN (n = 31) | 38.3 ± 1.4 | 27.9 ± 1.2 |
| WT Kumily (n = 60) | 38.7 ± 1.1 | |

Oil: oil content (% of seed weight), protein: Protein content (% of seed cake without oil)

D. Fatty Acid Profiles, Copy Number Measurements, and Phenotypic Observations of T3 Plants Carrying T-DNAs of Plasmids VC-LJB2755-2qcz rc and VC-LLM391-2qcz Rc Cultivated in Greenhouses During Winter.

T4 seed from T3 plants from the event LAODDN, which was homozygous for T-DNA from both VC-LJB2755-2qcz and VC-LLM391-2qcz rc (see Table 90) accumulated VLC-PUFAs (in particular ARA, EPA and DHA, see Table 91 and Table 92). The combination of EPA and DHA was up to approximately ten percent of the total fatty acid content in the seed for this event.

TABLE 90

Copy number measurement of T3 plants cultivated in the greenhouse of canola events containing the T-DNAs of plasmids VC-LJB2755-2qcz rc and VC-LLM391-2qcz rc. The events are indicated in the first column, along with the number of T1 plants that where measured per event. As the T3 plants underwent two cylces of selecting homozygous plants, all plants of all events are homozygous for all T-DNA insertions. A copy umber of ~2 therefore was indicative for one homozygous locus, a copy number of ~4 indicative for two homozygous loci or indicative for one omozygous locus containing two copies of the target gene measured by the assay, and so forth. Odd results of 3 and 5 indicate that at least some of the selected T1 plants carry a heterozygous locus.

Copy number assays targeting the T-DNA of VC-LJB2755-2qcz rc. Assays are listed according to the position of the assay target along the T-DNA, with targetc-AHAS located near the left T-DNA border and target j-p-LuPXR__i-Atss15 near the right T-DNA border.

| Event | c-AHAS | c-o3Des(Pi__GA) | j-i-Atss18__c- | j-i-Atss14__c- | c-d6Elo(Tp__GA) | j-i-Atss1__c- |
|---|---|---|---|---|---|---|
| LAODDN (n = 30) | 1.92 | | 2.0 | | | |

| | Copy number assays targeting the T-DNA of VC-LJB2755-2qcz rc. Assays are listed according to the position of the assay target along the T-DNA, with target c-AHAS located near the left T-DNA border and target j-p-LuPXR__i-Atss15 near the right T-DNA border. | | Copy number assays targeting the T-DNA of VC-LLM391-2qcz rc. Assays are listed according to the position of the assay target along the T-DNA, with target c-d4Des(Eg__GA) located near the left T-DNA border and target j-i-Atss1__c-d5Elo(Ot__GA3) near the right T-DNA border. | |
|---|---|---|---|---|
| Event | c-o3Des(Pir__GA) | j-p-LuPXR__i-Atss15 | c-d4Des(Eg__GA) | j-t-PvARC-p-LuCnl |
| LAODDN (n = 30) | | 1.9 | 1.8 | |

Copy number assays targeting the T-DNA of VC-LLM391-2qcz rc. Assays are listed according to the position of the assay target along the T-DNA, with target c-d4Des(Eg__GA) located near the left T-DNA border and target j-i-Atss1__c-d5Elo(Ot__GA3) near the right T-DNA border.

| Event | j-i-Atss2__c-d4Des(Tc__GA3) | c-d4Des(TcGA) | j-p-PvARC5__t-BnFAE | c-d5Elo(Ot__GA3) | j-i-Atss1__c-d5Elo(Ot__GA3) |
|---|---|---|---|---|---|
| LAODDN (n = 30) | | 1.9 | 2.1 | | 1.9 |

TABLE 91

Fatty acid profiles of T4 seeds harvested from T3 plants cultivated in the greenhouse of canola events containing the T-DNAs of plasmids VC-LJB2755-2qcz rc and VC-LLM391-2qcz rc The events are indicated in the first column, along with the number of T4 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 |
|---|---|---|---|---|---|---|---|---|---|---|
| LAODDN (n = 30) | 5.3 ± 0.5 | 0.3 ± 0 | 0 ± 0 | 3.3 ± 0.7 | 27.2 ± 2.5 | 37.7 ± 4.1 | 2.3 ± 5.1 | 5.1 ± 0.7 | 1.7 ± 0.3 | 0.4 ± 0.1 |

| Event | 20:0 | 20:1 n-9 | 20:2 n-6 | 20:3 n-3 | 20:3 n-6 | 20:4 n-3 | 20:4 n-6 | 20:5 n-3 |
|---|---|---|---|---|---|---|---|---|
| LAODDN (n = 30) | 0.8 ± 0.1 | 0.6 ± 0.1 | 0.1 ± 0.1 | 0 ± 0 | 1.2 ± 0.2 | 0.3 ± 0.5 | 1.3 ± 0.2 | 6.5 ± 0.8 |

| Event | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|
| LAODDN (n = 30) | 0.2 ± 0.2 | 0 ± 0 | 1 ± 0.3 | 2.7 ± 0.4 | 0 ± 0 | 1.3 ± 0.4 | 0.4 ± 0.1 | 0 ± 0 |

TABLE 92

Fatty acid profiles of one T4 seed batch per event harvested from T3 plants cultivated in the greenhouse of canola events containing the T-DNAs of plasmids VC-LJB2755-2qcz rc and VC-LLM391-2qcz rc. The events are indicated in the first column. Fatty acid profiles of T4 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAODDN (n = 1) | 5.2 | 0.2 | 0.0 | 3.7 | 24.2 | 39.5 | 0.4 | 4.8 | 2.0 | 0.5 | 0.9 | 0.6 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAODDN (n = 1) | 0.1 | 1.0 | 0.0 | 1.5 | 7.7 | 0.4 | 0.0 | 1.3 | 3.3 | 0.0 | 1.9 | 0.3 | 0.1 |

TABLE 93

Phenotypic rating of T3 plants cultivated in the greenhouse of canola events containing the T-DNAs of plasmids VC-LJB2755-2qcz rc and VC-LLM391-2qcz rc. The events are indicated in the first column, along with the number of T1 plants that where rated per event.

| Event | DFF | DF | DL | DP | DS | FC | LD | LGC | LF | NoL | PH |
|---|---|---|---|---|---|---|---|---|---|---|---|
| LAODDN (n = 30) | 43.5 ± 4.1 | 8.5 ± 0.5 | 7.8 ± 0.8 | 9 ± 0 | 7.9 ± 1 | 3 ± 0 | 4.6 ± 0.7 | 4.5 ± 0.7 | 8.8 ± 0.4 | 5 ± 0.8 | 115 ± 12.5 |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoL: number of lobes (#),
PH: plant height (cm)

E. Fatty Acid Profiles, Copy Number Measurements, and Phenotypic Observations of T3 Plants Carrying T-DNAs of Plasmids VC-LJB2755-2qcz rc and VC-LLM391-2qcz Rc Cultivated in Field Trials in USDA Growth Zones 8a-9a in the Winter.

Field data for T4 seed of two events carrying homozygous T-DNA insertions from VC-LJB2755-2qcz and VC-LLM391-2qcz rc (see Table 83 and Table 90 and Table 84, Table 87, Table 91) indicate these events do accumulate EPA, DHA and ARA when grown in the greenhouse and field, though as consistently observed, the field grown material did not accumulate the VLC-PUFAs (ARA, EPA, DHA) to the extent observed in the greenhouse (see Table 94 and Table 95 in comparison with Table 91, Table 92, Table 87 and Table 88). As observed in in Example 11 part F, higher oil content was observed compared to the summer field trials (Comparison Table 96 with Table 89). This phenomenon is analyzed in detail in Example 20.

TABLE 94

Fatty acid profiles of T4 seeds harvested from T3 cultivated in the field corresponding to USDA growth zones 8a-9a for field trials of canola events containing the T-DNAs of plasmids VC-LJB2755-2qcz rc and VC-LLM391-2qcz rc The events are indicated in the first column, along with the number of T4 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LAPBOW (n = 16) | 5.3 ± 0.2 | 0.4 ± 0 | 0 ± 0 | 2.4 ± 0.2 | 36.1 ± 3.1 | 31.3 ± 2 | 0.5 ± 0.1 | 7.9 ± 0.5 | 1.3 ± 0.3 |
| LAODDN (n = 47) | 5.5 ± 0.6 | 0.5 ± 0.2 | 0.2 ± 0.3 | 2.7 ± 0.5 | 36.8 ± 3.2 | 30.3 ± 2.2 | 0.6 ± 0.2 | 7.9 ± 0.5 | 1.3 ± 0.3 |
| WT Kumily (n = 83) | 5.1 ± 0.5 | 0.4 ± 0.1 | 0.1 ± 0.1 | 2.1 ± 0.5 | 59.1 ± 1.8 | 21.3 ± 1.5 | 0 ± 0.1 | 9.5 ± 0.7 | 0 ± 0.1 |

TABLE 94-continued

Fatty acid profiles of T4 seeds harvested from T3 cultivated in the field corresponding to USDA growth zones 8a-9a for field trials of canola events containing the T-DNAs of plasmids VC-LJB2755-2qcz rc and VC-LLM391-2qcz rc The events are indicated in the first column, along with the number of T4 seed aliquots representing a plot were measured per event. Per seed batch a random selection of ~30 seed was measured in two technical repeats.

| Event | 18:4 n-3 | 20:0 | 20:1 n-9 | 20:2 n-6 | 20:3 n-3 | 20:3 n-6 | 20:4 n-3 | 20:4 n-6 | 20:5 n-3 |
|---|---|---|---|---|---|---|---|---|---|
| LAPBOW (n = 16) | 0.4 ± 0.1 | 0.6 ± 0 | 0.7 ± 0 | 0.1 ± 0.1 | 0 ± 0 | 1.2 ± 0.1 | 0.8 ± 0.1 | 1.4 ± 0.2 | 4.5 ± 0.5 |
| LAODDN (n = 47) | 0.4 ± 0.1 | 0.6 ± 0.1 | 0.7 ± 0 | 0.1 ± 0.1 | 0 ± 0 | 1 ± 0.1 | 0.8 ± 0.1 | 1.2 ± 0.2 | 4.7 ± 0.7 |
| WT Kumily (n = 83) | 0 ± 0 | 0.6 ± 0.1 | 1 ± 0.1 | 0.1 ± 0 | 0 ± 0 | 0 ± 0 | 0 ± 0 | 0 ± 0.1 | 0.1 ± 0.1 |

| Event | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|
| LAPBOW (n = 16) | 0.2 ± 0 | 0 ± 0 | 0.7 ± 0.2 | 2.7 ± 0.2 | 0 ± 0 | 0.7 ± 0.2 | 0.3 ± 0.2 | 0.1 ± 0.1 |
| LAODDN (n = 47) | 0.2 ± 0 | 0 ± 0 | 0.4 ± 0.3 | 2.6 ± 0.3 | 0 ± 0 | 0.6 ± 0.2 | 0.2 ± 0.1 | 0.1 ± 0.1 |
| WT Kumily (n = 83) | 0.3 ± 0 | 0 ± 0 | 0 ± 0.1 | 0 ± 0.1 | 0 ± 0 | 0 ± 0 | 5.1 ± 0.5 | 0.4 ± 0.1 |

TABLE 95

Fatty acid profiles of one T4 seed batch per event harvested from T3 plants cultivated in the field corresponding to USDA growth zones 8a-9a for field trials of canola events containing the T-DNAs of plasmids VC-LJB2755-2qcz rc and VC-LLM391-2qcz rc. The events are indicated in the first column. Fatty acid profiles of T4 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPBOW (n = 1) | 5.3 | 0.4 | 0.0 | 2.3 | 31.5 | 34.0 | 0.5 | 7.3 | 1.8 | 0.6 | 0.6 | 0.7 | 0.1 |
| LAODDN (n = 1) | 5.6 | 0.4 | 0.0 | 2.1 | 33.8 | 31.1 | 0.7 | 8.0 | 1.5 | 0.5 | 0.5 | 0.7 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPBOW (n = 1) | 0.0 | 1.2 | 0.8 | 1.8 | 5.5 | 0.2 | 0.0 | 1.0 | 3.1 | 0.0 | 1.1 | 0.2 | 0.0 |
| LAODDN (n = 1) | 0.0 | 1.2 | 0.8 | 1.6 | 6.2 | 0.1 | 0.0 | 0.7 | 3.3 | 0.0 | 1.0 | 0.2 | 0.1 |

TABLE 96

Phenotypic rating of T3 plants cultivated in the field corresponding to USDA growth zones 8a-9a for trials of canola events containing the T-DNAs of plasmids VC-LJB2755-2qcz rc and VC-LLM391-2qcz rc. The events are indicated in the first column, along with the number of field plots that were rated per event.

| Event | Oil | protein |
|---|---|---|
| LAPBOW (n = 16) | 42.9 ± 4.2 | 23.3 ± 3.1 |
| LAODDN (n = 47) | 43.5 ± 3.8 | 22.7 ± 2.7 |
| WT Kumily (n = 83) | 45.3 ± 3.9 | |

Oil: oil content (% of seed weight), protein: Protein content (% of seed cake without oil)

F. Fatty Acid Profiles, Copy Number Measurements, and Phenotypic Observations of T4 Plants Carrying T-DNAs of Plasmids VC-LJB2755-2qcz rc and VC-LLM391-2qcz Rc Cultivated in Field Trials in USDA Zones 3a-4b and 5a During the Summer.

The data indicate that through the T5 generation the event LAODDN was still producing EPA and DHA at a level consistent with the field trial (described in part D). Also oil content was comparable between these two field trials.

TABLE 97

Fatty acid profiles of T5 seeds harvested from T4 cultivated in the field corresponding to USDA growth zones 3a-3b and 5a for field trials of canola events containing the T-DNAs of plasmids VC-LJB2755-2qcz rc and VC-LLM391-2qcz rc The events are indicated in the first column, along with the number of T4 seed aliquots representing a plot where measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LAODDN (n = 142) | 4.7 ± 0.4 | 0.2 ± 0.1 | 0 ± 0 | 2.8 ± 0.4 | 34.8 ± 3.5 | 33.8 ± 4.8 | 0.3 ± 0.3 | 7.7 ± 1 | 1.1 ± 0.4 | 0.2 ± 0.2 | 0.7 ± 0.1 | 0.8 ± 0.1 | 0.1 ± 0.1 | 0.1 ± 0.1 |
| WT Kumily (n = 56) | 4.5 ± 0.5 | 0.1 ± 0.1 | 0 ± 0 | 1.8 ± 1 | 60 ± 3.8 | 22.5 ± 3.6 | 0.6 ± 1.5 | 7.9 ± 2.2 | 0.1 ± 0.1 | 0 ± 0 | 0.8 ± 0.2 | 1 ± 0.4 | 0.1 ± 0 | 0 ± 0 |

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LAODDN (n = 142) | 1.2 ± 0.3 | 1.1 ± 1.2 | 1.4 ± 0.4 | 4.5 ± 1.9 | 0.3 ± 0.1 | 0 ± 0 | 0.5 ± 0.4 | 2.9 ± 0.5 | 0.1 ± 0.2 | 0.7 ± 0.2 | 0.1 ± 0.2 | 0.1 ± 0.1 |
| WT Kumily (n = 56) | 0.2 ± 0.8 | 0 ± 0 | 0 ± 0 | 0 ± 0.1 | 0.2 ± 0.2 | 0 ± 0 | 0 ± 0.1 | 0 ± 0 | 0 ± 0 | 0 ± 0 | 0 ± 0 | 0 ± 0 |

TABLE 98

Fatty acid profiles of one T5 seed batch per event harvested from T4 plants cultivated in the field corresponding to USDA growth zones 3a-3b and 5a for field trials of canola events containing the T-DNAs of plasmids VC-LJB2755-2qcz rc and VC-LLM391-2qcz rc. The events are indicated in the first column. Fatty acid profiles of T5 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LAODDN (n = 1) | 4.5 | 0.2 | 0.0 | 2.6 | 30.3 | 30.8 | 0.4 | 5.8 | 0.6 | 0.1 | 0.6 | 0.9 | 0.3 | 0.4 |

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LAODDN (n = 1) | 2.4 | 1.3 | 3.7 | 8.1 | 0.3 | 0.0 | 0.0 | 4.2 | 1.2 | 1.2 | 0.0 | 0.0 |

TABLE 99

Phenotypic rating of T4 plants cultivated in the greenhouse of canola events containing the T-DNAs of plasmids VC-LJB2755-2qcz rc and VC-LLM391-2qcz rc. The events are indicated in the first column, along with the number of field plots that were rated per event.

| Event | Oil | protein |
|---|---|---|
| LAODDN (n = 47) | 39.9 ± 4.4 | 25.4 ± 1.8 |
| WT Kumily (n = 56) | 40.6 ± 2.3 | 26.4 ± 1.3 |

Oil: oil content (% of seed weight), protein: Protein content (% of seed cake without oil)

Example 4: Plants Containing the T-DNA of Plasmid VC-LTM593-1qcz rc for Production of EPA and DHA in Seeds All genetic elements required for EPA and DHA synthesis described in this example, were transferred on a single T-DNA using a BiBAC plasmid into the plant genome. To this end, the plasmid VC-LTM593-1qcz rc where cloned into agrobacteria, and plant tissue was incubated according to example 6 with this agrobacterial culture. Due to the selectable herbicide resistance marker, regenerated plants contained the T-DNA of VC-LTM593-1qcz rc. The genetic elements of VC-LTM593-1qcz rc and the function of each element are listed in Table 11. For convenience, all enzymes expressed in seeds of plants carrying both T-DNA of VC-LTM593-1qcz rc that are required for EPA and DHA synthesis are additionally listed Table 130.

TABLE 130

List of genes essential of EPA and DHA synthesis carried by the T-DNA of plasmid VC-LTM593-1qcz rc.

| Genes encoding enzmyes for EPA and DHA synthesis | Length (bp) | Enzymatic function and source of encoded protein |
|---|---|---|
| c-d12Des(Ps_GA2) | 1197 | Delta-12 desaturase from *Phythophthora sojae* |
| c-d6Des(Ot_febit) | 1371 | Delta-6 desaturase from *Ostreococcus tauri* |
| c-d6Elo(Pp_GA2) | 873 | Delta-6 elongase from *Physcomitrella patens* |
| c-d6Elo(Tp_GA2) | 819 | Delta-6 elongase from *Thalassiosira pseudonana* |
| 2 copies of c-d5Des(Tc_GA2) | 1320 | Delta-5 desaturase from *Thraustochytrium* sp. ATCC21685 |
| c-o3Des(Pi_GA2) | 1086 | Omega-3-desaturase from *Phythophthora infestans* |
| 2 copies of c-o3Des(Pir_GA) | 1092 | Omega-3 desaturase from *Pythium irregulare* |
| c-d5Elo(Ot_GA3) | 903 | Delta-5 elongase from *Ostreococcus tauri* |
| c-d4Des(Pl_GA)2 | 1338 | Delta-4 desaturase from *Pavlova lutheri* |
| c-d4Des(Tc_GA3) | 1560 | Delta-4 desaturase from *Thraustochytrium* sp. |

Fatty acid Profile in selected T1 seed batches
A. Fatty Acid Profiles, Copy Number Measurements, and Phenotypic Observations of T1 Plants Carrying T-DNAs of Plasmids VC-LTM593-1qcz rc Cultivated in Greenhouses During Winter Specific events were examined further for copy number and displayed a variation in insertion number for the T-DNA from single insertion to partial double insertions along with double insertions. Additionally there were some variations in gene copy number (corresponding to the partial insertions and possible deletions), see Table 135, Table 136 and Table 137. The fatty acid profile data shown on Table 138 and Table 139 indicate an upper range of accumulation of combined EPA and DHA of eighteen percent of the total seed fatty acid content (event LBFDAU). In the event LBFDAU the percent of total seed fatty acid content being EPA is 15% and total seed fatty acid content being DHA is 3% in the T1. LBFDAU was analysed with a copy number indicative of a partial double copy. Another example of specific events having higher levels of EPA and DHA was LBFGKN with approximately 12 percent of the total seed fatty acid content being EPA and DHA, with 10 percent of the total seed fatty acid content being EPA and 2% being DHA. The T1 generation LBFGKN had only a single copy insertion event for VC-LTM593-1qcz rc, though data on Table 140, Table 141 and Table 142 indicate that double copy double locus events tended to accumulate more EPA and DHA combined than other copy and locus numbers with respect to the T2 seed fatty acid profile. This observation likely reflects the nature of insertion site effects and the various factors that affect the generation of elite events. Table 142 indicates that with respect to the aerial phenotype of the plants there was a range of flowering times, as indicated by DFF (days to the first flower) from 36-48. Event LBFDAU did not vary significantly from the majority of other events with a DFF value of 43, thus showing no significant effect on the aerial phenotype or significant impact on total oil or protein accumulation in the seed in the T1 plant and T2 seed.

TABLE 135

Copy number measurement of T1 plants cultivated in the greenhouse of canola events containing the T-DNAs of plasmids VC-LTM593-1qcz rc. The events are indicated in the first column, along with the number of T1 plants that where measured per event. The T1 plants underwent a selection from 250 segregating T1 seedlings, using zygocity analysis as illustrated in Table 137, keeping only plants that are homozygous for the desired number of loci (which are indicated in the last column of Table 137). A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result observed in the T0 generation (indicated in parentheses). For some events this was not the case because during selection of T1 plants, undesired loci have been segregated out while retaining only desired loci in a homozygous state.

Copy number assays targeting the T-DNA of VC-LTM593-1qcz rc. Assays are listed according to the position of the assay target along the T-DNA, with target c-AHAS located near the left T-DNA border and target c-d6Elo(Pp_GA) near the right T-DNA border.

| Event | c-AHAS | j-i-Atss1_c-d5Elo(Ot_GA3) | c-d4Des(Pl_GA)2 | j-p-LuPXR_i-Atss15 | j-p-PvARC5_t-BnSETL | c-d5Des(Tc_GA) | j-i-Atss18_c-o3Des(Pi_GA2) | j-p-BnSETL-v1_c-o3Des(Pir_GA) |
|---|---|---|---|---|---|---|---|---|
| LBFDGG | 2.1 | 2 | 2 | 1.8 | (T0: 1) | 4.2 | 2 | 1.9 |
| (n = 50) | (T0: 1.1) | | (T0: 1.3) | (T0: 1.1) | | (T0: 2.2) | (T0: 1.1) | |
| LBFGKN | 2.1 | 2.2 | 2.1 | 2.2 | (T0: 0.8) | 4.2 | 2.2 | 2.1 |
| (n = 50) | (T0: 1) | | (T0: 1.3) | (T0: 1.1) | | (T0: 2) | (T0: 1.2) | |
| LBFIHE | 2 | 2.2 | 2.1 | 2.1 | (T0: 1) | 4.1 | 2.2 | 2.3 |
| (n = 34) | (T0: 1) | | (T0: 1.1) | (T0: 1.2) | | (T0: 1.9) | (T0: 1.1) | |
| LBFLDI | 2.5 | 2.3 | 2.4 | 2.4 | (T0: 1) | 4.4 | 2.2 | 2.3 |
| (n = 60) | (T0: 1) | | (T0: 1.1) | (T0: 1) | | (T0: 1.9) | (T0: 1.2) | |
| LBFPNF | 1.9 | 2.1 | 2.1 | 2.1 | (T0: 1) | 5.6 | 1.9 | 2.1 |
| (n = 52) | (T0: 1.1) | | (T0: 1.1) | (T0: 1.3) | | (T0: 2.8) | (T0: 1) | |
| LBFNSQ | 2 | 2 | 1.9 | 1.9 | (T0: 1.6) | 7.1 | 3.8 | 4 |
| (n = 51) | (T0: 1.1) | | (T0: 1.2) | (T0: 1.1) | | (T0: 3.1) | (T0: 1.9) | |
| LBFDGL | 2.1 | 2.2 | 3.9 | 3.9 | (T0: 1.9) | 6.7 | 3.8 | 3.8 |
| (n = 57) | (T0: 1) | | (T0: 2) | (T0: 1.7) | | (T0: 2.9) | (T0: 2) | |
| LBFIEF | 4.2 | 3.7 | 3.6 | 3.9 | (T0: 2) | 6.4 | 3.8 | 4.2 |
| (n = 6) | (T0: 2.5) | | (T0: 2.7) | (T0: 2.7) | | (T0: 3.5) | (T0: 2.3) | |
| LBFBAV | 2 | 2.2 | 3.7 | 4 | (T0: 1.4) | 8.2 | 3.8 | 3.9 |
| (n = 50) | (T0: 1.1) | (T0: 1.3) | (T0: 1.5) | (T0: 1.7) | | (T0: 3.7) | (T0: 1.8) | |
| LBFPNC | 2.1 | 2 | 2.3 | 2 | (T0: 1.4) | 7.5 | 4.2 | 4 |
| (n = 32) | (T0: 1.1) | | (T0: 1.2) | (T0: 1) | | (T0: 3.4) | (T0: 1.7) | |

TABLE 135-continued

Copy number measurement of T1 plants cultivated in the greenhouse of canola events containing the T-DNAs of plasmids VC-LTM593-1qcz rc. The events are indicated in the first column, along with the number of T1 plants that where measured per event. The T1 plants underwent a selection from 250 segregating T1 seedlings, using zygocity analysis as illustrated in Table 137, keeping only plants that are homozygous for the desired number of loci (which are indicated in the last column of Table 137). A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result observed in the T0 generation (indicated in parentheses). For some events this was not the case because during selection of T1 plants, undesired loci have been segregated out while retaining only desired loci in a homozygous state.

| Event | | | | | | | | |
|---|---|---|---|---|---|---|---|---|
| LBFGHQ | 3.6 | 3.8 | 4.1 | 4 | (T0: 1.7) | 6.1 | 3.8 | 3.8 |
| (n = 46) | (T0: 1.8) | | (T0: 1.8) | (T0: 2.2) | | (T0: 3.1) | (T0: 1.7) | |
| LBFAZB | 3.9 | 4 | 3.9 | 3.9 | (T0: 1.3) | 6.6 | 3.7 | 4.1 |
| (n = 49) | (T0: 1.8) | (T0: 1.7) | (T0: 1.8) | (T0: 1-7) | | (T0: 3.1) | (T0: 1.8) | |
| LBFGKW | 3.8 | 3.8 | 4.2 | 4.1 | (T0: 1.6) | 7 | 3.9 | 4 |
| (n = 72) | (T0: 1.8) | | (T0: 2.1) | (T0: 1.9) | | (T0: 3.2) | (T0: 2) | |
| LBFNRU | 3.8 | 4 | 3.8 | 3.7 | (T0: 1.7) | 7 | 4 | 3.7 |
| (n = 58) | (T0: 1.9) | | (T0: 1.9) | (T0: 2) | | (T0: 3.2) | (T0: 1.7) | |
| LBFGIZ | 3.8 | 4.1 | 3.9 | 3.8 | (T0: 1.6) | 7 | 4.2 | 3.8 |
| (n = 43) | (T0: 1.9) | | (T0: 1.9) | (T0: 2.1) | | (T0: 2.8) | (T0: 1.8) | |
| LBFIGM | 4.1 | 3.9 | 3.8 | 3.8 | (T0: 1.5) | 7.6 | 3.9 | 3.9 |
| (n = 56) | (T0: 2) | | (T0: 2) | (T0: 1-7) | | (T0: 2.8) | (T0: 1.7) | |
| LBFNRR | 3.7 | 4.2 | 4 | 3.8 | (T0: 1.7) | 7.1 | 4.3 | 3.8 |
| (n = 61) | (T0: 1.9) | | (T0: 2.2) | (T0: 2) | | (T0: 2.8) | (T0: 2) | |
| LBFNTK | 4.1 | 4.1 | 3.9 | 3.9 | 4 | 7.6 | 4 | 3.9 |
| (n = 69) | (T0: 1.9) | | (T0: 2.1) | (T0: 2) | (T0: 1.7) | (T0: 2.9) | (T0: 1.8) | |
| LBFGJA | 3.7 | 3.7 | 3.9 | 3.6 | (T0: 1.7) | 7.6 | 3.4 | 3.8 |
| (n = 42) | (T0: 1.6) | | (T0: 2.1) | (T0: 2.1) | | (T0: 3.6) | (T0: 1.7) | |
| LBFIFV | 3.9 | 4 | 3.9 | 1.9 | (T0: 1.8) | 7.7 | 3.9 | 3.9 |
| (n = 58) | (T0: 1.7) | | (T0: 2.4) | (T0: 1) | | (T0: 3.9) | (T0: 1.8) | |
| LBFLER | 3.8 | 3.9 | 3.9 | 3.8 | (T0: 1.7) | 7.7 | 3.9 | 4 |
| (n = 52) | (T0: 1.9) | | (T0: 2.3) | (T0: 1.9) | | (T0: 3.3) | (T0: 2.2) | |
| LBFLDL | 3.8 | 3.9 | 3.8 | 3.8 | (T0: 1.8) | 7.8 | 3.9 | 3.8 |
| (n = 44) | (T0: 1.7) | | (T0: 2) | (T0: 1.8) | | (T0: 3.5) | (T0: 2.1) | |
| LBFNQW | 3.8 | 3.9 | 3.9 | 3.9 | (T0: 1.6) | 7.9 | 3.9 | 3.9 |
| (n = 51) | (T0: 1.8) | | (T0: 1.9) | (T0: 1.9) | | (T0: 3.4) | (T0: 1.8) | |
| LBFBAP | 2 | 2 | 2 | 1.8 | (T0: 1.1) | 7.5 | 3.8 | 3.9 |
| (n = 19) | (T0: 1.1) | (T0: 1.2) | (T0: 1) | (T0: 1.3) | | (T0: 2.8) | (T0: 1.8) | |
| LBFDAU | 2 | 2 | 3.8 | 3.8 | (T0: 1.5) | 7.3 | 3.8 | 3.9 |
| (n = 10) | (T0: 1.1) | | (T0: 1.9) | (T0: 1.8) | | (T0: 3.7) | (T0: 2) | |
| LBFPRA | 2.1 | 2 | 6 | 1.8 | (T0: 2) | 7.4 | 3.8 | 4.1 |
| (n = 16) | (T0: 2) | | (T0: 3) | (T0: 1.8) | | (T0: 4.7) | (T0: 2.8) | |
| LBFIFU | 2.2 | 2.5 | 2.4 | 2.4 | (T0: 1.7) | 6.5 | 2.6 | 3.2 |
| (n = 11) | (T0: 2) | | (T0: 2.2) | (T0: 2.1) | | (T0: 4.2) | (T0: 1.9) | |
| LBFDKD | 3.6 | 3.7 | 3.6 | 3.9 | (T0: 1.8) | 7.6 | 2.9 | 3.5 |
| (n = 2) | (T0: 1.6) | | (T0: 2.1) | (T0: 2.2) | | (T0: 3.4) | (T0: 2.1) | |
| LBFDJG | 3.6 | 3.7 | 4 | 3.7 | (T0: 1.9) | 8 | 3.6 | 4 |
| (n = 12) | (T0: 1.6) | | (T0: 1.8) | (T0: 1.6) | | (T0: 3.6) | (T0: 2) | |
| LBFLFK | 3.7 | 3.9 | 3.7 | 3.6 | (T0: 2) | 7.5 | 4.1 | 3.7 |
| (n = 15) | (T0: 2) | | (T0: 2.4) | (T0: 2.3) | | (T0: 5.2) | (T0: 2.2) | |
| LBFLCG | 3.8 | 3.9 | 3.7 | 3.7 | (T0: 1.7) | 9 | 3.8 | 3.9 |
| (n = 15) | (T0: 1.9) | | (T0: 2.3) | (T0: 1.9) | | (T0: 5.1) | (T0: 1.9) | |
| LBFPQM | 4 | 3.8 | 4.1 | 4.1 | (T0: 1.5) | 7.6 | 3.9 | 4 |
| (n = 12) | (T0: 2) | | (T0: 1.8) | (T0: 2) | | (T0: 3.7) | (T0: 2) | |
| LBFDHG | 4.2 | 4 | 3.8 | 3.8 | (T0: 1.6) | 7.7 | 3.9 | 3.7 |
| (n = 5) | (T0: 1.9) | | (T0: 2.3) | (T0: 1.8) | | (T0: 3.3) | (T0: 1.9) | |
| LBFCYO | (T0: 3) | | (T0: 2.2) | (T0: 2) | (T0: 2) | (T0: 3) | (T0: 3.4) | |
| (n = 0) | | | | | | | | |
| LBFBAJ | (T0: 1) | (T0: 1.1) | (T0: 1.1) | (T0: 1) | (T0: 1.7) | (T0: 4.8) | (T0: 2) | |
| (n = 0) | | | | | | | | |
| LBFDJI | (T0: 1.1) | | (T0: 1.2) | (T0: 1) | (T0: 1) | (T0: 3) | (T0: 2) | |
| (n = 0) | | | | | | | | |
| LBFGGO | (T0: 1) | | (T0: 1) | (T0: 1.1) | (T0: 1) | (T0: 2.6) | (T0: 1) | |
| (n = 0) | | | | | | | | |
| LBFLFP | (T0: 0.9) | | (T0: 1.2) | (T0: 1.2) | (T0: 1.8) | (T0: 3.5) | (T0: 2) | |
| (n = 0) | | | | | | | | |
| LBFNQV | (T0: 1.1) | | (T0: 1.2) | (T0: 1) | (T0: 1) | (T0: 2.7) | (T0: 1.8) | |
| (n = 0) | | | | | | | | |
| LBFNLT | (T0: 1.1) | | (T0: 1.2) | (T0: 1) | (T0: 1.8) | (T0: 3.3) | (T0: 1.8) | |
| (n = 0) | | | | | | | | |
| LBFLGC | (T0: 1) | | (T0: 1.1) | (T0: 1.1) | (T0: 1) | (T0: 2.5) | (T0: 1.1) | |
| (n = 0) | | | | | | | | |
| LBFLCW | (T0: 0.9) | | (T0: 1.2) | (T0: 1) | (T0: 0.8) | (T0: 3.6) | (T0: 1.7) | |
| (n = 0) | | | | | | | | |
| LBFZPJ | (T0: 2) | | (T0: 1.8) | (T0: 1.9) | (T0: 1) | (T0: 3.5) | (T0: 1) | |
| (n = 0) | | | | | | | | |
| LBFNSS | (T0: 1.1) | | (T0: 1) | (T0: 1.2) | (T0: 1.1) | (T0: 2.5) | (T0: 1.8) | |
| (n = 0) | | | | | | | | |
| LBGAOR | (T0: 1.1) | | (T0: 1.8) | (T0: 2) | (T0: 1.7) | (T0: 2.9) | (T0: 1.8) | |
| (n = 0) | | | | | | | | |

TABLE 135-continued

Copy number measurement of T1 plants cultivated in the greenhouse of canola events containing the T-DNAs of plasmids VC-LTM593-1qcz rc. The events are indicated in the first column, along with the number of T1 plants that where measured per event. The T1 plants underwent a selection from 250 segregating T1 seedlings, using zygocity analysis as illustrated in Table 137, keeping only plants that are homozygous for the desired number of loci (which are indicated in the last column of Table 137). A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result observed in the T0 generation (indicated in parentheses). For some events this was not the case because during selection of T1 plants, undesired loci have been segregated out while retaining only desired loci in a homozygous state.

| Event | | | | | | | | |
|---|---|---|---|---|---|---|---|---|
| LBFZOE (n = 0) | (T0: 1) | | (T0: 1) | (T0: 1.1) | (T0: 1.1) | (T0: 2.8) | (T0: 1) | |
| LBFDJS (n = 0) | (T0: 1) | | (T0: 1.2) | (T0: 1) | (T0: 1) | (T0: 2.9) | (T0: 1.2) | |
| LBFDKC (n = 0) | (T0: 1) | | (T0: 1) | (T0: 1.2) | (T0: 1.8) | (T0: 2.5) | (T0: 2.2) | |
| LBFDKA (n = 5) | 4.2 (T0: 1.6) | 3.8 | 5.4 (T0: 2.6) | 5.2 (T0: 3.1) | (T0: 2.4) | 10.1 (T0: 5.6) | 4.8 (T0: 3.1) | 6 |
| LBFLGH (n = 0) | (T0: 0.9) | | (T0: 1) | (T0: 1.1) | (T0: 1.1) | (T0: 2.9) | (T0: 2.3) | |
| LBFNUS (n = 0) | (T0: 1.1) | | (T0: 1) | (T0: 0.9) | (T0: 1.4) | (T0: 3.9) | (T0: 2.2) | |
| LBFLCH (n = 0) | (T0: 1.8) | | (T0: 2.1) | (T0: 2.1) | (T0: 2.3) | (T0: 5) | (T0: 3.1) | |
| LBFZMI (n = 0) | (T0: 3.3) | | (T0: 2.1) | (T0: 2) | (T0: 1.5) | (T0: 4.6) | (T0: 2.2) | |
| LBFIDT (n = 7) | 3.8 (T0: 1.5) | 4 | 4.3 (T0: 2.2) | 4.2 (T0: 1.9) | (T0: 1.5) | 8.5 (T0: 4.5) | 4 (T0: 2.5) | 4.3 |
| LBFAZW (n = 0) | (T0: 1.8) | (T0: 2) | (T0: 2.1) | (T0: 1.8) | (T0: 1.4) | (T0: 4.5) | (T0: 1.7) | |
| LBFBBI (n = 0) | (T0: 2) | (T0: 2) | (T0: 1.9) | (T0: 1.5) | (T0: 1.6) | (T0: 4.2) | (T0: 1.9) | |
| LBFAZW (n = 0) | (T0: 1.8) | (T0: 2) | (T0: 2.1) | (T0: 1.8) | (T0: 1.4) | (T0: 4.5) | (T0: 1.7) | |

Copy number assays targeting the T-DNA of VC-LTM593-1qcz rc. Assays are listed according to the position of the assay target along the T-DNA, with target c-AHAS located near the left T-DNA border and target c-d6Elo(Pp_GA) near the right T-DNA border.

| Event | j-i-Atss14_c-d12Des(Ps_GA) | c-d6Elo(Tp_GA) | j-t-StCAT_p2_p-LuPXR | j-i-Atss2_c-d6Des(Otfebit_GA) | c-d5Des(Tc_GA) | c-d6Elo(Pp_GA) | Conclusion from individual assays: number of T-DNA copies inserted into the genome |
|---|---|---|---|---|---|---|---|
| LBFDGG (n = 50) | 2 | 2.1 (T0: 1.1) | 2.2 (T0: 1) | 2.1 (T0: 1) | 4.2 (T0: 2.2) | 1.9 (T0: 1) | single copy |
| LBFGKN (n = 50) | 2.1 | 2.1 (T0: 1) | 2.2 (T0: 1) | 2.1 (T0: 1.1) | 4.2 (T0: 2) | 1.9 (T0: 1.1) | single copy |
| LBFIHE (n = 34) | 2.3 | 2.1 (T0: 1) | 2.1 (T0: 1.2) | 2.3 (T0: 1) | 4.1 (T0: 1.9) | 2.1 (T0: 1.1) | single copy |
| LBFLDI (n = 60) | 2.4 | 2.3 (T0: 0.8) | 2.3 (T0: 1) | 2.3 (T0: 0.9) | 4.4 (T0: 1.9) | 2.5 (T0: 1) | single copy |
| LBFPNF (n = 52) | 2 | 2 (T0: 1.2) | 4 (T0: 1.9) | 4.1 (T0: 1.7) | 5.6 (T0: 2.8) | 4.2 (T0: 1.9) | partial double copy |
| LBFNSQ (n = 51) | 3.9 | 3.7 (T0: 1.9) | 4.1 (T0: 1.9) | 3.8 (T0: 1.9) | 7.1 (T0: 3.1) | 2 (T0: 0.7) | partial double copy |
| LBFDGL (n = 57) | 4.1 | 3.8 (T0: 1.7) | 4 (T0: 1.9) | 3.8 (T0: 1.4) | 6.7 (T0: 2.9) | 1.8 (T0: 0.7) | partial double copy |
| LBFIEF (n = 6) | 4.1 | 3.6 (T0: 2.3) | 3.8 (T0: 2.6) | 3.7 (T0: 1.6) | 6.4 (T0: 3.5) | 2.1 (T0: 0.8) | partial double copy |
| LBFBAV (n = 50) | 3.9 | 4 (T0: 1.9) | 3.7 (T0: 2) | 4.1 (T0: 1.7) | 8.2 (T0: 3.7) | 6.3 (T0: 2.9) | partial double copy |
| LBFPNC (n = 32) | 3.8 | 3.8 (T0: 1.8) | 4.1 (T0: 1.8) | 4.2 (T0: 1.4) | 7.5 (T0: 3.4) | 4 (T0: 1.9) | partial double copy |
| LBFGHQ (n = 46) | 3.7 | 2.1 (T0: 1.1) | 2 (T0: 1.1) | 2 (T0: 1.1) | 6.1 (T0: 3.1) | 2 (T0: 1) | partial double copy |
| LBFAZB (n = 49) | 4 | 3.8 (T0: 1.7) | 4 (T0: 1.8) | 3.7 (T0: 1.3) | 6.6 (T0: 3.1) | 1.9 (T0: 0.6) | partial double copy |
| LBFGKW (n = 72) | 4 | 4 (T0: 1.7) | 3.6 (T0: 1.8) | 3.7 (T0: 1.5) | 7 (T0: 3.2) | 1.7 (T0: 0.6) | partial double copy |
| LBFNRU (n = 58) | 3.9 | 3.8 (T0: 1.7) | 4.2 (T0: 1.9) | 3.8 (T0: 1.6) | 7 (T0: 3.2) | 1.9 (T0: 0.8) | partial double copy |
| LBFGIZ (n = 43) | 3.9 | 3.8 (T0: 1.7) | 4.3 (T0: 1.5) | 3.8 (T0: 1.5) | 7 (T0: 2.8) | 1.9 (T0: 0.8) | partial double copy |
| LBFIGM (n = 56) | 3.8 | 3.8 (T0: 1.8) | 4.2 (T0: 2.2) | 4.1 (T0: 1.6) | 7.6 (T0: 2.8) | 1.9 (T0: 0.6) | partial double copy |
| LBFNRR (n = 61) | 4.1 | 3.9 (T0: 1.7) | 4.3 (T0: 1.6) | 3.9 (T0: 1.6) | 7.1 (T0: 2.8) | 1.9 (T0: 0.7) | partial double copy |
| LBFNTK (n = 69) | 4.1 | 3.8 (T0: 1.7) | 4.3 (T0: 1.9) | 4.1 (T0: 1.5) | 7.6 (T0: 2.9) | 1.9 (T0: 0.7) | partial double copy |

TABLE 135-continued

Copy number measurement of T1 plants cultivated in the greenhouse of canola events containing the T-DNAs of plasmids VC-LTM593-1qcz rc. The events are indicated in the first column, along with the number of T1 plants that where measured per event. The T1 plants underwent a selection from 250 segregating T1 seedlings, using zygocity analysis as illustrated in Table 137, keeping only plants that are homozygous for the desired number of loci (which are indicated in the last column of Table 137). A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result observed in the T0 generation (indicated in parentheses). For some events this was not the case because during selection of T1 plants, undesired loci have been segregated out while retaining only desired loci in a homozygous state.

| Event | | | | | | | |
|---|---|---|---|---|---|---|---|
| LBFGJA (n = 42) | 3.7 | 4.1 (T0: 1.9) | 3.9 (T0: 1.9) | 3.6 (T0: 1.9) | 7.6 (T0: 3.6) | 3.9 (T0: 2.1) | double copy |
| LBFIFV (n = 58) | 4 | 3.9 (T0: 2) | 4 (T0: 2.6) | 4.2 (T0: 1.8) | 7.7 (T0: 3.9) | 3.9 (T0: 2) | double copy |
| LBFLER (n = 52) | 4 | 4.1 (T0: 1.8) | 4.2 (T0: 2.3) | 4 (T0: 1.6) | 7.7 (T0: 3.3) | 3.8 (T0: 1.9) | double copy |
| LBFLDL (n = 44) | 4.1 | 4.1 (T0: 1.8) | 4.1 (T0: 2.1) | 3.9 (T0: 1.6) | 7.8 (T0: 3.5) | 3.8 (T0: 1.9) | double copy |
| LBFNQW (n = 51) | 4 | 4.2 (T0: 1.6) | 4.2 (T0: 2) | 3.9 (T0: 1.9) | 7.9 (T0: 3.4) | 3.9 (T0: 1.8) | double copy |
| LBFBAP (n = 19) | 3.8 | 5.7 (T0: 2.3) | 5.5 (T0: 2.3) | 5.7 (T0: 1.8) | 7.5 (T0: 2.8) | 4 (T0: 2.4) | partial triple copy |
| LBFDAU (n = 10) | 3.9 | 3.7 (T0: 1.8) | 3.9 (T0: 2.4) | 4.1 (T0: 1.7) | 7.3 (T0: 3.7) | 3.7 (T0: 1.9) | partial double copy |
| LBFPRA (n = 16) | 3.7 | 3.7 (T0: 2.4) | 3.9 (T0: 3.1) | 3.7 (T0: 2.3) | 7.4 (T0: 4.7) | 3.8 (T0: 2.8) | partial double copy |
| LBFIFU (n = 11) | 4.9 | 4.3 (T0: 2.3) | 4.2 | 4 (T0: 2.6) | 6.5 (T0: 4.2) | 3.8 (T0: 3) | partial double copy |
| LBFDKD (n = 2) | 3.6 | 3.8 (T0: 1.9) | 4.3 (T0: 2) | 4.3 (T0: 1.8) | 7.6 (T0: 3.4) | 4 (T0: 1.6) | double copy |
| LBFDJG (n = 12) | 3.9 | 4.1 (T0: 1.9) | 4.1 (T0: 2.2) | 3.7 (T0: 1.9) | 8 (T0: 3.6) | 4.5 (T0: 1.9) | double copy |
| LBFLFK (n = 15) | 3.8 | 3.8 (T0: 1.3) | 4.1 (T0: 2.4) | 3.9 (T0: 1.8) | 7.5 (T0: 5.2) | 4 (T0: 2) | double copy |
| LBFLCG (n = 15) | 3.9 | 3.7 (T0: 2) | 3.9 (T0: 2.5) | 5.6 (T0: 2.2) | 9 (T0: 5.1) | 3.9 (T0: 2) | double copy |
| LBFPQM (n = 12) | 3.8 | 3.8 (T0: 1.8) | 4 (T0: 2) | 4.2 (T0: 1.5) | 7.6 (T0: 3.7) | 4.1 (T0: 1.8) | double copy |
| LBFDHG (n = 5) | 3.6 | 3.8 (T0: 2) | 3.9 (T0: 2.3) | 3.9 (T0: 1.7) | 7.7 (T0: 3.3) | 3.9 (T0: 1.9) | double copy |
| LBFCYO (n = 0) | | (T0: 2) | (T0: 2.1) | (T0: 1.8) | (T0: 3) | (T0: 0.6) | partial double copy |
| LBFBAJ (n = 0) | | (T0: 2) | (T0: 2.5) | (T0: 1.8) | (T0: 4.8) | (T0: 2) | partial double copy |
| LBFDJI (n = 0) | | (T0: 1.5) | (T0: 2.5) | (T0: 2.1) | (T0: 3) | (T0: 1.7) | partial double copy |
| LBFGGO (n = 0) | | (T0: 2.1) | (T0: 2.1) | (T0: 2) | (T0: 2.6) | (T0: 1.9) | partial double copy |
| LBFLFP (n = 0) | | (T0: 1.8) | (T0: 2.1) | (T0: 1.7) | (T0: 3.5) | (T0: 1.7) | partial double copy |
| LBFNQV (n = 0) | | (T0: 1.7) | (T0: 2.3) | (T0: 1.7) | (T0: 2.7) | (T0: 2) | partial double copy |
| LBFNLT (n = 0) | | (T0: 1.8) | (T0: 2.2) | (T0: 1.8) | (T0: 3.3) | (T0: 1.9) | partial double copy |
| LBFLGC (n = 0) | | (T0: 3) | (T0: 2.6) | (T0: 2.2) | (T0: 2.5) | (T0: 1.8) | partial double copy |
| LBFLCW (n = 0) | | (T0: 1.5) | (T0: 2) | (T0: 1.6) | (T0: 3.6) | (T0: 1.5) | partial double copy |
| LBFZPJ (n = 0) | | (T0: 2.3) | (T0: 3) | (T0: 2.4) | (T0: 3.5) | (T0: 2.4) | partial double copy |
| LBFNSS (n = 0) | | (T0: 2.3) | (T0: 2.5) | (T0: 2) | (T0: 2.5) | (T0: 2) | partial double copy |
| LBGAOR (n = 0) | | (T0: 1.8) | (T0: 1.1) | (T0: 1) | (T0: 2.9) | (T0: 1.1) | partial double copy |
| LBFZOE (n = 0) | | (T0: 1.1) | (T0: 2.1) | (T0: 1.7) | (T0: 2.8) | (T0: 1.8) | partial double copy |
| LBFDJS (n = 0) | | (T0: 0.9) | (T0: 2.2) | (T0: 1.9) | (T0: 2.9) | (T0: 1.9) | partial double copy |
| LBFDKC (n = 0) | | (T0: 1.7) | (T0: 1.6) | (T0: 1.4) | (T0: 2.5) | (T0: 0.6) | partial double copy |
| LBFDKA (n = 5) | 5.7 | 5.7 (T0: 3.3) | 5.7 (T0: 3.9) | 5.9 (T0: 2.9) | 10.1 (T0: 5.6) | 5.7 (T0: 3.5) | partial triple copy |
| LBFLGH (n = 0) | | (T0: 2.5) | (T0: 3) | (T0: 2.1) | (T0: 2.9) | (T0: 2.5) | partial triple copy |
| LBFNUS (n = 0) | | (T0: 2.3) | (T0: 3.1) | (T0: 2.3) | (T0: 3.9) | (T0: 3.3) | partial triple copy |
| LBFLCH (n = 0) | | (T0: 2.3) | (T0: 5.3) | (T0: 3.3) | (T0: 5) | (T0: 3.4) | partial triple copy |
| LBFZMI (n = 0) | | (T0: 1.7) | (T0: 1.9) | (T0: 2.9) | (T0: 4.6) | (T0: 2.6) | partial triple copy |

TABLE 135-continued

Copy number measurement of T1 plants cultivated in the greenhouse of canola events containing the T-DNAs of plasmids VC-LTM593-1qcz rc. The events are indicated in the first column, along with the number of T1 plants that where measured per event. The T1 plants underwent a selection from 250 segregating T1 seedlings, using zygocity analysis as illustrated in Table 137, keeping only plants that are homozygous for the desired number of loci (which are indicated in the last column of Table 137). A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result observed in the T0 generation (indicated in parentheses). For some events this was not the case because during selection of T1 plants, undesired loci have been segregated out while retaining only desired loci in a homozygous state.

| | | | | | | | |
|---|---|---|---|---|---|---|---|
| LBFIDT (n = 7) | 4.3 | 4.3 (T0: 2.5) | 3.8 (T0: 3.8) | 4.2 (T0: 2.4) | 8.5 (T0: 4.5) | 3.9 (T0: 2.4) | partial triple copy |
| LBFAZW (n = 0) | | (T0: 2.5) | (T0: 3.3) | (T0: 2.4) | (T0: 4.5) | (T0: 2.5) | partial triple copy |
| LBFBBI (n = 0) | | (T0: 1.9) | (T0: 2.7) | (T0: 1.9) | (T0: 4.2) | (T0: 1.7) | partial triple copy |
| LBFAZW (n = 0) | | (T0: 2.5) | (T0: 3.3) | (T0: 2.4) | (T0: 4.5) | (T0: 2.5) | partial triple copy |

TABLE 136

Expected Mendelian segregation of the genotype in T1 seeds for some possible T-DNA insertion scenarios. Listed are the expected copy number segregation ratios for T1 seeds segregating for one or more unlinked genomic loci, which contain one or more linked copies of T-DNA insertions. sc: single copy, dc: double copy

| Locus configuration | Ratio of copy numbers (cn) expected T1 seed segregating for given locus configuration | | | | | | | | | | | | |
|---|---|---|---|---|---|---|---|---|---|---|---|---|---|
| | cn = 0 | cn = 1 | cn = 2 | cn = 3 | cn = 4 | cn = 5 | cn = 6 | cn = 7 | cn = 8 | cn = 9 | cn = 10 | cn = 11 | cn = 12 |
| 1 sc locus | 1 | 2 | 1 | | | | | | | | | | |
| 1 dc locus | 1 | | 2 | | 1 | | | | | | | | |
| 2 sc loci | 1 | 4 | 6 | 4 | 1 | | | | | | | | |
| 2 sc loci, 1 dc locus | 1 | 2 | 3 | 4 | 3 | 2 | 1 | | | | | | |
| 3 sc loci, 1 dc locus | 1 | 4 | 8 | 12 | 14 | 12 | 8 | 4 | 1 | | | | |

TABLE 137

Observed Medelian segregation of the genotype of T1 seeds of events from construct VC-LTM593-1qcz rc. The segregation has been analysed at three positions of the T-DNA. For each position, the number of seedlings have been counted that have a copy number (aritmetically rounded) of 0, 1, 2, 3, 4, 5, 6, 7, 8, 9, 10, 11, 12. The of seedlings counted for each copy number category are separated by colon, displaying the categories in the following order: 0 : 1 : 2 : 3 : 4 : 5 : 6 : 7 : 8 : 9 : 10 : 11 : 12. Listed are the observed copy number segregation ratios for T1 seeds segregating for one or more unlinked genomic loci, which contain one or more linked copies of T-DNA insertions. The observed frequencies for each assay have been compared against expected frequencies for various locus configurations listed in Table 136 using Chi-Square analysis. The last column displays the total number of loci that are segregating in the genome of a given event. Many events contain truncated insertions, as was evident when some assays indicate singl ecopy insertion at e.g. the left border (e.g. event LBFDAU, LPFPNC), while other positions on the T-DNA clearly indicate a double copy insertion that was either inserted in one locus (e.g. event LBFPNC), or in two loci (e.g. event LBFDAU)

| Event | Copy number ratios measured near the left border of the T-DNA using assay A1 | Copy number ratios measured using T-DNA internal assays targeting regions that had copy number results indicating truncated T-DNA insertions using assay A06, or A08, or A09, or A10 | Copy number ratios measured near the right border of the T-DNA using assay A12 | Most likely number of loci containing one or more T-DNA copies, tested using Chi-Square test |
|---|---|---|---|---|
| LBFDGG | 073 : 122 : 053 : 000 : 000 : 000 : 000 : 000 : 000 : 000 : 000 : 000 : 000 | A07 : 076 : 119 : 053 : 000 : 000 : 000 : 000 : 000 : 000 : 000 : 000 : 000 : 000 | 073 : 123 : 052 : 001 : 000 : 000 : 000 : 000 : 000 : 000 : 000 : 000 : 000 | one locus |
| LBFGKN | 057 : 131 : 059 : 001 : 000 : 000 : 000 : 000 : 000 : 000 : 000 : 000 : 000 | A07 : 057 : 130 : 059 : 001 : 000 : 000 : 000 : 000 : 000 : 000 : 000 : 000 : 000 | 057 : 130 : 060 : 000 : 000 : 000 : 000 : 000 : 000 : 000 : 000 : 000 : 000 | one locus |
| LBFIHE | 076 : 125 : 042 : 001 : 000 : 000 : 000 : 000 : 000 : 000 : 000 : 000 : 000 | A12 : 075 : 123 : 035 : 009 : 000 : 000 : 000 : 000 : 000 : 000 : 000 : 000 : 000 | 076 : 122 : 036 : 010 : 000 : 000 : 000 : 000 : 000 : 000 : 000 : 000 : 000 | one locus |

US 11,484,560 B2

TABLE 137-continued

Observed Medelian segregation of the genotype of T1 seeds of events from construct VC-LTM593-1qcz rc. The segregation has been analysed at three positions of the T-DNA. For each position, the number of seedlings have been counted that have a copy number (aritmetically rounded) of 0, 1, 2, 3, 4, 5, 6, 7, 8, 9, 10, 11, 12. The of seedlings counted for each copy number category are separated by colon, displaying the categories in the following order: 0 : 1 : 2 : 3 : 4 : 5 : 6 : 7 : 8 : 9 : 10 : 11 : 12. Listed are the observed copy number segregation ratios for T1 seeds segregating for one or more unlinked genomic loci, which contain one or more linked copies of T-DNA insertions. The observed frequencies for each assay have been compared against expected frequencies for various locus configurations listed in Table 136 using Chi-Square analysis. The last column displays the total number of loci that are segregating in the genome of a given event. Many events contain truncated insertions, as was evident when some assays indicate singl ecopy insertion at e.g. the left border (e.g. event LBFDAU, LPFPNC), while other positions on the T-DNA clearly indicate a double copy insertion that was either inserted in one locus (e.g. event LBFPNC), or in two loci (e.g. event LBFDAU)

| Event | Copy number ratios measured near the left border of the T-DNA using assay A1 | Copy number ratios measured using T-DNA internal assays targeting reagions that had copy number results indicating truncated T-DNA insertions using assay A06, or A08, or A09, or A10 | Copy number ratios measured near the right border of the T-DNA using assay A12 | Most likely number of loci containing one or more T-DNA copies, tested using Chi-Square test |
|---|---|---|---|---|
| LBFLDI | 068 : 101 : 059 : 018 : 003 : 000 : 000 : 000 : 000 : 000 : 000 : 000 : 000 | A12 : 075 : 094 : 062 : 015 : 002 : 000 : 000 : 000 : 000 : 000 : 000 : 000 : 000 | 068 : 106 : 053 : 018 : 002 : 001 : 000 : 000 : 000 : 000 : 000 : 000 : 000 | one locus |
| LBFPNF | 065 : 128 : 055 : 001 : 000 : 000 : 000 : 000 : 000 : 000 : 000 : 000 : 000 | A12 : 066 : 000 : 127 : 001 : 053 : 002 : 000 : 000 : 000 : 000 : 000 : 000 : 000 | 064 : 001 : 127 : 001 : 051 : 002 : 002 : 000 : 000 : 000 : 000 : 000 : 000 | one locus |
| LBFNSQ | 063 : 109 : 066 : 005 : 000 : 000 : 000 : 000 : 000 : 000 : 000 : 000 : 000 | A12 : 063 : 000 : 110 : 011 : 049 : 010 : 000 : 000 : 000 : 000 : 000 : 000 : 000 | 063 : 114 : 061 : 005 : 000 : 000 : 000 : 000 : 000 : 000 : 000 : 000 : 000 | one locus |
| LBFDGL | 072 : 113 : 062 : 001 : 000 : 000 : 000 : 000 : 000 : 000 : 000 : 000 : 000 | A12 : 072 : 000 : 108 : 007 : 061 : 000 : 001 : 000 : 000 : 000 : 000 : 000 : 000 | 073: 113 : 061 : 002 : 000 : 000 : 000 : 000 : 000 : 000 : 000 : 000 : 000 | one locus |
| LBFIEF | 042 : 000 : 018 : 020 : 013 : 002 : 004 : 000 : 001 : 000 : 000 : 000 : 000 | A12 : 042 : 000 : 025 : 015 : 012 : 005 : 000 : 001 : 000 : 000 : 000 : 000 : 000 | 041 : 032 : 020 : 005 : 001 : 000 : 000 : 000 : 000 : 000 : 000 : 000 : 000 | one locus |
| LBFBAV | 068 : 128 : 053 : 000 : 000 : 000 : 000 : 000 : 000 : 000 : 000 : 000 : 000 | A04 : 068 : 000 : 128 : 000 : 053 : 000 : 000 : 000 : 000 : 000 : 000 : 000 : 000 | 068 : 000 : 000 : 122 : 006 : 000 : 044 : 009 : 000 : 000 : 000 : 000 : 000 | one locus |
| LBFPNC | 043 : 074 : 035 : 001 : 000 : 000 : 000 : 000 : 000 : 000 : 000 : 000 : 000 | A12 : 043 : 002 : 072 : 001 : 034 : 001 : 000 : 000 : 000 : 000 : 000 : 000 : 000 | 043 : 000 : 074 : 001 : 034 : 000 : 001 : 000 : 000 : 000 : 000 : 000 : 000 | one locus |
| LBFGHQ | 067 : 000 : 113 : 007 : 051 : 001 : 000 : 000 : 001 : 000 : 000 : 000 : 000 | A12 : 065 : 110 : 057 : 001 : 000 : 000 : 000 : 000 : 000 : 000 : 000 : 000 : 000 | 066 : 104 : 059 : 003 : 003 : 001 : 000 : 000 : 000 : 000 : 000 : 000 : 000 | one locus |
| LBFAZB | 078 : 001 : 158 : 002 : 055 : 001 : 000 : 000 : 001 : 000 : 000 : 000 : 000 | A12 : 078 : 001 : 151 : 008 : 055 : 002 : 001 : 000 : 000 : 000 : 000 : 000 : 000 | 078 : 161 : 054 : 003 : 000 : 000 : 000 : 000 : 000 : 000 : 000 : 000 : 000 | one locus |
| LBFGKW | 047 : 000 : 124 : 007 : 070 : 000 : 001 : 000 : 000 : 000 : 000 : 000 : 000 | A13 : 047 : 000 : 124 : 012 : 065 : 000 : 000 : 000 : 000 : 000 : 000 : 000 : 000 | 047 : 129 : 073 : 000 : 000 : 000 : 000 : 000 : 000 : 000 : 000 : 000 : 000 | one locus |
| LBFNRU | 070 : 000 : 120 : 003 : 056 : 000 : 000 : 000 : 000 : 000 : 000 : 000 : 000 | A11 : 069 : 000 : 121 : 001 : 056 : 001 : 000 : 000 : 000 : 000 : 000 : 000 : 000 | 070 : 121 : 058 : 000 : 000 : 000 : 000 : 000 : 000 : 000 : 000 : 000 : 000 | one locus |
| LBFGIZ | 073 : 000 : 108 : 001 : 045 : 004 : 000 : 000 : 000 : 000 : 000 : 000 : 000 | A11 : 073 : 000 : 108 : 002 : 044 : 004 : 000 : 000 : 000 : 000 : 000 : 000 : 000 | 072 : 109 : 048 : 001 : 000 : 000 : 000 : 000 : 000 : 000 : 000 : 000 : 000 | one locus |
| LBFIGM | 055 : 000 : 133 : 004 : 056 : 000 : 001 : 000 : 000 : 000 : 000 : 000 : 000 | A04 : 054 : 000 : 133 : 004 : 056 : 001 : 000 : 000 : 000 : 000 : 000 : 000 : 000 | 055 : 137 : 057 : 000 : 000 : 000 : 000 : 000 : 000 : 000 : 000 : 000 : 000 | one locus |
| LBFNRR | 070 : 000 : 116 : 004 : 057 : 000 : 000 : 000 : 001 : 000 : 000 : 000 : 000 | A11 : 070 : 000 : 115 : 001 : 062 : 000 : 000 : 000 : 000 : 000 : 000 : 000 : 000 | 070 : 117 : 061 : 000 : 000 : 000 : 000 : 000 : 000 : 000 : 000 : 000 : 000 | one locus |
| LBFNTK | 054 : 003 : 119 : 005 : 063 : 004 : 000 : 000 : 000 : 000 : 000 : 000 : 000 | A04 : 053 : 003 : 115 : 003 : 070 : 002 : 000 : 000 : 000 : 000 : 000 : 000 : 000 | 053 : 122 : 072 : 000 : 000 : 000 : 000 : 000 : 000 : 000 : 000 : 000 : 000 | one locus |
| LBFGJA | 088 : 000 : 111 : 006 : 041 : 000 : 000 : 000 : 000 : 000 : 000 : 000 : 000 | A12 : 088 : 002 : 111 : 003 : 041 : 000 : 000 : 000 : 000 : 000 : 000 : 000 : 000 | 089 : 001 : 113 : 003 : 039 : 001 : 000 : 000 : 000 : 000 : 000 : 000 : 000 | one locus |
| LBFIFV | 070 : 000 : 119 : 000 : 056 : 002 : 000 : 000 : 000 : 000 : 000 : 000 : 000 | A04 : 070 : 119 : 057 : 001 : 000 : 000 : 000 : 000 : 000 : 000 : 000 : 000 : 000 | 070 : 000 : 119 : 000 : 056 : 001 : 001 : 000 : 000 : 000 : 000 : 000 : 000 | one locus |
| LBFLER | 073 : 000 : 123 : 002 : 051 : 000 : 000 : 000 : 000 : 000 : 000 : 000 : 000 | A13 : 074 : 000 : 121 :002 : 050 : 001 : 000 : 000 : 000 : 000 : 000 : 000 : 000 | 073 : 000 : 123 : 002 : 051 : 000 : 000 : 000 : 000 : 000 : 000 : 000 : 000 | one locus |

TABLE 137-continued

Observed Medelian segregation of the genotype of T1 seeds of events from construct VC-LTM593-1qcz rc. The segregation has been analysed at three positions of the T-DNA. For each position, the number of seedlings have been counted that have a copy number (aritmetically rounded) of 0, 1, 2, 3, 4, 5, 6, 7, 8, 9, 10, 11, 12. The of seedlings counted for each copy number category are separated by colon, displaying the categories in the following order: 0 : 1 : 2 : 3 : 4 : 5 : 6 : 7 : 8 : 9 : 10 : 11 : 12. Listed are the observed copy number segregation ratios for T1 seeds segregating for one or more unlinked genomic loci, which contain one or more linked copies of T-DNA insertions. The observed frequencies for each assay have been compared against expected frequencies for various locus configurations listed in Table 136 using Chi-Square analysis. The last column displays the total number of loci that are segregating in the genome of a given event. Many events contain truncated insertions, as was evident when some assays indicate singl ecopy insertion at e.g. the left border (e.g. event LBFDAU, LPFPNC), while other positions on the T-DNA clearly indicate a double copy insertion that was either inserted in one locus (e.g. event LBFPNC), or in two loci (e.g. event LBFDAU)

| Event | Copy number ratios measured near the left border of the T-DNA using assay A1 | Copy number ratios measured using T-DNA internal assays targeting reagions that had copy number results indicating truncated T-DNA insertions using assay A06, or A08, or A09, or A10 | Copy number ratios measured near the right border of the T-DNA using assay A12 | Most likely number of loci containing one or more T-DNA copies, tested using Chi-Square test |
|---|---|---|---|---|
| LBFLDL | 069 : 000 : 129 : 008 : 043 : 000 : 000 : 000 : 000 : 000 : 000 : 000 : 000 | A13 : 069 : 000 : 130 : 002 : 045 : 001 : 000 : 000 : 000 : 000 : 000 : 000 : 000 | 068 : 000 : 130 : 006 : 041 : 001 :001 :0 00 : 000 : 000 : 000 : 000 : 000 | one locus |
| LBFNQW | 070 : 001 : 123 : 007 : 045 : 002 : 000 : 000 : 000 : 000 : 000 : 000 : 000 | A13 : 070 : 000 : 123 : 001 : 053 : 001 : 000 : 000 : 000 : 000 : 000 : 000 : 000 | 070 : 001 : 122 : 005 : 047 : 003 : 000 : 000 : 000 : 000 : 000 : 000 : 000 | one locus |
| LBFBAP | 059 : 123 : 064 : 001 : 001 : 000 : 000 : 000 : 000 : 000 : 000 : 000 : 000 | A07 : 059 : 001 : 123 : 015 : 049 : 001 : 000 : 000 : 000 : 000 : 000 : 000 : 000 | 009 : 037 : 068 : 057 : 051 : 022 : 002 : 000 : 000 : 000 : 000 : 000 : 000 | double locus, isolation of one locus |
| LBFDAU | 059 : 123 : 062 : 000 : 000 : 000 : 000 : 000 : 000 : 000 : 000 : 000 : 000 | A12 : 013 : 069 : 090 : 062 : 010 : 000 : 000 : 000 : 000 : 000 : 000 : 000 : 000 | 013 : 072 : 087 : 062 : 010 : 000 : 000 : 000 : 000 : 000 : 000 : 000 : 000 | double locus |
| LBFPRA | 024 : 075 : 087 : 057 : 005 : 000 : 000 : 000 : 000 : 000 : 000 : 000 : 000 | A12 : 024 : 041 : 060 : 058 : 052 : 012 : 001 : 000 : 000 : 000 : 000 : 000 : 000 | 024 : 041 : 060 : 051 : 049 : 022 : 001 : 000 : 000 : 000 : 000 : 000 : 000 | double locus, isolation of one locus |
| LBFIFU | 019: 075 : 105 : 034 : 013 : 000 : 000 : 000 : 000 : 000 : 000 : 000 : 000 | A13 : 019 : 040 : 060 : 067 : 044 : 013 : 003 : 000 : 000 : 000 : 000 : 000 : 000 | 019 : 040 : 060 : 072 : 039 : 013 : 003 : 000 : 000 : 000 : 000 : 000 : 000 | double locus, isolation of one locus |
| LBFDKD | 007 : 031 : 045 : 018 : 002 : 000 : 000 : 000 : 000 : 000 : 000 : 000 : 000 | A07 : 007 : 031 : 046 : 017 : 002 : 000 : 000 : 000 : 000 : 000 : 000 : 000 : 000 | 007 : 031 : 044 : 017 : 003 : 000 : 000 : 000 : 000 : 000 : 000 : 000 : 000 | double locus |
| LBFDJG | 026 : 078 : 088 : 036 : 014 : 000 : 000 : 000 : 000 : 000 : 000 : 000 : 000 | A12 : 029 : 072 : 085 : 035 : 017 : 001 : 000 : 000 : 000 : 000 : 000 : 000 : 000 | 026 : 076 : 077 : 037 : 022 : 004 : 001 : 000 : 000 : 000 : 000 : 000 : 000 | double locus |
| LBFLFK | 018 : 062 : 096 : 058 : 015 : 000 : 000 : 000 : 000 : 000 : 000 : 000 : 000 | A11 : 018 : 061 : 096 : 059 : 015 : 000 : 000 : 000 : 000 : 000 : 000 : 000 : 000 | 018 : 061 : 098 : 057 : 015 : 000 : 000 : 000 : 000 : 000 : 000 : 000 : 000 | double locus |
| LBFLCG | 015 : 059 : 087 : 068 : 015 : 000 : 000 : 000 : 000 : 000 : 000 : 000 : 000 | A12 : 016 : 058 : 087 : 067 : 016 : 000 : 000 : 000 : 000 : 000 : 000 : 000 : 000 | 016 : 056 : 090 : 065 : 015 : 000 : 000 : 000 : 000 : 000 : 000 : 000 : 000 | double locus |
| LBFPQM | 008 : 058 : 094 : 060 : 014 : 000 : 000 : 000 : 000 : 000 : 000 : 000 : 000 | A12 : 008 : 058 : 094 : 062 : 012 : 000 : 000 : 000 : 000 : 000 : 000 : 000 : 000 | 008 : 058 : 095 : 061 : 012 : 000 : 000 : 000 : 000 : 000 : 000 : 000 : 000 | double locus |
| LBFDHG | 022 : 064 : 084 : 037 : 004 : 001 : 000 : 000 : 000 : 000 : 000 : 000 : 000 | A07 : 023 : 062 : 090 : 033 : 005 : 000 : 000 : 000 : 000 : 000 : 000 : 000 : 000 | 023 : 063 : 089 : 037 : 005 : 000 : 000 : 000 : 000 : 000 : 000 : 000 : 000 | double locus |
| LBFCYO | 091 : 001 : 002 : 013 : 090 : 001 : 006 : 031 : 001 : 000 : 000 : 000 : 000 | A14 : 059 : 126 : 051 : 000 : 000 : 000 : 000 : 000 : 000 : 000 : 000 : 000 : 000 | 059 : 126 : 051 : 000 : 000 : 000 : 000 : 000 : 000 : 000 : 000 : 000 : 000 | double locus |

TABLE 137-continued

Observed Medelian segregation of the genotype of T1 seeds of events from construct VC-LTM593-1qcz rc. The segregation has been analysed at three positions of the T-DNA. For each position, the number of seedlings have been counted that have a copy number (aritmetically rounded) of 0, 1, 2, 3, 4, 5, 6, 7, 8, 9, 10, 11, 12. The of seedlings counted for each copy number category are separated by colon, displaying the categories in the following order: 0 : 1 : 2 : 3 : 4 : 5 : 6 : 7 : 8 : 9 : 10 : 11 : 12. Listed are the observed copy number segregation ratios for T1 seeds segregating for one or more unlinked genomic loci, which contain one or more linked copies of T-DNA insertions. The observed frequencies for each assay have been compared against expected frequencies for various locus configurations listed in Table 136 using Chi-Square analysis. The last column displays the total number of loci that are segregating in the genome of a given event. Many events contain truncated insertions, as was evident when some assays indicate singl ecopy insertion at e.g. the left border (e.g. event LBFDAU, LPFPNC), while other positions on the T-DNA clearly indicate a double copy insertion that was either inserted in one locus (e.g. event LBFPNC), or in two loci (e.g. event LBFDAU)

| Event | Copy number ratios measured near the left border of the T-DNA using assay A1 | Copy number ratios measured using T-DNA internal assays targeting reagions that had copy number results indicating truncated T-DNA insertions using assay A06, or A08, or A09, or A10 | Copy number ratios measured near the right border of the T-DNA using assay A12 | Most likely number of loci containing one or more T-DNA copies, tested using Chi-Square test |
|---|---|---|---|---|
| LBFBAJ | 056 : 140 : 048 : 000 : 000 : 000 : 000 : 000 : 000 : 000 : 000 : 000 : 000 | A12 : 017 : 056 : 093 : 064 : 014 : 000 : 000 : 000 : 000 : 000 : 000 : 000 | 016 : 056 : 091 : 032 : 043 : 005 : 000 : 000 : 000 : 000 : 000 : 000 : 000 | double locus |
| LBFDJI | 151 : 285 : 171 : 003 : 000 : 000 : 000 : 000 : 000 : 000 : 000 : 000 : 000 | A12 : 051 : 073 : 118 : 157 : 149 : 036 : 023 : 002 : 001 : 000 : 000 : 000 | 049 : 152 : 228 : 129 : 041 : 003 : 000 : 000 : 000 : 000 : 000 : 000 : 000 | double locus |
| LBFGGO | 017 : 034 : 030 : 000 : 000 : 000 : 000 : 000 : 000 : 000 : 000 : 000 : 000 | A12 : 009 : 011 : 030 : 023 : 008 : 000 : 000 : 000 : 000 : 000 : 000 : 000 | 009 : 011 : 031 : 023 : 007 : 000 : 000 : 000 : 000 : 000 : 000 : 000 : 000 | double locus |
| LBFLFP | 047 : 094 : 053 : 001 : 000 : 000 : 000 : 000 : 000 : 000 : 000 : 000 : 000 | A04 : 046 : 092 : 056 : 001 : 000 : 000 : 000 : 000 : 000 : 000 : 000 : 000 | 010 : 038 : 069 : 049 : 027 : 001 : 001 : 000 : 000 : 000 : 000 : 000 : 000 | double locus |
| LBFNQV | 174 : 289 :138 : 000 : 000 : 000 : 000 : 000 : 000 : 000 : 000 : 000 : 000 | A04 : 174 : 286 : 138 : 002 : 000 : 000 : 000 : 000 : 000 : 000 : 000 : 000 | 049 : 163 : 210 : 126 : 048 : 003 : 000 : 000 : 000 : 000 : 000 : 000 : 000 | double locus |
| LBFNLT | 149 : 279 : 145 : 010 : 000 : 000 : 000 : 000 : 000 : 000 : 000 : 000 : 000 | A07 : 015 : 067 : 130 : 063 : 033 : 001 : 000 : 000 : 000 : 000 : 000 : 000 | 029 : 146 : 214 : 136 : 055 : 007 : 000 : 000 : 000 : 000 : 000 : 000 : 000 | double locus |
| LBFLGC | 064 : 121 : 057 : 005 : 002 : 000 : 000 : 000 : 000 : 000 : 000 : 000 : 000 | A12 : 013 : 034 : 059 : 060 : 049 : 026 : 006 : 000 : 002 : 000 : 000 : 000 | 013 : 068 : 112 : 048 : 008 : 000 : 000 : 000 : 000 : 000 : 000 : 000 : 000 | double locus |
| LBFLCW | 207 : 283 : 098 : 003 : 000 : 000 : 000 : 000 : 000 : 000 : 000 : 000 : 000 | A12 : 065 : 152 : 224 : 131 : 018 : 001 : 000 : 000 : 000 : 000 : 000 : 000 | 064 : 156 : 232 : 110 : 022 : 001 : 000 : 000 : 000 : 000 : 000 : 000 : 000 | double locus |
| LBFZPJ | 060 : 000 : 129 : 000 : 059 : 000 : 001 : 000 : 000 : 000 : 000 : 000 : 000 | A12 : 013 : 032 : 042 : 066 : 059 : 029 : 008 : 000 : 000 : 000 : 000 : 000 | 013 : 032 : 044 : 065 : 049 : 036 : 010 : 000 : 000 : 000 : 000 : 000 : 000 | double locus |
| LBFNSS | 155 : 359 : 142 : 000 : 000 : 000 : 000 : 000 : 000 : 000 : 000 : 000 : 000 | A12 : 044 : 094 : 127 : 183 : 113 : 058 : 033 : 003 : 002 : 000 : 000 : 000 | 042 : 163 : 268 : 141 : 039 : 003 : 001 : 000 : 000 : 000 : 000 : 000 : 000 | double locus |
| LBGAOR | 149 : 302 : 144 : 000 : 000 : 000 : 000 : 000 : 000 : 000 : 000 : 000 : 000 | A04 : 040 : 158 : 274 : 103 : 019 : 000 : 000 : 000 : 000 : 000 : 000 : 000 | 161 : 310 : 120 : 003 : 000 : 000 : 000 : 000 : 000 : 000 : 000 : 000 : 000 | double locus |
| LBFZOE | 026 : 060 : 035 : 000 : 000 : 000 : 000 : 000 : 000 : 000 : 000 : 000 : 000 | A12 : 010 : 025 : 051 : 026 : 008 : 002 : 000 : 000 : 000 : 000 : 000 : 000 | 010 : 025 : 049 : 031 : 006 : 000 : 000 : 000 : 000 : 000 : 000 : 000 : 000 | double locus |
| LBFDJS | 048 : 131 : 060 : 001 : 000 : 000 : 000 : 000 : 000 : 000 : 000 : 000 : 000 | A12 : 008 : 043 : 090 : 074 : 026 : 000 : 000 : 000 : 000 : 000 : 000 : 000 | 008 : 043 : 089 : 075 : 025 : 000 : 000 : 000 : 000 : 000 : 000 : 000 : 000 | double locus |
| LBFDKC | 001 : 109 : 133 : 001 : 000 : 000 : 000 : 000 : 000 : 000 : 000 : 000 : 000 | A07 : 001 : 000 : 109 : 008 : 126 : 001 : 000 : 000 : 000 : 000 : 000 : 000 | 001 : 108 : 132 : 004 : 000 : 000 : 000 : 000 : 000 : 000 : 000 : 000 : 000 | no wildtypes |
| LBFDKA | 015 : 072 : 101 : 052 : 008 : 000 : 000 : 000 : 000 : 000 : 000 : 000 : 000 | A12 : 001 : 012 : 041 : 054 : 076 : 045 : 018 : 001 : 000 : 000 : 000 : 000 | 001 : 012 : 041 : 053 : 069 : 050 : 019 : 003 : 000 : 000 : 000 : 000 : 000 | triple locus |
| LBFLGH | 061 : 137 : 051 : 000 : 000 : 000 : 000 : 000 : 000 : 000 : 000 : 000 : 000 | A12 : 015 : 034 : 052 : 068 : 039 : 026 : 012 : 002 : 001 : 000 : 000 : 000 | 014 : 033 : 053 : 060 : 045 : 030 : 012 : 001 : 000 : 000 : 000 : 000 : 000 | triple locus |
| LBFNUS | 054 : 137 : 058 : 000 : 000 : 000 : 000 : 000 : 000 : 000 : 000 : 000 : 000 | A12 : 003 : 016 : 048 : 054 : 034 : 008 : 003 : 000 : 000 : 000 : 000 : 000 | 004 : 020 : 071 : 081 : 060 : 010 : 003 : 000 : 000 : 000 : 000 : 000 : 000 | triple locus |
| LBFLCH | 019 : 077 : 090 : 052 : 011 : 000 : 000 : 000 : 000 : 000 : 000 : 000 : 000 | A12 : 019 : 039 : 013 : 006 : 050 : 050 : 021 : 008 : 019 : 013 : 009 : 002 : 000 | 019 : 039 : 013 : 041 : 063 : 027 : 026 : 013 : 007 : 000 : 000 : 000 : 000 | triple locus |

TABLE 137-continued

Observed Medelian segregation of the genotype of T1 seeds of events from construct VC-LTM593-1qcz rc. The segregation has been analysed at three positions of the T-DNA. For each position, the number of seedlings have been counted that have a copy number (aritmetically rounded) of 0, 1, 2, 3, 4, 5, 6, 7, 8, 9, 10, 11, 12. The of seedlings counted for each copy number category are separated by colon, displaying the categories in the following order: 0 : 1 : 2 : 3 : 4 : 5 : 6 : 7 : 8 : 9 : 10 : 11 : 12. Listed are the observed copy number segregation ratios for T1 seeds segregating for one or more unlinked genomic loci, which contain one or more linked copies of T-DNA insertions. The observed frequencies for each assay have been compared against expected frequencies for various locus configurations listed in Table 136 using Chi-Square analysis. The last column displays the total number of loci that are segregating in the genome of a given event. Many events contain truncated insertions, as was evident when some assays indicate singl ecopy insertion at e.g. the left border (e.g. event LBFDAU, LPFPNC), while other positions on the T-DNA clearly indicate a double copy insertion that was either inserted in one locus (e.g. event LBFPNC), or in two loci (e.g. event LBFDAU)

| Event | Copy number ratios measured near the left border of the T-DNA using assay A1 | Copy number ratios measured using T-DNA internal assays targeting reagions that had copy number results indicating truncated T-DNA insertions using assay A06, or A08, or A09, or A10 | Copy number ratios measured near the right border of the T-DNA using assay A12 | Most likely number of loci containing one or more T-DNA copies, tested using Chi-Square test |
|---|---|---|---|---|
| LBFZMI | 017 : 016 : 036 : 038 : 023 : 027 : 005 : 000 : 000 : 000 : 000 : 000 : 000 | A12 : 017 : 043 : 061 : 033 : 008 : 000 : 000 : 000 : 000 : 000 : 000 : 000 | 007 : 015 : 039 : 051 : 034 : 014 : 002 : 000 : 000 : 000 : 000 : 000 : 000 | triple locus |
| LBFIDT | 069 : 000 : 131 : 000 : 045 : 001 : 000 : 000 : 000 : 000 : 000 : 000 : 000 | A12 : 015 : 033 : 058 : 064 : 048 : 015 : 012 : 002 : 000 : 000 : 000 : 000 | 003 : 018 : 050 : 056 : 061 : 031 : 019 : 008 : 000 : 000 : 000 : 000 : 000 | triple locus, isolation of one locus |
| LBFAZW | 013 : 065 : 109 : 041 : 006 : 000 : 000 : 000 : 000 : 000 : 000 : 000 : 000 | A12 : 004 : 021 : 073 : 086 : 040 : 010 : 001 : 000 : 000 : 000 : 000 : 000 | 003 : 018 : 069 : 079 : 048 : 013 : 002 : 000 : 001 : 000 : 000 : 000 : 000 | trippel locus |
| LBFBBI | 005 : 057 : 139 : 040 : 004 : 000 : 000 : 000 : 000 : 000 : 000 : 000 : 000 | A12 : 009 : 030 : 074 : 066 : 051 : 014 : 001 : 000 : 000 : 000 : 000 : 000 | 005 : 065 : 127 : 044 : 004 : 000 : 000 : 000 : 000 : 000 : 000 : 000 : 000 | trippel locus |
| LBFAZW | 013 : 065 : 109 : 041 : 006 : 000 : 000 : 000 : 000 : 000 : 000 : 000 : 000 | A12 : 004 : 021 : 073 : 086 : 040 : 010 : 001 : 000 : 000 : 000 : 000 : 000 | 003 : 018 : 069 : 079 : 048 : 013 : 002 : 000 : 001 : 000 : 000 : 000 : 000 | trippel locus |

TABLE 138

Fatty acid profiles of T2 seeds harvested from T1 cultivated in the greenhouse of canola events containing the T-DNAs of plasmids VC-LTM593-1qcz rc. The events are indicated in the first column, along with the number of T2 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LBFDGG (n = 50) | 4.8 ± 0.2 | 0.2 ± 0 | 0 ± 0 | 2.9 ± 0.3 | 28.3 ± 1.5 | 35.6 ± 1 | 0.8 ± 0.1 | 4.5 ± 0.3 | 1.9 ± 0.2 | 0.4 ± 0.1 | 0.8 ± 0.1 | 0.7 ± 0 | 0.1 ± 0 | 0.1 ± 0 |
| LBFGKN (n = 50) | 4.6 ± 0.3 | 0.1 ± 0 | 0 ± 0 | 3 ± 0.2 | 28.3 ± 1.6 | 35.2 ± 0.7 | 1 ± 0.1 | 4.6 ± 0.3 | 2 ± 0.3 | 0.5 ± 0.2 | 0.8 ± 0 | 0.7 ± 0 | 0.2 ± 0 | 0.1 ± 0 |
| LBFIHE (n = 34) | 5.4 ± 0.9 | 0.2 ± 0.1 | 0 ± 0 | 3.1 ± 0.4 | 26.6 ± 2.1 | 34.7 ± 1.4 | 0.9 ± 0.2 | 3.9 ± 0.4 | 2.6 ± 0.9 | 0.3 ± 0.1 | 1 ± 0.1 | 0.9 ± 0.1 | 0.2 ± 0.1 | 0.1 ± 0 |
| LBFLDI (n = 60) | 6.6 ± 1.2 | 0.3 ± 0.1 | 0 ± 0 | 2.2 ± 0.2 | 31.1 ± 3.3 | 30 ± 1.9 | 0.7 ± 0.2 | 6 ± 0.6 | 1.1 ± 0.3 | 0.2 ± 0.1 | 0.8 ± 0.1 | 0.8 ± 0.1 | 0.4 ± 0.3 | 0.2 ± 0.1 |
| LBFPNF (n = 52) | 5 ± 0.2 | 0.2 ± 0 | 0 ± 0 | 2.5 ± 0.2 | 30.5 ± 1.3 | 27.8 ± 1.1 | 1.8 ± 0.2 | 4.5 ± 0.4 | 2.9 ± 0.3 | 0.4 ± 0.1 | 0.8 ± 0.1 | 0.7 ± 0.1 | 0.1 ± 0 | 0 ± 0 |
| LBFNSQ (n = 51) | 5 ± 0.4 | 0.1 ± 0 | 0 ± 0 | 2.7 ± 0.5 | 26.9 ± 1.6 | 35.7 ± 1.9 | 0.8 ± 0.2 | 5.4 ± 0.6 | 1.5 ± 0.2 | 0.3 ± 0.1 | 0.8 ± 0.1 | 0.4 ± 0.4 | 0.2 ± 0.1 | 0.1 ± 0 |
| LBFDGL (n = 57) | 4.9 ± 0.1 | 0.1 ± 0 | 0 ± 0 | 3 ± 0.4 | 26.9 ± 2.2 | 36.3 ± 1.9 | 0.6 ± 0.2 | 5.8 ± 0.7 | 1.5 ± 0.8 | 0.3 ± 0.1 | 0.8 ± 0.1 | 0.7 ± 0 | 0.2 ± 0 | 0.1 ± 0 |
| LBFIEF (n = 6) | 5 ± 0.2 | 0.1 ± 0 | 0 ± 0 | 3.4 ± 0.4 | 27.6 ± 2.9 | 36.2 ± 2.1 | 0.6 ± 0.1 | 5.7 ± 0.5 | 1.5 ± 0.2 | 0.4 ± 0.2 | 1 ± 0.1 | 0.7 ± 0 | 0.2 ± 0 | 0.1 ± 0.1 |
| LBFBAV (n = 50) | 5.1 ± 0.2 | 0.2 ± 0 | 0 ± 0 | 2.6 ± 0.3 | 29.5 ± 1.3 | 27.2 ± 1.4 | 1.6 ± 0.2 | 5.3 ± 0.3 | 1.6 ± 0.1 | 0.3 ± 0 | 0.8 ± 0.2 | 0.7 ± 0 | 0.1 ± 0 | 0.1 ± 0.1 |
| LBFPNC (n = 32) | 4.8 ± 0.3 | 0.1 ± 0 | 0 ± 0 | 3.9 ± 0.7 | 26.7 ± 1.7 | 35.6 ± 1 | 0.8 ± 0.1 | 3.3 ± 0.5 | 1.7 ± 0.3 | 0.2 ± 0.1 | 1.1 ± 0.2 | 0.7 ± 0 | 0.2 ± 0 | 0 ± 0 |
| LBFGHQ (n = 46) | 5.1 ± 0.2 | 0.1 ± 0.1 | 0 ± 0 | 2.4 ± 0.1 | 30.7 ± 1.3 | 35 ± 1.7 | 0.5 ± 0.1 | 7.7 ± 0.6 | 1.3 ± 0.2 | 0.4 ± 0.1 | 0.9 ± 0.3 | 0.8 ± 0.1 | 0.1 ± 0 | 0.1 ± 0 |
| LBFAZB (n = 49) | 4.9 ± 0.1 | 0.1 ± 0 | 0 ± 0 | 3.1 ± 0.2 | 28.4 ± 1.6 | 34.1 ± 1.1 | 1 ± 0.1 | 4.7 ± 0.4 | 1.9 ± 0.3 | 0.3 ± 0.1 | 0.8 ± 0.1 | 0.6 ± 0.1 | 0.1 ± 0.1 | 0.1 ± 0 |

TABLE 138-continued

Fatty acid profiles of T2 seeds harvested from T1 cultivated in the greenhouse of canola events containing the T-DNAs of plasmids VC-LTM593-1qcz rc. The events are indicated in the first column, along with the number of T2 seed batches that were measured per event. Per seed batch a random selection of ~30 seed was measured in two technical repeats.

| | | | | | | | | | | | | | | |
|---|---|---|---|---|---|---|---|---|---|---|---|---|---|---|
| LBFGKW (n = 72) | 5.1 ± 0.2 | 0.2 ± 0 | 0 ± 0 | 2.5 ± 0.2 | 30.1 ± 1.3 | 32.1 ± 1.6 | 1.1 ± 0.1 | 6.1 ± 0.4 | 1.7 ± 0.3 | 0.2 ± 0.1 | 0.8 ± 0.1 | 0.7 ± 0 | 0.1 ± 0 | 0.1 ± 0 |
| LBFNRU (n = 58) | 5 ± 0.2 | 0.2 ± 0 | 0 ± 0 | 2.6 ± 0.2 | 31.8 ± 2.5 | 29.2 ± 1.9 | 1 ± 0.1 | 7.1 ± 0.5 | 1.2 ± 0.2 | 0.2 ± 0 | 0.8 ± 0.1 | 0.8 ± 0 | 0.1 ± 0 | 0.1 ± 0 |
| LBFGIZ (n = 43) | 4.9 ± 0.6 | 0.2 ± 0.1 | 0 ± 0 | 2.6 ± 0.4 | 30.5 ± 3 | 30 ± 2.6 | 1 ± 0.2 | 6.2 ± 0.8 | 1.3 ± 0.2 | 0.2 ± 0 | 0.8 ± 0.1 | 0.7 ± 0.1 | 0.2 ± 0 | 0.2 ± 0 |
| LBFIGM (n = 56) | 4.8 ± 0.4 | 0.2 ± 0 | 0 ± 0 | 2.3 ± 0.2 | 31.9 ± 2.7 | 30.6 ± 2.7 | 1 ± 0.1 | 6.3 ± 0.7 | 1.3 ± 0.2 | 0.2 ± 0 | 0.7 ± 0.1 | 0.8 ± 0.1 | 0.1 ± 0 | 0.1 ± 0 |
| LBFNRR (n = 61) | 5 ± 0.2 | 0.2 ± 0 | 0 ± 0 | 2.8 ± 0.4 | 31.4 ± 1.5 | 30 ± 2.1 | 1.1 ± 0.1 | 7 ± 0.6 | 1.3 ± 0.2 | 0.3 ± 0 | 0.9 ± 0.1 | 0.8 ± 0.1 | 0.1 ± 0 | 0.1 ± 0 |
| LBFNTK (n = 69) | 5.1 ± 0.4 | 0.2 ± 0 | 0 ± 0 | 2.5 ± 0.2 | 29.6 ± 1.4 | 29 ± 1.8 | 1.3 ± 0.2 | 6.4 ± 0.6 | 1.5 ± 0.3 | 0.1 ± 0 | 0.8 ± 0.1 | 0.8 ± 0 | 0.1 ± 0 | 0.1 ± 0 |
| LBFGJA (n = 42) | 5.2 ± 0.2 | 0.2 ± 0 | 0 ± 0 | 3.1 ± 0.2 | 27.7 ± 0.8 | 34.5 ± 0.8 | 1.9 ± 0.2 | 3.3 ± 0.2 | 5.8 ± 0.9 | 0.5 ± 0.2 | 0.8 ± 0 | 0.7 ± 0.1 | 0.1 ± 0 | 0.1 ± 0 |
| LBFIFV (n = 58) | 4.8 ± 0.4 | 0.1 ± 0 | 0 ± 0 | 3.2 ± 0.3 | 27.6 ± 1.5 | 37.3 ± 0.9 | 0.8 ± 0.1 | 3.7 ± 0.2 | 1.8 ± 0.3 | 0.2 ± 0 | 0.9 ± 0.1 | 0.7 ± 0.2 | 0.1 ± 0 | 0.1 ± 0 |
| LBFLER (n = 52) | 4.7 ± 0.1 | 0.1 ± 0 | 0 ± 0 | 3.1 ± 0.2 | 28.7 ± 2 | 33.9 ± 1.1 | 1 ± 0.1 | 4.4 ± 0.3 | 1.9 ± 0.5 | 0.3 ± 0 | 0.9 ± 0 | 0.7 ± 0 | 0.1 ± 0 | 0.1 ± 0 |
| LBFLDL (n = 44) | 4.8 ± 0.1 | 0.1 ± 0 | 0 ± 0 | 3.4 ± 0.3 | 28 ± 1 | 34.6 ± 1 | 1 ± 0.2 | 4.2 ± 0.5 | 2.2 ± 0 | 0.3 ± 0 | 0.9 ± 0.1 | 0.7 ± 0 | 0.1 ± 0 | 0.1 ± 0 |
| LBFNQW (n = 51) | 4.8 ± 0.2 | 0.1 ± 0 | 0 ± 0 | 3.2 ± 0.3 | 27.6 ± 1.5 | 33.5 ± 1.1 | 1 ± 0.1 | 4.2 ± 0.3 | 2 ± 0.3 | 0.3 ± 0 | 1.3 ± 0.3 | 0.9 ± 0.1 | 0.2 ± 0.1 | 0.1 ± 0.1 |
| LBFBAP (n = 19) | 4.8 ± 0.1 | 0.1 ± 0 | 0 ± 0 | 3 ± 0.2 | 26 ± 0.9 | 33.8 ± 1 | 1.2 ± 0.1 | 3.4 ± 0.2 | 2.4 ± 0.3 | 0.3 ± 0 | 0.8 ± 0 | 0.7 ± 0 | 0.2 ± 0 | 0.1 ± 0 |
| LBFDAU (n = 10) | 5.2 ± 1 | 0.2 ± 0 | 0 ± 0 | 3.3 ± 0.3 | 20.5 ± 0.9 | 31.8 ± 0.5 | 0.9 ± 0.1 | 4.1 ± 0.2 | 2.5 ± 0.2 | 0.3 ± 0 | 0.9 ± 0.1 | 0.6 ± 0.1 | 0.2 ± 0 | 0.1 ± 0 |
| LBFPRA (n = 16) | 4.9 ± 0.2 | 0.2 ± 0 | 0 ± 0 | 2.6 ± 0.6 | 25.4 ± 2.2 | 31 ± 1.3 | 1.3 ± 0.2 | 5.4 ± 0.8 | 2 ± 0.4 | 0.2 ± 0.1 | 0.8 ± 0.1 | 0.8 ± 0 | 0.1 ± 0 | 0.1 ± 0 |
| LBFIFU (n = 11) | 4.7 ± 0.2 | 0.1 ± 0 | 0 ± 0 | 3.8 ± 0.9 | 25.9 ± 2.6 | 34.7 ± 1.3 | 1.1 ± 0.3 | 3.6 ± 0.6 | 2.7 ± 0.9 | 0.3 ± 0.1 | 0.9 ± 0.1 | 0.7 ± 0 | 0.1 ± 0 | 0.1 ± 0 |
| LBFDKD (n = 2) | 5.1 ± 0.2 | 0.2 ± 0 | 0 ± 0 | 3 ± 0.9 | 26.1 ± 3.9 | 35.6 ± 0.6 | 0.6 ± 0 | 4.8 ± 0.7 | 1.3 ± 0.4 | 0.2 ± 0.1 | 0.9 ± 0.2 | 0.8 ± 0 | 0.3 ± 0 | 0.2 ± 0 |
| LBFDJG (n = 12) | 4.4 ± 0.1 | 0.1 ± 0 | 0 ± 0 | 3.4 ± 0.3 | 27.3 ± 1.4 | 33.1 ± 1.9 | 1.1 ± 0.2 | 3.6 ± 0.1 | 2.1 ± 0.4 | 0.4 ± 0.1 | 0.9 ± 0.1 | 0.6 ± 0.2 | 0.1 ± 0 | 0 ± 0 |
| LBFLFK (n = 15) | 5.1 ± 0.3 | 0.2 ± 0 | 0 ± 0 | 2.5 ± 0.1 | 28.7 ± 1.6 | 29 ± 1.7 | 1.2 ± 0.2 | 5.6 ± 0.4 | 1.5 ± 0.2 | 0.2 ± 0 | 0.8 ± 0 | 0.7 ± 0 | 0.1 ± 0 | 0.1 ± 0 |
| LBFLCG (n = 15) | 4.9 ± 0.3 | 0.1 ± 0 | 0 ± 0 | 3.6 ± 0.3 | 25.8 ± 1.4 | 34.1 ± 0.8 | 0.9 ± 0.1 | 4.4 ± 0.2 | 1.9 ± 0.2 | 0.3 ± 0 | 0.9 ± 0 | 0.6 ± 0 | 0.1 ± 0 | 0.1 ± 0 |
| LBFPQM (n = 12) | 5.2 ± 0.3 | 0.1 ± 0 | 0 ± 0 | 3.8 ± 0.4 | 26.3 ± 1.2 | 31.6 ± 1 | 1.2 ± 0.1 | 4.3 ± 0.4 | 1.8 ± 0.2 | 0.2 ± 0 | 1.1 ± 0.1 | 0.9 ± 0.1 | 0.2 ± 0.1 | 0.2 ± 0 |
| LBFDHG (n = 5) | 5.4 ± 0.1 | 0.2 ± 0 | 0 ± 0 | 2.3 ± 0.2 | 24 ± 0.6 | 34 ± 0.7 | 1 ± 0.1 | 4.1 ± 0.2 | 2.7 ± 0.1 | 0.3 ± 0 | 0.7 ± 0 | 0.7 ± 0 | 0.1 ± 0 | 0.1 ± 0 |
| LBFDKA (n = 5) | 5.1 ± 0.3 | 0.1 ± 0 | 0 ± 0 | 3.7 ± 0.4 | 24.2 ± 2.8 | 29.7 ± 1.1 | 1.5 ± 0.3 | 4.4 ± 0.3 | 1.8 ± 0.1 | 0.2 ± 0 | 1.1 ± 0.1 | 0.9 ± 0.1 | 0.2 ± 0.1 | 0.2 ± 0 |
| LBFIDT (n = 7) | 5 ± 0.1 | 0.2 ± 0 | 0 ± 0 | 2.6 ± 0.1 | 27 ± 1.7 | 30.8 ± 1.2 | 1.1 ± 0.2 | 6.2 ± 0.4 | 1.8 ± 0.2 | 0.4 ± 0.1 | 0.8 ± 0 | 0.7 ± 0 | 0.1 ± 0 | 0.1 ± 0 |

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LBFDGG (n = 50) | 2.7 ± 0.2 | 1.5 ± 0.1 | 2.2 ± 0.3 | 7.7 ± 0.8 | 0.4 ± 0 | 0 ± 0 | 0.3 ± 0.1 | 1.9 ± 0.2 | 0.2 ± 0 | 1.4 ± 0.3 | 0.3 ± 0.1 | 0.2 ± 0.1 |
| LBFGKN (n = 50) | 2.8 ± 0.2 | 1.4 ± 0.1 | 2.3 ± 0.2 | 8.1 ± 0.9 | 0.4 ± 0 | 0 ± 0 | 0.3 ± 0 | 1.9 ± 0.2 | 0 ± 0 | 1.4 ± 0.3 | 0.2 ± 0 | 0.2 ± 0 |
| LBFIHE (n = 34) | 3.1 ± 0.3 | 1.5 ± 0.2 | 2.5 ± 0.4 | 8.4 ± 1 | 0.4 ± 0 | 0 ± 0 | 0.3 ± 0.1 | 1.6 ± 0.2 | 0.1 ± 0 | 1.5 ± 0.3 | 0.2 ± 0.1 | 0.3 ± 0.1 |
| LBFLDI (n = 60) | 2.6 ± 0.2 | 1.6 ± 0.2 | 1.7 ± 0.2 | 8.2 ± 1.7 | 0.4 ± 0 | 0 ± 0 | 0.3 ± 0.1 | 2.4 ± 0.5 | 0.1 ± 0 | 1.4 ± 0.3 | 0.3 ± 0 | 0.4 ± 0.1 |
| LBFPNF (n = 52) | 3.5 ± 0.3 | 1.5 ± 0.4 | 2.5 ± 0.2 | 9.8 ± 0.8 | 0.4 ± 0 | 0 ± 0 | 0.3 ± 0.3 | 2.7 ± 0 | 0.1 ± 0 | 1.2 ± 0.1 | 0.3 ± 0 | 0.2 ± 0.1 |
| LBFNSQ (n = 51) | 4.3 ± 0.6 | 2.2 ± 0.3 | 1.6 ± 0.4 | 6.8 ± 1.4 | 0.4 ± 0 | 0 ± 0 | 0.4 ± 0 | 1.7 ± 0.3 | 0.1 ± 0 | 1.3 ± 0.3 | 0.6 ± 0.2 | 0.5 ± 0.3 |
| LBFDGL (n = 57) | 4.7 ± 0.7 | 3 ± 0.5 | 0.8 ± 0.3 | 5.5 ± 1.8 | 0.4 ± 0 | 0 ± 0 | 0.3 ± 0.1 | 1.4 ± 0.3 | 0.1 ± 0 | 1 ± 0.4 | 0.9 ± 0.3 | 0.2 ± 0.1 |
| LBFIEF (n = 6) | 4.2 ± 0.3 | 2.5 ± 0.3 | 0.7 ± 0.3 | 5.2 ± 0.8 | 0.4 ± 0 | 0 ± 0 | 0.4 ± 0.1 | 1.6 ± 0.3 | 0.1 ± 0 | 1 ± 0.3 | 0.9 ± 0.2 | 0.2 ± 0 |
| LBFBAV (n = 50) | 10.9 ± 0.7 | 6.5 ± 0.5 | 0.1 ± 0.1 | 1.8 ± 0.7 | 0.4 ± 0 | 0 ± 0 | 0.1 ± 0.3 | 0.8 ± 0.1 | 0.1 ± 0.1 | 0.3 ± 0.5 | 3 ± 0.3 | 0.7 ± 0.1 |
| LBFPNC (n = 32) | 4.9 ± 0.9 | 2 ± 0.4 | 2.4 ± 0.7 | 6.9 ± 1.6 | 0.4 ± 0.1 | 0 ± 0 | 0.3 ± 0.1 | 1.9 ± 0.5 | 0.1 ± 0 | 0.9 ± 0.2 | 0.4 ± 0.2 | 0.4 ± 0.1 |
| LBFGHQ (n = 46) | 2.5 ± 0.3 | 1.7 ± 0.2 | 0.6 ± 0.1 | 4.9 ± 0.7 | 0.4 ± 0 | 0 ± 0 | 0.3 ± 0 | 1.9± 0.3 | 0.2 ± 0 | 1 ± 0.2 | 0.8 ± 0.1 | 0.3 ± 0.1 |
| LBFAZB (n = 49) | 6.3 ± 0.7 | 3.3 ± 0.3 | 0.8 ± 0.2 | 4.5 ± 0.9 | 0.3 ± 0 | 0 ± 0 | 0.4 ± 0 | 1.4 ± 0.2 | 0.1 ± 0 | 0.9 ± 0.2 | 1.5 ± 0.3 | 0.2 ± 0 |

TABLE 138-continued

Fatty acid profiles of T2 seeds harvested from T1 cultivated in the greenhouse of canola events containing the T-DNAs of plasmids VC-LTM593-1qcz rc. The events are indicated in the first column, along with the number of T2 seed batches that were measured per event. Per seed batch a random selection of ~30 seed was measured in two technical repeats.

| Event | | | | | | | | | | | | |
|---|---|---|---|---|---|---|---|---|---|---|---|---|
| LBFGKW (n = 72) | 6 ± 0.7 | 3.3 ± 0.4 | 0.5 ± 0.1 | 4.1 ± 0.8 | 0.4 ± 0 | 0 ± 0 | 0.4 ± 0.1 | 1.5 ± 0.3 | 0.1 ± 0 | 0.8 ± 0.2 | 1.7 ± 0.3 | 0.3 ± 0.1 |
| LBFNRU (n = 58) | 5.9 ± 0.7 | 3.6 ± 0.5 | 0.4 ± 0.1 | 4.2 ± 0.9 | 0.4 ± 0 | 0 ± 0 | 0.4 ± 0 | 1.7 ± 0.4 | 0.1 ± 0 | 0.9 ± 0.3 | 1.9 ± 0.4 | 0.3 ± 0.1 |
| LBFGIZ (n = 43) | 5.7 ± 0.8 | 3.5 ± 0.5 | 0.6 ± 0.1 | 5.3 ± 1.1 | 0.4 ± 0 | 0 ± 0 | 0.4 ± 0.1 | 2.1 ± 0.4 | 0.1 ± 0 | 1 ± 0.2 | 1.7 ± 0.4 | 0.4 ± 0.1 |
| LBFIGM (n = 56) | 5 ± 0.7 | 2.5 ± 0.3 | 1 ± 0.2 | 5.4 ± 1 | 0.4 ± 0 | 0 ± 0 | 0.4 ± 0.1 | 2 ± 0.5 | 0.4 ± 2.2 | 1 ± 0.2 | 1.2 ± 0.2 | 0.3 ± 0.1 |
| LBFNRR (n = 61) | 5.3 ± 1.2 | 3.5 ± 0.3 | 0.4 ± 0.1 | 4.4 ± 1.1 | 0.4 ± 0 | 0 ± 0 | 0.3 ± 0 | 1.7 ± 0.4 | 0 ± 0 | 0.8 ± 0.2 | 1.7 ± 0.3 | 0.3 ± 0.1 |
| LBFNTK (n = 69) | 6.7 ± 0.8 | 3.8 ± 0.5 | 0.6 ± 0.2 | 5 ± 0.9 | 0.4 ± 0 | 0 ± 0 | 0.5 ± 0.1 | 2 ± 0.4 | 0.1 ± 0 | 0.9 ± 0.2 | 1.8 ± 0.3 | 0.5 ± 0.1 |
| LBFGJA (n = 42) | 4.7 ± 0.6 | 1.5 ± 0.2 | 1.3 ± 0.2 | 3.8 ± 0.6 | 0.3 ± 0 | 0 ± 0 | 0.7 ± 0.1 | 1.4 ± 0.2 | 0.1 ± 0 | 0.8 ± 0.2 | 1.2 ± 0.2 | 0.1 ± 0 |
| LBFIFV (n = 58) | 6.3 ± 0.6 | 2.5 ± 0.2 | 1.3 ± 0.2 | 4.2 ± 0.7 | 0.4 ± 0 | 0 ± 0 | 0.4 ± 0.1 | 1.1 ± 0.2 | 0.1 ± 0 | 1.1 ± 0.3 | 1 ± 0.2 | 0.2 ± 0 |
| LBFLER (n = 52) | 5.9 ± 0.6 | 2.9 ± 0.3 | 1.1 ± 0.2 | 5.3 ± 0.7 | 0.4 ± 0 | 0 ± 0 | 0.5 ± 0.1 | 1.7 ± 0.2 | 0 ± 0 | 1 ± 0.2 | 1.1 ± 0.2 | 0.2 ± 0.1 |
| LBFLDL (n = 44) | 5.2 ± 0.6 | 2.5 ± 0.4 | 1.2 ± 0.3 | 5.5 ± 0.7 | 0.4 ± 0 | 0 ± 0 | 0.6 ± 0.1 | 1.9 ± 0.2 | 0.1 ± 0 | 0.8 ± 0.2 | 1 ± 0.2 | 0.2 ± 0 |
| LBFNQW (n = 51) | 5.3 ± 0.5 | 2.7 ± 0.4 | 1.1 ± 0.2 | 6.2 ± 1 | 0.4 ± 0 | 0 ± 0 | 0.5 ± 0.1 | 2 ± 0.3 | 0.1 ± 0 | 0.9 ± 0.2 | 0.8 ± 0.4 | 0.5 ± 0.1 |
| LBFBAP (n = 19) | 7.4 ± 0.7 | 2.9 ± 0.3 | 2.1 ± 0.3 | 6.2 ± 0.8 | 0.3 ± 0 | 0 ± 0 | 0.3 ± 0 | 1.7 ± 0.2 | 0.1 ± 0 | 1.1 ± 0.1 | 0.6 ± 0.1 | 0.4 ± 0.1 |
| LBFDAU (n = 10) | 4.2 ± 0.2 | 3.1 ± 0.3 | 1.6 ± 0.3 | 13.9 ± 1 | 0.4 ± 0 | 0 ± 0 | 0.2 ± 0 | 2.3 ± 0.2 | 0.1 ± 0 | 2.6 ± 0.4 | 0.4 ± 0.1 | 0.3 ± 0 |
| LBFPRA (n = 16) | 2.9 ± 0.6 | 1.6 ± 0.3 | 3 ± 0.3 | 12.3 ± 1.4 | 0.4 ± 0 | 0 ± 0 | 0.2 ± 0 | 2.7 ± 0.2 | 0 ± 0 | 1.4 ± 0.2 | 0.1 ± 0 | 0.4 ± 0.1 |
| LBFIFU (n = 11) | 4.2 ± 0.6 | 1.7 ± 0.3 | 2.7 ± 0.5 | 8 ± 1.8 | 0.3 ± 0 | 0 ± 0 | 0.4 ± 0.1 | 2 ± 0.3 | 0.1 ± 0.1 | 1.3 ± 0.4 | 0.3 ± 0.2 | 0.2 ± 0 |
| LBFDKD (n = 2) | 5.1 ± 1.6 | 3 ± 1.3 | 0.9 ± 0.4 | 5.7 ± 0.7 | 0.4 ± 0 | 0 ± 0 | 0.5 ± 0.1 | 2.2 ± 0.5 | 0.1 ± 0 | 1.1 ± 0.2 | 1.4 ± 0.7 | 0.3 ± 0 |
| LBFDJG (n = 12) | 6.1 ± 1.1 | 2.6 ± 0.4 | 1.6 ± 0.4 | 6.8 ± 1.4 | 0.4 ± 0 | 0 ± 0 | 0.4 ± 0.1 | 1.7 ± 0.2 | 0.1 ± 0 | 1.3 ± 0.4 | 1 ± 0.4 | 0.4 ± 0.1 |
| LBFLFK (n = 15) | 3.8 ± 0.3 | 2.4 ± 0.1 | 1.3 ± 0.1 | 9.9 ± 0.8 | 0.4 ± 0.1 | 0 ± 0 | 0.5 ± 0 | 3 ± 0.3 | 0.1 ± 0 | 1.8 ± 0.2 | 0.6 ± 0.1 | 0.3 ± 0.1 |
| LBFLCG (n = 15) | 3.7 ± 0.5 | 2.2 ± 0.3 | 1.4 ± 0.2 | 9 ± 0.7 | 0.3 ± 0 | 0 ± 0 | 0.4 ± 0.1 | 2.5 ± 0.2 | 0.1 ± 0 | 1.6 ± 0.3 | 0.6 ± 0.2 | 0.2 ± 0 |
| LBFPQM (n = 12) | 4.8 ± 0.6 | 3 ± 0.4 | 1.1 ± 0.2 | 8.2 ± 1.1 | 0.4 ± 0 | 0 ± 0 | 0.4 ± 0.1 | 2.2 ± 0.2 | 0.1 ± 0 | 1.5 ± 0.2 | 0.8 ± 0.1 | 0.5 ± 0.2 |
| LBFDHG (n = 5) | 3 ± 0.1 | 1.7 ± 0.1 | 1.7 ± 0.1 | 10.4 ± 0.8 | 0.4 ± 0 | 0 ± 0 | 0.6 ± 0.1 | 2.4 ± 0.1 | 0.3 ± 0 | 2.7 ± 0.2 | 0.5 ± 0 | 0.2 ± 0 |
| LBFDKA (n = 5) | 7.6 ± 0.6 | 5.1 ± 0.8 | 0.6 ± 0.1 | 6.6 ± 1 | 0.4 ± 0 | 0 ± 0 | 0.3 ± 0.1 | 2 ± 0.3 | 0.1 ± 0 | 1.3 ± 0.5 | 1.8 ± 0.2 | 0.9 ± 0 |
| LBFIDT (n = 7) | 4.5 ± 1.3 | 3 ± 0.9 | 1 ± 0.2 | 8.2 ± 0.6 | 0.4 ± 0 | 0 ± 0 | 0.5 ± 0.1 | 2.6 ± 0.2 | 0.1 ± 0 | 1.7 ± 0.2 | 1 ± 0.3 | 0.3 ± 0.1 |

TABLE 139

Fatty acid profiles of one T2 seed batch per event harvested from T1 plants cultivated in the greenhouse of canola events containing the T-DNAs of plasmids VC-LTM593-1qcz rc. The events are indicated in the first column. Fatty acid profiles of T2 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LBFDGG (n = 1) | 4.6 | 0.2 | 0.0 | 2.6 | 26.6 | 34.2 | 0.8 | 4.6 | 2.0 | 0.3 | 0.8 | 0.7 | 0.1 | 0.1 |
| LBFGKN (n = 1) | 4.7 | 0.2 | 0.0 | 3.0 | 25.0 | 34.6 | 0.8 | 4.3 | 2.2 | 0.3 | 0.8 | 0.7 | 0.2 | 0.1 |
| LBFIHE (n = 1) | 4.8 | 0.1 | 0.0 | 3.0 | 23.7 | 34.1 | 0.9 | 3.6 | 4.0 | 0.4 | 1.0 | 0.9 | 0.2 | 0.1 |
| LBFLDI (n = 1) | 6.4 | 0.1 | 0.0 | 2.1 | 28.5 | 28.4 | 0.9 | 5.9 | 1.2 | 0.2 | 0.7 | 0.7 | 0.3 | 0.2 |
| LBFPNF (n = 1) | 5.4 | 0.2 | 0.0 | 2.3 | 26.9 | 28.9 | 1.3 | 5.1 | 3.0 | 0.4 | 0.8 | 0.7 | 0.1 | 0.0 |
| LBFNSQ (n = 1) | 4.7 | 0.1 | 0.0 | 2.4 | 23.6 | 34.2 | 1.0 | 4.7 | 2.2 | 0.4 | 0.7 | 0.0 | 0.3 | 0.1 |
| LBFDGL (n = 1) | 4.9 | 0.1 | 0.0 | 2.5 | 23.9 | 32.2 | 1.0 | 6.0 | 1.7 | 0.3 | 0.7 | 0.7 | 0.1 | 0.1 |
| LBFIEF (n = 1) | 4.7 | 0.1 | 0.0 | 3.0 | 27.0 | 37.2 | 0.6 | 5.1 | 1.4 | 0.2 | 1.0 | 0.7 | 0.2 | 0.3 |
| LBFBAV (n = 1) | 5.9 | 0.2 | 0.0 | 2.5 | 23.9 | 27.6 | 1.0 | 5.7 | 1.8 | 0.3 | 0.9 | 0.7 | 0.1 | 0.3 |
| LBFPNC (n = 1) | 4.7 | 0.1 | 0.0 | 2.3 | 19.8 | 35.1 | 0.6 | 3.9 | 2.7 | 0.3 | 0.6 | 0.7 | 0.2 | 0.1 |
| LBFGHQ (n = 1) | 5.4 | 0.2 | 0.0 | 2.3 | 28.7 | 31.5 | 0.5 | 9.0 | 1.4 | 0.6 | 0.9 | 0.8 | 0.1 | 0.1 |
| LBFAZB (n = 1) | 5.1 | 0.1 | 0.0 | 3.1 | 26.6 | 30.1 | 1.6 | 4.7 | 2.5 | 0.4 | 0.8 | 0.6 | 0.0 | 0.1 |
| LBFGKW (n = 1) | 4.4 | 0.2 | 0.0 | 2.0 | 26.5 | 31.5 | 1.2 | 6.8 | 1.9 | 0.3 | 0.6 | 0.7 | 0.1 | 0.1 |
| LBFNRU (n = 1) | 5.0 | 0.2 | 0.0 | 2.5 | 27.2 | 26.6 | 0.9 | 8.0 | 1.4 | 0.3 | 0.8 | 0.7 | 0.1 | 0.2 |
| LBFGIZ (n = 1) | 5.2 | 0.2 | 0.0 | 2.3 | 27.3 | 31.2 | 0.7 | 6.1 | 1.5 | 0.2 | 0.7 | 0.4 | 0.2 | 0.2 |

TABLE 139-continued

Fatty acid profiles of one T2 seed batch per event harvested from T1 plants cultivated in the greenhouse of canola events containing the T-DNAs of plasmids VC-LTM593-1qcz rc. The events are indicated in the first column. Fatty acid profiles of T2 seed batches having the highest EPA + DHA levels per event are shown. Per seed batch, a random selection of ~30 seed was measured in two technical repeats.

| Event | | | | | | | | | | | | | | |
|---|---|---|---|---|---|---|---|---|---|---|---|---|---|---|
| LBFIGM (n = 1) | 4.9 | 0.1 | 0.0 | 2.5 | 28.9 | 29.6 | 1.6 | 5.8 | 1.8 | 0.3 | 0.8 | 0.8 | 0.1 | 0.1 |
| LBFNRR (n = 1) | 4.8 | 0.1 | 0.0 | 2.8 | 27.3 | 26.9 | 1.9 | 6.5 | 1.9 | 0.3 | 0.9 | 0.8 | 0.1 | 0.1 |
| LBFNTK (n = 1) | 4.9 | 0.2 | 0.0 | 2.4 | 29.0 | 27.5 | 1.1 | 6.8 | 1.4 | 0.2 | 0.7 | 0.7 | 0.2 | 0.1 |
| LBFGJA (n = 1) | 5.2 | 0.2 | 0.0 | 3.0 | 27.1 | 33.5 | 2.1 | 3.4 | 5.2 | 0.6 | 0.8 | 0.7 | 0.1 | 0.1 |
| LBFIFV (n = 1) | 4.8 | 0.1 | 0.0 | 3.4 | 21.6 | 34.4 | 0.8 | 3.5 | 2.8 | 0.3 | 0.9 | 0.7 | 0.2 | 0.1 |
| LBFLER (n = 1) | 5.1 | 0.2 | 0.0 | 2.8 | 22.8 | 32.5 | 1.1 | 3.7 | 4.1 | 0.5 | 0.8 | 0.7 | 0.1 | 0.1 |
| LBFLDL (n = 1) | 4.7 | 0.1 | 0.0 | 3.4 | 26.9 | 33.7 | 1.0 | 4.4 | 1.8 | 0.2 | 0.9 | 0.7 | 0.1 | 0.1 |
| LBFNQW (n = 1) | 4.8 | 0.1 | 0.0 | 2.7 | 24.8 | 33.0 | 1.1 | 4.3 | 2.0 | 0.3 | 1.6 | 0.9 | 0.2 | 0.1 |
| LBFBAP (n = 1) | 4.9 | 0.1 | 0.0 | 3.2 | 24.5 | 31.9 | 1.4 | 3.2 | 2.7 | 0.3 | 0.8 | 0.7 | 0.2 | 0.1 |
| LBFDAU (n = 1) | 4.6 | 0.2 | 0.0 | 3.4 | 18.7 | 31.8 | 0.9 | 4.1 | 2.9 | 0.4 | 0.8 | 0.7 | 0.2 | 0.1 |
| LBFPRA (n = 1) | 4.8 | 0.1 | 0.0 | 3.2 | 21.9 | 28.7 | 1.8 | 4.4 | 2.7 | 0.3 | 0.9 | 0.8 | 0.1 | 0.1 |
| LBFIFU (n = 1) | 4.8 | 0.1 | 0.0 | 3.2 | 22.4 | 34.7 | 0.9 | 4.5 | 2.5 | 0.3 | 0.7 | 0.6 | 0.2 | 0.1 |
| LBFDKD (n = 1) | 5.0 | 0.2 | 0.0 | 2.4 | 28.9 | 35.2 | 0.6 | 5.3 | 1.0 | 0.1 | 0.7 | 0.8 | 0.3 | 0.2 |
| LBFDJG (n = 1) | 4.4 | 0.1 | 0.0 | 3.3 | 25.4 | 32.3 | 1.2 | 3.5 | 2.3 | 0.5 | 0.9 | 0.7 | 0.1 | 0.1 |
| LBFLFK (n = 1) | 5.2 | 0.2 | 0.0 | 2.5 | 26.2 | 29.0 | 1.2 | 5.9 | 1.7 | 0.3 | 0.8 | 0.7 | 0.1 | 0.1 |
| LBFLCG (n = 1) | 5.0 | 0.2 | 0.0 | 4.4 | 22.6 | 34.7 | 0.7 | 4.1 | 2.1 | 0.3 | 1.1 | 0.6 | 0.1 | 0.1 |
| LBFPQM (n = 1) | 5.1 | 0.2 | 0.0 | 3.3 | 25.7 | 30.4 | 1.4 | 4.4 | 1.9 | 0.3 | 1.0 | 0.9 | 0.2 | 0.2 |
| LBFDHG (n = 1) | 5.4 | 0.2 | 0.0 | 2.1 | 23.9 | 33.5 | 1.1 | 4.0 | 2.6 | 0.3 | 0.7 | 0.7 | 0.1 | 0.1 |
| LBFDKA (n = 1) | 5.6 | 0.2 | 0.0 | 3.2 | 20.9 | 30.0 | 1.3 | 3.9 | 1.9 | 0.2 | 1.0 | 1.0 | 0.3 | 0.2 |
| LBFIDT (n = 1) | 5.1 | 0.2 | 0.0 | 2.6 | 26.4 | 32.0 | 1.0 | 5.7 | 2.0 | 0.4 | 0.8 | 0.7 | 0.1 | 0.1 |

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LBFDGG (n = 1) | 2.7 | 1.6 | 2.8 | 9.7 | 0.4 | 0.0 | 0.3 | 2.2 | 0.2 | 1.9 | 0.2 | 0.3 |
| LBFGKN (n = 1) | 3.1 | 1.7 | 2.5 | 10.4 | 0.3 | 0.0 | 0.4 | 2.4 | 0.1 | 2.0 | 0.2 | 0.2 |
| LBFIHE (n = 1) | 3.1 | 1.3 | 3.3 | 10.3 | 0.4 | 0.0 | 0.3 | 1.9 | 0.1 | 1.8 | 0.2 | 0.3 |
| LBFLDI (n = 1) | 3.0 | 1.9 | 1.7 | 10.8 | 0.3 | 0.0 | 0.4 | 3.3 | 0.2 | 1.7 | 0.4 | 0.4 |
| LBFPNF (n = 1) | 3.3 | 1.6 | 2.8 | 11.0 | 0.4 | 0.0 | 0.2 | 3.2 | 0.1 | 1.7 | 0.3 | 0.2 |
| LBFNSQ (n = 1) | 4.3 | 2.3 | 2.3 | 10.2 | 0.4 | 0.0 | 0.5 | 2.2 | 0.1 | 2.0 | 0.4 | 0.7 |
| LBFDGL (n = 1) | 4.6 | 2.9 | 1.4 | 10.1 | 0.4 | 0.0 | 0.3 | 2.0 | 0.2 | 2.2 | 1.0 | 0.3 |
| LBFIEF (n = 1) | 4.3 | 2.6 | 0.9 | 5.9 | 0.4 | 0.0 | 0.5 | 1.4 | 0.1 | 1.2 | 0.7 | 0.2 |
| LBFBAV (n = 1) | 10.2 | 7.6 | 0.3 | 4.2 | 0.5 | 0.0 | 0.0 | 2.0 | 0.0 | 1.1 | 2.6 | 0.4 |
| LBFPNC (n = 1) | 4.3 | 1.8 | 4.6 | 11.4 | 0.3 | 0.0 | 0.6 | 3.9 | 0.1 | 1.1 | 0.4 | 0.3 |
| LBFGHQ (n = 1) | 2.6 | 2.1 | 0.6 | 6.5 | 0.4 | 0.0 | 0.3 | 2.8 | 0.2 | 1.6 | 0.9 | 0.4 |
| LBFAZB (n = 1) | 5.4 | 2.9 | 1.6 | 8.7 | 0.4 | 0.0 | 0.4 | 2.2 | 0.1 | 1.5 | 0.9 | 0.3 |
| LBFGKW (n = 1) | 6.7 | 4.1 | 0.5 | 5.9 | 0.3 | 0.0 | 0.4 | 2.0 | 0.2 | 1.2 | 2.0 | 0.3 |
| LBFNRU (n = 1) | 6.0 | 4.6 | 0.4 | 7.0 | 0.4 | 0.0 | 0.4 | 3.0 | 0.1 | 1.8 | 1.9 | 0.3 |
| LBFGIZ (n = 1) | 5.3 | 3.1 | 1.0 | 7.4 | 0.4 | 0.0 | 0.5 | 2.8 | 0.1 | 1.4 | 1.4 | 0.5 |
| LBFIGM (n = 1) | 5.0 | 2.5 | 1.5 | 7.9 | 0.4 | 0.0 | 0.4 | 2.2 | 0.1 | 1.5 | 0.9 | 0.4 |
| LBFNRR (n = 1) | 5.4 | 3.7 | 0.8 | 8.9 | 0.4 | 0.0 | 0.3 | 2.5 | 0.1 | 1.6 | 1.1 | 0.5 |
| LBFNTK (n = 1) | 5.9 | 3.6 | 1.0 | 7.3 | 0.4 | 0.0 | 0.6 | 3.0 | 0.1 | 1.1 | 1.5 | 0.4 |
| LBFGJA (n = 1) | 4.2 | 1.6 | 1.5 | 5.4 | 0.3 | 0.0 | 0.7 | 1.6 | 0.2 | 1.2 | 1.0 | 0.2 |
| LBFIFV (n = 1) | 6.8 | 2.9 | 2.2 | 7.6 | 0.4 | 0.0 | 0.6 | 1.8 | 0.3 | 2.6 | 1.0 | 0.2 |
| LBFLER (n = 1) | 6.4 | 3.2 | 1.7 | 7.9 | 0.3 | 0.0 | 0.7 | 2.1 | 0.1 | 1.9 | 1.1 | 0.2 |
| LBFLDL (n = 1) | 4.6 | 2.6 | 1.2 | 7.8 | 0.4 | 0.0 | 0.6 | 2.4 | 0.1 | 1.3 | 0.8 | 0.3 |
| LBFNQW (n = 1) | 5.1 | 3.0 | 1.3 | 8.6 | 0.3 | 0.0 | 0.5 | 2.5 | 0.1 | 1.4 | 0.9 | 0.4 |
| LBFBAP (n = 1) | 7.6 | 3.1 | 2.5 | 7.6 | 0.3 | 0.0 | 0.3 | 1.9 | 0.0 | 1.3 | 0.7 | 0.4 |
| LBFDAU (n = 1) | 4.2 | 3.4 | 1.5 | 15.1 | 0.3 | 0.0 | 0.2 | 2.5 | 0.1 | 3.0 | 0.4 | 0.3 |
| LBFPRA (n = 1) | 3.6 | 2.0 | 3.4 | 15.6 | 0.4 | 0.0 | 0.2 | 2.5 | 0.0 | 1.8 | 0.1 | 0.5 |
| LBFIFU (n = 1) | 4.2 | 2.3 | 2.1 | 9.6 | 0.2 | 0.0 | 0.5 | 2.5 | 0.2 | 2.3 | 0.6 | 0.2 |
| LBFDKD (n = 1) | 4.0 | 2.1 | 1.2 | 6.2 | 0.4 | 0.0 | 0.6 | 2.5 | 0.1 | 1.0 | 0.9 | 0.3 |
| LBFDJG (n = 1) | 5.5 | 2.6 | 2.1 | 9.0 | 0.4 | 0.0 | 0.4 | 1.8 | 0.1 | 1.9 | 0.6 | 0.4 |
| LBFLFK (n = 1) | 3.4 | 2.4 | 1.3 | 11.4 | 0.4 | 0.0 | 0.5 | 3.4 | 0.1 | 2.3 | 0.6 | 0.3 |
| LBFLCG (n = 1) | 3.4 | 2.1 | 1.6 | 10.1 | 0.4 | 0.0 | 0.5 | 2.6 | 0.1 | 2.3 | 0.6 | 0.2 |
| LBFPQM (n = 1) | 4.3 | 2.5 | 1.8 | 10.2 | 0.4 | 0.0 | 0.4 | 2.6 | 0.1 | 1.8 | 0.6 | 0.5 |
| LBFDHG (n = 1) | 3.0 | 1.8 | 1.7 | 11.4 | 0.4 | 0.0 | 0.6 | 2.4 | 0.3 | 2.8 | 0.5 | 0.2 |
| LBFDKA (n = 1) | 8.3 | 5.8 | 0.7 | 7.6 | 0.3 | 0.0 | 0.4 | 2.2 | 0.1 | 1.8 | 2.0 | 0.9 |
| LBFIDT (n = 1) | 3.5 | 2.2 | 1.3 | 9.1 | 0.4 | 0.0 | 0.6 | 2.8 | 0.1 | 2.0 | 0.7 | 0.2 |

TABLE 140

Fatty acid profiles of T2 seeds harvested from T1 plants cultivated in the greenhouse of canola events containing the T-DNAs of plasmids VC-LTM593-1qcz rc. Plants of all events combined have been grouped into the categories indicated in the first column; as defined in Table 131. In addition to those categories, the catergory "dc" was sub-divided into the category dc sl: all T1 plants where the average of all copy number assays listed in Table 135 was 3.51-4.49, and the zygocity analysis listed in Table 137 revelead a single locus insertion of both copies, and into the category dc dl: all T1 plants where the average of all copy number assays listed in Table 135 was 3.51-4.49, and the zygocity analysis listed in Table 137 revelead a double locus insertion of both copies. The number of T1 plants fullfilling these criteria are displayed in parentheses. Per seed batch a random selection of ~30 seed was measured in two technical repeats.

| Category of T1 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| sc (n = 172) | 5.1 ± 0.9 | 0.2 ± 0.1 | 0 ± 0 | 2.8 ± 0.5 | 29.1 ± 3 | 33.8 ± 2.8 | 0.8 ± 0.2 | 4.8 ± 0.9 | 1.9 ± 0.7 | 0.3 ± 0.2 | 0.8 ± 0.1 | 0.8 ± 0.1 | 0.2 ± 0.2 | 0.1 ± 0.1 |
| dc (n = 813) | 4.9 ± 0.4 | 0.2 ± 0 | 0 ± 0 | 2.9 ± 0.5 | 29.1 ± 2.6 | 32 ± 3.1 | 1.1 ± 0.3 | 5.3 ± 1.3 | 1.9 ± 1 | 0.3 ± 0.1 | 0.9 ± 0.2 | 0.7 ± 0.1 | 0.1 ± 0 | 0.1 ± 0 |
| dc sl (n = 700) | 4.9 ± 0.4 | 0.2 ± 0 | 0 ± 0 | 2.8 ± 0.4 | 29.4 ± 2.5 | 31.9 ± 3.2 | 1.1 ± 0.3 | 5.4 ± 1.4 | 1.9 ± 1.1 | 0.3 ± 0.1 | 0.8 ± 0.2 | 0.7 ± 0.1 | 0.1 ± 0 | 0.1 ± 0 |
| dc dl (n = 64) | 5 ± 0.5 | 0.2 ± 0 | 0 ± 0 | 3.2 ± 0.6 | 26.3 ± 2.5 | 32.2 ± 2.4 | 1.1 ± 0.2 | 4.5 ± 0.7 | 1.9 ± 0.4 | 0.3 ± 0.1 | 0.9 ± 0.1 | 0.7 ± 0.1 | 0.1 ± 0 | 0.1 ± 0 |

| Category of T1 plants | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| sc (n = 172) | 2.8 ± 0.3 | 1.5 ± 0.2 | 2.1 ± 0.4 | 7.9 ± 1.3 | 0.4 ± 0 | 0 ± 0 | 0.3 ± 0.1 | 1.9 ± 0.4 | 0.1 ± 0.1 | 1.4 ± 0.3 | 0.3 ± 0.1 | 0.3 ± 0.1 |
| dc (n = 813) | 5.9 ± 1.7 | 3.1 ± 1.1 | 0.9 ± 0.5 | 5.1 ± 2.1 | 0.4 ± 0 | 0 ± 0 | 0.4 ± 0.1 | 1.7 ± 0.5 | 0.1 ± 0.6 | 1 ± 0.4 | 1.4 ± 0.7 | 0.3 ± 0.1 |
| dc sl (n = 700) | 6 ± 1.7 | 3.2 ± 1.2 | 0.9 ± 0.6 | 4.8 ± 1.7 | 0.4 ± 0 | 0 ± 0 | 0.4 ± 0.2 | 1.7 ± 0.5 | 0.1 ± 0.6 | 0.9 ± 0.3 | 1.4 ± 0.7 | 0.3 ± 0.2 |
| dc dl (n = 64) | 4.3 ± 1.1 | 2.5 ± 0.5 | 1.4 ± 0.3 | 9 ± 2 | 0.4 ± 0 | 0 ± 0 | 0.4 ± 0.1 | 2.4 ± 0.5 | 0.1 ± 0.1 | 1.7 ± 0.5 | 0.7 ± 0.3 | 0.3 ± 0.1 |

TABLE 141

Fatty acid profiles of T2 seeds harvested from T1 plants cultivated in the greenhouse of canola events containing the T-DNAs of plasmids VC-LTM593-1qcz rc. Plants of all events combined have been grouped into the categories indicated in the first column as defined in the description of Table 140. For each category, the fatty acid profile of the plant having the highest EPA + DHA levels was shown. Per seed batch a random selection of ~30 seed was measured in two technical repeats.

| Category of T1 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| sc (n = 1) | 6.4 | 0.1 | 0.0 | 3.0 | 23.7 | 34.1 | 0.9 | 3.6 | 4.0 | 0.4 | 1.0 | 0.9 | 0.2 | 0.1 |
| dc (n = 1) | 4.6 | 0.1 | 0.0 | 2.3 | 19.8 | 35.1 | 0.6 | 3.9 | 2.7 | 0.3 | 0.6 | 0.7 | 0.2 | 0.1 |
| dc sl (n = 1) | 4.8 | 0.1 | 0.0 | 2.3 | 19.8 | 35.1 | 0.6 | 3.9 | 2.7 | 0.3 | 0.6 | 0.7 | 0.2 | 0.1 |
| dc dl (n = 1) | 4.6 | 0.3 | 0.0 | 2.7 | 20.4 | 31.3 | 0.8 | 3.9 | 2.3 | 0.3 | 0.7 | 0.5 | 0.2 | 0.1 |

| Category of T1 plants | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| sc (n = 1) | 3.1 | 1.3 | 3.3 | 10.3 | 0.4 | 0.0 | 0.3 | 1.9 | 0.1 | 1.8 | 0.2 | 0.3 |
| dc (n = 1) | 4.3 | 1.8 | 4.6 | 11.4 | 0.3 | 0.0 | 0.6 | 3.9 | 0.1 | 1.1 | 0.4 | 0.3 |
| dc sl (n = 1) | 4.3 | 1.8 | 4.6 | 11.4 | 0.3 | 0.0 | 0.6 | 3.9 | 0.1 | 1.1 | 0.4 | 0.3 |
| dc dl (n = 1) | 3.9 | 2.5 | 2.4 | 13.7 | 0.3 | 0.0 | 0.3 | 2.6 | 0.2 | 2.9 | 0.4 | 0.2 |

TABLE 142

Phenotypic rating of T1 plants cultivated in the greenhouse of canola events containing the T-DNAs of plasmids VC-LTM593-1qcz rc. The events are indicated in the first column, along with the number of T1 plants that where rated per event.

| Event | DFF | DF | DL | DP | DS | FC | LD | LGC | LF | NoL | PH | TKW | SC | Oil | Protein |
|---|---|---|---|---|---|---|---|---|---|---|---|---|---|---|---|
| LBFDGG (n = 50) | 43.6 ± 2.7 | 9 ± 0 | 9 ± 0 | 9 ± 0 | 8.1 ± 1.6 | 3 ± 0 | 5 ± 0 | 5 ± 0 | 8.1 ± 1.6 | 4.5 ± 0.8 | 118.8 ± 6.1 | 4.4 ± 0.3 | 3.5 ± 0.9 | 36.1 | 30.2 |
| LBFGKN (n = 50) | 43.3 ± 1.7 | 9 ± 0 | 9 ± 0 | 9 ± 0 | 8.1 ± 0.7 | 3 ± 0 | 5 ± 0 | 5 ± 0 | 8.1 ± 0.7 | 5.1 ± 0.8 | 112.4 ± 4.1 | 4.4 ± 0.3 | 3 ± 0.8 | 36.9 | 30.1 |
| LBFIHE (n = 34) | 47.4 ± 5.1 | 9 ± 0 | 9 ± 0 | 9 ± 0 | 6.6 ± 1.6 | 3 ± 0 | 5 ± 0 | 5 ± 0 | 6.6 ± 1.6 | 5.6 ± 0.9 | 105.7 ± 6.3 | 4.2 ± 0.5 | 3.8 ± 0.6 | 36.0 | 29.4 |
| LBFLDI (n = 60) | 35.8 ± 2.9 | 9 ± 0 | 7.5 ± 0.6 | 8.9 ± 0.7 | 8.2 ± 1.1 | 3 ± 0 | 4 ± 0.5 | 4 ± 0 | 8.4 ± 1.2 | 5.4 ± 1.8 | 94 ± 5.1 | 3.6 ± 0.8 | 4.8 ± 1.8 | 36.9 | 30.1 |
| LBFPNF (n = 52) | 35.3 ± 2.2 | 9 ± 0 | 7.6 ± 0.6 | 8.8 ± 0.5 | 8.4 ± 0.6 | 3 ± 0 | 3.9 ± 0.3 | 4 ± 0 | 8.3 ± 1.2 | 5.3 ± 0.9 | 88.4 ± 7.9 | 3.6 ± 0.9 | 3.5 ± 0.7 | 39.1 | 28.3 |
| LBFNSQ (n = 51) | 45.2 ± 7 | 9 ± 0 | 7.7 ± 0.9 | 6.8 ± 1.3 | 6.8 ± 1.2 | 3 ± 0 | 5 ± 0.2 | 4.1 ± 0.5 | 8.7 ± 0.6 | 5 ± 1 | 109.6 ± 10.9 | 3.4 ± 0.3 | 4.4 ± 1.8 | 37.5 | 28.7 |
| LBFDGL (n = 57) | 43.9 ± 2.4 | 9 ± 0 | 9 ± 0 | 9 ± 0 | 7.7 ± 0.8 | 3 ± 0 | 5 ± 0 | 5 ± 0 | 7.7 ± 0.8 | 5.1 ± 0.8 | 109.4 ± 6.6 | 4.1 ± 0.4 | 2.8 ± 0.7 | 36.9 | 29.9 |
| LBFIEF (n = 6) | 47.2 ± 5 | 9 ± 0 | 9 ± 0 | 9 ± 0 | 4 ± 2 | 3 ± 0 | 5 ± 0 | 5 ± 0 | 4 ± 2 | 6.2 ± 0.8 | 98.3 ± 4.1 | 3.4 ± 0.3 | 3.8 ± 1 | 38.9 | 29.9 |
| LBFBAV (n = 50) | 46.6 ± 1.6 | 9 ± 0 | 7.4 ± 0.8 | 9 ± 0 | 8.9 ± 0.3 | 3 ± 0 | 5 ± 0 | 4 ± 0 | 9 ± 0.5 | 3.5 ± 0.5 | 125.1 ± 5.6 | 2.7 ± 0.3 | 3.9 ± 1 | 39.0 | 28.0 |
| LBFPNC (n = 32) | 44.6 ± 4.2 | 9 ± 0 | 9 ± 0 | 9 ± 0 | 8.3 ± 0.7 | 3 ± 0 | 5 ± 0 | 5 ± 0 | 8.3 ± 0.7 | 5.5 ± 0.9 | 105.6 ± 5.6 | 4.1 ± 0.3 | 2.8 ± 0.5 | 39.4 | 28.3 |
| LBFGHQ (n = 46) | 44.4 ± 4 | 9 ± 0 | 7.3 ± 1.9 | 9 ± 0 | 8.9 ± 0.3 | 3 ± 0 | 5 ± 0 | 4 ± 0.1 | 9 ± 0.7 | 3.9 ± 0.6 | 124.5 ± 6.2 | 2.6 ± 0.3 | 3.7 ± 0.9 | 38.3 | 27.8 |
| LBFAZB (n = 49) | 47.6 ± 3.2 | 9 ± 0 | 9 ± 0 | 9 ± 0 | 7.9 ± 0.8 | 3 ± 0 | 5 ± 0 | 5 ± 0 | 7.9 ± 0.8 | 5.1 ± 0.8 | 112.3 ± 4.9 | 3.9 ± 0.4 | 2.6 ± 0.6 | 38.2 | 29.4 |
| LBFGKW (n = 72) | 46.7 ± 1.9 | 9 ± 0 | 7.3 ± 0.5 | 9 ± 0 | 8.9 ± 0.3 | 3 ± 0 | 5 ± 0 | 4 ± 0 | 8.9 ± 0.3 | 4.1 ± 0.6 | 125.2 ± 6.2 | 2.6 ± 0.3 | 3.7 ± 0.8 | 38.8 | 27.9 |
| LBFNRU (n = 58) | 41.4 ± 1.7 | 9 ± 0 | 7.6 ± 0.6 | 8.9 ± 0.7 | 8.2 ± 0.7 | 3 ± 0 | 5 ± 0 | 4 ± 0 | 8.9 ± 0.8 | 5.6 ± 0.8 | 117 ± 5 | 2.6 ± 0.3 | 3.6 ± 1.3 | 39.5 | 27.6 |
| LBFGIZ (n = 43) | 41.5 ± 2.8 | 9 ± 0 | 7.6 ± 0.6 | 9 ± 0 | 8.3 ± 0.5 | 3 ± 0 | 5 ± 0 | 4 ± 0 | 8.9 ± 0.3 | 5.3 ± 0.9 | 113.5 ± 5.9 | 2.4 ± 0.2 | 3.9 ± 0.7 | 38.4 | 28.6 |
| LBFIGM (n = 56) | 36.1 ± 1.3 | 9 ± 0 | 6.7 ± 0.8 | 9 ± 0.3 | 8.8 ± 0.4 | 3 ± 0 | 2.7 ± 0.7 | 4 ± 0 | 8.8 ± 0.5 | 3.9 ± 0.7 | 107.6 ± 9 | 2.7 ± 0.3 | 3.4 ± 0.8 | 39.1 | 28.6 |
| LBFNRR (n = 61) | 41.3 ± 2.2 | 9 ± 0 | 7.8 ± 0.6 | 9 ± 0 | 8 ± 0.6 | 3 ± 0 | 5 ± 0 | 4 ± 0 | 9 ± 0 | 5.3 ± 0.6 | 116.5 ± 6.3 | 2.9 ± 0.3 | 3.2 ± 0.9 | 40.6 | 27.1 |
| LBFNTK (n = 69) | 34.5 ± 2.8 | 8 ± 0 | 6.6 ± 1.1 | 9 ± 0 | 8.7 ± 0.5 | 3 ± 0 | 2.4 ± 0.6 | 4 ± 0 | 8.8 ± 0.7 | 3.7 ± 0.6 | 93.4 ± 8.2 | 2.8 ± 0.3 | 3.8 ± 0.8 | 39.8 | 28.3 |
| LBFGJA (n = 42) | 45.1 ± 1 | 9 ± 0 | 9 ± 0 | 9 ± 0 | 7.6 ± 0.5 | 3 ± 0 | 5 ± 0 | 5 ± 0 | 7.6 ± 0.5 | 4.3 ± 1.1 | 113.3 ± 2.4 | 4.9 ± 0.2 | 2.4 ± 0.8 | 32.9 | 25.6 |
| LBFIFV (n = 58) | 42.4 ± 0.6 | 9 ± 0 | 9 ± 0 | 9 ± 0 | 8.8 ± 0.6 | 3 ± 0 | 5 ± 0 | 5 ± 0 | 8.8 ± 0.6 | 4.5 ± 0.8 | 113.1 ± 2.4 | 4.2 ± 0.2 | 2.6 ± 0.6 | 37.3 | 29.4 |
| LBFLER (n = 52) | 45.1 ± 3.5 | 9 ± 0 | 9 ± 0 | 9 ± 0 | 8.5 ± 0.7 | 3 ± 0 | 5 ± 0 | 5 ± 0 | 8.5 ± 0.7 | 5.6 ± 1 | 108.3 ± 6.8 | 3.9 ± 0.3 | 2.6 ± 0.7 | 40.8 | 27.7 |
| LBFLDL (n = 44) | 44.7 ± 3.7 | 9 ± 0 | 9 ± 0 | 9 ± 0 | 8.5 ± 0.6 | 3 ± 0 | 5 ± 0 | 5 ± 0 | 8.5 ± 0.6 | 5.1 ± 0.8 | 109.3 ± 5.3 | 4 ± 0.2 | 2.6 ± 0.8 | 38.6 | 29.2 |
| LBFNQW (n = 51) | 42.8 ± 1.9 | 9 ± 0 | 9 ± 0 | 9 ± 0 | 8.7 ± 0.5 | 3 ± 0 | 5 ± 0 | 5 ± 0 | 8.7 ± 0.5 | 5.7 ± 0.9 | 105.5 ± 6.3 | 4.1 ± 0.3 | 3.1 ± 0.5 | 38.4 | 28.9 |
| LBFBAP (n = 19) | 43.3 ± 1.8 | 9 ± 0 | 9 ± 0 | 9 ± 0 | 8.9 ± 0.2 | 3 ± 0 | 5 ± 0 | 5 ± 0 | 8.9 ± 0.2 | 4.6 ± 0.8 | 117.4 ± 6.1 | 4 ± 0.5 | 2.4 ± 0.5 | 38.7 | 28.8 |
| LBFDAU (n = 10) | 43.6 ± 1.7 | 9 ± 0 | 9 ± 0 | 9 ± 0 | 9 ± 0 | 3 ± 0 | 5 ± 0 | 5 ± 0 | 8.5 ± 1.6 | 4.4 ± 0.8 | 110 ± 5.8 | 4.5 ± 0.5 | 2.6 ± 0.5 | 34.5 | 30.2 |
| LBFPRA (n = 16) | 47.8 ± 2.5 | 9 ± 0 | 7.9 ± 0.8 | 7.8 ± 0.4 | 7.4 ± 0.8 | 3 ± 0 | 5.2 ± 0.4 | 4 ± 0 | 9 ± 0 | 5.6 ± 0.8 | 123.4 ± 4 | 4.2 ± 0.6 | 2.3 ± 0.8 | 38.1 | 28.2 |
| LBFIFU (n = 11) | 46.8 ± 6.4 | 9 ± 0 | 8.7 ± 0.9 | 8.7 ± 0.9 | 7.3 ± 1.1 | 3 ± 0 | 5 ± 0 | 5 ± 0 | 7.3 ± 1.1 | 5.6 ± 1.1 | 103.6 ± 8.1 | 3.8 ± 0.5 | 3.5 ± 0.9 | 37.4 | 28.7 |
| LBFDKD (n = 2) | 43 ± 4.2 | 9 ± 0 | 9 ± 0 | 9 ± 0 | 7.5 ± 0.7 | 3 ± 0 | 5 ± 0 | 5 ± 0 | 7.5 ± 0.7 | 5 ± 1.4 | 107.5 ± 10.6 | 4.3 ± 0.8 | 4 ± 1.4 | 36.6 | 31.2 |
| LBFDJG (n = 12) | 45.1 ± 1 | 9 ± 0 | 9 ± 0 | 9 ± 0 | 8.8 ± 0.6 | 3 ± 0 | 5 ± 0 | 5 ± 0 | 8.8 ± 0.6 | 4.3 ± 1 | 104.2 ± 29.8 | 3.8 ± 0.2 | 2.8 ± 0.5 | 37.7 | 29.8 |
| LBFLFK (n = 15) | 42.5 ± 5.5 | 9 ± 0 | 7.9 ± 1.2 | 8.7 ± 1.3 | 8.1 ± 1.3 | 3 ± 0 | 4.9 ± 0.5 | 4 ± 0 | 8.9 ± 0.4 | 5.1 ± 1.2 | 113.7 ± 9 | 4.1 ± 1 | 3.7 ± 0.6 | 39.3 | 27.2 |
| LBFLCG (n = 15) | 42.5 ± 0.6 | 9 ± 0 | 9 ± 0 | 9 ± 0 | 9 ± 0 | 3 ± 0 | 5 ± 0 | 5 ± 0 | 8.7 ± 1 | 4.5 ± 0.8 | 113.7 ± 2.3 | 4.3 ± 0.5 | 2.7 ± 0.8 | 37.7 | 29.1 |
| LBFPQM (n = 12) | 42.7 ± 2.5 | 9 ± 0 | 9 ± 0 | 9 ± 0 | 8.7 ± 0.5 | 3 ± 0 | 5 ± 0 | 5 ± 0 | 8.7 ± 0.5 | 5.5 ± 1 | 110 ± 6 | 4.2 ± 0.5 | 2.8 ± 0.4 | 39.2 | 27.7 |

TABLE 142-continued

Phenotypic rating of T1 plants cultivated in the greenhouse of canola events containing the T-DNAs of plasmids VC-LTM593-1qcz rc. The events are indicated in the first column, along with the number of T1 plants that where rated per event.

| Event | DFF | DF | DL | DP | DS | FC | LD | LGC | LF | NoL | PH | TKW | SC | Oil | Protein |
|---|---|---|---|---|---|---|---|---|---|---|---|---|---|---|---|
| LBFDHG (n = 5) | 44.8 ± 3 | 9 ± 0 | 9 ± 0 | 9 ± 0 | 6.4 ± 0.9 | 3 ± 0 | 5 ± 0 | 5 ± 0 | 6.4 ± 0.9 | 4.2 ± 0.8 | 115 ± 0 | 4.2 ± 0.2 | 5 ± 0 | 33.5 | 28.0 |
| LBFDKA (n = 5) | 48.6 ± 1.7 | 9 ± 0 | 9 ± 0 | 9 ± 0 | 9 ± 0 | 3 ± 0 | 5 ± 0 | 5 ± 0 | 9 ± 0 | 5.6 ± 0.9 | 108 ± 4.5 | 3.8 ± 0.2 | 2.4 ± 0.5 | 40.0 | 26.6 |
| LBFIDT (n = 7) | 46.3 ± 1.3 | 9 ± 0 | 7.7 ± 0.5 | 9 ± 0 | 8 ± 0 | 3 ± 0 | 5 ± 0 | 4 ± 0 | 9 ± 0 | 4.1 ± 0.7 | 125.7 ± 6.7 | 2.5 ± 0.2 | 3.7 ± 0.5 | 38.1 | 28.0 |

DFF: days to first flower (days),
DF: deformed flower (1 = deformed, 9 = normal),
DL: deformed leaf (1 = deformed, 9 = normal),
DP: deformed plant (1 = deformed, 9 = normal),
DS: deformed silique (1 = deformed, 9 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoL: number of lobes (#),
PH: plant height (cm),
TKW: thousand kernel weight (g),
SC: seed quality (1 = good, 9 = bad),
Oil: oil content (% of seed weight),
protein: Protein content (% of seed cake without oil)

TABLE 143

Phenotypic rating of T1 plants cultivated in the greenhouse of canola events containing the T-DNAs of plasmids VC-LTM593-1qcz rc. Plants of all events combined have been grouped into the categories indicated in the first column as defined in the description of Table 140. The number of T1 plants fullfilling these criteria are displayed in parentheses.

| Category of T1 plants | DFF | DF | DL | DP | DS | FC | LD | LGC | LF | NoL | PH | TKW | SC | oil | protein |
|---|---|---|---|---|---|---|---|---|---|---|---|---|---|---|---|
| sc (n = 177) | 41.5 ± 5.2 | 9 ± 0 | 8.6 ± 0.7 | 9 ± 0.4 | 7.9 ± 1.5 | 3 ± 0 | 4.8 ± 0.5 | 4.8 ± 0.4 | 8 ± 1.5 | 5.1 ± 1 | 109.1 ± 10.6 | 3.9 ± 0.6 | 3.8 ± 1.4 | 37 ± 1.4 | 29.5 ± 0.9 |
| dc (n = 781) | 43.4 ± 4.4 | 8.9 ± 0.3 | 8.1 ± 1.1 | 9 ± 0.3 | 8.4 ± 0.8 | 3 ± 0 | 4.6 ± 0.9 | 4.5 ± 0.5 | 8.6 ± 0.8 | 4.7 ± 1.1 | 112.2 ± 11 | 3.3 ± 0.8 | 3.2 ± 1 | 38 ± 2.1 | 28.5 ± 1.2 |
| dc sl (n = 677) | 43.1 ± 4.4 | 8.9 ± 0.3 | 8 ± 1.1 | 9 ± 0.2 | 8.5 ± 0.8 | 3 ± 0 | 4.6 ± 1 | 4.4 ± 0.5 | 8.7 ± 0.8 | 4.7 ± 1.1 | 112.3 ± 11 | 3.3 ± 0.8 | 3.2 ± 1 | 38.4 ± 1.8 | 28.3 ± 1.1 |
| dc dl (n = 55) | 43.3 ± 3.3 | 9 ± 0 | 8.7 ± 0.8 | 8.9 ± 0.6 | 8.4 ± 1 | 3 ± 0 | 5 ± 0.3 | 4.8 ± 0.4 | 8.5 ± 1.1 | 4.8 ± 1.1 | 110.8 ± 14.3 | 3.5 ± 0.7 | 3.2 ± 0.9 | 36.6 ± 2.7 | 28.9 ± 1.7 |

DFF: days to first flower (days),
DF: deformed flower (1 = deformed, 9 = normal),
DL: deformed leaf (1 = deformed, 9 = normal),
DP: deformed plant (1 = deformed, 9 = normal),
DS: deformed silique (1 = deformed, 9 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoL: number of lobes (#),
PH: plant height (cm),
TKW: thousand kernel weight (g),
SC: seed quality (1 = good, 9 = bad),
Oil: oil content (% of seed weight),
protein: Protein content (% of seed cake without oil)

B. Fatty Acid Profiles, Copy Number Measurements, and Phenotypic Observations of T1 Plants Carrying T-DNAs of Plasmids VC-LTM593-1qcz rc Cultivated in Field Trials in USDA Growth Zone 11 During Winter.

Certain events that had higher levels of EPA and DHA were tested in the field and examined for fatty acid profile, aerial phenotype (if any) and copy number in the T1 generation. A variety of constructs were examined including those with partial double copy insertions, single copy insertions and double copy insertions being represented (see Table 144). Table 145 indicates that LBFDAU had an EPA content of ca. 13% and a DHA content of ca. 3% of the total seed fatty acid content, and a maximum content for DHA of 3.6% and EPA of 17% of total seed fatty acids (Table 146). Measurements of single seeds from LBFDAU had as much as 26% EPA and 4.6% DHA, see Table 147. Overall the field performance of LBFDAU matched or exceeded that of the greenhouse.

TABLE 144

Copy number measurement of T1 plants cultivated in field, corresponding to USDA growth zone 11, during the winter for field trials of canola events containing the T-DNAs of plasmids VC-LTM593-1qcz rc. The events are indicated in the first column, along with the number of T1 plants that where measured per event. The T1 plants underwent a selection from ~80 segregating T1 seedlings, using zygocity analysis similar to the selection performed in the greenhouse (which was illustrated in Table 137), keeping only plants that are homozygous for the desired number of loci. A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result oberved in the T0 generation (indicated in parentheses). For some events this was not the case because during selection of T1 plants, undesired loci have been segregated out while retaining only desired loci in a homozygous state.

Copy number assays targeting the T-DNA of VC-LTM593-1qcz rc. Assays are listed according to the position of the assay target along the T-DNA, with target c-AHAS located near the left T-DNA border and target c-d6Elo(Pp_GA) near the right T-DNA border.

| Event | c-AHAS | j-i-Atss1_c-d5Elo(Ot_GA3) | c-d4Des(Pl_GA)2 | j-p-LuPXR_i-Atss15 | j-p-PvARC5_t-BnSETL | c-d5Des(Tc_GA) | j-i-Atss18_c-o3Des(Pi_GA2) | j-p-BnSETL-v1_c-o3Des(Pir_GA) |
|---|---|---|---|---|---|---|---|---|
| LBFDGG (n = 5) | 2 (T0: 1.1) | | | | | | | |
| LBFGKN (n = 12) | 2.1 (T0: 1) | | | | | | | |
| LBFIHE (n = 8) | 2.1 (T0: 1) | | | | | | | |
| LBFLDI (n = 13) | 2 (T0: 1) | | | | | | | |
| LBFPNF (n = 9) | 2 (T0: 1.1) | | | | | | | |
| LBFDAU (n = 4) | 2 (T0: 1.1) | | | | | | | |
| LBFPRA (n = 5) | 3.2 (T0: 2) | | | | | | | |
| LBFLFK (n = 4) | 3.9 (T0: 2) | | | | | | | |
| LBFLCG (n = 3) | 4.3 (T0: 1.9) | | | | | | | |
| LBFPQM (n = 1) | 3.7 (T0: 2) | | | | | | | |

Copy number assays targeting the T-DNA of VC-LTM593-1qcz rc. Assays are listed according to the position of the assay target along the T-DNA, with target c-AHAS located near the left T-DNA border and target c-d6Elo(Pp_GA) near the right T-DNA border.

| Event | j-i-Atss14_c-d12Des(Ps_GA) | c-d6Elo(Tp_GA) | j-t-StCAT_p2_p-LuPXR | j-i-Atss2_c-d6Des(Otfebit_GA) | c-d5Des(Tc_GA) | c-d6Elo(Pp_GA) | Conclusion from individual assays: number of T-DNA copies inserted into the genome |
|---|---|---|---|---|---|---|---|
| LBFDGG (n = 5) | | | 1.9 (T0: 1) | | | 1.9 (T0: 1) | single copy |
| LBFGKN (n = 12) | | | 2 (T0: 1) | | | 1.9 (T0: 1.1) | single copy |
| LBFIHE (n = 8) | | | 1.9 (T0: 1.2) | | | 1.9 (T0: 1.1) | single copy |
| LBFLDI (n = 13) | | | 1.9 (T0: 1) | | | 1.8 (T0: 1) | single copy |
| LBFPNF (n = 9) | | | 3.7 (T0: 1.9) | | | 3.3 (T0: 1.9) | partial double copy |
| LBFDAU (n = 4) | | | 3.8 (T0: 2.4) | | | 3.6 (T0: 1.9) | partial double copy |
| LBFPRA (n = 5) | | | 4.9 (T0: 3.1) | | | 4 (T0: 2.8) | partial double copy |
| LBFLFK (n = 4) | | | 3.4 (T0: 2.4) | | | 3.4 (T0: 2) | partial double copy |
| LBFLCG (n = 3) | | | 2.9 (T0: 2.5) | | | 3.4 (T0: 2) | partial double copy |
| LBFPQM (n = 1) | | | (T0: 2) | | | 3.9 (T0: 1.8) | partial double copy |

TABLE 145

Fatty acid profiles of T2 seeds harvested from T1 cultivated in the field, corresponding to USDA growth zone 11, during winter of canola events containing the T-DNAs of plasmids VC-LTM593-1qcz rc. The events are indicated in the first column, along with the number of T2 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LBFDGG (n = 5) | 4.4 ± 0.2 | 0.2 ± 0 | 0.1 ± 0 | 2.4 ± 0.1 | 32.3 ± 1.9 | 34.4 ± 1.6 | 0.7 ± 0 | 5.3 ± 0.6 | 1.5 ± 0.1 |
| LBFGKN (n = 12) | 4.8 ± 0.3 | 0.2 ± 0 | 0.1 ± 0 | 2.6 ± 0.3 | 27.8 ± 1.9 | 36 ± 1.3 | 0.5 ± 0.1 | 4.8 ± 0.7 | 1.5 ± 0.2 |
| LBFIHE (n = 8) | 4.9 ± 0.8 | 0.3 ± 0.1 | 0.1 ± 0 | 2.4 ± 0.4 | 30.8 ± 3.1 | 36.1 ± 1.2 | 0.5 ± 0.1 | 5.4 ± 1.3 | 1.5 ± 0.5 |
| LBFLDI (n = 13) | 4.5 ± 1.1 | 0.2 ± 0.1 | 0.1 ± 0 | 2.3 ± 0.6 | 30 ± 5.9 | 35.4 ± 6.1 | 0.5 ± 0.1 | 4.1 ± 0.8 | 1.3 ± 0.3 |
| LBFPNF (n = 9) | 4.7 ± 0.2 | 0.2 ± 0 | 0.1 ± 0 | 2.4 ± 0.3 | 29.2 ± 1.8 | 31.7 ± 1 | 1.1 ± 0.1 | 4 ± 0.6 | 2.6 ± 1.4 |
| LBFDAU (n = 4) | 4.6 ± 0.2 | 0.2 ± 0 | 0.1 ± 0 | 2.3 ± 0.3 | 24.3 ± 3.7 | 31.2 ± 2.5 | 0.8 ± 0.1 | 5.2 ± 0.6 | 2.2 ± 0.5 |
| LBFPRA (n = 5) | 4.8 ± 0.2 | 0.2 ± 0 | 0.1 ± 0 | 2.5 ± 0.4 | 25.1 ± 0.9 | 34.5 ± 2.4 | 0.9 ± 0.2 | 4.4 ± 0.7 | 2.2 ± 0.2 |
| LBFLFK (n = 4) | 5.1 ± 0.8 | 0.2 ± 0.1 | 0.1 ± 0 | 2.1 ± 0.4 | 2.7 ± 4.3 | 32.3 ± 0.5 | 0.8 ± 0.1 | 5.4 ± 0.8 | 1.9 ± 0.5 |
| LBFLCG (n = 3) | 4.8 ± 0.2 | 0.2 ± 0 | 0.1 ± 0 | 3 ± 0.3 | 26.4 ± 1.3 | 33.3 ± 1 | 0.8 ± 0 | 4.7 ± 0.7 | 2 ± 0.2 |
| LBFPQM (n = 1) | 5.0 | 0.2 | 0.1 | 2.7 | 26.1 | 30.8 | 1.0 | 4.3 | 2.3 |

| Event | 18:4 n-3 | 20:0 | 20:1 n-9 | 20:2 n-6 | 20:3 n-3 | 20:3 n-6 | 20:4 n-3 | 20:4 n-6 | 20:5 n-3 |
|---|---|---|---|---|---|---|---|---|---|
| LBFDGG (n = 5) | 0.4 ± 0.1 | 0.6 ± 0 | 0.7 ± 0 | 0.1 ± 0 | 0 ± 0 | 2 ± 0.2 | 1.1 ± 0.2 | 2.7 ± 0.3 | 6.9 ± 0.7 |
| LBFGKN (n = 12) | 0.4 ± 0.1 | 0.7 ± 0.1 | 0.7 ± 0 | 0.2 ± 0.1 | 0.1 ± 0 | 2.3 ± 0.2 | 1.1 ± 0.2 | 3.3 ± 0.4 | 8 ± 0.8 |
| LBFIHE (n = 8) | 0.3 ± 0.1 | 0.7 ± 0.1 | 0.7 ± 0.1 | 0.2 ± 0 | 0.1 ± 0 | 1.9 ± 0.5 | 0.9 ± 0.1 | 2.8 ± 0.7 | 6.4 ± 1.1 |
| LBFLDI (n = 13) | 0.3 ± 0.1 | 0.6 ± 0.1 | 0.7 ± 0.1 | 0.2 ± 0.1 | 0.1 ± 0 | 1.9 ± 0.5 | 0.8 ± 0.2 | 2.9 ± 0.8 | 6.4 ± 1.6 |
| LBFPNF (n = 9) | 0.6 ± 0.1 | 0.7 ± 0 | 0.7 ± 0 | 0.1 ± 0 | 0 ± 0 | 3.3 ± 0.4 | 1.2 ± 0.1 | 4.2 ± 0.5 | 8.4 ± 1.1 |
| LBFDAU (n = 4) | 0.4 ± 0.1 | 0.6 ± 0 | 0.7 ± 0.1 | 0.1 ± 0 | 0.1 ± 0 | 2.5 ± 0.4 | 1.7 ± 0.5 | 2.9 ± 0.4 | 13.4 ± 3.4 |
| LBFPRA (n = 5) | 0.4 ± 0.1 | 0.6 ± 0.1 | 0.7 ± 0 | 0.1 ± 0 | 0.1 ± 0 | 2.6 ± 0.6 | 1.3 ± 0.3 | 3.6 ± 0.6 | 10.7 ± 1.9 |
| LBFLFK (n = 4) | 0.4 ± 0 | 0.6 ± 0.1 | 0.7 ± 0.1 | 0.2 ± 0 | 0.1 ± 0 | 3.1 ± 0.6 | 1.7 ± 0.3 | 2.7 ± 0.5 | 9.5 ± 1.8 |
| LBFLCG (n = 3) | 0.5 ± 0.1 | 0.7 ± 0 | 0.7 ± 0 | 0.1 ± 0 | 0.1 ± 0 | 2.3 ± 0.1 | 1.2 ± 0.1 | 2.9 ± 0.2 | 9.9 ± 0.9 |
| LBFPQM (n = 1) | 0.5 | 0.7 | 0.6 | 0.1 | 0.1 | 3.4 | 1.8 | 2.8 | 10.8 |

| Event | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|
| LBFDGG (n = 5) | 0.3 ± 0 | 0 ± 0 | 0.3 ± 0 | 1.9 ± 0.2 | 0.1 ± 0 | 1.4 ± 0.3 | 0 ± 0 | 0.1 ± 0 |
| LBFGKN (n = 12) | 0.3 ± 0.1 | 0 ± 0 | 0.4 ± 0.1 | 1.9 ± 0.3 | 0.1 ± 0 | 1.8 ± 0.4 | 0.1 ± 0 | 0.2 ± 0 |
| LBFIHE (n = 8) | 0.3 ± 0 | 0 ± 0 | 0.5 ± 0.1 | 1.7 ± 0.3 | 0.1 ± 0 | 1.3 ± 0.2 | 0 ± 0.1 | 0.1 ± 0 |
| LBFLDI (n = 13) | 0.3 ± 0.1 | 0 ± 0 | 0.4 ± 0.1 | 1.6 ± 0.3 | 0.1 ± 0.1 | 1.3 ± 0.4 | 0.1 ± 0 | 0.1 ± 0 |
| LBFPNF (n = 9) | 0.3 ± 0 | 0 ± 0 | 0.5 ± 0.1 | 2.3 ± 0.4 | 0.1 ± 0 | 1.5 ± 0.3 | 0.1 ± 0.1 | 0.1 ± 0 |
| LBFDAU (n = 4) | 0.3 ± 0 | 0 ± 0 | 0.3 ± 0 | 2.7 ± 0.7 | 0.1 ± 0 | 2.7 ± 0.7 | 0.1 ± 0.1 | 0.2 ± 0 |
| LBFPRA (n = 5) | 0.3 ± 0 | 0 ± 0 | 0.5 ± 0.1 | 2.3 ± 0.3 | 0.1 ± 0 | 1.7 ± 0.2 | 0.1 ± 0.1 | 0.2 ± 0.1 |
| LBFLFK (n = 4) | 0.3 ± 0 | 0 ± 0 | 0.5 ± 0.2 | 2.9 ± 0.4 | 0.2 ± 0.1 | 2.1 ± 0.5 | 0.3 ± 0.1 | 0.2 ± 0 |
| LBFLCG (n = 3) | 0.3 ± 0 | 0 ± 0 | 0.7 ± 0.1 | 2.6 ± 0.3 | 0.2 ± 0 | 2.3 ± 0.5 | 0.2 ± 0 | 0.2 ± 0 |
| LBFPQM (n = 1) | 0.3 | 0.0 | 0.5 | 2.5 | 0.3 | 2.5 | 0.4 | 0.2 |

TABLE 146

Fatty acid profiles of one T2 seed batch per event harvested from T1 plants cultivated in the field, corresponding to USDA growth zone 11, during winter of canola events containing the T-DNAs of plasmids VC-LTM593-1qcz rc. The events are indicated in the first column. Fatty acid profiles of T2 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDGG (n = 1) | 4.5 | 0.21 | 0.1 | 2.4 | 29.86 | 33.45 | 0.71 | 5.74 | 1.69 | 0.45 | 0.62 | 0.74 | 0.12 |
| LBFGKN (n = 1) | 4.5 | 0.21 | 0.09 | 2.28 | 26.68 | 34.29 | 0.65 | 4.99 | 1.73 | 0.42 | 0.61 | 0.69 | 0.23 |
| LBFIHE (n = 1) | 4.8 | 0.22 | 0.09 | 2.95 | 26.2 | 38.09 | 0.52 | 3.19 | 2.12 | 0.22 | 0.78 | 0.69 | 0.15 |
| LBFLDI (n = 1) | 4.8 | 0.24 | 0.09 | 2.51 | 27.6 | 35.76 | 0.54 | 4.15 | 1.66 | 0.26 | 0.7 | 0.69 | 0.29 |
| LBFPNF (n = 1) | 4.9 | 0.27 | 0.13 | 2.11 | 26.29 | 31.14 | 0.91 | 5.04 | 1.72 | 0.68 | 0.67 | 0.7 | 0.11 |
| LBFDAU (n = 1) | 4.8 | 0.23 | 0.14 | 1.94 | 20.37 | 28.27 | 0.98 | 5.23 | 2.78 | 0.5 | 0.63 | 0.62 | 0.13 |
| LBFPRA (n = 1) | 4.7 | 0.16 | 0.14 | 1.92 | 25.56 | 32.27 | 1.21 | 4.87 | 2.09 | 0.44 | 0.51 | 0.66 | 0.13 |
| LBFLFK (n = 1) | 4.9 | 0.21 | 0.12 | 2.34 | 22.43 | 32.9 | 0.9 | 4.55 | 2.5 | 0.42 | 0.66 | 0.62 | 0.13 |
| LBFLCG (n = 1) | 5.0 | 0.27 | 0.12 | 2.65 | 24.88 | 32.2 | 0.74 | 5.16 | 2.3 | 0.46 | 0.69 | 0.65 | 0.14 |
| LBFPQM (n = 1) | 5.0 | 0.22 | 0.11 | 2.67 | 26.07 | 30.83 | 1.02 | 4.34 | 2.31 | 0.45 | 0.69 | 0.63 | 0.12 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDGG (n = 1) | 0.05 | 2.25 | 1.38 | 2.83 | 8.02 | 0.29 | 0 | 0.35 | 2.21 | 0.1 | 1.79 | 0 | 0.13 |
| LBFGKN (n = 1) | 0.1 | 2.43 | 1.22 | 3.34 | 9.74 | 0.31 | 0 | 0.48 | 2.27 | 0.17 | 2.31 | 0 | 0.23 |
| LBFIHE (n = 1) | 0 | 2.73 | 1.03 | 3.67 | 8.16 | 0.35 | 0 | 0.59 | 1.72 | 0.12 | 1.55 | 0 | 0.09 |
| LBFLDI (n = 1) | 0.1 | 2.63 | 1.16 | 3.5 | 8.32 | 0.31 | 0 | 0.47 | 1.89 | 0.19 | 1.85 | 0.15 | 0.21 |
| LBFPNF (n = 1) | 0.04 | 2.8 | 1.34 | 4.26 | 10.24 | 0.36 | 0 | 0.54 | 3.24 | 0.14 | 2.09 | 0.15 | 0.12 |
| LBFDAU (n = 1) | 0.13 | 3.08 | 2.3 | 2.51 | 17.57 | 0.36 | 0 | 0.29 | 3.16 | 0.09 | 3.62 | 0 | 0.25 |
| LBFPRA (n = 1) | 0.07 | 2.34 | 1.29 | 3.67 | 12.46 | 0.28 | 0 | 0.44 | 2.58 | 0.08 | 1.8 | 0.08 | 0.26 |
| LBFLFK (n = 1) | 0.07 | 3.86 | 2.18 | 2.37 | 11.06 | 0.3 | 0 | 0.76 | 3.2 | 0.24 | 2.66 | 0.46 | 0.21 |
| LBFLCG (n = 1) | 0.09 | 2.24 | 1.36 | 2.85 | 10.87 | 0.31 | 0 | 0.69 | 2.92 | 0.22 | 2.82 | 0.21 | 0.15 |
| LBFPQM (n = 1) | 0.07 | 3.4 | 1.75 | 2.78 | 10.78 | 0.3 | 0 | 0.54 | 2.53 | 0.27 | 2.5 | 0.4 | 0.23 |

TABLE 147

Fatty acid profiles of 95 single seeds of the one seedbatch of event LBFDAU shown in Table 146 having highest EPA + DHA levels.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|---|---|---|---|---|---|---|---|---|---|---|---|---|
| LBFDAU seed 1 | 4.2 | 0.2 | 0.2 | 2.1 | 11.3 | 26.5 | 1.2 | 3.8 | 4.3 | 0.6 | 0.7 | 0.5 | 0.1 | 0.1 | 3.3 | 3.0 | 1.9 | 26.2 | 0.4 | 0.0 | 0.6 | 3.7 | 0.2 | 4.9 | 0.0 | 0.2 |
| LBFDAU seed 2 | 5.5 | 0.3 | 0.1 | 2.5 | 14.3 | 25.0 | 0.8 | 4.5 | 2.5 | 0.5 | 0.7 | 0.5 | 0.2 | 0.1 | 3.0 | 2.5 | 2.5 | 23.6 | 0.5 | 0.0 | 0.5 | 3.8 | 0.3 | 5.8 | 0.0 | 0.2 |
| LBFDAU seed 3 | 5.1 | 0.3 | 0.1 | 2.0 | 16.0 | 25.5 | 1.2 | 4.4 | 3.4 | 0.6 | 0.7 | 0.5 | 0.1 | 0.1 | 3.4 | 2.5 | 2.5 | 23.1 | 0.3 | 0.0 | 0.6 | 3.3 | 0.1 | 4.2 | 0.0 | 0.2 |
| LBFDAU seed 4 | 6.7 | 0.4 | 0.2 | 3.8 | 15.8 | 23.5 | 1.5 | 4.9 | 3.3 | 0.9 | 1.2 | 0.5 | 0.0 | 0.0 | 1.7 | 1.3 | 1.9 | 21.2 | 0.7 | 0.0 | 0.8 | 3.5 | 0.4 | 5.8 | 0.0 | 0.2 |
| LBFDAU seed 5 | 5.4 | 0.4 | 0.2 | 1.5 | 16.1 | 24.4 | 1.0 | 5.4 | 3.4 | 0.8 | 0.6 | 0.5 | 0.1 | 0.1 | 2.9 | 2.1 | 3.5 | 22.0 | 0.3 | 0.0 | 0.5 | 3.7 | 0.2 | 4.8 | 0.0 | 0.2 |
| LBFDAU seed 6 | 5.5 | 0.3 | 0.1 | 1.9 | 16.6 | 25.6 | 0.9 | 5.4 | 3.3 | 0.7 | 0.6 | 0.5 | 0.1 | 0.1 | 2.9 | 2.1 | 2.4 | 21.8 | 0.4 | 0.0 | 0.4 | 3.4 | 0.2 | 4.4 | 0.0 | 0.2 |
| LBFDAU seed 7 | 5.0 | 0.4 | 0.2 | 2.4 | 16.3 | 25.3 | 1.1 | 4.6 | 3.5 | 0.6 | 0.7 | 0.5 | 0.1 | 0.1 | 3.6 | 3.1 | 2.0 | 21.9 | 0.5 | 0.0 | 0.5 | 3.5 | 0.0 | 4.3 | 0.0 | 0.1 |
| LBFDAU seed 8 | 5.3 | 0.3 | 0.1 | 2.3 | 17.4 | 26.0 | 1.2 | 4.1 | 3.7 | 0.7 | 0.7 | 0.5 | 0.1 | 0.1 | 2.6 | 2.0 | 2.7 | 21.7 | 0.5 | 0.0 | 0.4 | 3.1 | 0.2 | 4.0 | 0.0 | 0.2 |
| LBFDAU seed 9 | 5.3 | 0.2 | 0.2 | 2.4 | 14.3 | 27.8 | 1.0 | 4.0 | 4.2 | 0.6 | 0.7 | 0.5 | 0.1 | 0.1 | 3.6 | 2.9 | 2.3 | 21.1 | 0.4 | 0.0 | 0.5 | 2.8 | 0.3 | 4.4 | 0.0 | 0.1 |
| LBFDAU seed 10 | 6.7 | 0.5 | 0.2 | 2.8 | 15.8 | 23.3 | 0.8 | 5.7 | 2.9 | 0.8 | 0.9 | 0.5 | 0.0 | 0.0 | 3.1 | 2.4 | 2.2 | 19.8 | 0.8 | 0.0 | 0.6 | 4.7 | 0.1 | 5.4 | 0.0 | 0.0 |
| LBFDAU seed 11 | 5.9 | 0.6 | 0.2 | 3.4 | 19.3 | 22.2 | 1.5 | 4.0 | 3.1 | 0.7 | 0.9 | 0.6 | 0.0 | 0.1 | 3.0 | 2.1 | 2.0 | 20.8 | 0.8 | 0.0 | 0.2 | 4.6 | 0.0 | 4.2 | 0.0 | 0.0 |
| LBFDAU seed 12 | 5.2 | 0.4 | 0.2 | 2.2 | 16.1 | 25.2 | 0.8 | 5.5 | 3.3 | 0.7 | 0.8 | 0.5 | 0.1 | 0.1 | 3.7 | 2.9 | 2.4 | 20.1 | 0.4 | 0.0 | 0.4 | 4.2 | 0.2 | 4.7 | 0.0 | 0.2 |
| LBFDAU seed 13 | 4.3 | 0.2 | 0.1 | 2.0 | 17.5 | 27.7 | 1.2 | 4.9 | 2.9 | 0.5 | 0.6 | 0.6 | 0.1 | 0.1 | 2.9 | 2.3 | 2.6 | 20.7 | 0.3 | 0.0 | 0.4 | 3.6 | 0.2 | 4.1 | 0.0 | 0.2 |
| LBFDAU seed 14 | 4.2 | 0.3 | 0.1 | 2.0 | 16.4 | 27.9 | 0.9 | 5.1 | 2.9 | 0.7 | 0.6 | 0.5 | 0.1 | 0.1 | 3.5 | 3.2 | 2.0 | 20.5 | 0.3 | 0.0 | 0.4 | 3.7 | 0.1 | 4.3 | 0.0 | 0.2 |
| LBFDAU seed 15 | 4.5 | 0.4 | 0.1 | 1.5 | 17.0 | 25.7 | 1.1 | 5.3 | 2.9 | 0.6 | 0.5 | 0.6 | 0.1 | 0.1 | 3.4 | 2.4 | 2.9 | 19.7 | 0.3 | 0.0 | 0.5 | 4.8 | 0.3 | 5.1 | 0.0 | 0.3 |
| LBFDAU seed 16 | 4.7 | 0.6 | 0.2 | 2.0 | 17.2 | 25.9 | 1.1 | 5.9 | 3.0 | 0.7 | 0.7 | 0.5 | 0.1 | 0.0 | 3.2 | 2.6 | 2.3 | 20.1 | 0.6 | 0.0 | 0.7 | 3.4 | 0.1 | 4.3 | 0.0 | 0.2 |
| LBFDAU seed 17 | 4.5 | 0.3 | 0.1 | 2.3 | 18.4 | 27.0 | 1.5 | 4.6 | 3.4 | 0.7 | 0.7 | 0.6 | 0.1 | 0.0 | 2.7 | 1.9 | 2.8 | 20.8 | 0.5 | 0.0 | 0.6 | 2.8 | 0.1 | 3.5 | 0.0 | 0.2 |
| LBFDAU seed 18 | 5.1 | 0.2 | 0.2 | 2.9 | 16.1 | 27.1 | 1.5 | 4.7 | 4.2 | 0.7 | 0.7 | 0.6 | 0.1 | 0.0 | 2.3 | 2.3 | 2.1 | 19.5 | 0.7 | 0.0 | 0.4 | 3.4 | 0.0 | 4.8 | 0.0 | 0.2 |
| LBFDAU seed 19 | 4.5 | 0.3 | 0.1 | 1.7 | 18.7 | 27.0 | 1.4 | 4.5 | 2.9 | 0.4 | 0.5 | 0.6 | 0.1 | 0.1 | 3.1 | 2.1 | 2.9 | 19.8 | 0.2 | 0.0 | 0.5 | 3.7 | 0.2 | 4.3 | 0.0 | 0.4 |
| LBFDAU seed 20 | 5.3 | 0.2 | 0.1 | 2.6 | 17.9 | 26.4 | 1.1 | 4.4 | 2.9 | 0.5 | 0.7 | 0.6 | 0.1 | 0.1 | 3.4 | 2.7 | 2.3 | 20.8 | 0.3 | 0.0 | 0.7 | 3.0 | 0.1 | 3.3 | 0.0 | 0.2 |
| LBFDAU seed 21 | 5.2 | 0.3 | 0.2 | 2.1 | 16.3 | 27.8 | 0.7 | 5.1 | 3.5 | 0.7 | 0.7 | 0.6 | 0.2 | 0.1 | 3.1 | 2.4 | 2.7 | 19.7 | 0.4 | 0.0 | 0.5 | 3.6 | 0.2 | 4.0 | 0.0 | 0.1 |
| LBFDAU seed 22 | 4.8 | 0.2 | 0.1 | 2.4 | 17.7 | 28.9 | 0.9 | 4.9 | 3.1 | 0.5 | 0.7 | 0.6 | 0.1 | 0.1 | 2.4 | 2.1 | 3.1 | 19.9 | 0.3 | 0.0 | 0.4 | 3.0 | 0.1 | 3.8 | 0.0 | 0.2 |
| LBFDAU seed 23 | 4.5 | 0.2 | 0.1 | 1.6 | 19.4 | 26.9 | 1.3 | 5.6 | 2.8 | 0.5 | 0.5 | 0.7 | 0.1 | 0.1 | 3.0 | 2.3 | 2.7 | 19.1 | 0.2 | 0.0 | 0.4 | 3.7 | 0.1 | 3.7 | 0.0 | 0.2 |
| LBFDAU seed 24 | 6.6 | 0.6 | 0.2 | 3.4 | 18.4 | 23.0 | 1.0 | 3.9 | 4.6 | 1.1 | 1.1 | 0.7 | 0.0 | 0.0 | 3.6 | 2.0 | 1.6 | 17.9 | 0.7 | 0.0 | 0.9 | 3.7 | 0.0 | 4.8 | 0.0 | 0.0 |
| LBFDAU seed 25 | 5.2 | 0.3 | 0.2 | 2.1 | 16.0 | 26.6 | 0.9 | 4.9 | 3.7 | 0.8 | 0.7 | 0.6 | 0.1 | 0.0 | 3.9 | 2.6 | 2.8 | 18.0 | 0.6 | 0.0 | 0.7 | 4.6 | 0.3 | 4.4 | 0.0 | 0.1 |
| LBFDAU seed 26 | 5.5 | 0.6 | 0.2 | 2.6 | 19.9 | 23.4 | 2.1 | 3.8 | 3.0 | 0.6 | 0.8 | 0.6 | 0.0 | 0.0 | 4.0 | 2.0 | 2.8 | 18.5 | 0.6 | 0.0 | 1.0 | 3.8 | 0.2 | 3.9 | 0.0 | 0.2 |
| LBFDAU seed 27 | 4.5 | 0.3 | 0.1 | 1.7 | 19.5 | 26.6 | 1.5 | 5.2 | 2.3 | 0.5 | 0.5 | 0.6 | 0.1 | 0.1 | 3.6 | 2.5 | 2.6 | 18.6 | 0.3 | 0.0 | 0.5 | 4.1 | 0.2 | 3.8 | 0.0 | 0.4 |

TABLE 147-continued

Fatty acid profiles of 95 single seeds of the one seedbatch of event LBFDAU shown in Table 146 having highest EPA + DHA levels.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|---|---|---|---|---|---|---|---|---|---|---|---|---|
| LBFDAU seed 28 | 5.1 | 0.3 | 0.2 | 2.5 | 17.2 | 27.3 | 0.8 | 4.6 | 2.9 | 0.5 | 0.9 | 0.5 | 0.1 | 0.0 | 3.7 | 2.3 | 3.6 | 18.6 | 0.5 | 0.0 | 0.5 | 3.7 | 0.2 | 3.8 | 0.0 | 0.2 |
| LBFDAU seed 29 | 5.0 | 0.3 | 0.2 | 3.2 | 20.0 | 28.0 | 1.3 | 4.7 | 2.9 | 0.5 | 0.9 | 0.6 | 0.1 | 0.0 | 2.2 | 1.5 | 2.3 | 18.5 | 0.4 | 0.0 | 0.5 | 2.8 | 0.2 | 3.6 | 0.0 | 0.2 |
| LBFDAU seed 30 | 4.7 | 0.2 | 0.1 | 2.4 | 18.6 | 29.3 | 1.6 | 4.4 | 3.2 | 0.5 | 0.7 | 0.6 | 0.1 | 0.1 | 2.9 | 2.1 | 2.5 | 18.6 | 0.3 | 0.0 | 0.7 | 2.7 | 0.2 | 3.2 | 0.0 | 0.2 |
| LBFDAU seed 31 | 4.9 | 0.3 | 0.1 | 2.5 | 18.8 | 28.0 | 1.5 | 4.1 | 3.0 | 0.4 | 0.8 | 0.6 | 0.1 | 0.1 | 3.9 | 2.8 | 1.8 | 18.2 | 0.4 | 0.0 | 0.6 | 3.1 | 0.2 | 3.6 | 0.0 | 0.3 |
| LBFDAU seed 32 | 4.8 | 0.3 | 0.1 | 2.2 | 19.6 | 28.3 | 1.0 | 5.5 | 2.6 | 0.5 | 0.6 | 0.6 | 0.1 | 0.1 | 3.1 | 2.5 | 2.4 | 18.3 | 0.3 | 0.0 | 0.4 | 3.1 | 0.1 | 3.4 | 0.0 | 0.2 |
| LBFDAU seed 33 | 4.6 | 0.3 | 0.1 | 2.3 | 19.6 | 28.4 | 1.3 | 5.2 | 3.1 | 0.6 | 0.8 | 0.6 | 0.1 | 0.0 | 2.7 | 2.0 | 2.4 | 18.2 | 0.4 | 0.0 | 0.5 | 3.1 | 0.1 | 3.5 | 0.0 | 0.2 |
| LBFDAU seed 34 | 4.9 | 0.3 | 0.1 | 3.4 | 19.2 | 25.9 | 1.8 | 4.0 | 3.1 | 0.5 | 1.0 | 0.7 | 0.1 | 0.0 | 3.9 | 2.7 | 2.1 | 17.9 | 0.5 | 0.0 | 0.6 | 3.0 | 0.2 | 3.7 | 0.0 | 0.3 |
| LBFDAU seed 35 | 4.6 | 0.3 | 0.2 | 2.0 | 19.1 | 28.5 | 1.1 | 5.7 | 3.0 | 0.6 | 0.6 | 0.6 | 0.1 | 0.1 | 3.0 | 2.3 | 2.6 | 17.9 | 0.3 | 0.0 | 0.4 | 3.3 | 0.1 | 3.6 | 0.0 | 0.2 |
| LBFDAU seed 36 | 4.2 | 0.2 | 0.1 | 2.1 | 18.1 | 30.5 | 1.0 | 4.9 | 2.9 | 0.5 | 0.6 | 0.6 | 0.1 | 0.1 | 3.5 | 3.0 | 2.1 | 17.6 | 0.3 | 0.0 | 0.4 | 3.2 | 0.1 | 3.8 | 0.0 | 0.2 |
| LBFDAU seed 37 | 4.9 | 0.2 | 0.1 | 2.0 | 19.0 | 29.0 | 1.1 | 5.0 | 3.0 | 0.4 | 0.6 | 0.6 | 0.1 | 0.1 | 3.1 | 2.2 | 2.9 | 17.8 | 0.3 | 0.0 | 0.4 | 3.0 | 0.2 | 3.5 | 0.0 | 0.2 |
| LBFDAU seed 38 | 4.4 | 0.3 | 0.1 | 1.9 | 19.7 | 29.9 | 1.2 | 4.5 | 2.6 | 0.4 | 0.6 | 0.5 | 0.1 | 0.1 | 3.0 | 2.0 | 2.6 | 17.8 | 0.3 | 0.0 | 0.5 | 3.4 | 0.2 | 3.5 | 0.0 | 0.2 |
| LBFDAU seed 39 | 4.8 | 0.2 | 0.1 | 2.2 | 19.2 | 28.6 | 1.0 | 5.0 | 2.4 | 0.4 | 0.6 | 0.6 | 0.1 | 0.1 | 4.0 | 3.2 | 1.9 | 17.8 | 0.3 | 0.0 | 0.5 | 3.1 | 0.1 | 3.4 | 0.0 | 0.2 |
| LBFDAU seed 40 | 4.3 | 0.2 | 0.1 | 1.8 | 20.2 | 28.8 | 1.4 | 4.8 | 2.6 | 0.4 | 0.6 | 0.6 | 0.1 | 0.1 | 3.2 | 2.2 | 2.5 | 17.7 | 0.3 | 0.0 | 0.5 | 3.6 | 0.2 | 3.5 | 0.0 | 0.3 |
| LBFDAU seed 41 | 5.8 | 0.4 | 0.2 | 3.0 | 19.3 | 26.9 | 0.9 | 4.6 | 3.6 | 0.7 | 1.0 | 0.6 | 0.0 | 0.0 | 3.1 | 1.8 | 2.1 | 17.7 | 0.7 | 0.0 | 1.0 | 3.1 | 0.1 | 3.5 | 0.0 | 0.0 |
| LBFDAU seed 42 | 4.6 | 0.3 | 0.1 | 2.3 | 21.3 | 27.8 | 1.2 | 5.2 | 2.8 | 0.6 | 0.6 | 0.6 | 0.1 | 0.1 | 2.7 | 2.1 | 2.3 | 18.0 | 0.3 | 0.0 | 0.7 | 2.9 | 0.1 | 3.2 | 0.0 | 0.2 |
| LBFDAU seed 43 | 5.3 | 0.3 | 0.2 | 2.0 | 18.1 | 29.2 | 1.0 | 4.2 | 3.1 | 0.5 | 0.7 | 0.7 | 0.1 | 0.1 | 3.4 | 2.1 | 3.7 | 17.6 | 0.3 | 0.0 | 0.5 | 3.5 | 0.2 | 3.4 | 0.0 | 0.2 |
| LBFDAU seed 44 | 4.7 | 0.3 | 0.2 | 1.9 | 19.3 | 29.3 | 1.0 | 5.7 | 2.7 | 0.5 | 0.7 | 0.6 | 0.1 | 0.1 | 2.7 | 2.1 | 2.6 | 17.3 | 0.3 | 0.0 | 0.5 | 3.6 | 0.2 | 3.6 | 0.0 | 0.2 |
| LBFDAU seed 45 | 4.3 | 0.2 | 0.1 | 2.2 | 19.4 | 29.8 | 1.1 | 5.0 | 2.5 | 0.4 | 0.7 | 0.6 | 0.1 | 0.1 | 3.3 | 2.6 | 2.4 | 17.7 | 0.3 | 0.0 | 0.5 | 3.2 | 0.2 | 3.2 | 0.0 | 0.2 |
| LBFDAU seed 46 | 4.5 | 0.2 | 0.2 | 2.4 | 18.8 | 29.0 | 1.1 | 5.0 | 3.7 | 0.6 | 0.6 | 0.5 | 0.1 | 0.1 | 3.1 | 2.5 | 2.8 | 17.1 | 0.3 | 0.0 | 0.5 | 3.1 | 0.2 | 3.5 | 0.0 | 0.2 |
| LBFDAU seed 47 | 4.0 | 0.2 | 0.2 | 1.8 | 19.2 | 30.1 | 1.3 | 4.9 | 2.9 | 0.4 | 0.6 | 0.6 | 0.1 | 0.1 | 3.5 | 2.3 | 2.6 | 17.0 | 0.3 | 0.0 | 0.5 | 3.5 | 0.2 | 3.2 | 0.0 | 0.3 |
| LBFDAU seed 48 | 4.3 | 0.2 | 0.1 | 2.0 | 20.0 | 30.1 | 1.3 | 4.5 | 2.7 | 0.4 | 0.6 | 0.6 | 0.1 | 0.1 | 3.5 | 3.3 | 2.7 | 16.9 | 0.3 | 0.0 | 0.4 | 3.1 | 0.2 | 3.5 | 0.0 | 0.3 |
| LBFDAU seed 49 | 4.4 | 0.2 | 0.1 | 2.5 | 18.3 | 30.1 | 1.6 | 3.7 | 3.2 | 0.5 | 0.8 | 0.6 | 0.1 | 0.1 | 4.3 | 2.1 | 2.0 | 17.2 | 0.4 | 0.0 | 0.4 | 2.5 | 0.2 | 3.2 | 0.0 | 0.2 |
| LBFDAU seed 50 | 4.3 | 0.3 | 0.1 | 1.9 | 21.5 | 29.2 | 1.3 | 5.2 | 2.5 | 0.5 | 0.6 | 0.6 | 0.1 | 0.1 | 2.8 | 2.3 | 2.3 | 17.0 | 0.3 | 0.0 | 0.4 | 3.2 | 0.2 | 3.3 | 0.0 | 0.2 |
| LBFDAU seed 70 | 5.3 | 0.3 | 0.2 | 3.1 | 20.0 | 28.7 | 1.4 | 4.1 | 3.0 | 0.4 | 1.0 | 0.6 | 0.1 | 0.1 | 3.5 | 2.3 | 2.3 | 16.8 | 0.5 | 0.0 | 0.5 | 2.4 | 0.2 | 3.2 | 0.0 | 0.3 |

TABLE 147-continued

Fatty acid profiles of 95 single seeds of the one seedbatch of event LBFDAU shown in Table 146 having highest EPA + DHA levels.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|---|---|---|---|---|---|---|---|---|---|---|---|---|
| LBFDAU seed 71 | 4.2 | 0.2 | 0.1 | 2.0 | 22.1 | 29.1 | 1.7 | 4.9 | 2.3 | 0.3 | 0.6 | 0.6 | 0.1 | 0.1 | 2.9 | 2.3 | 2.2 | 16.7 | 0.3 | 0.0 | 0.7 | 2.7 | 0.2 | 3.3 | 0.0 | 0.3 |
| LBFDAU seed 72 | 4.7 | 0.2 | 0.1 | 2.4 | 21.4 | 28.0 | 2.2 | 4.8 | 2.5 | 0.4 | 0.7 | 0.6 | 0.1 | 0.1 | 3.1 | 2.2 | 2.4 | 17.2 | 0.4 | 0.0 | 0.5 | 2.7 | 0.2 | 2.8 | 0.0 | 0.3 |
| LBFDAU seed 73 | 4.7 | 0.3 | 0.1 | 2.1 | 20.9 | 28.1 | 1.0 | 5.4 | 3.1 | 0.6 | 0.6 | 0.6 | 0.1 | 0.1 | 2.9 | 2.1 | 2.6 | 16.3 | 0.3 | 0.0 | 0.6 | 3.4 | 0.2 | 3.7 | 0.0 | 0.2 |
| LBFDAU seed 74 | 5.0 | 0.2 | 0.1 | 2.1 | 18.5 | 29.7 | 1.6 | 4.8 | 2.9 | 0.5 | 0.7 | 0.6 | 0.1 | 0.1 | 3.9 | 2.9 | 2.4 | 16.7 | 0.3 | 0.0 | 0.5 | 2.8 | 0.2 | 3.3 | 0.0 | 0.2 |
| LBFDAU seed 75 | 4.8 | 0.2 | 0.1 | 1.9 | 20.1 | 29.2 | 1.1 | 5.1 | 2.6 | 0.4 | 0.6 | 0.7 | 0.1 | 0.1 | 3.4 | 2.4 | 2.7 | 16.7 | 0.3 | 0.0 | 0.7 | 3.2 | 0.2 | 3.2 | 0.0 | 0.2 |
| LBFDAU seed 76 | 4.3 | 0.2 | 0.1 | 1.9 | 21.6 | 28.7 | 1.5 | 5.1 | 2.6 | 0.4 | 0.5 | 0.6 | 0.1 | 0.1 | 3.3 | 2.3 | 2.6 | 16.6 | 0.3 | 0.0 | 0.6 | 2.9 | 0.2 | 3.3 | 0.0 | 0.4 |
| LBFDAU seed 77 | 4.7 | 0.3 | 0.2 | 1.9 | 19.0 | 31.0 | 0.7 | 4.6 | 2.7 | 0.5 | 0.6 | 0.6 | 0.1 | 0.0 | 3.3 | 2.2 | 2.5 | 16.1 | 0.4 | 0.0 | 0.6 | 3.8 | 0.3 | 3.7 | 0.0 | 0.1 |
| LBFDAU seed 78 | 4.3 | 0.2 | 0.1 | 2.1 | 21.0 | 29.5 | 1.4 | 5.1 | 2.6 | 0.4 | 0.6 | 0.6 | 0.1 | 0.1 | 3.4 | 2.5 | 2.3 | 16.7 | 0.3 | 0.0 | 0.4 | 3.1 | 0.1 | 2.9 | 0.0 | 0.2 |
| LBFDAU seed 79 | 4.5 | 0.3 | 0.1 | 2.0 | 21.0 | 29.6 | 1.4 | 5.5 | 2.5 | 0.5 | 0.6 | 0.6 | 0.1 | 0.1 | 2.7 | 1.9 | 2.7 | 16.2 | 0.3 | 0.0 | 0.5 | 3.2 | 0.2 | 3.5 | 0.0 | 0.3 |
| LBFDAU seed 80 | 5.0 | 0.3 | 0.1 | 2.3 | 20.6 | 28.3 | 0.9 | 5.8 | 2.8 | 0.6 | 0.9 | 0.6 | 0.0 | 0.1 | 3.0 | 2.4 | 2.5 | 16.2 | 0.4 | 0.0 | 0.5 | 3.3 | 0.1 | 3.3 | 0.0 | 0.2 |
| LBFDAU seed 81 | 6.2 | 0.5 | 0.2 | 2.9 | 20.3 | 27.1 | 0.8 | 5.6 | 3.0 | 0.9 | 0.6 | 0.6 | 0.1 | 0.1 | 3.0 | 2.1 | 2.1 | 15.4 | 0.7 | 0.0 | 0.5 | 3.5 | 0.0 | 3.9 | 0.0 | 0.0 |
| LBFDAU seed 82 | 4.1 | 0.2 | 0.1 | 2.2 | 21.5 | 30.4 | 1.4 | 4.8 | 2.6 | 0.4 | 0.6 | 0.6 | 0.1 | 0.1 | 3.1 | 2.4 | 2.3 | 16.1 | 0.4 | 0.0 | 0.5 | 2.6 | 0.2 | 3.1 | 0.0 | 0.4 |
| LBFDAU seed 83 | 4.7 | 0.3 | 0.2 | 2.2 | 20.6 | 30.6 | 1.0 | 5.5 | 2.8 | 0.5 | 0.6 | 0.6 | 0.1 | 0.1 | 2.7 | 2.0 | 2.7 | 15.5 | 0.4 | 0.0 | 0.5 | 2.7 | 0.2 | 3.2 | 0.0 | 0.2 |
| LBFDAU seed 84 | 4.3 | 0.3 | 0.1 | 2.2 | 20.9 | 31.0 | 1.6 | 4.5 | 2.7 | 0.3 | 0.6 | 0.6 | 0.1 | 0.0 | 3.3 | 2.2 | 2.1 | 15.6 | 0.3 | 0.0 | 0.9 | 2.8 | 0.2 | 3.0 | 0.0 | 0.3 |
| LBFDAU seed 85 | 4.1 | 0.2 | 0.1 | 1.9 | 22.2 | 30.6 | 1.3 | 4.6 | 2.5 | 0.5 | 0.5 | 0.6 | 0.1 | 0.0 | 2.9 | 1.7 | 3.1 | 15.6 | 0.3 | 0.0 | 0.7 | 3.0 | 0.2 | 2.9 | 0.0 | 0.3 |
| LBFDAU seed 86 | 4.4 | 0.3 | 0.1 | 2.0 | 21.6 | 30.5 | 1.2 | 5.4 | 2.3 | 0.4 | 0.6 | 0.6 | 0.1 | 0.1 | 2.9 | 2.1 | 2.2 | 15.3 | 0.4 | 0.0 | 0.7 | 3.3 | 0.1 | 3.1 | 0.0 | 0.2 |
| LBFDAU seed 87 | 4.8 | 0.2 | 0.1 | 2.4 | 22.3 | 29.6 | 1.1 | 5.2 | 2.3 | 0.4 | 0.7 | 0.6 | 0.1 | 0.1 | 3.2 | 2.6 | 2.2 | 15.6 | 0.3 | 0.0 | 0.5 | 2.7 | 0.1 | 2.7 | 0.0 | 0.3 |
| LBFDAU seed 88 | 4.8 | 0.2 | 0.1 | 2.2 | 22.0 | 30.2 | 1.3 | 4.9 | 2.7 | 0.6 | 0.6 | 0.6 | 0.1 | 0.0 | 3.2 | 2.2 | 2.5 | 15.1 | 0.4 | 0.0 | 0.4 | 2.5 | 0.2 | 3.0 | 0.0 | 0.3 |
| LBFDAU seed 89 | 5.2 | 0.3 | 0.2 | 2.0 | 20.3 | 29.7 | 1.1 | 5.1 | 3.2 | 0.6 | 0.6 | 0.6 | 0.1 | 0.0 | 3.1 | 1.9 | 3.4 | 14.8 | 0.4 | 0.0 | 0.6 | 3.3 | 0.2 | 3.2 | 0.0 | 0.2 |
| LBFDAU seed 90 | 4.7 | 0.2 | 0.1 | 2.4 | 23.0 | 30.3 | 1.1 | 5.3 | 2.1 | 0.5 | 0.7 | 0.6 | 0.1 | 0.1 | 3.0 | 2.2 | 2.2 | 15.1 | 0.3 | 0.0 | 0.4 | 2.7 | 0.1 | 2.5 | 0.0 | 0.3 |
| LBFDAU seed 91 | 5.0 | 0.3 | 0.2 | 2.3 | 21.9 | 30.6 | 1.3 | 5.2 | 2.4 | 0.7 | 0.8 | 0.6 | 0.1 | 0.1 | 2.9 | 2.1 | 2.4 | 14.7 | 0.4 | 0.0 | 0.4 | 2.7 | 0.2 | 2.8 | 0.0 | 0.3 |
| LBFDAU seed 92 | 4.8 | 0.2 | 0.1 | 2.5 | 24.6 | 29.6 | 1.3 | 5.2 | 2.1 | 0.5 | 0.7 | 0.7 | 0.1 | 0.1 | 3.2 | 2.2 | 2.4 | 13.5 | 0.3 | 0.0 | 0.5 | 2.2 | 0.1 | 2.5 | 0.0 | 0.3 |

C. Fatty Acid Profiles, Copy Number Measurements, and Phenotypic Observations of T2 Plants Carrying T-DNAs of Plasmids VC-LTM593-1qcz rc Cultivated in Greenhouses During the Summer The data in Table 148 indicate the copy number of the selected events was a single insertion which was homozygous in the T3 seed. Fatty acid profile measurements, see Table 149 and Table 150, indicated the combination of T-DNA from VC-LTM593-1qcz rc are capable of bringing in the VLC-PUFA pathway to successfully accumulate ARA, EPA and DHA. The data on Table 151 show that there was no significant impact on the aerial portion of the plant caused by VC-LTM593-1qcz rc.

TABLE 148

Copy number measurement of T2 plants cultivated in the greenhouse of canola events containing the T-DNAs of plasmids VC-LTM593-1qcz rc. The events are indicated in the first column, along with the number of T2 plants that where measured per event. For each event, T2 seedbatches of two homozygous T1 plants where selected for seeding. Comparison of the results with Table 135 confirmes homozygozity of all T2 plants.

Copy number assays targeting the T-DNA of VC-LTM593-1qcz rc. Assays are listed according to the position of the assay target along the T-DNA, with target c-AHAS located near the left T-DNA border and target c-d6Elo(Pp_GA) near the right T-DNA border.

| Event | c-AHAS | j-i-Atss1_c-d5Elo(Ot_GA3) | c-d4Des(Pl_GA)2 | j-p-LuPXR_i-Atss15 | j-p-PvARC5_t-BnSETL | c-d5Des(Tc_GA) | j-i-Atss18_c-o3Des(Pi_GA2) | c-o3Des(Pi_GA) |
|---|---|---|---|---|---|---|---|---|
| LBFDAU (n = 218) | 2.0 | 2.1 | 4.1 | | 3.8 | 8.1 | 4.0 | 4.0 |
| LBFDGG (n = 200) | 2.0 | 2.0 | 2.0 | | 2.0 | 4.0 | 2.0 | 2.0 |
| LBFGKN (n = 182) | 2.0 | 2.0 | 2.0 | | 2.0 | 4.2 | 2.1 | 1.9 |
| LBFIHE (n = 157) | 2.1 | 2.0 | 2.0 | | 2.1 | 4.3 | 2.0 | 2.0 |
| LBFLDI (n = 229) | 2.3 | 2.2 | 2.3 | | 2.3 | 4.7 | 2.3 | 2.3 |
| LBFPRA (n = 196) | 2.0 | 1.9 | 5.8 | | 3.9 | 7.9 | 4.0 | 4.1 |
| LBFDHG (n = 177) | 4.1 | 4.2 | 4.2 | | 4.0 | 8.3 | 4.1 | 4.1 |
| LBFLFK (n = 195) | 4.0 | 4.1 | 4.0 | | 4.0 | 8.2 | 4.0 | 4.0 |

Copy number assays targeting the T-DNA of VC-LTM593-1qcz rc. Assays are listed according to the position of the assay target along the T-DNA, with target c-AHAS located near the left T-DNA border and target c-d6Elo(Pp_GA) near the right T-DNA border.

| Event | j-p-BnSETL-v1_c-o3DES(Pir_GA) | j-i-Atss14_c-d12Des(Ps_GA) | c-d6Elo(Tp_GA) | j-t-StCAT_p2_p-LuPXR | j-i-Atss2_c-d6Des(Otfebit_GA) | c-d5Des(Tc_GA) | c-d6Elo(Pp_GA) | j-i-Atss18_c-d6Elo(Pp_GA2) |
|---|---|---|---|---|---|---|---|---|
| LBFDAU (n = 218) | | | 4.1 | 4.2 | 4.0 | 8.1 | 4.1 | 4.0 |
| LBFDGG (n = 200) | | | 2.1 | 2.1 | 2.0 | 4.0 | 2.2 | 2.1 |
| LBFGKN (n = 182) | | | 2.0 | 2.2 | 2.0 | 4.2 | 2.1 | 2.1 |
| LBFIHE (n = 157) | | | 2.2 | 2.1 | 2.0 | 4.3 | 2.1 | 2.0 |
| LBFLDI (n = 229) | | | 2.4 | 2.4 | 2.3 | 4.7 | 2.4 | 2.2 |
| LBFPRA (n = 196) | | | 3.9 | 4.0 | 3.9 | 7.9 | 4.0 | 1.9 |
| LBFDHG (n = 177) | | | 4.2 | 4.1 | 4.0 | 8.3 | 4.1 | 4.0 |
| LBFLFK (n = 195) | | | 4.0 | 4.0 | 4.0 | 8.2 | 4.0 | 4.0 |

TABLE 149

Fatty acid profiles of T3 seeds harvested from T2 cultivated in the greenhouse of canola events containing the T-DNAs of plasmid VC-LTM593-1qcz rc. The events are indicated in the first column, along with the number of T3 seed batches representing a plant measured per event. Per seed batch a random selection of ~15 seed was measured in five technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LBFDAU (n = 218) | 4.8 ± 0.2 | 0.2 ± 0 | 0 ± 0 | 4.2 ± 0.3 | 23 ± 1.6 | 31.5 ± 1.2 | 1.1 ± 0.2 | 4.6 ± 0.4 | 2.2 ± 0.4 |
| LBFDGG (n = 200) | 5 ± 0.2 | 0.2 ± 0 | 0 ± 0 | 3.2 ± 0.3 | 30.4 ± 2.2 | 34.1 ± 1.6 | 0.8 ± 0.1 | 5 ± 0.5 | 1.6 ± 0.2 |

TABLE 149-continued

Fatty acid profiles of T3 seeds harvested from T2 cultivated in the greenhouse of canola events containing the T-DNAs of plasmid VC-LTM593-1qcz rc. The events are indicated in the first column, along with the number of T3 seed batches representing a plant measured per event. Per seed batch a random selection of ~15 seed was measured in five technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LBFGKN (n = 182) | 4.8 ± 0.2 | 0.2 ± 0 | 0 ± 0 | 3.6 ± 0.4 | 28.3 ± 1.9 | 34.6 ± 1.6 | 0.7 ± 0.2 | 4.7 ± 0.5 | 1.8 ± 0.4 |
| LBFIHE (n = 157) | 4.9 ± 0.3 | 0.2 ± 0 | 0 ± 0 | 3.7 ± 0.6 | 25.9 ± 1.9 | 32.9 ± 1.8 | 0.8 ± 0.1 | 4.7 ± 0.6 | 2.4 ± 0.7 |
| LBFLDI (n = 229) | 5.9 ± 1 | 0.3 ± 0.1 | 0 ± 0.1 | 2.9 ± 0.3 | 27.8 ± 2.5 | 32.5 ± 1.8 | 0.7 ± 0.1 | 4.7 ± 0.5 | 1.7 ± 0.3 |
| LBFPRA (n = 196) | 5 ± 0.2 | 0.2 ± 0 | 0 ± 0 | 3.9 ± 0.7 | 23.2 ± 2 | 30.9 ± 1.9 | 1.1 ± 0.2 | 3.8 ± 0.6 | 2.6 ± 0.5 |
| LBFDHG (n = 177) | 5.7 ± 0.2 | 0.3 ± 0 | 0 ± 0 | 3.2 ± 0.5 | 24.1 ± 0.8 | 34.5 ± 1.4 | 0.8 ± 0.1 | 4.4 ± 0.3 | 2.5 ± 0.5 |
| LBFLFK (n = 195) | 5 ± 0.1 | 0.2 ± 0 | 0.1 ± 0.1 | 4 ± 0.4 | 25.9 ± 1.8 | 31.9 ± 1.3 | 1 ± 0.2 | 4.7 ± 0.4 | 1.8 ± 0.3 |

| Event | 18:4 n-3 | 20:0 | 20:1 n-9 | 20:2 n-6 | 20:3 n-3 | 20:3 n-6 | 20:4 n-3 | 20:4 n-6 | 20:5 n-3 |
|---|---|---|---|---|---|---|---|---|---|
| LBFDAU (n = 218) | 0.4 ± 0.1 | 1 ± 0.1 | 0.7 ± 0 | 0.1 ± 0 | 0.1 ± 0 | 4.5 ± 0.8 | 3.2 ± 0.6 | 1.4 ± 0.3 | 10.5 ± 1.4 |
| LBFDGG (n = 200) | 0.3 ± 0 | 0.9 ± 0.1 | 0.7 ± 0 | 0.1 ± 0 | 0.1 ± 0 | 2.4 ± 0.2 | 1.4 ± 0.2 | 2 ± 0.3 | 7 ± 0.8 |
| LBFGKN (n = 182) | 0.3 ± 0.2 | 0.9 ± 0.1 | 0.7 ± 0 | 0.2 ± 0.1 | 0.1 ± 0 | 2.4 ± 0.3 | 1.3 ± 0.2 | 2.4 ± 0.3 | 7.9 ± 0.9 |
| LBFIHE (n = 157) | 0.3 ± 0.1 | 0.8 ± 0.1 | 0.7 ± 0 | 0.2 ± 0.1 | 0.1 ± 0.1 | 2.7 ± 0.3 | 1.7 ± 0.3 | 2.5 ± 0.4 | 9.6 ± 1.3 |
| LBFLDI (n = 229) | 0.4 ± 0.1 | 0.8 ± 0.1 | 0.6 ± 0.1 | 0.1 ± 0 | 0.1 ± 0 | 2.4 ± 0.3 | 1.4 ± 0.2 | 2.4 ± 0.4 | 9.2 ± 1.5 |
| LBFPRA (n = 196) | 0.3 ± 0.1 | 0.9 ± 0.1 | 0.6 ± 0 | 0.1 ± 0 | 0.1 ± 0 | 3 ± 0.4 | 1.7 ± 0.2 | 3.5 ± 0.4 | 13.5 ± 2 |
| LBFDHG (n = 177) | 0.3 ± 0.1 | 0.9 ± 0.1 | 0.7 ± 0 | 0.1 ± 0 | 0.1 ± 0 | 3.1 ± 0.6 | 1.9 ± 0.4 | 1.5 ± 0.3 | 8.5 ± 1.2 |
| LBFLFK (n = 195) | 0.4 ± 0.1 | 1 ± 0.1 | 0.7 ± 0 | 0.1 ± 0 | 0.1 ± 0 | 4 ± 0.9 | 2.4 ± 0.5 | 1.4 ± 0.3 | 8.3 ± 1 |

| Event | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|
| LBFDAU (n = 218) | 0.4 ± 0 | 0 ± 0 | 0.4 ± 0.1 | 2.3 ± 0.3 | 0.2 ± 0.1 | 2.1 ± 0.4 | 0.6 ± 0.2 | 0.4 ± 0.1 |
| LBFDGG (n = 200) | 0.4 ± 0 | 0 ± 0 | 0.4 ± 0.1 | 2 ± 0.2 | 0.1 ± 0 | 1.3 ± 0.3 | 0.3 ± 0 | 0.1 ± 0 |
| LBFGKN (n = 182) | 0.4 ± 0 | 0 ± 0 | 0.4 ± 0.1 | 2 ± 0.2 | 0.1 ± 0.1 | 1.6 ± 0.3 | 0.3 ± 0.1 | 0.2 ± 0.1 |
| LBFIHE (n = 157) | 0.4 ± 0 | 0 ± 0 | 0.4 ± 0.1 | 2.2 ± 0.3 | 0.2 ± 0.1 | 2 ± 0.5 | 0.3 ± 0.1 | 0.3 ± 0.1 |
| LBFLDI (n = 229) | 0.3 ± 0 | 0 ± 0 | 0.5 ± 0.1 | 2.6 ± 0.4 | 0.1 ± 0 | 1.7 ± 0.4 | 0.3 ± 0.1 | 0.2 ± 0 |
| LBFPRA (n = 196) | 0.4 ± 0 | 0 ± 0 | 0.3 ± 0.1 | 2.6 ± 0.3 | 0.1 ± 0.1 | 1.7 ± 0.3 | 0.1 ± 0 | 0.3 ± 0.1 |
| LBFDHG (n = 177) | 0.4 ± 0 | 0 ± 0 | 0.8 ± 0.1 | 2.5 ± 0.3 | 0.2 ± 0.1 | 2.4 ± 0.3 | 0.8 ± 0.2 | 0.2 ± 0.1 |
| LBFLFK (n = 195) | 0.4 ± 0 | 0 ± 0 | 0.6 ± 0.1 | 2.7 ± 0.5 | 0.2 ± 0 | 1.5 ± 0.4 | 0.8 ± 0.3 | 0.3 ± 0.1 |

TABLE 150

Fatty acid profiles of one T3 seed batch per event harvested from T2 plants cultivated in the greenhouse of canola events containing the T-DNAs of plasmid VC-LTM593-1qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDAU (n = 1) | 5.1 | 0.3 | 0.0 | 4.7 | 20.6 | 27.6 | 1.1 | 4.3 | 2.5 | 0.5 | 1.3 | 0.6 | 0.2 |
| LBFDGG (n = 1) | 5.2 | 0.3 | 0.0 | 2.9 | 25.6 | 33.8 | 0.7 | 5.2 | 2.0 | 0.4 | 0.8 | 0.7 | 0.2 |
| LBFGKN (n = 1) | 4.8 | 0.2 | 0.0 | 3.7 | 26.5 | 30.2 | 1.2 | 4.9 | 2.3 | 0.3 | 0.8 | 0.6 | 0.2 |
| LBFIHE (n = 1) | 4.4 | 0.1 | 0.0 | 3.0 | 20.2 | 29.0 | 0.8 | 4.7 | 2.8 | 0.5 | 0.7 | 0.7 | 0.4 |
| LBFLDI (n = 1) | 6.7 | 0.3 | 0.0 | 3.0 | 22.2 | 28.3 | 1.1 | 4.0 | 2.7 | 0.7 | 0.8 | 0.5 | 0.1 |

TABLE 150-continued

Fatty acid profiles of one T3 seed batch per event harvested from T2 plants cultivated in the greenhouse of canola events containing the T-DNAs of plasmid VC-LTM593-1qcz rc. The events are indicated in the first column. Fatty acid profiles of T3 seed batches having the highest EPA + DHA levels per event are shown. Per seed batch, a random selection of ~30 seed was measured in two technical repeats.

| | | | | | | | | | | | | |
|---|---|---|---|---|---|---|---|---|---|---|---|---|
| LBFPRA (n = 1) | 5.0 | 0.2 | 0.0 | 3.5 | 20.0 | 27.6 | 1.4 | 3.1 | 3.4 | 0.4 | 0.8 | 0.6 | 0.1 |
| LBFDHG (n = 1) | 6.0 | 0.3 | 0.0 | 2.6 | 23.3 | 29.4 | 1.1 | 5.0 | 2.3 | 0.4 | 0.8 | 0.7 | 0.1 |
| LBFLFK (n = 1) | 4.9 | 0.2 | 0.2 | 3.8 | 23.0 | 31.9 | 1.0 | 4.4 | 2.3 | 0.5 | 0.9 | 0.7 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDAU (n = 1) | 0.1 | 4.0 | 2.8 | 1.6 | 14.1 | 0.5 | 0.0 | 0.4 | 2.8 | 0.3 | 3.5 | 0.5 | 0.3 |
| LBFDGG (n = 1) | 0.1 | 2.5 | 1.6 | 2.9 | 9.1 | 0.4 | 0.0 | 0.5 | 2.4 | 0.2 | 2.2 | 0.3 | 0.1 |
| LBFGKN (n = 1) | 0.1 | 2.5 | 1.4 | 3.2 | 10.9 | 0.3 | 0.0 | 0.4 | 2.4 | 0.1 | 2.5 | 0.2 | 0.3 |
| LBFIHE (n = 1) | 0.3 | 2.9 | 2.1 | 3.3 | 15.3 | 0.3 | 0.0 | 0.5 | 2.9 | 0.4 | 3.9 | 0.2 | 0.5 |
| LBFLDI (n = 1) | 0.1 | 3.2 | 2.1 | 2.5 | 13.8 | 0.4 | 0.0 | 0.5 | 3.4 | 0.3 | 2.7 | 0.5 | 0.2 |
| LBFPRA (n = 1) | 0.1 | 2.9 | 1.9 | 3.8 | 19.0 | 0.3 | 0.0 | 0.3 | 2.7 | 0.1 | 2.4 | 0.1 | 0.4 |
| LBFDHG (n = 1) | 0.1 | 2.8 | 1.9 | 1.6 | 12.8 | 0.4 | 0.0 | 0.7 | 3.3 | 0.4 | 3.3 | 0.6 | 0.3 |
| LBFLFK (n = 1) | 0.1 | 3.2 | 2.1 | 2.0 | 11.6 | 0.3 | 0.0 | 0.7 | 3.0 | 0.2 | 2.3 | 0.5 | 0.3 |

TABLE 151

Phenotypic rating of T1 plants cultivated in the greenhouse of canola events containing the T-DNAs of plasmids VC-LTM593-Iqcz rc.
The events are indicated in the first column, along with the number of T1 plants that where rated per event.

| Event | DFF | DF | DL | DP | DS | FC | LD | LGC |
|---|---|---|---|---|---|---|---|---|
| LBFDAU (n = 218) | 43.2 ± 2.9 | 9 ± 0 | 9 ± 0 | 8 ± 0 | 9 ± 0 | 3 ± 0 | 4 ± 0.1 | 5 ± 0 |
| LBFDGG (n = 200) | 43 ± 3.7 | 8.6 ± 1.5 | 8.5 ± 0.5 | 8 ± 0 | 8.6 ± 1.3 | 3 ± 0 | 4 ± 0 | 5 ± 0 |
| LBFGKN (n = 182) | 42.5 ± 4.3 | 8 ± 2.7 | 8.5 ± 1 | 7.6 ± 1.6 | 8.1 ± 1.9 | 2.9 ± 0.3 | 4.1 ± 0.8 | 5 ± 0.3 |
| LBFIHE (n = 157) | 51.1 ± 5.2 | 8.9 ± 0.4 | 8.9 ± 0.5 | 8.9 ± 0.5 | 5.2 ± 2.6 | 3 ± 0 | 5.1 ± 0.4 | 4.9 ± 0.4 |
| LBFLDI (n = 229) | 48.6 ± 4.5 | 9 ± 0 | 9 ± 0 | 9 ± 0 | 7.6 ± 2.5 | 3 ± 0 | 5 ± 0.1 | 5 ± 0.1 |
| LBFPRA (n = 196) | 51.2 ± 2.4 | 9 ± 0 | 9 ± 0 | 9 ± 0 | 5.8 ± 3.2 | 3 ± 0 | 5 ± 0 | 5 ± 0 |
| LBFDHG (n = 177) | 46 ± 3.5 | 9 ± 0 | 9 ± 0 | 8 ± 0 | 4.7 ± 1.6 | 3 ± 0 | 4 ± 0 | 5 ± 0 |
| LBFLFK (n = 195) | 42.3 ± 2.8 | 9 ± 0 | 9 ± 0 | 9 ± 0.3 | 8.9 ± 0.7 | 3 ± 0 | 4 ± 0.1 | 5 ± 0 |

| Event | LF | NoL | PH | TKW | SC | Oil | Protein |
|---|---|---|---|---|---|---|---|
| LBFDAU (n = 218) | 8.6 ± 0.8 | 5.1 ± 0.6 | 107.5 ± 7.6 | 3 ± 0.3 | 3.7 ± 1.2 | 35.6 | |
| LBFDGG (n = 200) | 8.7 ± 0.7 | 4.5 ± 0.5 | 112.1 ± 5.5 | 3 ± 0.3 | 3.7 ± 0.7 | N/A | |
| LBFGKN (n = 182) | 8.5 ± 1 | 5 ± 0 | 111.6 ± 15.2 | 3.3 ± 0.4 | 3.3 ± 0.6 | 36.1 | |
| LBFIHE (n = 157) | 5.2 ± 2.6 | 6.6 ± 1.1 | 139.4 ± 14.7 | 4 ± 0.5 | 3.8 ± 1.9 | 34.1 | |
| LBFLDI (n = 229) | 7.6 ± 2.5 | 6.2 ± 1.1 | 145.5 ± 15.9 | 4.2 ± 0.4 | 3.1 ± 1.3 | N/A | |
| LBFPRA (n = 196) | 5.8 ± 3.2 | 7.3 ± 1 | 138.7 ± 16.6 | 4.2 ± 0.4 | 2.4 ± 1.5 | 34.7 | |
| LBFDHG (n = 177) | 8.5 ± 0.8 | 5.2 ± 0.8 | 112.5 ± 5.4 | 3.4 ± 0.4 | 5.3 ± 1 | 32.3 | |
| LBFLFK (n = 195) | 8.7 ± 0.9 | 5.3 ± 0.5 | 113.4 ± 8 | 3.3 ± 0.3 | 3.9 ± 1.5 | 37.1 | |

DFF: days to first flower (days),
DF: deformed flower (1 = deformed, 9 = normal),
DL: deformed leaf (1 = deformed, 9 = normal),
DP: deformed plant (1 = deformed, 9 = normal),
DS: deformed silique (1 = deformed, 9 = norma
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high)
NoL: number of lobes (#),
PH: plant height (cm),
TKW: thousand kernel weight (g),
SC: seed quality (1 = good, 9 = bad),
Oil: oil content (% of seed weight),
protein: Protein content (% of seed cake without oil)

D. Fatty Acid Profiles, Copy Number Measurements, and Phenotypic Observations of T2 Plants Carrying T-DNAs of Plasmids VC-LTM593-1qcz rc Cultivated in Field Trials in USDA Growth Zones 3a-4b and 5a During the Summer Field data for the T3 seed from the events carrying the T-DNA from VC-LTM593-1qcz rc, shown in Table 152 and Table 153, indicate that the plants are capable of making VLC-PUFAs in the field (ARA, EPA and DHA), though not at the level observed in the greenhouse. ANOVA was conducted with using the software JMP 11.0. Analysis was conducted at the 95% confidence level using Tukey test. To compensate for unbalance in the data obtained from the field trial (e.g. due to e.g. weather), Least Square means instead of means where used in the statistical analysis. Common letters in the Table 154, Table 155 and Table 156 indicate no significant difference of the least square means. Table 154 shows the statistical analysis of agronomical parameters.

There was a difference in seed oil content observed compared to the greenhouse (e.g. comparing Table 154 with Table 151), indicating oil content and the fatty acid profile could be linked. These observations are in agreement with previous examples where it was observed that increased oil contents in the field grown plants concomitant with a decrease in VLC-PUFAs, in particular EPA, DHA and ARA. A more detailed description of the observations regarding oil content and VLC-PUFAs is given in Example 20.

For seed yield (kg per ha, data not shown), no statistically relevant difference was found comparing the events against wildtype Kumily (tested using Tukey, 0.05% level).

TABLE 152

Fatty acid profiles of T3 seeds harvested from T2 cultivated in the field, corresponding to USDA growth zones 3a-4b and 5a, for field trials of canola events containing the T-DNAs of plasmid VC-LTM593-1qcz rc. The events are indicated in the first column, along with the number of T3 seed aliquots representing a plot where measured per event. For event LBFGKN, 36 plots and 60 single plants from those plots where measured. Per seed batch a random selection of ~15 seed was measured in five technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LBFDAU (n = 16) | 4.7 ± 0.1 | 0.2 ± 0 | 0 ± 0 | 2.7 ± 0.1 | 28.6 ± 1.5 | 29.2 ± 0.7 | 1 ± 0.1 | 6.1 ± 0.3 | 1.6 ± 0.1 | 0.3 ± 0 | 0.7 ± 0 | 0.7 ± 0 | 0.1 ± 0 | 0.1 ± 0 |
| LBFDGG (n = 36) | 4.7 ± 0.1 | 0.2 ± 0 | 0 ± 0 | 2.5 ± 0.2 | 34.2 ± 1.9 | 32.3 ± 1.2 | 0.6 ± 0.1 | 7 ± 0.5 | 1.2 ± 0.1 | 0.2 ± 0 | 0.6 ± 0 | 0.8 ± 0 | 0.1 ± 0 | 0.1 ± 0 |
| LBFGKN (n = 36 + 60) | 4.6 ± 0.2 | 0.2 ± 0 | 0 ± 0 | 2.6 ± 0.2 | 33.7 ± 1.7 | 32.8 ± 1.4 | 0.6 ± 0.1 | 7.5 ± 0.6 | 0.9 ± 0.1 | 0.2 ± 0 | 0.7 ± 0 | 0.8 ± 0.1 | 0.2 ± 0 | 0.1 ± 0 |
| LBFIHE (n = 36) | 4.8 ± 0.2 | 0.2 ± 0 | 0 ± 0 | 2.6 ± 0.2 | 31.2 ± 1.7 | 33.9 ± 1.2 | 0.6 ± 0.1 | 6.7 ± 0.7 | 1.3 ± 0.2 | 0.3 ± 0 | 0.7 ± 0.1 | 0.8 ± 0 | 0.2 ± 0 | 0.1 ± 0 |
| LBFLDI (n = 36) | 4.9 ± 0.2 | 0.3 ± 0 | 0 ± 0 | 2.5 ± 0.2 | 33.4 ± 1.7 | 32.7 ± 1.2 | 0.6 ± 0.1 | 6.8 ± 0.6 | 1 ± 0.1 | 0.2 ± 0 | 0.7 ± 0.1 | 0.8 ± 0 | 0.2 ± 0 | 0.1 ± 0 |
| LBFIDT (n = 32) | 4.6 ± 0.1 | 0.2 ± 0 | 0 ± 0 | 2.7 ± 0.2 | 30 ± 1.4 | 29.9 ± 1 | 0.9 ± 0.1 | 6.5 ± 0.5 | 1.6 ± 0.1 | 0.3 ± 0 | 0.7 ± 0.1 | 0.7 ± 0 | 0.1 ± 0 | 0.1 ± 0 |
| LBFPRA (n = 36) | 4.8 ± 0.2 | 0.2 ± 0 | 0 ± 0 | 2.6 ± 0.2 | 28.4 ± 2.1 | 32.7 ± 1.4 | 0.8 ± 0.1 | 5.7 ± 0.4 | 1.6 ± 0.2 | 0.3 ± 0.1 | 0.7 ± 0 | 0.8 ± 0 | 0.2 ± 0 | 0.1 ± 0 |
| LBFDHG (n = 4) | 5.2 ± 0.1 | 0.2 ± 0 | 0 ± 0 | 2.4 ± 0.1 | 28.2 ± 1.4 | 29.5 ± 1 | 0.9 ± 0.2 | 6.5 ± 0 | 1.6 ± 0.1 | 0.3 ± 0 | 0.6 ± 0 | 0.7 ± 0 | 0.2 ± 0 | 0.1 ± 0 |
| LBFLFK (n = 36) | 4.7 ± 0.2 | 0.2 ± 0 | 0 ± 0 | 2.6 ± 0.2 | 30.1 ± 1.9 | 30.2 ± 1.1 | 0.9 ± 0.1 | 6.2 ± 0.4 | 1.5 ± 0.2 | 0.3 ± 0.1 | 0.6 ± 0 | 0.8 ± 0 | 0.1 ± 0 | 0.1 ± 0 |

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LBFDAU (n = 16) | 3.3 ± 0.3 | 2.2 ± 0.2 | 2 ± 0.2 | 10.7 ± 0.7 | 0.3 ± 0 | 0 ± 0 | 0.3 ± 0 | 2.9 ± 0.2 | 0.1 ± 0 | 1.6 ± 0.2 | 0.3 ± 0.1 | 0.3 ± 0 |
| LBFDGG (n = 36) | 2 ± 0.3 | 1.3 ± 0.2 | 1.9 ± 0.2 | 6.1 ± 0.7 | 0.3 ± 0 | 0 ± 0 | 0.3 ± 0 | 2.1 ± 0.2 | 0.1 ± 0 | 1.1 ± 0.2 | 0.2 ± 0.1 | 0.1 ± 0 |
| LBFGKN (n = 36 + 60) | 2.1 ± 0.3 | 1.2 ± 0.1 | 1.8 ± 0.2 | 6 ± 0.6 | 0.3 ± 0 | 0 ± 0 | 0.3 ± 0.1 | 2.1 ± 0.2 | 0.1 ± 0 | 1 ± 0.1 | 0.2 ± 0 | 0.2 ± 0 |
| LBFIHE (n = 36) | 2.1 ± 0.2 | 1.2 ± 0.1 | 2.4 ± 0.3 | 6.7 ± 0.6 | 0.3 ± 0 | 0 ± 0 | 0.3 ± 0.1 | 1.9 ± 0.2 | 0.1 ± 0 | 1.2 ± 0.2 | 0.2 ± 0.1 | 0.2 ± 0 |
| LBFLDI (n = 36) | 2 ± 0.3 | 1.2 ± 0.2 | 2 ± 0.2 | 6.2 ± 0.7 | 0.3 ± 0 | 0 ± 0 | 0.3 ± 0 | 2.1 ± 0.2 | 0.1 ± 0 | 1.1 ± 0.2 | 0.2 ± 0 | 0.2 ± 0 |
| LBFIDT (n = 32) | 4.4 ± 0.4 | 2.6 ± 0.2 | 1.5 ± 0.2 | 6.8 ± 0.7 | 0.3 ± 0 | 0 ± 0 | 0.6 ± 0.1 | 2.9 ± 0.3 | 0.1 ± 0 | 1.2 ± 0.2 | 1 ± 0.1 | 0.3 ± 0 |
| LBFPRA (n = 36) | 2.3 ± 0.3 | 1.2 ± 0.2 | 3.8 ± 0.5 | 9.6 ± 1 | 0.3 ± 0 | 0 ± 0 | 0.3 ± 0 | 2.4 ± 0.3 | 0.1 ± 0 | 1.1 ± 0.2 | 0.1 ± 0 | 0.2 ± 0.1 |
| LBFDHG (n = 4) | 2.9 ± 0 | 1.7 ± 0 | 2 ± 0.1 | 9.6 ± 0.4 | 0.3 ± 0 | 0 ± 0 | 0.6 ± 0.1 | 3.5 ± 0 | 0.2 ± 0 | 1.9 ± 0.2 | 0.5 ± 0.1 | 0.3 ± 0 |
| LBFLFK (n = 36) | 3.3 ± 0.3 | 1.9 ± 0.2 | 1.9 ± 0.2 | 8.2 ± 1 | 0.3 ± 0 | 0 ± 0 | 0.5 ± 0 | 3.2 ± 0.4 | 0.1 ± 0 | 1.4 ± 0.3 | 0.5 ± 0.1 | 0.3 ± 0.1 |

TABLE 153

Fatty acid profiles of one T3 seed batch per event harvested from T2 plants cultivated in USDA growth zones 3a-4b and 5a for field trials of canola events containing the T-DNAs of plasmid VC-LTM593-1qcz rc. The events are indicated in the first column. Fatty acid profiles of T3 seed batches representing a field plot having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDAU (n = 1) | 4.9 | 0.2 | 0.0 | 2.6 | 26.0 | 28.9 | 0.8 | 6.2 | 1.7 | 0.3 | 0.7 | 0.8 | 0.2 |
| LBFDGG (n = 1) | 5.0 | 0.3 | 0.0 | 2.7 | 30.1 | 33.1 | 0.5 | 6.5 | 1.5 | 0.3 | 0.7 | 0.8 | 0.2 |
| LBFGKN (n = 1) | 4.4 | 0.2 | 0.0 | 2.6 | 32.6 | 31.1 | 0.7 | 7.3 | 1.1 | 0.3 | 0.6 | 0.8 | 0.2 |
| LBFIHE (n = 1) | 4.8 | 0.2 | 0.0 | 2.5 | 28.0 | 33.9 | 0.6 | 6.3 | 1.6 | 0.3 | 0.8 | 0.8 | 0.2 |
| LBFLDI (n = 1) | 5.2 | 0.3 | 0.0 | 2.5 | 29.8 | 33.3 | 0.4 | 6.8 | 1.3 | 0.4 | 1.1 | 0.8 | 0.2 |
| LBFIDT (n = 1) | 4.7 | 0.2 | 0.0 | 2.6 | 28.6 | 28.8 | 1.0 | 7.1 | 1.6 | 0.3 | 0.7 | 0.7 | 0.1 |
| LBFPRA (n = 1) | 5.1 | 0.2 | 0.0 | 2.6 | 26.0 | 31.5 | 0.7 | 5.3 | 1.8 | 0.3 | 0.7 | 0.7 | 0.2 |
| LBFDHG (n = 1) | 5.1 | 0.2 | 0.0 | 2.4 | 29.0 | 28.4 | 1.0 | 6.6 | 1.6 | 0.3 | 0.6 | 0.8 | 0.1 |
| LBFLFK (n = 1) | 5.1 | 0.2 | 0.0 | 2.6 | 26.9 | 29.3 | 0.8 | 5.9 | 1.9 | 0.4 | 0.7 | 0.8 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDAU (n = 1) | 0.1 | 3.6 | 2.4 | 2.0 | 12.0 | 0.3 | 0.0 | 0.3 | 3.2 | 0.1 | 2.1 | 0.4 | 0.3 |
| LBFDGG (n = 1) | 0.1 | 2.1 | 1.4 | 2.4 | 7.5 | 0.3 | 0.0 | 0.4 | 2.4 | 0.1 | 1.6 | 0.2 | 0.1 |
| LBFGKN (n = 1) | 0.1 | 2.1 | 1.3 | 2.1 | 7.7 | 0.3 | 0.0 | 0.3 | 2.5 | 0.1 | 1.3 | 0.2 | 0.2 |
| LBFIHE (n = 1) | 0.1 | 2.4 | 1.5 | 2.7 | 8.2 | 0.3 | 0.0 | 0.4 | 2.3 | 0.1 | 1.6 | 0.2 | 0.2 |
| LBFLDI (n = 1) | 0.1 | 1.8 | 1.2 | 2.4 | 7.2 | 0.4 | 0.0 | 0.4 | 2.4 | 0.1 | 1.6 | 0.2 | 0.2 |
| LBFIDT (n = 1) | 0.1 | 4.3 | 2.6 | 1.5 | 8.1 | 0.3 | 0.0 | 0.6 | 3.4 | 0.1 | 1.4 | 1.0 | 0.4 |
| LBFPRA (n = 1) | 0.1 | 2.4 | 1.3 | 4.3 | 11.7 | 0.3 | 0.0 | 0.3 | 2.8 | 0.0 | 1.3 | 0.1 | 0.2 |
| LBFDHG (n = 1) | 0.1 | 2.9 | 1.7 | 1.9 | 10.2 | 0.3 | 0.0 | 0.5 | 3.5 | 0.2 | 1.9 | 0.5 | 0.3 |
| LBFLFK (n = 1) | 0.1 | 3.1 | 2.0 | 2.3 | 10.3 | 0.3 | 0.0 | 0.6 | 3.9 | 0.1 | 2.0 | 0.5 | 0.2 |

TABLE 154

Phenotypic rating of T2 plants cultivated in USDA growth zones 3a-4b and 5a for field trials of canola events containing the T-DNAs of plasmid VC-VC-LTM593-1qcz rc.

| Event | Stand | | First Vigor | | Last Flower | | Flower | | Maturity | | Height | | Plant Lodging | |
|---|---|---|---|---|---|---|---|---|---|---|---|---|---|---|
| LBFDAU (n = 16) | 23.7 | a | 5.7 | bcd | 43.8 | bc | 77.3 | abcde | 94.5 | a | 115.5 | b | 2.3 | ab |
| LBFDGG (n = 36) | 23.0 | a | 5.9 | bcd | 44.0 | bc | 77.1 | bcd | 94.3 | a | 116.2 | b | 2.3 | b |
| LBFDHG (n = 4) | 23.4 | | 5.8 | | 43.9 | | 77.2 | | | | 115.9 | | 2.3 | |
| LBFGKN (n = 36) | 22.8 | a | 6.3 | bcd | 43.3 | c | 76.5 | cde | 94.2 | a | 118.8 | b | 2.8 | ab |
| LBFIHE (n = 36) | 21.7 | a | 5.6 | cd | 45.7 | b | 79.7 | ab | 94.7 | a | 115.2 | b | 2.3 | b |
| LBFLFK (n = 36) | 22.5 | a | 5.1 | d | 45.6 | b | 78.0 | abc | 94.3 | a | 118.4 | b | 2.6 | ab |
| LBFPRA (n = 36) | 22.5 | a | 6.3 | bcd | 44.2 | bc | 78.1 | abc | 94.3 | a | 121.2 | b | 2.9 | ab |
| Topas | 24.8 | a | 5.2 | d | 48.1 | a | 80.9 | a | 95.3 | a | 139.7 | a | 3.2 | ab |
| Kumily | 28.2 | a | 6.9 | ab | 43.4 | c | 76.6 | cde | 94.2 | a | 119.9 | b | 2.8 | ab |
| Control 1 | 28.1 | a | 7.7 | a | 42.9 | c | 73.8 | e | 89.2 | b | 121.1 | b | 3.9 | a |
| Control 2 | 25.3 | a | 6.6 | abc | 40.7 | d | 74.3 | de | 90.3 | b | 119.1 | b | 3.8 | a |

TABLE 154-continued

Phenotypic rating of T2 plants cultivated in USDA growth zones 3a-4b and 5a for field trials of canola events containing the T-DNAs of plasmid VC-VC-LTM593-1qcz rc.

| Event | Shatter | | Agron Score | | Moisture | | TWK | | Oil | | Protein | |
|---|---|---|---|---|---|---|---|---|---|---|---|---|
| LBFDAU (n = 16) | 1.5 | a | 4.7 | ab | 9.0 | a | 3.5 | abcd | 38.5 | bc | 26.6 | c |
| LBFDGG (n = 36) | 1.6 | a | 4.2 | ab | 8.9 | a | 3.8 | a | 38.8 | abc | 26.3 | c |
| LBFDHG (n = 4) | 1.5 | | 4.4 | | 9.0 | | 3.7 | | 39.3 | abc | 26.5 | c |
| LBFGKN (n = 36) | 1.8 | a | 4.1 | ab | 8.5 | a | 3.7 | ab | 36.7 | c | 26.5 | c |
| LBFIHE (n = 36) | 1.6 | a | 4.1 | ab | 8.7 | a | 3.4 | bcd | 39.8 | ab | 26.5 | c |
| LBFLFK (n = 36) | 1.5 | a | 4.1 | ab | 8.6 | a | 3.7 | a | 38.3 | bc | 27.1 | c |
| LBFPRA (n = 36) | 1.9 | a | 4.2 | ab | 8.5 | a | 3.5 | abc | 39.2 | abc | 26.5 | c |
| Topas | 2.6 | a | 4.4 | a | 7.3 | b | 3.3 | cd | 37.8 | c | 26.9 | c |
| Kumily | 1.8 | a | 4.5 | a | 7.4 | b | 3.7 | ab | 39.8 | ab | 28.5 | a |
| Control 1 | 2.7 | a | 3.4 | b | 7.0 | b | 3.2 | d | 39.9 | ab | 27.1 | c |
| Control 2 | 2.7 | a | 3.4 | b | 7.0 | b | 3.1 | d | 40.7 | a | 27.4 | bc |

The events are indicated in the first column, along with the number of field plots that where rated per event.

Stand: the number of plants that emerged within a 1 meter section of row at GS 14 (4 leaves unfolded), rating of a seedlings ability to grow and develop at GS 14 (4 leaves unfolded, 1 = All plants at different growth stages and all plants appear unhealthy, 9 = All plants at same growth stage and all plants appear healthy), First flower: date at which plants are at GS 60 (days after emergence), Last flower: date at which plants are at GS 69 (days after emergence), Maturity: Days to Maturity (when average seed moisture is 30 to 35%, and 30 to 40% if the seeds in the pods have developed their mature seed color, either black or yellow), Plant Heigth: the average height (cm) of five plants in a plot measured from soil level to the top of the plant at GS 69 (cm), Lodging: rating of the average standability of plants in a plot at GS 83 (30% of pods ripe, 1 = 0-10% average lean of plants in plot from horizontal (standing erect), 9 = 81%+ average lean of plants in plot from horizontal (nearly prostrate)), Shatter: rating of the ability of plants to retain seed in the pod at GS 89 (all pods fully ripe, 1 = 0-10% perished pods, 9 = 81%+ perished pods), Agron Score: scale of 1-5 with 1 being the best, 5 the worst ranking of plant phenotype (measurements occurred post flower during pods formation and seed development), Moisture (% of seed weight), TKW: thousand kernel weight (g), Oil: oil content (% of seed weight), protein: Protein content (% of seed cake without oil).

TABLE 155

Compositional analysis of T3 seeds of T2 plants cultivated in USDA growth zones 3a-4b and 5a for field trials of canola events containing the T-DNAs of plasmid VC-VC-LTM593-1qcz rc. The events are indicated in the first column. The analysis has been done on 4 BULK, whereby each BULK is a representative sample of all seeds harvedted from 4 different geographic reagions. Alpha-Tocopherol (mg/100 g seed), Beta-Tocopherol (mg/100 g seed), Delta-Tocopherol (mg/100 g seed), Gamma-Tocopherol (mg/100 g seed), Tocopherol (mg/100 g seed), Sinapine (µg/g (ppm)), Phytate (% of seed weight (w/w)), Ash (% of seed weight (w/w)), Crude Fiber (% of seed weight (w/w)), ADF: acid detergent fiber (% of seed weight (w/w)), NDF: neutral detergent fiber (% of seed weight (w/w)). All results have been normalized to the seed weight of seeds having 0% moisture.

| Event | Alpha-Tocopherol | | Beta-Tocopherol | | Delta-Tocopherol | | Gamma-Tocopherol | | Tocopherols (VitE) | | Sinapine | |
|---|---|---|---|---|---|---|---|---|---|---|---|---|
| LBFDAU | 13.3 | ab | 0.25 | a | 0.58 | a | 29.5 | a | 43.7 | a | 0.64 | cd |
| LBFDGG | 14.1 | ab | 0.23 | a | 0.45 | bcd | 25.6 | b | 40.4 | abc | 0.69 | bcd |
| LBFGKN | 12.9 | b | 0.23 | a | 0.52 | abc | 26.9 | ab | 40.6 | abc | 0.70 | bc |
| LBFIHE | 13.2 | ab | 0.23 | a | 0.45 | bcd | 22.0 | cd | 35.9 | cde | 0.65 | cd |
| LBFLFK | 12.5 | b | 0.23 | a | 0.52 | abc | 25.7 | b | 38.9 | abc | 0.68 | bcd |
| LBFPRA | 13.6 | ab | 0.22 | a | 0.47 | bcd | 24.9 | bc | 39.2 | abc | 0.62 | d |
| Topas | 14.7 | ab | 0.25 | a | 0.36 | d | 16.6 | e | 31.9 | e | 0.69 | bcd |
| Kumily | 12.3 | b | 0.23 | a | 0.54 | ab | 24.4 | bc | 37.5 | bcd | 0.78 | a |
| Control 1 | 16.6 | a | 0.25 | a | 0.43 | cd | 24.1 | bc | 41.4 | ab | 0.73 | ab |
| Control 2 | 12.0 | b | 0.20 | a | 0.45 | bcd | 20.8 | d | 33.5 | de | 0.72 | ab |

| Event | Glucosinolate | | Phytate | | Ash | | Crude Fiber | | ADF | | NDF | |
|---|---|---|---|---|---|---|---|---|---|---|---|---|
| LBFDAU | 11.0 | bcd | 2.3 | B | 4.5 | ab | 9.4 | a | 11.8 | ab | 14.5 | a |
| LBFDGG | 13.1 | ab | 2.3 | B | 4.3 | ab | 9.2 | a | 10.9 | cd ef | 13.6 | ab |

TABLE 155-continued

Compositional analysis of T3 seeds of T2 plants cultivated in USDA growth zones 3a-4b and 5a for field trials of canola events containing the T-DNAs of plasmid VC-VC-LTM593-1qcz rc. The events are indicated in the first column. The analysis has been done on 4 BULK, whereby each BULK is a representative sample of all seeds harvedted from 4 different geographic reagions. Alpha-Tocopherol (mg/100 g seed), Beta-Tocopherol (mg/100 g seed), Delta-Tocopherol (mg/100 g seed), Gamma-Tocopherol (mg/100 g seed), Tocopherol (mg/100 g seed), Sinapine (μg/g (ppm)), Phytate (% of seed weight (w/w)), Ash (% of seed weight (w/w)), Crude Fiber (% of seed weight (w/w)), ADF: acid detergent fiber (% of seed weight (w/w)), NDF: neutral detergent fiber (% of seed weight (w/w)). All results have been normalized to the seed weight of seeds having 0% moisture.

| | | | | | | | | | | | | |
|---|---|---|---|---|---|---|---|---|---|---|---|---|
| LBFGKN | 11.3 | bc | 2.3 | b | 4.4 | ab | 9.3 | a | 11.0 | bc def | 13.5 | ab |
| LBFIHE | 15.7 | a | 2.2 | b | 4.7 | ab | 9.1 | a | 10.8 | cd ef | 13.4 | ab |
| LBFLFK | 12.6 | abc | 2.3 | b | 4.3 | b | 9.6 | a | 11.3 | ab cde | 13.7 | ab |
| LBFPRA | 10.9 | bcd | 2.2 | b | 4.3 | ab | 9.6 | a | 12.0 | a | 14.6 | a |
| Topas | 7.6 | d | 2.7 | a | 4.8 | a | 9.0 | a | 10.5 | ef | 12.9 | b |
| Kumily | 11.0 | bcd | 2.2 | b | 4.3 | b | 9.1 | a | 11.5 | abc | 14.3 | a |
| Control 1 | 9.5 | cd | 2.3 | b | 4.6 | ab | 8.6 | a | 10.2 | f | 12.8 | b |
| Control 2 | 11.9 | bc | 2.3 | b | 4.4 | ab | 9.2 | a | 10.6 | def | 13.8 | ab |

TABLE 156

Herbicde tolerance of T2 plants cultivated in USDA growth zones 3a-4b and 5a for field trials of canola events containing the T-DNAs of plasmid VC-VC-LTM593-1qcz rc. The events are indicated in the first column. IMI Injury: injury according to the scale detailed in Table 157 (DAT = days after treatment). Herbicide imazamox was aplied at a 2x rate of 70 g imazamox/ha. Brassica napus cv Kumily, which is the non-transgeneic comparator line that is otherwise isogenic to the events, was rated at 6 to 7, and was removed from the statistical analysis to make the Tukey test more sensitive to detect significant differences between events that are very similar in their tolerance.

| Event | IMI Injury 7 DAT | | IMI Injury 14 DAT | | IMI Injury 21 DAT | |
|---|---|---|---|---|---|---|
| LBFDAU | 2 | a | 1 | ab | 1 | a |
| LBFDGG | 2 | a | 1 | ab | 1 | a |
| LBFDHG | 2 | | 1 | | 1 | |
| LBFGKN | 2 | a | 1 | ab | 1 | a |
| LBFIHE | 2 | a | 2 | a | 1 | a |
| LBFLFK | 2 | a | 1 | b | 1 | a |
| LBFPRA | 2 | a | 1 | ab | 1 | a |
| Topas | 1 | a | 1 | b | 1 | a |
| Kumily | 6 | | 6 | | 7 | |

TABLE 157

Canola rating scale for herbicide

| % Injury | 1-7 Scale | Category | Injury Symptoms | Growth Rates and Recovery Effects |
|---|---|---|---|---|
| 0 | 1 | Excellent | None | None |
| 1-6 | 2 | Very Good | Leaf and petiole epinasty, chlorosis. | Minor or temporary growth effects. Injury and effects should be minor enough to not cause commercialization concerns. |
| 7-14 | 3 | Good | Leaf, petiole and stem epinasty, chlorosis, stem swelling. Leaf cupping be observed. | This would be the maximum allowable injury for commercial evaluations. Fairly temporary in nature without any effect on final yield and minimal delay in maturity, |
| 15-20 | 4 | Fair | Above symptoms plus stunting in height, smaller leaf size or | Appearance of unaffected new growth impeded for <7 days. Slight |

TABLE 157-continued

Canola rating scale for herbicide

| % Injury | 1-7 Scale | Category | Injury Symptoms | Growth Rates and Recovery Effects |
|---|---|---|---|---|
| | | | impact on LAI, in this class: Basal swelling may be observed. Expect recovery and seed production with this set of symptoms but delayed, reduced growth and reduced seed set. Plant stand may be non-uniform upon recovery. | delay in bolting and flower production. Yield impact minimal or small at harvest. |
| 21-40 | 5 | Poor | Injury in this class would be as above and more than evaluator's estimate of the level of commercial acceptance. | Significant delay in plant development significant malformations in growth and development vs. control. Malformations persist Serious reduction in maturity, height and harvest yield. |
| 41-79 | 6 | Non Tolerant | | Equivalent to suppression as a volunteer crop in a weed control assessment. Minimal regrowth following application. Plants survive but fail to flower and mature as normal. |
| 80-100 | 7 | Susceptible | Severe injury or death. | Severe injury or death. |

Figure 40:
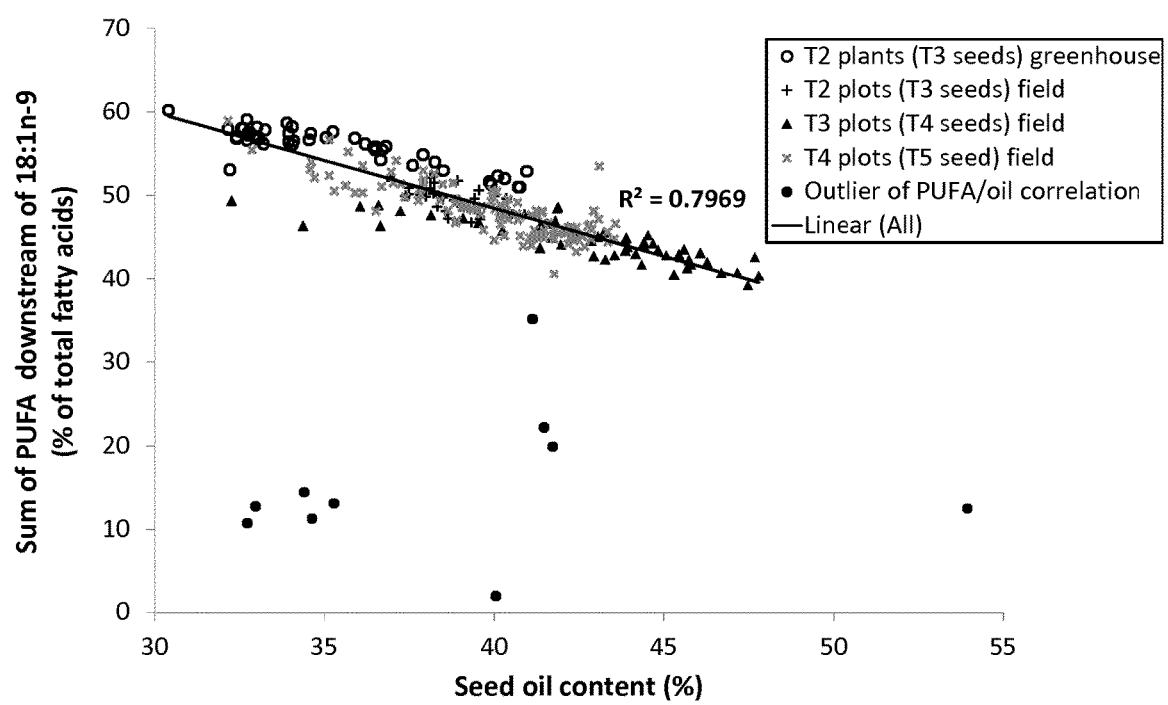
FIG. 40: The sum of all pathway fatty acids was negatively correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 41:
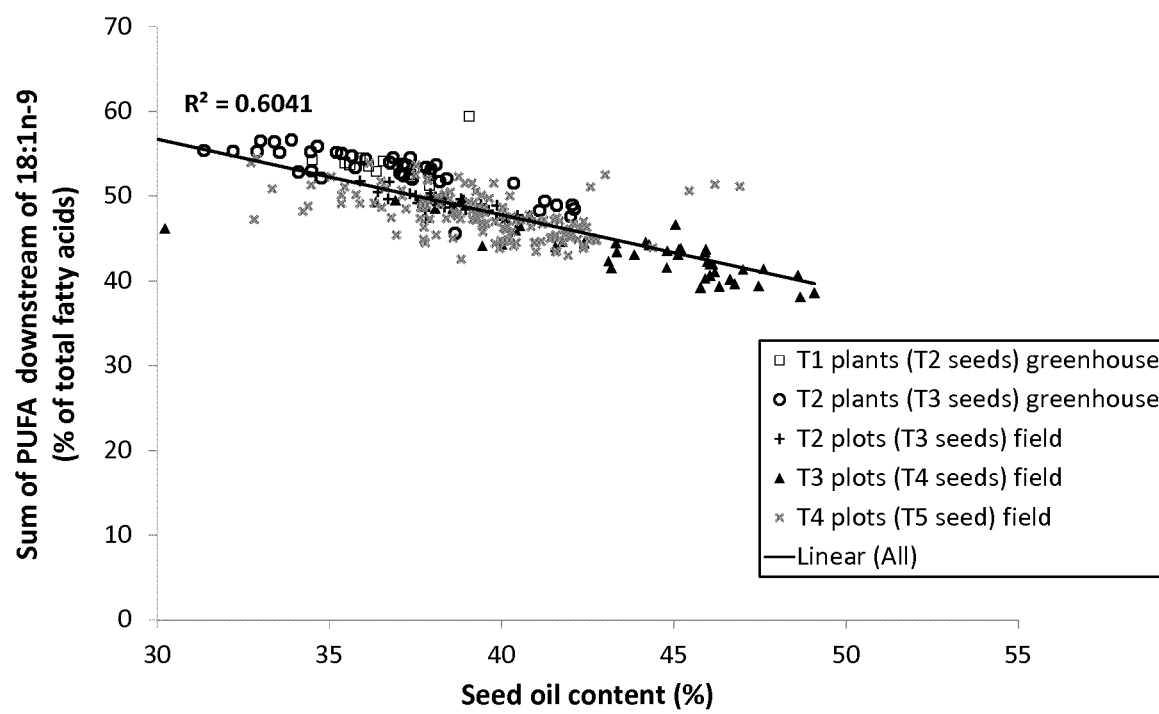
FIG. 41: The sum of all pathway fatty acids was negatively correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 42:
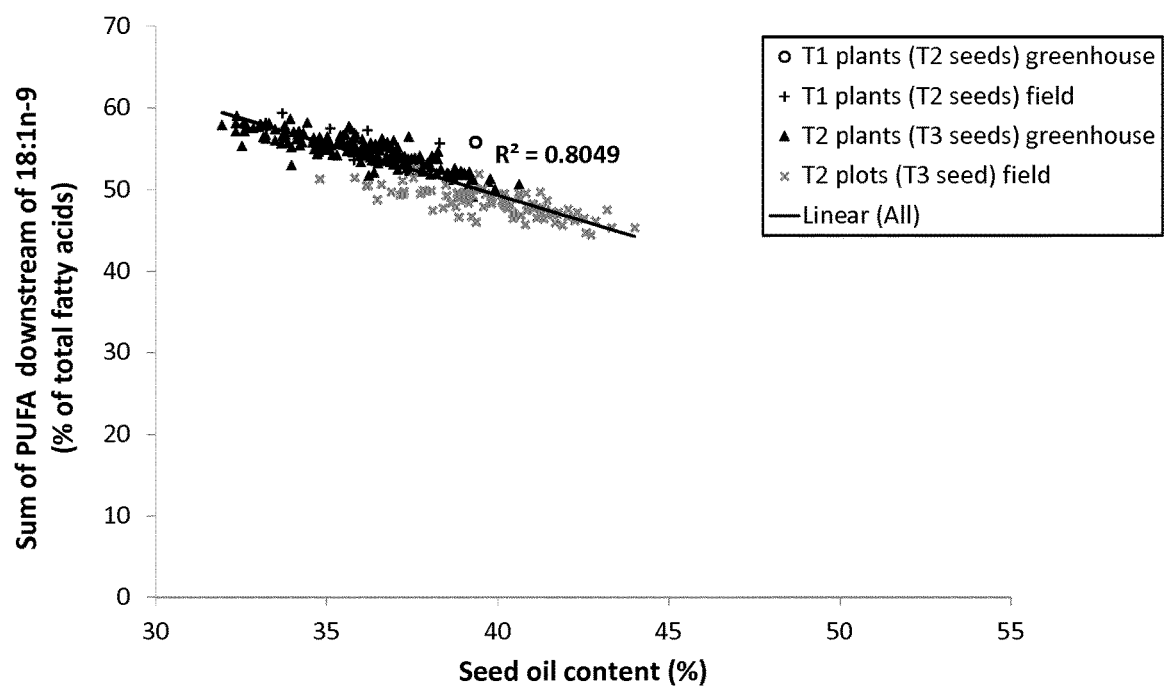
FIG. 42: The sum of all pathway fatty acids was negatively correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 43:
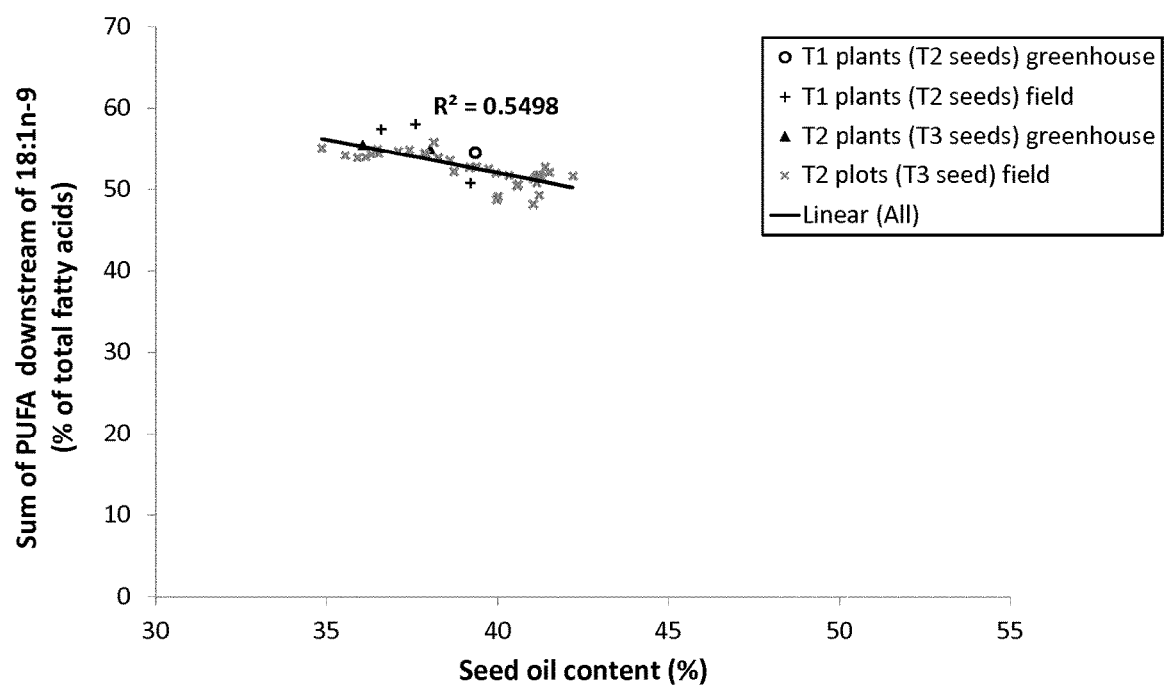
FIG. 43: The sum of all pathway fatty acids was negatively correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 44:
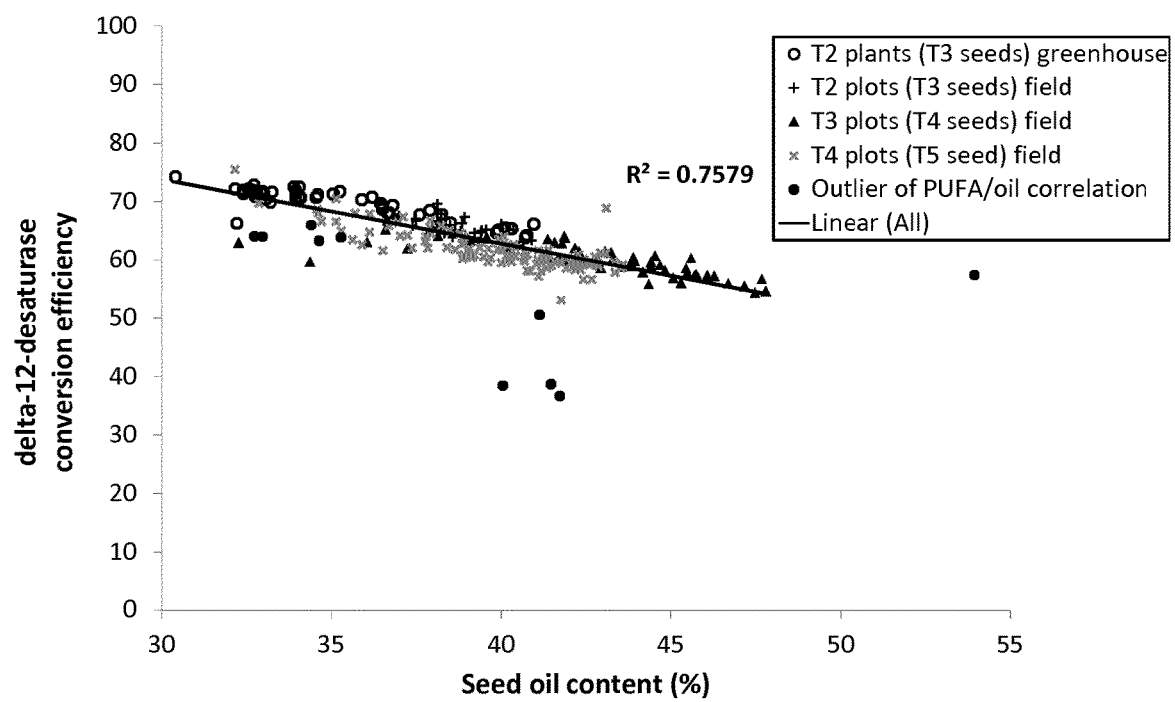
FIG. 44: The conversion efficiency of the delta-12-desaturase was negatively correlated with seed oil content. Shown are data of 3 generations of event LANPMZ. For the greenhouse data, one marker corresponds to one seed batch of one plant, for the field data, one marker corresponds to an analysis on a random selection of seeds representing one plot.
Figure 45:
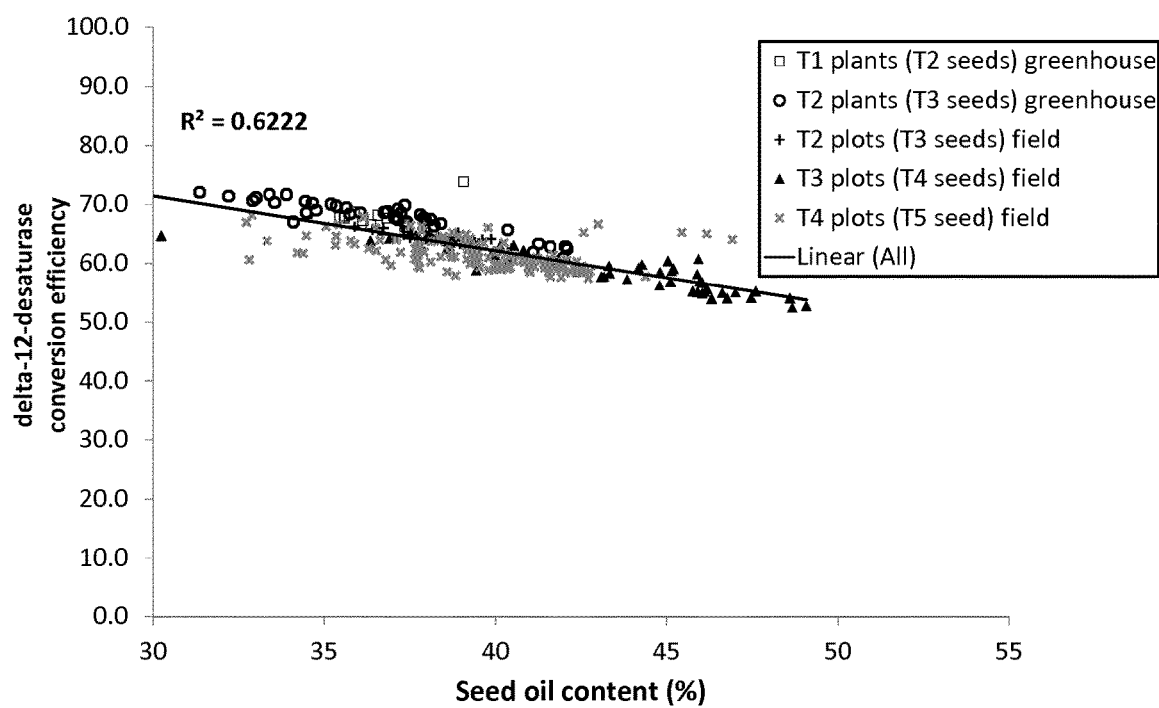
FIG. 45: The conversion efficiency of the delta-12-desaturase was negatively correlated with seed oil content. Shown are data of 4 generations of event LAODDN. For the greenhouse data, one marker corresponds to one seed batch of one plant, for the field data, one marker corresponds to an analysis on a random selection of seeds representing one plot.
Figure 46:
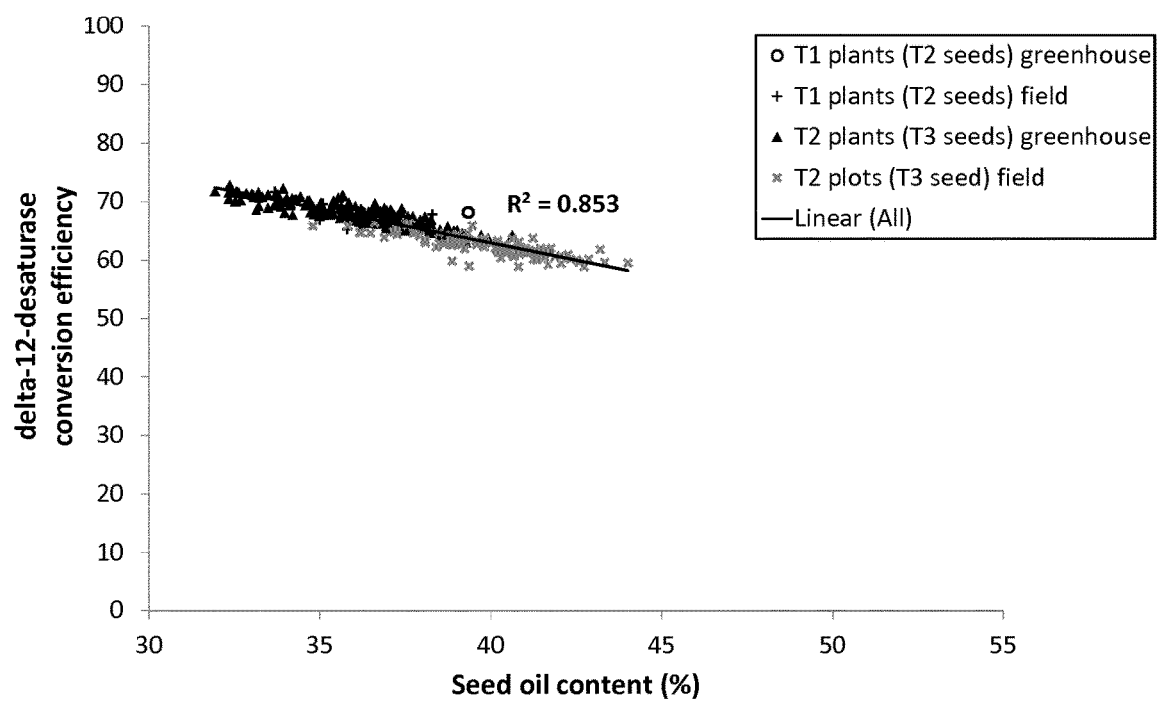
FIG. 46: The conversion efficiency of the delta-12-desaturase was negatively correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 47:
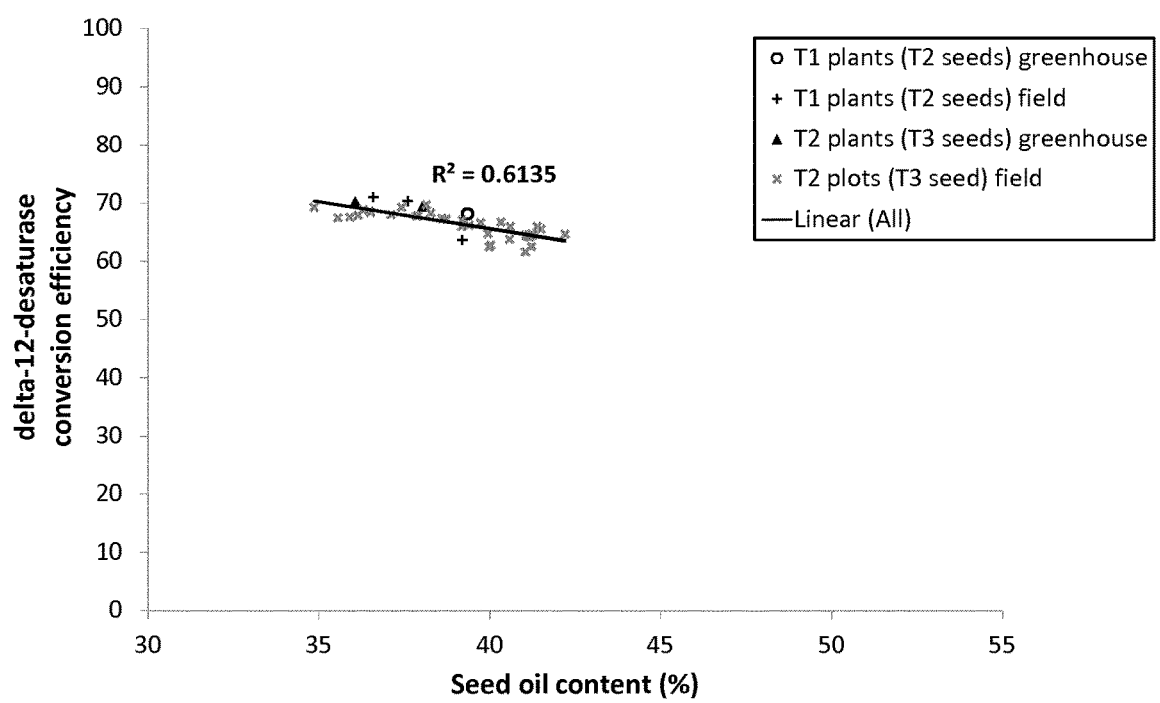
FIG. 47: The conversion efficiency of the delta-12-desaturase was negatively correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 48:
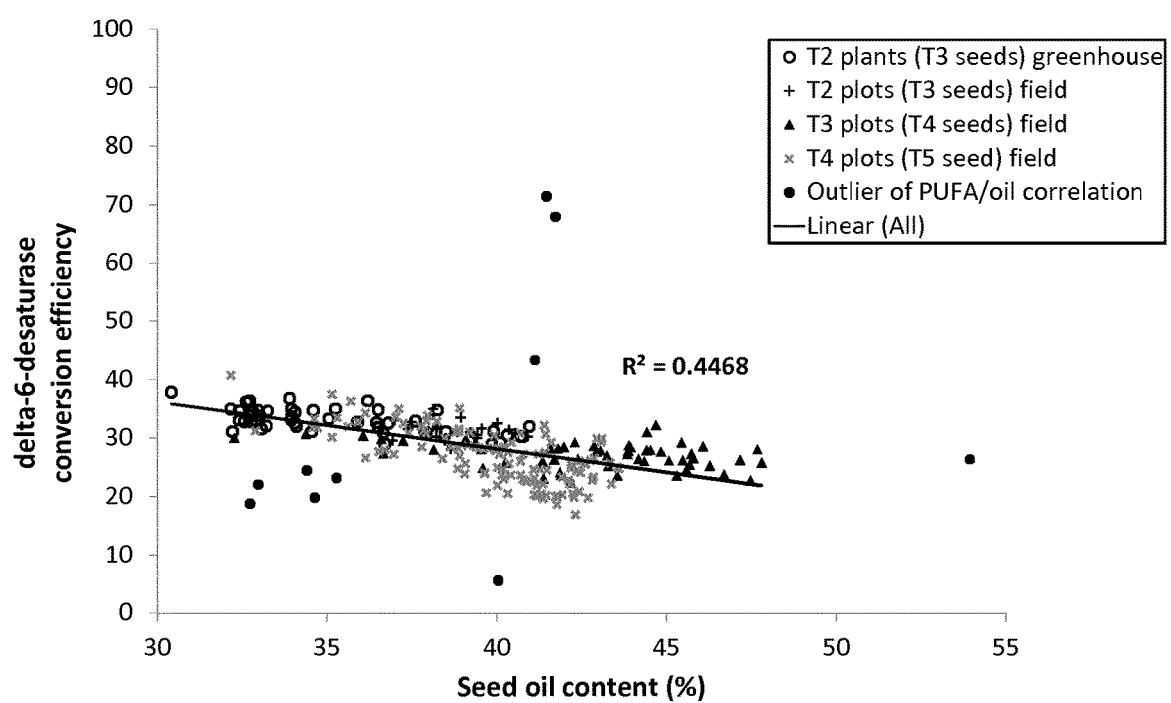
FIG. 48: The conversion efficiency of the delta-6-desaturase was negatively correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 49:
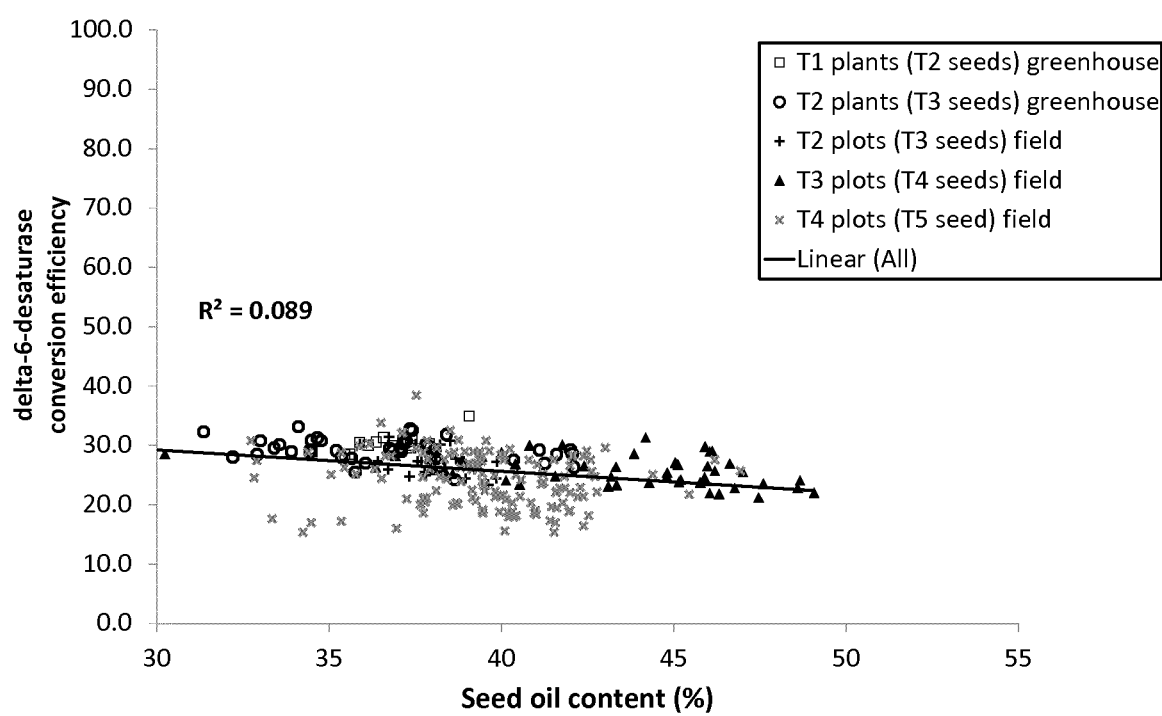
FIG. 49: The conversion efficiency of the delta-6-desaturase was negatively correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 50:
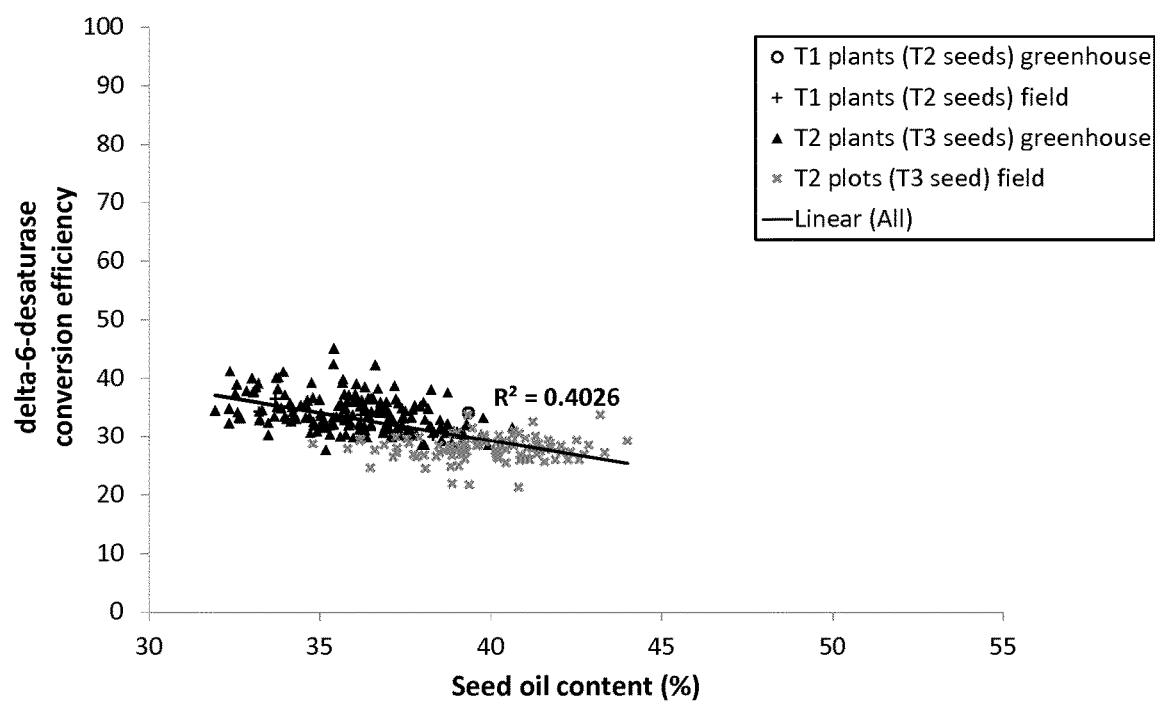
FIG. 50: The conversion efficiency of the delta-6-desaturase was negatively correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 51:
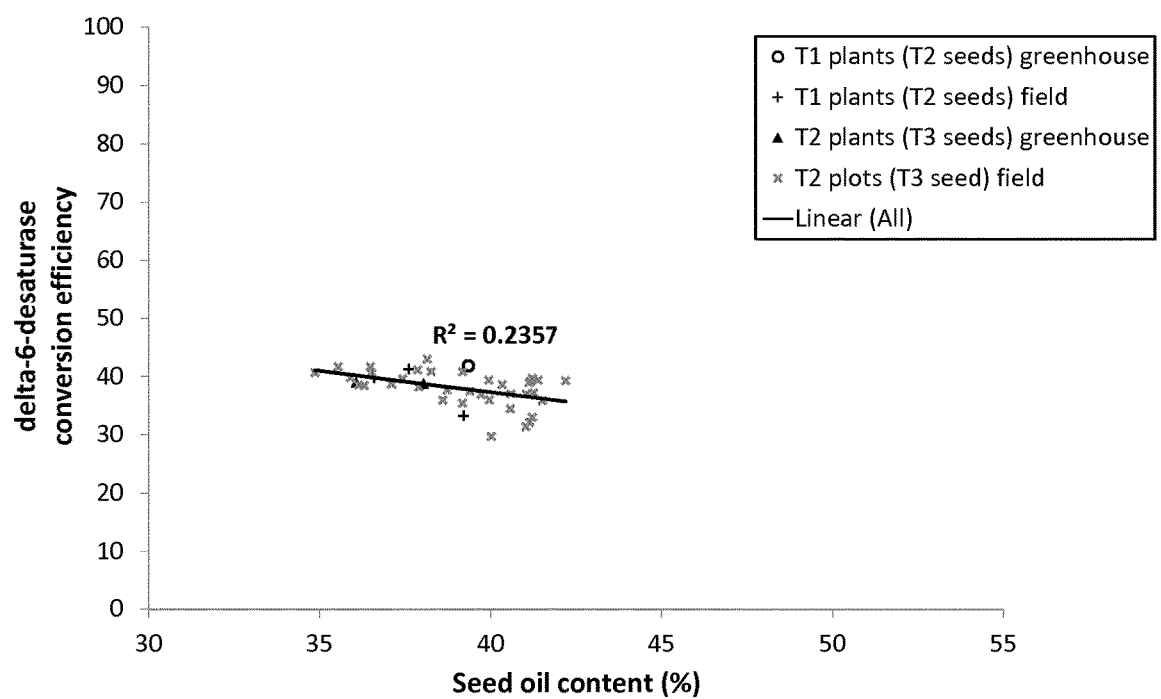
FIG. 51: The conversion efficiency of the delta-6-desaturase was negatively correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of one T2 seedbtach of one T1 plant, or a the analysis of a random selection of T3 seeds representing one plot.
Figure 52:
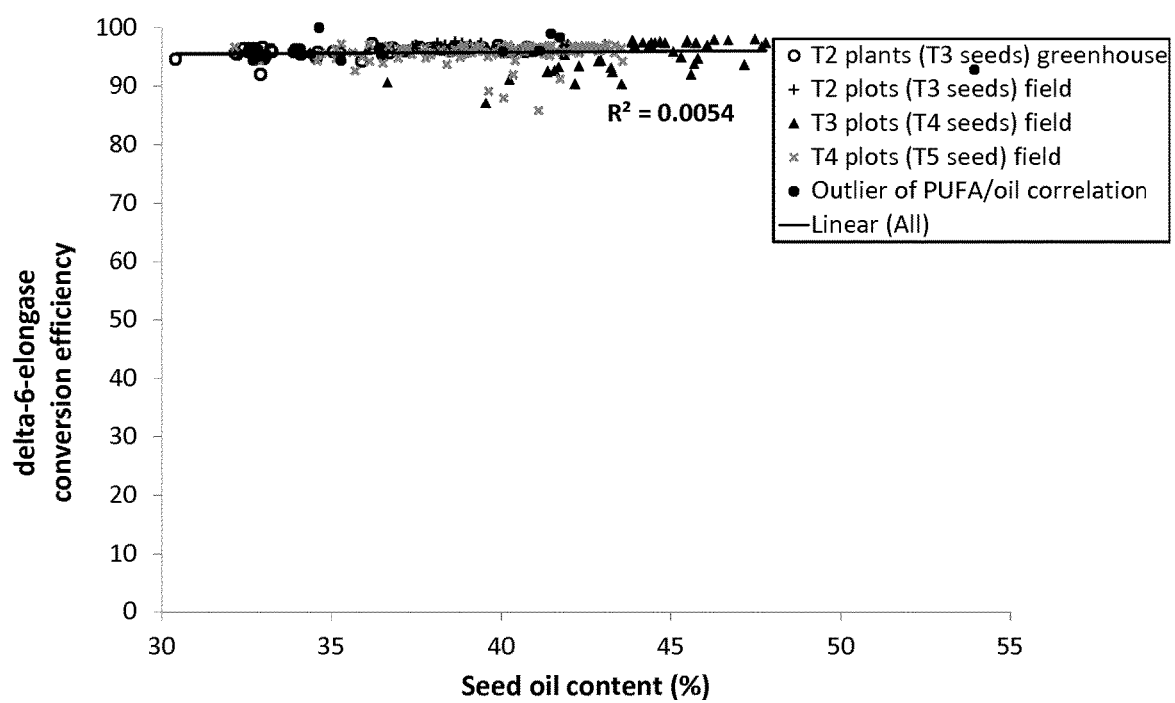
FIG. 52: The conversion efficiency of the delta-6 elongase was not negatively correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 53:
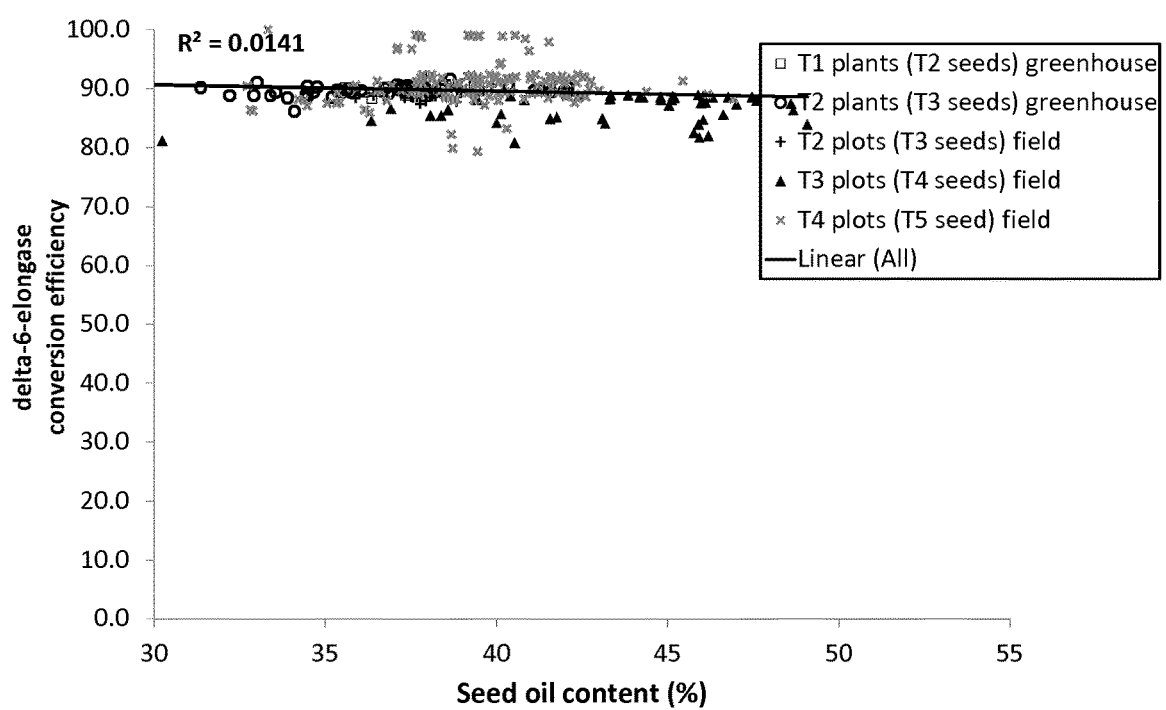
FIG. 53: The conversion efficiency of the delta-6 elongase was not negatively correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 54:
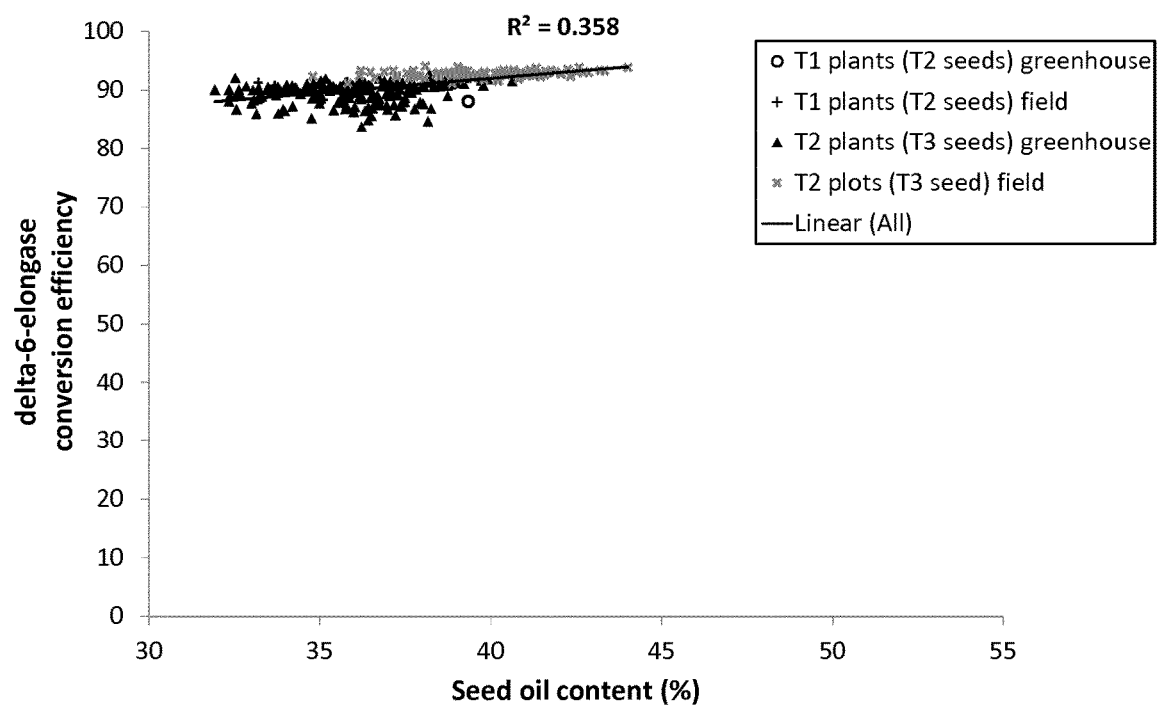
FIG. 54: The conversion efficiency of the delta-6 elongase was not negatively correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 55:
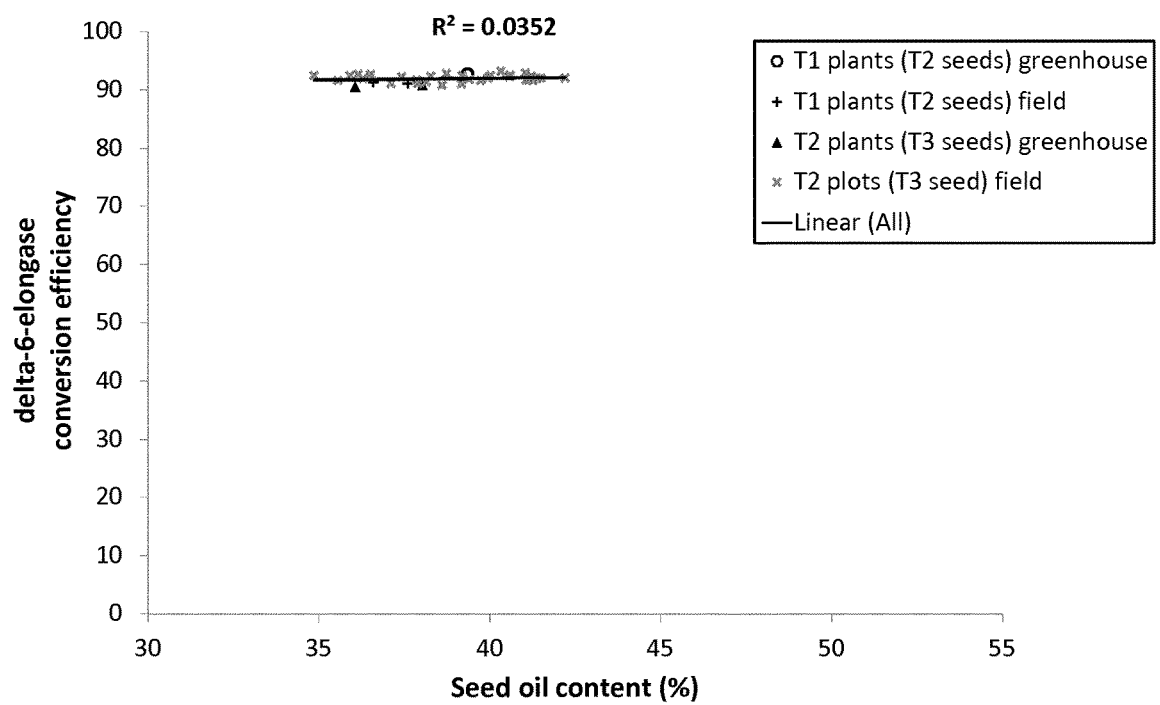
FIG. 55: The conversion efficiency of the delta-6 elongase was not negatively correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 56:
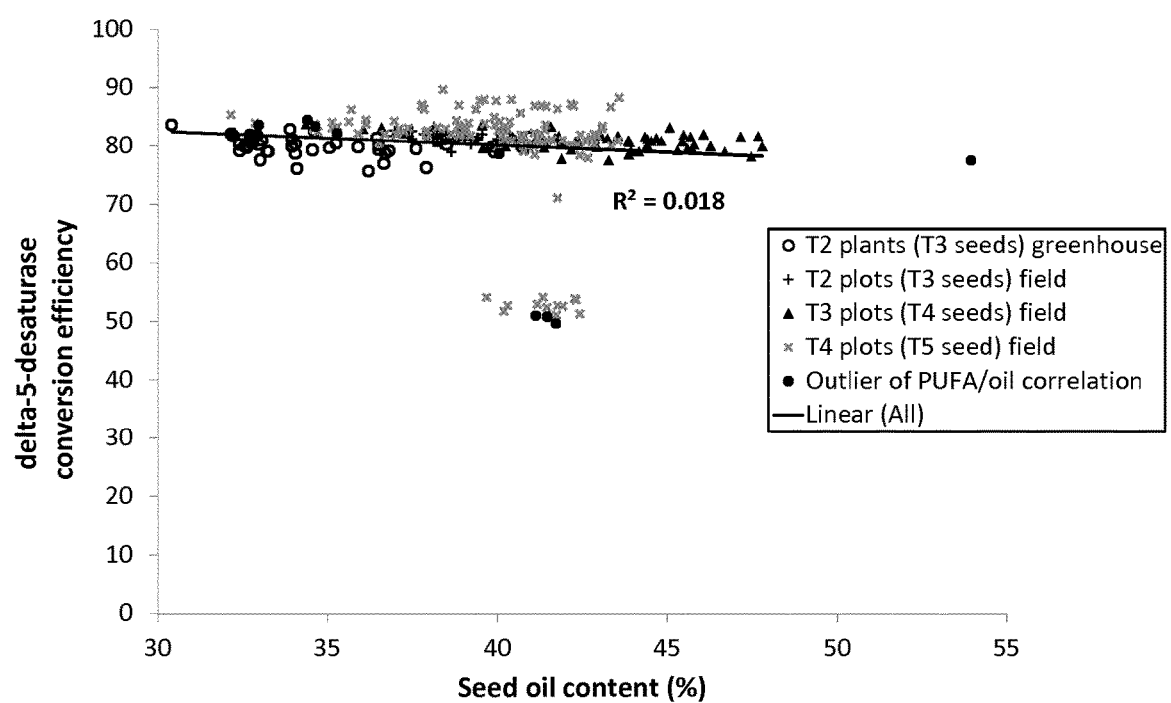
FIG. 56: The conversion efficiency of the delta-5-desaturase was not correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 57:
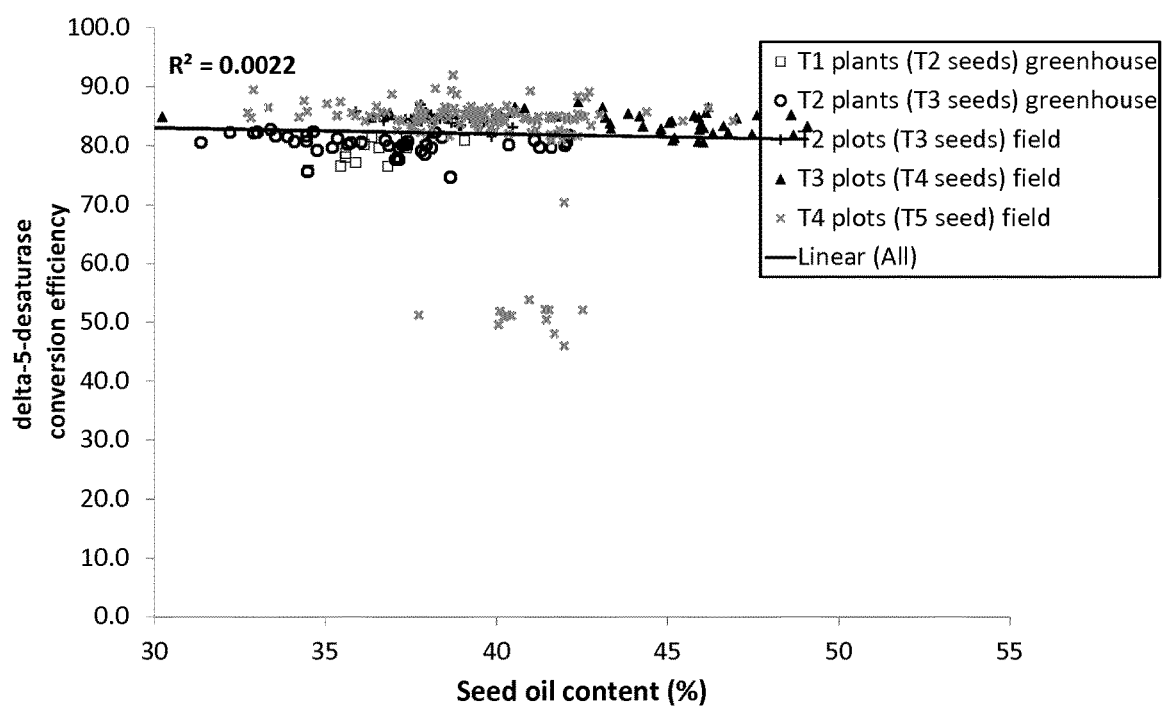
FIG. 57: The conversion efficiency of the delta-5-desaturase was not correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 58:
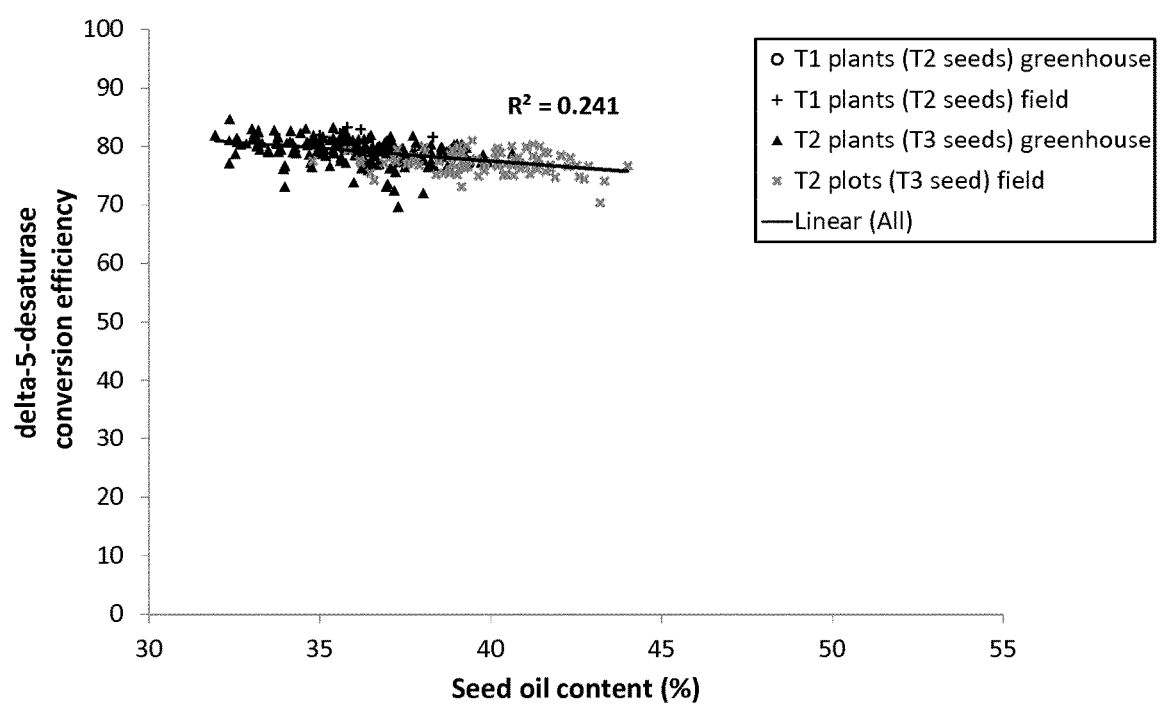
FIG. 58: The conversion efficiency of the delta-5-desaturase was not correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 59:
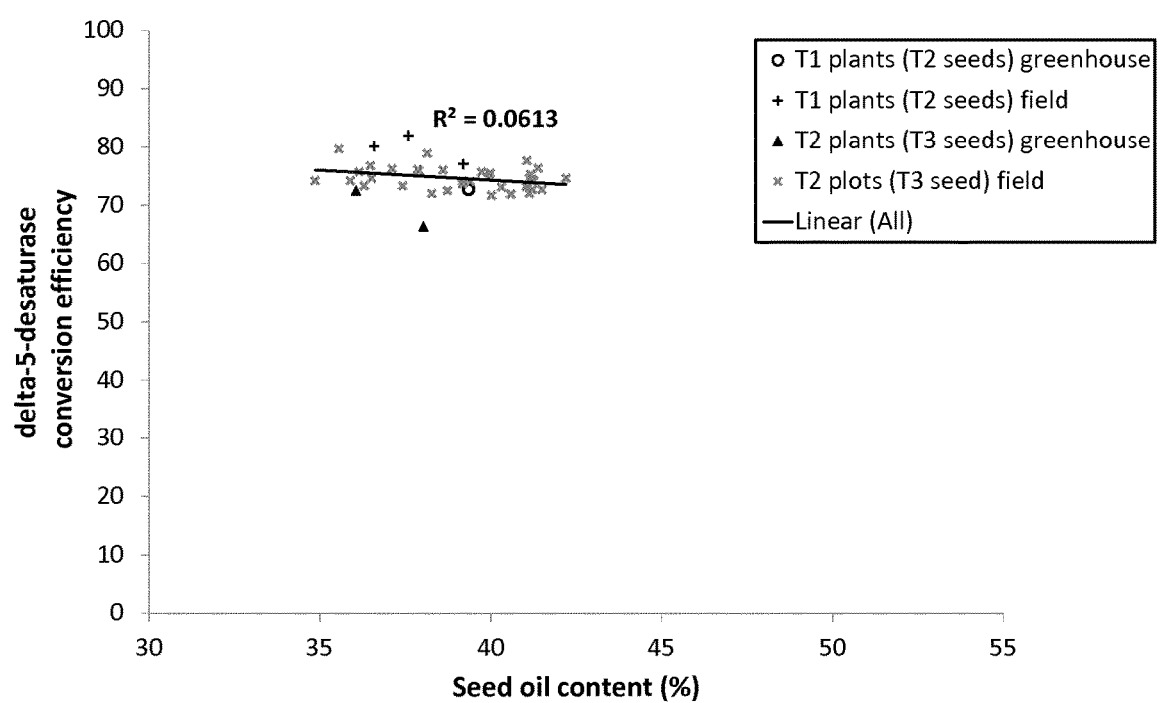
FIG. 59: The conversion efficiency of the delta-5-desaturase was not correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 60:
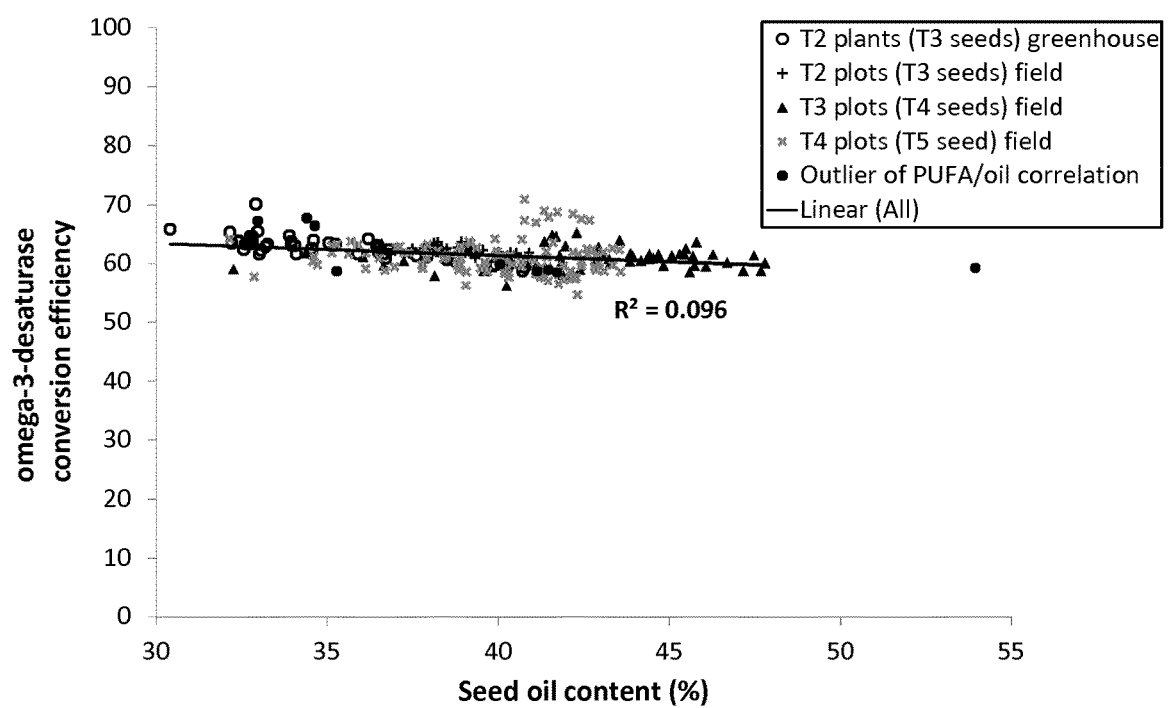
FIG. 60: The conversion efficiency of the omega-3-desaturase was not correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 61:
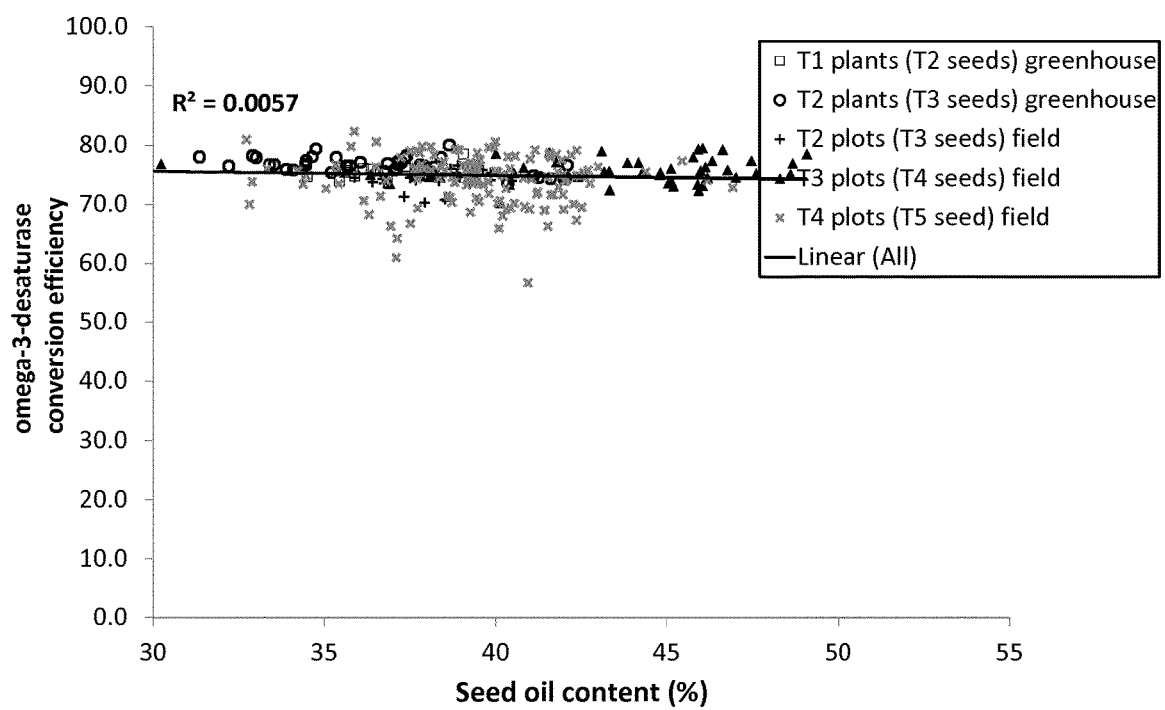
FIG. 61: The conversion efficiency of the omega-3-desaturase was not correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 62:
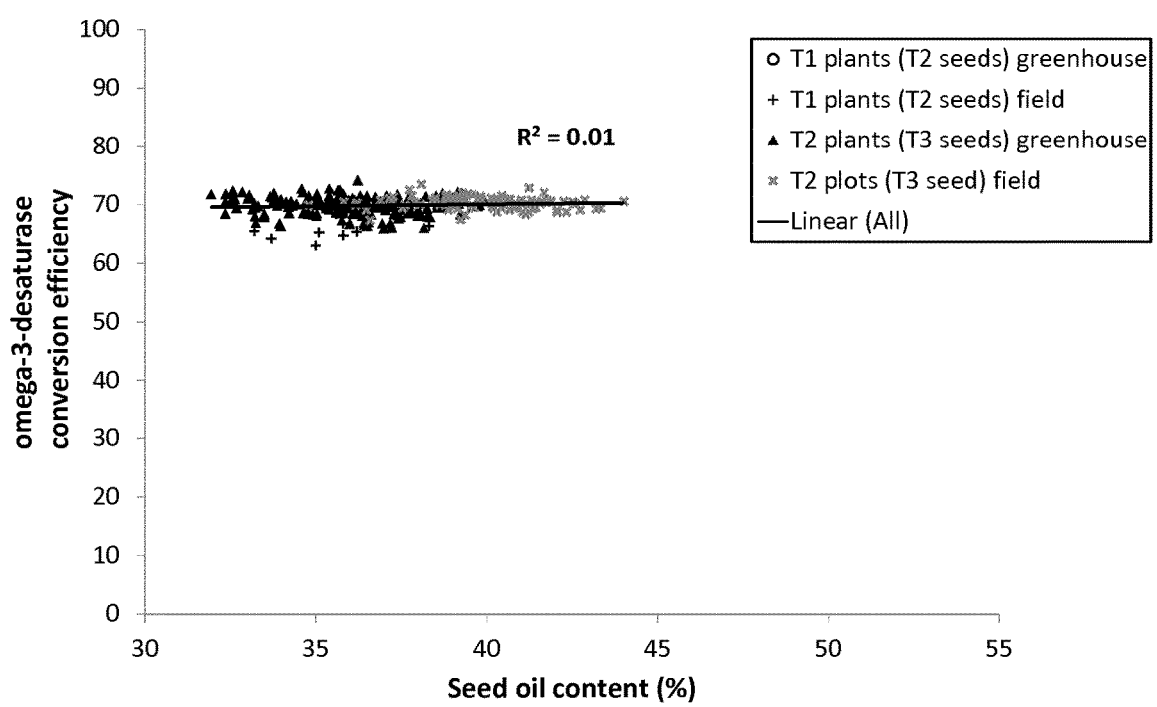
FIG. 62: The conversion efficiency of the omega-3-desaturase was not correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 63:
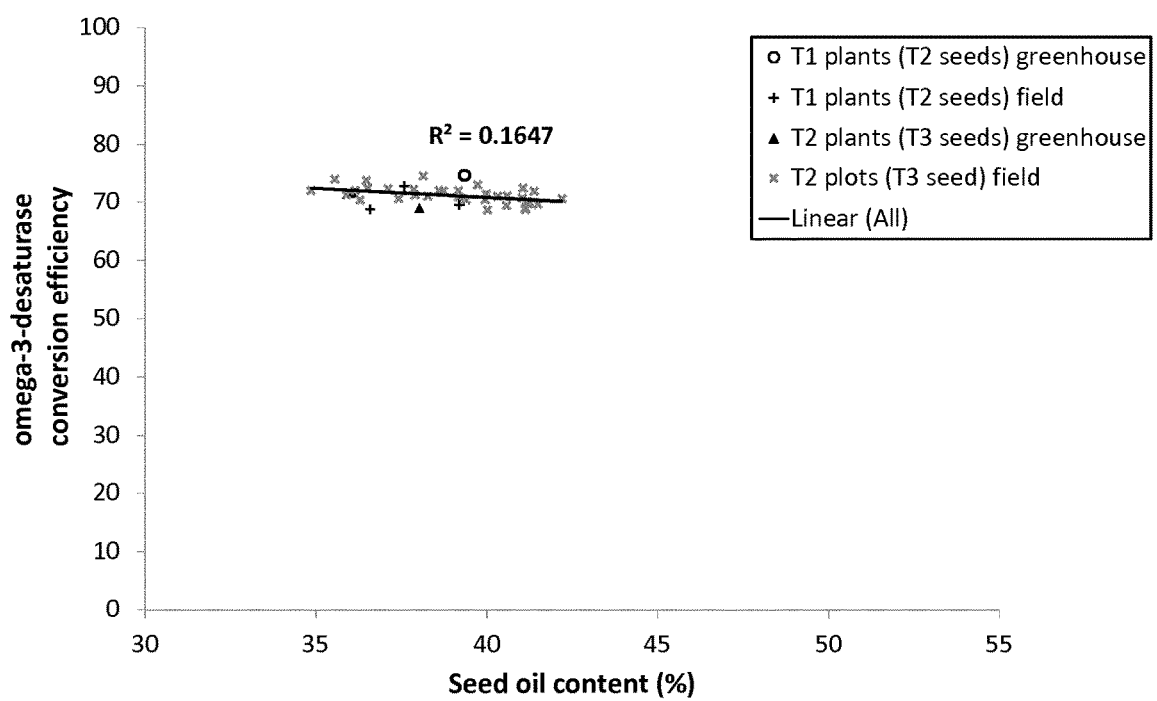
FIG. 63: The conversion efficiency of the omega-3-desaturase was not correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 64:
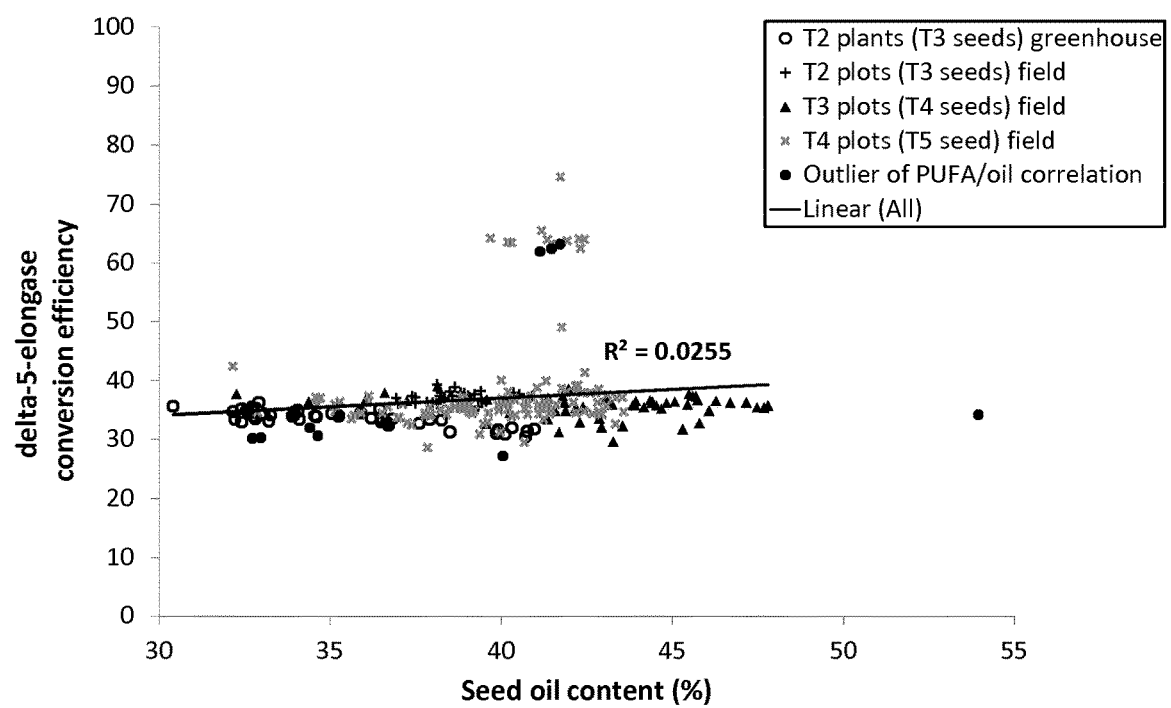
FIG. 64: The conversion efficiency of the delta-5-elongase was not correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 65:
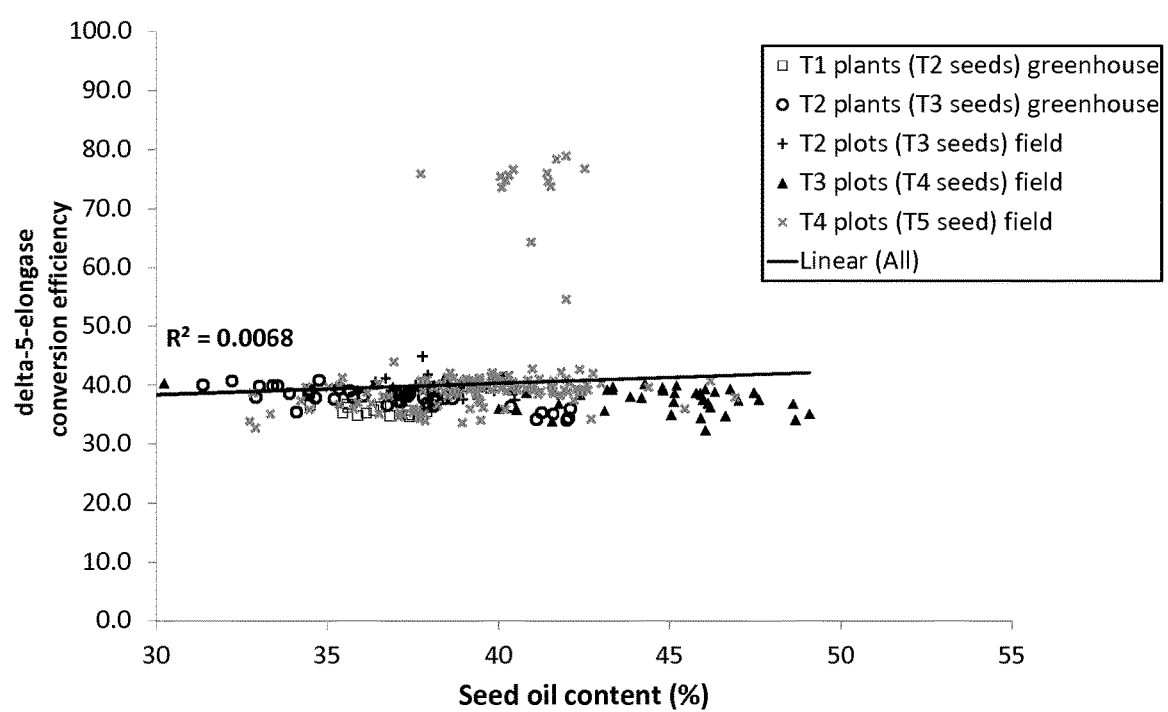
FIG. 65: The conversion efficiency of the delta-5-elongase was not correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 66:
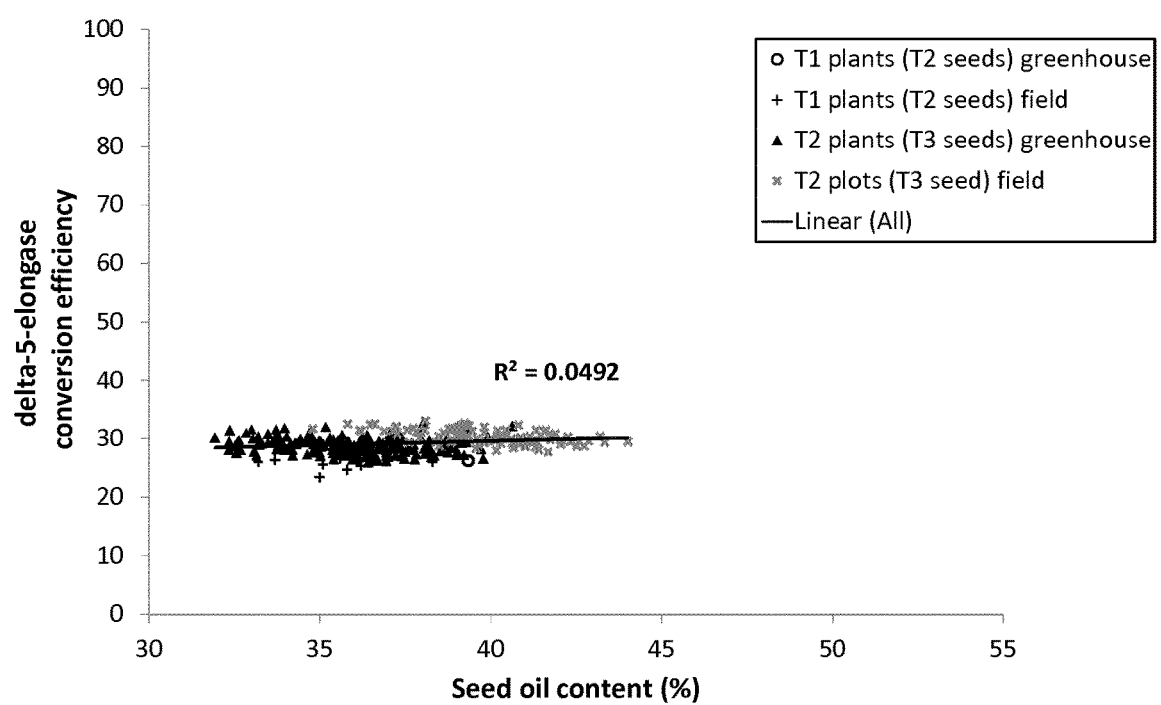
FIG. 66: The conversion efficiency of the delta-5-elongase was not correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 67:
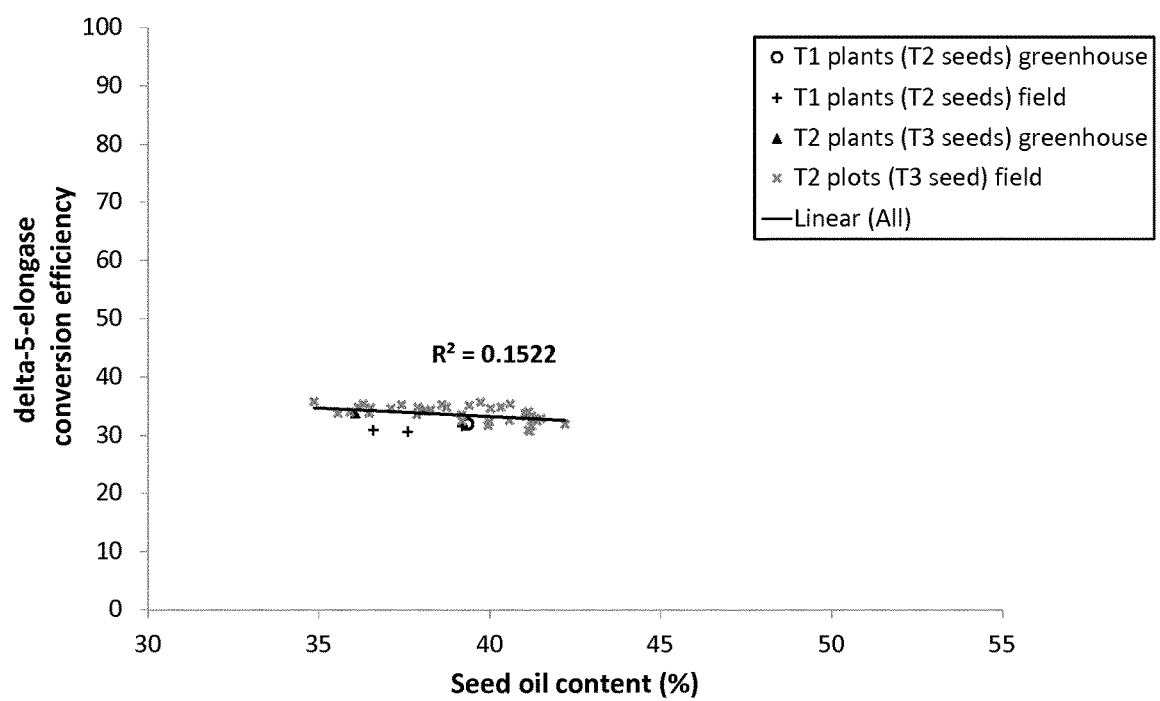
FIG. 67: The conversion efficiency of the delta-5-elongase was not correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of one T2 seedbtach of one T1 plant, or the analysis of a random selection of T3 seeds representing one plot.
Figure 68:
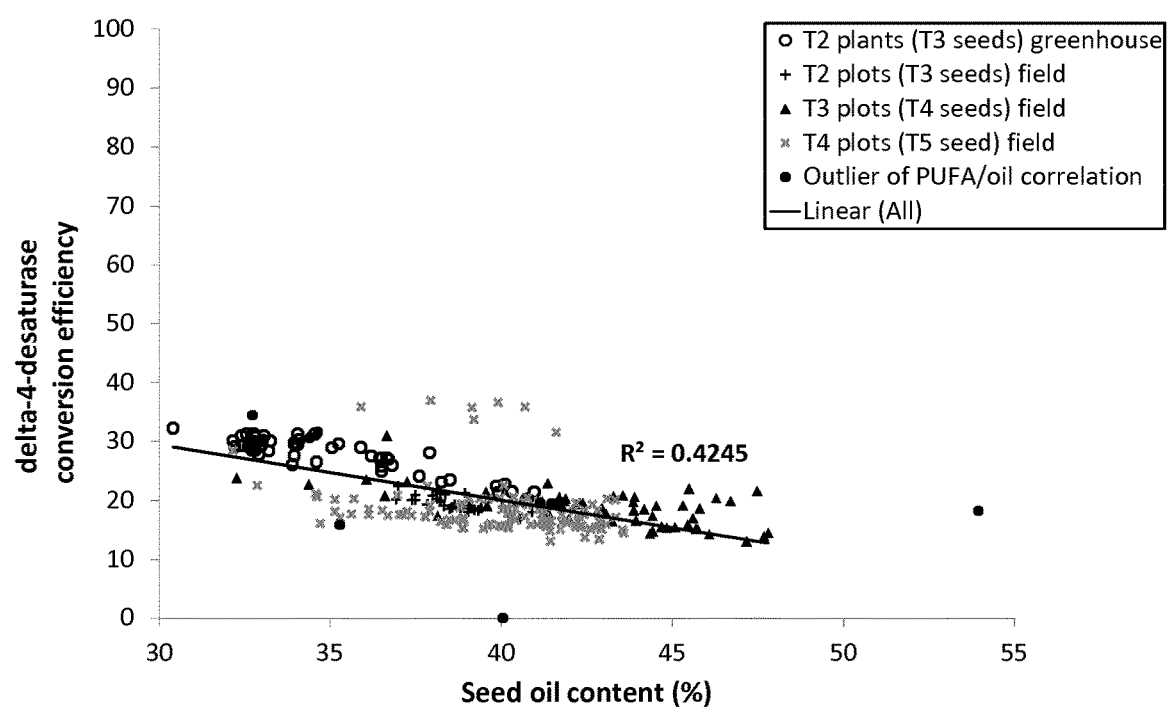
FIG. 68: The conversion efficiency of the delta-4-desaturase was negatively correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 69:
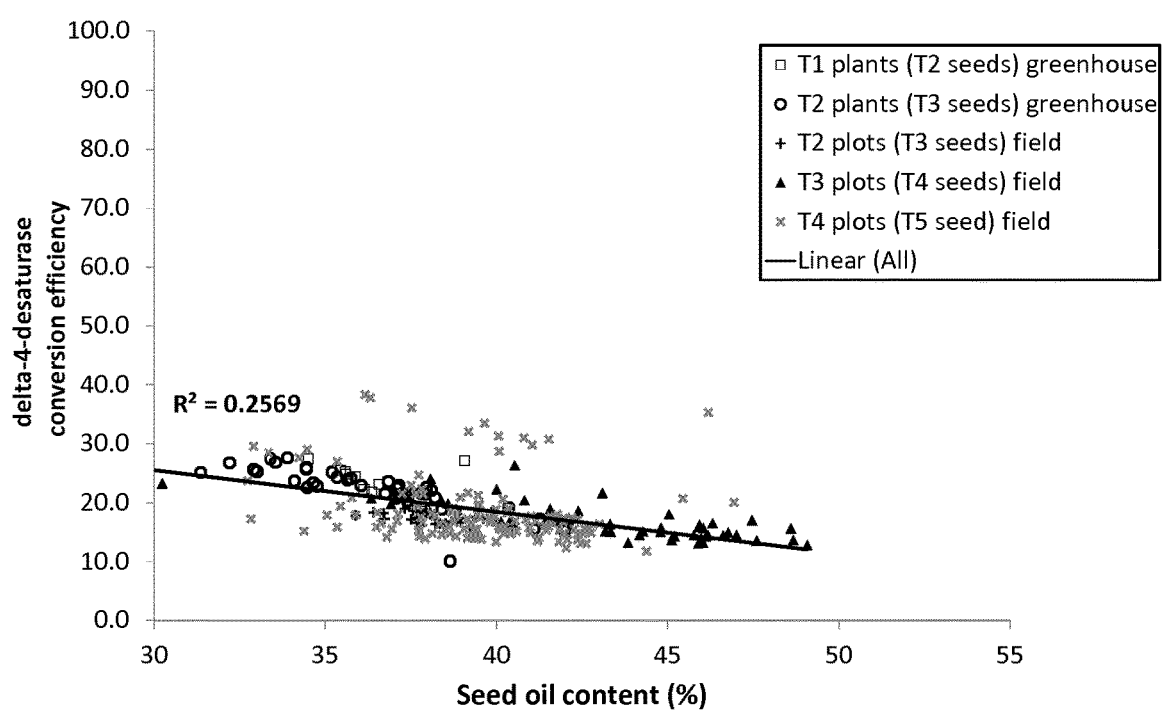
FIG. 69: The conversion efficiency of the delta-4-desaturase was negatively correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 70:
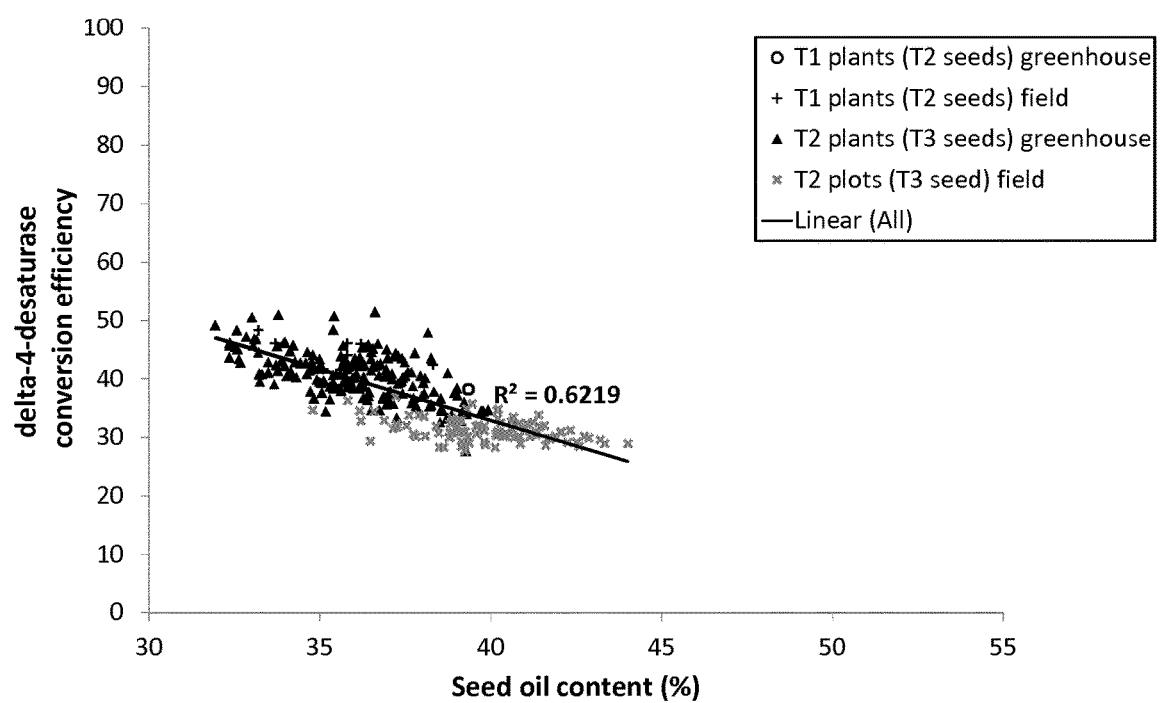
FIG. 70: The conversion efficiency of the delta-4-desaturase was negatively correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 71:
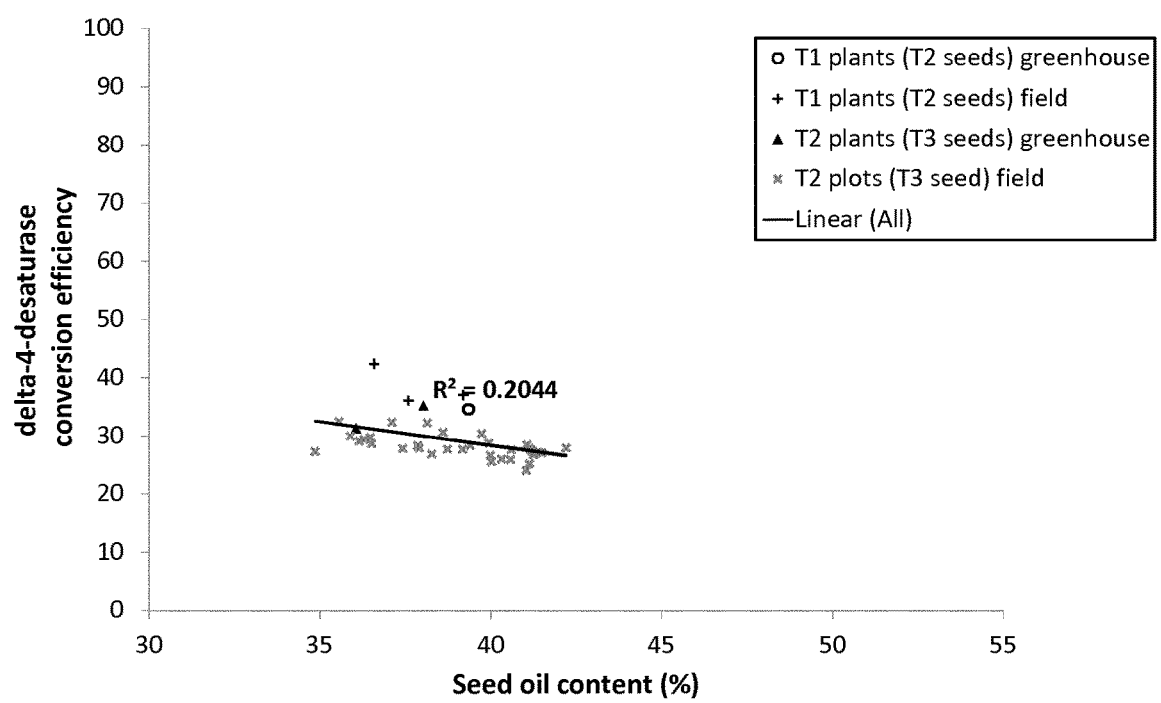
FIG. 71: The conversion efficiency of the delta-4-desaturase was negatively correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.

Example 5: Environmental Effects on VLC-PUFA Levels. Correlation Between Oil Content, VLC-PUFA Levels, and Delta-12-Desaturase Conversion Efficiency It was consistently observed that comparable populations yield higher VLC-PUFA levels in the greenhouse compared to the field. This trend usually coincides with lower oil content in the greenhouse compared to the field. To investigate this observation in more detail, oil content measured in all homozygous seed batches of the single copy event LANPMZ (event described in example 11) was plotted in FIG. 40 against the sum of all VLC-PUFA that are downstream of the delta-12-desaturase (i.e. delta-12-desaturase conversion efficiency, see FIG. 2). The same has been done for event LAODDN (event described in example 13), and is plotted FIG. 41. This analysis was also done for two events described in example 18, namely for event LBFGKN (FIG. 42), and for event LBFLFK (FIG. 43). For all transgenic events, a negative correlation was observed between oil content and delta-12-desaturase conversion efficiency. This correlation was consistent across all plants, whether grown in the greenhouse or in the field.

Figure 72:
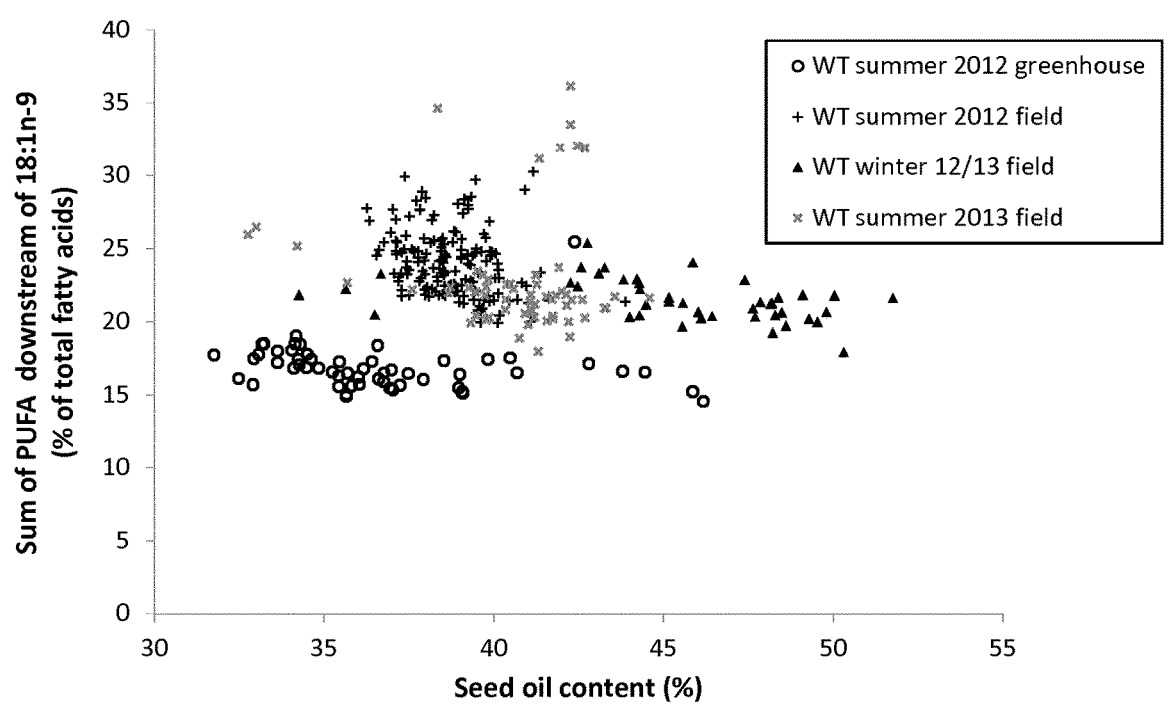
FIG. 72: The sum of all pathway fatty acids was not correlated with seed oil content in wildtype canola, but differs between greenhouse and field. Shown are data of three seasons. For the greenhouse data, one marker corresponds to one seedbatch of one plant, for the field data, one marker corresponds to an analysis on a random selection of seeds representing one plot.
Figure 73:
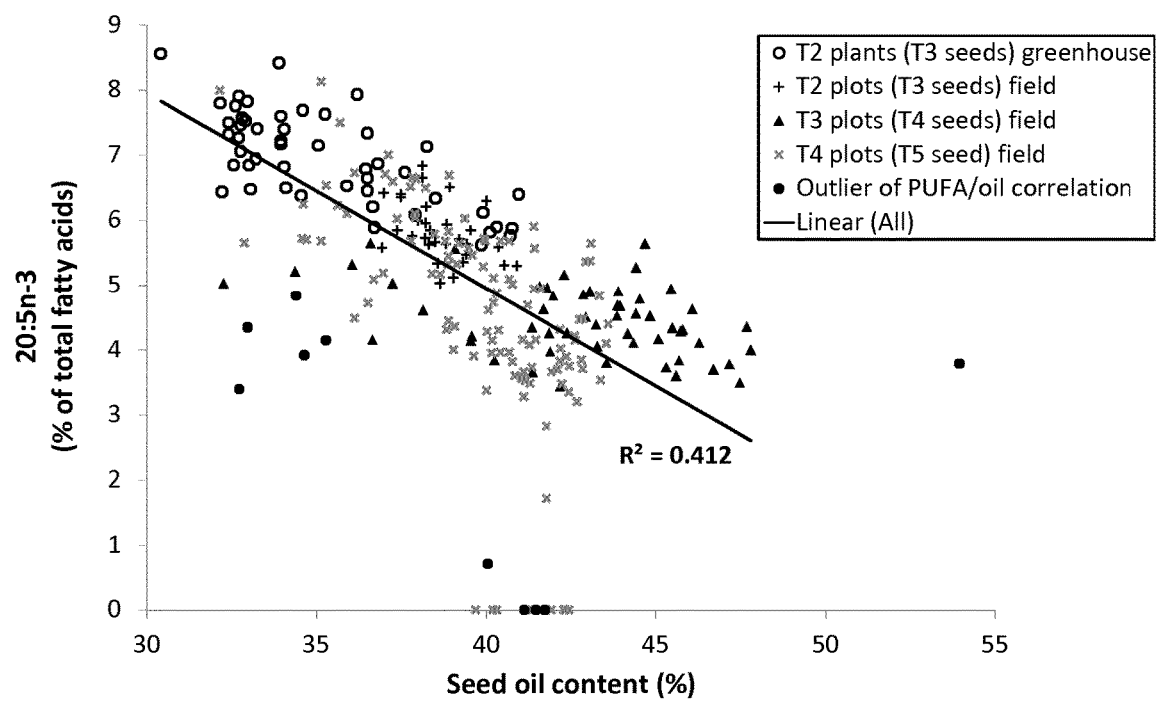
FIG. 73: The total fatty acid percentage of 20:5n-3 (EPA) correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 74:
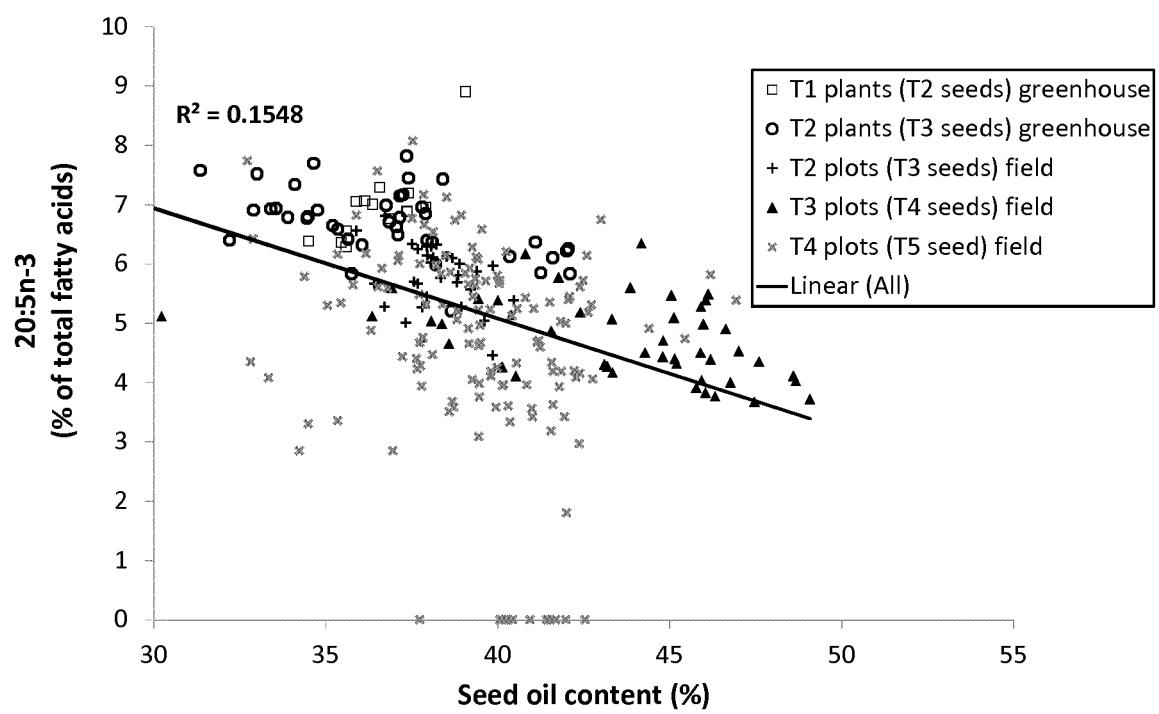
FIG. 74: The total fatty acid percentage of 20:5n-3 (EPA) correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 75:
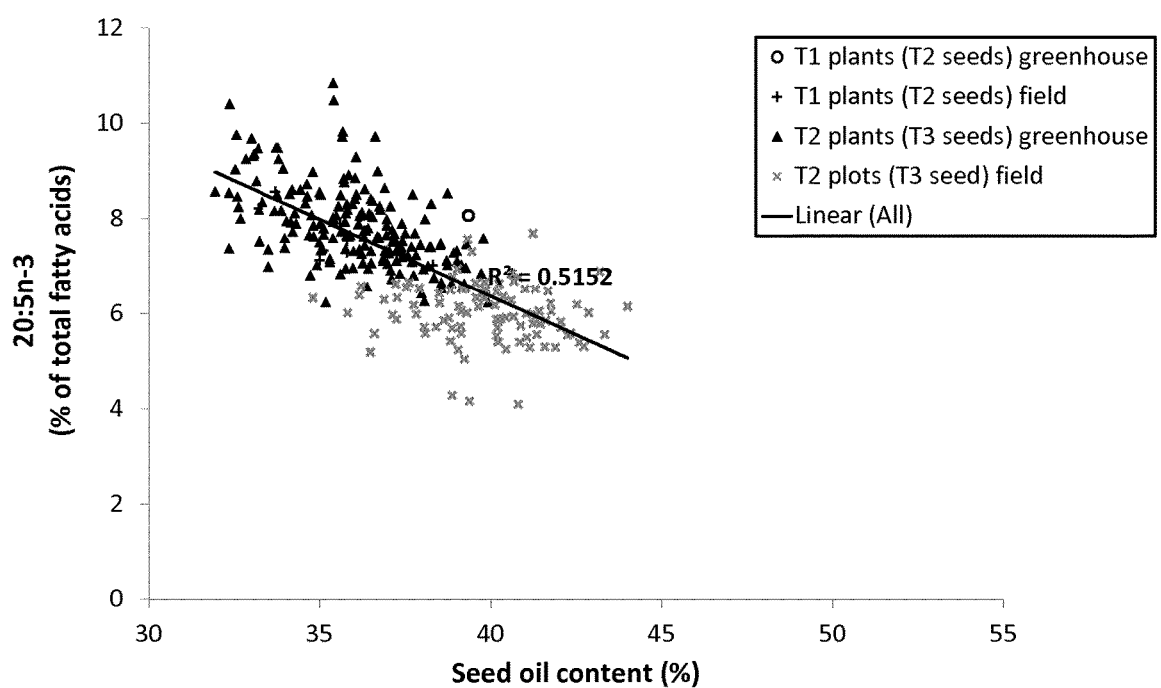
FIG. 75: The total fatty acid percentage of 20:5n-3 (EPA) correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 76:
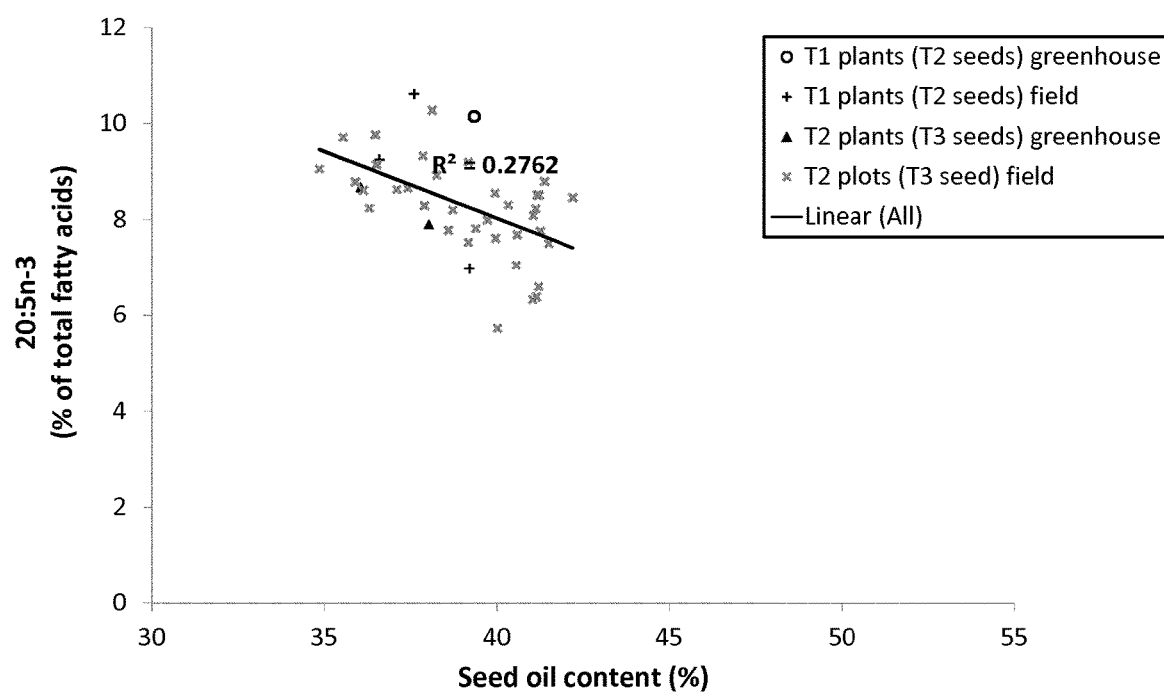
FIG. 76: The total fatty acid percentage of 20:5n-3 (EPA) correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 77:
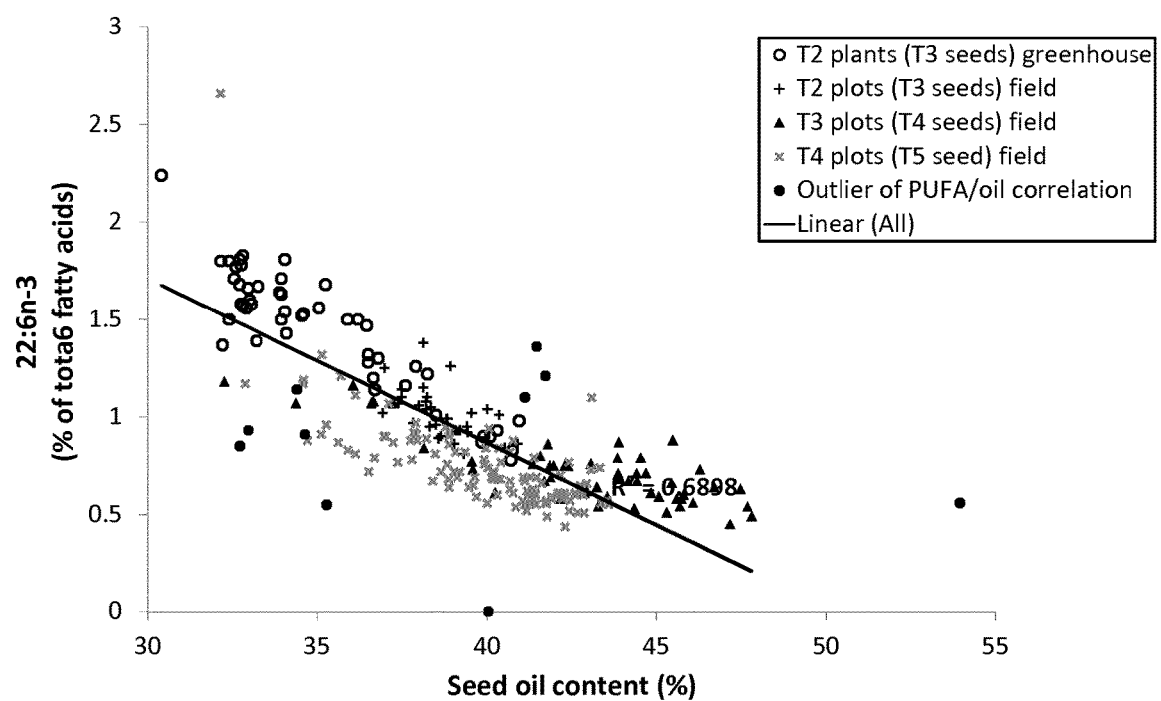
FIG. 77: The total fatty acid percentage of 22:6n-3 (DHA) correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 78:
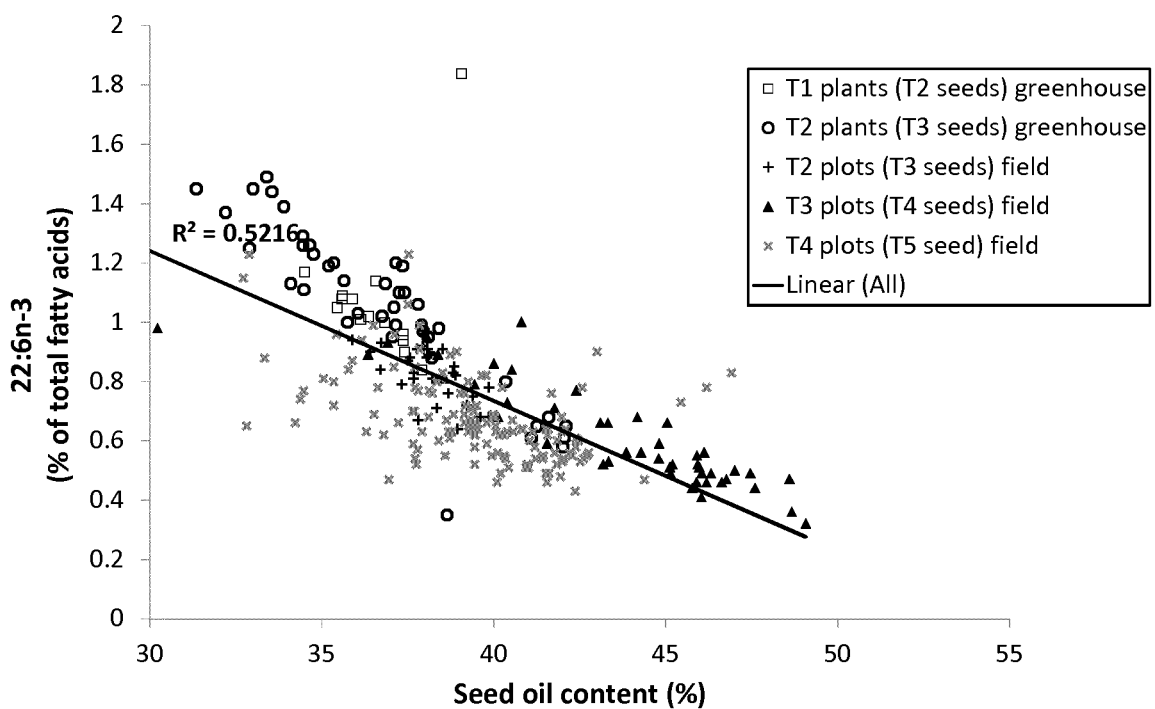
FIG. 78: The total fatty acid percentage of 22:6n-3 (DHA) correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 79:
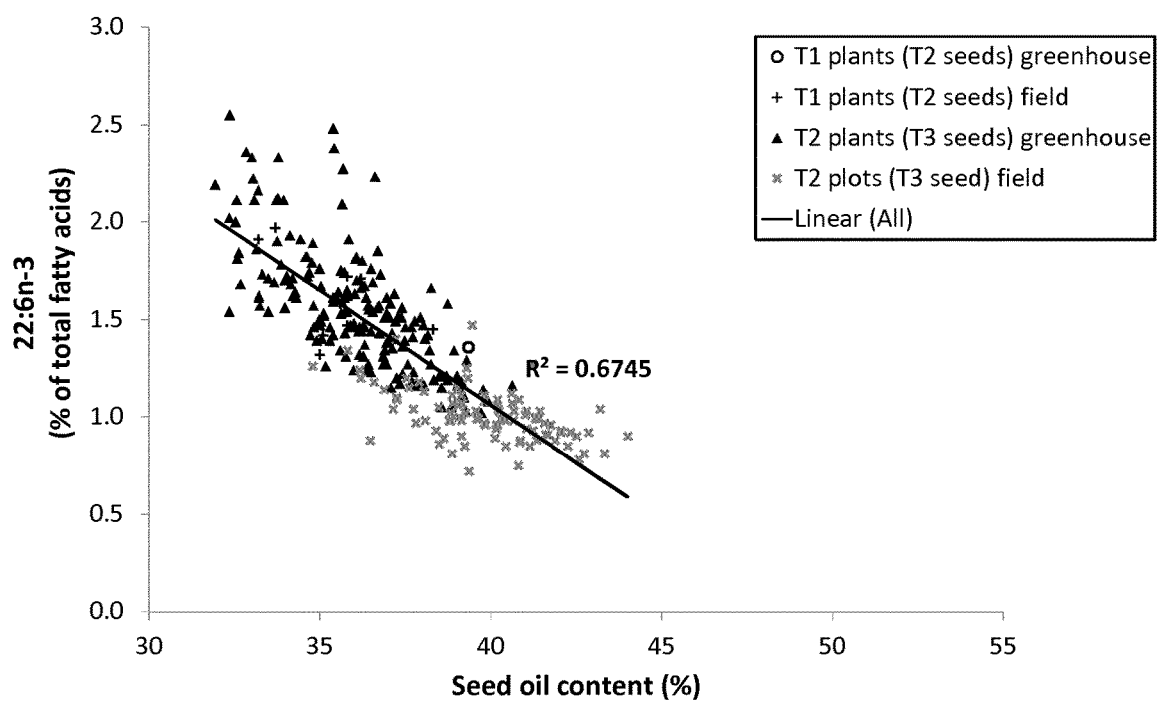
FIG. 79: The total fatty acid percentage of 22:6n-3 (DHA) correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 80:
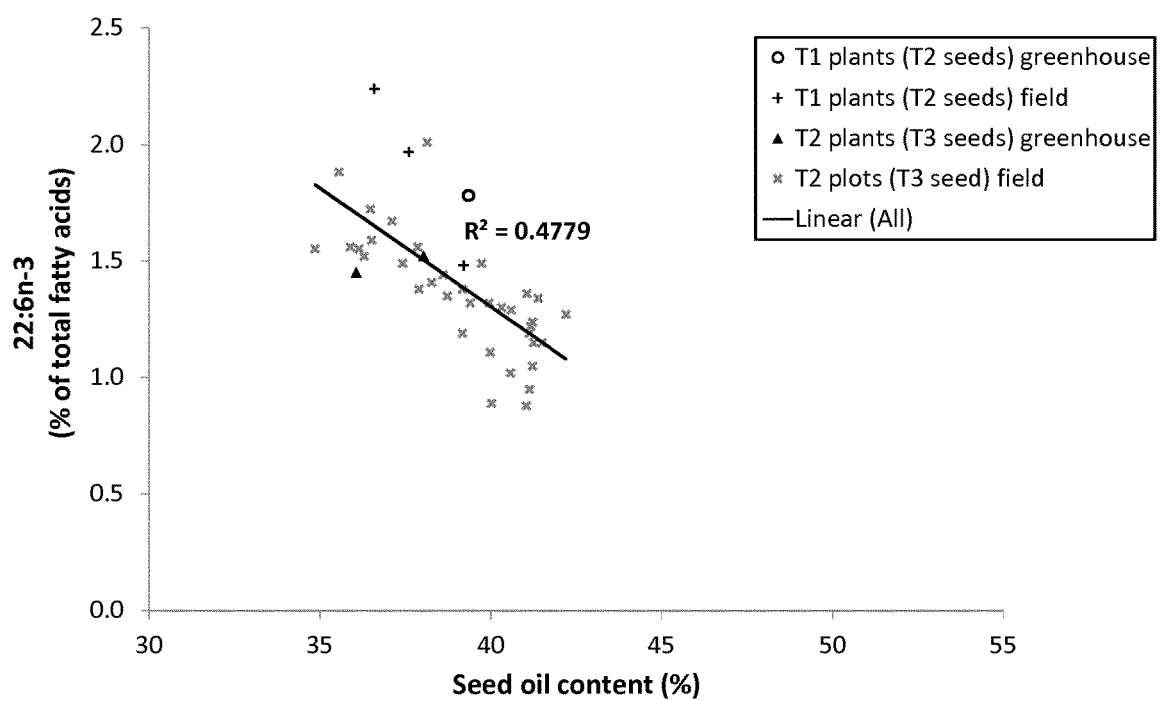
FIG. 80: The total fatty acid percentage of 22:6n-3 (DHA) correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 81:
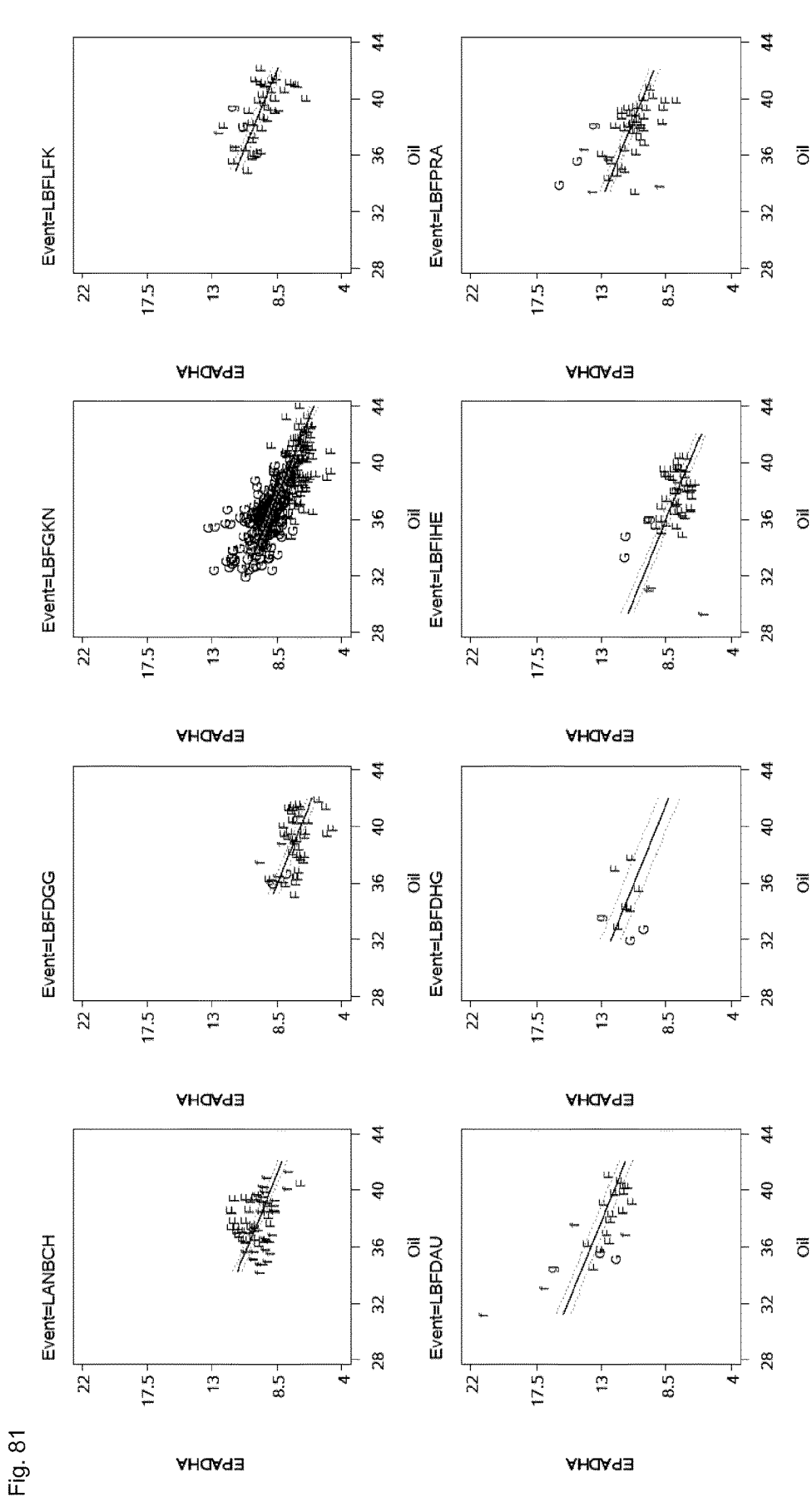
FIG. 81: The levels of EPA+DHA (20:5n-3 and 22:6n-3) correlated with seed oil content. Shown are data of homozygous plants (single plant: capital G or F, plots: lower case f, grown in greenhouses: G, grown in field trials: f and F). The data are described in more detail in Example 12 (event LANBCH), and Example 14 (all other events).
Figure 82:
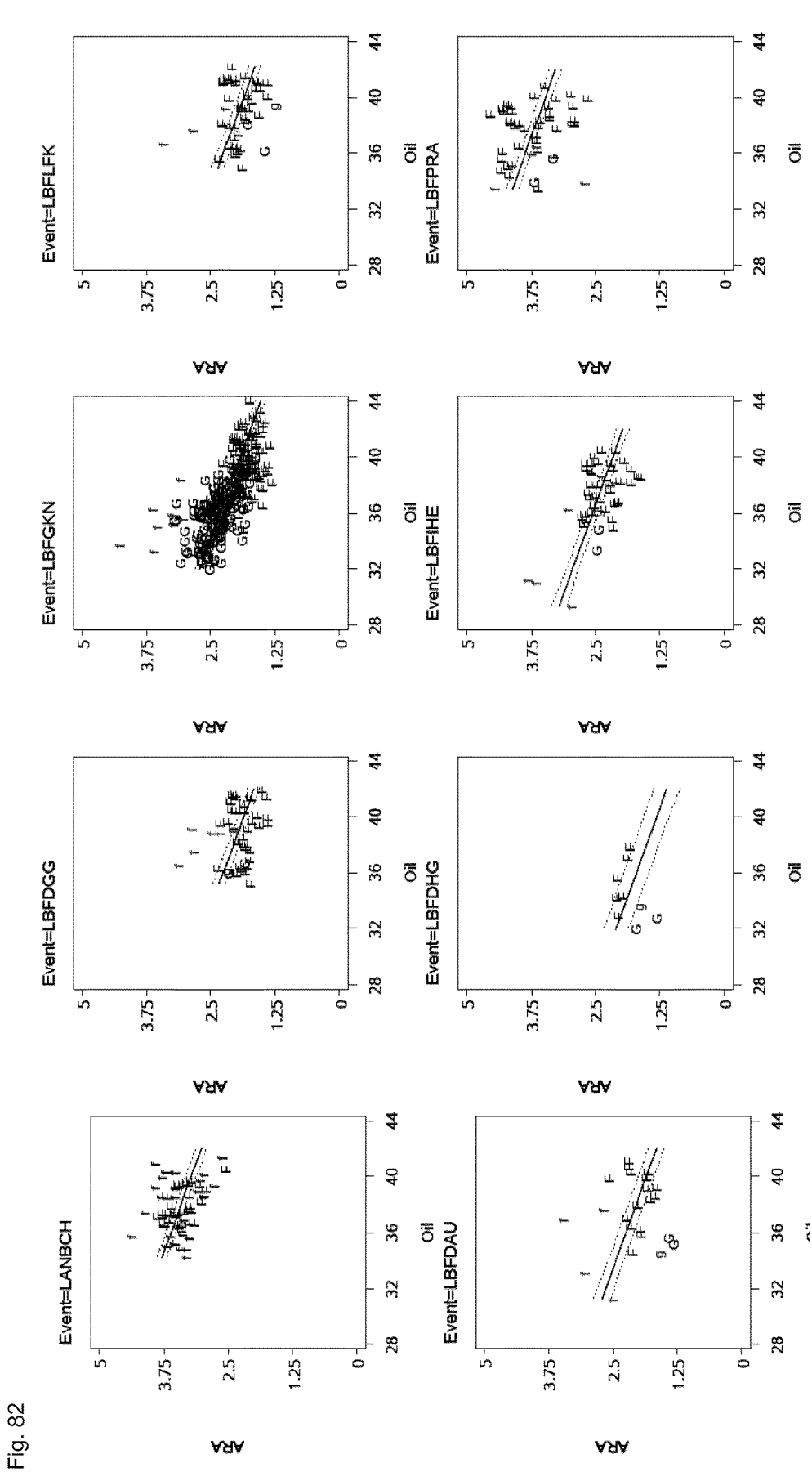
FIG. 82: The levels of ARA (20:4n-6) correlated with seed oil content. Shown are data of homozygous plants (single plant: capital G or F, plots: lower case f, grown in greenhouses: G, grown in field trials: f and F). The data are described in more detail in Example 12 (event LANBCH), and Example 14 (all other events).
Figure 83:
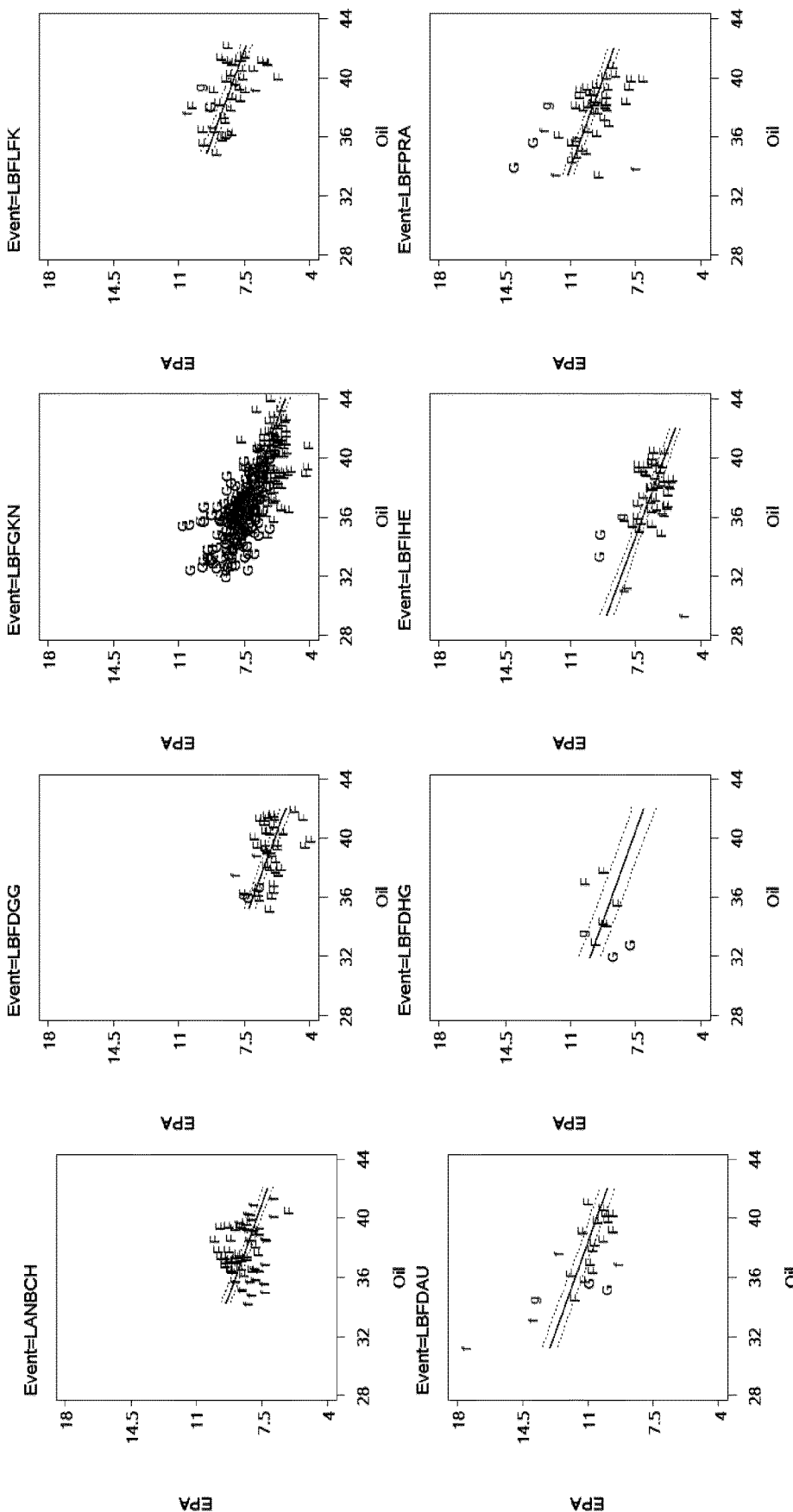
FIG. 83: The levels of EPA (20:5n-3) correlated with seed oil content. Shown are data of homozygous plants (single plant: capital G or F, plots: lower case f, grown in greenhouses: G, grown in field trials: f and F). The data are described in more detail in Example 12 (event LANBCH), and Example 14 (all other events).
Figure 84:
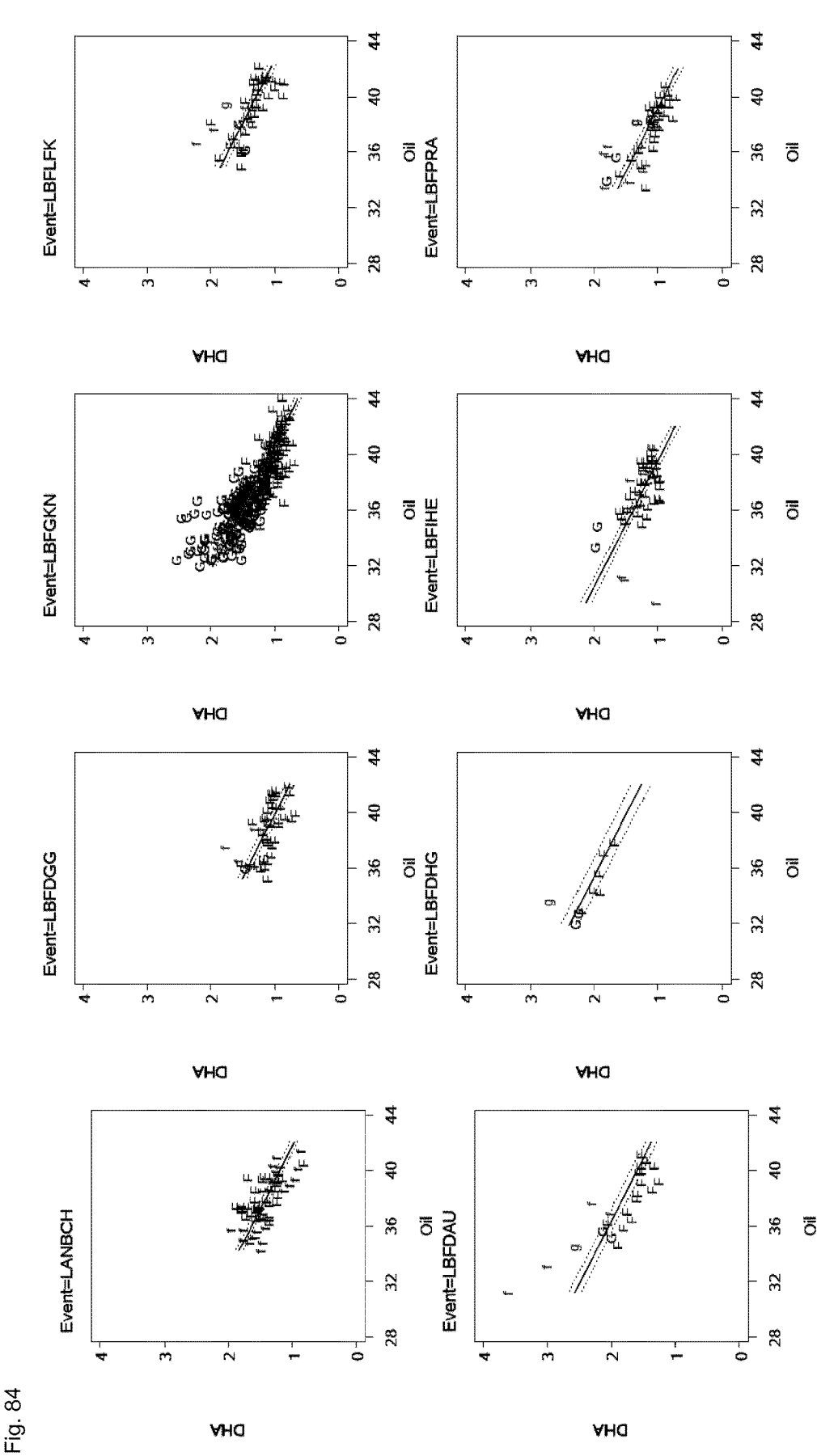
FIG. 84: The levels of DHA (22:6n-3) correlated with seed oil content. Shown are data of homozygous plants (single plant: capital G or F, plots: lower case f, grown in greenhouses: G, grown in field trials: f and F). The data are described in more detail in Example 12 (event LANBCH), and example 14 (all other events).

The same analysis for wildtype Kumily (FIG. 72) revealed no such correlation between delta-12-desaturase conversion efficiency and seed oil content. In addition, FIG. 72 shows a difference between greenhouse grown and field grown wildtype plants, in that field grown wildtype plants have higher delta-12-desaturase conversion efficiencies compared to greenhouse grown wildtype plants, regardless of oil content. Consequently, comparing FIG. 72 with FIG. 40 through FIG. 43, it can be concluded that the introduction of a transgenic delta-12-desaturase on a non-native, seed-specific promoter reduced the effect of the environment on delta-12-desaturase conversion efficiency. Surprisingly, this effect is dominant over the endogenous delta-12-desaturase and results in more consistent VLC-PUFA production across environmental conditions.

Example 6: In Vitro Demonstration of Enzyme Activity

Desaturase Enzyme Activity in Microsomes Isolated from Transgenic Yeast

Expression of desaturases and elongases was accomplished in *Saccharomyces cerevisiae*. Briefly, yeast strains containing the appropriate plasmid were grown overnight at 30° C. (in SD-medium-uracil+raffinose) and then used to inoculate a larger culture at a starting $OD_{600}$=0.2 (in SD-medium-uracil+raffinose+galactose). After 24 hours at 30° C. the culture (typically $OD_{600}$=0.6-0.8) was harvested by centrifugation and washed once in 25 mM Tris Buffer (pH 7.6). Preparation of crude extracts and microsomes from yeast expressing genes encoding desaturases and elongases was accomplished using standard procedures. Briefly, cells expressing desaturases were resuspended in 2 ml Desaturase Disruption Buffer (0.1M potassium phosphate pH 7.2, 0.33 M sucrose, 4 mM NADH, 1 mg/ml BSA (fatty acid free), 4000 U/ml catalase and protease inhibitors (Complete EDTA-free (Roche)) and disrupted using silica/zirconium beads in a Bead Beater. The crude extract was clarified by centrifugation twice at 8,000×g, 4° C.). After an additional centrifugation at 100,000×g (30 minutes at 4° C.) the microsomes were pelleted and ultimately resuspended in Desaturase Disruption Buffer (300 microliters). Protein concentrations in both the crude extract and microsomes were measured using the bicinchoninic acid (BCA) procedure (Smith, P. K., et al (1985) *Anal. Biochem.* (150): 76-85).

General Desaturase Activity Assays:

In the desaturase assay a [$^{14}$C]-labeled acyl-CoA was provided as a substrate and after the reaction the acyl-CoAs (and phospholipids) were hydrolyzed and methylated to fatty acid methyl esters (FAMEs), which were analyzed using argentation-TLC. The general assay conditions were modified from Banas et al. (Banas et al. (1997) *Physiology, Biochemistry and Molecular Biology of Plant Lipids* (Williams, J. P., Khan, M. U. and Lem, N. W. eds.) pp. 57-59).

The assay contained: 1 mg enzyme (crude extract) or 150·g (microsomal fraction), 10 nmol [$^{14}$C]-acyl-CoA (3000 dpm/nmol), 7.2 mM NADH (total), 0.36 mg BSA (total) in a buffer comprised of 0.1 M K-phosphate pH 7.2, 0.33 M sucrose, 4 mM NADH, 1 mg/ml BSA and protease inhibitors in a total volume of 200·l. After incubation at 30° C. for the desired time, 200·l of 2 M KOH in MeOH:H$_2$O (1:4) was added and incubated for 20 minutes at 90° C. Fatty acids were extracted by addition of 3 M HCl (200·l), 1.5 ml of MeOH:CHCl$_3$ (2:1) and CHCl$_3$ (500·l). The chloroform phase was recovered, dried under N$_2$(g) and fatty acids were methylated by addition of 2 ml MeOH containing 2% H$_2$SO$_4$ and incubation of 30 minutes at 90° C. FAMEs were extracted by addition of 2 ml H$_2$O and 2 ml hexane and separated by AgNO$_3$-TLC and Heptane:Diethyl ether:Acetic Acid (70:30:1) as a solvent. The radioactive lipids were visualized and quantified by electronic autoradiography using Instant Imager.

Delta-12 Desaturase (*Phytophthora sojae*), c-d12Des (Ps_GA) Enzyme Activity:

Enzyme assays were performed using re-suspended microsomes isolated from a yeast strain expressing the c-d12Des(Ps_GA) protein and compared to microsomes isolated from a control yeast strain containing an empty vector (LJB2126). In the presence of [$^{14}$C]18:1n-9-CoA, 16:0-lysphosphatidylcholine (LPC), and NADH membranes containing c-d12Des(Ps_GA) form an [$^{14}$C]18:2-fatty acid that can be isolated as a methyl ester and resolves on AgNO$_3$-TLC [heptane:diethyl ether (90:10)] similar to known synthetic standards. This enzyme activity requires NADH and was not observed in membranes isolated from the empty vector control strain. Control assays without 16:0-LPC contain a small-amount of activity, presumably due to endogenous 16:0-LPC found in yeast microsomes. Furthermore, separation of the phospholipids from the free-fatty acids after the enzymatic reaction and characterization of the isolabled fatty acid methyl esters demonstrated that all of the c-d12Des(Ps_GA) enzymatically produced 18:2n-6-fatty acid methyl ester (FAME) was found in the phosphatidylcholine fraction. c-d12Des(Ps_GA) enzyme activity may also be demonstrated using other [$^{14}$C]acyl-CoA's which may include, but are not limited to: [$^{14}$C]18:2n-6-CoA, [$^{14}$C]20:3n-6-CoA, [$^{14}$C]20:4n-6-CoA, [$^{14}$C]22:5n-3-CoA.

Delta-6 Desaturase (*Ostreococcus burl*), c-d6Des(Ot_Febit) Enzyme Activity:

c-d6Des(Ot_febit) enzyme activity and substrate specificity can be demonstrated in microsomes isolated from a yeast strain expressing the c-d6Des(Ot_febit) protein using an [$^{14}$C]acyl-CoA in the general assay described above. [$^{14}$C]Acyl-CoA's may include, but are not limited to: [$^{14}$C] 18:1n-9-CoA, [$^{14}$C]18:2n-6-CoA, [$^{14}$C]20:3n-6-CoA, [$^{14}$C] 20:4n-6-CoA, [$^{14}$C]22:5n-3-CoA. Isolated fatty acid methyl esters derived from enzymatic substrates and products can be resolved using AgNO$_3$-TLC and Heptane:Diethyl ether: Acetic Acid (70:30:1) as a solvent. Furthermore, the c-d6Des(Ot_febit) enzyme can be shown to directly desaturate an acyl-CoA substrate, as described in "Desaturase Headgroup (CoA vs PC) Preference", as suggested in previous reports (Domergue et al. (2005) Biochem. J. 389: 483-490).

Delta-5 Desaturase (*Thraustochytrium* ssp.), c-d5Des (Tc_GA2) Enzyme Activity:

c-d5Des(Tc_GA2) enzyme activity and substrate specificity can be demonstrated in microsomes isolated from a yeast strain expressing the c-d5Des(Tc_GA2) protein using an [$^{14}$C]acyl-CoA general assay as described above. [$^{14}$C] Acyl-CoA's may include, but are not limited to: [$^{14}$C]18: 1n-9-CoA, [$^{14}$C]18:2n-6-CoA, [$^{14}$C]20:3n-6-CoA, [$^{14}$C]20: 4n-6-CoA, [$^{14}$C]22:5n-3-CoA. Isolated fatty acid methyl esters derived from enzymatic substrates and products can be resolved using Reverse Phase-TLC (Silica gel 60 RP-18) and acetonitrile (100%) as a solvent.

Omega-3 Desaturase (*Phytophthora infestans*), c-o3Des (Pi_GA2) Enzyme Activity:

c-o3Des(Pi_GA2) enzyme activity and substrate specificity can be demonstrated in microsomes isolated from a yeast strain expressing the c-o3Des(Pi_GA2) protein using [$^{14}$C] acyl-CoA in the general assay described above. [$^{14}$C]Acyl-CoA's may include, but are not limited to: [$^{14}$C]18:1n-9-CoA, [$^{14}$C]18:2n-6-CoA, [$^{14}$C]20:3n-6-CoA, [$^{14}$C]20:4n-6-CoA, [$^{14}$C]22:5n-3-CoA. Isolated fatty acid methyl esters derived from enzymatic substrates and products can be resolved using Reverse Phase-TLC (Silica gel 60 RP-18) and acetonitrile (100%) as a solvent.

Omega-3 Desaturase (*Pythium irregulare*), c-o3Des (Pir_GA) Enzyme Activity:

c-o3Des(Pir_GA) enzyme activity and substrate specificity can be demonstrated in microsomes isolated from a yeast strain expressing the c-o3Des(Pir_GA) protein using an [$^{14}$C]acyl-CoA in the general assay described above. [$^{14}$C] Acyl-CoA's may include, but are not limited to: [$^{14}$C]18: 1n-9-CoA, [$^{14}$C]18:2n-6-CoA, [$^{14}$C]20:3n-6-CoA, [$^{14}$C]20: 4n-6-CoA, [$^{14}$C]22:5n-3-CoA. Isolated fatty acid methyl esters derived from enzymatic substrates and products can be resolved using Reverse Phase-TLC (Silica gel 60 RP-18) and acetonitrile (100%) as a solvent.

Delta-4 Desaturase (*Thraustochytrium* ssp.), c-d4Des (Tc_GA) Enzyme Activity:

c-d4Des(Tc_GA) enzyme activity and substrate specificity can be demonstrated in microsomes isolated from a yeast strain expressing the c-d4Des(Tc_GA) protein using an [$^{14}$C]acyl-CoA in the general assay described above. [$^{14}$C] Acyl-CoA's may include, but are not limited to: [$^{14}$C]18: 1n-9-CoA, [$^{14}$C]18:2n-6-CoA, [$^{14}$C]20:3n-6-CoA, [$^{14}$C]20: 4n-6-CoA, [$^{14}$C]22:5n-3-CoA. Isolated fatty acid methyl esters derived from enzymatic substrates and products can be resolved using Reverse Phase-TLC (Silica gel 60 RP-18) and acetonitrile (100%) as a solvent.

Delta-4 Desaturase (*Pavlova lutheri*), c-d4Des(Pl_GA)2 Enzyme Activity:

c-d4Des(Pl_GA)2 enzyme activity and substrate specificity can be demonstrated in microsomes isolated from a yeast strain expressing the c-d4Des(Pl_GA)2 protein using an [$^{14}$C]acyl-CoA in the general assay described above. [$^{14}$C]Acyl-CoA's may include, but are not limited to: [$^{14}$C] 18:1n-9-CoA, [$^{14}$C]18:2n-6-CoA, [$^{14}$C]20:3n-6-CoA, [$^{14}$C]

20:4n-6-CoA, [$^{14}$C]22:5n-3-CoA. Isolated fatty acid methyl esters derived from enzymatic substrates and products can be resolved using Reverse Phase-TLC (Silica gel 60 RP-.18) and acetonitrile (100%) as a solvent.

Delta-4 Desaturase (*Euglena gracilis*), c-d4Des(Eg) Enzyme Activity:

c-d4Des(Eg) enzyme activity and substrate specificity can be demonstrated in microsomes isolated from a yeast strain expressing the c-d4Des(Eg) protein using an [$^{14}$C]acyl-CoA in the general assay described above. [$^{14}$C]Acyl-CoA's may include, but are not limited to: [$^{14}$C]18:1n-9-CoA, [$^{14}$C]18:2n-6-CoA, [$^{14}$C]20:3n-6-CoA, [$^{14}$C]20:4n-6-CoA, [$^{14}$C]22:5n-3-CoA. Isolated fatty acid methyl esters derived from enzymatic substrates and products can be resolved using Reverse Phase-TLC (Silica gel 60 RP-18) and acetonitrile (100%) as a solvent.

Desaturase Activity in Microsomes Isolated from Transgenic *Brassica napus*.

Microsomes containing recombinant desaturases and elongases capable of synthesizing docosahexaenoic acid (22:6n-3) were isolated from immature seeds from transgenic *B. napus* using a procedure adopted from Bafor, M. et al. Biochem J. (1991) 280, 507-514. Briefly, immature seeds were first seperated from canola pods and then the developing embryos were isolated from the seed coat and transferred to ice-cold 0.1M Phosphate buffer (pH 7.2). The developing embryos were then washed with fresh Phosphate buffer, transferred to an ice-cold mortar, and ground to a homogenous solution in Extraction Buffer (0.1 M Phosphate, pH 7.2, 0.33 M sucrose, 1 mg/ml BSA (essentially fatty acid free), 4000 U/ml catalase, 4 mM NADH and protease inhibitor-Complete EDTA-free (Roche)). The lysed developing embryo's were diluted 20-fold with additional Extraction Buffer and passed through 2 layers of Miracloth into a centrifuge tube. Following centrifugation at 18,000×g for 10 minutes at 4° C., the clarified supernatant was passed through Miracloth into an ultracentrifuge tube. Following centrifugation at 105,000×g for 60 minutes at 4° C., the supernatant was removed from the microsomal pellet, which was then washed once with Extraction Buffer, and then using a Dounce homogenizer resuspended as a homogenous solution in Extraction Buffer (about 1 ml per 500 embryo's).

Enzyme activity can be demonstrated for the desaturases using the assays described above in "Desaturase Enzyme Activity in Microsomes Isolated from Transgenic Yeast" for microsomes isolated from yeast expression strains.

In summary in "Desaturase Enzyme Activity in Microsomes Isolated from Transgenic Yeast" we have provided a method that allows unambiguous demonstration of fatty acyl desaturase enzyme activity. We provide data demonstrating that: (1) gene c-d12Des(Ps_GA) encodes a delta-12 desaturase protein from *Phytophthora sojae* (c-d12Des(Ps_GA) that desaturates oleic acid (18:1n-9) to form linoleic acid (18:2n-6) in both microsomes isolated from a transgenic yeast (FIG. 24, panel A) and from a transgenic *B. napus* event (FIG. 25, panel A) expressing this protein, (2) gene c-o3Des(Pi_GA2) encodes a protein from *Phytophthora infestans* (c-o3Des(Pi_GA2)) that desaturates arachidonic acid (20:4n-6) to form eicosapentaenoic acid (20:5n-3) in microsomes isolated from a transgenic yeast (FIG. 24, panel B) expressing this protein, (3) gene c-o3Des (Pir_GA) encodes an omega-3 desaturase protein from *Pythium irregulare* (c-o3Des(Pir_GA)) that desaturates arachidonic acid (20:4n-6) to form eicosapentaenoic acid (20:5n-3) in microsomes isolated from a transgenic yeast (FIG. 24, panel B) expressing this protein, (4) a transgenic *B. napus* event containing genes encoding omega-3 desaturase proteins from both *Phytophthora infestans* (c-o3Des (Pi_GA2)) and *Pythium irregulare* (c-o3Des(Pir_GA)) that contains at least one enzyme, localized to the microsomes, capable of desaturating arachidonic acid (20:4n-6) to form eicosapentaenoic acid (20:5n-3) (FIG. 85, Panel C), (5) gene c-d4Des(Tc_GA) encodes a delta-4 desaturase protein from *Thraustochytrium* sp. (c-d4Des(Tc_GA)) that desaturates docosapentaenoic acid (22:5n-3) to form docosahexaenoic acid (22:6n-3) in microsomes isolated from a transgenic yeast (FIG. 24, panel C) expressing this protein, (6) gene c-d4Des(PI_GA)2 encodes a delta-4 desaturase protein from *Pavlova lutheri* (c-d4Des(PI_GA)2 that desaturates docosapentaenoic acid (22:5n-3) to form docosahexaenoic acid (22:6n-3) in microsomes isolated from a transgenic yeast (FIG. 24, panel D), (7) a transgenic *B. napus* event containing both the gene encoding the delta-4 desaturase protein from *Thraustochytrium* sp, gene c-d4Des(Tc_GA), and the gene c-d4-Des(PI_GA) from *Pavlova Lutheri* contains at least one enzyme, localized to the microsomes, capable of desaturating docosapentaenoic acid (22:5n-3) to form docosahexaenoic acid (22:6n-3) (FIG. 25, panel C), (8) a transgenic *B. napus* event containing the gene encoding a delta-6 desaturase protein from *Ostreococcus tauri* (c-d6Des(Ot_febit), capable of desaturating linoleic acid (18:2n-6) to form gamma-linolenic acid (18:3n-6) (FIG. 85, Panel A), and (9) a transgenic *B. napus* event containing the gene encoding a delta-5 desaturase protein from *Thraustachytrium* ssp. (c-dSDes(Tc_GA2), capable of desaturating dihomo-gamma-linolenic acid (20:3n-6) to form arachidonic acid (20:4n-6) (FIG. 85, Panel B). Except for the c-d12Des (Ps_GA), which has a known endogenous enzyme in *Brassica*, all other examples presented contain no detectable endogenous desaturase activity in microsomes isolated from either control yeast strains (FIG. 24) or control *Brassica* lines (FIG. 25 and FIG. 85).

Using the methods described in "Desaturase Enzyme Activity in Microsomes Isolated from Transgenic Yeast" for desaturase proteins the level of expression or detected enzyme activity may be influenced by the presence or absence of fusion tags to the native protein. Fusion tags or proteins to the desaturases may be attached the amino-terminus (N-terminal fusions) or the carboxy-terminus (C-terminal fusions) of the protein and may include but are not limited to: FLAG, hexa-Histidine, Maltose Binding Protein, and Chitin Binding Protein.

We have provided methods to establish enzyme catalyzed desaturation reactions required in an engineered pathway to biosynthesize docosohexaenoic acid (DHA, 22:6n-3) from oleic acid (18:1n-9) in canola. The methods presented in Example 21, "Desaturase Enzyme Activity in Microsomes Isolated from Transgenic Yeast" were developed to demonstrate desaturase activity in yeast strains expressing individual desaturases and can be further used to confirm the respective desaturase enzyme activities in transgenic canola, as described and demonstrated in Example 21, "Desaturase Activity in Microsomes Isolated from Transgenic *Brassica napus*". Furthermore these methods can be incorporated, by one skilled in the art, to measure desaturase enzyme activities in other organisms including, but not limited to: *Saccharomyces cerevisiae, Arabidopsis thaliana, Brassica* spp., *Camelina sativa, Carthamus tinctorius*, and *Salvia hispanica*.

Desaturase Headgroup (CoA vs PC) Preference

Fatty acid desaturases catalyze the abstraction of two hydrogen atoms from the hydrocarbon chain of a fatty acid to form a double bond in an unsaturated fatty acid and can be classified according to the backbone that their substrate was connected to: an acyl-CoA, an acyl-ACP (ACP, acyl carrier protein) or an acyl-lipid. To date a few examples exist where the acyl-CoA substrate has been confirmed. These involve purified enzymes and examples include a Linoleoyl-CoA Desaturase (Okayasu et al. (1981) Arch. Biochem. Biophys. 206: 21-28), a stearoyl-CoA desaturase from rat liver (Strittmatter et al (1974) Proc. Nat. Acad. Sci. USA 71: 4565-4569), and a Stearoyl-ACP desaturase from avocado (Shanklin J and Somerville C (1991) Proc Natl Acad Sci USA 88:2510-2514).

Alternatively, Heinz and coworkers have reported a strategy employing in vivo feeding of substrates to yeast strains expressing desaturases to examine substrate specificity of desaturases (Domergue et al. (2003) J. Biol. Chem. 278: 35115-35126, Domergue et al. (2005) Biochem. J. 389: 483-490). In these studies predictions of a desaturases's preference for acyl-lipid substrates were based on data obtained from a thorough analysis of the desaturated products in the CoA, phospholipid and neutral lipid pools over a growth time course. However, highly active endogenous acyltransferases which transfer acyl-groups between various pools (e.g. CoA, ACP, and lipid) may influence or convolute these data (Domergue et al. (2005) Biochem. J. 389: 483-490, Meesapyodsuk, D., Qui, X. (2012) Lipids 47: 227-237). Therefore this approach was still limited by the absence of direct evidence, such as obtained from in vitro assays, needed for conclusive determination of the substrate backbone utilized by the desaturase of interest.

Herein, we provide a previously unreported method to distinguish between enzymes that desaturate acyl-CoA fatty acids from enzymes that desaturate phospholipid linked fatty acids using microsomal preparations of proteins. We have improved upon initial reports of strategies to generate [$^{14}$C]-phosphatidylcholine analogs in situ (Stymne, S., and Stobart, A. K. (1986) Biochem. J. 240: 385-393, Griffiths, G., Stobart, A. K., and Stymne, S. (1988) Biochem. J. 252: 641-647) by: (1) monitoring the initial acyl-transfer reaction catalyzed by lysophosphatidyl choline acyl transferase (LP-CAT) to establish that all of the [$^{14}$C]-acyl-CoA has been consumed, and (2) including exogenous lysophosphatidyl choline (LPC). Our improvements therefore establish that only [$^{14}$C]-phosphatidylcholine analogs are present upon initiation of the desaturase assay and allow for testing of other phospholipids by adding their corresponding lysolipid. Furthermore, the assays testing for desaturation of acyl-phospholipid substrates, described in Demonstration of Phosphatidylcholine Specificity, can be complemented by testing in an assay developed to monitor desaturation of the substrate in the acyl-CoA form. Specifically, we have devised a strategy, described in Demonstration of acyl-CoA Specificity, in which the substrate to be tested remains in its acyl-CoA form and is not incorporated into phospholipids (e.g. phosphatidylcholine) by lysophosphatidyl choline acyl transferase (LPCAT). By comparing the relative desaturase activity, observed in assays where the substrate is in the acyl-phospholipid form compared to the acyl-CoA form, the actual backbone (e.g. phosphatidylcholine or CoA) covalently bound to the desaturated fatty acid product can be determined.

Demonstration of Phosphatidylcholine Specificity:

To test if a desaturase accepts an acyl-lipid (e.g. a phospholipid) substrate the enzyme reaction was performed as described above "Desaturase Enzyme Activity in Microsomes Isolated from Transgenic Yeast", but after a pre-incubation in the presence of exogenous lysophosphatidyl choline (LPC). The microsomal fraction of the yeast strain expressing the enzyme of interest was pre-incubated with a [$^{14}$C]-labelled acyl-CoA substrate in the presence of 16:0-lysophosphatidyl choline, which was typically 50·M but may vary from 0-500·M. During the pre-incubation endogenous lysophosphatidyl choline acyl transferase (LP-CAT), present in the microsomes, transfers the [$^{14}$C]fatty acid from CoA to 16:0-LPC generating, in situ, a [$^{14}$C]fatty acid-phosphatidylcholine (PC) (Jain et al. (2007) J. Biol. Chem. 282:30562-30569, Riekhof et al. (2007) J. Biol. Chem. 282:36853-36861, Tamaki et al. (2007) J. Biol. Chem. 282:34288-34298)). After a pre-incubation (typically 15 minutes, but may vary from 1-300 minutes) essentially all of the [$^{14}$C]-labelled acyl-CoA substrate was consumed, as measured by scintillation counting and TLC analysis of the aqueous phase.

The reaction was stopped and lipids were extracted using the method of Bligh and Dyer (Bligh, E. G., and Dyer, J. J. (1959) Can J. Biochem. Physiol. 37: 911-918), by addition of 200·l 0.15 M acetic acid and 1 ml MeOH:CHCl$_3$ (1:1). Part (about 10%) of the CHCl$_3$ phase (containing phosphatidyl choline (PC) and free fatty acids (FFA's)) was analyzed by scintillation counting and the rest was applied to a silica thin layer chromatography (TLC) plate. The plate was first developed in a polar solvent [CHCl$_3$:MeOH:acetic acid (90:15:10:3) and then in Heptane:diethylether:acetic acid (70:30:1) to measure incorporation into PC and the amount of FFA's (likely generated by thioesterases). PC and FFA's were scraped off the plate and methylated by addition of MeOH containing 2% H$_2$SO$_4$ at 90° C. for 30 minutes. The methyl esters were extracted in hexane and analyzed as described above for the respective enzymes (Example 21, "Desaturase Enzyme Activity in Microsomes Isolated from Transgenic Yeast"). The upper (aqueous) phase of the reaction mixture extraction contains acyl-CoA's and was hydrolyzed by addition of an equal volume of 2 M KOH in MeOH:H$_2$O (1:4) and incubated for 20 minutes at 90° C. Part of the aqueous phase was then analyzed by scintillation counting before fatty acids were extracted by addition of 3 M HCl (0.7 ml), 1.4 ml of MeOH) and CHCl$_3$ (1.9 ml). The chloroform phase was recovered, dried under N$_2$(g) and fatty acids were methylated by addition of 2 ml MeOH containing 2% H$_2$SO$_4$ and incubation of 30 minutes at 90° C. FAMEs were extracted by addition of 2 ml H$_2$O and 2 ml hexane and separated by AgNO$_3$-TLC and Heptane:Diethyl ether:acetic acid (70:30:1) as a solvent or Reverse Phase-TLC (Silica gel 60 RP-18 using acetonitrile (100%)). The radioactive lipids were visualized and quantified by electronic autoradiography using Instant Imager.

Delta-12 Desaturase (Phytophthora sojae), c-d12Des (Ps_GA) Substrate Preference:

The c-d12Des(Ps_GA) enzyme activity demonstrated in "Desaturase Enzyme Activity in Microsomes Isolated from Transgenic Yeast" can be further characterized to establish the backbone of the oleic acid substrate. In the desaturase assay described in "Desaturase Headgroup (CoA vs PC) Preference" containing 16:0-lysphosphatidylcholine (LPC) substantial desaturation was observed. A significantly reduced, but detectable, desaturase activity was observed in control reactions lacking 16:0-LPC which likely results from acylation of endogenous LPC present in the yeast microsomes containing the d12Des(Ps_GA) protein. However, a preincubation with 20:1n-9-CoA results in PC saturated with 20:1n-9, thus precluding incorporation of [$^{14}$C]-18:1n-9 into PC (described in "Demonstration of Acyl-CoA Specificity"). Additionally, separation of the phospholipids from the free-fatty acids after the enzymatic reaction and characterization of the isolable fatty acid methyl esters demonstrated that all of the d12Des(Ps_GA) enzymatically produced 18:2n-6-fatty acid methyl ester (FAME) was found in the phosphatidylcholine fraction (FIG. 26, Panel A and FIG. 86, Panel A). Furthermore, the d12Des(Ps_GA) activity was negligible in the assay for demonstration of acyl-CoA specificity (FIG. 86, Panel B), showing that 18:1n-9-acyl-CoA is not a preferred substrate for the delta-12 desaturase (*Phytophthora sojae*). In conclusion, delta-12 desaturase (*Phytophthora sojae*) clearly desaturates 18:1n-9 covalently bound to PC, but not an 18:1n-9-acyl CoA substrate.

Delta-4 Desaturase (*Thraustochytrium* Ssp.), c-d4Des (Tc_GA) Substrate Preference:

The c-d4Des(Tc_GA) enzyme activity demonstrated in "Desaturase Enzyme Activity in Microsomes Isolated from Transgenic Yeast" can be further characterized to establish the backbone of the docosopentaenoic acid substrate. In the desaturase assay described in "Desaturase Headgroup (CoA vs PC) Preference" without additional 16:0-lysphosphatidylcholine (LPC), desaturation was observed (FIG. 26, Panel B), and likely results from the presence of endogenous 16:0-LPC present in the membranes containing the c-d4Des (Tc_GA) protein. The c-d4Des(Tc_GA) desaturase activity was dramatically stimulated by including additional 16:0-LPC in the assay (FIG. 26, Panel B), consistent with the observation endogenous lysophosphatidyl choline acyl transferase (LPCAT), present in the microsomes, transfers the [$^{14}$C]22:5n-3 from CoA to 16:0-LPC generating a [$^{14}$C] 22:5n-3-phosphatidylcholine (PC) that was desaturated. Additionally, separation of the phospholipids from the free-fatty acids after the enzymatic reaction and characterization of the isolable fatty acid methyl esters demonstrated that essentially all of the c-d4Des(Tc_GA) enzymatically produced 22:6n-3-fatty acid methyl ester (FAME) was found in the phosphatidylcholine fraction (FIG. 26, Panel B and Panel C).

Demonstration of Acyl-CoA Specificity:

The assay conditions were as described above in "Desaturase Enzyme Activity in Microsomes Isolated from Transgenic Yeast". The microsomal fraction of the yeast strain expressing the enzyme of interest was pre-incubated with 10 nmol 20:1n-9-CoA (50 μM) and 0.5 mM DTNB (5,5'-dithiobis-(2-nitrobenzoic acid) for 10 min before addition of NADH and [$^{14}$C]labelled acyl-CoA substrate. The preincubation with 20:1n-9-CoA minimizes the incorporation of [$^{14}$C]labelled substrate into PC. DTNB prevents the reverse reaction of LPCAT and thereby the entering of acyl-CoA into PC via acyl exchange. This assay may also include alternative acyl-CoA's such as: 18:1n-9-CoA, 18:2n-6-CoA, 20:3n-6-CoA, 20:4n-6-CoA, 22:5n-3-CoA. The reaction was stopped and lipids were extracted using the method of Bligh and Dyer (Bligh, E. G., and Dyer, J. J. (1959) *Can J. Biochem. Physiol.* 37, 911-918), by addition of 200·1 0.15 M acetic acid and 1 ml MeOH:$CHCl_3$ (1:1). Part (about 10%) of the $CHCl_3$ phase (containing phosphatidyl choline (PC) and free fatty acids (FFA's)) was analyzed by scintillation counting and the rest was applied to a silica thin layer chromatography (TLC) plate. The plate was first developed in a polar solvent [$CHCl_3$:MeOH:acetic acid (90:15:10:3) and then in Heptane:diethylether:acetic acid (70:30:1) to measure incorporation into PC and the amount of FFA's (likely generated by thioesterases). PC and FFA's were scraped off the plate and methylated by addition of MeOH containing 2% $H_2SO_4$ at 90° C. for 30 minutes. The methyl esters were extracted in hexane and analyzed as described above for the respective enzymes "Desaturase Enzyme Activity in Microsomes Isolated from Transgenic Yeast". The upper (aqueous) phase of the reaction mixture extraction contains acyl-CoA's and was hydrolyzed by addition of an equal volume of 2 M KOH in MeOH:$H_2O$ (1:4) and incubated for 20 minutes at 90° C. Fatty acids were extracted by addition of 3 M HCl (0.7 ml), 1.4 ml of MeOH and $CHCl_3$ (1.9 ml). The chloroform phase was recovered, dried under $N_2$(g) and fatty acids were methylated by addition of 2 ml MeOH containing 2% $H_2SO_4$ and incubation of 30 minutes at 90° C. FAMEs were extracted by addition of 2 ml $H_2O$ and 2 ml hexane and separated by $AgNO_3$-TLC and Heptane:Diethyl ether:acetic acid (70:30:1) as a solvent or Reverse Phase-TLC (Silica gel 60 RP-18 using acetonitrile (100%)). The radioactive lipids were visualized and quantified by electronic autoradiography using Instant Imager.

To demonstrate acyl-CoA dependency both methods are tested. If desaturation does not occur in the method for determining PC-specificity (LPC addition and preincubation before adding NADH) and the method for determining acyl-CoA specificity (20:1-CoA and DTNB addition) leads to the desaturated product in the $H_2O$-phase (or product in any of the lipid pools PC/FFA/$H_2O$ since PC-dependent enzymes cannot be active if the substrate is not incorporated into PC (see FIG. 86, Panel B), it can be concluded that the enzyme was acyl-CoA dependent (see FIG. 27 and FIG. 87, Panels A and B). Similarly if a desaturase demonstrates activity in the PC-specific assay, but not in the assay where the substrate is presented as an acyl-CoA, then it can be concluded the enzyme utilizes a fatty acid covalently attached to phosphatidylcholine as a substrate.

Delta-9 Desaturase (*Saccharomyces cerevisiae*), d9Des(Sc) Substrate Preference:

Analysis of the [$^{14}$C]-distribution during of the d9Des(Sc) reaction, in the assay for demonstration of acyl-CoA dependency, shows that greater than 95% of the radioactivity (substrate and product) is present in the $H_2O$ (CoA) and FFA-pools (data not shown), indicating incorporation into PC was insignificant. During the reaction, product (16:1n-9) in the acyl-CoA pool increases linearly up to 60 minutes, showing that the enzyme preferentially converts 16:0 covalently bound to CoA (FIG. 87, Panel B). The amount of 16:1n-9 in the $H_2O$ fraction then levels out or slightly decreases, while the 16:1n-9 in the FFA pool increases, due to degradation of acyl-CoA by thioesterases present in the isolated membranes.

In the assay for demonstrating PC specificity, the d9Des (Sc) showed no activity (FIG. 87, Panel A), which indicates that when 16:0 fatty acid is attached to PC (or a FFA) it is not a preferred substrate.

The clear presence of desaturase activity in the "Acyl-CoA Specific" assay compared to the absence of activity in the "Phosphatidylcholine Specific" assay demonstrates that the delta-9 desaturase (*Saccharomyces cerevisiae*) utilizes 16:0 covalently attached to Coenzyme A. Interestingly, recent crystal structures of both the human and mouse stearoyl-coenzyme A desaturases have been reported with bound stearoyl-CoA confirming that this desaturase utilizes a coenzyme A substrate (Wang et al (2015) Nat Struct Mol Bio 22: 581-585 and Bai et al (2015) Nature 524: 252-257).

In summary, we presented a previously unreported method to distinguish between enzymes that desaturate acyl-CoA fatty acids from enzymes that desaturate phospholipid linked fatty acids. This embodiment of the invention t uses microsomal preparations of enzymes and does not, as in previous examples, require purification of the enzyme of interest. Furthermore, this embodiment allows isolation of the intact desaturated enzymatic product, allowing characterization of the backbone to which it was linked (e.g. lipid-, CoA-, or free fatty acid). An important consideration was that the endogenous lysophosphatidyl choline acyl transferase (LPCAT) present in yeast-derived microsomes can utilize a broad range of acyl-CoA's (Jain et al. (2007) *J. Biol. Chem.* 282:30562-30569, Riekhof et al. (2007) *J. Biol. Chem.* 282:36853-36861, Tamaki et al. (2007) *J. Biol. Chem.* 282:34288-34298)) making it suitable for generating an extensive variety of different phosphatidylcholine derivatives for assaying desaturase enzymes. LPCAT is able to accept 18:1n-9-CoA and 20:4n-6-CoA and this enzyme can acylate LPC with 22:5n-3-CoA. Microsomes isolated from any cells or tissue can be used in this embodiment of the invention, including but not limited to bacterial cells (e.g. *Escherichia coli, Psuedomonas aeruginosa, Bacillus thuringiensis*), mammalian tissue (e.g. liver) and plant tissue (e.g. leafs, roots, seeds, and pods) and could use exogenously supplied lysophosphatidyl choline acyl transferase from *Saccharomyces cerevisiae*, if necessary. Slight modifications to the general method presented here may include a pre-incubation with alternate acyl-CoA's, not the potential desaturase substrate, which could reduce the observed background due to endogenous LPC present in the membranes and also minimize thioesterase degradation of enzyme substrate or product acyl-CoA's.

Elongase Activity.

Expression of elongase enzymes in yeast was performed as described above for the desaturase enzymes in "Desaturase Enzyme Activity in Microsomes Isolated from Transgenic Yeast". Isolation of microsomes containing expressed elongases was generally as described above in "Desaturase Enzyme Activity in Microsomes Isolated from Transgenic Yeast" and by Denic (Denic, V. and Weissman (2007) Cell 130, 663-677). Briefly, cells from a yeast expression culture (50 ml) were resuspended in 1 ml of Elongase Disruption Buffer (20 mM Tris-HCl, pH 7.9, 10 mM $MgCl_2$, 1 mM EDTA, 5% glycerol, 0.3 M ammonium sulfate, protease inhibitor), mixed with 1 ml silica/zirconium beads (0.5 mm) and disrupted in a BeadBeater. After centrifugation (two times for 5 minutes at 8000×g, 4° C.) the crude extract was recovered and after a second centrifugation (100,000×g, 2 hours at 4° C.), the microsomal fraction was resuspended in 500·l of assay buffer (50 mM HEPES-KOH pH 6.8, 150 mM KOAc, 2 mM MgOAc, 1 mM $CaCl_2$, protease inhibitor). The protein concentrations in the microsomes were measured according to the BCA method. Resuspended microsomes were aliquoted and frozen in $N_2$(l) and stored at −80° C.

In the elongase assay [$^{14}$C]-labeled malonyl-CoA and non-labeled acyl-CoA were provided as substrates. After the reaction has proceeded an appropriate time, which may vary between 0-300 minutes depending on the purpose of the experiment, the reaction mixture was subjected to hydrolysis and methylation and the FAMEs were analyzed by RP-TLC combined with by electronic autoradiography using Instant Imager.

The assay contains about 170·g microsomal protein, 7.5 nmol [$^{14}$C]malonyl-CoA (3000 dpm/nmol), 5 nmol acyl-CoA in a total volume of 100·l. After incubation for the desired time at 30° C., the reaction was stopped with the addition of 100·l of 2 M KOH in MeOH (1:4) followed by a 20 minute incubation at 90° C. Fatty acids were extracted by addition of 3 M HCl (100·l), 0.75 ml of $MeOH:CHCl_3$ (2:1) and $CHCl_3$ (250·l). The chloroform phase was recovered, dried under $N_2$(g), and fatty acids were methylated by addition of 2 ml MeOH containing 2% $H_2SO_4$ and incubation of 30 minutes at 90° C. FAMEs were extracted by addition of 2 ml $H_2O$ and 2 ml hexane and separated by Reverse Phase-TLC (Silica gel 60 RP-18) using a solvent of acetonitrile:tetrahydrofuran (85:15). The radioactive lipids were visualized and quantified by electronic autoradiography using Instant Imager.

Furthermore, assays may include additional components (e.g. 1 mM NADPH, 2 mM $MgCl_2$, and 100·M cerulenin) to complete the fatty acid reduction cycle by endogenous yeast enzymes, but limit further elongation of the acyl-CoA.

Delta-6 Elongase (*Thalassiosira pseudonana*), c-d6Elo (Tp_GA2) Enzyme Activity:

c-d6Elo(Tp_GA2) enzyme activity and substrate specificity can be demonstrated in microsomes isolated from a yeast strain expressing the c-d6Elo(Tp_GA2) protein using [$^{14}$C]malonyl-CoA and an acyl-CoA in the general elongase assay described above. Acyl-CoA's may include, but are not limited to: 18:1n-9-CoA, 18:2n-6-CoA, 18:3n-6-CoA, 20:3n-6-CoA, 20:4n-6-CoA, 20:5n-3-CoA, 22:5n-3-CoA.

Delta-6 Elongase (*Physcomitrella patens*), c-d6Elo (Pp_GA2) Enzyme Activity:

c-d6Elo(Pp_GA2) enzyme activity and substrate specificity can be demonstrated in microsomes isolated from a yeast strain expressing the c-d6Elo(Tp_GA2) protein using [$^{14}$C]malonyl-CoA and an acyl-CoA in the general elongase assay described above. Acyl-CoA's may include, but are not limited to: 18:1n-9-CoA, 18:2n-6-CoA, 18:3n-6-CoA, 20:3n-6-CoA, 20:4n-6-CoA, 20:5n-3-CoA, 22:5n-3-CoA.

Delta-5 Elongase (*Ostreococcus tauri*), c-d5Elo(Ot_GA3) Enzyme Activity:

c-d5Elo(Ot_GA3) enzyme activity and substrate specificity can be demonstrated in microsomes isolated from a yeast strain expressing the c-d5Elo(Ot_GA3) protein using [$^{14}$C] malonyl-CoA and an acyl-CoA in the general elongase assay described above. Acyl-CoA's may include, but are not limited to: 18:1n-9-CoA, 18:2n-6-CoA, 18:3n-6-CoA, 20:3n-6-CoA, 20:4n-6-CoA, 20:5n-3-CoA, 22:5n-3-CoA.

In the presence of NADPH and [$^{14}$C]malonyl-CoA, 18:3n-6-CoA was elongated to 20:3n-6-CoA by the delta-6 Elongases isolated from *Thalassiosira pseudonana* (Tp) and *Physcomitrella patens* (Pp) as shown if FIG. 28, panels A and B. In both delta-6 elongase reactions the observed FAME-product co-migrates with 20:3n-6-methyl ester standards and was radioactive, consistent with transfer of two-carbons from [$^{14}$C]-malonyl-CoA to 18:3n-6-CoA. In the presence of NADPH the fatty acid reduction cycle was completed resulting in a saturated enzymatic product. However in the absence of NADPH a derivative of the direct enzymatic product, 3-keto-20:3n-6-CoA, was isolated as a FAME. The isolated enzymatic product was decarboxylated and converted to the 2-keto-19:3n-6-FAME as described previously (Bernert, J. T and Sprecher, H. (1977) J. Biol. Chem. 252:6736-6744 and Paul et al (2006) J. Biol. Chem. 281: 9018-9029). Appropriate controls demonstrate that this elongation reaction was dependent upon either the Delta-6 Elo (Tp) or the Delta-6 Elo (Pp) and not catalyzed by endogenous yeast enzymes.

In the presence of NADPH and [$^{14}$C]malonyl-CoA, 20:5n-3-CoA was elongated to 22:5n-3-CoA by the c-d5Elo (Ot_GA3), and containing either an N-terminal FLAG tag or a C-terminal FLAG tag, as shown in FIG. 28, panel C. In the Delta-5 elongase reaction the observed FAME-product co-migrates with a 22:5n-3-methyl ester standard and was radioactive, consistent with transfer of two-carbons from [$^{14}$C]-malonyl CoA to 20:5n-3-CoA. In the presence of NADPH the fatty acid reduction cycle was completed resulting in a saturated enzymatic product. However in the absence of NADPH a derivative of the direct 3-keto-22:5n-3-CoA product was isolated as a FAME. The isolated enzymatic product was decarboxylated and a 2-keto-21:5n-

3-FAME as described previously (Bernert, J. T and Sprecher, H. (1977) J. Biol. Chem. 252:6736-6744 and Paul et al (2006) J. Biol. Chem. 281: 9018-9029). Appropriate controls demonstrate that this elongation reaction was dependent upon the Delta-5 Elo (Ot) and not catalyzed by endogenous yeast enzymes.

Herein, using a highly sensitive elongase assay, we have demonstrated the enzyme activities of the Delta-6 Elongases used (FIG. 28, panel A and B) and a Delta-5 Elongase (FIG. 28, panel C), enzymes that are central to engineering canola to biosynthesize docosahexaenoic acid. For each of these elongases we have shown that in the presence of [$^{14}$C] malonyl-CoA and the appropriate fatty-acyl CoA ester substrate these enzymes can transfer two-carbons (containing [$^{14}$C]) from malonyl-CoA to the appropriate fatty-acyl-CoA ester to synthesize a new fatty acid which has been elongated by two carbons. In some cases a derivative (decarboxylated 2-keto compound) of the direct enzymatic product (3-KetoacylCoA ester) of the elongase was observed, however in the absence of NADPH only this decarboxylated 2-keto compound was observed, consistent with previous observations by Napier (Bernert, J. T and Sprecher, H. (1977) J. Biol. Chem. 252:6736-6744 and Paul et al (2006) J. Biol. Chem. 281: 9018-9029).

In summary we have provided a method that allows unequivocal demonstration of fatty acyl elongation enzyme activity. We provide data demonstrating that: (1) gene c-d6Elo(Tp_GA2) encodes a delta-6 elongase protein from *Thalassiosira pseudonana* (c-d6Elo(Tp_GA2)) that converts 18:3n-6-CoA to 20:3n-6-CoA in microsomes isolated from a transgenic yeast (FIG. 28, panel A), (2) gene c-d6Elo (Pp_GA2) encodes a delta-6 elongase protein from *Physcomitrella patens* (c-d6Elo(Pp_GA2)) that converts 18:3n-6-CoA to 20:3n-6-CoA in microsomes isolated from a transgenic yeast (FIG. 28, panel B), (3) a transgenic *B. napus* event containing both the gene encoding for the delta-6 elongase protein from *Thalassiosira pseudonana*, gene c-d6Elo(Tp_GA2), and the gene encoding for the gene the delta-6 elongase protein from *Physcomitrella patens*, gene c-d6Elo(Pp_GA2), contains at least one enzyme, localized to the microsomes, capable of elongating 18:3n-6-CoA to 20:3n-6-CoA (FIG. 28, panel A) (4) gene c-d5-Elo(Ot_GA3) encodes a delta-5 elongase protein from *Ostreococcus tauri* (c-d5Elo(Ot_GA3)) that converts 20:5n-3-CoA to 22:5n-3-CoA in microsomes isolated from both a transgenic yeast (FIG. 28, Panel C) and transgenic *B. napus* event (FIG. 29, Panel B). In all examples presented no endogenous elongase activity was detected in microsomes isolated from either control yeast strains (FIG. 28) or control *Brassica* lines (FIG. 29).

Using the methods described in "Elongase Activity" for elongase proteins the level of expression or detected enzyme activity may be influenced by the presence or absence of fusion tags to the native protein. Fusion tags or proteins to the desaturases may be attached the amino-terminus (N-terminal fusions) or the carboxy-terminus (C-terminal fusions) of the protein and may include but are not limited to: FLAG, hexa-Histidine, Maltose Binding Protein, and Chitin Binding Protein.

We have provided methods to establish enzyme catalyzed elongase reactions required in an engineered pathway to biosynthesize docosohexaenoic acid (DHA, 22:6n-3) from oleic acid (18:1n-9) in canola. The methods presented in Example 21 were developed to demonstrate elongase activity in yeast strains expressing individual elongases and can be further used to confirm the respective elongase enzyme activities in transgenic canola. Furthermore these methods can be incorporated, by one skilled in the art, to establish elongase enzyme activities in other organisms including, but not limited to: *Saccharomyces cerevisiae*, *Arabidopsis thaliana*, *Brassica* spp., *Camelina sativa*, *Carthamus tinctorius*, and *Salvia hispanica*.

REFERENCE LIST

Arondel, V., Lemieux, B., Hwang, I., Gibson, S., Goodman, H. M., and Somerville, C. R. (1992). Map-based cloning of a gene controlling omega-3 fatty acid desaturation in *Arabidopsis*. Science 258, 1353-1355.

Bafor, M., Smith, M. A., Jonsson, L., Stobart, K., and Stymne, S. Biochem J. (1991). Ricinoleic acid biosynthesis and triacylglycerol assembly in microsomal preparations from developing castor-bean (*Ricinus communis*) endosperm. 280, 507-514.

Bernert, J. T and Sprecher, H. (1977). Analysis of Partial Reactions in the Overall Chain Elongation of Saturated and Unsaturated Fatty Acids by Rat Liver Microsomes. J. Biol. Chem. 252, 6736-6744.

Banas, A., Bafor, M., Wiberg, E., Lenman, M., Ståhl, U., Stymne, S. (1997). Biosynthesis of an Acetylenic Fatty Acid in Microsomal Preparations from Developing Seeds of Crepis alpine. In: *Physiology, Biochemistry and Molecular Biology of Plant Lipids* (Williams, J. P., Kahn, M. U., Lem, N. W., eds.) pp. 57-59. Kluwer Academic Press, Dordrecht.

Bligh, E. G., and Dyer, J. J. (1959). A rapid method for total lipid extraction and purification. Can J. Biochem. Physiol. 37: 911-918

Broadwater, J. A., Whittle, E., and Shanklin, J. (2002). Desaturation and hydroxylation. Residues 148 and 324 of *Arabidopsis* FAD2, in addition to substrate chain length, exert a major influence in partitioning of catalytic specificity. J. Biol. Chem. 277, 15613-15620.

Broun, P., Shanklin, J., Whittle, E., and Somerville, C. (1998b). Catalytic plasticity of fatty acid modification enzymes underlying chemical diversity of plant lipids. Science 282, 1315-1317.

Calvo, A. M., Gardner, H. W., and Keller, N. P. (2001). Genetic connection between fatty acid metabolism and sporulation in *Aspergillus nidulans*. J. Biol. Chem. 276, 25766-25774.

Brown A J., Sweeney B., Mainwaring D O. and James D C. (2014) Synthetic Promoters for CHO Cell Engineering. Biotechnology and Bioengineering, 111, 8:1638-1647.

Cutler S R., Rodriguez P L., Finkelstein R R., and Abrams S R. (2010) Abscisic Acid: Emergence of a Core Signaling Network. Annual Review of Plant Biology 61:651-679.

Demekes T. and Jenkins R G. (2010) Influence of DNA extraction methods, PCR inhibitors and quantification methods on real-time PCR assay of biotechnology-derived traits. Analytical and Bioanalytical Chemistry 396, 1977-1990.

Domergue, F. Abbadi, A., Ott, C., Zank, T. K., Zahringer, U., and Heinz, E. (2003) Acyl Carriers Used as Substrates by the Desaturases and Elongases Involved in Very Long-chain Polyunsaturated Fatty Acids Biosynthesis Reconstituted in Yeast. J. Biol. Chem. 278, 35115-35126

Domergue, F., Abbadi, A., Zähringer, U., Moreau, H., Heinz, E. (2005) In vivo characterization of the first acyl-CoA D6-desaturase from a member of the plant kingdom, the microalga *Ostreococcus tauri*. Biochem. J. 389, 483-490.

Dubos C., Kelemen Z., Sebastian A., Bülow L., Huep G., Xu W., Grain D., Salsac F., Brousse C., Lepiniec L, Weisshaar B., Contreras-Moreira B. and Hehl R. BMC Genomics 15:317.

Focks N. and Benning C. (1998) wrinkled1: A novel, low-seed-oil mutant of Arabidopsis with a deficiency in the seed-specific regulation of carbohydrate metabolism. Plant Physiology 118, 1:91-101.

Ganas et al in Physiology, Biochemistry and Molecular Biology of Plant Lipids, Eds Williams, J. P., Khan, M. U. and Lem, N. W., Kluwer Academic Publishers, N L, 1996, 57-59

Griffiths, G., Stobart, A. K., and Stymne, S. (1988). • 6- and • 12-desaturase activities and phosphatidic acid formation in microsomal preparations from the developing cotyledons of common borage (Borago officinalis). Biochem. J. 252, 641-647

Hamilton C M (1997) A binary-BAC system for plant transformation with high-molecular-weight DNA. Gene 200: 107-116

Hattori T., Totsuka M., Hobo T., Kagaya Y., Yamamota-Toyoda A. (2002) Experimentally determined sequence requirement of ACGT containing abscisic acid response element. Plant and Cell Physiology 43, 1:136-140.

Higo K., Ugawa Y., Iwamoto M., Korenaga T. (1999) Plant Cis-acting regulatory DNA elements (PLACE) database: 1999. Nucleic Acids Research 27, 1:297-300.

Hinnebusch A. (2014) The Scanning Mechanism of Eukaryotic Translation Initiation. Annual Review of Biochemistry 83, 779-812

Jain, S., Stanford, N., Bhagwat, N., Seiler, B., Costanzo, M., Boone, C. and Peter, P. (2007). Identification of a Novel Lysophospholipid Acyltransferase in Saccaromyces cerevisiae. J. Biol. Chem. 282, 30562-30569.

Kargiotidou A., Deli D., Galanopoulou D., Tsaftaris A. and Farmaki T. (2008) Low temperature and light regulate delta 12 fatty acid desaturases (FAD2) at a transcriptional level in cotton (Gossypium hirsutum) Journal of Experimental Botany, 59, 8:2043-2056

Keller W., Konig P. and Richmond T J. (1995) Crystal Structure of a bZIP/DNA Complex at 2.2 Å: Determinants of DNA Specific Recognition. Journal of Molecular Biology 254, 657-667.

Kim W-C., Reca I-B., Kim Y S. Park S., Thomashow M F. Keegstra K. Han K-H. (2014) Transcription factors that directly regulate the expression of CSLA9 encoding mannan synthase in Arabidopsis thaliana. Plant Molecular Biology 84, 577-587

Knutzon, D. S., Thurmond, J. M., Huang, Y. S., Chaudhary, S., Bobik, E. G., Jr., Chan, G. M., Kirchner, S. J., and Mukerji, P. (1998). Identification of Delta5-dehydratase from Mortierella alpina by heterologous expression in Bakers' yeast and canola. J. Biol. Chem. 273, 29360-29366.

Komori, T., Imayama, T., Kato, N., Ishida, N., Ueki, j., and Komari, T. (2007). Current Status of Binary Vectors and Superbinary Vectors. Plant Physiology 145(4), 1155-1160, doi: dx.doi.org/10.1104/pp. 107.105734.

Kong F., Yamasaki T. and Ohama T. (2014) Expression levels of domestic cDNA cassettes integrated in the nuclear genomes of various Chlamydomonas reinhardtii strains. Journal of Bioscience and Bioengineering 117, 5:613-616.

Kozak M. Initiation of translation in prokaryotes and eukaryotes (1999) Gene 234, 187-208. Livak K. and Schmittgen T D. (2001) Analysis of Relative Gene Expression Data Using Real-Time Quantitative PCR and the 2-deltadeltaCT Method. Methods 25, 402-408.

López Y., Patil A., Nakai K. (2013) Identification of novel motif patterns to decipher the promoter architecture of co-expressed genes in Arabidopsis thaliana. BMC Systems Biology 7(Suppl 3):S10

Machens F., Becker M., Umrath F., Hehl R. (2014) Identification of a novel type of WRKY transcription factor binding site in elicitor-responsive cis-sequences from Arabidopsis thaliana. Plant Molecular Biology 84, 371-385

Mantle, P. G. and Nisbet, L. J. (1976). Differentiation of Claviceps purpurea in axenic culture. J. Gen. Microbiol. 93, 321-334.

Meggendorfer M., Weierich C., Wolff H., Brack-Werner R., Cremer T. (2010) Functional nuclear topography of transcriptionally inducible extra-chromosomal transgene clusters. Chromosome Research 18, 401-417.

Meesapyodsuk, D., Qui, X. (2012). The Front-end Desaturase: Structure, Function, Evolution and Biotechnological Use Lipids 47, 227-237

Mendel, J. G. (1866). Versuche Ober Pflanzenhybriden Verhandlungen des naturforschenden Vereines in Brünn, Bd. IV für das Jahr, 1865 Abhandlungen:3-47.

Mey, G., Oeser, B., Lebrun, M. H., and Tudzynski, P. (2002). The biotrophic, non-appressorium-forming grass pathogen Claviceps purpurea needs a Fus3/Pmk1 homologous mitogen-activated protein kinase for colonization of rye ovarian tissue. Mol. Plant Microbe Interact. 15, 303-312.

Muino J M., Smaczniak C., Angenent G C., Kaufmann K. and van Dijk A D J. (2014) Structural determinants of DNA recognition by plant MADS-domain transcription factors. Nucleic Acids Research 42, 4:2138-2146.

Murashige T. and Skoog F. (1962) A Revised Medium for Rapid Growth and Bio Assays with Tobacco Tissue Cultures. Physiologia Plantarum 15, 3:473-497

Nakagawa S., Niimura Y., Gojobori T., Tanaka H., and Miura K-I. (2008) Diversity of preferred nucleotide sequences around the translation initiation codon in eukaryote genomes. Nucleic Acids Research 36, 3:861-871

Nishikata K., Cox R S III., Shimoyama S., Yoshida Y., Matsui M., Makita Y. and Toyoda T. (2013) Database Construction for PromoterCAD: Synthetic Promoter Design for Mammals and Plants ACS Synthetic Biology 3, 192-196.

Okayasu, T.; Nagao, M.; Ishibashi, T.; and Imai, Y. (1981) Purification and Parial Characterization of Linoleoyl-CoA Desaturase from Rat Liver Microsomes Arch. Biochem. Biophys. 206, 21-28.

Okuley, J., Lightner, J., Feldmann, K., Yadav, N., Lark, E., and Browse, J. (1994). Arabidopsis FAD2 gene encodes the enzyme that was essential for polyunsaturated lipid synthesis. Plant Cell 6, 147-158.

Parker S. C. J., Hansen L., Abaan H. O, Tullius T. D., Margulies E. H. (2009) Local DNA Topography Correlates with Functional Noncoding Regions of the Human Genome. Science 324, 389-392.

Paul, S., Gable, K., Beaudoin, F., Cahoon, E. Jaworski, J., Napier, J. A., and Dunn, T. M. (2006). Members of the Arabidopsis FAE1-like 3-Ketoacyl-CoA Synthase Gene Family Substitute for the Elop Proteins of Saccharomyces cerevisiae. J. Biol. Chem. 281, 9018-9029.

Qi, B., Fraser, T., Mugford, S., Dobson, G., Sayanova, O., Butler, J., Napier, J. A., Stobart, A. K., and Lazarus, C. M.

(2004). Production of very long chain polyunsaturated omega-3 and omega-6 fatty acids in plants. Nat. Biotechnol. 22, 739-745.

Ramamoorthy S., Garapati H. S., Mishra R. K. (2014) Length and sequence dependent accumulation of simple sequence repeats in vertebrates: Potential role in genome organization and regulation. Gene 551, 167-175.

Riekhof, W. R., Wu, J., Gijón, M. A., Zarini, S., Murphy, R. C. and Voelker, D. R. Lysophosphatidylcholine Metabolism in *Saccaromyces cerevisiae*: The Role of P-Type ATPases In Transport and A Broad Specificity Acyltransferase in Acylation. J. Biol. Chem. 2007, 282:36853-36861.

Ruiz-Lopez N., Haslam R P., Napier J A. and Sayanova O. (2014) Successful high-level accumulation of fish oil omega-3 long-chain polyunsaturated fatty acids in a transgenic oilseed crop. The Plant Journal 77, 198-208.

Ruuska S A., Girke T., Benning C., and John B. Ohlrogge. Contrapuntal Networks of Gene Expression during *Arabidopsis* Seed Filling The Plant Cell 14, 6:1191-1206.

Sánchez-García A. Mancha M., Heinz E., Martínez-Rivas J. M. (2004) Differential temperature regulation of three sunflower microsomal oleate desaturase (FAD2) isoforms overexpressed in *Saccharomyces cerevisiae* European Journal of Lipid Science and Technology 106, 583-590

Sarkar A K. and Lahiri A. (2013) Specificity determinants for the abscisic acid response element. FEBS Open Bio 3, 101-105.

Shanklin J, Somerville C. (1991) Stearoyl-acyl-carrier-protein desaturase from higher plants was structurally unrelated to the animal and fungal homologs. Proc Natl Acad Sci USA 88, 2510-2514.

Shanklin, J. and Cahoon, E. B. (1998). DESATURATION AND RELATED MODIFICATIONS OF FATTY ACIDS1. Annu. Rev. Plant Physiol Plant Mol. Biol. 49, 611-641.

Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C. (1985). Measurement of protein using bicinchonic acid. Anal. Biochem. 150, 76-85.

Strittmatter, P.; Spatz, L.; Corcoran, D.; Rogers, M. J.; Setlow, B.; and Redline, R. (1974) Purification and properties of rat liver microsomal stearyl coenzyme A desaturase. Proc. Nat. Acad. Sci. USA 71, 4565-4569.

Stymne, S. and Stobart, A. K. (1986) Biosynthesis of •-linolenic acid in cotyledons and microsomal preparations of the developing seeds of common borage (*Borago officinalis*). Biochem. J. 240, 385-393.

Tamaki, H., Shimada, A., Ito, Y., Ohya, M., Takase, J., Miyashita, M., Miyagawa, H., Nozaki, H., Nakayama, R. and Hidehiko Kumagai (2007) LPT1 Encodes a Membrane-bound O-Acyltransferase Involved in the Acylation of Lysophospholipids in the Yeast *Saccharomyces cerevisiae*. J. Biol. Chem. 282, 34288-34298.

Tang G-Q., Novitzky W P., Griffin H C., Huber S C., and Dewey R E. (2005) Oleate desaturase enzymes of soybean: evidence of regulation through differential stability and phosphorylation. The Plant Journal 44, 433-446.

Tudzynski, P., Correia, T., and Keller, U. (2001). Biotechnology and genetics of ergot alkaloids. Appl. Microbiol. Biotechnol. 57, 593-605.

Wachter E., Quante T., Merusi C., Arczewska A., Stewart F., Webb S., Bird A. (2014) Synthetic CpG islands reveal DNA sequence determinants of chromatin structure. eLIFE e03397. DOI: 10.7554/eLife.03397.

Xiao G., Zhang Z Q., Yin C F., Liu R Y., Wu X M., Tan T L., Chen S Y., Lu C M. and Guan C Y. (2014) Characterization of the promoter and 5'-UTR intron of oleic acid desaturase (FAD2) gene in *Brassica napus*. Gene 545, 45-55.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11484560B2). An electronic copy of the "Sequence Listing" will also be available from the USPTO upon request and payment of the fee set forth in 37 CFR 1.19(b)(3).

The invention claimed is:

1. An assay method for simulating a plant metabolic property of a plant grown under field conditions, comprising:

i) providing a transgenic plant of order Brassicales expressing a delta-12 desaturase heterologous to the transgenic plant, wherein said delta-12 desaturase has at least 96% total amino acid sequence identity to the amino acid sequence as set forth in SEQ ID NO: 328, and wherein the transgenic plant also expresses at least one or more enzymes of unsaturated fatty acid metabolism heterologous to the transgenic plant, of which enzymes at least one is capable of using linoleic acid as a substrate, and of which enzymes at least one is connected to a plant metabolic property, ii) growing the transgenic plant under greenhouse conditions;

iii) measuring said plant metabolic property for said transgenic plant, wherein the measured metabolic property simulates the plant metabolic property measurement for the transgenic plant grown under field conditions; and iv) selecting transgenic offspring of the transgenic plant for field trials and conducing field trials on said selected transgenic offspring to produce a commercially viable transgenic plant variety of order Brassicales having said simulated plant metabolic property, wherein number of field trials required for development of said commercially viable transgenic plant variety is reduced compared to a corresponding control plant not expressing said delta-12 desaturase, wherein said transgenic offspring expresses the delta-12 desaturase and the at least one or more enzymes of unsaturated fatty acid metabolism, wherein the plant metabolic property is production of polyunsaturated fatty acids comprising VLC-PUFAs,
wherein the transgenic plant exhibits a negative correlation between seed oil content and delta-12-desaturase conversion efficiency whether grown in greenhouse or in field conditions, and wherein VLC-PUFA production levels in the transgenic plant and said selected transgenic offspring is consistent across different environmental conditions as compared to a corresponding control plant not expressing said delta-12-desaturase and grown under similar environmental conditions.

2. The assay method according to claim 1, wherein the Delta-12 desaturase is obtained from an organism of class oomycetes.

3. The assay method of claim 1, wherein the delta-12 desaturase expressed by the transgenic plant has 100% total amino acid sequence identity to the amino acid sequence as set forth in SEQ ID NO: 328.

* * * * *